(12) United States Patent
Alam et al.

(10) Patent No.: US 11,548,867 B2
(45) Date of Patent: Jan. 10, 2023

(54) AMIDO COMPOUNDS AS AHR MODULATORS

(71) Applicant: IDEAYA BIOSCIENCES, INC., South San Francisco, CA (US)

(72) Inventors: Muzaffar Alam, South San Francisco, CA (US); Hilary Plake Beck, South San Francisco, CA (US); Michael Patrick Dillon, South San Francisco, CA (US); Marcos Gonzalez-Lopez, South San Francisco, CA (US); Alice Chen Rico, South San Francisco, CA (US); James Clifford Sutton, Jr., South San Francisco, CA (US)

(73) Assignee: IDEA YA BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 16/631,738

(22) PCT Filed: Jul. 18, 2018

(86) PCT No.: PCT/US2018/042747
§ 371 (c)(1),
(2) Date: Jan. 16, 2020

(87) PCT Pub. No.: WO2019/018562
PCT Pub. Date: Jan. 24, 2019

(65) Prior Publication Data
US 2021/0115016 A1    Apr. 22, 2021

Related U.S. Application Data

(60) Provisional application No. 62/534,543, filed on Jul. 19, 2017.

(51) Int. Cl.
*C07D 401/12* (2006.01)
*C07D 215/12* (2006.01)
(Continued)

(52) U.S. Cl.
CPC ......... *C07D 401/12* (2013.01); *C07D 215/12* (2013.01); *C07D 217/18* (2013.01);
(Continued)

(58) Field of Classification Search
CPC .. C07D 401/12; C07D 215/12; C07D 217/18; C07D 401/14; C07D 403/12;
(Continued)

(56) References Cited

U.S. PATENT DOCUMENTS 6,060,477 A    5/2000  Piazza et al.
6,184,231 B1 *  2/2001  Hewawasam ........ C07D 215/54
                                                   514/312
(Continued)

FOREIGN PATENT DOCUMENTS

CN    103864792 A    6/2014
EP       719765 A2    7/1996
(Continued)

OTHER PUBLICATIONS

National Center for Biotechnology Information. PubChem Compound Summary for CID 89798261. https://pubchem.ncbi.nlm.nih.gov/compound/89798261. Create Date Feb. 13, 2015. (Year: 2015).*
(Continued)

*Primary Examiner* — Daniel R Carcanague
(74) *Attorney, Agent, or Firm* — Mintz, Levin, Cohn, Ferris, Glovsky & Popeo, P.C.

(57) ABSTRACT

Provided herein are compounds, compositions and methods of using the compounds and compositions for the treatment of diseases modulated, as least in part, by AhR. The compounds are represented by formulae Formula (I), (II), (III), (iv): wherein the letters and symbols a, b, c, d, e, f, g, Z, $R^{1b}$, $R^{2a}$ and $R^{2b}$ have the meanings provided in the specification.

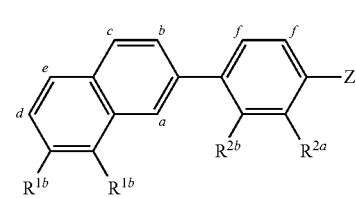

I

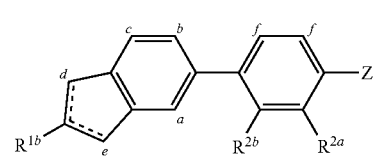

II

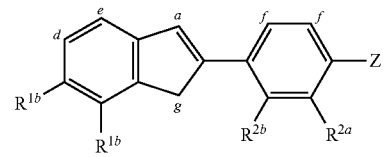

III

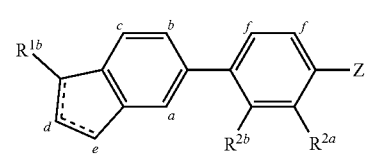

IV

19 Claims, No Drawings

(51) Int. Cl.
*C07D 217/18* (2006.01)
*C07D 401/14* (2006.01)
*C07D 403/12* (2006.01)
*C07D 405/12* (2006.01)
*C07D 413/12* (2006.01)
*C07D 413/14* (2006.01)
*C07D 471/04* (2006.01)
*C07D 487/04* (2006.01)

(52) U.S. Cl.
CPC ......... *C07D 401/14* (2013.01); *C07D 403/12* (2013.01); *C07D 405/12* (2013.01); *C07D 413/12* (2013.01); *C07D 413/14* (2013.01); *C07D 471/04* (2013.01); *C07D 487/04* (2013.01)

(58) Field of Classification Search
CPC .. C07D 405/12; C07D 413/12; C07D 413/14; C07D 471/04; C07D 487/04
See application file for complete search history.

(56) References Cited

U.S. PATENT DOCUMENTS

| | | | |
|---|---|---|---|
| 6,271,390 | B1 | 8/2001 | Sircar et al. |
| 10,815,250 | B2 * | 10/2020 | Alam ............ C07D 471/04 |
| 2005/0026976 | A1 | 2/2005 | Curtin et al. |
| 2006/0189606 | A1 | 8/2006 | Karp et al. |
| 2007/0161626 | A1 | 7/2007 | Halley et al. |
| 2008/0182844 | A1 | 7/2008 | Bjergarde et al. |
| 2009/0163489 | A1 | 6/2009 | Booker et al. |
| 2010/0215579 | A1 | 8/2010 | Kung et al. |
| 2010/0239496 | A1 | 9/2010 | Gangdharmath et al. |
| 2011/0071150 | A1 | 3/2011 | Alam et al. |
| 2011/0195044 | A1 | 8/2011 | Romine |
| 2011/0263612 | A1 | 10/2011 | Whitten et al. |
| 2012/0028963 | A1 | 2/2012 | Lee et al. |
| 2012/0178622 | A1 * | 7/2012 | Gross ............ C07D 413/10 504/100 |
| 2012/0258974 | A1 | 10/2012 | Belardinelli et al. |
| 2014/0228367 | A1 | 8/2014 | Flynn |
| 2014/0343051 | A1 | 11/2014 | Sauvageau et al. |
| 2015/0094307 | A1 * | 4/2015 | Schmidt ............ A61K 31/427 514/235.8 |
| 2016/0102077 | A1 | 4/2016 | Boral et al. |
| 2017/0158690 | A1 | 6/2017 | Wu et al. |
| 2017/0239296 | A1 | 8/2017 | Boitano et al. |
| 2019/0270754 | A1 * | 9/2019 | Alam ............ C07D 491/107 |
| 2021/0002297 | A1 * | 1/2021 | Alam ............ C07D 498/12 |
| 2021/0079001 | A1 * | 3/2021 | Beck ............ C07D 487/04 |
| 2021/0254006 | A1 * | 8/2021 | Alam ............ C12N 5/0647 |

FOREIGN PATENT DOCUMENTS

| | | | |
|---|---|---|---|
| WO | WO-9618617 | A1 | 6/1996 |
| WO | WO-9807726 | A1 | 2/1998 |
| WO | WO-9848800 | A1 | 11/1998 |
| WO | WO 2003007959 | * | 1/2003 ............ C07D 401/04 |
| WO | WO-2003082186 | A1 | 10/2003 |
| WO | WO-2004012736 | A1 | 2/2004 |
| WO | WO-2004024897 | A2 | 3/2004 |
| WO | WO-2004046122 | A2 | 6/2004 |
| WO | WO-2005013950 | A2 | 2/2005 |
| WO | WO-2005021548 | A2 | 3/2005 |
| WO | WO-2005034869 | A2 | 4/2005 |
| WO | WO-2005105761 | A1 | 11/2005 |
| WO | WO-2006076009 | A2 | 7/2006 |
| WO | WO-2006078283 | A2 | 7/2006 |
| WO | WO-2006080821 | A1 | 8/2006 |
| WO | WO-2006105081 | A2 | 10/2006 |
| WO | WO-2008005457 | A2 | 1/2008 |
| WO | WO-2008054599 | A2 | 5/2008 |
| WO | WO-2008092861 | A1 | 8/2008 |
| WO | WO-2008115262 | A2 | 9/2008 |
| WO | WO-2008116129 | A2 | 9/2008 |
| WO | WO-2009005551 | A2 | 1/2009 |
| WO | WO-2009112445 | A1 | 9/2009 |
| WO | WO-2009129267 | A2 | 10/2009 |
| WO | WO-2010064875 | A2 | 6/2010 |
| WO | WO-2010093808 | A1 | 8/2010 |
| WO | WO-2010104851 | A1 | 9/2010 |
| WO | WO-2010106436 | A2 | 9/2010 |
| WO | WO-2010115736 | A2 | 10/2010 |
| WO | WO-2010118009 | A1 | 10/2010 |
| WO | WO-2010124097 | A2 | 10/2010 |
| WO | WO-2011052923 | A2 | 5/2011 |
| WO | WO-2011133750 | A1 | 10/2011 |
| WO | WO-2011138665 | A1 | 11/2011 |
| WO | WO-2011146401 | A1 | 11/2011 |
| WO | WO-2012067863 | A1 | 5/2012 |
| WO | WO-2012069856 | A1 | 5/2012 |
| WO | WO-2013036749 | A1 | 3/2013 |
| WO | WO-2013175281 | A1 | 11/2013 |
| WO | WO-2014048165 | A1 | 4/2014 |
| WO | WO-2014131855 | A1 | 9/2014 |
| WO | WO-2014143609 | A1 | 9/2014 |
| WO | WO-2017039318 | A1 | 3/2017 |
| WO | WO-2017049165 | A1 | 3/2017 |
| WO | WO-2017161001 | A1 | 9/2017 |
| WO | WO-2017184547 | A1 * | 10/2017 ......... A61K 31/4709 |
| WO | WO-2018054989 | A1 | 3/2018 |
| WO | WO-2019018562 | A1 | 1/2019 |
| WO | WO-2020018848 | A1 * | 1/2020 ........... C12N 5/0647 |

OTHER PUBLICATIONS

Wang; Journal of the American Chemical Society 2011, 133, 9878-9891, with supporting information, 331 pages in total. (Year: 2011).*

Murray; Nat Rev Cancer 2014, 14, 801-814. https://doi.org/10.1038/nrc3846 (Year: 2014).*

International Search Report in PCT/US2018/042747 dated Oct. 29, 2018, 4 pages.

Written Opinion of the International Searching Authority in PCT/US2018/042747 dated Oct. 29, 2018, 7 pages.

Abuzar et al., Synthesis of Substituted Benzimidazoles as Potential Anthelminthics, Archiv der Pharmazie, 1982, 315(10), 866-871.

Ackermann et al., Copper-Catalyzed N-Arylation/Hydroamin(d)ation Domino Synthesis of Indoles and its Application to the Preparation of a Chek1/KDR Kinase Inhibitor Pharmacophore, Advanced Synthesis and Catalysis, 2009, 351(7-8), 1064-1072.

Åkerbladh et al., Synthesis of 4-Quinolones via a Carbonylative Sonogashira Cross-Coupling Using Molybdenum Hexacarbonyl as a CO Source, Journal of Organic Chemistry, 2015, 80(3), 1464-1471.

Angelbello et al., Development of pharmacophore models for small molecules targeting RNA: Application to the RNA repeat expansion in myotonic dystrophy type 1., Bioorganic and Medicinal Chemistry Letters, 2016, 26(23), 5792-5796.

Atwell et al., Potential antitumor agents. 57. 2-Phenylquinoline-8-carboxamides as minimal DNA-intercalating antitumor agents with in vivo solid tumor activity, Journal of Medicinal Chemistry, 1989, 32(2), 396-401.

Bowser et al., Novel anti-infection agents: small-molecule inhibitors of bacterial transcription factors, Bioorganic and Medicinal Chemistry Letters, 2007, 17(20), 5652-5655.

Cai et al., Candidate PET Radioligand Development for Neurofibrillary Tangles: Two Distinct Radioligand Binding Sites Identified in Postmortem Alzheimer's Disease Brain, ACS Chemical Neuroscience, 2016, 7(7), 897-911.

Chai et al., Molecular Modeling of Small Molecules as BVDV RNA-Dependent RNA Polymerase Allosteric Inhibitors, Bulletin of the Korean Chemical Society (2013), 34(3), 837-850.

Chapman et al., Small molecule modulators of HIV Rev/Rev response element interaction identified by random screening, Antiviral Research, 2002, 54(3), 149-162.

Chua et al., Antitumor Benzothiazoles. 7. Synthesis of 2-(4-Acylaminophenyl)benzothiazoles and Investigations into the Role

(56) References Cited

OTHER PUBLICATIONS of Acetylation in the Antitumor Activities of the Parent Amines, Journal of Medicinal Chemistry, 1999, 42(3), 381-392.
Cichero et al., Benzimidazole-based derivatives as privileged scaffold developed for the treatment of the RSV infection: a computational study exploring the potency and cytotoxicity profiles, Journal of Enzyme Inhibition and Medicinal Chemistry, 2017, 32(1), 375-402.
Haikarainen et al., para-Substituted 2-phenyl-3,4-dihydroquinazolin-4-ones as potent and selective tankyrase inhibitors, ChemMedChem, 2013, 8(12), 1978-1985.
Halland et al., Discovery of N [4-(1H Pyrazolo[3;4 b]pyrazin-6-yl)-phenyl]-sulfonamides as Highly Active and Selective SGK1 Inhibitors, ACS Medicinal Chemistry Letters (2015); 6(1); 73-78.
Hilal et al., A QSAR study for 2-(4-aminophenyl)benzothiazoles: using DFT optimisation of geometry of molecules, Molecular Simulation, 2011, 37(1), 62-71.
Hu et al., Palladium-catalyzed cyclization of o-alkynyltrifluoroacetanilides followed by isocyanide insertion: synthesis of 2-substituted 1H-indole-3-carboxamides, Chemical Communications, 2012, 48(59), 7371-7373.
International Search Report for PCT/US2019/042487 dated Oct. 29, 2018, 4 pages.
Kaila et al., Synthesis and Biological Evaluation of Quinoline Salicylic Acids As P-Selectin Antagonists, Journal of Medicinal Chemistry, 2007, 50(1), 21-39.
Lamie et al., Design and synthesis of three series of novel antitumor-azo derivatives, Medicinal Chemistry Research, 2017, 26(6), 1228-1240.
Lee et al., 7-Fluoroindazoles as Potent and Selective Inhibitors of Factor Xa, Journal of Medicinal Chemistry (2008); 51(2); 282-297.
Mqadmi et al., Prevention of complement-mediated immune hemolysis by a small molecule compound, Biochemical and Biophysical Research Communications, 2004, 325(4), 1465-1471.
O'Connor et al., Lysis of egg phosphatidylcholine vesicles by tricyclic carboxamide antitumor agents, Chemico-Biological Interactions, 1990, 75(1), 93-104.
Okamura et al., Quinoline and benzimidazole derivatives: candidate probes for in vivo imaging of tau pathology in Alzheimer's disease, Journal of Neuroscience, 2005, 25(47), 10857-10862.
Özkay et al., Antimicrobial activity of a new combination system of benzimidazole and various azoles, Archiv der Pharmazie, 2011, 344(4), 264-271.
Peng et al., A convenient one-pot procedure for the synthesis of 2-aryl quinazolines using active MnO2 as oxidant, Journal of Heterocyclic Chemistry, 2010, 47(5), 1240-1245.
Peng et al., Discovery of 2-(2-aminopyrimidin-5-yl)-4-morpholino-N-(pyridin-3-yl)quinazolin-7-amines as novel PI3K/mTOR inhibitors and anticancer agents, European Journal of Medicinal Chemistry, 2016, 108, 644-654.
Pi et al., Exploration of Biaryl Carboxylic Acids as Proton Shuttles for the Selective Functionalization of Indole C—H Bonds, Journal of Organic Chemistry, 2018, 83(10), 5791-5800.
Ran et al., A selectivity study on mTOR/PI3Ka inhibitors by homology modeling and 3D-QSAR, Journal of Molecular Modeling (2012); 18(1); 171-186.
Richards et al., Substituted 2-phenyl-benzimidazole derivatives: novel compounds that suppress key markers of allergy, European Journal of Medicinal Chemistry, 2006, 41(8), 950-969.
Rios et al., Identification of novel benzimidazole derivatives as anti-Trypanosoma cruzi agents: solid-phase synthesis, structure-activity relationships and molecular docking studies, Future Medicinal Chemistry, 2013, 5(15), 1719-1732.
Rios, Natalia et al., Microwave-Assisted Solid-Phase Synthesis of a 1,2-Disubstituted Benzimidazole Library by Using a Phosphonium Linker, Journal of Heterocyclic Chemistry, 2013, 50(3), 720-726.
Rostamizadeh et al., Amino acid-based ionic liquid immobilized on α-Fe2O3-MCM-41: An efficient magnetic nanocatalyst and recyclable reaction media for the synthesis of quinazolin-4(3H)-one derivatives, Journal of Molecular Catalysis A: Chemical, 2013, 374-375, 102-110.
Rzuczek et al., Studying a Drug-like, RNA-Focused Small Molecule Library Identifies Compounds That Inhibit RNA Toxicity in Myotonic Dystrophy, ACS Chemical Biology, 2015, 10(12), 2706-2715.
Sandlin et al., Use of the NP-40 Detergent-Mediated Assay in Discovery of Inhibitors of β-Hematin Crystallization, Antimicrobial Agents and Chemotherapy, 2011, 55(7), 3363-3369.
Sharif et al., Oxidative synthesis of quinazolinones and benzothiadiazine 1,1-dioxides from 2-aminobenzamide and 2-aminobenzenesulfonamide with benzyl alcohols and aldehydes, RSC Advances, 2014, 4(1), 8-17.
Shilova et al., Modified method for determining aromatic diamines during the synthesis of oligomeric para-aramids, Fibre Chemistry, 2012, 43(5), 376-380.
Singh et al., Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives, Synthesis, 2000, (10), 1380-1390.
Singh et al., Molecular dynamics simulations and statistical coupling analysis of GPI12 in L. major: functional co-evolution and conservedness reveals potential drug-target sites, Molecular BioSystems, 2015, 11(3), 958-968.
Tago et al., Synthesis and preliminary evaluation of 2-arylhydroxyquinoline derivatives for tau imaging, Journal of Labelled Compounds and Radiopharmaceuticals, 2014, 57(1), 18-24.
Tonelli et al., Antiviral activity of benzimidazole derivatives. II. Antiviral activity of 2-phenylbenzimidazole derivatives, Bioorganic and Medicinal Chemistry, 2010, 18(8), 2937-2953.
Tonelli et al., Pharmacophore modeling, resistant mutant isolation, docking, and MM-PBSA analysis: Combined experimental/computer-assisted approaches to identify new inhibitors of the bovine viral diarrhea virus (BVDV), Bioorganic and Medicinal Chemistry, 2010, 18(6), 2304-2316.
Uttarwar et al., Synthesis and pharmacological screening of derivatives of benzimidazole linked with quinoline and tetrazole, Journal of Chemical and Pharmaceutical Research, 2013, 5(4), 41-46.
Verheijen et al., Discovery of 4-Morpholino-6-aryl-1H-pyrazolo[3;4-d]pyrimidines as Highly Potent and Selective ATP-Competitive Inhibitors of the Mammalian Target of Rapamycin (mTOR): Optimization of the 6-Aryl Substituent, Journal of Medicinal Chemistry (2009); 52(24); 8010-8024.
Wang et al., Synthesis and antitumor activities evaluation of m-(4-morpholinoquinazolin-2-yl)benzamides in vitro and in vivo, European Journal of Medicinal Chemistry, 2015, 96, 382-395.
Written Opinion of the International Searching Authority/US for PCT/US2019/042487 dated Oct. 29, 2018, 7 pages.
Chemical Abstracts STN Record for CAS Registry No. 2143075-18-5, Acetamide, N-[4-[4-(3-chloropropyl)-2-quinolinyl]phenyl]-, retrieved Jul. 3, 2018.
Chemical Abstracts STN Record for CAS Registry No. 2143075-17-4, Acetamide, N-[4-[4-(3-hydroxypropyl)-2-quinolinyl]phenyl]-, retrieved Jul. 3, 2018.
Chemical Abstracts STN Record for CAS Registry No. 2143074-51-3, Acetamide, N-[4-[4-(chloromethyl)-2-quinolinyl]phenyl]-, retrieved Jul. 3, 2018.
Chemical Abstracts STN Record for CAS Registry No. 2143074-49-9, Acetamide, N-[4-(4-formyl-2-quinolinyl)phenyl]-, retrieved Jul. 3, 2018.
Chemical Abstracts STN Record for CAS Registry No. 2143074-47-7, Acetamide, N-[4-[4-(hydroxymethyl)-2-quinolinyl]phenyl]-, retrieved Jul. 3, 2018.
Chemical Abstracts STN Record for CAS Registry No. 2143074-24-0, Acetamide, N-[4-(4-acetyl-2-quinolinyl)phenyl]-, retrieved Jul. 3, 2018.
Chemical Abstracts STN Record for CAS Registry No. 2143073-90-7, Acetamide, N-[4-[6-chloro-(4-carboxy)-2-quinolinyl]phenyl-, retrieved Jul. 3, 2018.
Chemical Abstracts STN Record for CAS Registry No. 2143073-78-1, Acetamide, N-[4-[8-chloro-(4-carboxy)-2-quinolinyl]phenyl-, retrieved Jul. 3, 2018.

(56) References Cited

OTHER PUBLICATIONS

Chemical Abstracts STN Record for CAS Registry No. 2143072-43-7, Acetamide, N-[4-[4-(4-morpholinyl)-2-quinolinyl]phenyl]-, retrieved Jul. 3, 2018.
Chemical Abstracts STN Record for CAS Registry No. 2143072-41-5, Acetamide, N-[6-[6-chloro-4-(4-morpholinylcarbonyl)-2-quinolinyl]-3-pyridinyl]-, retrieved Jul. 3, 2018.
Chemical Abstracts STN Record for CAS Registry No. 2143072-39-1, Acetamide, N-[5-[6-chloro-4-(4-morpholinylcarbonyl)-2-quinolinyl]-2-pyridinyl]-, retrieved Jul. 3, 2018.
Chemical Abstracts STN Record for CAS Registry No. 2143072-37-9, Acetamide, N-[4-[6-chloro-4-(4-morpholinylcarbonyl)-2-quinolinyl]phenyl]-, retrieved Jul. 3, 2018.
Chemical Abstracts STN Record for CAS Registry No. 2143072-35-7, Acetamide, N-[4-[8-chloro-4-(4-morpholinylcarbonyl)-2-quinolinyl]phenyl]-, retrieved Jul. 3, 2018.
Chemical Abstracts STN Record for CAS Registry No. 2143072-33-5, Acetamide, N-[5-[8-chloro-4-(4-morpholinylcarbonyl)-2-quinolinyl]-2-pyridinyl]-, retrieved Jul. 3, 2018.
Chemical Abstracts STN Record for CAS Registry No. 2143072-31-3, Acetamide, N-[4-[8-chloro-4-(4-morpholinylcarbonyl)-2-quinolinyl]phenyl]-, retrieved Jul. 3, 2018.
Chemical Abstracts STN Record for CAS Registry No. 1965250-06-9(Component: 1584711-32-9), Butanamide, N-[2,6-dimethyl-4-(2-quinolinyl)phenyl]-3,3-dimethyl-, hydrochloride (1:1), retrieved Jul. 3, 2018.
Chemical Abstracts STN Record for CAS Registry No. 1932700-88-3, Acetamide, N-[5-(1-oxido-2-quinoxalinyl)-2-pyridinyl]-, retrieved Jul. 3, 2018.
Chemical Abstracts STN Record for CAS Registry No. 1838191-55-1, Carbamic acid, N-[4-(1-oxido-1,2,4-benzotriazin-3-yl)phenyl]-, 1,1-dimethylethyl ester, retrieved Jul. 3, 2018.
Chemical Abstracts STN Record for CAS Registry No. 1710372-24-9, Acetamide, N-[4-[6,7-dimethoxy-4-(4-morpholinyl)-2-quinazolinyl]phenyl]-, retrieved Jul. 3, 2018.
Chemical Abstracts STN Record for CAS Registry No. 1646550-42-6, Acetamide, N-[4-(1,4-dihydro-4-oxo-2-quinolinyl)phenyl]-, retrieved Jul. 3, 2018.
Chemical Abstracts STN Record for CAS Registry No. 1628638-52-7, 4-Quinazolinecarboxylic acid, 2-[4-(acetylamino)phenyl]-, retrieved Jul. 3, 2018.
Chemical Abstracts STN Record for CAS Registry No. 1584716-39-1, Butanamide, N-[4-(7-fluoro-2-quinolinyl)-2,6-dimethylphenyl]-3,3-dimethyl-, retrieved Jul. 3, 2018.
Chemical Abstracts STN Record for CAS Registry No. 1584713-72-3, Butanamide, N-[4-(3-isoquinolinyl)-2,6-dimethylphenyl]-3,3-dimethyl-, retrieved Jul. 3, 2018.
Chemical Abstracts STN Record for CAS Registry No. 1584713-69-8, Butanamide, N-[4-(6,8-difluoro-2-quinolinyl)-2,6-dimethylphenyl]-3,3-dimethyl-, retrieved Jul. 3, 2018.
Chemical Abstracts STN Record for CAS Registry No. 1584713-68-7, Butanamide, N-[4-(8-fluoro-2-quinolinyl)-2,6-dimethylphenyl]-3,3-dimethyl-, retrieved Jul. 3, 2018.
Chemical Abstracts STN Record for CAS Registry No. 1584713-67-6, Butanamide, N-[4-(6-fluoro-2-quinolinyl)-2,6-dimethylphenyl]-3,3-dimethyl-, retrieved Jul. 3, 2018.
Chemical Abstracts STN Record for CAS Registry No. 1584712-77-5(Component: 1584711-33-0), Butanamide, N-[2,6-dimethyl-4-(3-quinolinyl)phenyl]-3,3-dimethyl-, hydrochloride (1:1), retrieved Jul. 3, 2018.
Chemical Abstracts STN Record for CAS Registry No. 1584711-33-0, Butanamide, N-[2,6-dimethyl-4-(3-quinolinyl)phenyl]-3,3-dimethyl-, retrieved Jul. 3, 2018.
Chemical Abstracts STN Record for CAS Registry No. 1584711-32-9, Butanamide, N-[2,6-dimethyl-4-(2-quinolinyl)phenyl]-3,3-dimethyl-, retrieved Jul. 3, 2018.
Chemical Abstracts STN Record for CAS Registry No. 1396754-97-4, 6-Quinoxalinecarboxylic acid, 2-[4-(acetylamino)phenyl]-3-[methyl(1-methylethyl)amino]-, methyl ester, retrieved Jul. 3, 2018.
Chemical Abstracts STN Record for CAS Registry No. 1396754-95-2, 6-Quinoxalinecarboxylic acid, 2-[4-(acetylamino)phenyl]-3-[methyl(1-methylethyl)amino]-, retrieved Jul. 3, 2018.
Chemical Abstracts STN Record for CAS Registry No. 1338254-84-4, Acetamide, N-[4-[3-[[(ethylamino)carbonyl]amino]-8-methyl-6-isoquinolinyl]phenyl]-, retrieved Jul. 3, 2018.
Chemical Abstracts STN Record for CAS Registry No. 1312162-84-7, Acetamide, N-[4-(2-quinolinyl)phenyl]-, retrieved Jul. 3, 2018.
Chemical Abstracts STN Record for CAS Registry No. 1278576-77-4, Acetamide, N-[4-[4-(propylamino)-7-(trifluoromethyl)-2-quinazolinyl]phenyl]-, retrieved Jul. 3, 2018.
Chemical Abstracts STN Record for CAS Registry No. 1269359-75-2, Acetamide, N-[2-ethyl-4-(3-quinolinyl)phenyl]-, retrieved Jul. 3, 2018.
Chemical Abstracts STN Record for CAS Registry No. 1262586-43-5, Acetamide, N-[4-(3,4-dihydro-4-oxo-2-quinazolinyl)-2-nitrophenyl]-, retrieved Jul. 3, 2018.
Chemical Abstracts STN Record for CAS Registry No. 1262537-37-0, Acetamide, N-[4-[8-(trifluoromethyl)-2-quinazolinyl]phenyl]-, retrieved Jul. 3, 2018.
Chemical Abstracts STN Record for CAS Registry No. 1262537-35-8, Acetamide, N-[4-(5-fluoro-2-quinazolinyl)phenyl]-, retrieved Jul. 3, 2018.
Chemical Abstracts STN Record for CAS Registry No. 1262537-31-4, Acetamide, N-[4-(2-quinazolinyl)phenyl]-, retrieved Jul. 3, 2018.
Chemical Abstracts STN Record for CAS Registry No. 1200688-04-5, Acetamide, N-[4-(2-chloro-3-quinolinyl)phenyl]-, retrieved Jul. 3, 2018.
Chemical Abstracts STN Record for CAS Registry No. 1172225-25-0, Propanamide, N-[4-(3-chloro-4-methyl-2-quinolinyl)phenyl]-, retrieved Jul. 3, 2018.
Chemical Abstracts STN Record for CAS Registry No. 1171992-98-5(Component: 1172225-25-0), Propanamide, N-[4-(3-chloro-4-methyl-2-quinolinyl)phenyl]-, hydrochloride (1:1), retrieved Jul. 3, 2018.
Chemical Abstracts STN Record for CAS Registry No. 1154425-67-8, Acetamide, N-[4-(1,4-dihydro-3-hydroxy-4-oxo-2-quinolinyl)phenyl]-, retrieved Jul. 3, 2018.
Chemical Abstracts STN Record for CAS Registry No. 1115422-05-3, 4-Quinolinecarboxamide, 2-[4-(acetylamino)phenyl]-N-butyl-6-methyl-, retrieved Jul. 3, 2018.
Chemical Abstracts STN Record for CAS Registry No. 1115421-97-0, 4-Quinolinecarboxamide, 2-[4-(acetylamino)phenyl]-6-methyl-N-(3-methylbutyl)-, retrieved Jul. 3, 2018.
Chemical Abstracts STN Record for CAS Registry No. 1115421-96-9, 4-Quinolinecarboxamide, 2-[4-(acetylamino)phenyl]-6-methyl-N-propyl-, retrieved Jul. 3, 2018.
Chemical Abstracts STN Record for CAS Registry No. 1115421-75-4, 4-Quinolinecarboxamide, N-butyl-2-[4-[(1-oxopropyl)amino]phenyl]-, retrieved Jul. 3, 2018.
Chemical Abstracts STN Record for CAS Registry No. 1115421-68-5, 4-Quinolinecarboxamide, N-(1-methylethyl)-2-[4-[(1-oxopropyl)amino]phenyl]-, retrieved Jul. 3, 2018.
Chemical Abstracts STN Record for CAS Registry No. 1115421-66-3, Propanamide, N-[4-[4-[(4-methyl-1-piperidinyl)carbonyl]-2-quinolinyl]phenyl]-, retrieved Jul. 3, 2018.
Chemical Abstracts STN Record for CAS Registry No. 1115352-50-5, 4-Quinolinecarboxamide, 2-[4-(acetylamino)phenyl]-6-methyl-N-(1-methylethyl)-, retrieved Jul. 3, 2018.
Chemical Abstracts STN Record for CAS Registry No. 1115352-49-2, Acetamide, N-[4-[6-methyl-4-(1-pyrrolidinylcarbonyl)-2-quinolinyl]phenyl]-, retrieved Jul. 3, 2018.
Chemical Abstracts STN Record for CAS Registry No. 1115352-48-1, Acetamide, N-[4-[6-methyl-4-[(4-methyl-1-piperidinyl)carbonyl]-2-quinolinyl]phenyl]-, retrieved Jul. 3, 2018.
Chemical Abstracts STN Record for CAS Registry No. 1115352-40-3, Acetamide, N-[4-[4-(4-morpholinylcarbonyl)-2-quinolinyl]phenyl]-, retrieved Jul. 3, 2018.
Chemical Abstracts STN Record for CAS Registry No. 1115352-28-7, Propanamide, N-[4-[4-(4-morpholinylcarbonyl)-2-quinolinyl]phenyl]-, retrieved Jul. 3, 2018.

(56) References Cited

OTHER PUBLICATIONS

Chemical Abstracts STN Record for CAS Registry No. 1115352-27-6, 4-Quinolinecarboxamide, N-(3-methylbutyl)-2-[4-[(1-oxopropyl)amino]phenyl]-, retrieved Jul. 3, 2018.
Chemical Abstracts STN Record for CAS Registry No. 1115352-24-3, Propanamide, N-[4-[4-(1-pyrrolidinylcarbonyl)-2-quinolinyl]phenyl]-, retrieved Jul. 3, 2018.
Chemical Abstracts STN Record for CAS Registry No. 1115352-20-9, 4-Quinolinecarboxamide, N-(1-methylpropyl)-2-[4-[(1-oxopropyl)amino]phenyl]-, retrieved Jul. 3, 2018.
Chemical Abstracts STN Record for CAS Registry No. 1115317-41-3, 4-Quinolinecarboxamide, 2-[4-(acetylamino)phenyl]-6-methyl-N-(1-methylpropyl)-, retrieved Jul. 3, 2018.
Chemical Abstracts STN Record for CAS Registry No. 1115317-24-2, 4-Quinolinecarboxamide, 2-[4-[(1-oxopropyl)amino]phenyl]-N-propyl-, retrieved Jul. 3, 2018.
Chemical Abstracts STN Record for CAS Registry No. 1100946-38-0, Butanamide, N-[4-(4,7-dichloro-2-quinazolinyl)phenyl]-3-methyl-, retrieved Jul. 3, 2018.
Chemical Abstracts STN Record for CAS Registry No. 1086059-92-8, Acetamide, N-[5-[4-(4-pyridinyl)-6-quinolinyl]-2-pyridinyl]-, retrieved Jul. 3, 2018.
Chemical Abstracts STN Record for CAS Registry No. 1086057-80-8, Acetamide, N-[4-methyl-5-[4-(4-pyridinyl)-6-quinolinyl]-2-pyridinyl]-, retrieved Jul. 3, 2018.
Chemical Abstracts STN Record for CAS Registry No. 1041114-37-7, Acetamide, N-[2-methoxy-4-(6-methoxy-2-naphthalenyl)phenyl]-, retrieved Jul. 3, 2018.
Chemical Abstracts STN Record for CAS Registry No. 1041113-23-8, Acetamide, N-[2-hydroxy-4-(6-hydroxy-2-naphthalenyl)phenyl]-, retrieved Jul. 3, 2018.
Chemical Abstracts STN Record for CAS Registry No. 1034346-07-0, 4-Isoquinolinecarboxylic acid, 3-[4-[(1-oxopropyl)amino]phenyl]-, methyl ester, retrieved Jul. 3, 2018.
Chemical Abstracts STN Record for CAS Registry No. 1031980-47-8, Acetamide, N-[4-[4-(1-piperidinylcarbonyl)-2-quinolinyl]phenyl]-, retrieved Jul. 3, 2018.
Chemical Abstracts STN Record for CAS Registry No. 1031980-35-4, 4-Quinolinecarboxamide, 2-[4-(acetylamino)phenyl]-N-(3-methylbutyl)-, retrieved Jul. 3, 2018.
Chemical Abstracts STN Record for CAS Registry No. 1031980-23-0, Acetamide, N-[4-[4-(1-pyrrolidinylcarbonyl)-2-quinolinyl]phenyl]-, retrieved Jul. 3, 2018.
Chemical Abstracts STN Record for CAS Registry No. 1031980-20-7, Acetamide, N-[4-[4-[(4-methyl-1-piperidinyl)carbonyl]-2-quinolinyl]phenyl]-, retrieved Jul. 3, 2018.
Chemical Abstracts STN Record for CAS Registry No. 1031980-11-6, 4-Quinolinecarboxamide, 2-[4-(acetylamino)phenyl]-N-(1-methylpropyl)-, retrieved Jul. 3, 2018.
Chemical Abstracts STN Record for CAS Registry No. 1031980-08-1, Propanamide, N-[4-[4-(1-piperidinylcarbonyl)-2-quinolinyl]phenyl]-, retrieved Jul. 3, 2018.
Chemical Abstracts STN Record for CAS Registry No. 1031980-05-8, 4-Quinolinecarboxamide, N-[2-(dimethylamino)ethyl]-2-[4-[(1-oxopropyl)amino]phenyl]-, retrieved Jul. 3, 2018.
Chemical Abstracts STN Record for CAS Registry No. 1031966-41-2, 4-Quinolinecarboxamide, 2-[4-(acetylamino)phenyl]-N-(1-methylethyl)-, retrieved Jul. 3, 2018.
Chemical Abstracts STN Record for CAS Registry No. 1030102-11-4, Acetamide, N-[4-[6-methyl-4-(1-piperidinylcarbonyl)-2-quinolinyl]phenyl]-, retrieved Jul. 3, 2018.
Chemical Abstracts STN Record for CAS Registry No. 2088628-56-0, Carbamic acid, N-[4-(2-quinoxalinyl)phenyl]-, methyl ester, retrieved Jul. 3, 2018.
Chemical Abstracts STN Record for CAS Registry No. 1931921-69-5, Carbamic acid, N-[4-(6-methoxy-2-quinolinyl)phenyl]-, 1,1-dimethylethyl ester, retrieved Jul. 3, 2018.
Chemical Abstracts STN Record for CAS Registry No. 1852602-87-9, Carbamic acid, N-[5-[7-amino-4-(4-morpholinyl)-2-quinazolinyl]-4-(trifluoromethyl)-2-pyridinyl]-, 1,1-dimethylethyl ester, retrieved Jul. 3, 2018.
Chemical Abstracts STN Record for CAS Registry No. 1852602-86-8, Carbamic acid, N-[5-[4-(4-morpholinyl)-7-nitro-2-quinazolinyl]-4-(trifluoromethyl)-2-pyridinyl]-, 1,1-dimethylethyl ester, retrieved Jul. 3, 2018.
Chemical Abstracts STN Record for CAS Registry No. 1839104-88-9, Carbamic acid, N-[4-(4-chloro-6-quinolinyl)phenyl]-, 1,1-dimethylethyl ester, retrieved Jul. 3, 2018.
Chemical Abstracts STN Record for CAS Registry No. 1839104-87-8, Carbamic acid, N-[4-(6-quinolinyl)phenyl]-, 1,1-dimethylethyl ester, retrieved Jul. 3, 2018.
Chemical Abstracts STN Record for CAS Registry No. 1707147-10-1, Carbamic acid, N-[4-[6-[(2R)-2,3-dihydroxypropoxy]-2-quinolinyl]phenyl]-N-methyl-, 1,1-dimethylethyl ester, retrieved Jul. 3, 2018.
Chemical Abstracts STN Record for CAS Registry No. 1707146-90-4, Carbamic acid, N-[4-(6-hydroxy-2-quinolinyl)phenyl]-N-methyl-, 1,1-dimethylethyl ester, retrieved Jul. 3, 2018.
Chemical Abstracts STN Record for CAS Registry No. 1684447-75-3, Carbamic acid, N-methyl-N-[4-(2-naphthalenyl)phenyl]-, 1,1-dimethylethyl ester, retrieved Jul. 3, 2018.
Chemical Abstracts STN Record for CAS Registry No. 1646550-43-7, Carbamic acid, N-[4-(1,4-dihydro-4-oxo-2-quinolinyl)phenyl]-, 1,1-dimethylethyl ester, retrieved Jul. 3, 2018.
Chemical Abstracts STN Record for CAS Registry No. 1609025-38-8, 6-Quinoxalinecarboxylic acid, 3-[4-[[(1,1-dimethylethoxy)carbonyl]methylamino]phenyl]-2-phenyl-, methyl ester, retrieved Jul. 3, 2018.
Chemical Abstracts STN Record for CAS Registry No. 1609025-37-7, 6-Quinoxalinecarboxylic acid, 3-[4-[[(1,1-dimethylethoxy)carbonyl]methylamino]phenyl]-2-phenyl-, retrieved Jul. 3, 2018.
Chemical Abstracts STN Record for CAS Registry No. 1609025-36-6, 6-Quinoxalinecarboxylic acid, 3-[4-[[(1,1-dimethylethoxy)carbonyl]amino]phenyl]-2-phenyl-, methyl ester, retrieved Jul. 3, 2018.
Chemical Abstracts STN Record for CAS Registry No. 1461720-18-2, 4-Piperidinecarboxylic acid, 1-[3-[4-[[(1,1-dimethylethoxy)carbonyl]amino]phenyl]-6-methyl-2-quinolinyl]-, retrieved Jul. 3, 2018.
Chemical Abstracts STN Record for CAS Registry No. 1451074-30-8, Carbamic acid, N-[4-[6-(2-hydroxyethoxy)-2-quinolinyl]phenyl]-, 1,1-dimethylethyl ester, retrieved Jul. 3, 2018.
Chemical Abstracts STN Record for CAS Registry No. 1437281-31-6, Carbamic acid, N-[4-[7-(2-hydroxyethoxy)-2-quinoxalinyl]phenyl]-N-methyl-, 1,1-dimethylethyl ester, retrieved Jul. 3, 2018.
Chemical Abstracts STN Record for CAS Registry No. 1417912-62-9, Carbamic acid, N-[3-ethoxy-4-(2-formyl-3-quinolinyl)phenyl]-, 1,1-dimethylethyl ester, retrieved Jul. 3, 2018.
Chemical Abstracts STN Record for CAS Registry No. 1578483-92-7, Carbamic acid, N-[5-(3-chloro-6-isoquinolinyl)-2-pyridinyl]-N-methyl-, 1,1-dimethylethyl ester, retrieved Jul. 3, 2018.
Chemical Abstracts STN Record for CAS Registry No. 1563178-53-9, Carbamic acid, N-[4-(7-hydroxy-2-quinolinyl)phenyl]-, 1,1-dimethylethyl ester, retrieved Jul. 3, 2018.
Chemical Abstracts STN Record for CAS Registry No. 1563178-42-6, Carbamic acid, N-[4-(7-methoxy-2-quinolinyl)phenyl]-N-methyl-, 1,1-dimethylethyl ester, retrieved Jul. 3, 2018.
Chemical Abstracts STN Record for CAS Registry No. 1394971-34-6, 6-Quinoxalinecarboxylic acid, 2-[6-[[(1,1-dimethylethoxy)carbonyl]amino]-3-pyridinyl]-3-[methyl(1-methylethyl)amino]-, methyl ester, retrieved Jul. 3, 2018.
Chemical Abstracts STN Record for CAS Registry No. 1374109-76-8, Carbamic acid, N-[4-[6-(dimethylamino)-2-quinolinyl]-2-fluorophenyl]-, 1,1-dimethylethyl ester, retrieved Jul. 3, 2018.
Chemical Abstracts STN Record for CAS Registry No. 1374109-59-7, Carbamic acid, N-ethyl-N-[5-(6-hydroxy-2-quinolinyl)-2-pyridinyl]-, 1,1-dimethylethyl ester, retrieved Jul. 3, 2018.

(56) References Cited

OTHER PUBLICATIONS

Chemical Abstracts STN Record for CAS Registry No. 1374109-51-9, Carbamic acid, N-[5-(6-hydroxy-2-quinolinyl)-2-pyridinyl]-N-methyl-, 1,1-dimethylethyl ester, retrieved Jul. 3, 2018.
Chemical Abstracts STN Record for CAS Registry No. 1374109-46-2, Carbamic acid, N-[5-(6-hydroxy-2-quinolinyl)-2-pyridinyl]-, 1,1-dimethylethyl ester, retrieved Jul. 3, 2018.
Chemical Abstracts STN Record for CAS Registry No. 1374109-42-8, Carbamic acid, N-ethyl-N-[4-(6-hydroxy-2-quinolinyl)phenyl]-, 1,1-dimethylethyl ester, retrieved Jul. 3, 2018.
Chemical Abstracts STN Record for CAS Registry No. 1374109-40-6, Carbamic acid, N-ethyl-N-[4-[6-(3-fluoro-2-hydroxypropoxy)-2-quinolinyl]phenyl]-, 1,1-dimethylethyl ester, retrieved Jul. 3, 2018.
Chemical Abstracts STN Record for CAS Registry No. 1313359-28-2, Carbamic acid, N-[4-(4-fluoro-2-quinolinyl)phenyl]-N-methyl-, 1,1-dimethylethyl ester, retrieved Jul. 3, 2018.
Chemical Abstracts STN Record for CAS Registry No. 1268864-80-7, 6-Quinoxalinecarboxylic acid, 2-[6-[[(1,1-dimethylethoxy)carbonyl]amino]-3-pyridinyl]-3-[methyl(1-methylethyl)amino]-, retrieved Jul. 3, 2018.
Chemical Abstracts STN Record for CAS Registry No. 1254254-87-9, Carbamic acid, N-[4-[6-[2-(fluoro-18F)ethoxy]-2-naphthalenyl]phenyl]-N-methyl-, 1,1-dimethylethyl ester, retrieved Jul. 3, 2018.
Chemical Abstracts STN Record for CAS Registry No. 1254254-85-7, Carbamic acid, N-[4-[6-(2-hydroxyethoxy)-2-naphthalenyl]phenyl]-N-methyl-, 1,1-dimethylethyl ester, retrieved Jul. 3, 2018.
Chemical Abstracts STN Record for CAS Registry No. 1254254-84-6, Carbamic acid, N-[4-[6-[2-[[(1,1-dimethylethyl)dimethylsilyl]oxy]ethoxy]-2-naphthalenyl]phenyl]-N-methyl-, 1,1-dimethylethyl ester, retrieved Jul. 3, 2018.
Chemical Abstracts STN Record for CAS Registry No. 1246277-89-3, Carbamic acid, N-[4-[5-(3,4-dihydro-2,4-dioxo-1(2H)-pyrimidinyl)-7-(1,1-dimethylethyl)-8-methoxy-2-quinolinyl]phenyl]-, 1,1-dimethylethyl ester, retrieved Jul. 3, 2018.
Chemical Abstracts STN Record for CAS Registry No. 1246094-00-7, Carbamic acid, N-[4-(3-isoquinolinyl)phenyl]-N-methyl-, 1,1-dimethylethyl ester, retrieved Jul. 3, 2018.
Chemical Abstracts STN Record for CAS Registry No. 1246093-99-1, Carbamic acid, N-methyl-N-[4-(3-quinolinyl)phenyl]-, 1,1-dimethylethyl ester, retrieved Jul. 3, 2018.
Chemical Abstracts STN Record for CAS Registry No. 1246093-98-0, Carbamic acid, N-methyl-N-[4-(4-nitro-2-quinolinyl)phenyl]-, 1,1-dimethylethyl ester, retrieved Jul. 3, 2018.
Chemical Abstracts STN Record for CAS Registry No. 1246092-74-9, Carbamic acid, N-[5-(2-quinolinyl)-2-pyridinyl]-, 1,1-dimethylethyl ester, retrieved Jul. 3, 2018.
Chemical Abstracts STN Record for CAS Registry No. 1246092-52-3, Carbamic acid, N-[4-(6-methoxy-2-quinolinyl)-2-nitrophenyl]-N-methyl-, 1,1-dimethylethyl ester, retrieved Jul. 3, 2018.
Chemical Abstracts STN Record for CAS Registry No. 1246092-48-7, Carbamic acid, N-[2-fluoro-4-(6-methoxy-2-quinolinyl)phenyl]-, 1,1-dimethylethyl ester, retrieved Jul. 3, 2018.
Chemical Abstracts STN Record for CAS Registry No. 1246092-20-5, Carbamic acid, N-[4-[6-(2-fluoroethoxy)-2-quinolinyl]phenyl]-N-methyl-, 1,1-dimethylethyl ester, retrieved Jul. 3, 2018.
Chemical Abstracts STN Record for CAS Registry No. 1246092-18-1, Carbamic acid, N-[4-(6-methoxy-2-quinolinyl)phenyl]-N-methyl-, 1,1-dimethylethyl ester, retrieved Jul. 3, 2018.
Chemical Abstracts STN Record for CAS Registry No. 2143074-02-4, Carbamate, tert-butyl (4-(4-morpholinoquinolin-2-yl)phenyl), retrieved Jul. 3, 2018.
Chemical Abstracts STN Record for CAS Registry No. 2143074-00-2, Carbamate, tert-butyl (4-(4-chloroquinolin-2-yl)phenyl), retrieved Jul. 3, 2018.
Chemical Abstracts STN Record for CAS Registry No. 1054481-89-8, 1,6-Naphthyridine-4-carboxylic acid, 2-[4-[[(1,1-dimethylethoxy)carbonyl]amino]phenyl]-3-methoxy-, methyl ester, retrieved Jul. 3, 2018.

Chemical Abstracts STN Record for CAS Registry No. 884347-88-0, Carbamic acid, N-[4-(2-quinolinyl)phenyl]-, 1,1-dimethylethyl ester, retrieved Jul. 3, 2018.
Chemical Abstracts STN Record for CAS Registry No. 131408-97-4, Acetamide, N-[4-(6-methoxy-1,2,4-benzotriazin-3-yl)phenyl]-, retrieved Jul. 3, 2018.
Chemical Abstracts STN Record for CAS Registry No. 111030-30-9, Acetamide, N-[4-[3-(2-chlorophenyl)-2-quinoxalinyl]phenyl]-, retrieved Jul. 3, 2018.
Chemical Abstracts STN Record for CAS Registry No. 109810-73-3, Acetamide, N-[4-(2-naphthalenyl)phenyl]-, retrieved Jul. 3, 2018.
Chemical Abstracts STN Record for CAS Registry No. 109571-09-7, Cinchoninic acid, 2-(p-acetamidophenyl)-, nitro deriv. (6Cl), retrieved Jul. 3, 2018.
Chemical Abstracts STN Record for CAS Registry No. 109534-09-0, Acetamide, N-[4-(1,2,4-benzotriazin-3-yl)phenyl]-, retrieved Jul. 3, 2018.
Chemical Abstracts STN Record for CAS Registry No. 109500-69-8, Acetamide, N-[4-(4-oxido-1,2,4-benzotriazin-3-yl)phenyl]-, retrieved Jul. 3, 2018.
Chemical Abstracts STN Record for CAS Registry No. 109289-07-8, Cinchoninic acid, 2-(p-acetamidophenyl)-, dinitro deriv. (6Cl), retrieved Jul. 3, 2018.
Chemical Abstracts STN Record for CAS Registry No. 107027-29-2, 8-Quinolinecarboxamide, 2-[4-(acetylamino)phenyl]-N-[2-(dimethylamino)ethyl]-, retrieved Jul. 3, 2018.
Chemical Abstracts STN Record for CAS Registry No. 107027-07-6(Component: 107027-29-2), 8-Quinolinecarboxamide, 2-[4-(acetylamino)phenyl]-N-[2-(dimethylamino)ethyl]-, hydrochloride (1:2), retrieved Jul. 3, 2018.
Chemical Abstracts STN Record for CAS Registry No. 102750-30-1, Acetamide, N-[4-[3-[4-(dimethylamino)phenyl]-2-quinoxalinyl]phenyl]-, retrieved Jul. 3, 2018.
Chemical Abstracts STN Record for CAS Registry No. 102173-92-2, Acetamide, N-[4-(6-ethoxy-2-quinolinyl)phenyl]-, retrieved Jul. 3, 2018.
Chemical Abstracts STN Record for CAS Registry No. 101731-25-3, Acetamide, N-[4-(6-methoxy-2-quinolinyl)phenyl]-, retrieved Jul. 3, 2018.
Chemical Abstracts STN Record for CAS Registry No. 101731-08-2, Acetamide, N-[4-(4-methyl-2-quinolinyl)phenyl]-, retrieved Jul. 3, 2018.
Chemical Abstracts STN Record for CAS Registry No. 101444-13-7, Acetamide, N-[4-(3-quinolinyl)phenyl]-, retrieved Jul. 3, 2018.
Chemical Abstracts STN Record for CAS Registry No. 97015-87-7, Acetamide, N-[4-(3-phenyl-2-quinoxalinyl)phenyl]-, retrieved Jul. 3, 2018.
Chemical Abstracts STN Record for CAS Registry No. 95223-13-5, Acetamide, N-[2,6-dibromo-4-(3-phenyl-2-quinoxalinyl)phenyl]-, retrieved Jul. 3, 2018.
Chemical Abstracts STN Record for CAS Registry No. 95139-52-9, Acetamide, N-[4-[3-(4-chlorophenyl)-2-quinoxalinyl]phenyl]-, retrieved Jul. 3, 2018.
Chemical Abstracts STN Record for CAS Registry No. 95139-33-6, Acetamide, N-[4-[3-(4-bromophenyl)-2-quinoxalinyl]phenyl]-, retrieved Jul. 3, 2018.
Chemical Abstracts STN Record for CAS Registry No. 69406-94-6, 6-Quinoxalinecarboxylic acid, 2-[4-(acetylamino)phenyl]-3-phenyl-, retrieved Jul. 3, 2018.
Chemical Abstracts STN Record for CAS Registry No. 64375-03-7, 6-Quinoxalinecarboxylic acid, 3-[4-(acetylamino)phenyl]-2-phenyl-, retrieved Jul. 3, 2018.
Chemical Abstracts STN Record for CAS Registry No. 17286-66-7, Acetamide, N-[4-(2-quinoxalinyl)phenyl]-, retrieved Jul. 3, 2018.
Chemical Abstracts STN Record for CAS Registry No. 16025-19-7, Acetamide, N-[4-(3-methyl-2-quinoxalinyl)phenyl]-, retrieved Jul. 3, 2018.
Chemical Abstracts STN Record for CAS Registry No. 1507-22-8, Acetamide, N-[4-(4-methyl-2-quinazolinyl)phenyl]-, retrieved Jul. 3, 2018.
Chemical Abstracts STN Record for CAS Registry No. 859929-20-7, 4-Quinolinecarboxylic acid, 6-[4-(acetylamino)phenyl]-2-methyl-, retrieved Jul. 3, 2018.

(56) References Cited

OTHER PUBLICATIONS

Chemical Abstracts STN Record for CAS Registry No. 855754-15-3, 4-Quinolinecarboxylic acid, 6-[4-(acetylamino)phenyl]-2-phenyl-, retrieved Jul. 3, 2018.
Chemical Abstracts STN Record for CAS Registry No. 757984-68-2, Acetamide, N-[4-[4-(dimethylamino)-6-methoxy-2-quinazolinyl]-3-fluorophenyl]-, retrieved Jul. 3, 2018.
Chemical Abstracts STN Record for CAS Registry No. 757984-67-1, Acetamide, N-[4-[6-chloro-4-(dimethylamino)-2-quinazolinyl]-3-fluorophenyl]-, retrieved Jul. 3, 2018.
Chemical Abstracts STN Record for CAS Registry No. 713527-54-9, Acetamide, N-[4-(3,4-dihydro-6,7-dimethyl-3-oxo-2-quinoxalinyl)phenyl]-, retrieved Jul. 3, 2018.
Chemical Abstracts STN Record for CAS Registry No. 701290-17-7, Acetamide, N-[4-(3,4-dihydro-4-oxo-2-quinazolinyl)phenyl]-, retrieved Jul. 3, 2018.
Chemical Abstracts STN Record for CAS Registry No. 1030102-06-7, 4-Quinolinecarboxamide, 2-[4-(acetylamino)phenyl]-N-[2-(dimethylamino)ethyl]-6-methyl-, retrieved Jul. 3, 2018.
Chemical Abstracts STN Record for CAS Registry No. 1030101-81-5, 4-Quinolinecarboxamide, 2-[4-(acetylamino)phenyl]-N-butyl-, retrieved Jul. 3, 2018.
Chemical Abstracts STN Record for CAS Registry No. 2143074-28-4, 4-quinolinecarbonyl chloride, 2-[4-[(2,2,2-trifluoroacetyl)amino]phenyl]-, retrieved Jul. 3, 2018.
Chemical Abstracts STN Record for CAS Registry No. 2143074-26-2, 4-quinolinecarboxylic acid, 2-[4-[(2,2,2-trifluoroacetyl)amino]phenyl]-, retrieved Jul. 3, 2018.
Chemical Abstracts STN Record for CAS Registry No. 1374109-35-9, Acetamide, 2,2,2-trifluoro-N-[4-(6-hydroxy-2-quinolinyl) phenyl]-, retrieved Jul. 3, 2018.
Chemical Abstracts STN Record for CAS Registry No. 1374109-28-0, Acetamide, 2,2,2-trifluoro-N-[4-(6-hydroxy-2-quinolinyl)phenyl]-N-methyl-, retrieved Jul. 3, 2018.
Chemical Abstracts STN Record for CAS Registry No. 1374109-06-4, Acetamide, 2,2,2-trifluoro-N-[4-(7-hydroxy-2-quinolinyl)phenyl]-N-methyl-, retrieved Jul. 3, 2018.
Chemical Abstracts STN Record for CAS Registry No. 1374108-89-0, Acetamide, 2,2,2-trifluoro-N-[4-[7-[2-hydroxy-1-(hydroxymethyl)ethoxy]-2-quinolinyl]phenyl]-N-methyl-, retrieved Jul. 3, 2018.
Chemical Abstracts STN Record for CAS Registry No. 1278575-57-7, Acetamide, N-[4-[4-(ethylamino)-7-(trifluoromethyl)-2-quinazolinyl]phenyl]-2,2,2-trifluoro-, retrieved Jul. 3, 2018.
Chemical Abstracts STN Record for CAS Registry No. 924900-46-9, 4-Quinolinecarboxylic acid, 3-hydroxy-7,8-dimethyl-2-[4-[(2,2,2-trifluoroacetyl)amino]phenyl]-, retrieved Jul. 3, 2018.
Chemical Abstracts STN Record for CAS Registry No. 913243-18-2, 4-Quinolinecarboxylic acid, 2-[4-[(2-chloroacetyl)amino]phenyl]-, retrieved Jul. 3, 2018.
Chemical Abstracts STN Record for CAS Registry No. 913243-03-5, 4-Quinolinecarboxylic acid, 2-[4-[(2-chloro-1-oxopropyl)amino]phenyl]-, retrieved Jul. 3, 2018.
Chemical Abstracts STN Record for CAS Registry No. 901217-98-9, 4-Quinolinecarboxylic acid, 2-[4-[(2-bromo-2-methyl-1-oxopropyl)amino]phenyl]-, retrieved Jul. 3, 2018.
Chemical Abstracts STN Record for CAS Registry No. 339298-39-4, Acetamide, 2-chloro-N-[2-[4-[(chloroacetyl)amino]phenyl]-4-phenyl-6-quinazolinyl]-(9Cl), retrieved Jul. 3, 2018.
Chemical Abstracts STN Record for CAS Registry No. 332410-00-1, Propanamide, N-[4-(6-bromo-4-phenyl-2-quinolinyl)phenyl]-3-chloro-, retrieved Jul. 3, 2018.
Chemical Abstracts STN Record for CAS Registry No. 332403-61-9, Acetamide, 2,2,2-trifluoro-N-[4-phenyl-2-[4-[(trifluoroacetyl)amino]phenyl]-6-quinazolinyl]-(9Cl), retrieved Jul. 3, 2018.
Chemical Abstracts STN Record for CAS Registry No. 16166-03-3, Acetamide, 2,2-dichloro-N-[4-(3-methyl-2-quinoxalinyl)phenyl]-, retrieved Jul. 3, 2018.
Chemical Abstracts STN Record for CAS Registry No. 16025-21-1, Acetamide, 2-chloro-N-[4-(3-methyl-2-quinoxalinyl)phenyl]-, retrieved Jul. 3, 2018.
Chemical Abstracts STN Record for CAS Registry No. 2056072-30-9, 4-Piperidinecarboxamide, N-[4-(6-isoquinolinyl)phenyl]-N-methyl-, retrieved Jul. 3, 2018.
Chemical Abstracts STN Record for CAS Registry No. 1092328-14-7, 1-Piperidinecarboxamide, N-[4-(6-chloro-4-phenyl-2-quinolinyl)phenyl]-, retrieved Jul. 3, 2018.
Chemical Abstracts STN Record for CAS Registry No. 877756-11-1, 2-Pyrrolidinecarboxamide, N-[4-(6-quinolinyl)phenyl]-, (2R)-, retrieved Jul. 3, 2018.
Chemical Abstracts STN Record for CAS Registry No. 877756-10-0, 2-Pyrrolidinecarboxamide, N-[4-(3-quinolinyl)phenyl]-, (2R)-, retrieved Jul. 3, 2018.
Chemical Abstracts STN Record for CAS Registry No. 877602-73-8, Absolute stereochemistry. 2-Pyrrolidinecarboxamide, N-[4-(2-naphthalenyl)phenyl]-, (2R)-, retrieved Jul. 3, 2018.
Chemical Abstracts STN Record for CAS Registry No. 877599-55-8(Component: 877756-11-1), 2-Pyrrolidinecarboxamide, N-[4-(6-quinolinyl)phenyl]-, hydrochloride (1:1), (2R)-, retrieved Jul. 3, 2018.
Chemical Abstracts STN Record for CAS Registry No. 877599-54-7(Component: 877756-10-0), 2-Pyrrolidinecarboxamide, N-[4-(3-quinolinyl)phenyl]-, hydrochloride (1:1), (2R)-, retrieved Jul. 3, 2018.
Chemical Abstracts STN Record for CAS Registry No. 877599-47-8(Component: 877602-73-8), 2-Pyrrolidinecarboxamide, N-[4-(2-naphthalenyl)phenyl]-, hydrochloride (1:1), (2R)-, retrieved Jul. 3, 2018.
Chemical Abstracts STN Record for CAS Registry No. 489459-01-0, 5-Quinoxalinecarboxamide, 3-[4-[(4-morpholinylcarbonyl)amino]phenyl]-, retrieved Jul. 3, 2018.
Chemical Abstracts STN Record for CAS Registry No. 1378231-82-3, 1 H-1,2,3-Triazole-4-carboxamide, 1-(2-fluoroethyl)-N[4-(2-quinolinyl)phenyl]-, retrieved Jul. 3, 2018.
Chemical Abstracts STN Record for CAS Registry No. 1206051-02-6, 2-Pyrazinecarboxamide, N-[4-( 3,4-dihydro-4-oxo-2-quinazolinyl]-3,4-dihydro-3-oxo-, retrieved Jul. 3, 2018.
Chemical Abstracts STN Record for CAS Registry No. 1205963-08-1, 3-Pyridinecarboxamide, 5-amino-N-[4-(3,4-dihydro-4-oxo-2-quinazolinyl)phenyl]-, retrieved Jul. 3, 2018.
Chemical Abstracts STN Record for CAS Registry No. 1205862-86-7, 5-Thiazolecarboxamide, N-[4-(3,4-dihydro-4-oxo-2-quinazolinyl)phenyl]-2,4-dimethyl-, retrieved Jul. 3, 2018.
Chemical Abstracts STN Record for CAS Registry No. 1205862-58-3, 4-Pyridinecarboxamide, N-[4-(3,4-dihydro-4-oxo-2-quinazolinyl)phenyl]-1,2-dihydro-6-hydroxy-2-oxo-, retrieved Jul. 3, 2018.
Chemical Abstracts STN Record for CAS Registry No. 1205862-54-9, 2-Pyridinecarboxamide, 4-amino-N-[4-(3,4-dihydro-4-oxo-2-quinazolinyl)phenyl]-, retrieved Jul. 3, 2018.
Chemical Abstracts STN Record for CAS Registry No. 1205862-44-7, 2-Pyridinecarboxamide, N-[4-(3,4-dihydro-4-oxo-2-quinazolinyl)phenyl]-, retrieved Jul. 3, 2018.
Chemical Abstracts STN Record for CAS Registry No. 1205862-03-8, 3-Pyridinecarboxamide, N-[4-(3,4-dihydro-4-oxo-2-quinazolinyl)phenyl]-, retrieved Jul. 3, 2018.
Chemical Abstracts STN Record for CAS Registry No. 1205470-69-4, 3-Pyridinecarboxamide, 2-amino-N-[4-(3,4-dihydro-4-oxo-2-quinazolinyl)phenyl]-, retrieved Jul. 3, 2018.
Chemical Abstracts STN Record for CAS Registry No. 1205377-42-9, 2-Pyrazinecarboxamide, 3-amino-N-[4-(3,4-dihydro-4-oxo-2-quinazolinyl)phenyl]-, retrieved Jul. 3, 2018.
Chemical Abstracts STN Record for CAS Registry No. 1205059-95-5, 2-Pyridinecarboxamide, 4-chloro-N-[4-(3,4-dihydro-4-oxo-2-quinazolinyl)phenyl]-, retrieved Jul. 3, 2018.
Chemical Abstracts STN Record for CAS Registry No. 1111019-64-7, 3-Pyridinecarboxamide, N-[4-(2-quinolinyl)phenyl]-, retrieved Jul. 3, 2018.
Chemical Abstracts STN Record for CAS Registry No. 900917-71-7, 1H-Pyrazole-4-carboxamide, 1,3-diphenyl-N-[4-(2-quinoxalinyl)phenyl]-, retrieved Jul. 3, 2018.

(56) References Cited

OTHER PUBLICATIONS

Chemical Abstracts STN Record for CAS Registry No. 489458-99-3, 5-Quinoxalinecarboxamide, 3-[4-[(3-pyridinylcarbonyl)amino]phenyl]-, retrieved Jul. 3, 2018.
Chemical Abstracts STN Record for CAS Registry No. 1417914-47-6, 2-Quinolinecarboxaldehyde, 3-[2-ethoxy-4-(2-oxo-1-pyrrolidinyl)phenyl]-, retrieved Jul. 3, 2018.
Chemical Abstracts STN Record for CAS Registry No. 1375243-12-1, 4(3H)-Quinazolinone, 6-(1-methylethyl)-2-[4-(2-oxo-3-oxazolidinyl)phenyl]-, retrieved Jul. 3, 2018.
Chemical Abstracts STN Record for CAS Registry No. 1246092-27-2, 2-Oxazolidinone, 3-[4-(2-quinolinyl)phenyl]-, retrieved Jul. 3, 2018.
Chemical Abstracts STN Record for CAS Registry No. 1197503-42-6, 4(3H)-Quinazolinone, 2-[4-(2-oxo-3-oxazolidinyl)phenyl]-, retrieved Jul. 3, 2018.
Chemical Abstracts STN Record for CAS Registry No. 1170775-69-5, 2-Pyrrolidinone, 1-[4-(4-methyl-2-quinolinyl)phenyl]-, retrieved Jul. 3, 2018.
Chemical Abstracts STN Record for CAS Registry No. 1170444-26-4(Component: 1170775-69-5), 2-Pyrrolidinone, 1-[4-(4-methyl-2-quinolinyl)phenyl]-, hydrochloride (1:1), retrieved Jul. 3, 2018.
Chemical Abstracts STN Record for CAS Registry No. 1016727-18-6, 7-Quinazolinecarboxylic acid, 3,4-dihydro-4-oxo-2-[4-(2-oxo-1-pyrrolidinyl)phenyl]-, retrieved Jul. 3, 2018, retrieved Jul. 3, 2018.
Chemical Abstracts STN Record for CAS Registry No. 701221-07-0, Acetamide, N-[4-(6-chloro-4-phenyl-2-quinolinyl)phenyl]-, retrieved Jul. 3, 2018.
Chemical Abstracts STN Record for CAS Registry No. 667435-07-6, Butanamide, N-[4-(3,4-dihydro-4-oxo-2-quinazolinyl)phenyl]-3-methyl-, retrieved Jul. 3, 2018.
Chemical Abstracts STN Record for CAS Registry No. 667435-06-5, Propanamide, N-[4-(3,4-dihydro-4-oxo-2-quinazolinyl)phenyl]-2-methyl-, retrieved Jul. 3, 2018.
Chemical Abstracts STN Record for CAS Registry No. 426815-70-5, Acetamide, N-[4-(3,4-dihydro-3-oxo-2-quinoxalinyl)phenyl]-, retrieved Jul. 3, 2018.
Chemical Abstracts STN Record for CAS Registry No. 371960-52-0, Acetamide, N-[2-[4-(acetylamino)phenyl]-4-phenyl-7-quinazolinyl]-, retrieved Jul. 3, 2018.
Chemical Abstracts STN Record for CAS Registry No. 371940-44-2, Acetamide, N-[4-[6-hydroxy-4-(4-morpholinyl)-2-quinazolinyl]phenyl]-, retrieved Jul. 3, 2018.
Chemical Abstracts STN Record for CAS Registry No. 356083-44-8, Propanamide, N-[4-(2-quinoxalinyl)phenyl]-, retrieved Jul. 3, 2018.
Chemical Abstracts STN Record for CAS Registry No. 355402-31-2, Acetamide, N-[4-(4-phenyl-2-quinazolinyl)phenyl]-, retrieved Jul. 3, 2018.
Chemical Abstracts STN Record for CAS Registry No. 312697-03-3, Acetamide, N-[4-(6-methyl-4-phenyl-2-quinazolinyl)phenyl]-, retrieved Jul. 3, 2018.
Chemical Abstracts STN Record for CAS Registry No. 299962-92-8, Acetamide, N-[2-[4-(acetylamino)phenyl]-4-phenyl-6-quinazolinyl]-, retrieved Jul. 3, 2018.
Chemical Abstracts STN Record for CAS Registry No. 298187-85-6, 4-Quinolinecarboxylic acid, 2-[4-(acetylamino)phenyl]-, retrieved Jul. 3, 2018.
Chemical Abstracts STN Record for CAS Registry No. 275375-79-6, Acetamide, N-[4-[4-(5-chloro-2-hydroxyphenyl)-1,2-dihydro-2-oxo-6-(trifluoromethyl)-3-quinolinyl]phenyl]-, retrieved Jul. 3, 2018.
Chemical Abstracts STN Record for CAS Registry No. 1016520-10-7, 7-Quinazolinecarboxylic acid, 2-[4-(acetylamino)phenyl]-3,4-dihydro-4-oxo-, retrieved Jul. 3, 2018.
Chemical Abstracts STN Record for CAS Registry No. 958814-14-7, Acetamide, N-[4-(1,4-dihydroxy-2-naphthalenyl)phenyl]-, retrieved Jul. 3, 2018.
Chemical Abstracts STN Record for CAS Registry No. 951609-55-5, Butanamide, N-[4-(6-methyl-2-quinolinyl)phenyl]-, retrieved Jul. 3, 2018.
Chemical Abstracts STN Record for CAS Registry No. 951600-08-1, Pentanamide, N-[4-(6-methyl-2-quinolinyl)phenyl]-, retrieved Jul. 3, 2018.
Chemical Abstracts STN Record for CAS Registry No. 924900-45-8, 4-Quinolinecarboxylic acid, 2-[4-(acetylamino)phenyl]-3-hydroxy-7,8-dimethyl-, retrieved Jul. 3, 2018.
Chemical Abstracts STN Record for CAS Registry No. 899293-98-2, Butanamide, N-[4-(3,4-dihydro-4-oxo-2-quinazolinyl)phenyl]-2-ethyl-, retrieved Jul. 3, 2018.
Chemical Abstracts STN Record for CAS Registry No. 883041-74-5, 4-Quinolinecarboxylic acid, 2-[4-(acetylamino)phenyl]-7-methyl-, retrieved Jul. 3, 2018.
Chemical Abstracts STN Record for CAS Registry No. 1029725-12-9, Acetamide, N-[4-[6-methyl-4-(4-morpholinylcarbonyl)-2-quinolinyl]phenyl]-, retrieved Jul. 3, 2018.
Chemical Abstracts STN Record for CAS Registry No. 1016727-26-6, 7-Quinazolinecarboxylic acid, 3,4-dihydro-2-[4-[(2-methyl-1-oxopropyl)amino]phenyl]-4-oxo-, retrieved Jul. 3, 2018.
Chemical Abstracts STN Record for CAS Registry No. 1378231-82-3, 1-(2-fluoroethyl)-N-(4-(quinolin-2-yl)phenyl-1H-1,2,3-triazole-4-carboxamide, retrieved Jun. 22, 2020.
Chemical Abstracts STN Record for CAS Registry No. 667435-07-6, 3-methyl-N-(4-(4-oxo-3,4-dihydroquinazolin-2-yl)phenyl)butanamide, retrieved Jun. 22, 2020.
Chemical Abstracts STN Record for CAS Registry No. 1197503-42-6, 3-(4-(4-oxo-3,4-dihydroquinazolin-2-yl)phenyl)oxazolidin-2-one, retrieved Jun. 22, 2020.
Chemical Abstracts STN Record for CAS Registry No. 1710372-24-9, N-(4-(6,7-dimethoxy-4-morpholinoquinazolin-2-yl)phenyl)acetamide, retrieved Jun. 22, 2020.

* cited by examiner

AMIDO COMPOUNDS AS AHR MODULATORS

CROSS-REFERENCES TO RELATED APPLICATIONS

This application is an application claiming priority benefit under 35 U.S.C. § 119(e) of U.S. Provisional Application No. 62/534,543, filed Jul. 19, 2017, which is incorporated herein by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The aryl hydrocarbon receptor (AhR) is a helix-loop-helix ligand-activated transcription factor that mediates biological responses to aromatic hydrocarbons. AhR is localized in the cytoplasm, where upon binding to a hydrocarbon based ligand agonist such as 2,3,7,8-tetrachlorodibenzo-p-dioxin (TCDD), it migrates to the nucleus and forms a heterodimer with aryl hydrocarbon receptor nuclear translocator (ARNT). Formation of the AhR/ARNT complex subsequently enables binding to and transcription of the xenobiotic response element (XRE) and associated genes. AhR can also activate a non-XRE dependent protein-protein interaction pathway.

Through its XRE-dependent and independent activity, AhR modulates numerous critical innate and adaptive immune responses. Chief among those responses, AhR agonists promote development of IL-17 producing T-helper cells (Th17) and regulatory T-cells (Tregs). AhR activation further induces trans-differentiation of Th117 cells to Tregs and enhances the suppressive activity of Tregs. Studies have also demonstrated that AhR agonism results in suppression of innate inflammatory responses mediated by macrophages (e.g. Reduced LPS-induced IL-1b, IL-6, IL-12 and TNFa expression) and dendritic cells (DCs) (inhibits activation of DCs and promotes expression of IL-10).

To mount an effective anti-tumor immune response, antigen presenting cells (APCs) are required to process, present and consequently activate helper CD4+ T-cells (Th) and cytotoxic CD8+ T-cells (Tc) which act in concert to effectively lyse tumor cells. Tumor cells have developed several mechanisms to evade the immune mediated lysis of Th and Tc. One such mechanism is the release of high concentrations of kynurenine and other potential AhR ligands in the tumor microenvironment (TME). High AhR ligand concentrations activate the AhR in the TME resulting in suppression of APCs, Th and Tc directly, as well as recruitment, generation and activation of Tregs and Th17 which further suppress the activity of Th and Tc. Through this mechanism, tumor cells are capable of evading anti-tumor immune responses. An antagonist of the AhR pathway would therefore block the AhR-dependent immune evasion mechanisms employed by malignant cells and restore effective anti-tumor immunity.

Recent insights into tumor immunobiology has revealed that malignant cells employ a composite of immune-evasion mechanisms. Blocking or enhancing these mechanisms through a combination of therapeutic applications such as immune check point inhibition and vaccines has been demonstrated pre-clinically and clinically to provide an optimal restoration of the anti-tumor immune response. While it is expected that AhR antagonism in monotherapy will restore anti-tumor immunity, a combination of an AhR modulator with a check point inhibitor and/or vaccine is predicted to work in concert with other therapeutics to potentiate the immunotherapeutic response.

Immune mechanisms regulated by AhR have also been associated with autoimmune and inflammatory diseases such as multiple sclerosis and inflammatory bowel diseases. The activation of AhR by agonists could therefore be beneficial for the therapeutic treatment of autoimmune and inflammatory diseases. While agonists of AhR are described in the art, there remains a need for improved compositions and methods for immunological modulation of treating autoimmune and inflammatory diseases via modulation of AhR.

BRIEF SUMMARY OF THE INVENTION

Provided herein are compounds, compositions and methods of using the compounds and compositions for the treatment of diseases modulated, as least in part, by AhR. The compounds are represented by formulae:

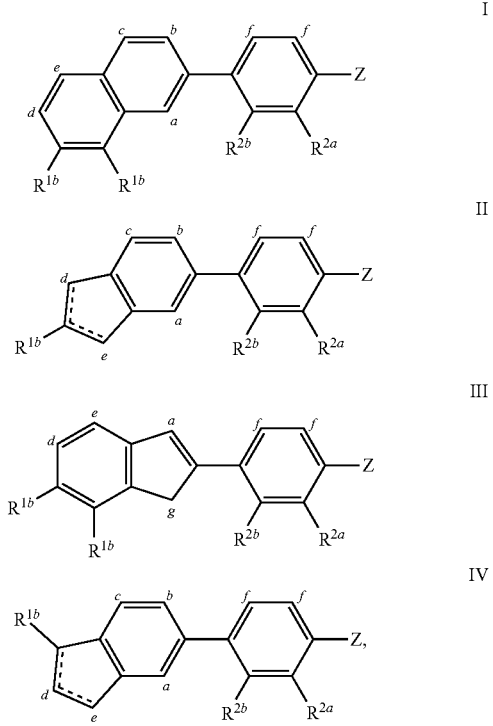

wherein the letters and symbols a, b, c, d, e, f, g, Z, $R^{1b}$, $R^{2a}$ and $R^{2b}$ have the meanings provided below.

BRIEF DESCRIPTION OF THE DRAWINGS

Not Applicable

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The present invention is drawn to, inter alia, small molecule compounds having AhR modulator activity, as well as compositions thereof, and methods of using the compounds and compositions for the treatment and prevention of the diseases, disorders and conditions described herein.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "deuteroalkyl", by itself or as part of another substituent, refers to an alkyl group wherein from one to five hydrogen atoms have been replaced by deuterium.

An example of a "deuteroalkyl" group is —$CD_3$.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "heterocycloalkyl" refers to a ring having from four to eight carbon ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized, unless stated otherwise. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

As used herein, a wavy line, "⌇", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached, wherein the ring may containing one or two additional heteroatoms independently selected from N, O, S, SO, and $SO_2$. Accordingly, a group represented as dialkylamino or —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently, unless stated otherwise. Non-limiting examples of aryl groups include phenyl, naphthyl and biphenyl.

The term "heteroaryl" refers to aromatic groups (or rings) that contain from one to five heteroatoms as ring vertices selected from N, O, and S, wherein the nitrogen and sulfur atoms are optionally oxidized, and the nitrogen atom(s) are optionally quaternized, unless stated otherwise. A heteroaryl group can be attached to the remainder of the molecule through a heteroatom. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^{3}$H), iodine-125 ($^{125}$I) or carbon-14 ($^{14}$C), or non-radioactive isotopes, such as deuterium ($^{2}$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an AhR modulator, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an AhR modulator or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an AhR modulator or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an AhR modulator (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of AhR, either directly or indirectly. A modulator may act alone, or it may use a cofactor, e.g., a protein, metal ion, or small molecule. Examples of modulators include small molecule compounds and other bioorganic molecules.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

AhR and Modulation Thereof

Identification of AhR Modulators Possessing Desirable Characteristics

The present invention is drawn, in part, to the identification of AhR modulators with at least one property or characteristic that is of therapeutic relevance. Candidate AhR modulators can be identified by using, for example, an art-accepted assay or model, examples of which are will be apparent to the skilled artisan. The assay used to determine the AhR modulatory activity of the compounds described herein is set forth in the Experimental section.

After identification, candidate modulators can be further evaluated by using techniques that provide data regarding characteristics of the modulators (e.g., pharmacokinetic parameters). Comparisons of the candidate modulators to a reference standard (which may the "best-of-class" of current modulators) are indicative of the potential viability of such candidates.

AhR modulators that can serve as reference or benchmark compounds include CH223191, StemRegenin-1, kynurenine, ITE, GNF351, and CB7993113. Other reference compounds subsequently identified by the skilled artisan can also be used to assess the viability of candidate AhR modulators.

Methods and Compounds

Provided herein are methods of treating cancer in a subject in need thereof, said method comprising administering to said subject an effective amount of a compound having the formula (I), (II), (III) or (IV):

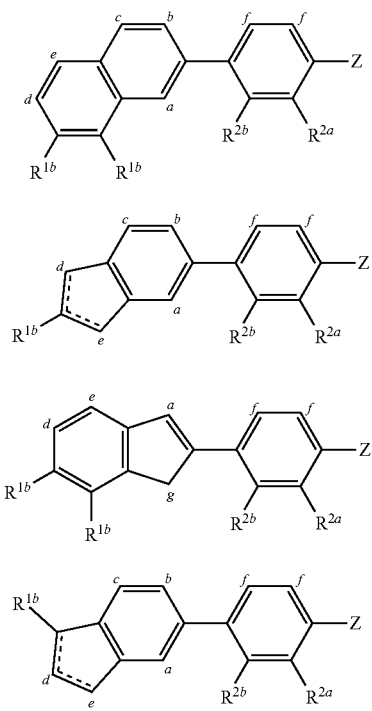

or a pharmaceutically acceptable salt, solvate or hydrate thereof, wherein the dashed bonds are single or double bonds;

each of ring vertices a, b and c is independently selected from the group consisting of $C(R^{1a})$ and N;

each of ring vertices d and e is independently selected from the group consisting of $C(R^{1b})$ and N;

each ring vertex f is selected from the group consisting of $C(R^{2c})$, $C(R^{2d})$ and N;

ring vertex g is selected from the group consisting of O, S and $N(R^{1a})$;

Z is selected from the group consisting of:

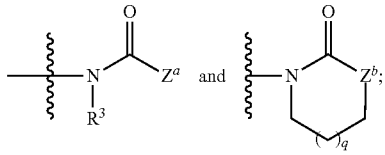

$Z^a$ is selected from the group consisting of:
(i) a 5- or 6-membered heteroaryl group having at least one nitrogen atom as a ring member, which is optionally substituted with from 1 to 4 $R^4$;
(ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy; and
(iii) a $C_{1-8}$ alkyl group, $C_{1-8}$ haloalkyl group, or a $C_{1-8}$ alkoxy group;

$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;

the subscript q is 0, 1 or 2;

each $R^{1a}$ and $R^{1b}$ is independently selected from the group consisting of hydrogen, deuterium, halogen, —CN, —NO$_2$, —$R^c$, —CO$_2R^a$, —CONR$^aR^b$, —C(O)R$^a$, —OC(O)NR$^aR^b$, —NR$^bC(O)R^a$, —NR$^bC(O)_2R^c$, —NR$^aC(O)NR^aR^b$, —NR$^aR^b$, —OR$^a$, and —S(O)$_2$NR$^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-OR$^d$, $C_{1-3}$ alkylene-CO$_2R^d$, $C_{1-3}$ alkylene-NR$^dR^e$, $C_{1-3}$ alkylene-CONR$^dR^e$, $C_{1-3}$ alkylene-OC(O)NR$^dR^e$, and $C_{1-3}$ alkylene-NR$^eC(O)_2R^f$; each $R^{3a}$ is independently H or F;

each $R^4$ is independently selected from the group consisting of halogen, —CN, —$R^f$, —CO$_2R^d$, —CONR$^dR^e$, —C(O)R$^d$, —OC(O)NR$^dR^e$, —NR$^eC(O)R^d$, —NR$^eC(O)_2R^f$, —NR$^dC(O)NR^dR^e$, —NR$^dR^e$, —OR$^d$, —S(O)$_2$NR$^dR^e$, —X$^1$—CN, —X$^1$—CO$_2R^d$, —X$^1$—CONR$^dR^e$, —X$^1$—C(O)R$^d$, —X$^1$—OC(O)NR$^dR^e$, —X$^1$—NR$^eC(O)R^d$, —X$^1$—NR$^eC(O)_2R^f$, —X$^1$—NR$^dC(O)NR^dR^e$, —X$^1$—NR$^dR^e$, —X$^1$—OR$^d$, —X$^1$—Y and —X$^1$—S(O)$_2$NR$^dR^e$; wherein each $X^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine;

each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O and S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl;

and wherein the aliphatic and cyclic portions of $R^d$, $R^e$ and $R^f$ are optionally further substituted with from one to three halogen, hydroxy, methyl, amino, methylamino, dimethylamino or carboxylic acid groups;

with the proviso that, for the compounds of formula I, the compound is other than:

2-(4-acetamidophenyl)-N-(2-(dimethylamino)ethyl)quinoline-8-carboxamide;

3-methyl-N-(4-(4-oxo-3,4-dihydroquinazolin-2-yl)phenyl) butanamide, and tautomer thereof;

3-(4-(4-oxo-3,4-dihydroquinazolin-2-yl)phenyl)oxazolidin-2-one, and tautomer thereof; or N-(4-(6,7-dimethoxy-4-morpholinoquinazolin-2-yl)phenyl) acetamide.

In some related embodiments, the compounds useful in the methods herein are those compounds of formulae (I), (II), (III) or (IV), or a pharmaceutically acceptable salt, solvate or hydrate thereof, wherein the dashed bonds are single or double bonds wherein one of the dashed bonds is a single bond and the other of the dashed bonds is a double bond; each of ring vertices a, b and c is independently selected from the group consisting of $C(R^{1a})$ and N;

each of ring vertices d and e is independently selected from the group consisting of $C(R^{1b})$, N, NH, $N(C_{1-4}$ alkyl) and $N(C_{1-4}$ haloalkyl), provided at least of d and e is other than $C(R^{1b})$;

each ring vertex f is selected from the group consisting of $C(R^{2c})$, $C(R^{2d})$ and N;

ring vertex g is selected from the group consisting of O, S and $N(R^{1a})$;

Z is selected from the group consisting of:

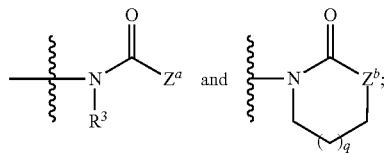

$Z^a$ is selected from the group consisting of:
 (i) a 5- or 6-membered heteroaryl group having at least one nitrogen atom as a ring member, which is optionally substituted with from 1 to 4 $R^4$;
 (ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy; and
 (iii) a $C_{1-8}$ alkyl group, $C_{1-8}$ haloalkyl group, or a $C_{1-8}$ alkoxy group;

$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;

the subscript q is 0, 1 or 2;

each $R^{1a}$ and $R^{1b}$ is independently selected from the group consisting of hydrogen, deuterium, halogen, —CN, —$NO_2$, —$R^c$, —$CO_2R^a$, —$CONR^aR^b$, —$C(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$; each $R^{3a}$ is independently H or F;

each $R^4$ is independently selected from the group consisting of halogen, —CN, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^dC(O)NR^dR^e$, —$NR^dR^e$, —$OR^d$, —$S(O)_2NR^dR^e$, —$X^1$—CN, —$X^1$—$CO_2R^d$, —$X^1$—$CONR^dR^e$, —$X^1$—$C(O)R^d$, —$X^1$—$OC(O)NR^dR^e$, —$X^1$—$NR^eC(O)R^d$, —$X^1$—$NR^eC(O)_2R^f$, —$X^1$—$NR^dC(O)NR^dR^e$, —$X^1$—$NR^dR^e$, —$X^1$—$OR^d$, —$X^1$—Y and —$X^1$—$S(O)_2NR^dR^e$; wherein each $X^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine;

each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O and S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl;

and wherein the aliphatic and cyclic portions of $R^d$, $R^e$ and $R^f$ are optionally further substituted with from one to three halogen, hydroxy, methyl, amino, methylamino, dimethylamino or carboxylic acid groups;

with the proviso that, for the compounds of formula I, the compound is other than:

2-(4-acetamidophenyl)-N-(2-(dimethylamino)ethyl)quinoline-8-carboxamide;

3-methyl-N-(4-(4-oxo-3,4-dihydroquinazolin-2-yl)phenyl) butanamide, and tautomer thereof, namely, N-(4-(4-hydroxyquinazolin-2-yl)phenyl)-3-methylbutanamide;

3-(4-(4-oxo-3,4-dihydroquinazolin-2-yl)phenyl)oxazolidin-2-one, and tautomer thereof, namely, 3-(4-(4-hydroxyquinazolin-2-yl)phenyl)oxazolidin-2-one; or N-(4-(6,7-dimethoxy-4-morpholinoquinazolin-2-yl)phenyl) acetamide.

In one group of embodiments, the compound is a compound of formula (II), (III), or (IV), wherein one of the dashed bonds is a single bond and the other of the dashed bonds is a double bond;

each of ring vertices d and e is independently selected from the group consisting of $C(R^{1b})$, N, NH, $N(C_{1-4}$ alkyl) and $N(C_{1-4}$ haloalkyl), provided at least of d and e is other than $C(R^{1b})$; and each $R^{1b}$ is independently selected from the group consisting of hydrogen, deuterium, halogen, —$NO_2$, —$R^c$, —$C(O)R^a$, —$OC(O)NR^aR^b$, —$NR^bC(O)R^a$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, and wherein the aliphatic and cyclic portions of $R^a$, $R^b$ and $R^c$ are optionally further substituted with from one to three halogen, hydroxy, methyl, amino, methylamino, and dimethylamino and at least one of $R^{1b}$ is other than hydrogen; (and embodiments thereof disclosed herein below).

In one group of embodiments, Z is selected from the group consisting of:

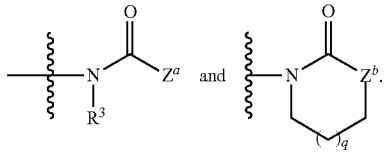

In one group of embodiments, the compounds of formulae (I), (II), (III) and (IV), wherein one of ring vertices a, b, c, d and e is N. In certain selected embodiments, each ring vertex f is CH.

In another group of embodiments, the compounds of formulae (I), (II), (III) and (IV), wherein two of ring vertices a, b, c, d and e is N. In certain selected embodiments, each ring vertex f is CH.

In yet another group of embodiments, the compounds of formulae (I), (II), (III) and (IV), wherein three of ring vertices a, b, c, d and e is N. In certain selected embodiments, each ring vertex f is CH.

Returning to the compounds of formulae (I), (II), (III) and (IV), and the embodiments noted above, in one further selected group of embodiments, Z is

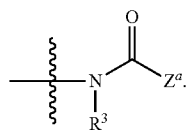

In some embodiments, $Z^a$ is selected from the group consisting of pyrazole, imidazole, oxazole, isoxazole, 1,2,3-triazole, 1,2,4-triazole, pyridine, pyrimidine, pyridazine and pyrazine, each of which is optionally substituted with from 1 to 2 $R^4$. In other embodiments, $Z^a$ is selected from the group consisting of tetrahydropyran, tetrahydrothiopyran, morpholine, piperidine and piperazine.

In still other embodiments, compounds of formula (I) are provided and are represented by formulae Ia, Ib, Ic, Id, Ie, If, Ig, and Ih:

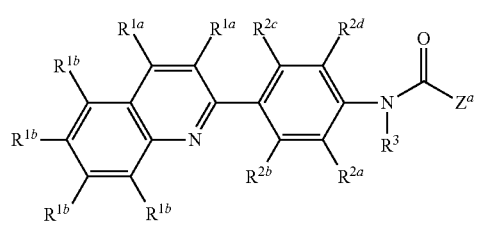

Ia

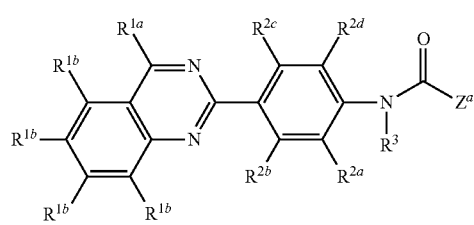

Ib

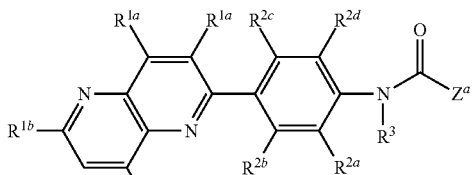

Ic

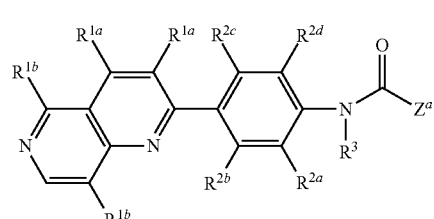

Id

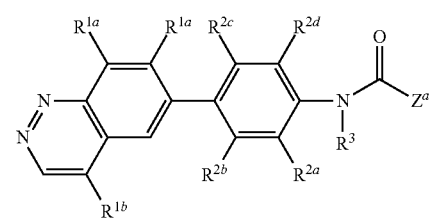

Ie

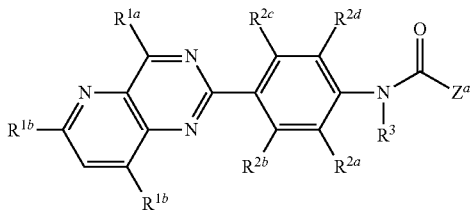

If

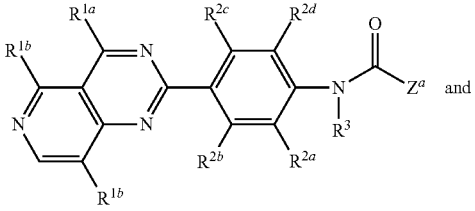

Ig

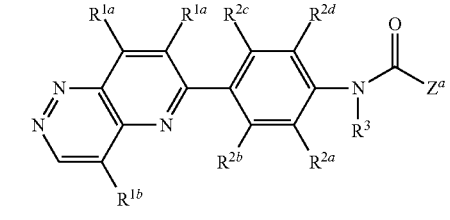

Ih

In other selected embodiments, compounds are provided having formula Ib, wherein $Z^a$ is pyrazole or pyridine, each of which is optionally substituted with from 1 to 3 $R^4$.

In still other selected embodiments, compounds are provided having formula Ic, wherein $Z^a$ is pyrazole or pyridine, each of which is optionally substituted with from 1 to 3 $R^4$.

In yet selected embodiments, compounds are provided having formula Id, wherein $Z^a$ is pyrazole or pyridine, each of which is optionally substituted with from 1 to 3 $R^4$.

In other selected embodiments, compounds are provided having formula If, wherein $Z^a$ is pyrazole or pyridine, each of which is optionally substituted with from 1 to 3 $R^4$.

In some selected embodiments, compounds are provided having formula Ig, wherein $Z^a$ is pyrazole or pyridine, each of which is optionally substituted with from 1 to 3 $R^4$.

In still other selected embodiments, compounds are provided having formula Ia1:

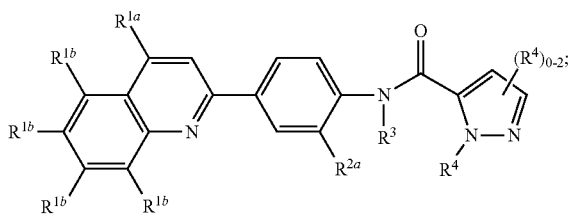

Ia1 wherein each $R^{1a}$ and $R^{1b}$ is independently selected from the group consisting of H, halogen, —$R^c$, —OC(O)$NR^aR^b$, —$NR^bC(O)R^a$, —$NR^bC(O)_2R^c$, —$NR^aC(O)NR^aR^b$, —$NR^aR^b$ and —$OR^a$;

$R^{2a}$ is selected from the group consisting of H, F and $CH_3$;

each $R^4$ is independently selected from the group consisting of halogen, —CN, —$R^f$, —$CO_2R^d$, —$CONR^dR^e$, —$NR^eC(O)_2R^f$, —$NR^dC(O)NR^dR^e$, —$NR^dR^e$, —$OR^d$, —$X^1$—CN, —$X^1$—$CO_2R^d$, —$X^1$—$CONR^dR^e$, —$X^1$—$NR^dR^e$, —$X^1$—$OR^d$ and —$X^1$—Y.

In yet other selected embodiments, compounds are provided having formula Ib1:

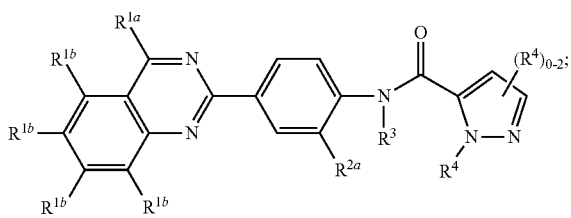

Ib1 wherein each $R^{1a}$ and $R^{1b}$ is independently selected from the group consisting of H, halogen, —$R^c$, —OC(O)$NR^aR^b$, —$NR^bC(O)R^a$, —$NR^bC(O)_2R^c$, —$NR^aC(O)NR^aR^b$, —$NR^aR^b$ and —$OR^a$;

$R^{2a}$ is selected from the group consisting of H, F and $CH_3$;

each $R^4$ is independently selected from the group consisting of halogen, —CN, —$R^f$, —$CO_2R^d$, —$CONR^dR^e$, —$NR^eC(O)_2R^f$, —$NR^dC(O)NR^dR^e$, —$NR^dR^e$, —$OR^d$, —$X^1$—CN, —$X^1$—$CO_2R^d$, —$X^1$—$CONR^dR^e$, —$X^1$—$NR^dR^e$, —$X^1$—$OR^d$ and —$X^1$—Y.

In other selected embodiments, compounds are provided having formula If1:

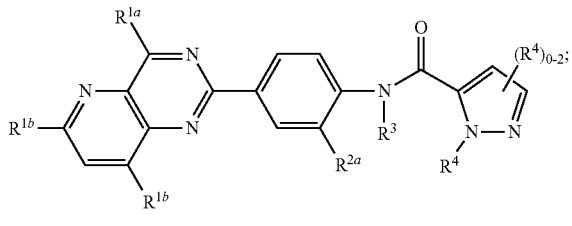

If1 wherein each $R^{1a}$ and $R^{1b}$ is independently selected from the group consisting of H, halogen, —$R^c$, —OC(O)$NR^aR^b$, —$NR^bC(O)R^a$, —$NR^bC(O)_2R^c$, —$NR^aC(O)NR^aR^b$, —$NR^aR^b$ and —$OR^a$;

$R^{2a}$ is selected from the group consisting of H, F and $CH_3$;

each $R^4$ is independently selected from the group consisting of halogen, —CN, —$R^f$, —$CO_2R^d$, —$CONR^dR^e$, —$NR^eC(O)_2R^f$, —$NR^dC(O)NR^dR^e$, —$NR^dR^e$, —$OR^d$, —$X^1$—CN, —$X^1$—$CO_2R^d$, —$X^1$—$CONR^dR^e$, —$X^1$—$NR^dR^e$, —$X^1$—$OR^d$ and —$X^1$—Y.

In yet other selected embodiments, compounds are provided having formula Ig1:

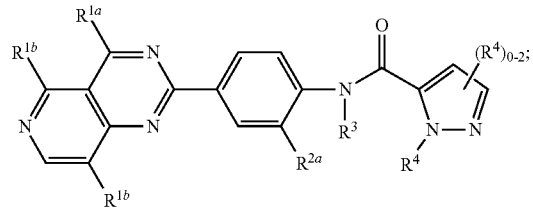

Ig1 wherein each $R^{1a}$ and $R^{1b}$ is independently selected from the group consisting of H, halogen, —$R^c$, —OC(O)$NR^aR^b$, —$NR^bC(O)R^a$, —$NR^bC(O)_2R^c$, —$NR^aC(O)NR^aR^b$, —$NR^aR^b$ and —$OR^a$;

$R^{2a}$ is selected from the group consisting of H, F and $CH_3$;

each $R^4$ is independently selected from the group consisting of halogen, —CN, —$R^f$, —$CO_2R^d$, —$CONR^dR^e$, —$NR^eC(O)_2R^f$, —$NR^dC(O)NR^dR^e$, —$NR^dR^e$, —$OR^d$, —$X^1$—CN, —$X^1$—$CO_2R^d$, —$X^1$—$CONR^dR^e$, —$X^1$—$NR^dR^e$, —$X^1$—$OR^d$ and —$X^1$—Y.

In some selected embodiments, provided herein are compounds in Table 1 having +++ or ++++ activity.

Compounds:

Group A Embodiments

Group A1:

In one group of embodiments, compounds provided herein are represented by formula (I):

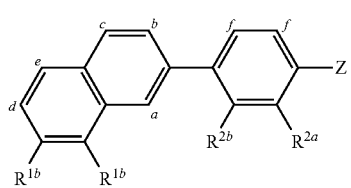

I or a pharmaceutically acceptable salt, solvate or hydrate thereof, wherein:
each of ring vertices a, b and c is independently selected from the group consisting of $C(R^{1a})$ and N;
ring vertex d is $C(R^{1b})$;
ring vertex e is selected from the group consisting of $C(R^{1b})$ and N;
each ring vertex f is selected from the group consisting of $C(R^{2c})$, $C(R^{2d})$ and N;
Z is selected from the group consisting of:

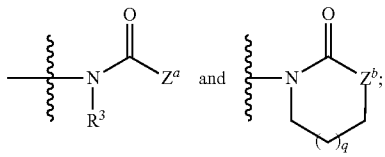

$Z^a$ is selected from the group consisting of:
(i) a 5- or 6-membered heteroaryl group having at least one nitrogen atom as a ring member, which is substituted with from 0 to 4 $R^4$;
(ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy;
(iii) a $C_{1-8}$ alkyl group, $C_{1-8}$ haloalkyl group, or a $C_{1-8}$ alkoxy group;
$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;
the subscript q is 0, 1 or 2;
each $R^{1a}$ and $R^{1b}$ is independently selected from the group consisting of hydrogen, deuterium, halogen, —CN, —NO$_2$, —$R^c$, —CO$_2R^a$, —CONR$^aR^b$, —C(O)R$^a$, —OC(O)NR$^aR^b$, —NR$^bC(O)R^a$, —NR$^bC(O)_2R^c$, —NR$^aC(O)NR^aR^b$, —NR$^aR^b$, —OR$^a$, and —S(O)$_2$NR$^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and 5- or 6-membered heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups; and at least one $R^{1b}$ is selected from the group consisting of $C_{1-4}$ haloalkyl, $C_{1-4}$ haloalkoxy and —CN;
each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;
$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-CO$_2R^d$, $C_{1-3}$ alkylene-NR$^dR^e$, $C_{1-3}$ alkylene-CONR$^dR^e$, $C_{1-3}$ alkylene-OC(O)NR$^dR^e$, and $C_{1-3}$ alkylene-NR$^eC(O)_2R^f$;

each $R^4$ is independently selected from the group consisting of halogen, —CN, —$R^f$, —CO$_2R^d$, —CONR$^dR^e$, —C(O)R$^d$, —OC(O)NR$^dR^e$, —NR$^eC(O)R^d$, —NR$^eC(O)_2R^f$, —NR$^dC(O)NR^dR^e$, —NR$^dR^e$, —OR$^d$, —S(O)$_2$NR$^dR^e$, —X$^1$—CN, —X$^1$—CO$_2R^d$, —X$^1$—CONR$^dR^e$, —X$^1$—C(O)R$^d$, —X$^1$—OC(O)NR$^dR^e$, —X—NR$^eC(O)R^d$, —X—NR$^eC(O)_2R^f$, —X—NR$^dC(O)NR^dR^e$, —X—NR$^dR^e$, —X$^1$—OR$^d$, —X$^1$—P(O)(OH)$_2$, —X$^1$—Y and —X$^1$—S(O)$_2$NR$^dR^e$; wherein each $X^1$ is independently $C_{1-6}$alkylene and Y is selected from the group consisting of pyrazolyl, imidazolyl, 1,2,3-triazolyl, 1,2,4-triazolyl, tetrazolyl, piperidinyl, pyrrolidinyl, tetrahydrofuranyl, tetrahydropyranyl and morpholinyl;
each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;
each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, phenyl and 5- or 6-membered heteroaryl;
wherein the aliphatic and cyclic portions of $R^d$, $R^e$ and $R^f$ are optionally further substituted with from one to three halogen, hydroxy, methyl, amino, methylamino, dimethylamino and carboxylic acid groups;
with the proviso that the compound is other than:
N-[4-[8-(trifluoromethyl)-2-quinazolinyl]phenyl]acetamide;
N-[4-[4-(5-chloro-2-hydroxyphenyl)-1,2-dihydro-2-oxo-6-(trifluoromethyl)-3-quinolinyl]phenyl]acetamide and tautomer thereof, namely N-(4-(4-(5-chloro-2-hydroxyphenyl)-2-hydroxy-6-(trifluoromethyl)quinolin-3-yl)phenyl)acetamide;
N-[4-[4-(propylamino)-7-(trifluoromethyl)-2-quinazolinyl]phenyl]acetamide; or
N-[4-[4-(ethylamino)-7-(trifluoromethyl)-2-quinazolinyl]phenyl]-2,2,2-trifluoroacetamide.
Within this group of embodiments, further embodiments are provided wherein d is selected from the group consisting of C(CN), C(C$_{1-4}$ haloalkyl) and C(C$_{1-4}$ haloalkoxy), and in still further embodiments, d is C(CF$_3$).
In still other embodiments, the compounds are represented by a formula selected from the group consisting of:

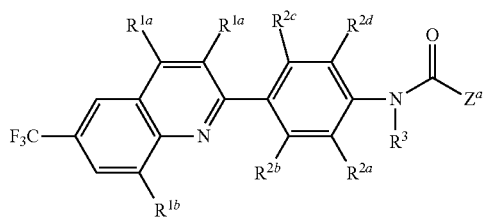

I-1a

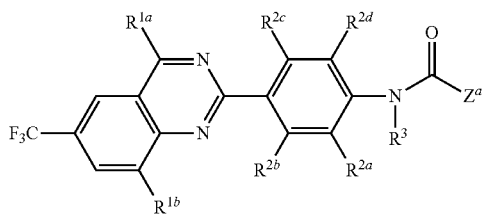

I-1b

19

-continued

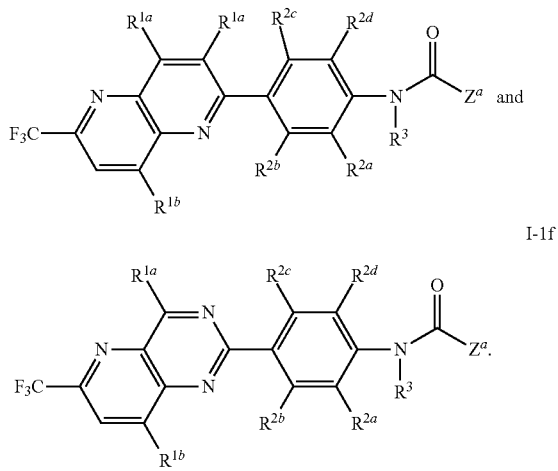

In some embodiments of formulae I-1a, I-1b, I-1c and I-1f, $Z^a$ is selected from the group consisting of pyrazolyl, imidazolyl, oxazolyl, isoxazolyl, 1,2,3-triazolyl, 1,2,4-triazolyl, pyridinyl, pyrimidinyl, pyridazinyl and pyrazinyl, each of which is substituted with from 0 to 2 $R^4$.

In still further selected embodiments, compounds herein are represented by formula I-1a, wherein $Z^a$ is pyrazolyl or pyridinyl, each of which is substituted with 0 to 3 $R^4$. In other selected embodiments, compounds herein are represented by formula I-1b, wherein $Z^a$ is pyrazolyl or pyridinyl, each of which is substituted with 0 to 3 $R^4$. In yet further selected embodiments, compounds herein are represented by formula I-1c, wherein $Z^a$ is pyrazolyl or pyridinyl, each of which is substituted with 0 to 3 $R^4$. In other further selected embodiments, compounds herein are represented by formula I-1f, wherein $Z^a$ is pyrazolyl or pyridinyl, each of which is substituted with 0 to 3 $R^4$.

With reference to the Group A embodiments of formula I, or the embodiments above, provided as formulae I-1a, I-1b, I-1c and I-1f, in some selected embodiments, each $R^4$ is independently selected from the group consisting of halogen, —CN, —$R^f$, —$CO_2R^d$, —$CONR^dR^e$, —$OR^d$, —$X^1$—CN, —$X^1$—$CO_2R^d$, —$X^1$—$CONR^dR^e$, —$X^1$—$OR^d$, and —$X^1$—Y; wherein each $X^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; each $R^d$ and $R^e$ is independently selected from hydrogen or $C_{1-8}$ alkyl; and each $R^f$ is independently selected from the group consisting of $C_{1-8}$ alkyl.

With reference to the Group A embodiments of formula I, or the embodiments above, provided as formulae I-1a, I-1b, I-1c and I-1f, in some selected embodiments, each $R^{1a}$ is hydrogen. In other selected embodiments, only one of $R^{2a}$, $R^{2b}$, $R^{2c}$ and $R^{2d}$ is other than hydrogen. In still other selected embodiments, only one of $R^{2a}$, $R^{2b}$, $R^{2c}$ and $R^{2d}$ is other than hydrogen, and is selected from the group consisting of F and $CH_3$. In other selected embodiments, $Z^a$ is pyrazolyl or pyridinyl, each of which is substituted with 0 to 3 $R^4$; each $R^{1a}$ is hydrogen; one of $R^{2a}$, $R^{2b}$, $R^{2c}$ and $R^{2d}$ is other than hydrogen; and $R^3$ is hydrogen or methyl.

20

Group B Embodiments

Group B1:
In one group of embodiments, compounds provided herein are represented by the formula:

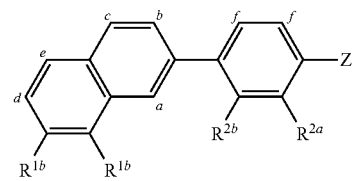

I or a pharmaceutically acceptable salt, solvate or hydrate thereof, wherein:
each of ring vertices a, b and c is independently selected from the group consisting of $C(R^{1a})$ and N;
each of ring vertices d and e is independently selected from the group consisting of $C(R^{1b})$ and N;
each ring vertex f is selected from the group consisting of $C(R^{2c})$, $C(R^{2d})$ and N;
Z is:

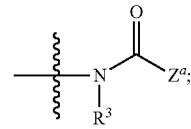

$Z^a$ is a 5- or 6-membered heteroaryl group having at least one nitrogen atom as a ring member, which is substituted with from 0 to 4 $R^4$;
each $R^{1a}$ and $R^{1b}$ is independently selected from the group consisting of hydrogen, deuterium, halogen, —CN, —$NO_2$, —$R^c$, —$CO_2R^a$, —$CONR^aR^b$, —$C(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and 5- or 6-membered heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups;
each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;
$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$;

each R⁴ is independently selected from the group consisting of halogen, —CN, —R^f, —CO₂R^d, —CONR^dR^e, —C(O)R^d, —OC(O)NR^dR^e, —NR^eC(O)R^d, —NR^eC(O)₂R^f, —NR^dC(O)NR^dR^e, —NR^dR^e, —OR^d, —S(O)₂NR^dR^e, —X¹—CN, —X¹—CO₂R^d, —X¹—CONR^dR^e, —X¹—C(O)R^d, —X¹—OC(O)NR^dR^e, —X¹—NR^eC(O)R^d, —X—NR^eC(O)₂R^f, —X¹—NR^dC(O)NR^dR^e, —X¹—NR^dR^e, —X¹—OR^d, —X¹—P(O)(OH)₂, —X¹—Y and —X¹—S(O)₂NR^dR^e; wherein each X¹ is independently C₁₋₆alkylene and Y is selected from the group consisting of pyrazolyl, imidazolyl, 1,2,3-triazolyl, 1,2,4-triazolyl, tetrazolyl, piperidinyl, pyrrolidinyl, tetrahydrofuranyl, tetrahydropyranyl and morpholinyl;

each R^d and R^e is independently selected from hydrogen, C₁₋₈ alkyl, and C₁₋₈ haloalkyl, or when attached to the same nitrogen atom are optionally combined with the nitrogen atom to form a five or six-membered ring having from 0 to 2 additional heteroatoms as ring members selected from N, O or S;

each R^f is independently selected from the group consisting of C₁₋₈ alkyl, C₁₋₈ haloalkyl, C₁₋₈ deuteroalkyl, C₃₋₆ cycloalkyl, heterocycloalkyl, phenyl and 5- or 6-membered heteroaryl;

wherein the aliphatic and cyclic portions of R^d, R^e and R^f are optionally further substituted with from one to three halogen, hydroxy, methyl, amino, methylamino, dimethylamino and carboxylic acid groups;

and wherein the compound is other than:
3-[4-[(3-pyridinylcarbonyl)amino]phenyl]-5-quinoxalinecarboxamide;
1,3-diphenyl-N-[4-(2-quinoxalinyl)phenyl]-1H-pyrazole-4-carboxamide;
N-[4-(2-quinolinyl)phenyl]-3-pyridinecarboxamide;
4-chloro-N-[4-(3,4-dihydro-4-oxo-2-quinazolinyl)phenyl]-2-pyridinecarboxamide, or tautomers thereof, namely, 4-chloro-N-[4-(4-hydroxy-2-quinazolinyl)phenyl]-2-pyridinecarboxamide;
3-amino-N-[4-(3,4-dihydro-4-oxo-2-quinazolinyl)phenyl]-2-pyrazinecarboxamide, or tautomers thereof, namely, 3-amino-N-[4-(4-hydroxy-2-quinazolinyl)phenyl]-2-pyrazinecarboxamide;
2-amino-N-[4-(3,4-dihydro-4-oxo-2-quinazolinyl)phenyl]-3-pyridinecarboxamide, or tautomers thereof, namely, 2-amino-N-[4-(4-hydroxy-2-quinazolinyl)phenyl]-3-pyridinecarboxamide;
N-[4-(3,4-dihydro-4-oxo-2-quinazolinyl)phenyl]-3-pyridinecarboxamide, or tautomers thereof, namely, N-[4-(4-hydroxy-2-quinazolinyl)phenyl]-3-pyridinecarboxamide;
N-[4-(3,4-dihydro-4-oxo-2-quinazolinyl)phenyl]-2-pyridinecarboxamide, or tautomers thereof, namely, N-[4-(4-hydroxy-2-quinazolinyl)phenyl]-2-pyridinecarboxamide;
4-amino-N-[4-(3,4-dihydro-4-oxo-2-quinazolinyl)phenyl]-2-pyridinecarboxamide, or tautomers thereof, namely, 4-amino-N-[4-(4-hydroxy-2-quinazolinyl)phenyl]-2-pyridinecarboxamide;
N-[4-(3,4-dihydro-4-oxo-2-quinazolinyl)phenyl]-1,2-dihydro-6-hydroxy-2-oxo-4-pyridinecarboxamide, or tautomers thereof, namely, N-[4-(4-hydroxy-2-quinazolinyl)phenyl]-2,6-dihydroxy-4-pyridinecarboxamide;
N-[4-(3,4-dihydro-4-oxo-2-quinazolinyl)phenyl]-2,4-dimethyl-5-thiazolecarboxamide, or tautomers thereof, namely, N-[4-(4-hydroxy-2-quinazolinyl)phenyl]-2,4-dimethyl-5-thiazolecarboxamide;
5-amino-N-[4-(3,4-dihydro-4-oxo-2-quinazolinyl)phenyl]-3-pyridinecarboxamide, or tautomers thereof, namely, 5-amino-N-[4-(4-hydroxy-2-quinazolinyl)phenyl]-3-pyridinecarboxamide;
N-[4-(3,4-dihydro-4-oxo-2-quinazolinyl)phenyl]-3,4-dihydro-3-oxo-2-pyrazinecarboxamide, or tautomers thereof, namely, N-[4-(4-hydroxy-2-quinazolinyl)phenyl]-3-hydroxy-2-pyrazinecarboxamide; and
1-(2-fluoroethyl)-N-(4-(quinolin-2-yl)phenyl-1H-1,2,3-triazole-4-carboxamide.

In one selected group of embodiments, at least one R¹ᵇ is selected from the group consisting of C₁₋₄ haloalkyl, C₁₋₄ haloalkoxy and —CN. In another selected group of embodiments, each R¹ᵃ is hydrogen. In still another selected group of embodiments, each of R²ᵃ, R²ᵇ, R²ᶜ and R²ᵈ is selected from the group consisting of hydrogen, F and CH₃.

In some particular embodiments, compounds provided herein are represented by a formula selected from the group consisting of:

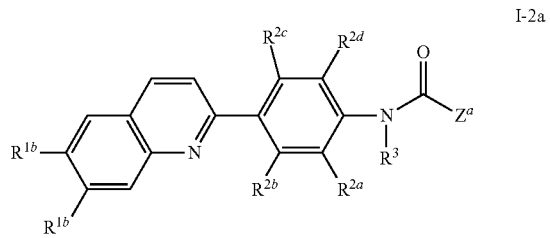

I-2a

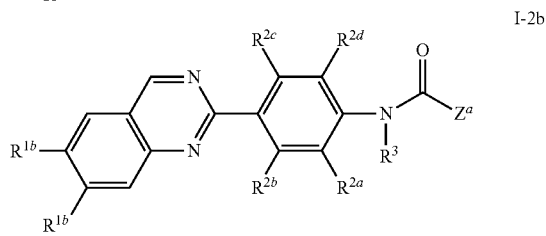

I-2b

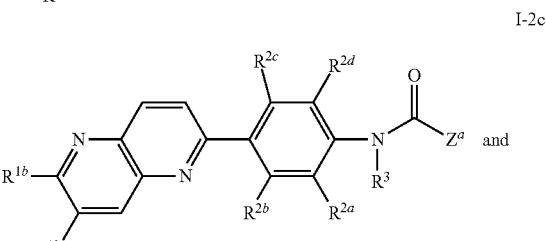

I-2c and

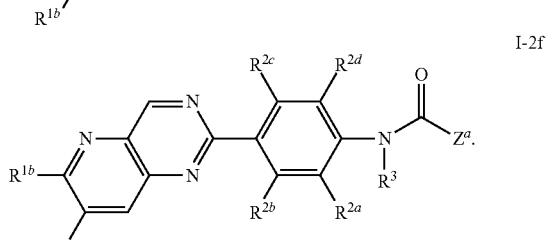

I-2f

In certain of these embodiments, the compound has formula I-2a, wherein one R¹ᵇ is CF₃. In other of these embodiments, the compound has formula I-2b, wherein one R¹ᵇ is CF₃. In still other of these embodiments, the compound has formula I-2c, wherein one R¹ᵇ is CF₃. In yet other of these embodiments, the compound has formula I-2f, wherein one R¹ᵇ is CF₃.

In some embodiments of formulae I-2a, I-2b, I-2c and I-2f, compounds provided herein are those wherein Z^a is pyrazolyl and is substituted with 0 to 2 $R^4$; one or two of $R^{2a}$, $R^{2b}$, $R^{2c}$ and $R^{2d}$ is selected from the group consisting of F and $CH_3$; and one $R^{1b}$ is selected from the group consisting of $C_{1-4}$ haloalkyl and $C_{1-4}$ haloalkoxy.

Group B2:

In one group of embodiments, provided herein are compounds of formula:

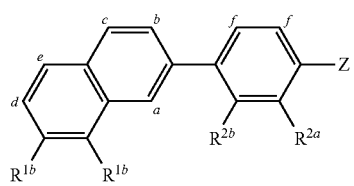

I or a pharmaceutically acceptable salt, solvate or hydrate thereof, wherein;

each of ring vertices a, b and c is independently selected from the group consisting of $C(R^{1a})$ and N;

each of ring vertices d and e is independently selected from the group consisting of $C(R^{1b})$ and N;

each ring vertex f is selected from the group consisting of $C(R^{2c})$, $C(R^{2d})$ and N;

Z is:

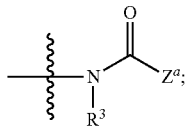

$Z^a$ is a 5- or 6-membered heteroaryl group having at least one nitrogen atom as a ring member, which is substituted with from 0 to 4 $R^4$;

each $R^{1a}$ and $R^{1b}$ is independently selected from the group consisting of hydrogen, deuterium, halogen, —CN, —$NO_2$, —$R^c$, —$CO_2R^a$, —$C(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^c$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and 5- or 6-membered heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups; and at least one $R^{1a}$ and $R^{1b}$ is other than hydrogen;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$;

each $R^4$ is independently selected from the group consisting of halogen, —CN, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^dC(O)NR^dR^e$, —$NR^dR^e$, —$OR^d$, —$S(O)_2NR^dR^e$, —X—CN, —$X^1$—$CO_2R^d$, —$X^1$—$CONR^dR^e$, —$X^1$—$C(O)R^d$, —$X^1$—$OC(O)NR^dR^e$, —$X^1$—$NR^eC(O)R^d$, —$X^1$—$NR^eC(O)_2R^f$, —$X^1$—$NR^dC(O)NR^dR^e$, —$X^1$—$NR^dR^e$, —$X^1$—$OR^d$, —$X^1$—$P(O)(OH)_2$, —$X^1$—Y and —$X^1$—$S(O)_2NR^dR^e$; wherein each $X^1$ is independently $C_{1-6}$alkylene and Y is selected from the group consisting of pyrazolyl, imidazolyl, 1,2,3-triazolyl, 1,2,4-triazolyl, tetrazolyl, piperidinyl, pyrrolidinyl, tetrahydrofuranyl, tetrahydropyranyl and morpholinyl;

each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, and 5- or 6-membered heteroaryl;

wherein the aliphatic and cyclic portions of $R^d$, $R^e$ and $R^f$ are optionally further substituted with from one to three halogen, hydroxy, methyl, amino, methylamino, dimethylamino and carboxylic acid groups.

In this group of embodiments, further selected embodiments are those wherein each $R^{1a}$ is hydrogen and at least one $R^{1b}$ is other than hydrogen. Also in this group of embodiments are further selected embodiments wherein the compound has a formula selected from the group consisting of:

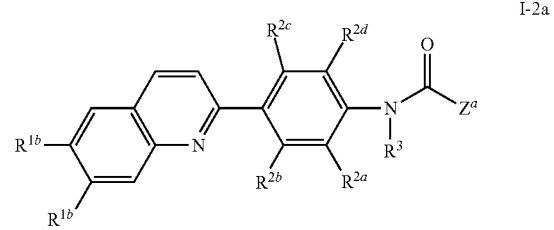

I-2a

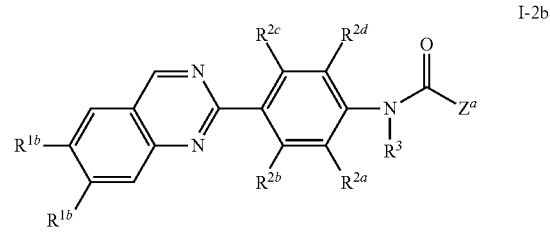

I-2b

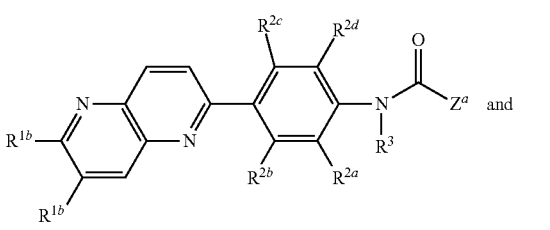

I-2c and

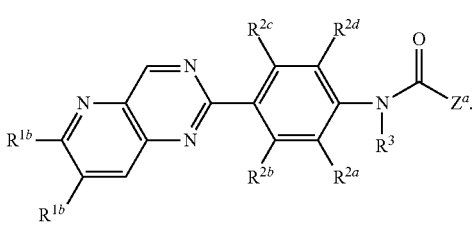

I-2f

In some selected embodiments, $Z^a$ is selected from the group consisting of pyrazolyl, imidazolyl, oxazolyl, isoxazolyl, 1,2,3-triazolyl, 1,2,4-triazolyl, pyridinyl, pyrimidinyl, pyridazinyl and pyrazinyl, each of which is substituted with from 0 to 2 $R^4$. In other selected embodiments, only one of $R^{2a}$, $R^{2b}$, $R^{2c}$ and $R^{2d}$ is other than hydrogen. In yet other selected embodiments, $Z^a$ is pyrazolyl or pyridinyl and is substituted with 0 to 2 $R^4$.

With reference to those embodiments just described as having formula I-2a, I-2b, I-2c or I-2f, further selected embodiments are those wherein one $R^{1b}$ is selected from the group consisting of $C_{1-4}$ haloalkyl, $C_{1-4}$ haloalkoxy and —CN. In other selected embodiments, $R^3$ is hydrogen or $CH_3$. In still other selected embodiments, only one of $R^{2a}$, $R^{2b}$, $R^{2c}$ and $R^{2d}$ is other than hydrogen; one $R^{1b}$ is selected from the group consisting of $C_{1-4}$ haloalkyl, $C_{1-4}$ haloalkoxy and —CN; and $R^3$ is hydrogen or $CH_3$.

With reference to the Group B, B1 or B2 embodiments of formula I, or the embodiments above, provided as formulae I-2a, I-2b, I-2c and I-2f, in some selected embodiments, each $R^4$ is independently selected from the group consisting of halogen, —CN, —$R^f$, —$CO_2R^d$, —$CONR^dR^e$, —$OR^d$, —$X^1$—CN, —$X^1$—$CO_2R^d$, —$X^1$—$CONR^dR^e$, —$X^1$—$OR^d$, and —$X^1$—Y; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen or $C_{1-8}$ alkyl; and each $R^f$ is independently selected from the group consisting of $C_{1-8}$ alkyl.

Group C Embodiments

Group $C_1$:

In another group of embodiments, compounds provided herein have the formula:

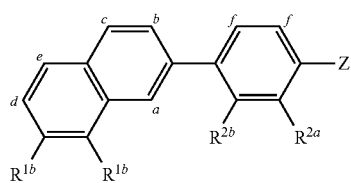

I or a pharmaceutically acceptable salt, solvate or hydrate thereof, wherein;
each of ring vertices a, b and c is independently selected from the group consisting of $C(R^{1a})$ and N;
each of ring vertices d and e is independently selected from the group consisting of $C(R^{1b})$ and N;
each ring vertex f is selected from the group consisting of $C(R^{2c})$, $C(R^{2d})$ and N;

Z is:

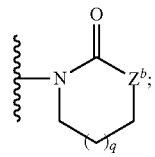

$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;
the subscript q is 0, 1 or 2;
each $R^{1a}$ and $R^{1b}$ is independently selected from the group consisting of hydrogen, deuterium, halogen, —CN, —$NO_2$, —$R^c$, —$CO_2R^a$, —$CONR^aR^b$, —$C(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and 5- or 6-membered heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups;
each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;
$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$;
each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;
each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, phenyl and 5- or 6-membered heteroaryl;
wherein the aliphatic and cyclic portions of $R^d$, $R^e$ and $R^f$ are optionally further substituted with from one to three halogen, hydroxy, methyl, amino, methylamino, dimethylamino and carboxylic acid groups;
and wherein the compound is other than:
1-[4-(4-methyl-2-quinolinyl)phenyl]-2-pyrrolidinone;
3-[2-ethoxy-4-(2-oxo-1-pyrrolidinyl)phenyl]-2-quinolinecarboxaldehyde;
2-[4-(2-oxo-3-oxazolidinyl)phenyl]-4(3H)-quinazolinone or tautomer thereof, namely 3-(4-(4-hydroxyquinazolin-2-yl)phenyl)oxazolidin-2-one;
3-[4-(2-quinolinyl)phenyl]-2-oxazolidinone;

6-(1-methylethyl)-2-[4-(2-oxo-3-oxazolidinyl)phenyl]-4 (3H)-quinazolinone or tautomer thereof, namely 3-(4-(4-hydroxy-6-isopropylquinazolin-2-yl)phenyl)oxazolidin-2-one;

3,4-dihydro-4-oxo-2-[4-(2-oxo-1-pyrrolidinyl)phenyl]-7-quinazolinecarboxylic acid, or tautomer thereof, namely 4-hydroxy-2-(4-(2-oxopyrrolidin-1-yl)phenyl)quinazoline-7-carboxylic acid;

2-[4-(2-oxo-3-oxazolidinyl)phenyl]-4(3H)-quinazolinone or tautomer thereof, namely 3-(4-(4-hydroxyquinazolin-2-yl)phenyl)oxazolidine-2,4-dione; or 3-[4-(2-quinolinyl)phenyl]-2-oxazolidinone.

In this group of embodiments, some selected embodiments are those compounds wherein at least one $R^{1b}$ is selected from the group consisting of $C_{1-4}$ haloalkyl, $C_{1-4}$ haloalkoxy and —CN. Other selected embodiments, are those compounds having a formula selected from the group consisting of:

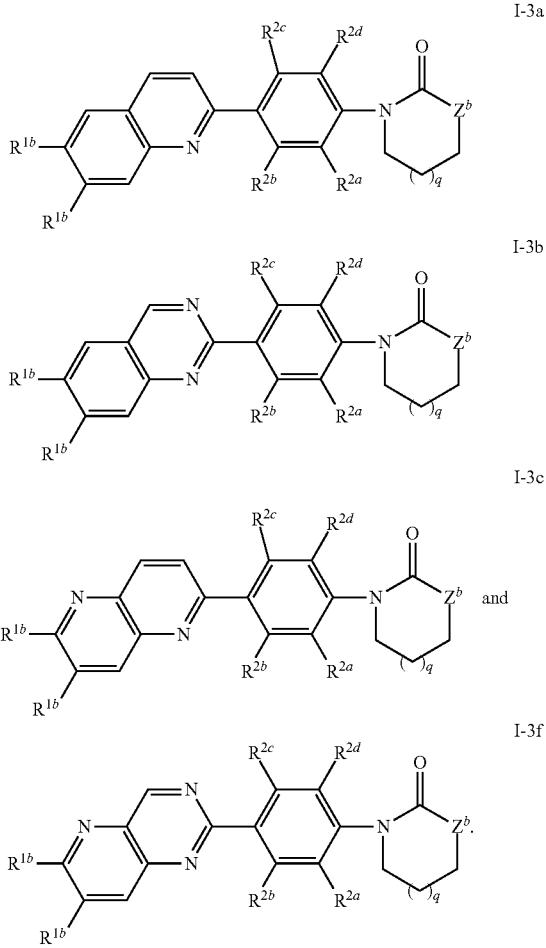

Within this group of embodiments and the selected embodiments having formula I-3a, I-3b, I-3c or I-3f, further selected embodiments are those wherein $Z^b$ is selected from the group consisting of O, NH, N(CH$_3$) and CH$_2$. In still other selected embodiments, q is 0 or 1. In this other selected embodiments, only one of $R^{2a}$, $R^{2b}$, $R^{2c}$ and $R^{2d}$ is other than hydrogen. In yet other selected embodiments, one $R^{1b}$ is CF$_3$. In one particular group of embodiments, $Z^b$ is selected from the group consisting of O, NH, N(CH$_3$) and CH$_2$; q is 0 or 1; only one of $R^{2a}$, $R^{2b}$, $R^{2c}$ and $R^{2d}$ is other than hydrogen; and one $R^{1b}$ is CF$_3$.

Group $C_2$:

In another group of embodiments, compounds provided herein have the formula:

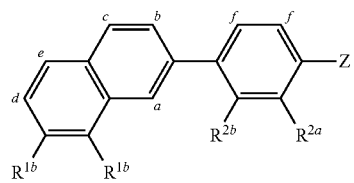

I or a pharmaceutically acceptable salt, solvate or hydrate thereof, wherein;

each of ring vertices a, b and c is independently selected from the group consisting of $C(R^{1a})$ and N;

each of ring vertices d and e is independently selected from the group consisting of $C(R^{1b})$ and N;

each ring vertex f is selected from the group consisting of $C(R^{2c})$, $C(R^{2d})$ and N;

Z is:

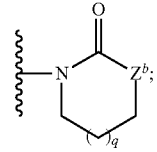

$Z^b$ is selected from the group consisting of O, NR$^z$ and C(R$^z$)$_2$, wherein each R$^z$ is independently selected from the group consisting of H, $C_{1-4}$ alkyl, $C_{1-4}$ haloalkyl and $C_{1-4}$ alkoxy;

the subscript q is 0, 1 or 2;

each $R^{1a}$ and $R^{1b}$ is independently selected from the group consisting of hydrogen, deuterium, halogen, —CN, —NO$_2$, —R$^c$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^c$, and —S(O)$_2$NR$^a$R$^b$; wherein each R$^a$ and R$^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each R$^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and 5- or 6-membered heteroaryl, and wherein the aliphatic and cyclic portions of R$^a$, R$^b$ and R$^c$ are optionally further substituted with from one to three halogen, hydroxy, methyl, amino, methylamino, dimethylamino and carboxylic acid groups; and at least one $R^{1b}$ is other than hydrogen;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

R$^3$ is selected from the group consisting of hydrogen, deuterium, $C_{1-3}$ alkyl, $C_{1-3}$ deuteroalkyl, $C_{1-3}$ alkylene- OR$^d$, C$_{1-3}$ alkylene-CO$_2$R$^d$, C$_{1-3}$ alkylene-NR$^d$R$^e$, C$_{1-3}$ alkylene-CONR$^d$R$^e$, C$_{1-3}$ alkylene-OC(O)NR$^d$R$^e$, and C$_{1-3}$ alkylene-NR$^e$C(O)$_2$R$^f$;

each R$^d$ and R$^e$ is independently selected from hydrogen, C$_{1-8}$ alkyl, and C$_{1-8}$ haloalkyl, or when attached to the same nitrogen atom are optionally combined with the nitrogen atom to form a five or six-membered ring having from 0 to 2 additional heteroatoms as ring members selected from N, O or S;

each R$^f$ is independently selected from the group consisting of C$_{1-8}$ alkyl, C$_{1-8}$ haloalkyl, C$_{1-8}$ deuteroalkyl, C$_{3-6}$ cycloalkyl, heterocycloalkyl, phenyl and 5- or 6-membered heteroaryl;

wherein the aliphatic and cyclic portions of R$^d$, R$^e$ and R$^f$ are optionally further substituted with from one to three halogen, hydroxy, methyl, amino, methylamino, dimethylamino and carboxylic acid groups and wherein the compound is other than:

6-(1-methylethyl)-2-[4-(2-oxo-3-oxazolidinyl)phenyl]-4(3H)-quinazolinone or tautomer thereof, namely 3-(4-(4-hydroxy-6-isopropylquinazolin-2-yl)phenyl)oxazolidin-2-one.

In this group of embodiments, some selected embodiments are those compounds wherein at least one R$^{1b}$ is selected from the group consisting of C$_{1-4}$ haloalkyl, C$_{1-8}$ haloalkoxy and —CN. Other selected embodiments, are those compounds having a formula selected from the group consisting of:

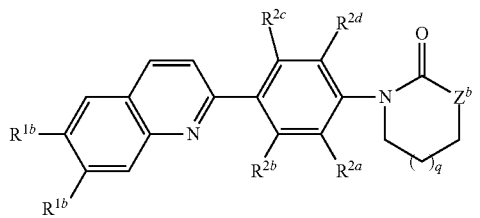

I-3a

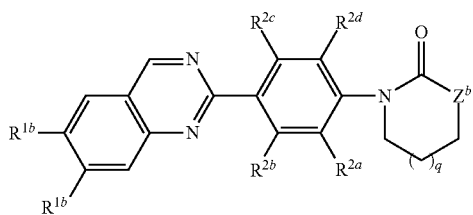

I-3b

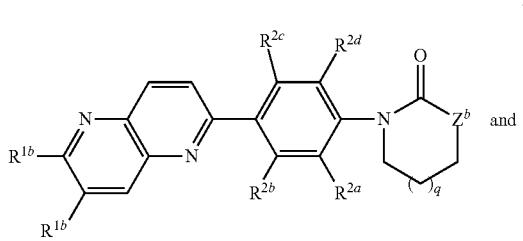

I-3c and

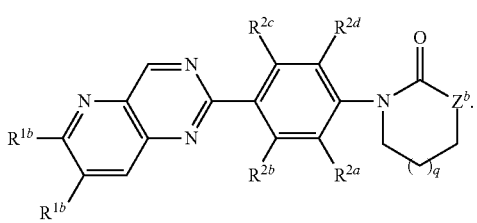

I-3f

Within this group of embodiments and the selected embodiments having formula I-31, I-3b, I-3c or I-3f, further selected embodiments are those wherein Z$^b$ is selected from the group consisting of O, NH, N(CH$_3$) and CH$_2$. In still other selected embodiments, q is 0 or 1. In this other selected embodiments, only one of R$^{2a}$, R$^{2b}$, R$^{2c}$ and R$^{2d}$ is other than hydrogen. In yet other selected embodiments, one R$^{1b}$ is CF$_3$. In one particular group of embodiments, Z$^b$ is selected from the group consisting of O, NH, N(CH$_3$) and CH$_2$; q is 0 or 1; only one of R$^{2a}$, R$^{2b}$, R$^{2c}$ and R$^{2d}$ is other than hydrogen; and one R$^{1b}$ is CF$_3$.

Group D Embodiments

In another group of embodiments, compounds provided herein have the formula:

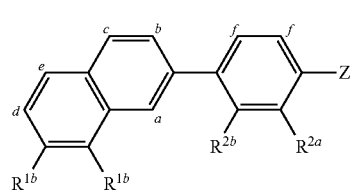

I or a pharmaceutically acceptable salt, solvate or hydrate thereof, wherein:

each of ring vertices a, b and c is independently selected from the group consisting of C(R$^{1a}$) and N;

each of ring vertices d and e is selected from the group consisting of C(R$^{1b}$) and N;

each ring vertex f is selected from the group consisting of C(R$^{2c}$), C(R$^{2d}$) and N;

Z is:

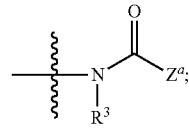

Z$^a$ is pyrazolyl, which is substituted with from 0 to 4 R$^4$;

each R$^{1a}$ and R$^{1b}$ is independently selected from the group consisting of hydrogen, deuterium, halogen, —CN, —NO$_2$, —R$^c$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^a$, and —S(O)$_2$NR$^a$R$^b$; wherein each R$^a$ and R$^b$ is independently selected from hydrogen, C$_{1-8}$ alkyl, and C$_{1-8}$ haloalkyl, or when attached to the same nitrogen atom are optionally combined with the nitrogen atom to form a five or six-membered ring having from 0 to 2 additional heteroatoms as ring members selected from N, O or S; each R$^c$ is independently selected from the group consisting of C$_{1-8}$ alkyl, C$_{1-8}$ haloalkyl, C$_{1-8}$ deuteroalkyl, C$_{2-6}$ alkenyl, C$_{2-6}$ alkynyl, C$_{3-6}$ cycloalkyl, 5- or 6-membered heterocycloalkyl, phenyl and 5- or 6-membered heteroaryl, and wherein the aliphatic and cyclic portions of R$^a$, R$^b$ and R$^c$ are optionally further substituted with from one to three halogen, hydroxy, methyl, amino, methylamino, dimethylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$;

each $R^4$ is independently selected from the group consisting of halogen, —CN, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^dC(O)NR^dR^e$, —$NR^dR^e$, —$OR^d$, —$S(O)_2NR^dR^e$, —$X^1$—CN, —$X^1$—$CO_2R^d$, —$X^1$—$CONR^dR^e$, —$X^1$—$C(O)R^d$, —$X^1$—$OC(O)NR^dR^e$, —$X^1$—$NR^eC(O)R^d$, —$X$—$NR^eC(O)_2R^f$, —$X^1$—$NR^dC(O)NR^dR^e$, —$X^1$—$NR^dR^e$, —$X^1$—$OR^d$, —$X^1$—$P(O)(OH)_2$, —$X^1$—Y and —$X^1$—$S(O)_2NR^dR^e$; wherein each $X^1$ is independently $C_{1-6}$alkylene and Y is selected from the group consisting of pyrazolyl, imidazolyl, 1,2,3-triazolyl, 1,2,4-triazolyl, tetrazolyl, piperidinyl, pyrrolidinyl, tetrahydrofuranyl, tetrahydropyranyl and morpholinyl;

each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, and 5- or 6-membered heteroaryl;

wherein the aliphatic and cyclic portions of $R^d$, $R^e$ and $R^f$ are optionally further substituted with from one to three halogen, hydroxy, methyl, amino, methylamino, dimethylamino and carboxylic acid groups.

In this group of embodiments, some selected embodiments are those compounds wherein $Z^a$ is substituted with 1 or 2 $R^4$. In still other selected embodiments, compounds are provided having a formula selected from the group consisting of:

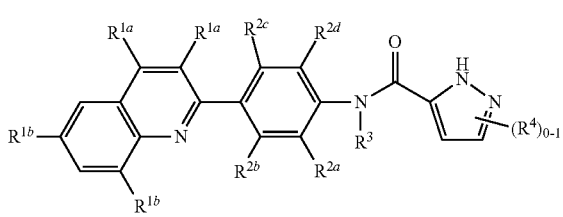

I-4a

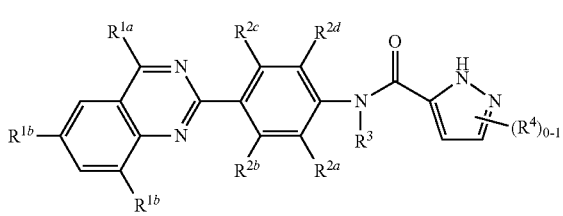

I-4b

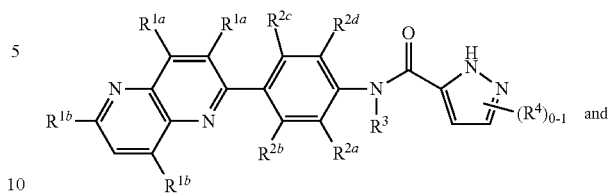

I-4c

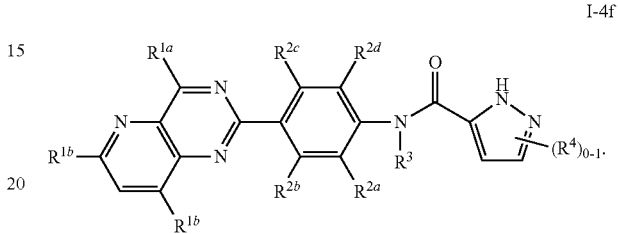

I-4f

For those embodiments provided as having formula I-4a, I-4b, I-4c or I-4f, certain selected embodiments are those wherein $R^{2a}$, $R^{2b}$, $R^{2c}$ and $R^{2d}$ are each independently selected from the group consisting of H, F and $CH_3$. In some selected embodiments, the compounds are represented by formula I-4a. In other selected embodiments, the compounds are represented by formula I-4b. In still other selected embodiments, the compounds are represented by formula I-4c. In yet other selected embodiments, the compounds are represented by formula I-4f.

For those embodiments described as having formula I-4a, I-4b, I-4c or I-4f, some further embodiments are those wherein only one of $R^{2a}$, $R^{2b}$, $R^{2c}$ and $R^{2d}$ is other than hydrogen. In still further embodiments, one $R^{1b}$ is selected from the group consisting of $C_{1-4}$ haloalkyl and $C_{1-4}$ haloalkoxy. In yet further embodiments, each $R^{1a}$ is hydrogen. In further embodiments, $R^3$ is selected from the group consisting of H and $CH_3$. In some selected further embodiments, the compounds described as having formula I-4a, I-4b, I-4c or I-4f, are those wherein each $R^{1a}$ is hydrogen; one $R^{1b}$ is selected from the group consisting of $C_{1-4}$ haloalkyl and $C_{1-4}$ haloalkoxy; one or two of $R^{2a}$, $R^{2b}$, $R^{2c}$ and $R^{2d}$ is other than hydrogen; and $R^3$ is selected from the group consisting of hydrogen, $C_{1-3}$ alkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$.

With reference to the Group D embodiments of formula I, or the embodiments above, provided as formulae I-4a, I-4b, I-4c and I-4f, in some selected embodiments, each $R^4$ is independently selected from the group consisting of halogen, —CN, —$R^f$, —$CO_2R^d$, —$CONR^dR^e$, —$OR^d$, —$X^1$—CN, —$X^1$—$CO_2R^d$, —$X^1$—$CONR^dR^e$, —$X^1$—$OR^d$, and —$X^1$—Y; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen or $C_{1-8}$ alkyl; and each $R^f$ is independently selected from the group consisting of $C_{1-8}$ alkyl.

Group E Embodiments

In another group of embodiments, compounds provided herein have the formula (II):

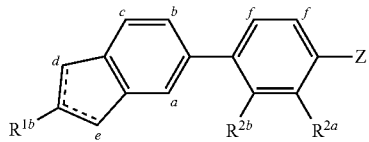

II or a pharmaceutically acceptable salt, solvate or hydrate thereof, wherein
one of the two dashed bonds is a single bond and the other of the two dashed bonds is a double bond;
each of ring vertices a, b and c is independently selected from the group consisting of $C(R^{1a})$ and N;
each of ring vertices d and e is independently selected from the group consisting of $C(R^{1b})$, N, NH, $N(C_{1-4}$ alkyl) and $N(C_{1-4}$ haloalkyl) provided at least of d and e is other than $C(R^{1b})$;
each ring vertex f is selected from the group consisting of $C(R^{2c})$, $C(R^{2d})$ and N;
Z is selected from the group consisting of:

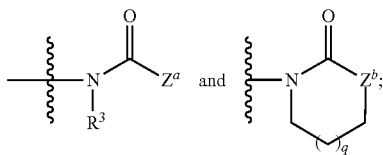

$Z^a$ is selected from the group consisting of:
(i) a 5- or 6-membered heteroaryl group having at least one nitrogen atom as a ring member, which is optionally substituted with from 1 to 4 $R^4$;
(ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy; and
(iii) a $C_{1-8}$ alkyl group, $C_{1-8}$ haloalkyl group, or a $C_{1-8}$ alkoxy group; $Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;
the subscript q is 0, 1 or 2;
each $R^{1a}$ and $R^{1b}$ is independently selected from the group consisting of hydrogen, deuterium, halogen, —$NO_2$, —$R^c$, —$C(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, and $C_{2-6}$ alkynyl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$; and each $R^4$ is independently selected from the group consisting of halogen, —CN, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^dC(O)NR^dR^e$, —$NR^dR^e$, —$OR^d$, —$S(O)_2NR^dR^e$, —$X^1$—CN, —$X^1$—$CO_2R^d$, —$X^1$—$CONR^dR^e$, —$X^1$—$C(O)R^d$, —$X^1$—$OC(O)NR^dR^e$, —$X^1$—$NR^eC(O)R^d$, —$X^1$—$NR^eC(O)_2R^f$, —$X^1$—$NR^dC(O)NR^dR^e$, —$X^1$—$NR^dR^e$, —$X^1$—$OR^d$, —$X^1$—Y and —$X^1$—$S(O)_2NR^dR^e$; wherein each $X^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl; and wherein the aliphatic and cyclic portions of $R^d$, $R^e$ and $R^f$ are optionally further substituted with from one to three halogen, hydroxy, methyl, amino, methylamino, dimethylamino and carboxylic acid groups; provided the compound of Formula (II) is other than:

carbamic acid, N-[4-(1H-pyrrolo[2,3-b]pyridin-5-yl)phenyl]-1,1-dimethylethyl ester;

2,2,2-trifluoro-N-(4-(2-hydroxy-5-methyl-1H-imidazo[4,5-b]pyridin-6-yl)phenyl)-acetamide or its tautomer namely, acetamide, N-[4-(2,3-dihydro-5-methyl-2-oxo-1H-imidazo[4,5-b]pyridin-6-yl)phenyl]-2,2,2-trifluoro-);

carbamic acid, [5-(3-bromo-1H-pyrrolo[2,3-b]pyridin-5-yl)-2-pyridinyl]-1,1-dimethylethyl ester;

N-(4-(2-hydroxy-5-methyl-3H-imidazo[4,5-b]pyridin-6-yl)phenyl)pentanamide or its tautomer namely, pentanamide, N-[4-(2,3-dihydro-5-methyl-2-oxo-1H-imidazo[4,5-b]pyridin-6-yl)phenyl]-;

N-(4-(2-hydroxy-5-methyl-1H-imidazo[4,5-b]pyridin-6-yl)phenyl)pentanamide;

N-(4-(2-hydroxy-5-methyl-1H-imidazo[4,5-b]pyridin-6-yl)phenyl)acetamide or its tautomer namely, acetamide, N-[4-(2,3-dihydro-5-methyl-2-oxo-1H-imidazo[4,5-b]pyridin-6-yl)phenyl]; or N-(4-(2-hydroxy-5-methyl-3H-imidazo[4,5-b]pyridin-6-yl)phenyl)acetamide.

Group F Embodiments

In another group of embodiments, compounds provided herein have the formula (II):

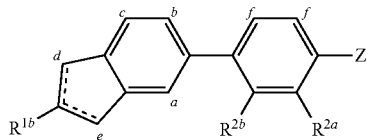

II or a pharmaceutically acceptable salt, solvate or hydrate thereof, wherein one of the dashed bonds is a single bond and the other of the dashed bonds is a double bond;

each of ring vertices a, b and c is independently selected from the group consisting of $C(R^{1a})$ and N;

each of ring vertices d and e is independently selected from the group consisting of $C(R^{1b})$, N, NH, $N(C_{1-4}$ alkyl) and $N(C_{1-4}$ haloalkyl) provided at least of d and e is other than $C(R^{1b})$;

each ring vertex f is selected from the group consisting of $C(R^{2c})$, $C(R^{2d})$ and N;

Z is selected from the group consisting of:

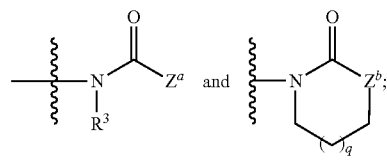

$Z^a$ is selected from the group consisting of:
(i) a 5- or 6-membered heteroaryl group having at least one nitrogen atom as a ring member, which is optionally substituted with from 1 to 4 $R^4$; and
(ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy;

$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;

the subscript q is 0, 1 or 2;

each $R^{1a}$ and $R^{1b}$ is independently selected from the group consisting of hydrogen, deuterium, halogen, —CN, —NO$_2$, —$R^c$, —CONR$^a$R$^b$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^a$, and —S(O)$_2$NR$^a$R$^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, phenyl and heteroaryl, and wherein the aliphatic and cyclic portions of $R^a$, $R^b$ and $R^c$ are optionally further substituted with from one to three halogen, hydroxy, methyl, amino, methylamino, dimethylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-OR$^d$, $C_{1-3}$ alkylene-CO$_2$R$^d$, $C_{1-3}$ alkylene-NR$^d$R$^e$, $C_{1-3}$ alkylene-CONR$^d$R$^e$, $C_{1-3}$ alkylene-OC(O)NR$^d$R$^e$, and $C_{1-3}$ alkylene-NR$^e$C(O)$_2$R$^f$; and each $R^4$ is independently selected from the group consisting of halogen, —CN, —$R^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$R$^e$, —OR$^d$, —S(O)$_2$NR$^d$R$^e$, —X$^1$—CN, —X$^1$—CO$_2$R$^d$, —X$^1$—CONR$^d$R$^e$, —X$^1$—C(O)R$^d$, —X$^1$—OC(O)NR$^d$R$^e$, —X$^1$—NR$^e$C(O)R$^d$, —X$^1$—NR$^e$C(O)$_2$R$^f$, —X$^1$—NR$^d$C(O)NR$^d$R$^e$, —X$^1$—NR$^d$R$^e$, —X$^1$—OR$^d$, —X$^1$—Y and —X$^1$—S(O)$_2$NR$^d$R$^e$; wherein each $X^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl; and wherein the aliphatic and cyclic portions of $R^d$, $R^e$ and $R^f$ are optionally further substituted with from one to three halogen, hydroxy, methyl, amino, methylamino, dimethylamino and carboxylic acid groups.

Group F1 Embodiments

Within Group F, in one selected group of embodiments, compounds of formula (II) are represented by a formula selected from the group consisting of II-1a to II-1h:

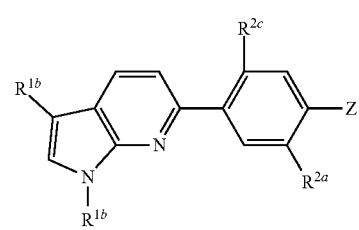

II-1a

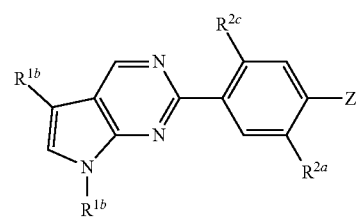

II-1b

-continued

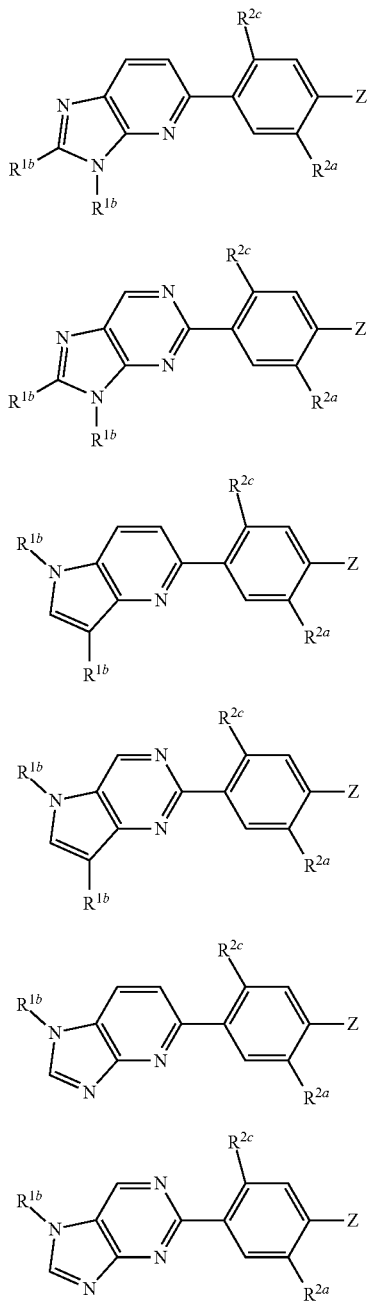

II-1c

II-1d

II-1e

II-1f

II-1g

II-1h

In certain of these embodiments, the compound has formula II-1a. In other of these embodiments, the compound has formula II-1b. In still other of these embodiments, the compound has formula II-1c. In yet other of these embodiments, the compound has formula II-1d. In certain of these embodiments, the compound has formula II-1e. In certain of these embodiments, the compound has formula II-1f. In certain of these embodiments, the compound has formula II-1g. In certain of these embodiments, the compound has formula II-1h.

Groups E, F and F1 Embodiments (i) Within E, F and F1 groups of embodiments and embodiments contained within Group F1, in one selected group of embodiments, Z is:

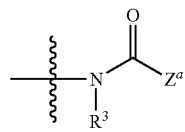

wherein $Z^a$ is a 5- or 6-membered heteroaryl group having at least one nitrogen atom as a ring member, which is optionally substituted with from 1 to 4 $R^4$.

Within this group of embodiments, in another selected group of embodiments compounds are provided wherein $Z^a$ is selected from the group consisting of pyrazolyl, imidazolyl, oxazolyl, isoxazolyl, 1,2,3-triazolyl, 1,2,4-triazolyl, pyridinyl, pyrimidinyl, pyridazinyl and pyrazinyl, each of which is substituted with from 0 to 2 $R^4$.

Within this group of embodiments, in yet another selected group of embodiments compounds are provided wherein $Z^a$ is pyrazolyl or pyridinyl, each of which is substituted with 0 to 3 $R^4$.

Within this group of embodiments, in still another selected group of embodiments compounds are provided wherein $Z^a$ is pyrazolyl substituted with 0 to 3 $R^4$. With this group of embodiments in further embodiments compounds are provided wherein $Z^a$ is pyrazol-5-yl substituted with 1 or 2 $R^4$.

Within this group of embodiments, in still another further selected group of embodiments compounds are provided wherein $Z^a$ is pyridinyl substituted with 0 to 3 $R^4$.

With this group of embodiments in further embodiments compounds are provided wherein $Z^a$ is pyridin-3yl or pyridin-4-yl substituted with 1 or 2 $R^4$. Within this group of embodiments in still further embodiments compounds are provided wherein $Z^a$ is pyridin-3-yl or pyridin-4-yl substituted with 1 or 2 $R^4$ wherein at least 1 $R^4$ is located carbon at the 2-position of the pyridin-3-yl or pyridin-4-yl ring.

Within these groups of embodiments, in further selected group of embodiments compounds are provided wherein $R^3$ is selected from the group consisting of hydrogen, $C_{1-3}$ alkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$. In a further selected group of embodiments, compounds are provided wherein $R^3$ is hydrogen or methyl.

Within these groups of embodiments, in further selected group of embodiments compounds are provided each $R^4$ is independently selected from the group consisting of halogen, —CN, —$R^f$, —$CO_2R^d$, —$CONR^dR^e$, —$OR^d$, —$X^1$—CN, —$X^1$—$CO_2R^d$, —$X$—$CONR^dR^e$, —$X^1$—$OR^d$, and —$X^1$—Y; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen or $C_{1-8}$ alkyl; and each $R^f$ is independently selected from the group consisting of $C_{1-8}$ alkyl.

(ii) Within E, F and F1 groups of embodiments and embodiments contained within Group F1, in another selected group of embodiments, Z is:

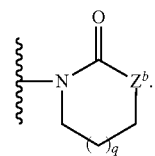

Within this group of embodiments, in further selected group of embodiments compounds are provided wherein $Z^a$ is $C(R^z)_2$, wherein each $R^z$ is independently selected from the group consisting of H, $C_{1-4}$ alkyl, $C_{1-4}$ haloalkyl and $C_{1-4}$ alkoxy. In still other selected embodiments, q is 1 or 2.

Within this group of embodiments, in another further selected group of embodiments compounds are provided wherein $Z^a$ is $N(R^z)$, wherein each $R^z$ is independently selected from the group consisting of H, $C_{1-4}$ alkyl, $C_{1-4}$ haloalkyl and $C_{1-4}$ alkoxy. In still other selected embodiments, q is 1 or 2.

Within this group of embodiments, in further embodiments, compounds are provided wherein $Z^b$ is selected from the group consisting of NH, $N(CH_3)$ and $CH_2$. In still other selected embodiments, q is 1 or 2.

Within this group of embodiments, in yet another further selected group of embodiments compounds are provided wherein $Z^a$ is O. In still other selected embodiments, q is 1 or 2.

(iii) Within E, F and F1 groups of embodiments and groups of embodiments contained therein above (i.e., (i) and (ii) and embodiments therein), in some selected embodiments, each $R^{1a}$ is hydrogen.

(iv) Within E, F and F1 groups of embodiments and groups of embodiments contained therein above (i.e., (i), (ii), and (iii) and embodiments therein), in other selected embodiments, only one or two of $R^{2a}$, $R^{2b}$, $R^{2c}$ and $R^{2d}$ are other than hydrogen. In still other selected embodiments, only one or two of $R^{2a}$, $R^{2b}$, $R^{2c}$ and $R^{2d}$ is other than hydrogen, and are selected from the group consisting of F and $CH_3$. In still other selected embodiments, only $R^{2a}$ is other than hydrogen, and is selected from the group consisting of F and $CH_3$.

(v) Within Groups E, F and F1 and groups of embodiments contained therein, in another selected group of embodiments (i.e., (i), (ii), (iii), and (iv) and embodiments therein), at least one $R^{1b}$ is selected from the group consisting of $C_{1-4}$ haloalkyl or $C_{1-4}$ haloalkoxy.

(vi) Within Groups E, F and F1 and groups of embodiments contained therein above (i.e., (i), (ii), (iii), (iv), and (v) and embodiments therein), in another selected group of embodiments, one of $R^{1b}$ is other than hydrogen and is $C_{1-4}$ haloalkyl (e.g. $CF_3$) or $C_{1-4}$ haloalkoxy (e.g., trifluoromethoxy), each $R^{1a}$ is hydrogen, one of $R^{2a}$, $R^{2b}$, $R^{2c}$ and $R^{2d}$ are other than hydrogen and are independently selected from the group consisting of F and $CH_3$.

In a further group of embodiments, $R^{2a}$ is methyl.

Group G Embodiments

In another group of embodiments, compounds provided herein have the formula (III):

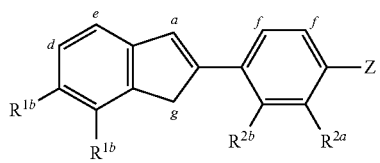

III or a pharmaceutically acceptable salt, solvate or hydrate thereof, wherein:
ring vertex a is selected from the group consisting of $C(R^{1a})$ and N;

each of ring vertices d and e is independently selected from the group consisting of $C(R^{1b})$ and N;
each ring vertex f is selected from the group consisting of $C(R^{2c})$, $C(R^{2d})$ and N;
ring vertex g is selected from the group consisting of O, S and $N(R^{1a})$;
Z is selected from the group consisting of:

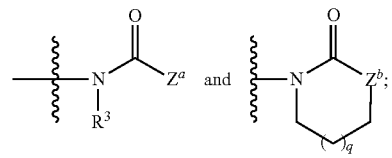

$Z^a$ is selected from the group consisting of:
  (i) a 5- or 6-membered heteroaryl group having at least one nitrogen atom as a ring member, which is optionally substituted with from 1 to 4 $R^4$;
  (ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy; and
  (iii) a $C_{1-8}$ alkyl group, $C_{1-8}$ haloalkyl group, or a $C_{1-8}$ alkoxy group; $Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;
the subscript q is 0, 1 or 2;
each $R^{1a}$ and $R^{1b}$ is independently selected from the group consisting of hydrogen, deuterium, halogen, $-R^c$, $-OC(O)NR^aR^b$, $-NR^bC(O)_2R^c$, $-NR^aC(O)NR^aR^b$, and $-S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, and $C_{2-6}$ alkynyl, and wherein the aliphatic and cyclic portions of $R^a$, $R^b$ and $R^c$ are optionally further substituted with from one to three halogen, hydroxy, methyl, amino, methylamino, and dimethylamino groups; and at least one of $R^{1b}$ is other than hydrogen;
each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;
$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$; and
each $R^4$ is independently selected from the group consisting of halogen, $-CN$, $-R^f$, $-CO_2R^d$, $-CONR^dR^e$, $-C(O)R^d$, $-OC(O)NR^dR^e$, $-NR^eC(O)R^d$, $-NR^dC(O)NR^dR^e$, $-NR^dR^e$, $-OR^d$, $-S(O)_2NR^dR^e$, $-X^1-CN$, $-X^1-CO_2R^d$, $-X^1-CONR^dR^e$, $-X^1-C(O)R^d$, $-X^1-OC(O)NR^dR^e$, $-X^1-NR^eC(O)R^d$, $-X^1-NR^eC(O)_2R^f$, $-X^1-NR^dC(O)NR^dR^e$, $-X^1-NR^dR^e$, $-X^1-OR^d$, $-X^1-Y$ and $-X^1-S(O)_2NR^dR^e$; wherein each $X^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl;

and wherein the aliphatic and cyclic portions of $R^d$, $R^e$ and $R^f$ are optionally further substituted with from one to three halogen, hydroxy, methyl, methylamino, and carboxylic acid groups provided the compound of formula (III) is other than:

acetamide, N-[2-methyl-4-(1-methyl-1H-indol-2-yl)phenyl]-;
acetamide, N-[4-(5-bromo-1H-pyrrolo[3,2-b]pyridin-2-yl)phenyl]-;
propanamide, N-[4-(5-chloro-1H-indol-2-yl)phenyl]-;
butanamide, N-[4-(5-chloro-1H-indol-2-yl)phenyl]-2-ethyl-;
propanamide, N-[4-(5-chloro-1H-indol-2-yl)phenyl]-2-methyl-;
butanamide, N-[4-(5-chloro-1H-indol-2-yl)phenyl]-3-methyl-;
propanamide, N-[4-(5-fluoro-1H-indol-2-yl)phenyl]-2-methyl-;
butanamide, N-[4-(5-fluoro-1H-indol-2-yl)phenyl]-3-methyl-;
butanamide, 2-ethyl-N-[4-(5-fluoro-1H-indol-2-yl)phenyl]-;
butanamide, N-[4-(5-chloro-1H-indol-2-yl)phenyl]-;
butanamide, N-[4-(5-fluoro-1H-indol-2-yl)phenyl]-;
pentanamide, N-[4-(5-chloro-1H-indol-2-yl)phenyl]-;
pentanamide, N-[4-(5-fluoro-1H-indol-2-yl)phenyl]-;
propanamide, N-[4-(5-fluoro-1H-indol-2-yl)phenyl]-;
acetamide, N-[4-(3-methyl-1H-indol-2-yl)phenyl]-;
acetamide, N-[4-(1,3-dimethyl-1H-indol-2-yl)phenyl]-;
carbamic acid, N-[4-(3-chloro-6-methoxy-1H-indol-2-yl)phenyl]-1-methylethyl ester;
1H-pyrazole-5-carboxamide, N-[4-(5-fluoro-1H-indol-2-yl)phenyl]-1-methyl-;
1H-pyrazole-5-carboxamide, N-[4-(5-chloro-1H-indol-2-yl)phenyl]-1-methyl-;
2-pyrazinecarboxamide, N-[4-(5-fluoro-1H-indol-2-yl)phenyl]-;
4-pyridinecarboxamide, N-[4-(5-fluoro-1H-indol-2-yl)phenyl]-;
2-pyrazinecarboxamide, N-[4-(5-chloro-1H-indol-2-yl)phenyl]-;
tert-butyl (4-(5-methylfuro[3,2-b]pyridin-2-yl)phenyl)carbamate;
4,5-dichloro-N-(4-(5-methylfuro[3,2-b]pyridin-2-yl)phenyl)isothiazole-3-carboxamide
4,5-dichloro-N-(4-(6-methylbenzo[d]thiazol-2-yl)phenyl)isothiazole-3-carboxamide
N-(4-(5-(trifluoromethyl)-1H-benzo[d]imidazol-2-yl)phenyl)acetamide;
N-(4-(5-(trifluoromethyl)-1H-benzo[d]imidazol-2-yl)phenyl)propionamide;
2-chloro-N-(4-(5-(trifluoromethyl)-1H-benzo[d]imidazol-2-yl)phenyl)acetamide;
N-(4-(1-methyl-5-(trifluoromethyl)-1H-benzo[d]imidazol-2-yl)phenyl)acetamide;
N-(4-(1-methyl-5-(trifluoromethyl)-1H-benzo[d]imidazol-2-yl)phenyl)propionamide;
N-(4-(1-butyl-5-methyl-1H-benzo[d]imidazol-2-yl)phenyl)acetamide; or
N-(4-(1-methyl-5,6-(dichloro)-1H-benzo[d]imidazol-2-yl)phenyl)acetamide.

Group H Embodiments

In another group of embodiments, compounds provided herein have the formula (III):

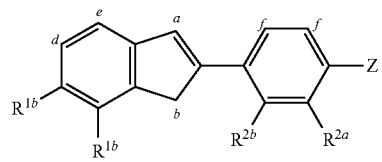

III or a pharmaceutically acceptable salt, solvate or hydrate thereof, wherein:

ring vertex a is selected from the group consisting of $C(R^{1a})$ and N;

each of ring vertices d and e is independently selected from the group consisting of $C(R^{1b})$ and N;

each ring vertex f is selected from the group consisting of $C(R^{2c})$, $C(R^{2d})$ and N;

ring vertex g is selected from the group consisting of O, S and $N(R^{1a})$;

Z is selected from the group consisting of:

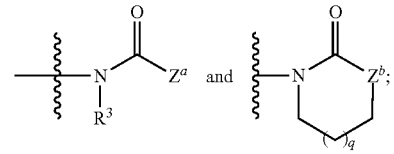

$Z^a$ is a 5- or 6-membered heteroaryl group having at least one nitrogen atom as a ring member, which is optionally substituted with from 1 to 4 $R^4$;

$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;

the subscript q is 0, 1 or 2;

each $R^{1a}$ and $R^{1b}$ is independently selected from the group consisting of hydrogen, deuterium, halogen, —$R^c$, —$CONR^aR^b$, —$C(O)R^a$, —$OC(O)NR^aR^b$, —$NR^bC(O)_2R^c$, —$NR^aC(O)NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each $R^c$ is independently selected from the group consisting of $C_{1-8}$ alkyl, $C_{1-8}$ haloalkyl, $C_{1-8}$ deuteroalkyl, $C_{2-6}$ alkenyl, $C_{2-6}$ alkynyl, $C_{3-6}$ cycloalkyl, 5- or 6-membered heterocycloalkyl, phenyl and heteroaryl, and wherein the aliphatic and cyclic portions of $R^a$, $R^b$ and $R^c$ are optionally further substituted with from one to three halogen, hydroxy, methyl, amino, methylamino, and dimethylamino groups and at least one of $R^{1b}$ is other than hydrogen;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$; and each $R^4$ is independently selected from the group consisting of halogen, —CN, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^dC(O)NR^dR^e$, —$NR^dR^e$, —$OR^d$, —$S(O)_2NR^dR^e$, —$X^1$—CN, —$X^1$—$CO_2R^d$, —$X^1$—$CONR^dR^e$, —$X^1$—$C(O)R^d$, —$X^1$—$OC(O)NR^dR^e$, —$X^1$—$NR^eC(O)R^d$, —$X^1$—$NR^eC(O)_2R^f$, —$X^1$—$NR^dC(O)NR^dR^e$, —$X^1$—$NR^dR^e$, —$X^1$—$OR^d$, —$X^1$—Y and —$X^1$—$S(O)_2NR^dR^e$; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each $R^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl;

and wherein the aliphatic and cyclic portions of $R^d$, $R^e$ and $R^f$ are optionally further substituted with from one to three halogen, hydroxy, methyl, amino, methylamino, dimethylamino and carboxylic acid groups provided the compound of formula (III) is other than:

1H-pyrazole-5-carboxamide, N-[4-(5-fluoro-1H-indol-2-yl)phenyl]-1-methyl-;
1H-pyrazole-5-carboxamide, N-[4-(5-chloro-1H-indol-2-yl)phenyl]-1-methyl-;
4-pyridinecarboxamide, N-[4-(5-fluoro-1H-indol-2-yl)phenyl]-;
2-pyrazinecarboxamide, N-[4-(5-chloro-1H-indol-2-yl)phenyl]-;
2-pyrazinecarboxamide, N-[4-(5-fluoro-1H-indol-2-yl)phenyl]-;
4,5-dichloro-N-(4-(5-methylfuro[3,2-b]pyridin-2-yl)phenyl)isothiazole-3-carboxamide; or
4,5-dichloro-N-(4-(6-methylbenzo[d]thiazol-2-yl)phenyl)isothiazole-3-carboxamide.

Group H1 Embodiments

Within Group H, in one selected group of embodiments, compounds of formula (III) are represented by a formula selected from the group consisting of III-1a to III-1d:

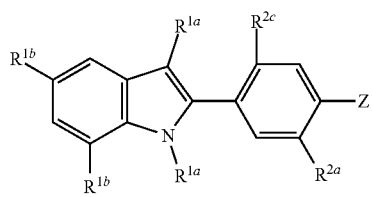

III-1a

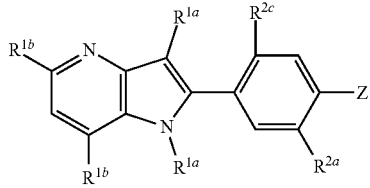

III-1b

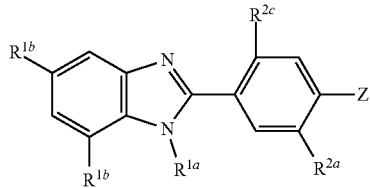

III-1c

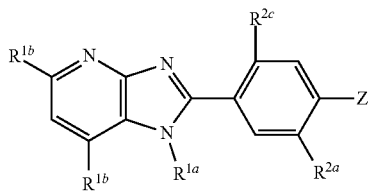

III-1d

In certain of these embodiments, the compound has formula III-1a. In other of these embodiments, the compound has formula III-1b. In still other of these embodiments, the compound has formula III-1c. In yet other of these embodiments, the compound has formula III-1d.

Group H2 Embodiments

Within Group H, in another selected group of embodiments, compounds of formula (III) are represented by a formula selected from the group consisting of III-2a to III-2h:

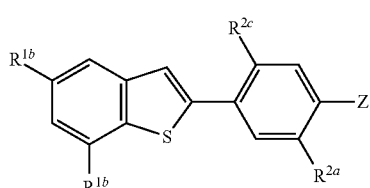

III-2a

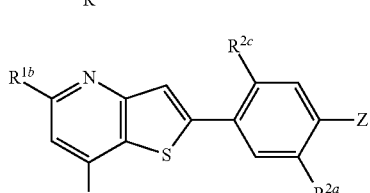

III-2b

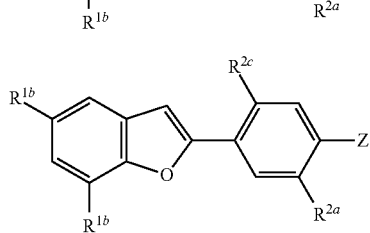

III-2c

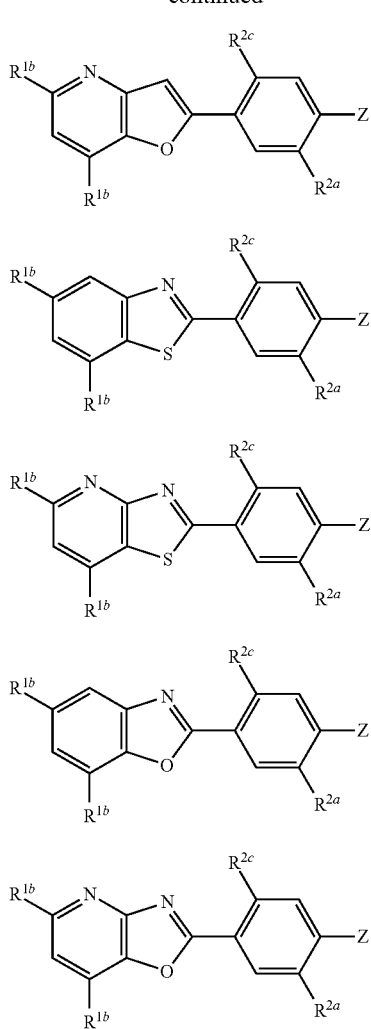

In certain of these embodiments, the compound has formula III-2a. In other of these embodiments, the compound has formula III-2b. In still other of these embodiments, the compound has formula III-2c. In yet other of these embodiments, the compound has formula III-2d. In yet other of these embodiments, the compound has formula III-2e. In yet other of these embodiments, the compound has formula III-2f. In yet other of these embodiments, the compound has formula III-2g. In yet other of these embodiments, the compound has formula III-2h.

Groups G, H, H1 and H2 Embodiments:

(i) Within Groups G, H, H1 and H2 and groups of embodiments contained within Groups H1 and H2, in one selected group of embodiments, Z is:

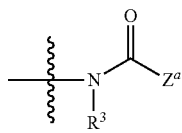

wherein $Z^a$ is a 5- or 6-membered heteroaryl group having at least one nitrogen atom as a ring member, which is optionally substituted with from 1 to 4 $R^4$.

Within this group of embodiments, in another selected group of embodiments compounds are provided wherein $Z^a$ is selected from the group consisting of pyrazolyl, imidazolyl, oxazolyl, isoxazolyl, 1,2,3-triazolyl, 1,2,4-triazolyl, pyridinyl, pyrimidinyl, pyridazinyl and pyrazinyl, each of which is substituted with from 0 to 2 $R^4$.

Within this group of embodiments, in another selected group of embodiments compounds are provided wherein $Z^a$ is pyrazolyl or pyridinyl, each of which is substituted with 0 to 3 $R^4$.

Within this group of embodiments, in still another selected group of embodiments compounds are provided wherein $Z^a$ is pyrazolyl substituted with 0 to 3 $R^4$. With this group of embodiments in further embodiments compounds are provided wherein $Z^a$ is pyrazol-5-yl substituted with 1 or 2 $R^4$.

Within this group of embodiments, in still another further selected group of embodiments compounds are provided wherein $Z^a$ is pyridinyl substituted with 0 to 3 $R^4$.

With this group of embodiments in further embodiments compounds are provided wherein $Z^a$ is pyridin-3yl or pyridin-4-yl substituted with 1 or 2 $R^4$. With this group of embodiments in still further embodiments compounds are provided wherein $Z^a$ is pyridin-3yl or pyridin-4-yl substituted with 1 or 2 $R^4$ wherein at least 1 $R^4$ is located carbon at the 2-position of the pyridin-3yl or pyridin-4-yl ring.

Within these group of embodiments, in further selected group of embodiments compounds are provided wherein $R^3$ is selected from the group consisting of hydrogen, $C_{1-3}$ alkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$. In one selected group of embodiments compounds are provided wherein $R^3$ is hydrogen or methyl.

Within these groups of embodiments, in further selected group of embodiments compounds are provided each $R^4$ is independently selected from the group consisting of halogen, —CN, —$R^f$, —$CO_2R^d$, —$CONR^dR^e$, —$OR^d$, —$X^1$—CN, —$X^1$—$CO_2R^d$, —$X^1$—$CONR^dR^e$, —$X^1$—$OR^d$, and —$X^1$—Y; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen or $C_{1-8}$ alkyl; and each $R^f$ is independently selected from the group consisting of $C_{1-8}$ alkyl.

(ii) Within Groups G, H, H1 and H2 and groups of embodiments contained within Groups H1 and H2, in another selected group of embodiments, Z is:

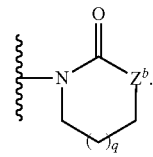

Within this group of embodiments, in further selected group of embodiments compounds are provided wherein $Z^a$ is $C(R^z)_2$, wherein each $R^z$ is independently selected from the group consisting of H, $C_{1-4}$ alkyl, $C_{1-4}$ haloalkyl and $C_{1-4}$ alkoxy. In still other selected embodiments, q is 1 or 2.

Within this group of embodiments, in another further selected group of embodiments compounds are provided wherein $Z^a$ is $N(R^z)$, wherein each $R^z$ is independently selected from the group consisting of H, $C_{1-4}$ alkyl, $C_{1-4}$ haloalkyl and $C_{1-4}$ alkoxy. In still other selected embodiments, q is 1 or 2.

Within this group of embodiments, in further embodiments, compounds are provided wherein $Z^b$ is selected from the group consisting of NH, N(CH$_3$) and CH$_2$. In still other selected embodiments, q is 1 or 2.

Within this group of embodiments, in yet another further selected group of embodiments compounds are provided wherein $Z^a$ is O. In still other selected embodiments, q is 1 or 2.

(iii) Within Groups G, H, H1, and H2 and groups of embodiments contained therein above (i.e., (i) and (ii) and embodiments therein), in some selected embodiments, only one or two of $R^{2a}$, $R^{2b}$, $R^{2c}$ and $R^{2d}$ is other than hydrogen.

(iv) Within Groups G, H, H1, and H2 and groups of embodiments contained therein above (i.e., (i) and (ii) and embodiments therein), in some selected embodiments, only one or two of $R^{2a}$, $R^{2b}$, $R^{2c}$ and $R^{2d}$ is other than hydrogen, and are independently selected from the group consisting of F and CH$_3$.

(v) Within Groups G, H, H1, and H2 and groups of embodiments contained therein (i.e., (i), (ii), (iii), and (iv) and embodiments therein), in some selected embodiments, in another selected group of embodiments, at least one $R^{1b}$ is selected from the group consisting of halo, $C_{1-4}$ haloalkyl, or $C_{1-4}$ haloalkoxy.

(vi) Within Groups G, H, H1, and H2 and groups of embodiments contained therein (i.e., (i), (ii), (iii), (iv) and (v) and embodiments therein), in another selected group of embodiments, one or two of $R^{1b}$ are other than hydrogen and are independently selected from hydrogen, halo, $C_{1-4}$ haloalkyl (e.g. CF$_3$) and $C_{1-4}$ haloalkoxy (e.g., trifluoromethoxy), each $R^{1a}$ is hydrogen or methyl, one or two of $R^{2a}$, $R^{2b}$, $R^{2c}$ and $R^{2d}$ are other than hydrogen and are independently selected from the group consisting of F and CH$_3$. In some selected embodiments, $R^{2a}$ is methyl.

Group I Embodiments

In another group of embodiments, compounds provided herein have the formula (IV):

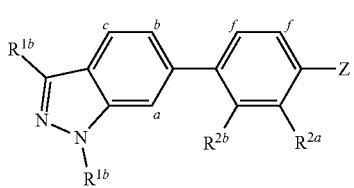

IV or a pharmaceutically acceptable salt, solvate or hydrate thereof, wherein:
each of ring vertices a, b and c is independently selected from the group consisting of C($R^{1a}$) and N;
each ring vertex f is selected from the group consisting of C($R^{2c}$), C($R^{2d}$) and N;
Z is selected from the group consisting of:

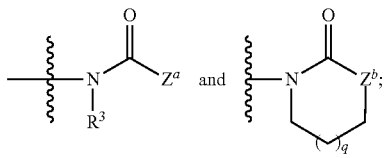

$Z^a$ is selected from the group consisting of:
(i) a 5- or 6-membered heteroaryl group having at least one nitrogen atom as a ring member, which is optionally substituted with from 1 to 4 $R^4$;
(ii) a 5-, 6- or 7-membered heterocycloalkyl group, which is optionally substituted with hydroxyl, deuterium, $C_{1-4}$ alkyl, $C_{1-4}$ haloalkyl, $C_{1-4}$ deuteroalkyl, and $C_{1-4}$ alkoxy; and
(iii) a C alkyl group, $C_{1-8}$ haloalkyl group, or a $C_{1-8}$ alkoxy group;
$Z^b$ is selected from the group consisting of O, NR$^z$ and C(R$^z$)$_2$, wherein each R$^z$ is independently selected from the group consisting of H, $C_{1-4}$ alkyl, $C_{1-4}$ haloalkyl and $C_{1-4}$ alkoxy;
the subscript q is 0, 1 or 2;
each $R^{1a}$ and $R^{1b}$ is independently selected from the group consisting of hydrogen, deuterium, halogen, —CN, —NO$_2$, —R$^c$, —C(O)R$^a$, —OC(O)NR$^a$R$^b$, —NR$^b$C(O)R$^a$, —NR$^b$C(O)$_2$R$^c$, —NR$^a$C(O)NR$^a$R$^b$, —OR$^a$, and —S(O)$_2$NR$^a$R$^b$; wherein each R$^a$ and R$^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each R$^c$ is independently selected from the group consisting of $C_{1-8}$ alkyl, $C_{1-8}$ haloalkyl, $C_{1-8}$ deuteroalkyl, $C_{2-6}$ alkenyl, and $C_{2-6}$ alkynyl, and wherein the aliphatic and cyclic portions of R$^a$, R$^b$ and R$^c$ are optionally further substituted with from one to three halogen, hydroxy, methyl, amino, methylamino, dimethylamino and carboxylic acid groups;
each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;
$R^3$ is selected from the group consisting of hydrogen, deuterium, $C_{1-3}$ alkyl, $C_{1-3}$ deuteroalkyl, $C_{1-3}$ alkylene-OR$^d$, $C_{1-3}$ alkylene-CO$_2$R$^d$, $C_{1-3}$ alkylene-NR$^d$R$^e$, $C_{1-3}$ alkylene-CONR$^d$R$^e$, $C_{1-3}$ alkylene-OC(O)NR$^d$R$^e$, and $C_{1-3}$ alkylene-NR$^e$C(O)$_2$R$^f$; and
each $R^4$ is independently selected from the group consisting of halogen, —CN, —R$^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$R$^e$, —OR$^d$, —S(O)$_2$NR$^d$R$^e$, —X$^1$—CN, —X$^1$—CO$_2$R$^d$, —X$^1$—CONR$^d$R$^e$, —X$^1$—C(O)R$^d$, —X$^1$—OC(O)NR$^d$R$^e$, —X$^1$—NR$^e$C(O)R$^d$, —X$^1$—NR$^e$C(O)$_2$R$^f$, —X$^1$—NR$^d$C(O)NR$^d$R$^e$, —X$^1$—NR$^d$R$^e$, —X$^1$—OR$^d$, —X$^1$—Y and —X$^1$—S(O)$_2$NR$^d$R$^e$; wherein each X$^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and
each R$^d$ and R$^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;
each R$^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl;
and wherein the aliphatic and cyclic portions of R$^d$, R$^e$ and R$^f$ are optionally further substituted with from one to three halogen, hydroxy, methyl, amino, methylamino, dimethylamino and carboxylic acid groups provided the compound of Formula (II) is other than:
acetamide, N-[2-bromo-6-(1-methyl-1H-indazol-5-yl)-3-pyridinyl]-2,2,2-trifluoro-; carbamic acid, N-[4-(3-methyl-1H-pyrazolo[4,3-c]pyridin-6-yl)phenyl]-,1,1-dimethylethyl ester;
carbamic acid, N-[4-(3-methyl-1H-pyrazolo[3,4-b]pyrazin-6-yl)phenyl]-,1,1-dimethylethyl ester;
carbamic acid, N-[4-[4-chloro-1-(2,2,2-trifluoroethyl)-1H-pyrazolo[3,4-d]pyrimidin-6-yl]phenyl]-,1,1-dimethylethyl ester;
acetamide, N-[4-(4-cyano-3H-imidazo[4,5-c]pyridin-6-yl)-2-(trifluoromethyl)phenyl]-; or 4-pyridinecarboxamide, 3-fluoro-N-[4-(5-methyl-1H-indazol-6-yl)phenyl]-.

Group J Embodiments

In another group of embodiments, compounds provided herein have the formula (IV):

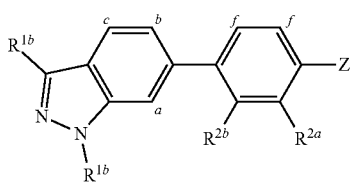

IV or a pharmaceutically acceptable salt, solvate or hydrate thereof, wherein:
each of ring vertices a, b and c is independently selected from the group consisting of $C(R^{1a})$ and N;
each ring vertex f is selected from the group consisting of $C(R^{2c})$, $C(R^{2d})$ and N;
Z is selected from the group consisting of:

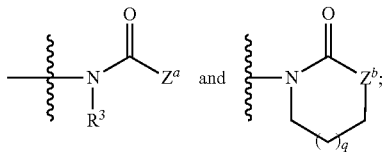

$Z^a$ is a 5- or 6-membered heteroaryl group having at least one nitrogen atom as a ring member, which is optionally substituted with from 1 to 4 $R^4$;
$Z^b$ is selected from the group consisting of O, $NR^z$ and $C(R^z)_2$, wherein each $R^z$ is independently selected from the group consisting of H, $C_{1-4}$ alkyl, $C_{1-4}$ haloalkyl and $C_{1-4}$ alkoxy;
the subscript q is 0, 1 or 2;
each $R^{1a}$ and $R^{1b}$ is independently selected from the group consisting of hydrogen, deuterium, halogen, —CN, —NO$_2$, —$R^c$, —C(O)$R^a$, —OC(O)NR$^a$R$^b$, —NR$^b$C(O)R$^a$, —NR$^b$C(O)$_2$R$^c$, —NR$^a$C(O)NR$^a$R$^b$, —NR$^a$R$^b$, —OR$^a$, and —S(O)$_2$NR$^a$R$^b$; wherein each R$^a$ and R$^b$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S; each R$^c$ is independently selected from the group consisting of $C_{1-8}$ alkyl, $C_{1-8}$ haloalkyl, $C_{1-8}$ deuteroalkyl, $C_{2-6}$ alkenyl, and $C_{2-6}$ alkynyl, and wherein the aliphatic and cyclic portions of R$^a$, R$^b$ and R$^c$ are optionally further substituted with from one to three halogen, hydroxy, methyl, amino, methylamino, dimethylamino and carboxylic acid groups;

each $R^{2a}$, $R^{2b}$, $R^{2c}$ and $R^{2d}$ is independently selected from the group consisting of hydrogen, halogen, $C_{1-3}$ alkyl, $C_{1-3}$ deuteroalkyl, $C_{1-3}$ haloalkyl, $C_{1-3}$ alkoxy, $C_{1-3}$ deuteroalkoxy and $C_{1-3}$ haloalkoxy;

$R^3$ is selected from the group consisting of hydrogen, deuterium, $C_{1-3}$ alkyl, $C_{1-3}$ deuteroalkyl, $C_{1-3}$ alkylene-OR$^d$, $C_{1-3}$ alkylene-CO$_2$R$^d$, $C_{1-3}$ alkylene-NR$^d$R$^e$, $C_{1-3}$ alkylene-CONR$^d$R$^e$, $C_{1-3}$ alkylene-OC(O)NR$^d$R$^e$, and $C_{1-3}$ alkylene-NR$^e$C(O)$_2$R$^f$; and each $R^4$ is independently selected from the group consisting of halogen, —CN, —R$^f$, —CO$_2$R$^d$, —CONR$^d$R$^e$, —C(O)R$^d$, —OC(O)NR$^d$R$^e$, —NR$^e$C(O)R$^d$, —NR$^e$C(O)$_2$R$^f$, —NR$^d$C(O)NR$^d$R$^e$, —NR$^d$R$^e$, —OR$^d$, —S(O)$_2$NR$^d$R$^e$, —X$^1$—CN, —X$^1$—CO$_2$R$^d$, —X$^1$—CONR$^d$R$^e$, —X$^1$—C(O)R$^d$, —X$^1$—OC(O)NR$^d$R$^e$, —X$^1$—NR$^e$C(O)R$^d$, —X$^1$—NR$^e$C(O)$_2$R$^f$, —X$^1$—NR$^d$C(O)NR$^d$R$^e$, —X$^1$—NR$^d$R$^e$, —X$^1$—OR$^d$, —X$^1$—Y and —X$^1$—S(O)$_2$NR$^d$R$^e$; wherein each X$^1$ is independently $C_{1-6}$alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each R$^d$ and R$^e$ is independently selected from hydrogen, $C_{1-8}$ alkyl, and $C_{1-8}$ haloalkyl, or when attached to the same nitrogen atom are optionally combined with the nitrogen atom to form a five or six-membered ring having from 0 to 2 additional heteroatoms as ring members selected from N, O or S;

each R$^f$ is independently selected from the group consisting of $C_{1-8}$ alkyl, $C_{1-8}$ haloalkyl, $C_{1-8}$ deuteroalkyl, $C_{3-6}$ cycloalkyl, heterocycloalkyl, aryl and heteroaryl;

and wherein the aliphatic and cyclic portions of R$^d$, R$^e$ and R$^f$ are optionally further substituted with from one to three halogen, hydroxy, methyl, amino, methylamino, dimethylamino and carboxylic acid groups provided the compound of formula (IV) is other than 4-pyridinecarboxamide, 3-fluoro-N-[4-(5-methyl-1H-indazol-6-yl)phenyl]-.

Group J1 Embodiments

Within Group J, in one selected embodiment, compounds of formula (IV) are represented by a formula selected from the group consisting of IV-1a and IV-1b:

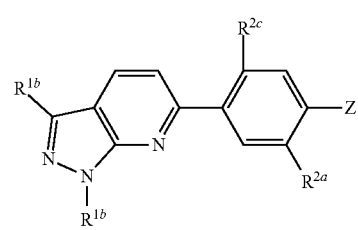

IV-1a

-continued

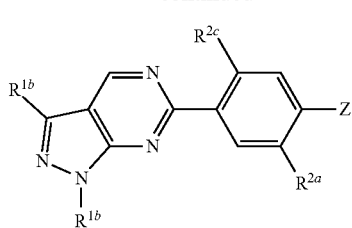

IV-1b

In certain of these embodiments, the compound has formula IV-1a. In other of these embodiments, the compound has formula IV-1b.

Group I, J and J1 Embodiments (i) Within I, J and J1 groups of embodiments and embodiments contained within Group J1, in one selected group of embodiments, Z is:

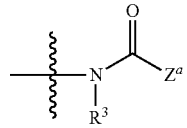

wherein $Z^a$ is a 5- or 6-membered heteroaryl group having at least one nitrogen atom as a ring member, which is optionally substituted with from 1 to 4 $R^4$.

Within this group of embodiments, in another selected group of embodiments compounds are provided wherein $Z^a$ is selected from the group consisting of pyrazolyl, imidazolyl, oxazolyl, isoxazolyl, 1,2,3-triazolyl, 1,2,4-triazolyl, pyridinyl, pyrimidinyl, pyridazinyl and pyrazinyl, each of which is substituted with from 0 to 2 $R^4$.

Within this group of embodiments, in another selected group of embodiments compounds are provided wherein $Z^a$ is pyrazolyl or pyridinyl, each of which is substituted with 0 to 3 $R^4$.

Within this group of embodiments, in still another selected group of embodiments compounds are provided wherein $Z^a$ is pyrazolyl substituted with 0 to 3 $R^4$. With this group of embodiments in further embodiments compounds are provided wherein $Z^a$ is pyrazol-5-yl substituted with 1 or 2 $R^4$.

Within this group of embodiments, in still another further selected group of embodiments compounds are provided wherein $Z^a$ is pyridinyl substituted with 0 to 3 $R^4$. With this group of embodiments in further embodiments compounds are provided wherein $Z^a$ is pyridin-3yl or pyridin-4-yl substituted with 1 or 2 $R^4$. With this group of embodiments in still further embodiments compounds are provided wherein $Z^a$ is pyridin-3yl or pyridin-4-yl substituted with 1 or 2 $R^4$ wherein at least 1 $R^4$ is located carbon at the 2-position of the pyridin-3-yl or pyridin-4-yl ring.

Within these groups of embodiments, in further selected group of embodiments compounds are provided wherein $R^3$ is selected from the group consisting of hydrogen, $C_{1-3}$ alkyl, $C_{1-3}$ alkylene-$OR^d$, $C_{1-3}$ alkylene-$CO_2R^d$, $C_{1-3}$ alkylene-$NR^dR^e$, $C_{1-3}$ alkylene-$CONR^dR^e$, $C_{1-3}$ alkylene-$OC(O)NR^dR^e$, and $C_{1-3}$ alkylene-$NR^eC(O)_2R^f$. In one selected group of embodiments compounds are provided wherein $R^3$ is hydrogen or methyl.

Within these groups of embodiments, in further selected group of embodiments compounds are provided each $R^4$ is independently selected from the group consisting of halogen, —CN, —$R^f$, —$CO_2R^d$, —$CONR^dR^e$, —$OR^d$, —$X^1$—CN, —$X^1$—$CO_2R^d$, —$X$—$CONR^dR^e$, —$X$—$OR^d$, and —$X^1$—Y; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen or $C_{1-8}$ alkyl; and each $R^f$ is independently selected from the group consisting of $C_{1-8}$ alkyl.

(ii) Within I, J and J1 groups of embodiments and embodiments contained within Group J1, in another selected group of embodiments, Z is:

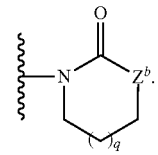

Within this group of embodiments, in further selected group of embodiments compounds are provided wherein $Z^a$ is $C(R^z)_2$, wherein each $R^z$ is independently selected from the group consisting of H, $C_{1-4}$ alkyl, $C_{1-4}$ haloalkyl and $C_{1-4}$ alkoxy. In still other selected embodiments, q is 1 or 2.

Within this group of embodiments, in another further selected group of embodiments compounds are provided wherein $Z^a$ is $N(R^z)$, wherein each $R^z$ is independently selected from the group consisting of H, $C_{1-4}$ alkyl, $C_{1-4}$ haloalkyl and $C_{1-4}$ alkoxy. In still other selected embodiments, q is 1 or 2.

Within this group of embodiments, in further embodiments, compounds are provided wherein $Z^b$ is selected from the group consisting of NH, N(CH$_3$) and CH$_2$. In still other selected embodiments, q is 1 or 2.

Within this group of embodiments, in yet another further selected group of embodiments compounds are provided wherein $Z^a$ is O. In still other selected embodiments, q is 1 or 2.

(iii) Within I, J, and J1 groups of embodiments and groups of embodiments contained therein above (i.e., (i) and (ii) and embodiments therein), in some selected embodiments, each $R^{1a}$ is hydrogen.

(iv) Within I, J, and J1 groups of embodiments and groups of embodiments contained therein above (i.e., (i), (ii) and (iii) and embodiments therein), only one or two of $R^{2a}$, $R^{2b}$, $R^{2c}$ and $R^{2d}$ are other than hydrogen. In still other selected embodiments, only one or two of $R^{2a}$, $R^{2b}$, $R^{2c}$ and $R^{2d}$ are other than hydrogen, and is selected from the group consisting of F and CH$_3$.

(v) Within I, J, and J1 groups of embodiments and groups of embodiments contained therein above (i.e., (i), (ii), (iii) and (iv) and embodiments therein), in another selected group of embodiments, at least one $R^{1b}$ is selected from the group consisting of $C_{1-4}$ alkyl, $C_{1-4}$ haloalkyl or $C_{1-4}$ haloalkoxy.

(vi) Within I, J, and J1 groups of embodiments and groups of embodiments contained therein above (i.e., (i), (ii), (iii), (iv) and (v) and embodiments therein), in another selected group of embodiments, one of $R^{1b}$ is other than hydrogen and is $C_{1-4}$ alkyl (e.g., methyl), $C_{1-4}$ haloalkyl (e.g. CF$_3$) or $C_{1-4}$ haloalkoxy (e.g., trifluoromethoxy), each $R^{1a}$ is hydrogen, one or two of $R^{2a}$, $R^{2b}$, $R^{2c}$ and $R^{2d}$ are other than hydrogen and are independently selected from the group consisting of F and $CH_3$. In a further group of embodiments, $R^{2a}$ is methyl.

With reference to the embodiments of Groups E, F, G, H, I and J, and the subgroups of embodiments discussed therein, selected embodiments are those wherein each $R^4$, when present, is independently selected from the group consisting of halogen, —CN, —$R^f$, —$CO_2R^d$, —$CONR^dR^e$, —$OR^d$, —$X^1$—CN, —$X^1$—$CO_2R^d$, —$X^1$—$CONR^dR^e$, —$X^1$—$OR^d$, and —$X^1$—Y; wherein each $X^1$ is independently $C_{1-6}$ alkylene and Y is selected from the group consisting of pyrazole, imidazole, 1,2,3-triazole, 1,2,4-triazole, tetrazole, piperidine, pyrrolidine, tetrahydrofuran, tetrahydropyran and morpholine; and each $R^d$ and $R^e$ is independently selected from hydrogen or $C_{1-8}$ alkyl; and each $R^f$ is independently selected from the group consisting of $C_{1-8}$ alkyl.

Therapeutic and Prophylactic Uses

The present invention contemplates the use of the AhR modulators described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-Related Disorders.

In accordance with the present invention, an AhR modulator can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer may be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an AhR modulator and at least one additional therapeutic or diagnostic agent, examples of which are set forth elsewhere herein.

Immune-Related Disorders and Disorders with an Inflammatory Component.

As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the AhR modulators described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The AhR modulators provided herein can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The AhR modulators can also be used to stimulate the immune system of patients suffering from iatrogenically-induced immune suppression, including those who have undergone bone marrow transplants, chemotherapy, or radiotherapy.

In particular embodiments of the present disclosure, the AhR modulators are used to increase or enhance an immune response to an antigen by providing adjuvant activity. In a particular embodiment, at least one antigen or vaccine is administered to a subject in combination with at least one AhR modulator as provided herein to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one AhR modulator as provided herein.

Microbial-Related Disorders.

By inhibiting the immunosuppressive and anti-inflammatory activity of AhR, the present disclosure contemplates the use of the AhR modulators described herein in the treatment and/or prevention of any viral, bacterial, fungal, parasitic or other infective disease, disorder or condition for which treatment with an AhR modulator may be beneficial. Examples of such diseases and disorders include HIV and AIDS, staphylococcal and streptococcal infections (e.g., *Staphylococcus aureus* and *Streptococcus sanguinis*, respectively), leishmania, toxoplasma, trichomonas, giardia, *Candida albicans, Bacillus anthracis*, and *Pseudomonas aeruginosa*. Compounds of the invention can be used to treat sepsis, decrease or inhibit bacterial growth, and reduce or inhibit inflammatory cytokines.

CNS-Related and Neurological Disorders.

Inhibition of AhR may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders.

Embodiments provided herein also contemplate the administration of the AhR modulators described herein to a subject for the treatment or prevention of any other disorder that may benefit from at least some level of AhR modulation. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the AhR modulators provided herein may be used to inhibit statin-induced adenosine production, or reduce or decrease increases in blood glucose caused by a statin in a subject taking a statin (e.g., lovastatin and pravastatin)

Pharmaceutical Compositions

The AhR modulators provided herein may be in the form of compositions suitable for administration to a subject. In general, such compositions are "pharmaceutical compositions" comprising an AhR modulator(s) and one or more pharmaceutically acceptable or physiologically acceptable diluents, carriers or excipients. In certain embodiments, the AhR modulator is present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., a modulator of AhR function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release.

Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an AhR modulator as provided herein and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an AhR modulator, including implants (e.g., implantable pumps) and catheter systems, slow injection pumps and devices, all of which are well known to the skilled artisan.

Depot injections, which are generally administered subcutaneously or intramuscularly, may also be utilized to release the AhR modulators disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the AhR modulators in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The AhR modulators contemplated by the present invention may be in the form of any other suitable pharmaceutical composition (e.g., sprays for nasal or inhalation use) currently known or developed in the future.

Routes of Administration

The present invention contemplates the administration of one or more AhR modulators as provided herein, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the AhR modulators disclosed herein over a defined period of time.

Particular embodiments of the present invention contemplate oral administration.

Combination Therapy

The present invention contemplates the use of AhR modulators in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the AhR modulators are administered or applied sequentially, e.g., where one agent is administered prior to one or more other agents. In other embodiments, the AhR modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The AhR modulators of the present invention may be used in combination with at least one other (active) agent in any manner appropriate under the circumstances. In one embodiment, treatment with the at least one active agent and at least one AhR modulator of the present invention is maintained over a period of time. In another embodiment, treatment with the at least one active agent is reduced or discontinued (e.g., when the subject is stable), while treatment with an AhR modulator of the present invention is maintained at a constant dosing regimen. In a further embodiment, treatment with the at least one active agent is reduced or discontinued (e.g., when the subject is stable), while treatment with an AhR modulator of the present invention is reduced (e.g., lower dose, less frequent dosing or shorter treatment regimen). In yet another embodiment, treatment with the at least one active agent is reduced or discontinued (e.g., when the subject is stable), and treatment with the AhR modulator of the present invention is increased (e.g., higher dose, more frequent dosing or longer treatment regimen). In yet another embodiment, treatment with the at least one active agent is maintained and treatment with the AhR modulator of the present invention is reduced or discontinued (e.g., lower dose, less frequent dosing or shorter treatment regimen). In yet another embodiment, treatment with the at least one active agent and treatment with the AhR modulator of the present invention are reduced or discontinued (e.g., lower dose, less frequent dosing or shorter treatment regimen).

Oncology-Related Disorders.

The present invention provides methods for treating and/or preventing a proliferative condition, cancer, tumor, or precancerous disease, disorder or condition with an AhR modulator and at least one additional therapeutic or diagnostic agent.

In certain embodiments, the present invention provides methods for tumor suppression of tumor growth comprising administration of an AhR modulator described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more AhR modulators described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylomithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with an AhR modulator include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors.

The present invention contemplates the use of the modulators of AhR function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints checkpoints include but are not limited to CTLA-4, PD-1/L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present invention contemplates the use of the AhR modulators described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

The present invention encompasses pharmaceutically acceptable salts, acids or derivatives of any of the above.

Metabolic and Cardiovascular Diseases.

The present invention provides methods for treating and/or preventing certain cardiovascular- and/or metabolic-related diseases, disorders and conditions, as well as disorders associated therewith, with an AhR modulator and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the AhR modulators described herein include various supplements and herbs (e.g., garlic, policosanol, and guggul).

The present invention encompasses pharmaceutically acceptable salts, acids or derivatives of any of the above.

Immune-Related Disorders and Disorders Having an Inflammatory Component.

The present invention provides methods for treating and/or preventing immune-related diseases, disorders and conditions; and diseases, disorders and conditions having an inflammatory component; with an AhR modulator and at least one additional therapeutic or diagnostic agent.

Examples of therapeutic agents useful in combination therapy are specific to the underlying disease, disorder or condition, and are known to the skilled artisan.

Microbial Diseases.

The present invention provides methods for treating and/or preventing viral, bacterial, fungal and parasitic diseases, disorders and conditions, as well as disorders associated therewith, with an AhR modulator and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an AhR modulator include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscamet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the AhR modulators described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the AhR modulators described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the AhR modulators described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The AhR modulators provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of an AhR modulator, as provided herein, may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the AhR modulators contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired AhR modulator is contained in a "unit dosage form". The phrase "unit dosage form" refers to physically discrete units, each unit containing a predetermined amount of the AhR modulator, either alone or in combination with one or more additional agents, sufficient to produce the desired effect. It will be appreciated that the parameters of a unit dosage form will depend on the particular agent and the effect to be achieved.

Kits

The present invention also contemplates kits comprising an AhR modulator, and pharmaceutical compositions thereof. The kits are generally in the form of a physical structure housing various components, as described below, and may be utilized, for example, in practicing the methods described above.

A kit can include one or more of the AhR modulators disclosed herein (provided in, e.g., a sterile container), which may be in the form of a pharmaceutical composition suitable for administration to a subject. The AhR modulators can be provided in a form that is ready for use (e.g., a tablet or capsule) or in a form requiring, for example, reconstitution or dilution (e.g., a powder) prior to administration. When the AhR modulators are in a form that needs to be reconstituted or diluted by a user, the kit may also include diluents (e.g., sterile water), buffers, pharmaceutically acceptable excipients, and the like, packaged with or separately from the AhR modulators. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

Other common chemical abbreviations are used herein, for example, AcCl: acetyl chloride; Ar: argon; $CH_2Cl_2$: dichloromethane; $CH_3CN$: acetonitrile; $CH_3OH$: methanol; DCM: dichloromethane; DIEA: diisopropyl ethylamine; DMAP: 4-dimethylaminopyridine; DMF: dimethyl formamide; DMSO: dimethyl sulfoxide; equiv.: equivalent(s); $Et_3N$: triethylamine; $Et_2O$: diethyl ether; EtOAc: ethyl acetate; EtOH: ethanol; HATU: 1-[bis(dimethylamino) methylene]-1H-1,2,3-triazolo[4,5-b]pyridinium 3-oxid hexafluorophosphate, N-[(dimethylamino)-1H-1,2,3-triazolo-[4,5-b]pyridin-1-ylmethylene]-N-methylmethanaminium hexafluorophosphate N-oxide; HCl: hydrogen chloride; $H_2O$: water; IPA: isopropyl alcohol; $iPr_2O$: diisopropyl ether; $K_2CO_3$: potassium carbonate; $LiBH_4$: lithium borohydride; LiHMDS: lithium hexamethyldisilazane: MeOH: methanol; $MgSO_4$: magnesium sulfate; $NaBH_4$: sodium borohydride; $NaBH_3CN$: sodium cyanoborohydride; NaCl: sodium chloride; NaH: sodium hydride; $NaHCO_3$: sodium bicarbonate; NaOEt: sodium ethoxide; NaOH: sodium hydroxide; NaOMe: sodium methoxide; $Na_2SO_4$: sodium sulfate; n-BuOH: n-butanol; $NH_4Cl$: ammonium chloride; Pd/C: palladium on carbon; $Pd(OH)_2$: palladium hydroxide; $POCl_3$: phosphoryl trichloride; PPTS: pyridinium p-toluenesulfonate; RT: room temperature; $SOCl_2$: thionyl chloride; TFA: trifluoroacetic acid; TfOH: triflic acid; THF: tetrahydrofuran; and THP: tetrahydropyran.

Example 001: 1-methyl-N-(2-methyl-4-(6-(trifluoromethyl)quinolin-2-yl)phenyl)-1H-pyrazole-5-carboxamide

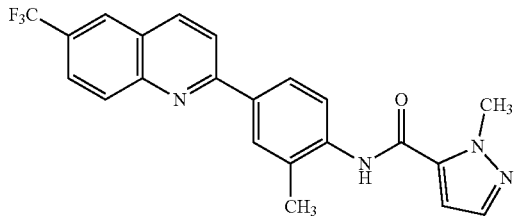 [SMILES: Cc1cc(-c2ccc3cc(C(F)(F)F)ccc3n2)ccc1NC(=O)c1ccnn1C]

A mixture of 2-methyl-4-(6-(trifluoromethyl)quinolin-2-yl)aniline (10 g, 33.08 mmol, 1.00 equiv), 1-methyl-1H-pyrazole-5-carboxylic acid (4.4 g, 34.89 mmol, 1.05 equiv), DIPEA (8.5 g, 65.77 mmol, 2.00 equiv) and HATU (4.4 g, 11.57 mmol, 1.50 equiv) in DMF (200 mL) was stirred overnight at room temperature. The reaction was quenched by the addition of 600 mL of water, extracted three times with 200 mL of ethyl acetate and the combined organic layers washed with 50 mL of water. Volatiles were eliminated under reduced pressure. The crude product was purified by recrystallization with methanol to afford the desired final product as a yellow solid in 76% yield. (ES, m/z): $[M+H]^+$ 411; $^1$H-NMR (DMSO-$d_6$, 300 MHz, ppm): δ2.40 (s, 3H), δ4.12 (s, 3H), δ7.12-7.13 (d, 1H), δ7.57-7.61 (m, 2H), δ8.00-8.04 (d, 1H), δ8.19-8.36 (m, 4H), δ8.54 (s, 1H), δ8.66-8.69 (d, 1H), δ10.00 (s, 1H).

Step 1: ethyl (E)-3-(2-amino-5-(trifluoromethyl) phenyl)acrylate

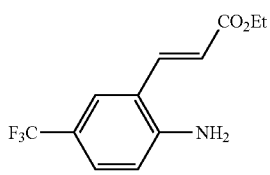 [SMILES: CCOC(=O)/C=C/c1cc(C(F)(F)F)ccc1N]

A mixture of 2-bromo-4-(trifluoromethyl)aniline (40 g, 166.65 mmol, 1.00 equiv), ethyl prop-2-enoate (34 g, 339.61 mmol, 2.00 equiv), DIPEA (64 g, 495.20 mmol, 3.00 equiv), P(O-tol)$_3$ (10 g, 0.20 equiv) and Pd(OAc)$_2$ (4 g, 17.82 mmol, 0.10 equiv) in DMF (400 mL) was stirred at 100° C. overnight. The reaction was quenched by the addition of 1200 mL of water and extracted with ethyl acetate (3×200 mL). The organic layers were combined and concentrated under reduced pressure and the resulting residue was purified by silica gel column chromatography with ethyl acetate/ petroleum ether (1:10) to afford ethyl (E)-3-(2-amino-5-(trifluoromethyl)phenyl)acrylate as a yellow solid in 86% yield.

Step 2: 6-(trifluoromethyl)quinolin-2(1H)-one

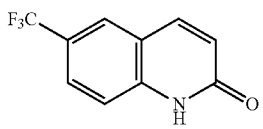 [SMILES: O=c1ccc2cc(C(F)(F)F)ccc2[nH]1]

Over a solution of ethyl (E)-3-(2-amino-5-(trifluoromethyl)phenyl)acrylate (37 g, 142.73 mmol, 1.00 equiv) in dioxane (92.7 mL), HCl (12N, 28 mL) was added. The resulting solution was stirred for 3 h at 100° C. and quenched by the addition of 200 mL of water. The solids were collected by filtration to afford the desired final product as a yellow solid in 89% yield.

Step 3: 2-chloro-6-(trifluoromethyl)quinoline

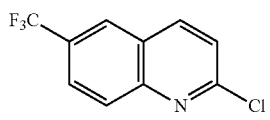 [SMILES: FC(F)(F)c1ccc2nc(Cl)ccc2c1]

Phosphoryl trichloride (135 mL) was added over 6-(trifluoromethyl)-1,2-dihydroquinolin-2-one (27 g, 126.67 mmol, 1.00 equiv). The reaction mixture was stirred for 1 h at 120° C. and concentrated under vacuum. Water (100 mL) was added and the resulting solid was collected by filtration to afford the desired final product in 68% yield.

Step 4: 2-methyl-4-(6-(trifluoromethyl)quinolin-2-yl)aniline

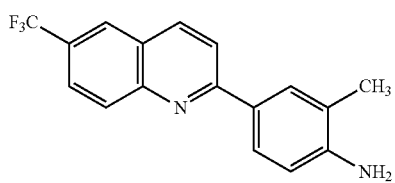 [SMILES: Cc1cc(-c2ccc3cc(C(F)(F)F)ccc3n2)ccc1N]

Over a solution of 2-chloro-6-trifluoromethyl)quinoline (20 g, 86.36 mmol, 1.00 equiv) and 2-methyl-4-(4,4,5,5-tetramethyl-1,3,2-dioxaborolan-2-yl)aniline (24 g, 102.95 mmol, 1.20 equiv) in ethylene glycol dimethyl ether (400 mL) and water (80 mL), sodium carbonate (27.4 g, 258.51 mmol, 3.00 equiv) and Pd(PPh$_3$)$_4$ (5 g, 4.33 mmol, 0.05 equiv) were added. The resulting solution was stirred for 3 h at 90° C. and the reaction quenched by addition of 200 mL of water. Extraction with ethyl acetate (3×200 mL) followed by evaporation of volatiles under reduced pressure afforded a residue that was purified by silica gel chromatography with ethyl acetate/petroleum ether (1:5) to afford the desired product as a yellow solid in 67% yield.

Example 002: N,1-Dimethyl-N-(2-methyl-4-(6-(trifluoromethyl)quinolin-2-yl)phenyl)-1H-pyrazole-5-carboxamide

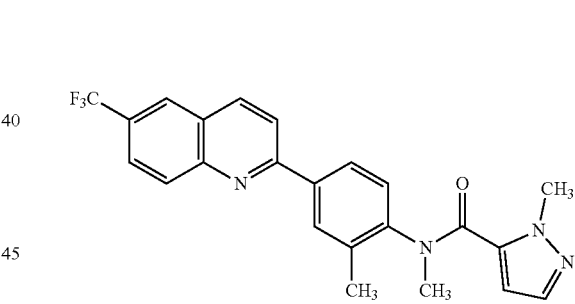

Over a solution of 1-methyl-N-(2-methyl-4-(6-(trifluoromethyl)quinolin-2-yl)phenyl)-1H-pyrazole-5-carboxamide (100 mg, 0.24 mmol, 1 equiv) in DMF (1 mL, 0.01 mmol, 0.056 equiv), NaH (9.8 mg, 0.41 mmol) was added. The resulting solution was stirred for 30 min at room temperature. CH$_3$I (34.6 mg, 0.24 mmol, 1 equiv) was added and the reaction mixture stirred for an additional hour at room temperature. The reaction was quenched with a saturated solution of NH$_4$Cl (20 mL) and extracted with ethyl acetate (3×20 ml). The organic layers were combined and concentrated under reduced pressure. The resulting residue was purified by preparative TLC with dichloromethane/ methanol (40/1) to afford the desired final product as a white solid in 69% yield. LCMS (ES, m/z): [M+H]$^+$ 425; $^1$H-NMR (400 MHz, DMSO-d$_6$, ppm): δ 8.70-8.68 (d, 1H), δ8.55 (s, 1H), δ8.34-8.32 (d, 1H), δ8.28-8.25 (d, 2H), δ8.18-8.16 (d, 1H), δ 8.05-8.02 (d, 1H), δ7.50-7.48 (d, 1H), δ7.15 (s, 1H), δ5.55-5.54 (d, 1H), δ4.01 (s, 3H), δ3.33 (s, 3H), δ2.28 (s, 3H)

Example 003: 1-methyl-N-(4-(quinoxalin-2-yl)phenyl)-1H-pyrazole-5-carboxamide

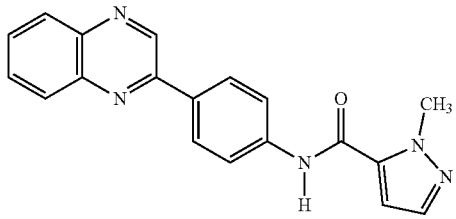 [SMILES: Cn1nccc1C(=O)Nc1ccc(-c2cnc3ccccc3n2)cc1]

A THF solution of 4-(quinoxalin-2-yl)aniline, 1-methyl-1H-pyrazole-5-carboxylic acid, DIPEA and T3P was stirred at room temperature for 15 hours. The reaction was quenched with water and extracted twice with ethyl acetate. The organic layers were combined and washed with a saturated solution of NaHCO$_3$, water and brine. The resulting solution was dried with anhydrous MgSO$_4$ and concentrated under reduced pressure to afford a residue that was purified by chromatography in silca gel (hexanes/ethyl acetate from 10% to 100%) to afford the desired final product as a yellow solid in 37% yield. LCMS (ES, m/z): [M+H]$^+$ 330; $^1$H-NMR (400 MHz, DMSO-d$_6$, ppm): 9.38 (s, 1H), 8.30 (d, 2H), 8.18 (m, 2H), 7.83 (m, 5H), 7.58 (d, 1H), 6.73 (d, 1H), 4.3 (s, 3H).

Step 1: 4-(quinoxalin-2-yl)aniline

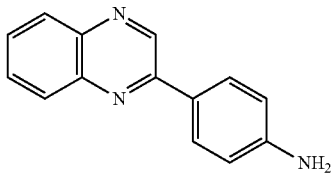 [SMILES: Nc1ccc(-c2cnc3ccccc3n2)cc1]

The title compound was prepared analogously to Example 001, step 4, where 2-bromoquinoxaline was substituted in place of 2-chloro-6-(trifluoromethyl)quinoline and 4-(4,4,5,5-tetramethyl-1,3,2-dioxaborolan-2-yl)aniline was substituted in place of 3-methyl-4-(tetramethyl-1,3,2-dioxaborolan-2-yl)aniline. Yield=68%.

Example 004: N-Ethyl-1-methyl-N-(2-methyl-4-(6-(trifluoromethyl)quinolin-2-yl)phenyl)-1H-pyrazole-5-carboxamide

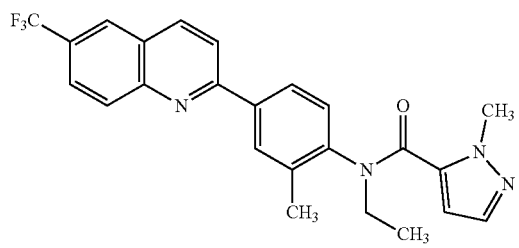

The title compound was prepared analogously to Example 002, where ethyl iodide was substituted in place of methyl iodide. LCMS (ES, m/z): [M+H]$^+$ 439; $^1$H-NMR (400 MHz, DMSO-d$_6$, ppm): δ 8.70-8.68 (d, 1H), δ8.55 (s, 1H), δ8.34-8.32 (d, 1H), δ8.28-8.25 (d, 2H), δ8.19-8.17 (d, 1H), δ8.05-8.02 (d, 1H), δ7.47-7.45 (d, 1H), δ7.15 (s, 1H), δ5.53 (s, 1H). δ4.11-4.01 (m, 1H), δ3.93 (s, 3H), δ3.69-3.60 (m, 1H), δ2.52 (s, 3H), δ1.24-1.20 (t, 3H).

Example 005: N-(2-fluoro-3-methyl-4-(6-(trifluoromethyl)quinolin-2-yl)phenyl)-1-methyl-1H-pyrazole-5-carboxamide

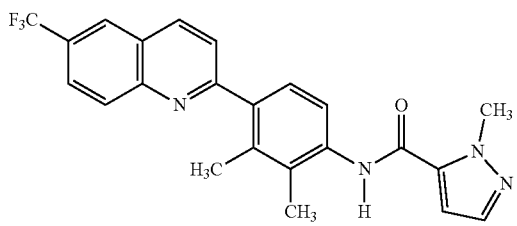 [SMILES: Cc1c(NC(=O)c2ccnn2C)ccc(-c2ccc3cc(C(F)(F)F)ccc3n2)c1C]

Pd(PPh$_3$)$_4$ (49.9 mg, 0.04 mmol, 0.1 equiv) was added to a solution of 2-chloro-6-(trifluoromethyl)quinoline (100 mg, 0.43 mmol, 1 equiv), N-(2-fluoro-3-methyl-4-(4,4,5,5-tetramethyl-1,3,2-dioxaborolan-2-yl)phenyl)-1-methyl-1H-pyrazole-5-carboxamide (170.6 mg, 0.47 mmol, 1.1 equiv) and Na$_2$CO$_3$ (91.5 mg, 0.86 mmol, 2 equiv) in DME (2 mL) and H$_2$O (0.5 mL). After stirring at 90° C. for three hours, the reaction was quenched with water (10 ml). The aqueous layer was extracted with EtOAc (2×20 mL) and the combined organic layers concentrated under reduced pressure. The residue was purified by preparative TLC (dichloromethane/MeOH=40:1) to afford the desired product as a white solid in 63% yield. LCMS (ES, m/z): [M+H]$^+$ 429; $^1$H-NMR (DMSO-d$_6$, 300 MHz, ppm): δ2.35-2.36 (d, 3H), δ4.11 (s, 3H), δ7.14-7.15 (d, 1H), δ7.44-7.47 (d, 1H), δ7.56-7.57 (d, 1H), δ7.60-7.65 (m, 1H), δ7.91-7.94 (d, 1H), δ8.04-8.08 (m, 1H), δ8.25-8.28 (d, 1H), δ8.61 (s, 1H), δ8.69-8.72 (d, 1H), δ10.21 (s, 1H)

Step 1: 4-bromo-2-fluoro-3-methylaniline

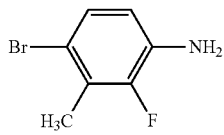

To a stirred solution of 2-fluoro-3-methylaniline (4 g, 31.96 mmol, 1 equiv) in acetonitrile (100 mL), NBS (6.2 g, 35.03 mmol, 1.096 equiv) was added in portions at 10° C. under nitrogen atmosphere. The resulting mixture was stirred at room temperature for 1 hour and concentrated under reduced pressure. The residue was purified by silica gel column chromatography, with ethyl acetate/petroleum ether (1:30) as eluent to afford 4-bromo-2-fluoro-3-methylaniline as a red solid in 86% yield.

Step 2: N-(4-bromo-2-fluoro-3-methylphenyl)-1-methyl-1H-pyrazole-5-carboxamide

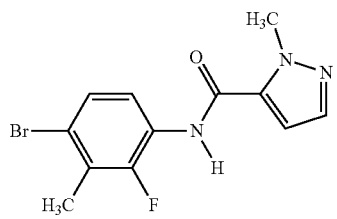 [SMILES: Cc1c(Br)ccc(NC(=O)c2ccnn2C)c1F]

To a solution of 4-bromo-2-fluoro-3-methylaniline (3 g, 14.70 mmol, 1 equiv), 1-methyl-1H-pyrazole-5-carboxylic acid (2.2 g, 17.44 mmol, 1.186 equiv) and DIPEA (3.8 g, 29.3 mmol, 1.994 equiv) in DMF (60.0 mL, 0.44 mmol, 0.028 equiv), HATU (8.4 g, 22.01 mmol, 1.497 equiv) was added. The resulting mixture was stirred at room temperature overnight. The reaction was quenched by the addition of water (180 mL) and the aqueous layer extracted with EtOAc (2×100 mL). The organic layers were combined and concentrated under reduced pressure. The residue was purified by silica gel column chromatography, with EtOAc/PE (1:10) to afford N-(4-bromo-2-fluoro-3-methylphenyl)-1-methyl-1H-pyrazole-5-carboxamide as a yellow solid in 83% yield.

Step 3: N-(2-fluoro-3-methyl-4-(4,4,5,5-tetramethyl-1,3,2-dioxaborolan-2-yl)phenyl)-1-methyl-1H-pyrazole-5-carboxamide

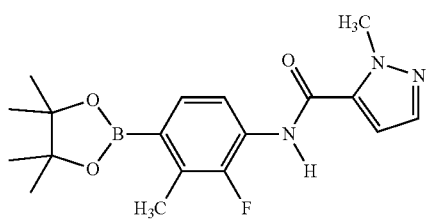 [SMILES: Cc1c(B2OC(C)(C)C(C)(C)O2)ccc(NC(=O)c2ccnn2C)c1F]

To a mixture of N-(4-bromo-2-fluoro-3-methylphenyl)-1-methyl-1H-pyrazole-5-carboxamide (3.8 g, 12.1 mmol, 1 equiv), 4,4,5,5-tetramethyl-2-(tetramethyl-1,3,2-dioxaborolan-2-yl)-1,3,2-dioxaborolane (3.4 g, 13.39 mmol, 1.1 equiv) and KOAc (3.6 g, 36.52 mmol, 3 equiv) in 1,4-dioxane (76 mL), Pd(dppf)Cl$_2$ (0.9 g, 1.22 mmol, 0.1 equiv) was added. The resulting mixture was stirred at 80° C. for 5 hours followed by elimination of volatiles under reduced pressure. The residue was purified by silica gel column chromatography with EtOAc/petroleum ether (1:15) to afford the desired final product as a yellow solid in 87% yield.

Example 006: N-(2-fluoro-3-methyl-4-(6-(trifluoromethyl)quinolin-2-yl)phenyl)-N,1-dimethyl-1H-pyrazole-5-carboxamide

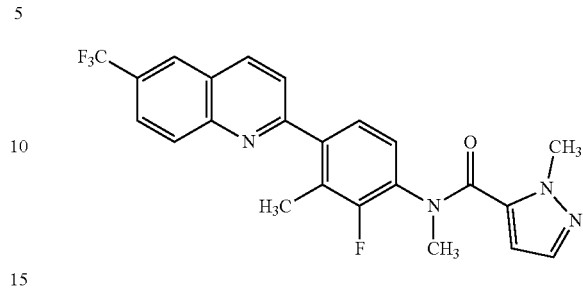

The title compound was prepared analogously to Example 002, where N-(2-fluoro-3-methyl-4-(6-(trifluoromethyl)quinolin-2-yl)phenyl)-1-methyl-1H-pyrazole-5-carboxamide was substituted in place of 1-methyl-N-(2-methyl-4-(6-(trifluoromethyl)quinolin-2-yl)phenyl)-1H-pyrazole-5-carboxamide. LCMS (ES, m/z): [M+H]$^+$ 443; $^1$H-NMR (DMSO-d$_6$, 300 MHz, ppm): δ2.25-2.26 (d, 3H), δ3.38 (s, 3H), δ3.98 (s, 3H), δ5.85 (s, 1H), δ7.29 (s, 1H), δ7.43-7.8 (m, 2H), δ7.87-7.90 (d, 1H), δ8.04-8.08 (d, 1H), δ8.24-827 (d, 1H), δ8.61 (s, 1H), δ8.69-8.72 (d, 1H)

Example 007: N-(2-fluoro-6-methyl-4-(6-(trifluoromethyl)quinolin-2-yl)phenyl)-N,1-dimethyl-1H-pyrazole-5-carboxamide

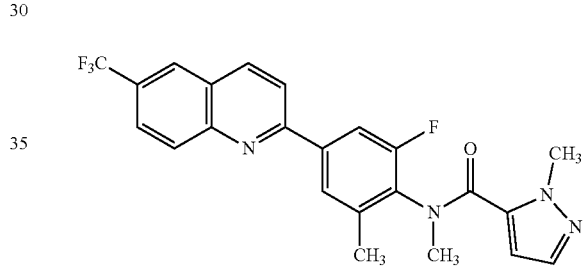

The title compound was prepared analogously to Example 002, where N-(2-fluoro-6-methyl-4-(6-(trifluoromethyl)quinolin-2-yl)phenyl)-1-methyl-1H-pyrazole-5-carboxamide was substituted in place of N,1-Dimethyl-N-(2-methyl-4-(6-(trifluoromethyl)quinolin-2-yl)phenyl)-1H-pyrazole-5-carboxamide. LCMS (ES, m/z): [M+H]$^+$ 443; $^1$H-NMR (400 MHz, DMSO-d$_6$, ppm): δ 8.73-8.70 (d, 1H), δ8.56 (s, 1H), δ8.37-8.35 (d, 1H), δ8.29-8.27 (d, 1H), δ8.17 (s, 1H), δ8.07-8.04 (m, 2H), δ7.21-7.20 (d, 1H), δ5.70-5.69 (d, 1H), δ3.99-3.95 (d, 3H), δ3.36-3.31 (d, 3H), δ2.41 (s, 3H)

Example 008: N-(2-fluoro-6-methyl-4-(6-(trifluoromethyl)quinolin-2-yl)phenyl)-1-methyl-1H-pyrazole-5-carboxamide

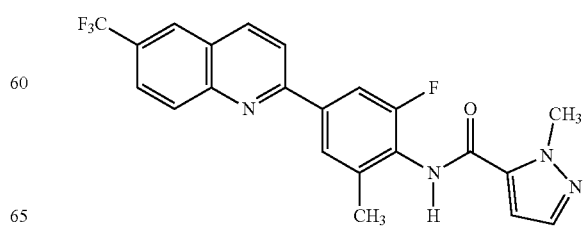

The title compound was prepared analogously to Example 001, where N-(2-fluoro-6-methyl-4-(6-(trifluoromethyl)quinolin-2-yl)phenyl)-1-methyl-1H-pyrazole-5-carboxamide was substituted in place of 1-methyl-N-(2-methyl-4-(6-(trifluoromethyl)quinolin-2-yl)phenyl)-1H-pyrazole-5-carboxamide. LCMS (ES, m/z): [M+H]$^+$ 429; $^1$H-NMR (300 MHz, DMSO-d$_6$, ppm): δ2.40 (s, 3H), δ4.11 (s, 3H), δ7.14 (s, 1H), δ7.58-7.59 (d, 1H), δ8.03-8.18 (m, 3H), δ8.29-8.32 (d, 1H), δ8.39-8.42 (d, 1H), δ8.57 (s, 1H), δ8.71-8.74 (d, 1H), δ10.09 (s, 1H)

Step 1: 4-bromo-2-fluoro-6-methylaniline

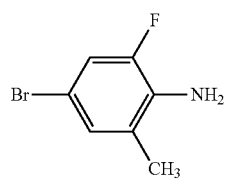

The title compound was prepared analogously to Example 005, step 1, where 2-fluoro-6-methylaniline was substituted in place of 2-fluoro-3-methylaniline. Yield=98%.

Step 2: 2-fluoro-6-methyl-4-(4,4,5,5-tetramethyl-1,3,2-dioxaborolan-2-yl)aniline

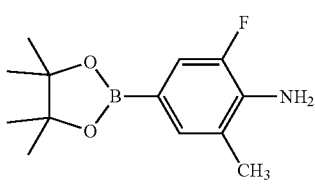 [SMILES: Cc1cc(B2OC(C)(C)C(C)(C)O2)cc(F)c1N]

The title compound was prepared analogously to Example 005, step 2, where 4-bromo-2-fluoro-6-methylaniline was substituted in place of 4-bromo-2-fluoro-3-methylaniline. Yield=85%.

Example 009: tert-butyl methyl(2-methyl-4-(6-(trifluoromethyl)quinazolin-2-yl)phenyl)carbamate

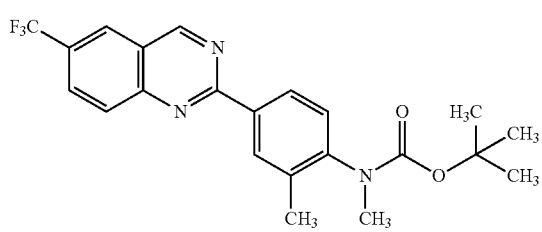 [SMILES: Cc1cc(-c2ncc3cc(C(F)(F)F)ccc3n2)ccc1N(C)C(=O)OC(C)(C)C]

To a solution of 2-chloro-6-(trifluoromethyl)quinazoline (4 g, 17.20 mmol, 1 equiv) and tert-butyl N-methyl-N-[2-methyl-4-(tetramethyl-1,3,2-dioxaborolan-2-yl)phenyl]carbamate (5.97 g, 17.20 mmol, 1 equiv) in toluene (80 mL) and EtOH (40 mL), K$_2$CO$_3$ (7.13 g, 51.59 mmol, 3 equiv) and Pd(PPh$_3$)$_4$ (1.99 g, 1.72 mmol, 0.1 equiv) were added. The resulting mixture was stirred at 100° C. overnight. The reaction was quenched by the addition of water (200 mL) and the resulting mixture was extracted with EtOAc (2×100 mL). The combined organic layers were concentrated under reduced pressure and the residue purified by silica gel column chromatography with EtOAc/petroleum ether (1/20) as eluent to afford the desired product as a white solid in 70% yield. LCMS (ES, m/z): [M+H]$^+$ 418; $^1$H-NMR (300 MHz, CDCl$_3$, ppm): δ1.36-1.55 (m, 9H), δ2.36 (s, 3H), δ3.21 (s, 3H), δ7.29 (s, 1H), δ8.06-8.10 (q, 1H), δ8.21-8.26 (t, 2H), δ8.46-8.49 (d, 1H), δ8.52 (s, 1H), δ9.56 (s, 1H)

Step 1: tert-butyl methyl(2-methyl-4-(4,4,5,5-tetramethyl-1,3,2-dioxaborolan-2-yl)phenyl)carbamate

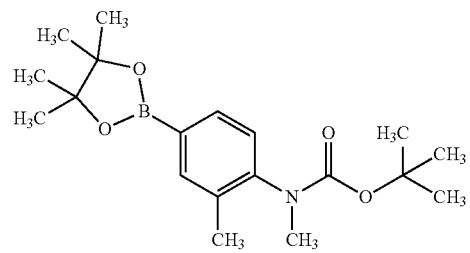 [SMILES: Cc1cc(B2OC(C)(C)C(C)(C)O2)ccc1N(C)C(=O)OC(C)(C)C]

The title compound was prepared analogously to Example 005, step 3, where tert-butyl (4-bromo-2-methylphenyl)(methyl)carbamate was substituted in place of N-(4-bromo-2-fluoro-3-methylphenyl)-1-methyl-1H-pyrazole-5-carboxamide. Yield=62%.

Example 010: N,1-dimethyl-N-(2-methyl-4-(6-(trifluoromethoxy)quinolin-2-yl)phenyl)-1H-pyrazole-5-carboxamide

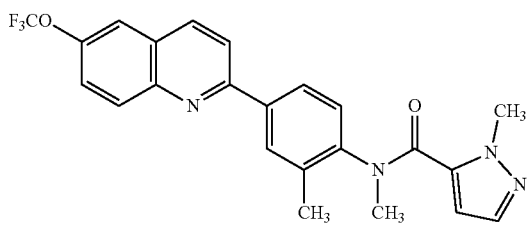 [SMILES: Cc1cc(-c2ccc3cc(OC(F)(F)F)ccc3n2)ccc1N(C)C(=O)c1ccnn1C]

The title compound was prepared analogously to Example 002 where 1-methyl-N-(2-methyl-4-(6-(trifluoromethoxy)quinolin-2-yl)phenyl)-1H-pyrazole-5-carboxamide was substituted in place of N,1-dimethyl-N-(2-methyl-4-(6-(trifluoromethyl)quinolin-2-yl)phenyl)-1H-pyrazole-5-carboxamide. Yield=14%. LCMS (ES, m/z): [M+H]$^+$ 441; $^1$H-NMR (400 MHz, CDCl$_3$, ppm): δ 8.30-8.28 (d, 2H), δ8.12 (s, 1H), δ8.04-8.02 (d, 1H), δ7.96-7.94 (d, 1H), δ7.70 (s, 1H), δ7.65-7.62 (d, 1H), δ7.35-7.32 (d, 1H), δ7.09 (s, 1H), δ5.53 (s, 1H), δ4.20 (s, 3H), δ3.43 (s, 3H), δ2.31 (s, 3H)

Example 011: 1-methyl-N-(2-methyl-4-(6-(trifluoromethoxy)quinolin-2-yl)phenyl)-1H-pyrazole-5-carboxamide

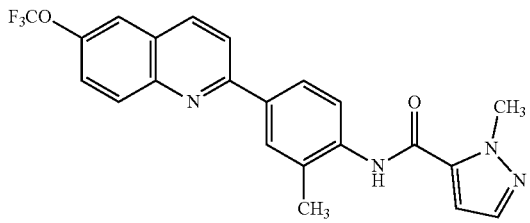 [SMILES: Cc1cc(-c2ccc3cc(OC(F)(F)F)ccc3n2)ccc1NC(=O)c1ccnn1C]

The title compound was prepared analogously to Example 005 where 2-chloro-6-(trifluoromethoxy)quinoline was substituted in place of 2-chloro-6-(trifluoromethyl)quinoline. Yield=53%. LCMS (ES, m/z): [M+1]$^+$ 427; $^1$H-NMR: (400 MHz, DMSO-d$_6$, ppm): δ 9.97 (s, 1H), δ 8.58-8.56 (d, 1H), δ8.30-8.15 (m, 4H), δ8.08 (s, 1H), δ7.79-7.76 (m, 1H), δ7.60-7.56 (d, 2H), δ7.12-7.11 (d, 1H), δ4.11 (s, 3H), δ2.39 (s, 3H).

Step 1: Ethyl (E)-3-(2-amino-5-(trifluoromethoxy)phenyl)acrylate

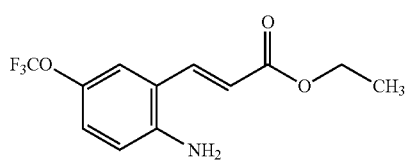 [SMILES: CCOC(=O)/C=C/c1cc(OC(F)(F)F)ccc1N]

The title compound was prepared analogously to Example 001, step 1, where 2-bromo-4-(trifluoromethoxy)aniline was substituted in place of 2-bromo-4-(trifluoromethyl)aniline. Yield=90%.

Step 2: 6-(Trifluoromethoxy)quinolin-2(1H)-one

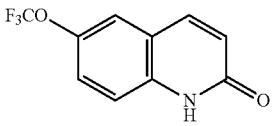

The title compound was prepared analogously to Example 001, step 2, where Ethyl (E)-3-(2-amino-5-(trifluoromethoxy)phenyl)acrylate was substituted in place of ethyl (E)-3-(2-amino-5-(trifluoromethyl)phenyl)acrylate. Yield=98%.

Step 3: 2-Chloro-6-(trifluoromethoxy)quinoline

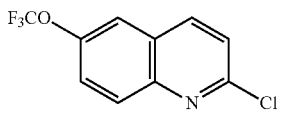 [SMILES: FC(F)(F)Oc1ccc2nc(Cl)ccc2c1]

The title compound was prepared analogously to Example 001, step 3, where 6-(trifluoromethoxy)quinolin-2(1H)-one was substituted in place of 6-(trifluoromethyl)-1,2-dihydroquinolin-2-one. Yield=98%.

Example 012: N-(4-(8-chloroquinolin-2-yl)-2-methylphenyl)-1-methyl-1H-pyrazole-5-carboxamide

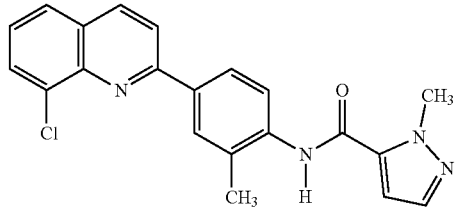 [SMILES: Cc1cc(-c2ccc3cccc(Cl)c3n2)ccc1NC(=O)c1ccnn1C]

The title compound was prepared analogously to Example 003, step 1, where 4-(8-chloroquinolin-2-yl)-2-methylaniline was substituted in place of 4-(quinoxalin-2-yl)aniline. Yield=28%. LCMS (ES, m/z): [M+H]$^+$ 377; $^1$H-NMR (400 MHz, CDCl$_3$, ppm): 8.29 (s, 1H), 8.28 (d, 1H), 8.20 (d, 1H), 8.13 (dd, 1H), 8.00 (d, 1H), 7.88 (dd, 1H), 7.77 (dd, 1H), 7.70 (s, 1H), 7.56 (d, 1H), 7.46 (m, 1H), 6.73 (d, 1H), 4.30 (s, 3H), 2.45 (s, 3H).

Step 1: 4-(8-chloroquinolin-2-yl)-2-methylaniline

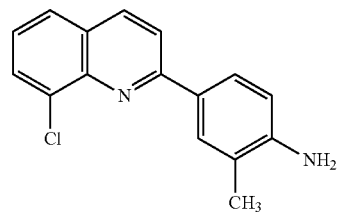 [SMILES: Cc1cc(-c2ccc3cccc(Cl)c3n2)ccc1N]

The title compound was prepared analogously to Example 014, step 1, where 2,8-chloroquinoline was substituted in place of 2-chloro-6-fluoroquinoline and 2-methyl-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=98%.

Example 013: 1-methyl-N-(2-methyl-4-(1,6-naphthyridin-2-yl)phenyl)-1H-pyrazole-5-carboxamide

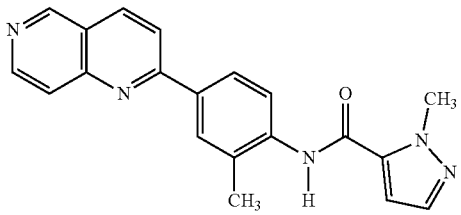

The title compound was prepared analogously to Example 003, where 2-Methyl-4-(1,6-naphthyridin-2-yl)aniline was substituted in place of 4-(quinoxalin-2-yl)aniline. LCMS (ES, m/z): [M+1]$^+$344; $^1$H-NMR (400 MHz, CDCl$_3$, ppm):

9.28 (s, 1H). 8.75 (d, 1H), 8.36 (d, 1H), 8.24 (d, 1H), 8.17 (s, 1H), 8.04 (m, 3H), 7.69 (s, 1H), 7.53 (s, 1H), 6.69 (s, 1H), 4.25 (s, 3H), 2.47 (s, 3H).

Step 1: 2-Methyl-4-(1,6-naphthyridin-2-yl)aniline

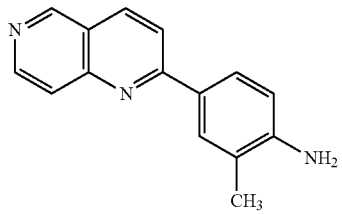

The title compound was prepared analogously to Example 014, where 2-chloro-1,6-naphthyridine was substituted in place of 2-chloro-6-fluoroquinoline and 2-methyl-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=89%.

Example 014: N-(4-(6-fluoroquinolin-2-yl)-2-methylphenyl)-1-methyl-1H-pyrazole-5-carboxamide

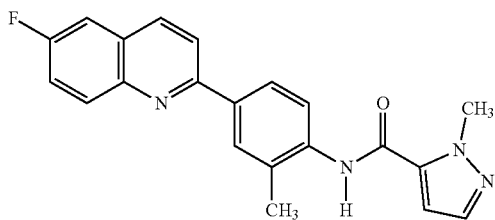 [SMILES: Cc1cc(-c2ccc3cc(F)ccc3n2)ccc1NC(=O)c1ccnn1C]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline. Yield=88%. LCMS (ES, m/z): [M+H]$^+$ 361; $^1$H-NMR (300 MHz, CDCl$_3$, ppm): δ2.47 (s, 3H), δ4.27 (s, 3H), δ6.70-6.71 (d, 1H), δ7.44-7.56 (m, 3H), δ7.69 (s, 1H), δ7.90-7.93 (d, 1H), δ8.00-8.03 (q, 1H), δ8.15-8.22 (m, 4H)

Step 1: tert-butyl (4-(6-fluoroquinolin-2-yl)-2-methylphenyl)carbamate

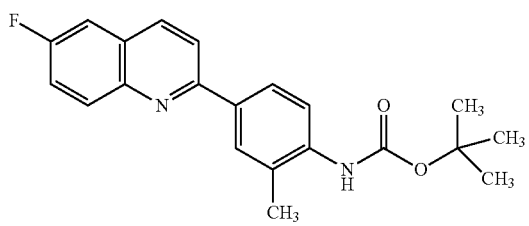 [SMILES: Cc1cc(-c2ccc3cc(F)ccc3n2)ccc1NC(=O)OC(C)(C)C]

A solution of 2-chloro-6-fluoroquinoline (81 mg, 0.45 mmol), tert-butyl (2-methyl-4-(4,4,5,5-tetramethyl-1,3,2-dioxaborolan-2-yl)phenyl)carbamate (164 mg, 0.49 mmol), bis(triphenylphosphine)palladium (II) chloride (16 mg, 0.022 mmol) and K$_2$CO$_3$ (123 mg, 0.89 mmol) in ethanol (4 mL) and water (1 mL), was heated at 80 degrees for 4 hours. The reaction was cooled down to room temperature and diluted with water, extracted with ethyl acetate three times, dried with MgSO$_4$, filtered and concentrated under reduced pressure. Purification of the resulting crude material by silica gel chromatography, afforded the desired final product as a white solid in 88% yield.

Step 2: 4-(6-fluoroquinolin-2-yl)-2-methylaniline

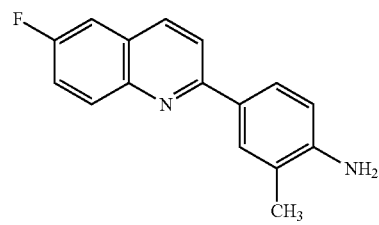

TFA (0.15 mL) was added over a solution of tert-butyl (4-(6-fluoroquinolin-2-yl)-2-methylphenyl)carbamate (139 mg, 0.39 mmol) in dichloromethane (5 mL) at room temperature. The mixture was stirred for 6 hours and the reaction stopped by addition of water. The pH of the mixture was brought to neutral by addition of 1M NaOH and extracted three times with CH$_2$Cl$_2$. The combined organic layers were washed with brine, dried over MgSO$_4$ and concentrated under reduced pressure to afford a crude material that was purified by silica gel chromatography to afford the desired final product as a yellow solid in 81% yield.

Example 015: tert-butyl (2-methyl-4-(4-methylquinolin-2-yl)phenyl)carbamate

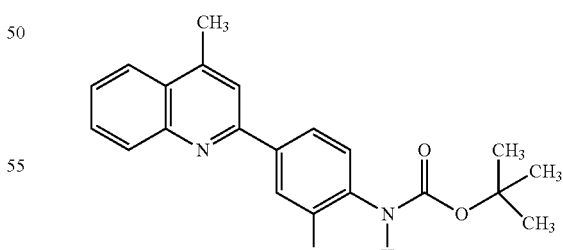

The title compound was prepared analogously to Example 014, step 1, where 2-chloro-4-methylquinoline was substituted in place of 2-chloro-6-fluoroquinoline. Yield=31%. LCMS (ES, m/z): [M+H]$^+$ 349; $^1$H-NMR (300 MHz, CDCl$_3$, ppm): 8.19 (d, 1H), 8.06 (m, 2H), 7.96 (m, 2H), 7.70 (m, 2H), 7.53 (m, 1H), 6.41 (s, 1H), 2.76 (s, 3H), 2.38 (s, 3H), 1.55 (s, 9H).

Example 016: 1-Methyl-N-(2-methyl-4-(4-methylquinolin-2-yl)phenyl)-1H-pyrazole-5-carboxamide

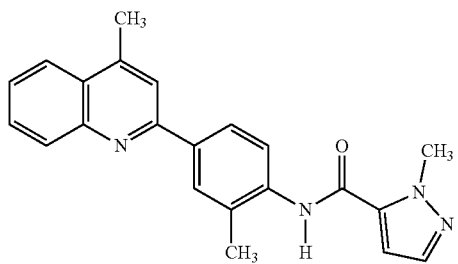 [SMILES: Cc1cc(-c2cc(C)c3ccccc3n2)ccc1NC(=O)c1ccnn1C]

The title compound was prepared analogously to Example 003, where 2-methyl-4-(4-methylquinolin-2-yl)aniline was substituted in place of 4-(quinoxalin-2-yl)aniline. Yield=41%. LCMS (ES, m/z): [M+H]⁺ 357; ¹H-NMR (300 MHz, CDCl₃, ppm): 8.20 (m, 2H), 8.01 (d, 2H), 7.82-7.47 (m, 5H), 7.26 (s, 1H), 6.70 (s, 1H), 4.25 (s, 3H), 2.81 (s, 3H), 2.46 (s, 3H)

Step 1: 2-methyl-4-(4-methylquinolin-2-yl)aniline

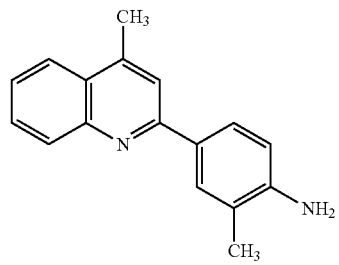 [SMILES: Cc1cc(-c2cc(C)c3ccccc3n2)ccc1N]

The title compound was prepared analogously to Example 014, step 2, where tert-butyl (2-methyl-4-(4-methylquinolin-2-yl)phenyl)carbamate was substituted in place of tert-butyl (4-(6-fluoroquinolin-2-yl)-2-methylphenyl)carbamate. Yield=84%.

Example 017: tert-butyl (2-methyl-4-(8-methylquinolin-2-yl)phenyl)carbamate

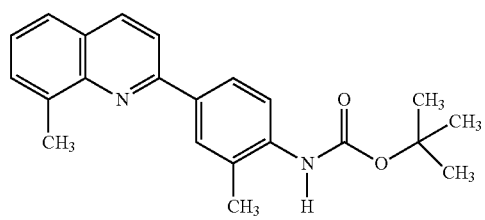 [SMILES: Cc1cc(-c2ccc3cccc(C)c3n2)ccc1NC(=O)OC(C)(C)C]

The title compound was prepared analogously to Example 014, step 1, where 2-chloro-8-methylquinoline was substituted in place 2-chloro-6-fluoroquinoline. Yield=26%. LCMS (ES, m/z): [M+H]⁺ 349; ¹H-NMR (300 MHz, CDCl₃, ppm): 8.16 (d, 1H), 8.12 (s, 1H), 8.04 (s, 2H), 7.87 (d, 1H), 7.64 (d, 1H), 7.56 (d, 1H), 7.39 (m, 1H), 6.40 (s, 1H), 2.91 (3H), 2.39 (s, 3H), 1.56 (s, 9H)

Example 018: N-(4-(8-fluoroquinolin-2-yl)-2-methylphenyl)-1-methyl-1H-pyrazole-5-carboxamide

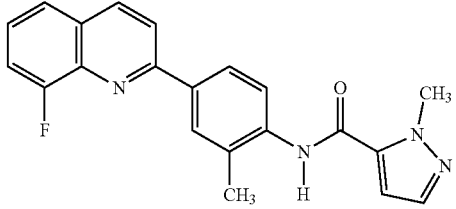

The title compound was prepared analogously to Example 003, where 4-(8-fluoroquinolin-2-yl)-2-methylaniline was substituted in place 4-(quinoxalin-2-yl)aniline. Yield=33%. LCMS (ES, m/z): [M+H]⁺ 361; ¹H-NMR (CDCl₃, 400 MHz, ppm): 2.50 (s, 3H), 4.30 (s, 3H), 6.7 (s, 1H), 7.47 (m, 2H), 7.56 (d, 1H), 7.68 (m, 2H), 7.95 (d, 1H), 8.06 (dd, 1H), 8.25 (m, 3H).

Step 1: tert-butyl (4-(8-fluoroquinolin-2-yl)-2-methylphenylcarbamate

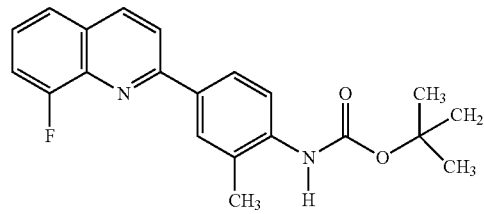 [SMILES: Cc1cc(-c2ccc3cccc(F)c3n2)ccc1NC(=O)OC(C)(C)C]

The title compound was prepared analogously to Example 014, step 1, where 2-chloro-8-fluoroquinoline was substituted in place 2-chloro-6-fluoroquinoline. Yield=28%

Step 2: 4-(8-fluoroquinolin-2-yl)-2-methylaniline

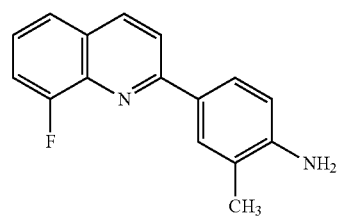 [SMILES: Cc1cc(-c2ccc3cccc(F)c3n2)ccc1N]

The title compound was prepared analogously to Example 014, step 2, where tert-butyl (4-(8-fluoroquinolin-2-yl)-2-methylphenyl)carbamate was substituted in place of tert-butyl (4-(6-fluoroquinolin-2-yl)-2-methylphenyl)carbamate. Yield=33%.

Example 019: N-(4-(7-fluoroquinolin-2-yl)-2-methylphenyl)-1-methyl-1H-pyrazole-5-carboxamide

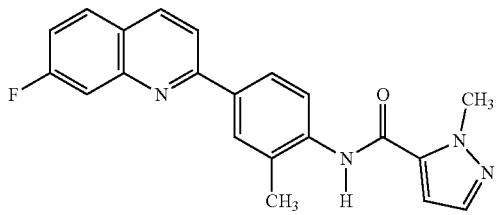 [SMILES: Cc1cc(-c2ccc3ccc(F)cc3n2)ccc1NC(=O)c1ccnn1C]

The title compound was prepared analogously to Example 003, where 4-(7-fluoroquinolin-2-yl)-2-methylaniline was substituted in place 4-(quinoxalin-2-yl)aniline. Yield=46%. LCMS (ES, m/z): [M+H]$^+$ 361; $^1$H-NMR (CDCl$_3$, 400 MHz, ppm): 8.21 (m, 3H), 8.01 (dd, 1H), 7.85 (m, 3H), 7.67 (s, 1H), 7.54 (d, 1H), 7.33 (m, 1H), 6.69 (d, 1H), 4.25 (s, 3H), 2.46 (s, 3H).

Step 1: tert-butyl (4-(7-fluoroquinolin-2-yl)-2-methylphenyl)carbamate

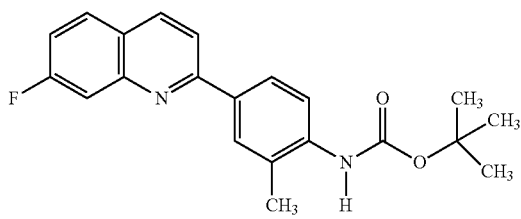 [SMILES: Cc1cc(-c2ccc3ccc(F)cc3n2)ccc1NC(=O)OC(C)(C)C]

The title compound was prepared analogously to Example 014, step 1, where 2-chloro-7-fluoroquinoline was substituted in place 2-chloro-6-fluoroquinoline. Yield=65%

Step 2: 4-(7-fluoroquinolin-2-yl)-2-methylaniline

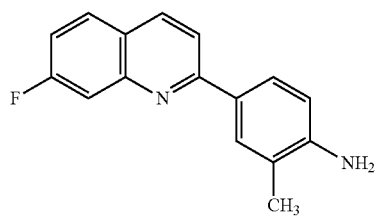 [SMILES: Cc1cc(-c2ccc3ccc(F)cc3n2)ccc1N]

The title compound was prepared analogously to Example 014, step 2, where tert-butyl (4-(7-fluoroquinolin-2-yl)-2-methylphenyl)carbamate was substituted in place of tert-butyl (4-(6-fluoroquinolin-2-yl)-2-methylphenyl)carbamate. Yield=79%.

Example 020: 1-Methyl-N-(2-methyl-4-(8-methylquinolin-2-yl)phenyl)-1H-pyrazole-5-carboxamide

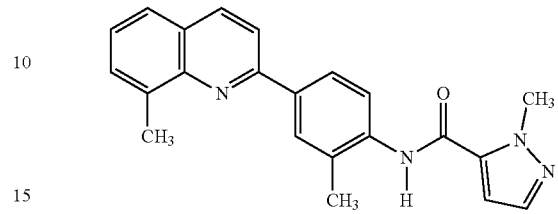

The title compound was prepared analogously to Example 003, where 2-Methyl-4-(8-methylquinolin-2-yl)aniline was substituted in place of 4-(quinoxalin-2-yl)aniline. Yield=22%. LCMS (ES, m/z): [M+H]$^+$ 357; $^1$H-NMR (CDCl$_3$, 400 MHz, ppm): 2.37 (s, 3H), 2.85 (s, 3H), 4.18 (s, 3H), 6.6 (d, 1H), 7.18 (s, 1H), 7.32 (m, 1H), 7.45 (d, 1H), 7.50 (d, 1H), 7.57 (m, 1H), 7.81 (d, 1H), 8.00-8.15 (m, 4H).

Step 1: tert-butyl (2-methyl-4-(8-methylquinolin-2-yl)phenyl)carbamate

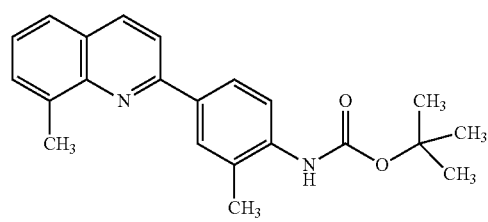 [SMILES: Cc1cc(-c2ccc3cccc(C)c3n2)ccc1NC(=O)OC(C)(C)C]

The title compound was prepared analogously to Example 014, step 1, where tert-butyl (2-methyl-4-(8-methylquinolin-2-yl)phenyl)carbamate was substituted in place of tert-butyl (4-(6-fluoroquinolin-2-yl)-2-methylphenyl)carbamate. Yield=82%

Step 2: 2-Methyl-4-(8-methylquinolin-2-yl)aniline

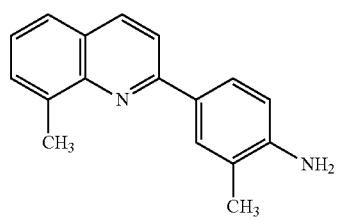

The title compound was prepared analogously to Example 014, step 2, where tert-butyl (2-methyl-4-(8-methylquinolin-2-yl)phenyl)carbamate was substituted in place of tert-butyl (4-(6-fluoroquinolin-2-yl)-2-methylphenyl)carbamate. Yield=82%

Example 021: N-(4-(Isoquinolin-6-yl)-2-methylphenyl)-1-methyl-1H-pyrazole-5-carboxamide

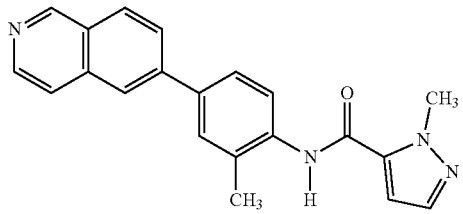

The title compound was prepared analogously to Example 003, where 4-(isoquinolin-6-yl)-2-methylaniline was substituted in place of 4-(quinoxalin-2-yl)aniline. Yield=7%. LCMS (ES, m/z): [M+H]$^+$ 343; $^1$H-NMR (CDCl$_3$, 400 MHz, ppm): 2.48 (s, 3H), 4.28 (s, 3H), 6.75 (d, 1H), 7.58 (d, 1H), 7.7 (m, 3H), 7.95 (d, 1H), 8.05 (dd, 1H), 8.15 (m, 3H), 8.55 (d, 1H), 9.37 (s, 1H).

Step 1: 4-(isoquinolin-6-yl)-2-methylaniline

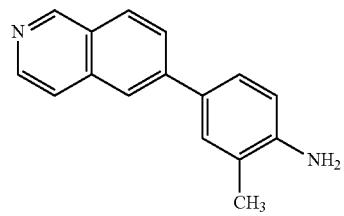 [SMILES: Cc1cc(-c2ccc3cnccc3c2)ccc1N]

The title compound was prepared analogously to Example 014, step 1, where 6-bromoisoquinoline was substituted in place 2-chloro-6-fluoroquinoline and 2-methyl-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=46%

Example 022: tert-butyl (4-(8-fluoroquinolin-2-yl)-2-methylphenyl)carbamate

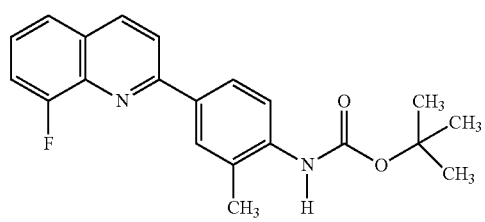 [SMILES: Cc1cc(-c2ccc3cccc(F)c3n2)ccc1NC(=O)OC(C)(C)C]

The title compound was prepared analogously to Example 014, step 1, where 2-chloro-8-fluoroquinoline was substituted in place 2-chloro-6-fluoroquinoline. Yield=28%. LCMS (ES, m/z): [M+H]$^+$ 353; $^1$H-NMR (CDCl$_3$, 400 MHz, ppm): 8.21 (dd, 1H), 8.13 (d, 1H), 8.08 (d, 1H), 7.95 (m, 2H), 7.59 (m, 1H), 7.42 (m, 2H), 6.43 (s, 1H), 2.38 (s, 3H), 1.55 (s, 9H)

Example 023: N-(4-(6-fluoroquinolin-2-yl)-2-methylphenyl)benzamide

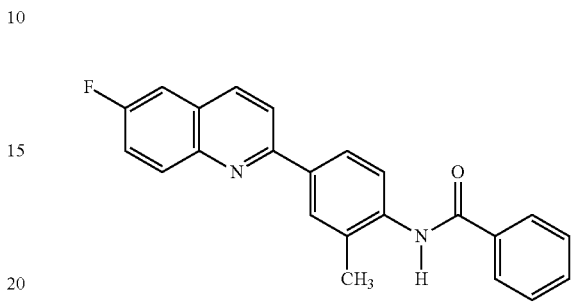

To a solution of 4-(6-fluoroquinolin-2-yl)-2-methylaniline (100 mg, 0.40 mmol, 1 equiv) and benzoyl chloride (61.3 mg, 0.44 mmol, 1.1 equiv) in CH$_2$Cl$_2$ (1 mL) at room temperature, triethylamine (80.2 mg, 0.79 mmol, 2 equiv) was added. The reaction mixture was stirred at room temperature for 3 hours and quenched with water (10 mL). The resulting mixture was extracted with dichloromethane (3×20 mL) and concentrated under reduced pressure. The residue was purified by recrystallization from dichloromethane/hexane=1:10 to afford the desired product as a white solid in 92% yield. LCMS (ES, m/z): [M+H]$^+$ 357; $^1$H-NMR (DMSO-d$_6$, 400 MHz, ppm): δ3.01 (s, 3H), δ7.54-7.61 (m, 4H), δ7.62-7.73 (m, 1H), δ7.81-7.84 (m, 1H), δ8.01-8.03 (t, 2H), δ8.12-8.17 (m, 2H), δ8.21-8.24 (m, 2H), δ8.45-8.47 (d, 1H), δ9.98 (s, 1H)

Example 024: methyl (4-(6-fluoroquinolin-2-yl)-2-methylphenyl)carbamate

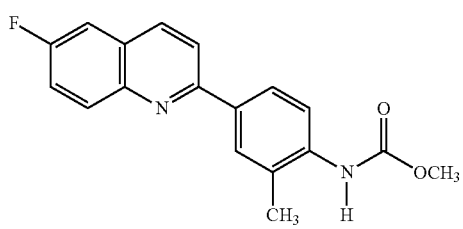 [SMILES: COC(=O)Nc1ccc(-c2ccc3cc(F)ccc3n2)cc1C]

The title compound was prepared analogously to Example 005 where 2-chloro-6-fluoroquinoline was substituted in place of 2-chloro-6-(trifluoromethyl)quinoline and (4-((methoxycarbonyl)amino)-3-methylphenyl)boronic acid was substituted in place of N-(2-fluoro-3-methyl-4-(4,4,5,5-tetramethyl-1,3,2-dioxaborolan-2-yl)phenyl)-1-methyl-1H-pyrazole-5-carboxamide. Yield=15%. LCMS (ES, m/z): [M+H]$^+$ 311; $^1$H-NMR (CD$_3$OD, 300 MHz, ppm): δ2.38 (s, 3H), δ3.78 (s, 3H), δ7.54-7.62 (m, 2H), δ7.69-7.71 (d, 1H), δ7.93-7.96 (m, 1H), δ7.99-8.02 (m, 2H), δ8.10-8.15 (m, 1H), δ8.33-8.35 (d, 1H)

Example 025: N-(4-(6-fluoroquinolin-2-yl)-2-methylphenyl)tetrahydro-2H-pyran-4-carboxamide

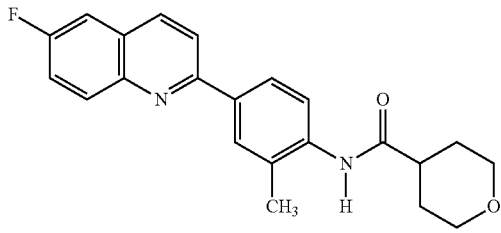

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and tetrahydro-2H-pyran-4-carboxylic acid was substituted in place of 1-methyl-1H-pyrazole-5-carboxylic acid. Yield=68%. LCMS (ES, m/z): [M+H]$^+$ 365; $^1$H-NMR (300 MHz, CD$_3$OD, ppm): 8.36-8.34 (d, 1H), 8.18-8.13 (m, 1H), 8.07-7.97 (m, 3H), 7.65-7.56 (m, 3H), 4.08-4.04 (m, 2H), 3.59-3.51 (m, 2H), 2.84-2.74 (m, 1H), 2.40 (s, 3H), 2.00-1.87 (m, 4H)

Example 026: N-(4-(6-fluoroquinolin-2-yl)-2-methylphenyl)picolinamide

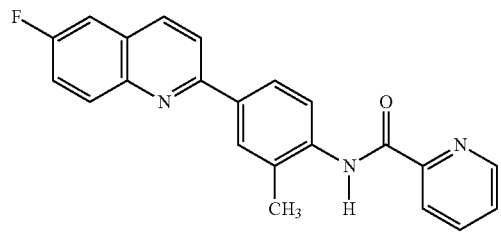 [SMILES: Cc1cc(-c2ccc3cc(F)ccc3n2)ccc1NC(=O)c1ccccn1]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and picolinic acid was substituted in place of 1-methyl-1H-pyrazole-5-carboxylic acid. Yield=87%. LCMS (ES, m/z): [M+H]$^+$ 358; $^1$H-NMR (300 MHz, CDCl$_3$, ppm): 10.34 (s, 1H), 8.68-8.67 (t, 1H), 8.61-8.58 (d, 1H), 8.38-8.35 (m, 1H), 8.21-8.18 (m, 3H), 8.06-8.00 (m, 1H), 7.99-7.94 (m, 2H), 7.63-7.31 (m, 3H), 2.60 (s, 3H)

Example 027: N-(4-(6-fluoroquinolin-2-yl)-2-methylphenyl)nicotinamide

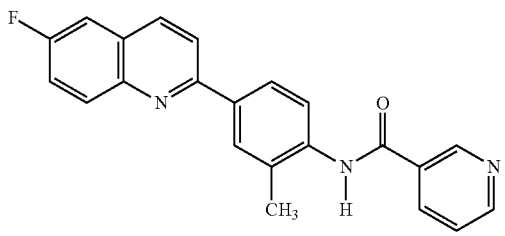 [SMILES: Cc1cc(-c2ccc3cc(F)ccc3n2)ccc1NC(=O)c1cccnc1]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and nicotinic acid was substituted in place of 1-methyl-1H-pyrazole-5-carboxylic acid. Yield=55%. LCMS (ES, m/z): [M+H]$^+$ 358; $^1$H-NMR (300 MHz, CDCl$_3$, ppm): 9.19 (s, 1H), 8.85-8.34 (d, 1H), 8.32-8.8.18 (m, 5H), 8.06-8.02 (m, 1H), 7.95-7.89 (m, 2H), 7.57-7.46 (m, 3H), 2.52 (s, 3H)

Example 028: N-(4-(6-fluoroquinolin-2-yl)-2-methylphenyl)isonicotinamide

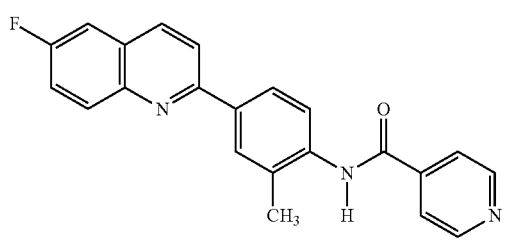 [SMILES: Cc1cc(-c2ccc3cc(F)ccc3n2)ccc1NC(=O)c1ccncc1]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and pyridine-4-carboxylic acid was substituted in place of 1-methyl-1H-pyrazole-5-carboxylic acid. Yield=59%. LCMS (ES, m/z): [M+H]$^+$ 358; $^1$H-NMR (300 MHz, CDCl$_3$, ppm): 8.88-8.86 (d, 2H), 8.23-8.16 (m, 4H), 8.05-8.02 (d, 1H), 7.94-7.88 (m, 2H), 7.79-7.77 (d, 2H), 7.57-7.45 (m, 2H), 2.51 (s, 3H).

Example 029: N-(4-(6-fluoroquinolin-2-yl)-2-methylphenyl)pyridazine-4-carboxamide

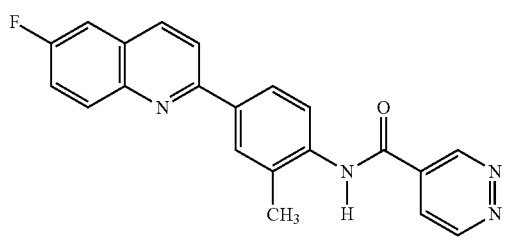 [SMILES: Cc1cc(-c2ccc3cc(F)ccc3n2)ccc1NC(=O)c1ccnnc1]

4-(6-fluoroquinolin-2-yl)-2-methylaniline (100 mg, 0.40 mmol, 1 equiv) and pyridazine-4-carboxylic acid (73.8 mg, 0.59 mmol, 1.5 equiv) were dissolved in dichloromethane (5 mL) and diisopropylethylamine (102.5 mg, 0.79 mmol, 2 equiv) and HATU (226.1 mg, 0.59 mmol, 1.5 equiv) were added next. The resulting solution was stirred at room temperature overnight and quenched by the addition of 5 mL of water. Extraction with dichloromethane (2×5 ml) and elimination of volatiles under reduced pressure, afford a residue that was purified by preparative TLC with dichloromethane/methanol (25:1) to afford the desired product as a white solid in 58% yield. LCMS (ES, m/z): [M+H]$^+$ 359; $^1$H-NMR (300 MHz, CDCl$_3$, ppm): δ2.25 (s, 3H), δ7.63-7.66 (m, 1H), δ7.68-7.73 (m, 1H), δ7.81-7.84 (m, 1H), δ8.13-8.17 (m, 3H), δ8.22-8.24 (m, 2H), δ8.46-8.48 (d, 1H), δ9.53-9.54 (d, 1H), δ9.70 (s, 1H), δ10.47 (s, 1H)

Example 030: N-(4-(6-fluoroquinolin-2-yl)-2-methylphenyl)pyrimidine-5-carboxamide

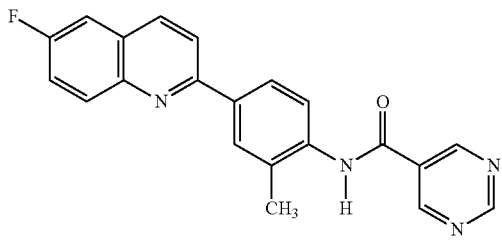 [SMILES: Cc1cc(-c2ccc3cc(F)ccc3n2)ccc1NC(=O)c1cncnc1]

The title compound was prepared analogously to Example 029 where pyrimidine-5-carboxylic acid was substituted in place of pyridazine-4-carboxylic acid. Yield=38%. LCMS (ES, m/z): [M+H]$^+$ 359; $^1$H-NMR (400 MHz, DMSO-d$_6$, ppm): δ2.42 (s, 3H), δ7.64-7.81 (m, 2H), δ7.81-7.84 (m, 1H), δ8.14-8.17 (m, 2H), δ8.23-8.25 (m, 2H), δ8.46-8.48 (d, 1H), δ9.33 (s, 2H), δ9.40 (s, 1H), δ10.33 (s, 1H).

Example 031: N-(4-(6-fluoroquinolin-2-yl)-2-methylphenyl)pyridazine-3-carboxamide

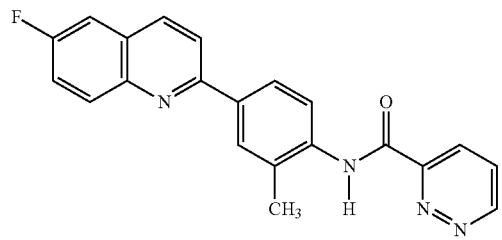 [SMILES: Cc1cc(-c2ccc3cc(F)ccc3n2)ccc1NC(=O)c1cccnn1]

The title compound was prepared analogously to Example 029 where pyridazine-3-carboxylic acid was substituted in place of pyridazine-4-carboxylic acid. Yield=42%. LCMS (ES, m/z): [M+H]$^+$ 359; $^1$H-NMR (300 MHz, DMSO-d$_6$, ppm): δ2.47 (s, 3H), δ7.67-7.74 (m, 1H), δ7.80-7.84 (m, 1H), δ7.93-8.00 (m, 1H), δ8.01-8.04 (m, 1H), δ8.13-8.18 (m, 2H), δ8.22-8.24 (m, 2H), δ8.36-8.39 (m, 1H), δ8.45-8.51 (m, 1H), δ9.50-9.56 (m, 1H), δ10.73 (s, 1H).

Example 032: N-(4-(6-fluoroquinolin-2-yl)-2-methylphenyl)pyrazine-2-carboxamide

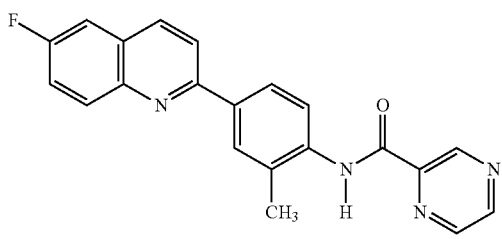

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and pyrazine-2-carboxylic acid was substituted in place of 1-methyl-1H-pyrazole-5-carboxylic acid. Yield=85%. LCMS (ES, m/z): [M+H]$^+$ 359; $^1$H-NMR (400 MHz, DMSO-d$_6$, ppm): δ2.45 (s, 3H), δ7.67-7.73 (m, 1H), δ7.78-7.83 (m, 1H), δ7.96-8.03 (m, 1H), δ8.12-8.18 (m, 2H), δ8.21-8.23 (m, 2H), δ8.45-8.47 (d, 1H), δ8.86 (s, 1H), δ8.98-8.99 (d, 1H), δ9.35 (s, 1H), δ10.36 (s, 1H).

Example 033: N-(4-(6-fluoroquinolin-2-yl)-2-methylphenyl)-1-methyl-1H-imidazole-2-carboxamide

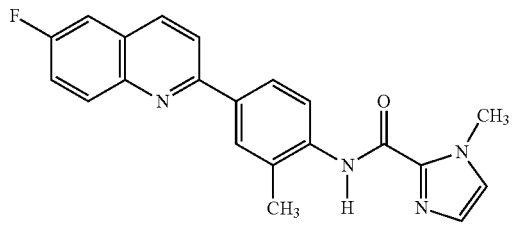 [SMILES: Cc1cc(-c2ccc3cc(F)ccc3n2)ccc1NC(=O)c1nccn1C]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and 1-methyl-1H-imidazole-2-carboxylic acid was substituted in place of 1-methyl-1H-pyrazole-5-carboxylic acid. Yield=39%. LCMS (ES, m/z): [M+H]$^+$ 361; $^1$H-NMR (300 MHz, DMSO-d$_6$, ppm): δ9.84 (s, 1H), δ8.46-8.43 (d, 1H), δ8.22-8.19 (m, 2H), δ8.16-8.11 (m, 2H), δ7.99-7.96 (d, 1H), δ7.83-7.82 (m, 1H), δ7.72-7.69 (m, 1H), δ7.49 (s, 1H), δ7.12 (s, 1H), δ4.03 (s, 3H), δ2.08 (s, 3H)

Example 034: N-(4-(6-fluoroquinolin-2-yl)-2-methylphenyl)-1-methyl-1H-imidazole-5-carboxamide

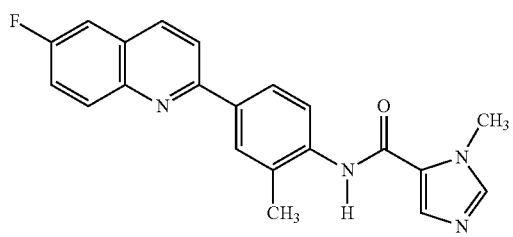 [SMILES: Cc1cc(-c2ccc3cc(F)ccc3n2)ccc1NC(=O)c1cncn1C]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and 1-methyl-1H-imidazole-5-carboxylic acid was substituted in place of 1-methyl-1H-pyrazole-5-carboxylic acid. LCMS (ES, m/z): [M+1]$^+$ 361; $^1$H-NMR (300 MHz, CD$_3$OD, ppm): δ8.40-8.37 (d, 1H), δ8.19-8.17 (m, 1H), δ8.16-8.08 (m, 1H), δ8.05-8.02 (t, 2H), δ7.85-7.83 (d, 2H), δ7.66-7.57 (m, 3H), δ3.99 (s, 3H), δ2.46 (s, 3H)

Example 035: N-(4-(6-fluoroquinolin-2-yl)-2-methylphenyl)-1-methyl-1H-imidazole-4-carboxamide

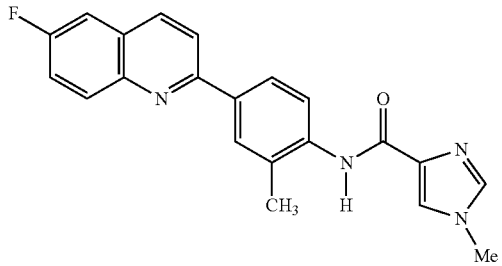 [SMILES: Cc1cc(-c2ccc3cc(F)ccc3n2)ccc1NC(=O)c1cn(C)cn1]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and pyrimidine-5-carboxylic acid was substituted in place of 1-methyl-1H-pyrazole-5-carboxylic acid. Yield=39%. LCMS (ES, m/z): [M+H]$^+$ 361; $^1$H-NMR (300 MHz, DMSO-d$_6$, ppm): δ9.41 (s, 1H), δ8.45-8.42 (d, 1H), δ8.21-8.11 (m, 5H), δ7.87 (s, 1H), δ7.83-7.79 (m, 2H), δ7.72-7.65 (m, 1H), δ3.76 (s, 3H), δ2.28 (s, 3H)

Example 036: N-(4-(6-fluoroquinolin-2-yl)-2-methylphenyl)oxazole-4-carboxamide

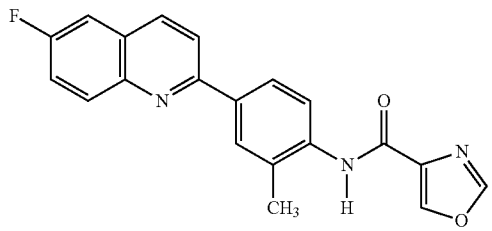 [SMILES: Cc1cc(-c2ccc3cc(F)ccc3n2)ccc1NC(=O)c1cocn1]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and 1,3-oxazole-4-carboxylic acid was substituted in place of 1-methyl-1H-pyrazole-5-carboxylic acid. Yield=33%. LCMS (ES, m/z): [M+H]$^+$ 348; $^1$H-NMR (300 MHz, DMSO-d$_6$, ppm): δ2.40 (s, 3H), δ7.66-7.73 (m, 1H), δ7.79-7.84 (m, 2H), δ8.12-8.16 (m, 2H), δ8.19-8.23 (m, 2H), δ8.44-8.47 (d, 1H), δ8.65-8.66 (d, 1H), δ8.84-8.85 (d, 1H), δ9.71 (s, 1H)

Example 037: N-(4-(6-fluoroquinolin-2-yl)-2-methylphenyl)isoxazole-5-carboxamide

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and 1,2-oxazole-5-carboxylic acid was substituted in place of 1-methyl-1H-pyrazole-5-carboxylic acid. Yield=34%. LCMS (ES, m/z): [M+H]$^+$ 348; $^1$H-NMR (300 MHz, DMSO-d6, ppm): δ2.38 (s, 3H), δ7.28-7.29 (d, 1H), δ7.55-7.57 (d, 1H), δ7.68-7.73 (m, 1H), δ7.81-7.84 (m, 1H), δ8.13-8.17 (m, 2H), δ8.22-8.24 (m, 2H), δ8.46-48 (d, 1H), δ8.84-8.85 (d, 1H), δ10.51 (s, 1H)

Example 038: N-(4-(6-fluoroquinolin-2-yl)-2-methylphenyl)-5-methylisoxazole-4-carboxamide

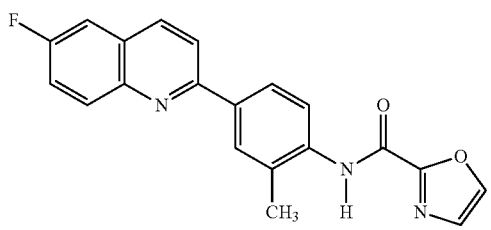 [SMILES: Cc1cc(-c2ccc3cc(F)ccc3n2)ccc1NC(=O)c1ncco1]

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and 5-methyl-1,2-oxazole-4-carboxylic acid was substituted in place of 1-methyl-1H-pyrazole-5-carboxylic acid. Yield=16%. LCMS (ES, m/z): [M+H]$^+$ 362; $^1$H-NMR (300 MHz, DMSO-d$_6$, ppm): δ2.38 (s, 3H), δ2.70-2.73 (d, 3H), δ7.55-7.58 (m, 1H), δ7.66-7.73 (m, 1H), δ7.80-7.84 (m, 1H), δ8.12-8.17 (m, 2H), δ8.21-8.24 (m, 2H), δ8.44-8.47 (d, 1H), δ9.08 (s, 1H), δ9.81 (s, 1H)

Example 039: N-(4-(6-fluoroquinolin-2-yl)-2-methylphenyl)oxazole-2-carboxamide

The title compound was prepared analogously to Example 001 where 4-(6-fluoroquinolin-2-yl)-2-methylaniline was substituted in place of 2-methyl-4-(6-(trifluoromethyl)quinolin-2-yl)aniline and 1,3-oxazole-2-carboxylic acid was substituted in place of 1-methyl-1H-pyrazole-5-carboxylic acid. Yield=14%. LCMS (ES, m/z): [M+H]$^+$ 348; $^1$H-NMR (300 MHz, DMSO-d$_6$, ppm): δ2.40 (s, 3H), δ7.58 (s, 1H), δ7.65-7.73 (m, 2H), δ7.81-7.84 (m, 1H), δ8.12-8.17 (m, 2H), δ8.21-8.23 (m, 2H), δ8.44-8.48 (m, 2H), δ10.38 (s, 1H)

Example 040: N-(4-(6-fluoroquinolin-2-yl)-2-methylphenyl)acetamide

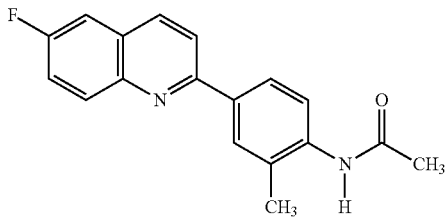 [SMILES: CC(=O)Nc1ccc(-c2ccc3cc(F)ccc3n2)cc1C]

Triethylamine (80.2 mg, 0.79 mmol, 2.000 equiv) was added over a solution of 4-(6-fluoroquinolin-2-yl)-2-methylaniline (100 mg, 0.40 mmol, 1 equiv) and acetyl chloride (34.2 mg, 0.44 mmol, 1.099 equiv) in $CH_2Cl_2$ (1 mL) at room temperature. The reaction mixture was stirred at room temperature for 3 hours and quenched by addition of water (10 mL). The mixture was extracted with $CH_2Cl_2$ (3×20 mL) and the organic layers combined and concentrated under reduced pressure. The residue was purified by recrystallization from dichloromethane/hexane=1/10 to afford the desired final product as a white solid in 77% yield. LCMS (ES, m/z): $[M+H]^+$ 295; $^1$H-NMR (DMSO-$d_6$, 400 MHz, ppm): δ2.11 (s, 3H), δ2.34 (s, 3H), δ7.66-7.71 (m, 2H), δ7.79-7.82 (m, 1H), δ8.04-8.06 (m, 1H), δ8.10-8.14 (m, 2H), δ8.16-8.19 (d, 1H), δ8.42-8.44 (d, 1H), δ9.37 (s, 1H).

Example 041: N-(4-(6-fluoroquinolin-2-yl)-2-methylphenyl)morpholine-4-carboxamide

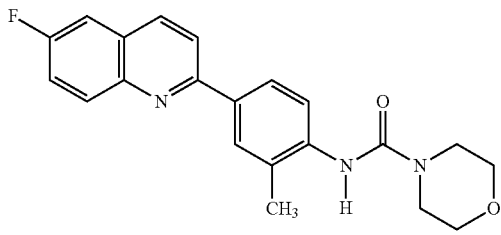 [SMILES: Cc1cc(-c2ccc3cc(F)ccc3n2)ccc1NC(=O)N1CCOCC1]

To a −15° C. solution of 4-(6-fluoroquinolin-2-yl)-2-methylaniline (100 mg, 0.40 mmol, 1 equiv), in dichloromethane (3 mL) was added triphosgene (46.9 mg, 0.16 mmol, 0.4 equiv), followed by triethylamine (100.3 mg, 0.99 mmol, 2.501 equiv). The reaction mixture was stirred at 0° C. for 30 minutes and morpholine (38.0 mg, 0.44 mmol, 1.1 equiv) was added. The reaction mixture was stirred at room temperature for one additional hour and quenched by the slow addition of 10 mL of water. The resulting solution was extracted with $CH_2Cl_2$ (3×20 mL), the organic layers were combined and concentrated under reduced pressure to afford a residue that was purified by recrystallization from dichloromethane and hexane. The desired final product was isolated as a yellow solid in 80% yield. LCMS (ES, m/z): $[M+H]^+$ 366; $^1$H-NMR (DMSO-$d_6$, 400 MHz, ppm): δ2.31 (s, 3H), δ3.44-3.46 (t, 4H), δ3.62-3.65 (t, 4H), δ7.44-7.46 (d, 1H), δ7.66-7.70 (m, 1H), δ7.78-7.81 (m, 1H), δ8.03-8.05 (m, 1H), δ8.10-8.14 (m, 2H), δ8.16-8.18 (d, 2H), δ8.41-8.43 (d, 1H).

Example 042: N-(5-(6-fluoroquinolin-2-yl)-3-methylpyridin-2-yl)-1-methyl-1H-pyrazole-5-carboxamide

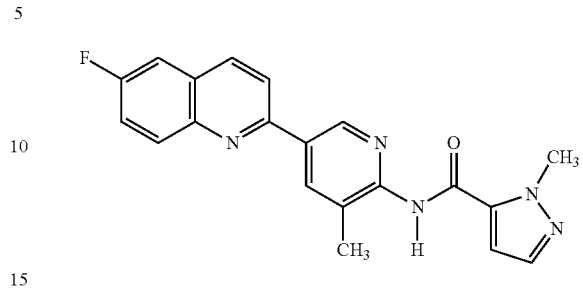

The title compound was prepared analogously to Example 001, where 5-(6-fluoroquinolin-2-yl)-3-methylpyridin-2-amine was substituted in place of 2-methyl-4-(6-(trifluoromethyl)quinolin-2-yl)aniline. Yield=31%. LCMS (ES, m/z): $[M+H]^+$ 362; $^1$H-NMR (DMSO-$d_6$, 300 MHz, ppm): δ2.35 (s, 3H), δ4.08-4.11 (d, 3H), δ7.15-7.16 (d, 1H), δ7.55-7.56 d, 1H), δ7.70-7.77 (m, 1H), δ7.84-8.88 (m, 1H), δ8.16-8.21 (m, 1H), δ8.29-8.32 (d, 1H), δ8.51-8.54 (d, 1H), δ8.59-8.60 (d, 1H), δ9.18-9.19 (d, 1H), δ10.72 (s, 1H).

Step 1:
5-(6-fluoroquinolin-2-yl)-3-methylpyridin-2-amine

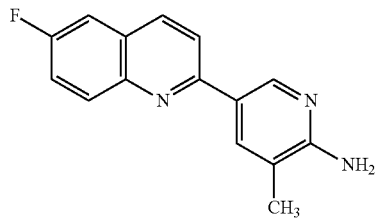 [SMILES: Cc1cc(-c2ccc3cc(F)ccc3n2)cnc1N]

To a solution of 2-chloro-6-fluoroquinoline (200 mg, 1.1 mmol, 1 equiv), 3-methyl-5-(4,4,5,5-tetramethyl-1,3,2-dioxaborolan-2-yl)pyridin-2-amine (387 mg, 1.7 mmol, 1.501 equiv), $Na_2CO_3$ (351 mg, 3.3 mmol, 2.998 equiv) in DME (4 ml) and $H_2O$ (0.8 ml), $Pd(PPh_3)_4$ (127 mg, 0.01 mmol, 0.100 equiv) was added. The reaction was heated at 90° C. for 3 hours, and quenched with water (10 mL). The aqueous layer was extracted with EtOAc (3×20 mL), the organic layers were combined and concentrated under reduced pressure. The residue was purified by preparative TLC with dichloromethane/MeOH=(20:1) to afford the desired product as a yellow solid in 64% yield.

Example 043: N-(5-(6-fluoroquinolin-2-yl)-4-methylpyridin-2-yl)-1-methyl-1H-pyrazole-5-carboxamide

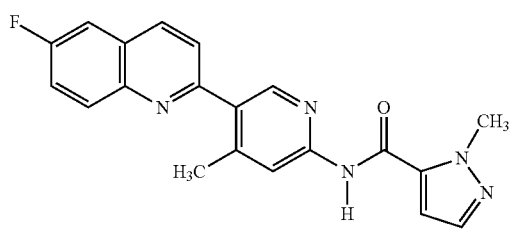 [SMILES: Cc1cc(NC(=O)c2ccnn2C)ncc1-c1ccc2cc(F)ccc2n1]

The title compound was prepared analogously to Example 001 where 5-(6-fluoroquinolin-2-yl)-4-methylpyridin-2-amine was substituted in place of 2-methyl-4-(6-(trifluoromethyl)quinolin-2-yl)aniline. Yield=30%. LCMS (ES, m/z): [M+H]+ 362; $^1$H-NMR (DMSO-d$_6$, 400 MHz, ppm): δ2.49 (s, 3H), δ4.14 (s, 3H), δ7.34-7.35 (d, 1H), δ7.54-7.55 (d, 1H), δ7.71-7.76 (m, 1H), δ7.86-7.89 (t, 2H), δ8.13-8.17 (m, 1H), δ8.20 (s, 1H), δ8.48-8.50 (d, 1H), δ8.65 (s, 1H), δ10.94 (s, 1H).

Step 1: 4-methyl-5-(4,4,5,5-tetramethyl-1,3,2-dioxaborolan-2-yl)pyridin-2-amine

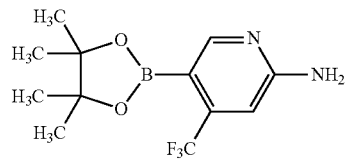

A solution of 5-bromo-4-methylpyridin-2-amine (10 g, 53.47 mmol, 1 equiv), 4,4,5,5-tetramethyl-2-(tetramethyl-1,3,2-dioxaborolan-2-yl)-1,3,2-dioxaborolane (14.9 g, 58.68 mmol, 1.097 equiv), KOAc (15.7 g, 159.97 mmol, 2.992 equiv) and Pd(dppf)Cl$_2$ (3.9 g, 5.33 mmol, 0.100 equiv) in 1,4-dioxane (250 ml), was stirred at 115° C. under nitrogen atmosphere overnight. The mixture was allowed to cool down to room temperature and filtered. The filtrate was concentrated under vacuum and the residue was diluted with 100 mL of petroleum ether. The solids were collected by filtration and washed with petroleum ether affording the desired product as a yellow solid in 19% yield.

Step 2: 5-(6-fluoroquinolin-2-yl)-4-methylpyridin-2-amine

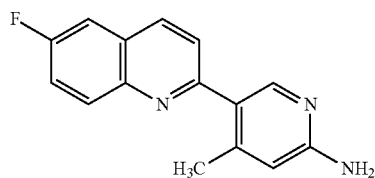

The title compound was prepared analogously to Example 042, step 1 where 4-methyl-5-(4,4,5,5-tetramethyl-1,3,2-dioxaborolan-2-yl)pyridin-2-amine was substituted in place of 3-methyl-5-(4,4,5,5-tetramethyl-1,3,2-dioxaborolan-2-yl)pyridin-2-amine. Yield=75%.

Example 044: N-(5-(6-fluoroquinolin-2-yl)-6-methylpyridin-2-yl)-1-methyl-1H-pyrazole-5-carboxamide

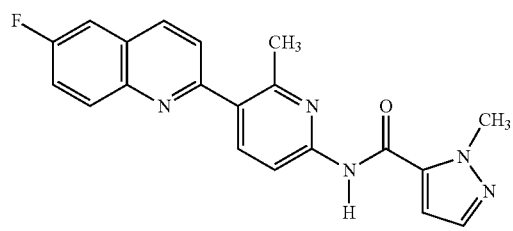 [SMILES: Cc1nc(NC(=O)c2ccnn2C)ccc1-c1ccc2cc(F)ccc2n1]

The title compound was prepared analogously to Example 001 where 5-(6-fluoroquinolin-2-yl)-6-methylpyridin-2-amine was substituted in place of 2-methyl-4-(6-(trifluoromethyl)quinolin-2-yl)aniline. Yield=27%. LCMS (ES, m/z): [M+H]+ 362; $^1$H-NMR (400 MHz, DMSO-d$_6$, ppm): δ2.62 (s, 3H), δ4.14 (s, 3H), δ7.37-7.38 (d, 1H), δ7.54-7.55 (d, 1H), δ7.71-7.76 (m, 1H), δ7.85-7.89 (m, 2H), δ8.03-8.05 (d, 1H), δ8.12-8.18 (m, 2H), δ8.48-8.50 (d, 1H), δ10.96 (s, 1H).

Step 1: 6-methyl-5-(4,4,5,5-tetramethyl-1,3,2-dioxaborolan-2-yl)pyridin-2-amine

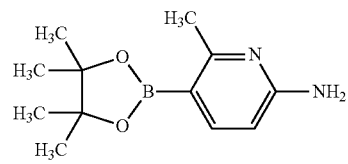

The title compound was prepared analogously to Example 043, step 1 where 5-bromo-6-methylpyridin-2-amine was substituted in place of 5-bromo-4-methylpyridin-2-amine. Yield=36%.

Step 2: 5-(6-fluoroquinolin-2-yl)-6-methylpyridin-2-amine

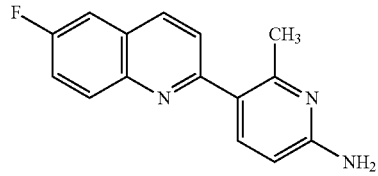 [SMILES: Cc1nc(N)ccc1-c1ccc2cc(F)ccc2n1]

The title compound was prepared analogously to Example 042, step 1, where 6-methyl-5-(4,4,5,5-tetramethyl-1,3,2-dioxaborolan-2-yl)pyridin-2-amine was substituted in place of 3-methyl-5-(4,4,5,5-tetramethyl-1,3,2-dioxaborolan-2-yl)pyridin-2-amine. Yield=90%

Example 045: N-(6-(6-fluoroquinolin-2-yl)-2-methylpyridin-3-yl)-1-methyl-1H-pyrazole-5-carboxamide

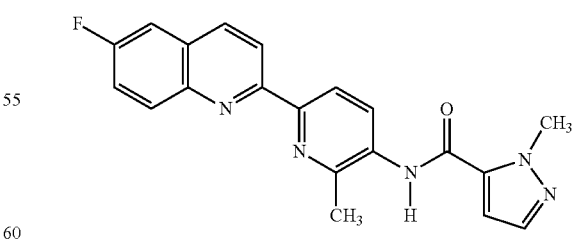

The title compound was prepared analogously to Example 001 where 6-(6-fluoroquinolin-2-yl)-2-methylpyridin-3-amine was substituted in place of 2-methyl-4-(6-(trifluoromethyl)quinolin-2-yl)aniline. Yield=17%. LCMS (ES, m/z): [M+H]+ 362; $^1$H-NMR (400 MHz, CDCl$_3$, ppm): 8.64-8.61 (d, 2H), 8.58-8.54 (t, 1H), 8.34 (s, 1H), 8.27-8.25 (d, 1H), 7.80 (s, 1H), 7.55-7.53 (m, 2H), 7.52-7.47 (m, 1H), 6.77 (s, 1H), 4.25 (s, 3H), 2.73 (s, 3H).

Step 1: 2-methyl-6-(tributylstannyl)pyridin-3-amine

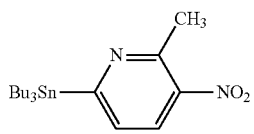

Over a solution of 6-bromo-2-methyl-3-nitropyridine (400 mg, 1.84 mmol, 1.00 equiv), Pd(dppf)Cl$_2$ (150 mg, 0.21 mmol, 0.10 equiv), and KOAc (2 g, 20.38 mmol, 3.00 equiv) in toluene (6 mL), bis(tributyltin) (3.2 g, 7.83 mmol, 3.00 equiv) was added. The resulting solution was stirred for 12 hours at 110° C. The reaction was cooled down to room temperature and stopped by the addition of water. Extraction with ethyl acetate three times followed by evaporation of volatiles under reduced pressure afforded a crude material that was purified by neutral alumina gel with ethyl acetate/petroleum ether (1:100) to afford the desired product as colorless oil in 25% yield.

Step 2: 6-fluoro-2-(6-methyl-5-nitropyridin-2-yl)quinoline

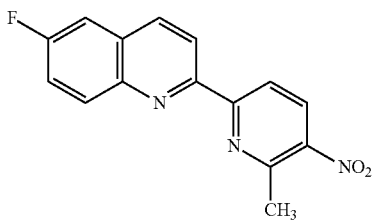

Pd(PPh$_3$)$_4$ (54 mg, 0.05 mmol, 0.10 equiv) was added over a solution of 2-chloro-6-fluoroquinoline (84 mg, 0.46 mmol, 1.00 equiv) and 2-methyl-3-nitro-6-(tributylstannyl)pyridine (200 g, 468.20 mmol, 1.00 equiv) in toluene (2 mL). The resulting mixture was stirred for 12 h at 110° C. The reaction was cooled down to room temperature, quenched with water and extracted with ethyl acetate three times. The combined organic layers were dried with MgSO$_4$ and concentrated under reduced pressure. The resulting residue was purified by silica gel chromatography with ethyl acetate/petroleum ether (1:2) to afford the desired final product as a colorless oil in 91% yield.

Step 3: 6-(6-fluoroquinolin-2-yl)-2-methylpyridin-3-amine

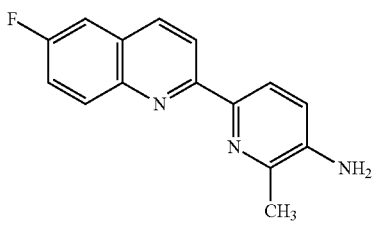

Over a mixture of 6-fluoro-2-(6-methyl-5-nitropyridin-2-yl)quinoline (140 mg, 0.49 mmol, 1.00 equiv) in water (2 mL), Fe (28 mg, 3.00 equiv) and NH$_4$Cl (133 mg, 2.49 mmol, 5.00 equiv) were added. The resulting solution was stirred for 2 h at 100° C. and extracted with ethyl acetate three times. The organic layers were combined, dried with MgSO$_4$ and the volatiles evaporated under reduced pressure. The residue was purified by TLC with dichloromethane/methanol (20:1) to afford the desired product as a white solid in 58% yield.

Example 046: N-(6-(6-fluoroquinolin-2-yl)-5-methylpyridin-3-yl)-1-methyl-1H-pyrazole-5-carboxamide

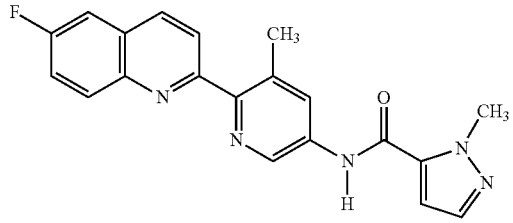 [SMILES: Cc1cc(NC(=O)c2ccnn2C)cnc1-c1ccc2cc(F)ccc2n1]

The title compound was prepared analogously to Example 001 where 6-(6-fluoroquinolin-2-yl)-5-methylpyridin-3-amine was substituted in place of 2-methyl-4-(6-(trifluoromethyl)quinolin-2-yl)aniline. Yield=39%. LCMS (ES, m/z): [M+H]$^+$ 362; $^1$H-NMR (400 MHz, CDCl$_3$, ppm): δ2.76 (s, 3H), δ4.26 (s, 3H), δ7.20-7.26 (m, 1H), δ7.49-7.53 (m, 3H), δ8.05-8.07 (d, 1H), δ8.18-8.20 (m, 1H), δ8.26-8.38 (d, 1H), δ8.75 (s, 1H), δ9.20 (s, 2H)

Step 1: 3-methyl-5-nitro-2-(tributylstannyl)pyridine

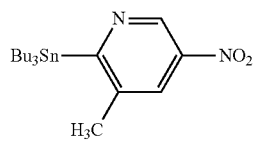

The title compound was prepared analogously to Example 045, step 1, where 2-bromo-3-methyl-5-nitropyridine was substituted in place of 6-bromo-2-methyl-3-nitropyridine. Yield=36%.

Step 2: 6-fluoro-2-(3-methyl-5-nitropyridin-2-yl)quinoline

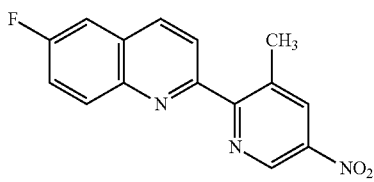 [SMILES: Cc1cc([N+](=O)[O-])cnc1-c1ccc2cc(F)ccc2n1]

The title compound was prepared analogously to Example 045, step 2, where 3-methyl-5-nitro-2-(tributylstannyl)pyridine was substituted in place of 2-methyl-3-nitro-6-(tributylstannyl)pyridine. Yield=30%.

Step 3:
6-(6-fluoroquinolin-2-yl)-5-methylpyridin-3-amine

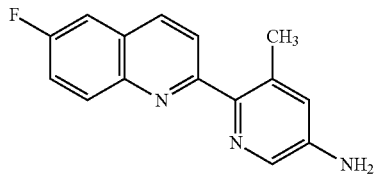

The title compound was prepared analogously to Example 045, step 3, where 6-fluoro-2-(3-methyl-5-nitropyridin-2-yl)quinoline was substituted in place of 6-fluoro-2-(6-methyl-5-nitropyridin-2-yl)quinoline. Yield=61%.

Example 047: N-(4-(6-fluoroquinolin-2-yl)-2-(trifluoromethoxy)phenyl)-1-methyl-1H-pyrazole-5-carboxamide

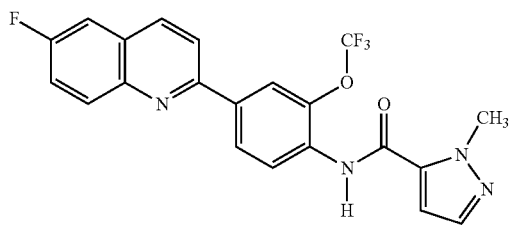 [SMILES: Cn1nccc1C(=O)Nc1ccc(-c2ccc3cc(F)ccc3n2)cc1OC(F)(F)F]

The title compound was prepared analogously to Example 003, where 4-(6-fluoroquinolin-2-yl)-2-(trifluoromethoxy)aniline was substituted in place of 4-(quinoxalin-2-yl)aniline. Yield=33%. LCMS (ES, m/z): [M+H]$^+$ 431; $^1$H-NMR (400 MHz, CDCl$_3$, ppm): 8.66 (d, 1H), 8.29-8.08 (m, 5H), 7.89 (d, 1H), 7.58-7.43 (m, 3H), 6.69 (d, 1H), 4.27 (s, 3H).

Step 1: 4-(6-fluoroquinolin-2-yl)-2-(trifluoromethoxy)aniline

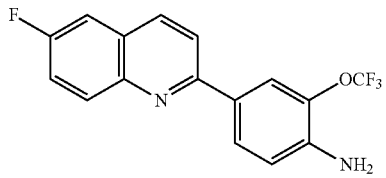 [SMILES: Nc1ccc(-c2ccc3cc(F)ccc3n2)cc1OC(F)(F)F]

The title compound was prepared analogously to Example 014, step 1, where 4-(4,4,5,5-tetramethyl-1,3,2-dioxaborolan-2-yl)-2-(trifluoromethoxy)aniline was substituted in place of tert-butyl (2-methyl-4-(4,4,5,5-tetramethyl-1,3,2-dioxaborolan-2-yl)phenyl)carbamate. Yield=34%.

Example 048: N-(4-(6-fluoroquinolin-2-yl)-2-(trifluoromethyl)phenyl)-1-methyl-1H-pyrazole-5-carboxamide

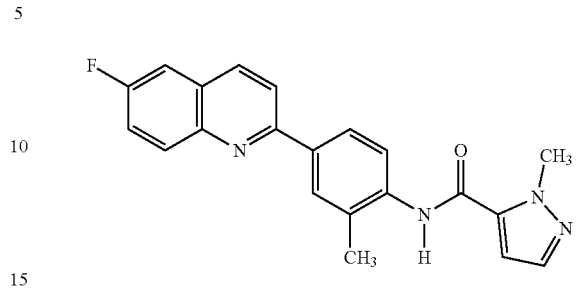

The title compound was prepared analogously to Example 003, where 4-(6-fluoroquinolin-2-yl)-2-(trifluoromethyl)aniline was substituted in place of 4-(quinoxalin-2-yl)aniline. Yield=24%. LCMS (ES, m/z): [M+H]$^+$ 415; $^1$H-NMR (400 MHz, CDCl$_3$, ppm): 8.61 (m, 2H), 8.39 (dd, 1H), 8.23 (m, 3H), 7.94 (d, 1H), 7.54 (m, 3H), 6.71 (s, 1H), 4.30 (s, 3H)

Step 1: 4-(6-fluoroquinolin-2-yl)-2-(trifluoromethyl)aniline

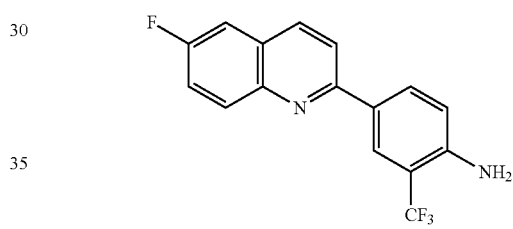

The title compound was prepared analogously to Example 014, step 1, where 4-(4,4,5,5-tetramethyl-1,3,2-dioxaborolan-2-yl)-2-(trifluoromethyl)aniline was substituted in place of tert-butyl (2-methyl-4-(4,4,5,5-tetramethyl-1,3,2-dioxaborolan-2-yl)phenyl)carbamate. Yield=98%.

Example 049: N-(4-(8-chloro-6-fluoroquinolin-2-yl)-2-methylphenyl)-1-methyl-1H-pyrazole-5-carboxamide

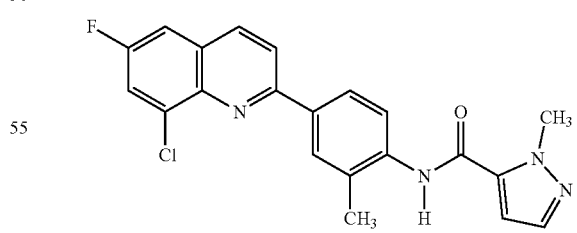

The title compound was prepared analogously to Example 001 where 4-(8-chloro-6-fluoroquinolin-2-yl)-2-methylaniline was substituted in place of 2-methyl-4-(6-(trifluoromethyl)quinolin-2-yl)aniline. Yield=42%. LCMS (ES, m/z): [M+H]$^+$ 395; $^1$H-NMR (400 MHz, CDCl$_3$, ppm): δ8.10-8.06 (m, 2H), δ7.64-7.57 (m, 3H), δ7.56-7.54 (m, 2H), δ7.44-7.43 (d, 2H), δ6.68 (s, 1H), δ4.26 (s, 3H), δ2.42 (s, 3H).

Step 1: N-(2-bromo-4-fluorophenyl)cinnamamide

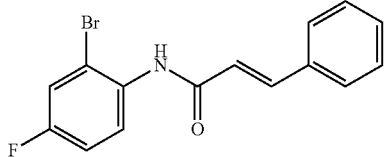 [SMILES: O=C(/C=C/c1ccccc1)Nc1ccc(F)cc1Br]

Pyridine (10.39 g, 131.35 mmol, 1.00 equiv) was added over a solution of 4-dimethylaminopyridine (1.618 g, 13.24 mmol, 0.10 equiv) in dichloromethane (80 mL). The reaction mixture was cooled down to 0° C. and a solution of cinnamoyl chloride (21.85 g, 131.15 mmol, 1.00 equiv) in dichloromethane (66 mL) was added. The resulting solution was stirred for 15 min at 0° C. and a solution of 2-bromo-4-fluoroaniline (25.0 g, 131.57 mmol, 1.00 equiv) in dichloromethane (125 mL) was added dropwise. The cooling bath was removed and the mixture was allowed to react at room temperature for one additional hour. After quenching with 100 mL of H₂O, the solids were collected by filtration to afford the desired product as yellow solid in 88% yield.

Step 2: 8-bromo-6-fluoroquinolin-2(1H)-one

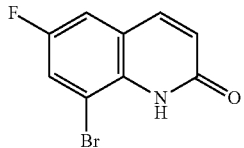

AlCl₃ (44.89 g, 336.66 mmol, 3.00 equiv) was added over N-(2-bromo-4-fluorophenyl)cinnamamide (36 g, 112.45 mmol, 1.00 equiv) and the resulting mixture was stirred for 1 h at 100° C. The reaction was quenched by the addition of 500 mL of ice/water and the solids collected by filtration to afford the desired product as a white solid in 91% yield Step 3: 8-bromo-2-chloro-6-fluoroquinoline

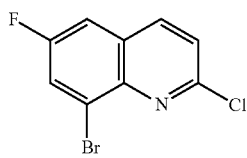

The title compound was prepared analogously to Example 001, step 3, where 8-bromo-6-fluoroquinolin-2(1H)-one was substituted in place of 6-(trifluoromethyl)quinolin-2(1H)-one. Yield=84%.

Step 4: 8-bromo-6-fluoro-2-(3-methyl-4-nitrophenyl)quinoline

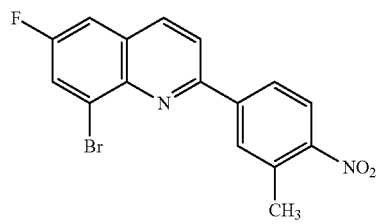 [SMILES: Cc1cc(-c2ccc3cc(F)cc(Br)c3n2)ccc1[N+](=O)[O-]]

The title compound was prepared analogously to Example 001, step 4, where 8-bromo-2-chloro-6-fluoroquinoline was substituted in place of 2-chloro-6-(trifluoromethyl)quinoline and 4,4,5,5-tetramethyl-2-(3-methyl-4-nitrophenyl)-1,3,2-dioxaborolane was substituted in place of 2-methyl-4-(4,4,5,5-tetramethyl-1,3,2-dioxaborolan-2-yl)aniline. Yield=96%.

Step 5: 4-(8-chloro-6-fluoroquinolin-2-yl)-2-methylaniline

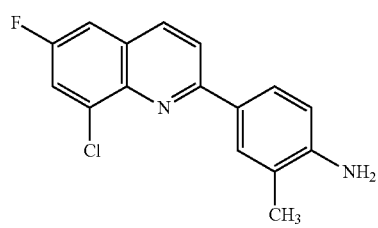 [SMILES: Cc1cc(-c2ccc3cc(F)cc(Cl)c3n2)ccc1N]

The title compound was prepared analogously to Example 045, step 3, where 8-bromo-6-fluoro-2-(3-methyl-4-nitrophenyl)quinoline was substituted in place of 6-fluoro-2-(6-methyl-5-nitropyridin-2-yl)quinoline.

Example 050: N-(4-(6-fluoroquinolin-2-yl)-3-methylphenyl)-1-methyl-1H-pyrazole-5-carboxamide

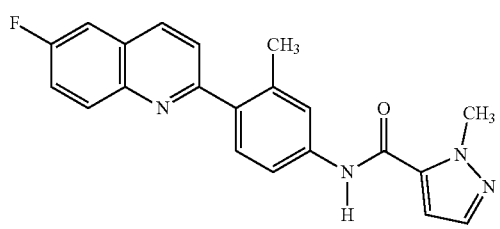 [SMILES: Cc1cc(NC(=O)c2ccnn2C)ccc1-c1ccc2cc(F)ccc2n1]

The title compound was prepared analogously to Example 003, where 4-(6-fluoroquinolin-2-yl)-3-methylaniline was substituted in place of 4-(quinoxalin-2-yl)aniline. Yield=16%; LCMS (ES, m/z): [M+H]⁺ 361; ¹H-NMR (400 MHz, CDCl₃, ppm): 8.19 (d, 2H), 7.80 (s, 1H), 7.54 (m, 7H), 6.72 (s, 1H), 4.24 (s, 3H), 2.46 (s, 3H).

Step 1:
6-fluoro-2-(2-methyl-4-nitrophenyl)quinoline

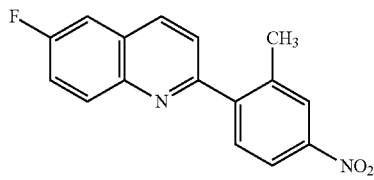 [SMILES: Cc1cc([N+](=O)[O-])ccc1-c1ccc2cc(F)ccc2n1]

The title compound was prepared analogously to Example 014, step 1, where 4,4,5,5-tetramethyl-2-(3-methyl-4-nitrophenyl)-1,3,2-dioxaborolane was substituted in place of tert-butyl (2-methyl-4-(4,4,5,5-tetramethyl-1,3,2-dioxaborolan-2-yl)phenyl)carbamate. Yield=65%.

Step 2: 4-(6-fluoroquinolin-2-yl)-3-methylaniline

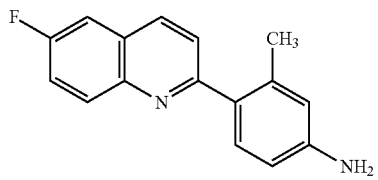

6-fluoro-2-(2-methyl-4-nitrophenyl)quinoline (308 mg, 1.15 mmol) was dissolved in MeOH (15 mL) at room temperature. Zn dust (226 mg, 3.46 mmol) and ammonium chloride (185 mg, 3.46 mmol) were added and the resulting mixture stirred at room temperature for 18 hours. The reaction mixture was filtered and the volatiles evaporated. The resulting residue was purified by chromatography on silica gel with ethyl acetate in hexanes (0 to 100%) to afford the desired product as a yellow solid in 95% yield.

Example 051: N-(4-(8-bromo-6-fluoroquinolin-2-yl)-2-methylphenyl)-1-methyl-1H-pyrazole-5-carboxamide

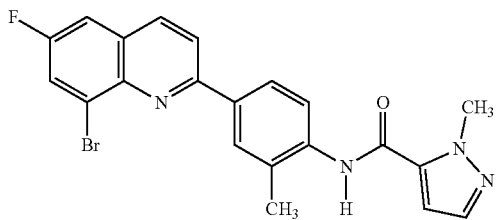 [SMILES: Cc1cc(-c2ccc3cc(F)cc(Br)c3n2)ccc1NC(=O)c1ccnn1C]

The title compound was prepared analogously to Example 001 where 4-(8-bromo-6-fluoroquinolin-2-yl)-2-methylaniline was substituted in place of 2-methyl-4-(6-(trifluoromethyl)quinolin-2-yl)aniline. Yield=63%. LCMS (ES, m/z): [M+H]⁺ 439, 441; ¹H-NMR (400 MHz, CDCl₃, ppm): δ2.47 (s, 3H), δ4.26 (s, 3H), δ6.69-6.70 (d, 1H), δ7.43-7.45 (m, 1H), δ7.54-7.55 (d, 1H), δ7.65 (s, 1H), δ7.87-7.90 (m, 1H), δ7.96-7.98 (d, 1H), δ8.10-8.21 (m, 3H), δ8.25 (s, 1H)

Step 1:
4-(8-bromo-6-fluoroquinolin-2-yl)-2-methylaniline

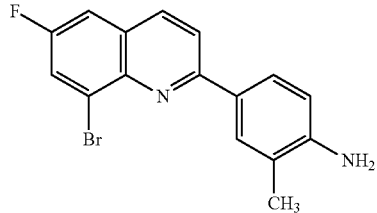 [SMILES: Cc1cc(-c2ccc3cc(F)cc(Br)c3n2)ccc1N]

The title compound was prepared analogously to Example 045, step 3, where 8-bromo-6-fluoro-2-(3-methyl-4-nitrophenyl)quinoline was substituted in place of 6-fluoro-2-(6-methyl-5-nitropyridin-2-yl)quinoline. Yield=38%.

Example 052: N-(4-(6-fluoro-8-methylquinolin-2-yl)-2-methylphenyl)-1-methyl-1H-pyrazole-5-carboxamide

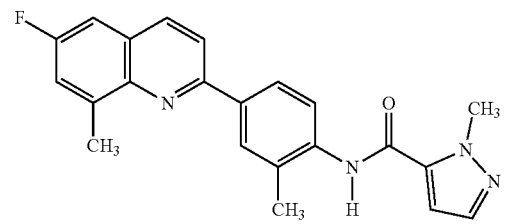

Pd(dppf)Cl₂ (16.7 mg, 0.02 mmol, 0.1 equiv) was added over a solution of N-(4-(8-bromo-6-fluoroquinolin-2-yl)-2-methylphenyl)-1-methyl-1H-pyrazole-5-carboxamide (100 mg, 0.23 mmol, 1 equiv), methylboronic acid (27.3 mg, 0.46 mmol, 2 equiv) and K₂CO₃ (62.9 mg, 0.46 mmol, 2 equiv) in toluene (2 mL). The resulting solution was stirred at 100° C. overnight and then quenched by the addition of 5 mL of water. The mixture was extracted with ethyl acetate (2×5 mL) and the organic layers combined and concentrated under reduced pressure. The residue was purified by silica gel chromatography with dichloromethane/methanol (30/1) to afford the desired final product as a white solid in 48% yield. LCMS (ES, m/z): [M+H]⁺ 375; ¹H-NMR (400 MHz, DMSO-d₆, ppm): δ2.37 (s, 3H), δ2.85 (s, 3H), δ4.11 (s, 3H), δ7.10-7.11 (d, 1H), δ7.53-7.64 (m, 4H), δ8.17-8.23 (m, 3H), δ8.41-8.43 (d, 1H), δ9.97 (s, 1H)

Example 053: N-(4-(8-cyclopropyl-6-fluoroquinolin-2-yl)-2-methylphenyl)-1-methyl-1H-pyrazole-5-carboxamide

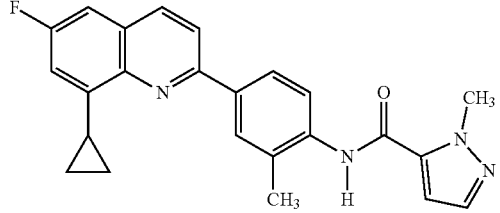 [SMILES: Cc1cc(-c2ccc3cc(F)cc(C4CC4)c3n2)ccc1NC(=O)c1ccnn1C]

The title compound was prepared analogously to Example 052, where cyclopropylboronic acid was substituted in place of methylboronic acid. Yield=42%. LCMS (ES, m/z): [M+H]+ 401; 1H-NMR (400 MHz, CDCl3, ppm): δ0.90-0.94 (m, 2H), δ1.26-1.29 (m, 2H), δ2.46 (s, 3H), δ3.47-3.56 (m, 1H), δ4.26 (s, 3H), δ6.68-6.69 (d, 1H), δ6.91-6.94 (m, 1H), δ7.20-7.23 (m, 1H), δ7.54 (s, 1H), δ7.63 (s, 1H), δ7.91-7.93 (d, 1H), δ8.08-8.18 (m, 4H)

Example 054: N-(4-(8-cyano-6-fluoroquinolin-2-yl)-2-methylphenyl)-1-methyl-1H-pyrazole-5-carboxamide

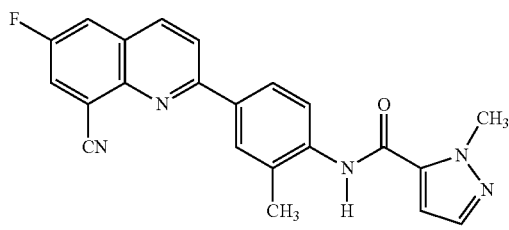 [SMILES: Cc1cc(-c2ccc3cc(F)cc(C#N)c3n2)ccc1NC(=O)c1ccnn1C]

Over a solution of N-[4-(8-bromo-6-fluoroquinolin-2-yl)-2-methylphenyl]-1-methyl-1H-pyrazole-5-carboxamide (100 mg, 0.23 mmol, 1 equiv) in DMSO (2 mL), CuCN (81.6 mg, 0.91 mmol, 4.002 equiv) was added. The resulting solution was stirred for 4 hr at 140° C. and then quenched by the addition of 6 mL of water. The mixture was extracted with ethyl acetate and the combined organic layers (2×4 ml) concentrated. The residue was purified by preparative TLC with dichloromethane/methanol (20/1) to afford the desired product as a white solid in 41% yield. LCMS (ES, m/z): [M+H]+ 386; H-NMR (400 MHz, DMSO-d6, ppm): δ2.39 (s, 3H), δ4.11 (s, 3H), δ7.12 (s, 1H), δ7.57-7.63 (m, 2H), δ8.23-8.29 (m, 3H), δ8.40-8.47 (m, 2H), δ8.60-8.62 (d, 1H)

Example 055: N-(4-(6-fluoro-8-isopropylquinolin-2-yl)-2-methylphenyl)-1-methyl-1H-pyrazole-5-carboxamide

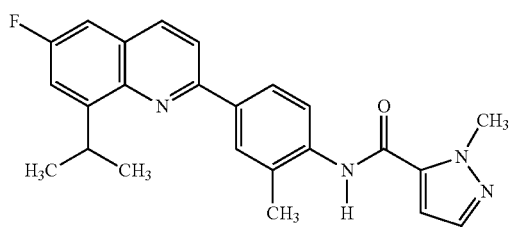 [SMILES: Cc1cc(-c2ccc3cc(F)cc(C(C)C)c3n2)ccc1NC(=O)c1ccnn1C]

A solution of N-(4-(6-fluoro-8-(prop-1-en-2-yl)quinolin-2-yl)-2-methylphenyl)-1-methyl-1H-pyrazole-5-carboxamide (45 mg, 0.11 mmol, 1 equiv) and 10% Pd on carbon (10 mg) in MeOH (5 mL) and THF (5 mL) was hydrogenated at atmospheric pressure and room temperature for 2 hours. The solids were filtered out and the organic solution concentrated. The residue was purified by preparative TLC with dichloromethane/methanol (30/1) to afford the desired product as a white solid in 22% yield. LCMS (ES, m/z): [M+H]+ 403; 1H-NMR (300 MHz, DMSO-d6, ppm): δ1.29-1.40 (d, 6H), δ2.36 (s, 3H), δ4.09 (s, 3H), δ4.36-4.42 (m, 1H), δ7.09 (s, 1H), δ7.50-7.62 (m, 4H), δ8.14-8.21 (m, 3H), δ8.39-8.42 (d, 1H), δ9.95 (s, 1H)

Step 1: N-(4-(6-fluoro-8-(prop-1-en-2-yl)quinolin-2-yl)-2-methylphenyl)-1-methyl-1H-pyrazole-5-carboxamide

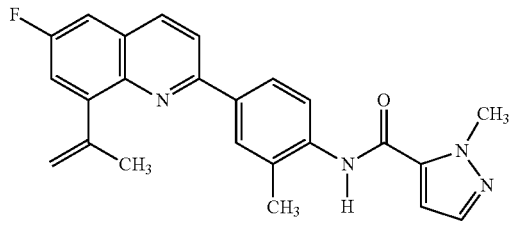 [SMILES: C=C(C)c1cc(F)cc2ccc(-c3ccc(NC(=O)c4ccnn4C)c(C)c3)nc12]

The title compound was prepared analogously to Example 052, where 4,4,5,5-tetramethyl-2-(prop-1-en-2-yl)-1,3,2-dioxaborolane acid was substituted in place of methylboronic acid. Yield=38%.

Example 056: N-(4-(8-methoxyquinolin-2-yl)-2-methylphenyl)-1-methyl-1H-pyrazole-5-carboxamide

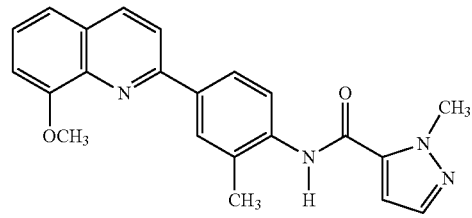 [SMILES: COc1cccc2ccc(-c3ccc(NC(=O)c4ccnn4C)c(C)c3)nc12]

The title compound was prepared analogously to Example 001, where 4-(8-methoxyquinolin-2-yl)-2-methylaniline was substituted in place of 2-methyl-4-(6-(trifluoromethyl)quinolin-2-yl)aniline. Yield=74%. LCMS (ES, m/z): [M+H]+ 373; 1H-NMR (300 MHz, CDCl3, ppm): δ2.44 (s, 3H), δ4.11 (s, 3H), δ4.25 (s, 3H), δ6.68 (s, 1H), δ7.07-7.09 (d, 1H), δ7.39-7.48 (m, 2H), δ7.52-7.53 (d, 1H), δ7.57 (s, 1H), δ7.90-7.92 (d, 1H), δ7.98-8.01 (d, 1H), δ8.11-8.20 (m, 3H).

Step 1: 8-methoxy-2-(3-methyl-4-nitrophenyl)quinoline

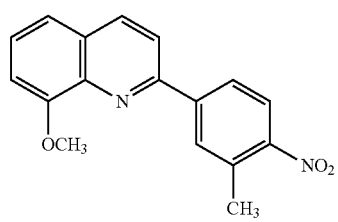 [SMILES: COc1cccc2ccc(-c3ccc([N+](=O)[O-])c(C)c3)nc12]

The title compound was prepared analogously to Example 001, step 4 where 2-chloro-8-(methoxy)quinoline was substituted in place of 2-chloro-6-(trifluoromethyl)quinoline. Yield=73%.

Step 2: 4-(8-methoxyquinolin-2-yl)-2-methylaniline

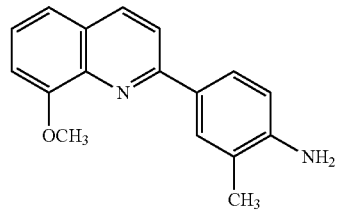

The title compound was prepared analogously to Example 045, step 3 where 8-methoxy-2-(3-methyl-4-nitrophenyl)quinoline was substituted in place of 6-fluoro-2-(6-methyl-5-nitropyridin-2-yl)quinoline. Yield=99%.

Example 057: 1-methyl-N-(2-methyl-4-(5-(trifluoromethyl)quinolin-2-yl)phenyl)-1H-pyrazole-5-carboxamide

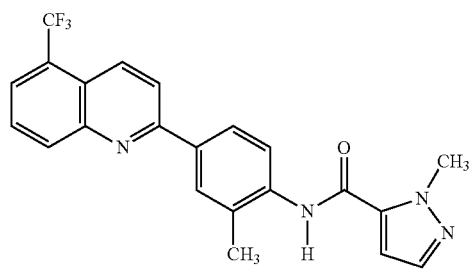 [SMILES: Cc1cc(-c2ccc3c(C(F)(F)F)cccc3n2)ccc1NC(=O)c1ccnn1C]

The title compound was prepared analogously to Example 001, step 4, where 2-chloro-5-(trifluoromethyl)quinoline was substituted in place of 2-chloro-6-(trifluoromethyl)quinoline and 1-methyl-N-[2-methyl-4-(tetramethyl-1,3,2-dioxaborolan-2-yl)phenyl]-1H-pyrazole-5-carboxamide was substituted in place of 2-methyl-4-(4,4,5,5-tetramethyl-1,3,2-dioxaborolan-2-yl)aniline. Yield=63%. LCMS: (ES, m/z): [M+H]$^+$ 411; $^1$H-NMR: (400 MHz, DMSO-d$_6$, ppm): δ9.99 (s, 1H), δ8.57-8.55 (d, 1H), δ8.41-8.38 (d, 2H), δ8.26 (s, 1H), δ8.19-8.17 (d, 1H), δ8.09-8.07 (d, 1H), δ7.96-7.92 (t, 1H), δ7.61-7.56 (m, 2H), δ7.12-7.11 (d, 1H), δ4.11 (s, 3H), δ2.08 (s, 3H).

Step 1: ethyl (E)-3-(2-amino-6-(trifluoromethyl)phenyl)acrylate

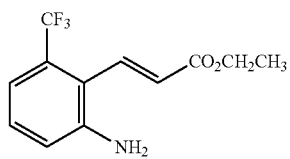

The title compound was prepared analogously to Example 001, step 1, where 2-bromo-3-(trifluoromethyl)aniline was substituted in place of 2-bromo-4-(trifluoromethyl)aniline. Yield=69%.

Step 2: 5-(trifluoromethyl)quinolin-2(1H)-one

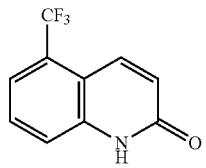 [SMILES: O=c1ccc2c(C(F)(F)F)cccc2[nH]1]

The title compound was prepared analogously to Example 001, step 2, where ethyl (E)-3-(2-amino-6-(trifluoromethyl)phenyl)acrylate was substituted in place of (E)-3-(2-amino-5-(trifluoromethyl)phenyl)acrylate. Yield=35%.

Step 3: 2-chloro-5-(trifluoromethyl)quinoline

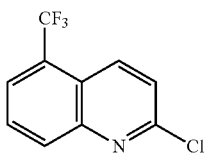

The title compound was prepared analogously to Example 001, step 3, where 5-(trifluoromethyl)quinolin-2(1H)-one was substituted in place of 6-(trifluoromethyl)-1,2-dihydroquinolin-2-one. Yield=52%.

Example 058: N-(4-(6-fluoro-8-(trifluoromethyl)quinolin-2-yl)-2-methylphenyl)-1-methyl-1H-pyrazole-5-carboxamide

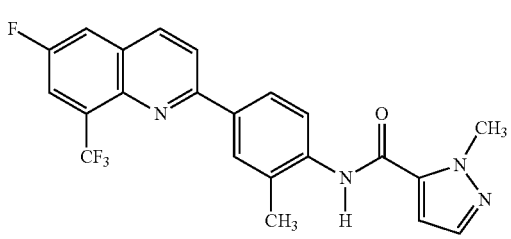 [SMILES: Cc1cc(-c2ccc3cc(F)cc(C(F)(F)F)c3n2)ccc1NC(=O)c1ccnn1C]

The title compound was prepared analogously to Example 001 where 4-(6-fluoro-8-(trifluoromethyl) quinolin-2-yl)-2-methylaniline was substituted in place of 2-methyl-4-(6-(trifluoromethyl)quinolin-2-yl)aniline. Yield=51%. LCMS (ES, m/z): [M+H]$^+$ 429; $^1$H-NMR (400 MHz, CDCl$_3$, ppm): δ2.46 (s, 3H), δ4.26 (s, 3H), δ6.68-6.69 (d, 1H), δ7.54 (s, 1H), δ7.61-7.64 (m, 2H), δ7.86-7.88 (m, 1H), δ8.02-8.04 (d, 1H), δ8.10-8.11 (d, 1H), δ8.12-8.22 (m, 3H)

Step 1: ethyl (E)-3-(2-amino-5-fluoro-3-(trifluoromethyl)phenyl)acrylate

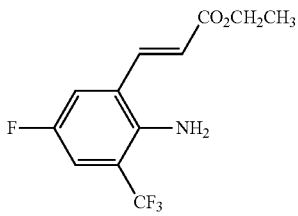

The title compound was prepared analogously to Example 001, step 1, where 2-bromo-4-fluoro-6-(trifluoromethyl)aniline was substituted in place of 2-bromo-4-(trifluoromethyl)aniline. Yield=23%.

Step 2:
6-fluoro-8-(trifluoromethyl)quinolin-2(1H)-one

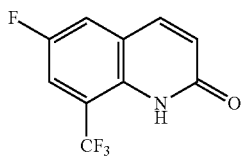

The title compound was prepared analogously to Example 001, step 2, where ethyl (E)-3-(2-amino-5-fluoro-3-(trifluoromethyl)phenyl)acrylate was substituted in place of (E)-3-(2-amino-5-(trifluoromethyl)phenyl)acrylate. Yield=81%.

Step 3:
2-chloro-6-fluoro-8-(trifluoromethyl)quinoline

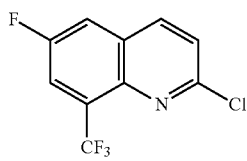 [SMILES: Fc1cc(C(F)(F)F)c2nc(Cl)ccc2c1]

The title compound was prepared analogously to Example 001 step 3, where 6-fluoro-8-(trifluoromethyl)quinolin-2(1H)-one was substituted in place of 6-(trifluoromethyl)-1,2-dihydroquinolin-2-one. Yield=34%.

Step 4: 4-(6-fluoro-8-(trifluoromethyl)quinolin-2-yl)-2-methylaniline

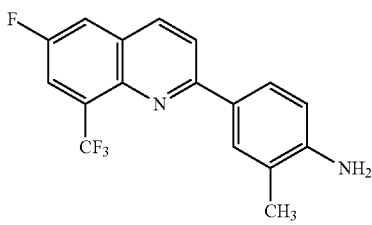 [SMILES: Cc1cc(-c2ccc3cc(F)cc(C(F)(F)F)c3n2)ccc1N]

The title compound was prepared analogously to Example 001, step 4, where 2-chloro-6-fluoro-8-(trifluoromethyl)quinoline was substituted in place 2-chloro-6-(trifluoromethyl)quinoline. Yield=88%.

Example 059: 1-methyl-N-(2-methyl-4-(8-methyl-1,6-naphthyridin-2-yl)phenyl)-1H-pyrazole-5-carboxamide

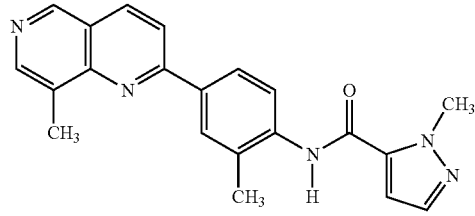 [SMILES: Cc1cc(-c2ccc3cncc(C)c3n2)ccc1NC(=O)c1ccnn1C]

The title compound was prepared analogously to Example 001, where 2-methyl-4-(8-methyl-1,6-naphthyridin-2-yl)aniline was substituted in place of 2-methyl-4-(6-(trifluoromethyl)quinolin-2-yl)aniline. Yield=20%. LCMS (ES, m/z): [M+H]$^+$ 358; $^1$H-NMR (DMSO-d$_6$, 300 MHz, ppm): δ2.27 (s, 3H), δ2.83 (s, 3H), δ4.20 (s, 3H), δ7.12 (s, 1H), δ7.56-7.64 (m, 2H), δ8.23-8.26 (d, 1H), δ8.30 (s, 1H), δ8.34-8.37 (d, 1H), δ8.61-8.64 (d, 2H), δ9.24 (s, 1H), δ10.00 (s, 1H).

Step 1: ethyl (E)-3-(4-amino-5-methylpyridin-3-yl)acrylate

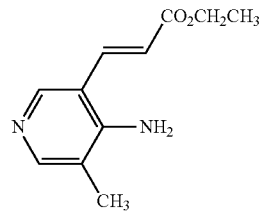

The title compound was prepared analogously to Example 001, step 1, where 3-bromo-5-methylpyridin-4-amine was substituted in place of 2-bromo-4-(trifluoromethyl)aniline. Yield=52%.

Step 2: 8-methyl-1,6-naphthyridin-2(1H)-one

EtONa (2.9 g, 4.00 equiv) was added over a solution of ethyl 3-(4-amino-5-methylpyridin-3-yl)acrylate (2.2 g, 10.67 mmol, 1.00 equiv) in ethanol (66 mL). The resulting solution was stirred for 2 h at 80° C. The reaction was then quenched by the addition of 100 mL of saturated NH$_4$Cl and extracted with ethyl acetate (3×50 mL). The organic layers were combined and concentrated under reduced pressure to afford the desired final product as a white solid in 9% yield.

Step 3: 2-chloro-8-methyl-1,6-naphthyridine

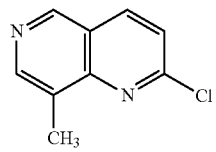

Over a solution of 8-methyl-1,2-dihydro-1,6-naphthyridin-2-one (130 mg, 0.81 mmol, 1.00 equiv) in toluene (5 mL), PPh$_3$ (638.8 mg, 2.44 mmol, 3.00 equiv) and Cl$_3$CCN (116 mg, 1.00 equiv) were added. The solution was stirred at 110° C. for 3 hours. The pH value of the solution was adjusted to 7 with 2N HCl and extracted with ethyl acetate (3×20 mL). The organic layers were combined and concentrated under reduced pressure. The resulting residue was purified by preparative TLC with dichloromethane/methanol (25:1) as eluent to afford the final product as a yellow solid in 21% yield.

Step 4:
2-methyl-4-(8-methyl-1,6-naphthyridin-2-yl)aniline

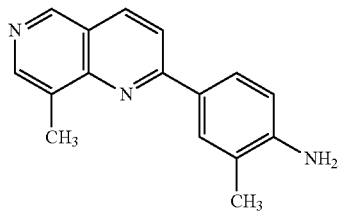 [SMILES: Cc1cc(-c2ccc3cncc(C)c3n2)ccc1N]

The title compound was prepared analogously to Example 001, step 4, where 2-chloro-8-methyl-1,6-naphthyridine was substituted in place of 2-chloro-6-(trifluoromethyl)quinoline and 2-methyl-4-(4,4,5,5-tetramethyl-1,3,2-dioxaborolan-2-yl)aniline was substituted in place of 3-methyl-4-(tetramethyl-1,3,2-dioxaborolan-2-yl)aniline. Yield=72%.

Example 060: N-(4-(4-chloroisoquinolin-6-yl)-2-methylphenyl)-1-methyl-1H-pyrazole-5-carboxamide

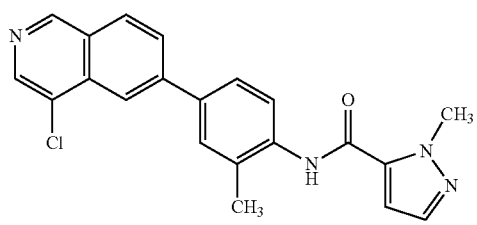 [SMILES: Cc1cc(-c2ccc3cncc(Cl)c3c2)ccc1NC(=O)c1ccnn1C]

The title compound was prepared analogously to Example 001, where 4-(4-chloroisoquinolin-6-yl)-2-methylaniline was substituted in place of 2-methyl-4-(6-(trifluoromethyl)quinolin-2-yl)aniline. Yield=89%. LCMS (ES, m/z): [M+H]$^+$ 377; 1H-NMR: (300 MHz, DMSO-d$_6$, ppm): δ2.37 (s, 3H), δ4.10 (s, 3H), δ7.09-7.10 (d, 1H), δ7.54-7.56 (m, 2H), δ7.75-7.84 (m, 2H), δ8.18-8.37 (m, 3H), δ8.68 (s, 1H), δ9.35 (s, 1H), δ9.98 (s, 1H)

Step 1:
4-chloro-6-(3-methyl-4-nitrophenyl)isoquinoline

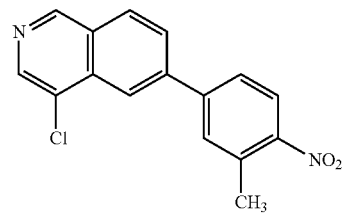

Na$_2$CO$_3$ (524.5 mg, 4.95 mmol, 2 equiv) and Pd(dppf)Cl$_2$ (181.0 mg, 0.25 mmol, 0.1 equiv) were added to a solution of 6-bromo-4-chloroisoquinoline (600 mg, 2.47 mmol, 1 equiv) and 4,4,5,5-tetramethyl-2-(3-methyl-4-nitrophenyl)-1,3,2-dioxaborolane (976.4 mg, 3.71 mmol, 1.5 equiv) in DME (6 ml) and water (1.5 mL). The mixture was stirred at 50° C. for four hours. Volatiles were removed under reduced pressure and the residue was purified by silica gel column chromatography with petroleum ether/ethyl acetate (10:1) to afford the desired final product as a brown solid (700 mg, 95%)

Step 2: 4-(4-chloroisoquinolin-6-yl)-2-methylaniline

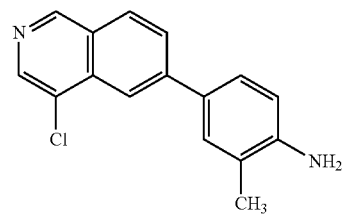 [SMILES: Cc1cc(-c2ccc3cncc(Cl)c3c2)ccc1N]

The title compound was prepared analogously to Example 045, step 3 where 4-chloro-6-(3-methyl-4-nitrophenyl)isoquinoline was substituted in place of 6-fluoro-2-(6-methyl-5-nitropyridin-2-yl)quinoline. Yield=58%.

Example 061: 1-methyl-N-(2-methyl-4-(4-methylisoquinolin-6-yl)phenyl)-1H-pyrazole-5-carboxamide

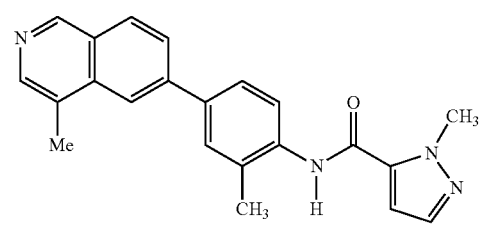 [SMILES: Cc1cc(-c2ccc3cncc(C)c3c2)ccc1NC(=O)c1ccnn1C]

To a solution of N-[4-(4-chloroisoquinolin-6-yl)-2-methylphenyl]-1-methyl-1H-pyrazole-5-carboxamide (300 mg, 0.80 mmol, 1 equiv) in DMF (3 mL), methylboronic acid (143.0 mg, 2.39 mmol, 3 equiv) was added, followed by KOAc (234.4 mg, 2.39 mmol, 3 equiv) and Pd(dppf)Cl$_2$ (58.3 mg, 0.08 mmol, 0.1 equiv). The resulting mixture was heated at 140 degree ° C. overnight. The reaction was quenched with water, extracted with CH$_2$Cl$_2$ (2×5 mL) and the organic layers combined and concentrated under vacuum. The residue was purified by Prep-TLC with dichloromethane/MeOH (20:1) to afford the desired product as a white solid in 47% yield. LCMS (ES, m/z): [M+H]$^+$ 357; $^1$H-NMR (400 MHz, DMSO-d$_6$, ppm): δ2.37 (s, 3H), δ2.69 (s, 3H), δ4.10 (s, 3H), δ7.09-7.10 (d, 1H), δ7.55-7.56 (d, 1H), δ7.60 (s, 1H), δ7.77-7.81 (m, 1H), δ7.89 (s, 1H), δ8.06-8.08 (m, 1H), δ8.20-8.25 (m, 2H), δ8.34 (s, 1H), δ9.19 (s, 1H), δ9.98 (s, 1H)

Example 062: 1-methyl-N-(2-methyl-4-(4-methylcinnolin-6-yl)phenyl)-1H-pyrazole-5-carboxamide

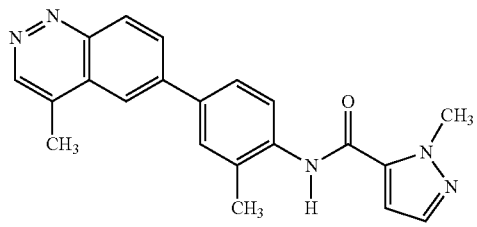 [SMILES: Cc1cc(-c2ccc3nncc(C)c3c2)ccc1NC(=O)c1ccnn1C]

The title compound was prepared analogously to Example 001, where 2-methyl-4-(4-methylcinnolin-6-yl)aniline was substituted in place of 2-methyl-4-(6-(trifluoromethyl)quinolin-2-yl)aniline. Yield=31%. LCMS (ES, m/z): [M+H]$^+$ 358; $^1$H-NMR (300 MHz, DMSO-d$_6$, ppm): δ2.38 (s, 3H), δ2.78 (s, 3H), δ4.11 (s, 3H), δ7.11 (s, 1H), δ7.53-7.56 (d, 2H), δ7.81-7.84 (d, 1H), δ7.91 (s, 1H), δ8.30-8.33 (d, 1H), δ8.39 (s, 1H), δ8.49-8.52 (d, 1H), δ9.26 (s, 1H), δ9.98 (s, 1H)

Step 1: 4-(4-chlorocinnolin-6-yl)-2-methylaniline

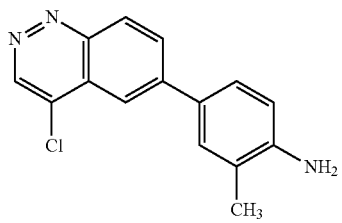 [SMILES: Cc1cc(-c2ccc3nncc(Cl)c3c2)ccc1N]

The title compound was prepared analogously to Example 042, step 1 where 2-methyl-4-(4,4,5,5-tetramethyl-1,3,2-dioxaborolan-2-yl)aniline was substituted in place of 3-methyl-5-(tetramethyl-1,3,2-dioxaborolan-2-yl)pyridin-2-amine and 6-bromo-4-chlorocinnoline was substituted in place of 2-chloro-6-fluoroquinoline. Yield=58%.

Step 2: 2-methyl-4-(4-methylcinnolin-6-yl)aniline

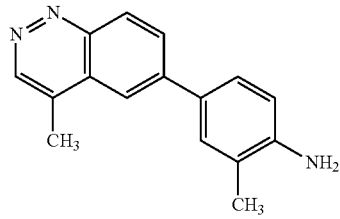 [SMILES: Cc1cc(-c2ccc3nncc(C)c3c2)ccc1N]

K$_2$CO$_3$ (276.7 mg, 2.00 mmol, 3 equiv) and Pd(dppf)Cl$_2$ (48.8 mg, 0.07 mmol, 0.1 equiv) were added to a solution of 4-(4-chlorocinnolin-6-yl)-2-methylaniline (180 mg, 0.67 mmol, 1 equiv) and methylboronic acid (119.8 mg, 2.00 mmol, 3 equiv) in DMF (2 mL). The resulting mixture was stirred under nitrogen at 140° C. overnight. The reaction was quenched by the addition of water (20 mL). The resulting mixture was extracted with ethyl acetate (2×20 mL) and the combined organic layers were combined and concentrated under reduced pressure. The residue was purified by preparative TLC (CH$_2$Cl$_2$/MeOH=20/1) to afford the desired product as a yellow solid in 30% yield Example 063: N-(4-(6-(1H-tetrazol-5-yl)quinolin-2-yl)-2-methylphenyl)-1-methyl-1H-pyrazole-5-carboxamide

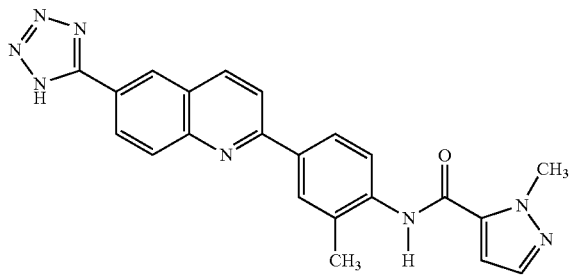 [SMILES: Cc1cc(-c2ccc3cc(-c4nnn[nH]4)ccc3n2)ccc1NC(=O)c1ccnn1C]

To a solution of N-[4-(6-cyanoquinolin-2-yl)-2-methylphenyl]-1-methyl-1H-pyrazole-5-carboxamide (100 mg, 0.27 mmol, 1 equiv) in DMF (5 mL, 0.07 mmol, 0.251 equiv), NH$_4$Cl (145.6 mg, 2.72 mmol, 10 equiv) and NaN$_3$ (88.5 mg, 1.36 mmol, 5 equiv) were added. The resulting solution was stirred overnight at 120° C. The reaction was quenched by the addition of 20 mL of water, extracted with ethyl acetate (3×20 ml). The organic layers were combined and concentrated under reduced pressure. The crude product was purified by preparative HPLC (Column: XBridge C18 OBD, 100 Å, 5 μm, 19 mm×250 mm; mobile phase=A: Water (10 mmol/L NH$_4$HCO$_3$), mobile phase B=acetonitrile; flow rate=25 mL/min; gradient: 5% B to 55% B in 7 min; Detector=254/220 nm; retention time=5.78 minutes) to afford the desired product as a yellow solid in 33% yield. LCMS (ES, m/z): [M+H]$^+$ 411; $^1$H-NMR (300 MHz, DMSO-d$_6$, ppm): δ2.40 (s, 3H), δ4.12 (s, 3H), δ7.11-7.12 (d, 1H), δ7.57-7.60 (t, 2H), δ8.14-8.41 (m, 5H), δ8.63-8.66 (d, 1H), δ8.73-8.74 (d, 1H), δ9.99 (s, 1H)

Example 064: N-(4-(6-bromoquinolin-2-yl)-2-methylphenyl)-1-methyl-1H-pyrazole-5-carboxamide

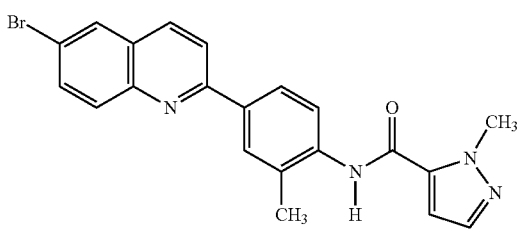

The title compound was prepared analogously to Example 001, where 4-(6-bromoquinolin-2-yl)-2-methylaniline was substituted in place of 2-methyl-4-(6-(trifluoromethyl)quinolin-2-yl)aniline. Yield=52%.

Step 1: 4-(6-bromoquinolin-2-yl)-2-methylaniline

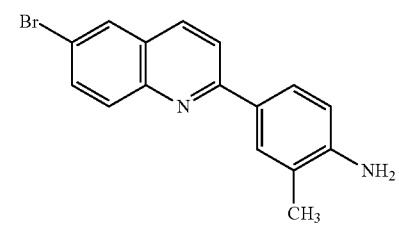

The title compound was prepared analogously to Example 001, step 4, where 6-bromo-2-chloroquinoline was substituted in place of 2-chloro-6-(trifluoromethyl)quinoline. Yield=70%.

Example 065: N-(4-(6-Chloroquinolin-2-yl)-2-methylphenyl)-1-methyl-1H-pyrazole-5-carboxamide

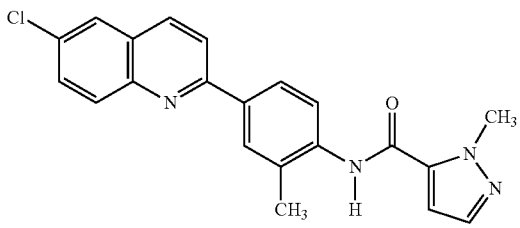 [SMILES: Cc1cc(-c2ccc3cc(Cl)ccc3n2)ccc1NC(=O)c1ccnn1C]

The title compound was prepared analogously to Example 003, where 4-(6-Chloroquinolin-2-yl)-2-methylaniline was substituted in place of 4-(quinoxalin-2-yl)aniline. Yield=35%. LCMS (ES, m/z): [M+H]$^+$ 377; $^1$H-NMR (400 MHz, CDCl$_3$, ppm): 8.20 (m, 4H), 8.01 (dd, 1H), 7.92 (d, 1H), 7.84 (d, 1H), 7.68 (m, 2H), 7.54 (d, 1H), 6.69 (d, 1H), 4.26 (s, 3H), 2.47 (s, 3H)

Step 1: 4-(6-Chloroquinolin-2-yl)-2-methylaniline

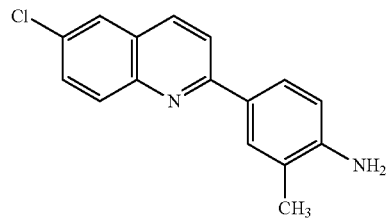 [SMILES: Cc1cc(-c2ccc3cc(Cl)ccc3n2)ccc1N]

The title compound was prepared analogously to Example 014, step 1, where 2,6-dichloroquinoline was substituted in place of 2-chloro-6-fluoroquinoline and 2-methyl-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=57%

Example 066: N-(2-fluoro-4-(6-fluoroquinolin-2-yl)phenyl)-1-methyl-1H-pyrazole-5-carboxamide

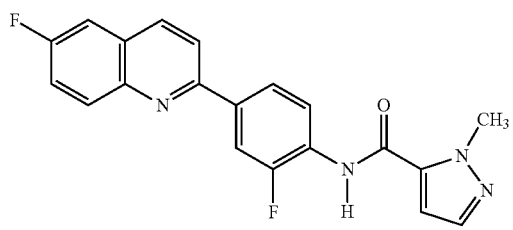 [SMILES: Cn1nccc1C(=O)Nc1ccc(-c2ccc3cc(F)ccc3n2)cc1F]

The title compound was prepared analogously to Example 003, where 2-fluoro-4-(6-fluoroquinolin-2-yl)aniline was substituted in place of 4-(quinoxalin-2-yl)aniline. Yield=20%. LCMS (ES, m/z): [M+H]$^+$ 365; $^1$H-NMR (400 MHz, CDCl$_3$, ppm): 8.56 (dd, 1H), 8.15 (m, 3H), 7.96 (m, 2H), 7.89 (d, 1H), 7.48 (m, 3H), 6.73 (d, 1H), 4.25 (s, 3H)

Step 1: 2-Fluoro-4-(6-fluoroquinolin-2-yl)aniline

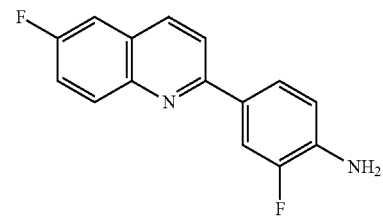 [SMILES: Nc1ccc(-c2ccc3cc(F)ccc3n2)cc1F]

The title compound was prepared analogously to Example 014, step 1, where 2-chloro-6-fluoroquinoline was substituted in place of 1-methyl-N-(2-methyl-4-(6-(trifluoromethyl)quinolin-2-yl)phenyl)-1H-pyrazole-5-carboxamide and 2-fluoro-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=79%

Example 067: N-(5-fluoro-4-(6-fluoroquinolin-2-yl)-2-methylphenyl)-1-methyl-1H-pyrazole-5-carboxamide

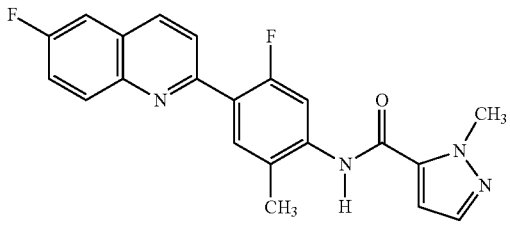 [SMILES: Cc1cc(-c2ccc3cc(F)ccc3n2)c(F)cc1NC(=O)c1ccnn1C]

The title compound was prepared analogously to Example 003, where 2-fluoro-4-(6-fluoroquinolin-2-yl)-5-methylaniline was substituted in place of 4-(quinoxalin-2-yl)aniline. Yield=32%. LCMS (ES, m/z): [M+H]$^+$ 379; $^1$H-NMR (400 MHz, CDCl$_3$, ppm): 8.4-7.92 (m, 5H), 7.67 (s, 1H), 7.50 (m, 3H), 6.69 (d, 1H), 4.26 (s, 3H), 2.42 (s, 3H)

Step 1:
5-fluoro-4-(6-fluoroquinolin-2-yl)-2-methylaniline

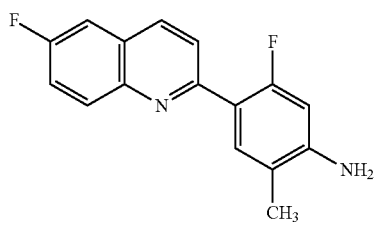 [SMILES: Cc1cc(-c2ccc3cc(F)ccc3n2)c(F)cc1N]

The title compound was prepared analogously to Example 014, step 1, where 2-fluoro-5-methyl-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=43%

Example 068: N-(4-(6-cyclopropylquinolin-2-yl)-2-methylphenyl)-1-methyl-1H-pyrazole-5-carboxamide

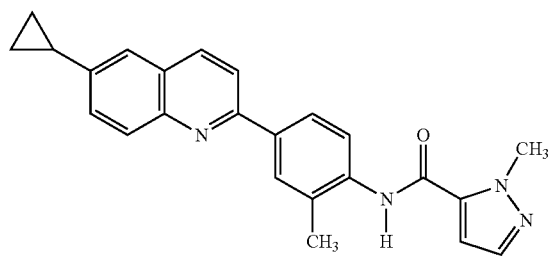 [SMILES: Cc1cc(-c2ccc3cc(C4CC4)ccc3n2)ccc1NC(=O)c1ccnn1C]

The title compound was prepared analogously to Example 052, where N-(4-(6-bromoquinolin-2-yl)-2-methylphenyl)-1-methyl-1H-pyrazole-5-carboxamide was substituted in place of N-(4-(8-bromo-6-fluoroquinolin-2-yl)-2-methylphenyl)-1-methyl-1H-pyrazole-5-carboxamide and cyclopropylboronic acid was substituted in place of methylboronic acid. Yield=53%; LCMS (ES, m/z): [M+H]$^+$ 383; $^1$H-NMR (400 MHz, CDCl$_3$, ppm): δ0.86-0.89 (m, 2H), δ1.08-1.19 (m, 2H), δ2.09-2.15 (m, 1H), δ2.47 (s, 3H), δ4.28 (s, 3H), δ6.70 (s, 1H), δ7.45-7.48 (m, 1H), δ7.52-7.56 (m, 2H), δ7.65 (s, 1H), δ7.84-7.86 (d, 1H), δ8.00-8.08 (m, 1H), δ8.10-8.19 (m, 4H).

Example 069: N-(4-(6-cyclopropylquinolin-2-yl)-2-methylphenyl)-N,1-dimethyl-1H-pyrazole-5-carboxamide

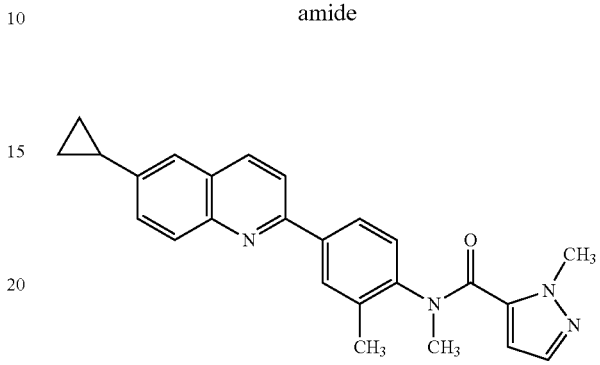

The title compound was prepared analogously to Example 002, where N-(4-(6-cyclopropylquinolin-2-yl)-2-methylphenyl)-1-methyl-1H-pyrazole-5-carboxamide was substituted in place of 1-methyl-N-(2-methyl-4-(6-(trifluoromethyl)quinolin-2-yl)phenyl)-1H-pyrazole-5-carboxamide. Yield=62%. LCMS (ES, m/z): [M+H]$^+$ 397; $^1$H-NMR (DMSO-d$_6$, 400 MHz, ppm): δ0.84-8.86 (m, 2H), δ1.06-1.09 (m, 2H), δ2.09-2.19 (m, 1H), δ2.25 (s, 3H), δ3.33 (s, 3H), δ4.00 (s, 3H), δ5.53-5.54 (d, 1H), δ7.14-7.15 (d, 1H), δ7.39-7.48 (d, 1H), δ7.49-7.55 (d, 1H), δ7.68-7.69 (d, 1H), δ7.94-7.96 (d, 1H), δ8.07-8.11 (m, 2H), δ8.18 (s, 1H), δ8.33-8.35 (d, 1H).

Example 070: 1-methyl-N-(2-methyl-4-(quinolin-2-yl)phenyl)-1H-pyrazole-5-carboxamide

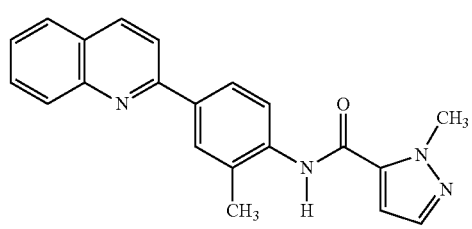 [SMILES: Cc1cc(-c2ccc3ccccc3n2)ccc1NC(=O)c1ccnn1C]

N-[4-(6-bromoquinolin-2-yl)-2-methylphenyl]-1-methyl-1H-pyrazole-5-carboxamide (70 mg, 0.17 mmol, 1 equiv) and 10% Pd on carbon (14 mg) were dissolved in ethyl acetate (5 mL). The mixture was hydrogenated at atmospheric pressure overnight. The solids were filtered out and the solution concentrated. The crude product was purified by preparative TLC (dichloromethane/MeOH=20/1) to afford the desired product as a white solid in 56% yield. LCMS (ES, m/z): [M+H]$^+$ 343; $^1$H-NMR: (DMSO-d$_6$, 300 MHz, ppm): δ2.38 (s, 3H), δ4.11 (s, 3H), δ7.10-7.11 (d, 1H), δ7.54-7.63 (m, 3H), δ7.76-7.81 (m, 1H), δ8.00-8.02 (d, 1H), δ8.07-8.10 (d, 1H), δ8.14-8.17 (d, 2H), δ8.20-8.23 (d, 1H), δ8.45-8.48 (d, 1H), δ9.97 (s, 1H).

Example 071: 1-methyl-N-(2-methyl-4-(6-morpholinoquinolin-2-yl)phenyl)-1H-pyrazole-5-carboxamide

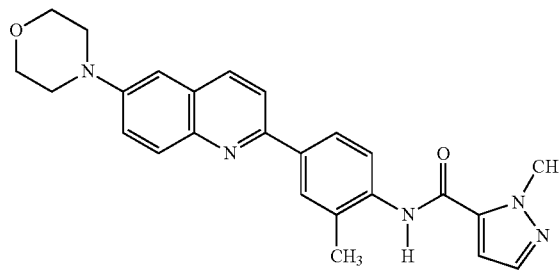

A mixture of N-[4-(6-bromoquinolin-2-yl)-2-methylphenyl]-1-methyl-1H-pyrazole-5-carboxamide (150 mg, 0.36 mmol, 1 equiv), morpholine (155.1 mg, 1.78 mmol, 5 equiv), t-BuONa (102.7 mg, 1.07 mmol, 3.001 equiv), Xantphos (41.2 mg, 0.07 mmol, 0.2 equiv), $Pd_2(dba)_3 \cdot CHCl_3$ (36.9 mg, 0.04 mmol, 0.1 equiv) in dioxane (3 mL) was stirred at 100° C. for 4 h. The reaction was then quenched by the addition of 10 mL of water and the resulting solution was extracted with ethyl acetate (3×20 mL) and the combined organic layers were concentrated. The residue was purified by preparative TLC with dichloromethane/methanol (20:1) to afford the desired product as a white solid. Yield=26%. LCMS (ES, m/z): $[M+H]^+$ 428; $^1$H-NMR (DMSO-$d_6$, 300 MHz, ppm): δ2.36 (s, 3H), δ3.27-3.32 (m, 4H), δ3.79-3.82 (t, 4H), δ4.10 (s, 3H), δ7.10 (s, 1H), δ7.23-7.24 (d, 1H), δ7.49-7.52 (d, 1H), δ7.55-7.56 (d, 1H), δ7.63-7.67 (t, 1H), δ7.92-7.95 (d, 1H), δ8.03-8.10 (m, 2H), δ8.16 (s, 1H), δ8.22-8.25 (d, 1H), δ9.94 (s, 1H).

Example 072: N-(4-(6-ethynylquinolin-2-yl)-2-methylphenyl)-1-methyl-1H-pyrazole-5-carboxamide

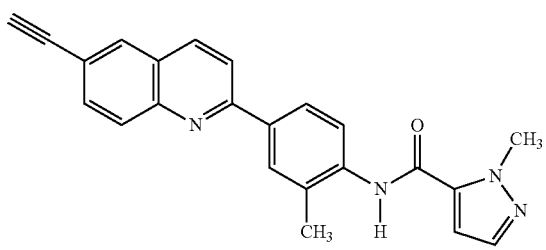 [SMILES: C#Cc1ccc2nc(-c3ccc(NC(=O)c4ccnn4C)c(C)c3)ccc2c1]

To a stirred mixture of 1-methyl-N-(2-methyl-4-(6-((trimethylsilyl)ethynyl)quinolin-2-yl)phenyl)-1H-pyrazole-5-carboxamide (100 mg, 0.23 mmol, 1 equiv) in MeOH (4 mL) was added $K_2CO_3$ (3.2 mg, 0.02 mmol, 0.1 equiv). The resulting mixture was stirred at room temperature for 1 hour. The reaction was quenched by the addition of water (20 mL) and the resulting mixture was extracted with EtOAc (2×10 mL). The combined organic layers were concentrated under reduced pressure. The crude product was recrystallized with MeOH (5 mL) to afford the desired product as a yellow solid in 98% yield. LCMS: (ES, m/z): $[M+H]^+$ 367; $^1$H-NMR: (300 MHz, DMSO-$d_6$, ppm): δ2.39 (s, 3H), δ4.11 (s, 3H), δ4.39 (s, 1H), δ7.11-7.12 (d, 1H), δ7.55-7.58 (q, 2H), δ7.78-7.81 (q, 1H), δ8.05-8.08 (d, 1H), δ8.15-8.25 (m, 4H), δ8.46-8.49 (d, 1H), δ9.98 (s, 1H).

Step 1: 1-methyl-N-(2-methyl-4-(6-((trimethylsilyl)ethynyl)quinolin-2-yl)phenyl)-1H-pyrazole-5-carboxamide

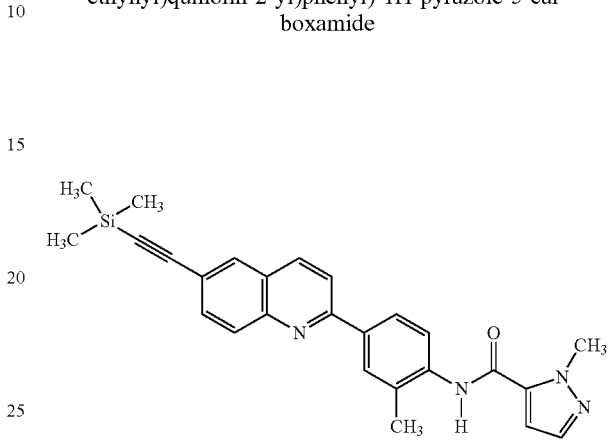

$Et_3N$ (108.1 mg, 1.07 mmol, 3 equiv), CuI (6.8 mg, 0.04 mmol, 0.1 equiv) and $Pd(PPh_3)_2Cl_2$ (25.0 mg, 0.04 mmol, 0.1 equiv) were added to a solution of N-[4-(6-bromoquinolin-2-yl)-2-methylphenyl]-1-methyl-1H-pyrazole-5-carboxamide (150 mg, 0.36 mmol, 1 equiv) and ethynyltrimethylsilane (174.9 mg, 1.78 mmol, 5 equiv) in 1,4-dioxane (1.5 mL). The resulting mixture was stirred under nitrogen at 120° C. for 5 hours. The reaction was quenched by the addition of water (20 mL) and extracted with EtOAc (2×20 mL). The combined organic layers were concentrated under reduced pressure and the residue purified by preparative TLC (dichloromethane/MeOH=35/1) to afford the desired product as a white solid in 77% yield.

Example 073: N-(4-(6-cyanoquinolin-2-yl)-2-methylphenyl)-1-methyl-1H-pyrazole-5-carboxamide

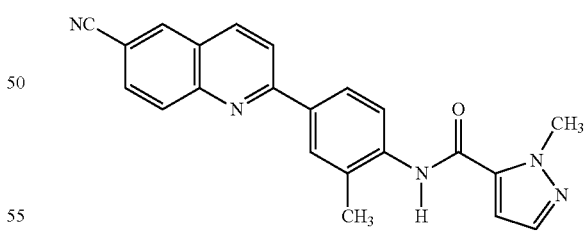

The title compound was prepared analogously to Example 054, where N-[4-(6-bromoquinolin-2-yl)-2-methylphenyl]-1-methyl-1H-pyrazole-5-carboxamide was substituted in place of N-[4-(8-bromo-6-fluoroquinolin-2-yl)-2-methylphenyl]-1-methyl-1H-pyrazole-5-carboxamide.
Yield=58%. LCMS: (ES, m/z): $[M+H]^+$ 368; $^1$H-NMR (400 MHz, CDCl$_3$, ppm): δ2.47 (s, 3H), δ4.26 (s, 3H), δ6.69-6.70 (d, 1H), δ7.54-7.55 (d, 1H), δ7.67 (s, 1H), δ7.85-7.88 (q, 1H), δ8.00-8.02 (d, 1H), δ8.05-8.07 (q, 1H), δ8.19 (s, 1H), δ8.23-8.28 (m, 4H).

Example 074: 2-(3-methyl-4-(1-methyl-1H-pyrazole-5-carboxamido)phenyl)quinoline-6-carboxamide

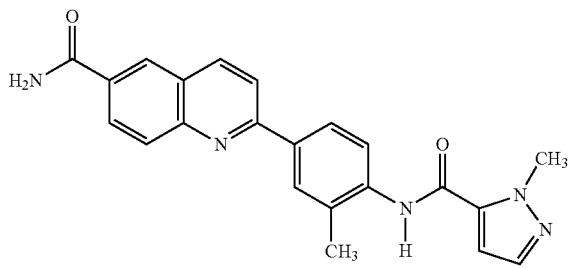 [SMILES: Cc1cc(-c2ccc3cc(C(N)=O)ccc3n2)ccc1NC(=O)c1ccnn1C]

To a solution of N-[4-(6-cyanoquinolin-2-yl)-2-methylphenyl]-1-methyl-1H-pyrazole-5-carboxamide (90 mg, 0.24 mmol, 1 equiv) in MeOH (10 mL) was added NaOH (19.6 mg, 0.49 mmol, 2 equiv) dissolved in 1 mL of water and $H_2O_2$ (0.5 mL). The resulting mixture was stirred under nitrogen at room temperature overnight. The precipitated solids were collected by filtration and washed with water (3×100 mL). The resulting solid was dried to afford the desired product as a yellow solid in 78% yield. LCMS (ES, m/z): [M+H]$^+$ 386; $^1$H-NMR (300 MHz, DMSO-$d_6$, ppm): δ2.39 (s, 3H), δ4.11 (s, 3H), δ7.11 (s, 1H), δ7.50-7.71 (m, 3H), δ8.14-8.26 (m, 6H), δ8.56-8.70 (m, 2H), δ9.99 (s, 1H)

Example 075: N-(4-(6-aminoquinolin-2-yl)-2-methylphenyl)-1-methyl-1H-pyrazole-5-carboxamide

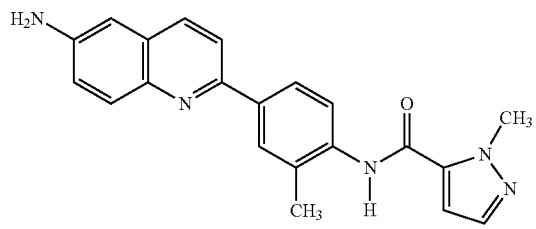 [SMILES: Cc1cc(-c2ccc3cc([N+](=O)[O-])ccc3n2)ccc1NC(=O)c1ccnn1C]

A mixture of 1-methyl-N-[2-methyl-4-(6-nitroquinolin-2-yl)phenyl]-1H-pyrazole-5-carboxamide (100 mg, 0.26 mmol, 1.00 equiv) and 10% palladium on carbon (40 mg) in methanol (8 mL) and tetrahydrofuran (4 mL) was hydrogenated for 2 hours at 60° C. The solids were filtered out and the solution concentrated under reduced pressure. The residue was purified by preparative TLC with ethyl acetate/petroleum ether (1:5) to afford the desired product as a white solid in 76% yield. LCMS (ES, m/z): [M+H]$^+$ 358; $^1$H-NMR (DMSO-$d_6$, 300 MHz ppm): δ2.35 (s, 3H), δ4.11 (s, 3H), δ5.66 (s, 2H), δ6.82-6.83 (s, 1H), δ7.10 (s, 1H), δ7.19-7.20 (d, 1H), δ7.46-7.49 (d, 1H), δ7.55-7.56 (s, 1H), δ7.76-7.78 (d, 1H), δ7.90-7.93 (d, 1H), δ8.01-8.04 (d, 2H), δ8.11 (s, 1H), δ9.93 (s, 1H)

Example 076: 1-methyl-N-(2-methyl-4-(6-nitroquinolin-2-yl)phenyl)-1H-pyrazole-5-carboxamide

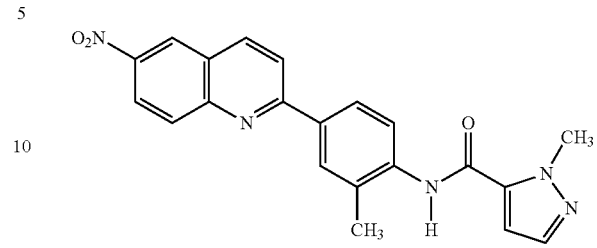

The title compound was prepared analogously to Example 001 where 2-methyl-4-(6-nitroquinolin-2-yl)aniline was substituted in place of 2-methyl-4-(6-(trifluoromethyl)quinolin-2-yl)aniline. Yield=65%. LCMS (ES, m/z): [M+H]$^+$ 388; $^1$H-NMR (DMSO-$d_6$, 300 MHz ppm): 2.40 (s, 3H), δ4.12 (s, 3H), δ7.11-7.12 (d, 1H), δ7.57-7.63 (m, 2H), δ8.21-8.30 (m, 3H), δ8.38-8.41 (d, 1H), δ8.41-8.46 (d, 1H), δ8.78-8.81 (d, 1H), δ9.08-9.09 (s, 1H), δ10.00 (s, 1H).

Step 1: Ethyl (E)-3-(2-amino-5-nitrophenyl)acrylate

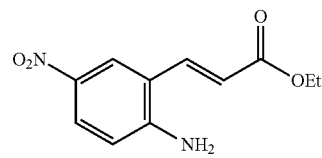 [SMILES: CCOC(=O)/C=C/c1cc([N+](=O)[O-])ccc1N]

The title compound was prepared analogously to Example 001, step 1, where 2-bromo-4-nitroaniline was substituted in place of 2-bromo-4-(trifluoromethyl)aniline. Yield=64%.

Step 2: 6-nitroquinolin-2(1H)-one

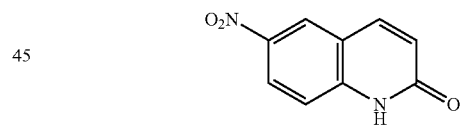

The title compound was prepared analogously to Example 001, step 2, where ethyl (E)-3-(2-amino-5-nitrophenyl)acrylate was substituted in place of 2-bromo-4-(trifluoromethyl)aniline. Yield=99%.

Step 3: 2-chloro-6-nitroquinoline

The title compound was prepared analogously to Example 001, step 3, where 6-nitroquinolin-2(1H)-one was substituted in place of 6-(trifluoromethyl)quinolin-2(1H)-one. Yield=93%.

Step 4: 2-methyl-4-(6-nitroquinolin-2-yl)aniline

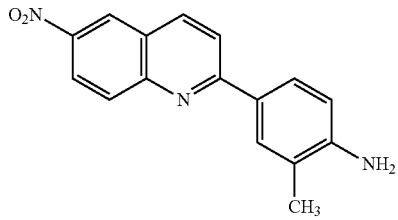 [SMILES: Cc1cc(-c2ccc3cc([N+](=O)[O-])ccc3n2)ccc1N]

The title compound was prepared analogously to Example 001, step 4, where 2-chloro-6-nitroquinoline was substituted in place of 2-chloro-6-(trifluoromethyl)quinoline. Yield=54%.

Example 077: N-(2-fluoro-4-(6-(trifluoromethyl) quinolin-2-yl)phenyl)-1-methyl-1H-pyrazole-5-carboxamide

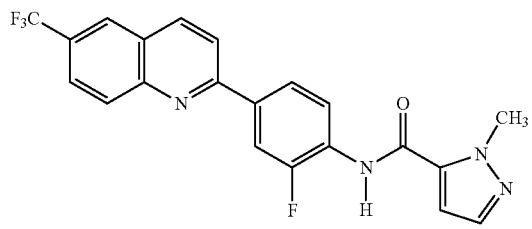 [SMILES: Cn1nccc1C(=O)Nc1ccc(-c2ccc3cc(C(F)(F)F)ccc3n2)cc1F]

The title compound was prepared analogously to Example 003, where 2-fluoro-4-(6-(trifluoromethyl)quinolin-2-yl) aniline was substituted in place of 4-(quinoxalin-2-yl)aniline. Yield=37%. LCMS (ES, m/z): [M+H]$^+$ 415; $^1$H-NMR (400 MHz, CDCl$_3$, ppm): 8.61 (dd, 1H), 8.35 (d, 2H), 8.19 (m, 2H), 8.01 (m, 3H), 7.92 (dd, 1H), 7.55 (d, 1H), 6.75 (d, 1H), 4.27 (s, 3H)

Step 1: 2-fluoro-4-(6-(trifluoromethyl)quinolin-2-yl) aniline

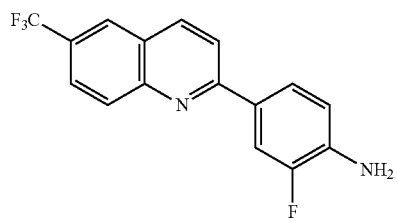 [SMILES: Nc1ccc(-c2ccc3cc(C(F)(F)F)ccc3n2)cc1F]

The title compound was prepared analogously to Example 014, where 2-chloro-6-(trifluoromethyl)quinoline was substituted in place of 2-chloro-6-fluoroquinoline and (4-amino-3-fluorophenyl)boronic acid was substituted in place of tert-butyl (2-methyl-4-(4,4,5,5-tetramethyl-1,3,2-dioxaborolan-2-yl)phenyl)carbamate. Yield=94%.

Example 078: 1-methyl-N-(2-methyl-4-(7-(trifluoromethyl)quinolin-2-yl)phenyl)-1H-pyrazole-5-carboxamide

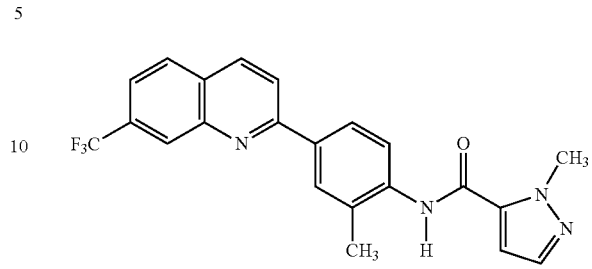

The title compound was prepared analogously to Example 001, where 2-methyl-4-(7-(trifluoromethyl)quinolin-2-yl) aniline was substituted in place of 2-methyl-4-(6-(trifluoromethyl)quinolin-2-yl)aniline. Yield=68%. LCMS (ES, m/z): [M+H]$^+$ 411; $^1$H-NMR (400 MHz, DMSO-d$_6$, ppm): δ9.98 (s, 1H), δ8.64-8.61 (d, 1H), δ8.42 (s, 1H), δ8.39-8.36 (d, 1H), δ8.28-8.26 (d, 2H), δ8.21-8.18 (d, 1H), δ7.88-7.86 (m, 1H), δ7.60-7.56 (m, 2H), δ7.11 (s, 1H), δ4.11 (s, 3H), δ2.33 (s, 3H).

Step 1: Ethyl (E)-3-(2-amino-4-(trifluoromethyl) phenyl)acrylate

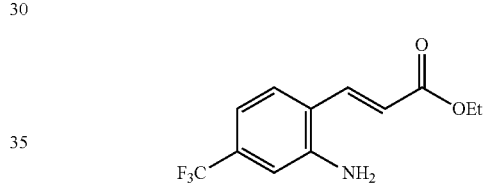

The title compound was prepared analogously to Example 001, step 1, where 2-bromo-5-(trifluoromethyl)aniline was substituted in place of 2-bromo-4-(trifluoromethyl)aniline. Yield=93%.

Step 2: 7-(trifluoromethyl)quinolin-2(1H)-one

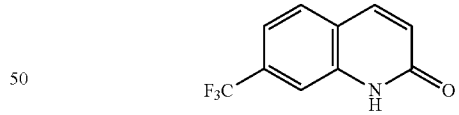

The title compound was prepared analogously to Example 001, step 2, where Ethyl (E)-3-(2-amino-4-(trifluoromethyl) phenyl)acrylate was substituted in place of (E)-3-(2-amino-5-(trifluoromethyl)phenyl)acrylate. Yield=99%.

Step 3: 2-chloro-7-(trifluoromethyl)quinoline

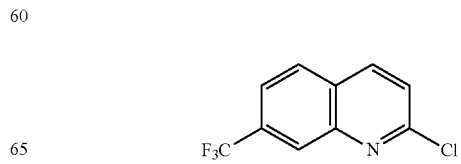

The title compound was prepared analogously to Example 001, step 3, where 7-(trifluoromethyl)quinolin-2(1H)-one was substituted in place of 6-(trifluoromethyl)-1,2-dihydroquinolin-2-one. Yield=85%.

Step 4: 2-methyl-4-(7-(trifluoromethyl)quinolin-2-yl)aniline

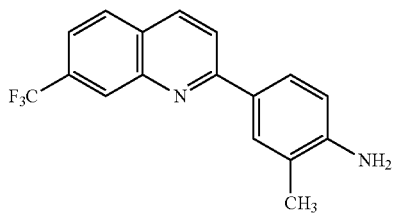 [SMILES: Cc1cc(-c2ccc3ccc(C(F)(F)F)cc3n2)ccc1N]

The title compound was prepared analogously to Example 001, step 4, where 2-chloro-7-(trifluoromethyl)quinoline was substituted in place of 2-chloro-6-(trifluoromethyl)quinoline. Yield=58%.

Example 079: 1-methyl-N-(2-methyl-4-(6-methylquinolin-2-yl)phenyl)-1H-pyrazole-5-carboxamide

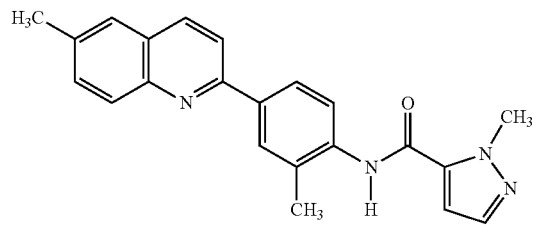

The title compound was prepared analogously to Example 001, where 2-methyl-4-(6-methylquinolin-2-yl)aniline was substituted in place of 2-methyl-4-(6-(trifluoromethyl)quinolin-2-yl)aniline. Yield=48%. LCMS (ES, m/z): [M+H]+ 357; $^1$H-NMR (300 MHz, CDCl$_3$, ppm): δ2.46 (s, 3H), δ2.58 (s, 3H), δ4.27 (s, 3H), δ6.70-6.71 (d, 1H), δ7.55-7.61 (m, 3H), δ7.68 (s, 1H), δ7.84-7.87 (d, 1H), δ7.99-8.03 (q, 1H), δ8.09-8.19 (m, 4H)

Step 1: 2-methyl-4-(6-methylquinolin-2-yl)aniline

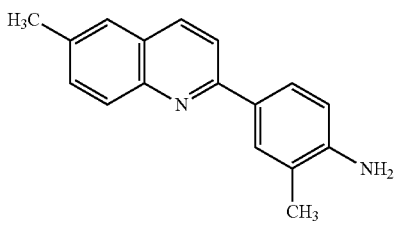 [SMILES: Cc1ccc2nc(-c3ccc(N)c(C)c3)ccc2c1]

The title compound was prepared analogously to Example 001, step 4, where 2-chloro-6-methylquinoline was substituted in place of 2-chloro-6-(trifluoromethyl)quinoline. Yield=72%.

Example 080: 2,2,2-trifluoro-N-(2-methyl-4-(6-(trifluoromethyl)quinolin-2-yl)phenyl)acetamide

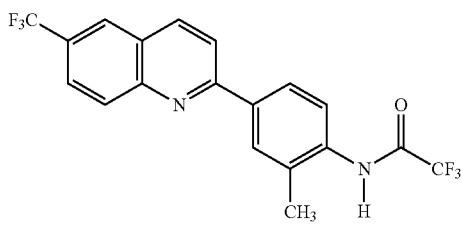 [SMILES: Cc1cc(-c2ccc3cc(C(F)(F)F)ccc3n2)ccc1NC(=O)C(F)(F)F]

To a solution of (Z)-2,2,2-trifluoro-N-(2-methyl-4-(6-(trifluoromethyl)quinolin-2-yl)phenyl)acetimidoyl chloride in THF was added an excess of a concentrated NH$_4$OH solution. The mixture was stirred at room temperature for 5 minutes. The reaction mixture was diluted with water, extracted with ethyl acetate and dried over MgSO$_4$. The volatiles were removed under reduced pressure to afford the desired product as a white solid in 93% yield. LCMS (ES, m/z): [M+H]+ 399; $^1$H-NMR (400 MHz, DMSO-d$_6$, ppm): 11.12 (s, 1H), 8.70 (d, 1H), 8.55 (s, 1H), 8.40-8.15 (m, 4H), 8.03 (dd, 1H), 7.50 (d, 1H), 3.31 (s, 3H)

Step 1: (Z)-2,2,2-Trifluoro-N-(2-methyl-4-(6-(trifluoromethyl)quinolin-2-yl)phenyl)acetimidoyl chloride

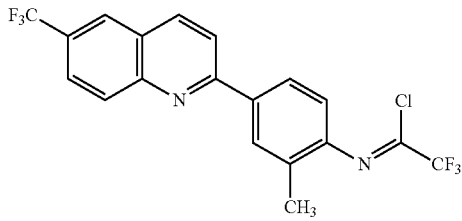 [SMILES: Cc1cc(-c2ccc3cc(C(F)(F)F)ccc3n2)ccc1/N=C(\Cl)C(F)(F)F]

To a solution of Ph$_3$P in CCl$_4$ at 0° C. was added Et$_3$N and stirred for 10 min. Trifluoroacetic acid was added and stirred for another 10 min at 0 degree. Then a solution of 2-methyl-4-(6-(trifluoromethyl)quinolin-2-yl)aniline in CCl$_4$ was added dropwise. The mixture was heated under reflux for 1 hour and the solvent removed in vacuo. The residue was chromatographed eluting with 0-100% EtOAc-Hexanes to obtain the desired product as a light yellow powder in 18% yield.

Example 081: 2,2,2-Trifluoro-N-methyl-N-(2-methyl-4-(6-(trifluoromethyl)quinolin-2-yl)phenyl)acetamide

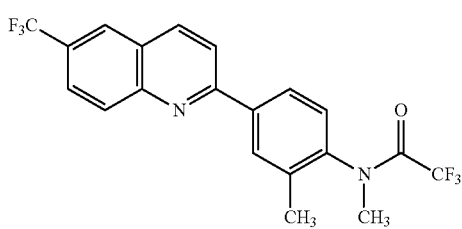 [SMILES: Cc1cc(-c2ccc3cc(C(F)(F)F)ccc3n2)ccc1N(C)C(=O)C(F)(F)F]

The title compound was prepared analogously to Example 002, where 2,2,2-trifluoro-N-(2-methyl-4-(6-(trifluoromethyl)quinolin-2-yl)phenyl)acetamide was substituted in place of 1-methyl-N-(2-methyl-4-(6-(trifluoromethyl)quinolin-2-yl)phenyl)-1H-pyrazole-5-carboxamide. Yield=46%. LCMS (ES, m/z): [M+H]⁺ 413; ¹H-NMR (400 MHz, CDCl₃, ppm): 8.40 (m, 2H), 8.21 (s, 2H), 8.10-7.90 (m, 3H), 7.37 (d, 1H), 3.36 (s, 3H), 2.43 (s, 3H)

Example 082: 1-Methyl-N-(2-methyl-4-(1-methyl-1H-indol-6-yl)phenyl)-1H-pyrazole-5-carboxamide

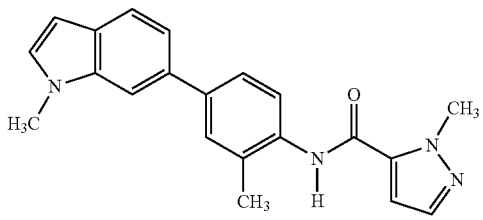 [SMILES: Cc1cc(-c2ccc3ccn(C)c3c2)ccc1NC(=O)c1ccnn1C]

The title compound was prepared analogously to Example 003, where 2-Methyl-4-(1-methyl-1H-indol-6-yl)aniline was substituted in place of 4-(quinoxalin-2-yl)aniline. Yield=32%. LCMS (ES, m/z): [M+H]⁺ 345; ¹H-NMR (400 MHz, CDCl₃, ppm): 7.95 (d, 1H), 7.68 (d, 1H), 7.62-7.47 (m, 5H), 7.37 (dd, 1H), 7.10 (d, 1H), 6.67 (s, 1H), 6.50 (d, 1H), 4.26 (s, 3H), 3.85 (s, 3H), 2.40 (s, 3H)

Step 1:
1-methyl-6-(3-methyl-4-nitrophenyl)-1H-indole

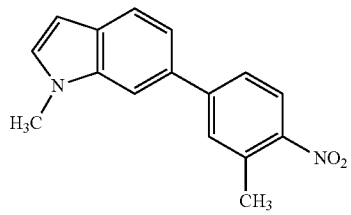

The title compound was prepared analogously to Example 014, step 1, where 6-bromo-1-methyl-1H-indole was substituted in place of 2-chloro-6-fluoroquinoline and 4,4,5,5-tetramethyl-2-(3-methyl-4-nitrophenyl)-1,3,2-dioxaborolane was substituted in place of tert-butyl (2-methyl-4-(4,4,5,5-tetramethyl-1,3,2-dioxaborolan-2-yl)phenyl)carbamate. Yield=74%

Step 2: 2-Methyl-4-(1-methyl-1H-indol-6-yl)aniline

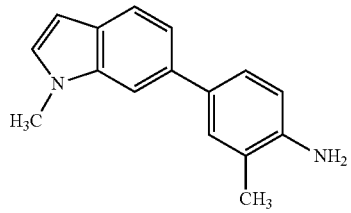 [SMILES: Cc1cc(-c2ccc3ccn(C)c3c2)ccc1[N+](=O)[O-]]

The title compound was prepared analogously to Example 050, step 2, where 1-methyl-6-(3-methyl-4-nitrophenyl)-1H-indole was substituted in place of 6-fluoro-2-(2-methyl-4-nitrophenyl)quinoline. Yield=95%.

Example 083: 1-methyl-N-(2-methyl-4-(1-methyl-1H-indol-5-yl)phenyl)-1H-pyrazole-5-carboxamide

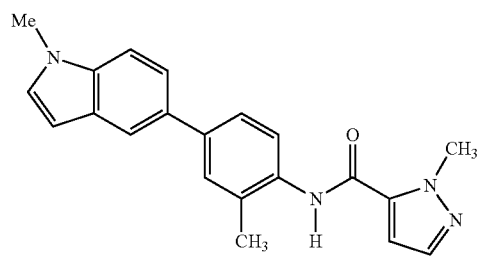 [SMILES: Cc1cc(-c2ccc3c(ccn3C)c2)ccc1NC(=O)c1ccnn1C]

The title compound was prepared analogously to Example 001, where 2-methyl-4-(1-methyl-1H-indol-5-yl)aniline was substituted in place of 2-methyl-4-(6-(trifluoromethyl)quinolin-2-yl)aniline. LCMS (ES, m/z): [M+H]⁺ 345; ¹H-NMR (300 MHz, DMSO-d₆, ppm): 9.89 (s, 1H), 7.85 (s, 1H), 7.61-7.47 (m, 5H), 7.39-7.36 (m, 2H), 7.08 (s, 1H), 6.50-6.49 (d, 1H), 4.10 (s, 3H), 3.83 (s, 3H), 2.31 (s, 3H).

Step 1: 2-methyl-4-(1-methyl-1H-indol-5-yl)aniline

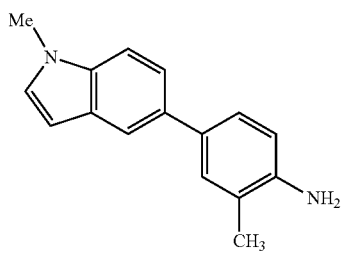 [SMILES: Cc1cc(-c2ccc3c(ccn3C)c2)ccc1N]

The title compound was prepared analogously to Example 001, step 4, where 5-bromo-1-methyl-1H-indole was substituted in place of 2-chloro-6-(trifluoromethyl)quinoline. Yield=9%.

Example 084: 1-methyl-N-(2-methyl-4-(1-(2,2,2-trifluoroethyl)-1H-pyrrolo[3,2-b]pyridin-5-yl)phenyl)-1H-pyrazole-5-carboxamide

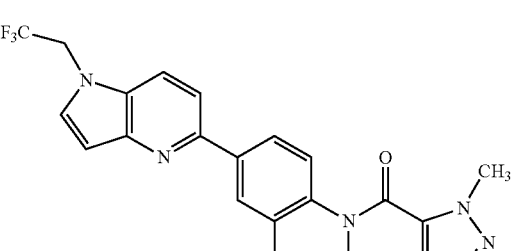

The title compound was prepared analogously to Example 001 where 2-methyl-4-(1-(2,2,2-trifluoroethyl)-1H-pyrrolo

[3,2-b]pyridin-5-yl)aniline was substituted in place of 2-methyl-4-(6-(trifluoromethyl)quinolin-2-yl)aniline. Yield=55%. LCMS (ES, m/z): [M+H]+ 414; ¹H-NMR (400 MHz, CDCl₃, ppm): δ2.41 (s, 3H), δ4.25 (s, 3H), δ4.65-4.71 (q, 2H), δ6.67-6.68 (d, 1H), δ6.89-6.90 (d, 1H), δ7.37-7.38 (d, 1H), δ7.51-7.53 (d, 1H), δ7.63-7.66 (d, 2H), δ7.74-7.76 (m, 1H), δ7.83-7.86 (m, 1H), δ7.98 (s, 1H), δ8.03-8.05 (d, 1H)

Step 1: 5-chloro-1-(2,2,2-trifluoroethyl)-1H-pyrrolo[3,2-b]pyridine

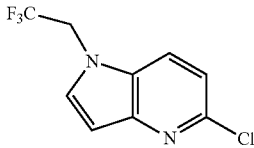 [SMILES: FC(F)(F)Cn1ccc2nc(Cl)ccc21]

A mixture of 5-chloro-1H-pyrrolo[3,2-b]pyridine (1 g, 6.55 mmol, 1 equiv), 1,1,1-trifluoro-2-iodoethane (1.4 g, 6.55 mmol, 1 equiv) and Cs₂CO₃ (2.1 g, 6.55 mmol, 1 equiv) in 10 mL of DMF was stirred for 4 hours at 60° C. The reaction was then quenched by the addition of 30 mL of water, extracted with 10 mL of ethyl acetate and the combined organic layers concentrated under reduced pressure. The residue was purified by silica gel chromatography with ethyl acetate/petroleum ether (1/10) to afford the desired final product as a colorless oil in 42% yield.

Step 2: 2-methyl-4-(1-(2,2,2-trifluoroethyl)-1H-pyrrolo[3,2-b]pyridin-5-yl)aniline

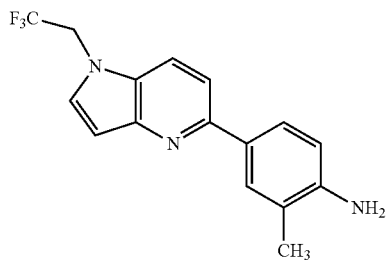

The title compound was prepared analogously to Example 001, step 4, where 5-chloro-1-(2,2,2-trifluoroethyl)-1H-pyrrolo[3,2-b]pyridine was substituted in place of 2-chloro-6-(trifluoromethyl)quinoline. Yield=11%.

Example 085: 1-methyl-N-(2-methyl-4-(1-methyl-1H-pyrrolo[3,2-b]pyridin-5-yl)phenyl)-1H-pyrazole-5-carboxamide

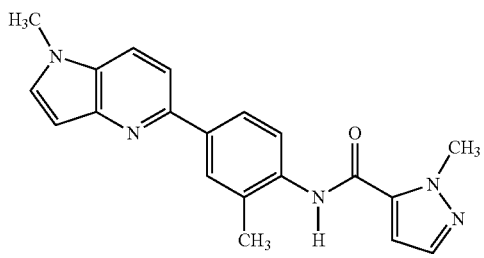 [SMILES: Cc1cc(-c2ccc3c(ccn3C)n2)ccc1NC(=O)c1ccnn1C]

The title compound was prepared analogously to Example 001 where 2-methyl-4-(1-methyl-1H-pyrrolo[3,2-b]pyridin-5-yl)aniline was substituted in place of 2-methyl-4-(6-(trifluoromethyl)quinolin-2-yl)aniline. Yield=51%. LCMS (ES, m/z): [M+H]+ 346; ¹H-NMR (DMSO-d₆, 300 MHz, ppm): δ2.28 (s, 3H), δ3.99 (s, 3H), δ4.10 (s, 3H), δ6.78-6.79 (d, 1H), δ7.10-7.11 (d, 1H), δ7.57-7.62 (m, 2H), δ7.90-7.93 (d, 1H), δ7.98-8.05 (m, 3H), δ8.54-8.57 (d, 1H), δ10.02 (s, 1H)

Step 1: 5-chloro-1-methyl-1H-pyrrolo[3,2-b]pyridine

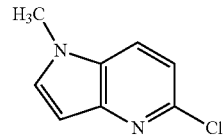

A mixture of 5-chloro-1H-pyrrolo[3,2-b]pyridine (450 mg, 2.95 mmol, 1 equiv), Cs₂CO₃ (960.9 mg, 2.95 mmol, 1 equiv) and iodomethane (418.6 mg, 2.95 mmol, 1.000 equiv) in DMF (11.2 mL), was stirred for 4 h at 60° C. The reaction was quenched by the addition of 30 mL of water, extracted with 10 ml of ethyl acetate and the combined organic layers concentrated under reduced pressure. The residue was purified by silica gel chromatography with ethyl acetate/petroleum ether (1:10) as eluent to afford the desired final product as a yellow oil in 81% yield.

Step 2: 2-methyl-4-(1-methyl-1H-pyrrolo[3,2-b]pyridin-5-yl)aniline

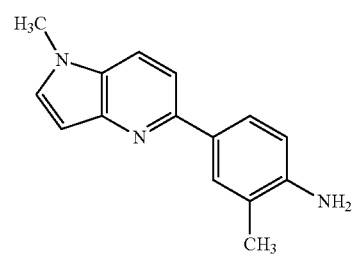 [SMILES: Cc1cc(-c2ccc3c(ccn3C)n2)ccc1N]

The title compound was prepared analogously to Example 001, step 4, where 5-chloro-1-methyl-1H-pyrrolo[3,2-b]pyridine was substituted in place of 2-chloro-6-(trifluoromethyl)quinoline. Yield=18%.

Example 086: 1-methyl-N-(2-methyl-4-(1-methyl-3-(trifluoromethyl)-1H-indol-6-yl)phenyl)-1H-pyrazole-5-carboxamide

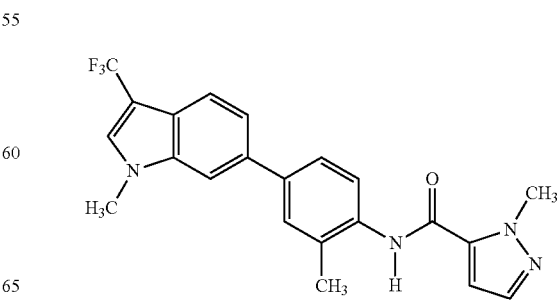

A mixture of 6-chloro-1-methyl-3-(trifluoromethyl)-1H-indole (300 mg, 1.28 mmol, 1 equiv), 1-methyl-N-[2-methyl-4-(tetramethyl-1,3,2-dioxaborolan-2-yl)phenyl]-1H-pyrazole-5-carboxamide (438.2 mg, 1.28 mmol, 1 equiv), K$_3$PO$_4$ (545.2 mg, 2.57 mmol, 2 equiv) and Pd-XPhos-G2 (100.9 mg, 0.13 mmol, 0.1 equiv) was dissolved in DMF (3.0 mL). The reaction mixture was irradiated in a microwave reactor for 1 h at 140° C. After dilution with water (20 mL), the aqueous layer was extracted with EtOAc (2×20 mL) and the combined organic layers concentrated under reduced pressure. The residue was purified by preparative TLC (dichloromethane/MeOH=30:1) to afford the desired final product as a white solid in 6% yield. LCMS (ES, m/z): [M+H]$^+$ 413; $^1$H-NMR (400 MHz, DMSO-d$_6$, ppm): δ2.34 (s, 3H), δ3.94 (s, 3H), δ4.11 (s, 3H), δ7.09 (s, 1H), δ7.43-7.45 (d, 1H), δ7.55-7.59 (m, 2H), δ7.62-7.71 (m, 2H), δ7.72 (s, 1H), δ7.91 (s, 1H), δ8.03 (s, 1H), δ9.91 (s, 1H)

Step 1: 6-chloro-3-iodo-1H-indole

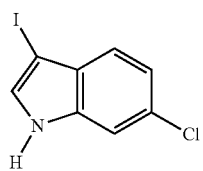

Over a solution of 6-chloro-1H-indole (5 g, 32.98 mmol, 1.00 equiv) in DMF (135 mL), potassium hydroxide (4.64 g, 82.69 mmol, 2.50 equiv) was added. A solution of I$_2$ (8.42 g, 1.00 equiv) in DMF (60 mL) was added to this solution and the resulting mixture stirred for 1 hour at room temperature. After dilution with 400 mL of H$_2$O, the aqueous layer was extracted with ethyl acetate (2×200 mL) and the organic layers combined and concentrated. The residue was purified by silica gel chromatography with ethyl acetate/petroleum ether (1:20) as eluent to afford the desired product as a white solid. Yield=79%.

Step 2: 6-chloro-3-iodo-1-methyl-1H-indole

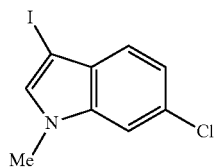

The title compound was prepared analogously to Example 088, step 2, where 6-chloro-3-iodo-1H-indole was substituted in place of 5-(3-methyl-4-nitrophenyl)-1H-indole and methyl iodide was substituted in place of 2,2,2-trifluoroethyl trifluoromethanesulfonate. Yield=99%.

Step 3: 6-chloro-1-methyl-3-(trifluoromethyl)-1H-indole

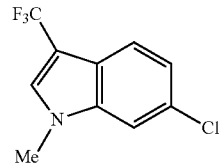 [SMILES: Cn1cc(I)c2ccc(Cl)cc21]

A mixture of 6-chloro-3-iodo-1-methyl-1H-indole (1 g, 3.43 mmol, 1 equiv), CuI (3266.5 mg, 17.15 mmol, 5 equiv), KF (996.5 mg, 17.15 mmol, 5 equiv), and TMSCF$_3$ (2264.0 mg, 17.15 mmol, 5 equiv) in NMP (20 mL) was stirred overnight at 100° C. The reaction was quenched by the addition of 60 mL of water, extracted with ethyl acetate (2×20 mL) and the organic layers combined and concentrated. The residue was purified by silica gel chromatography with ethyl acetate/petroleum ether (1:100) as eluent to afford the desired product as a colorless oil in 99% yield.

Example 087: N,1-dimethyl-N-(2-methyl-4-(1-methyl-3-(trifluoromethyl)-1H-indol-6-yl)phenyl)-1H-pyrazole-5-carboxamide

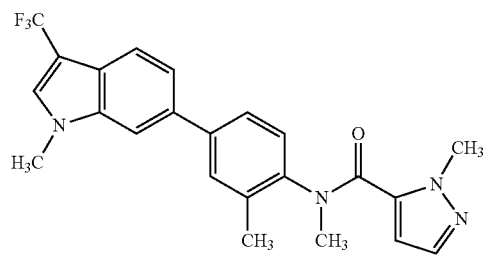 [SMILES: Cc1cc(-c2ccc3c(C(F)(F)F)cn(C)c3c2)ccc1N(C)C(=O)c1ccnn1C]

The title compound was prepared analogously to Example 002, where 1-methyl-N-(2-methyl-4-(1-methyl-3-(trifluoromethyl)-1H-indol-6-yl)phenyl)-1H-pyrazole-5-carboxamide was substituted in place of 1-methyl-N-(2-methyl-4-(6-(trifluoromethyl)quinolin-2-yl)phenyl)-1H-pyrazole-5-carboxamide. Yield=23%. LCMS (ES, m/z): [M+H]$^+$ 427; $^1$H-NMR (400 MHz, CDCl$_3$, ppm): δ2.27 (s, 3H), δ3.44 (s, 3H), δ3.91 (s, 3H), δ4.21 (s, 3H), δ5.52 (s, 1H), δ7.19-7.28 (m, 2H), δ7.46-7.58 (m, 5H), δ7.81-7.83 (d, 1H)

Example 088: 1-methyl-N-(2-methyl-4-(1-(2,2,2-trifluoroethyl)-1H-indol-5-yl)phenyl)-1H-pyrazole-5-carboxamide

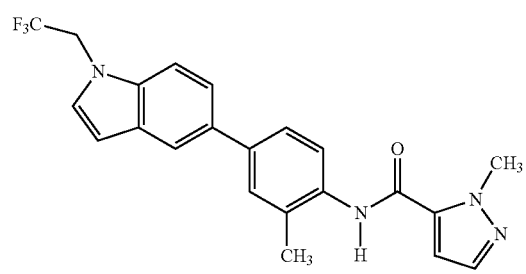 [SMILES: Cc1cc(-c2ccc3c(ccn3CC(F)(F)F)c2)ccc1NC(=O)c1ccnn1C]

The title compound was prepared analogously to Example 001 where 2-methyl-4-(1-(2,2,2-trifluoroethyl)-1H-indol-5-yl)aniline was substituted in place of 2-methyl-4-(6-(trifluoromethyl)quinolin-2-yl)aniline. Yield=31%. LCMS (ES, m/z): [M+H]⁺ 413; ¹H-NMR (400 MHz, CDCl₃, ppm): δ2.40 (s, 3H), δ4.25 (s, 3H), δ4.64-4.70 (m, 2H), δ6.65-6.67 (m, 2H), δ7.14 (s, 1H), δ7.40-7.54 (m, 6H), δ7.83 (s, 1H), δ7.92-7.94 (d, 1H)

Step 1: 5-(3-methyl-4-nitrophenyl)-1H-indole

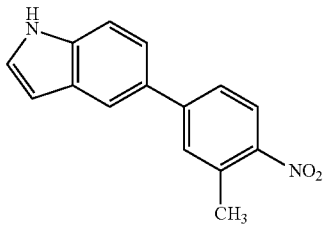 [SMILES: Cc1cc(-c2ccc3[nH]ccc3c2)ccc1[N+](=O)[O-]]

A mixture of 5-(tetramethyl-1,3,2-dioxaborolan-2-yl)-1H-indole (1000 mg, 4.11 mmol, 1 equiv), 4-bromo-2-methyl-1-nitrobenzene (888.6 mg, 4.11 mmol, 1.000 equiv), K₂CO₃ (1137.0 mg, 8.23 mmol, 2 equiv) and Pd(dppf)Cl₂ (301.0 mg, 0.41 mmol, 0.1 equiv) in dioxane (10.0 mL) was stirred at 80° C. for 2 hours. The reaction was concentrated under reduced pressure and the resulting residue was purified by silica gel chromatography with ethyl acetate/petroleum ether (1:10) as eluent to afford the desired product as a yellow solid in 48% yield.

Step 2: 5-(3-methyl-4-nitrophenyl)-1-(2,2,2-trifluoroethyl)-1H-indole

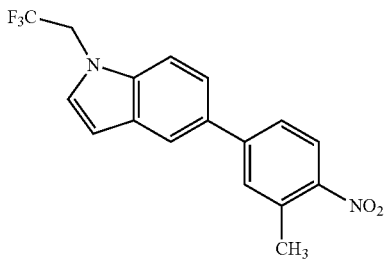 [SMILES: Cc1cc(-c2ccc3c(ccn3CC(F)(F)F)c2)ccc1[N+](=O)[O-]]

5-(3-methyl-4-nitrophenyl)-1H-indole (400 mg, 1.59 mmol, 1 equiv) was dissolved in DMF (5 mL). NaH (63.4 mg, 1.59 mmol, 1 equiv, 60%) was added and the mixture stirred for 0.5 hours. 2,2,2-trifluoroethyl trifluoromethanesulfonate (368.0 mg, 1.59 mmol, 1 equiv) was added and the resulting solution was stirred for 4 additional hours at room temperature. After quenching with 20 mL of saturated NH₄Cl solution, the aqueous layer was extracted with 10 ml of ethyl acetate twice and the combined organic layers concentrated. The residue was purified by silica gel chromatography with ethyl acetate/petroleum ether (1/5) as eluent to afford the desired final product in 62% yield.

Step 3: 2-methyl-4-(1-(2,2,2-trifluoroethyl)-1H-indol-5-yl)aniline

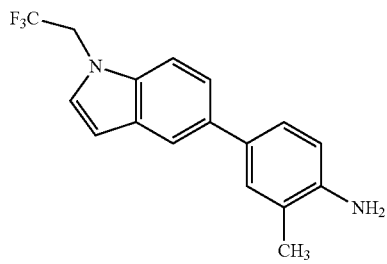 [SMILES: Cc1cc(-c2ccc3c(ccn3CC(F)(F)F)c2)ccc1N]

The title compound was prepared analogously to Example 045, step 3, where 5-(3-methyl-4-nitrophenyl)-1-(2,2,2-trifluoroethyl)-1H-indole was substituted in place of 6-fluoro-2-(6-methyl-5-nitropyridin-2-yl)quinoline. Yield=53%.

Example 089: 1-Methyl-N-(2-methyl-4-(1-methyl-1H-benzo[d]imidazol-6-yl)phenyl)-1H-pyrazole-5-carboxamide

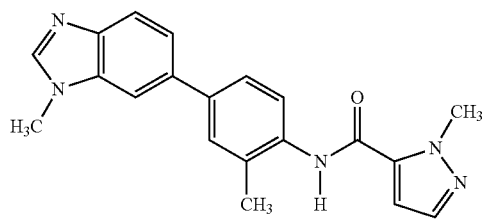 [SMILES: Cc1cc(-c2ccc3ncn(C)c3c2)ccc1NC(=O)c1ccnn1C]

The title compound was prepared analogously to Example 003, where 2-Methyl-4-(1-methyl-H-benzo[d]imidazol-6-yl)aniline was substituted in place of 4-(quinoxalin-2-yl)aniline. LCMS (ES, m/z): [M+H]⁺ 346; ¹H-NMR (400 MHz, CDCl₃, ppm): 9.90 (s, 1H), 8.21 (s, 1H), 7.90 (s, 1H), 7.75-7.66 (m, 2H), 7.65-7.52 (m, 3H), 7.43 (d, 1H), 7.09 (s, 1H), 4.10 (s, 3H), 3.91 (s, 3H), 2.33 (s, 3H)

Step 1: 1-Methyl-6-(3-methyl-4-nitrophenyl)-1H-benzo[d]imidazole

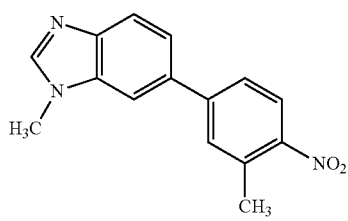

The title compound was prepared analogously to Example 014, step 1, where 6-chloro-1-methyl-1H-benzo[d]imidazole was substituted in place of 2-chloro-6-fluoroquinoline and 4,4,5,5-tetramethyl-2-(3-methyl-4-nitrophenyl)-1,3,2-dioxaborolane was substituted in place of tert-butyl (2-methyl-4-(4,4,5,5-tetramethyl-1,3,2-dioxaborolan-2-yl)phenyl)carbamate. Yield=79%.

Step 2: 2-Methyl-4-(1-methyl-1H-benzo[d]imidazol-6-yl)aniline

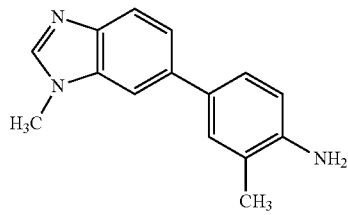 [SMILES: Cc1cc(-c2ccc3ncn(C)c3c2)ccc1[N+](=O)[O-]]

The title compound was prepared analogously to Example 050, step 2, where 1-Methyl-6-(3-methyl-4-nitrophenyl)-1H-benzo[d]imidazole was substituted in place of 6-fluoro-2-(2-methyl-4-nitrophenyl)quinoline. Yield=95%.

Example 090: 1-Methyl-N-(2-methyl-4-(1-methyl-1H-indazol-6-yl)phenyl)-1H-pyrazole-5-carboxamide

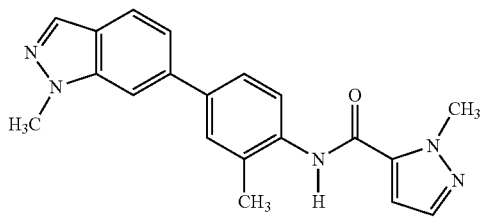 [SMILES: Cc1cc(-c2ccc3cnn(C)c3c2)ccc1NC(=O)c1ccnn1C]

The title compound was prepared analogously to Example 003, 2-Methyl-4-(1-methyl-1H-indazol-6-yl)aniline was substituted in place of 4-(quinoxalin-2-yl)aniline. Yield=18%. LCMS (ES, m/z): [M+H]+ 346; 1H-NMR (400 MHz, CDCl3, ppm): 8.05-7.96 (m, 2H), 7.78 (d, 1H), 7.63-7.52 (m, 5H), 7.41 (dd, 1H), 6.68 (d, 1H), 4.25 (s, 3H), 4.15 (s, 3H), 2.42 (s, 3H)

Step 1: 1-Methyl-6-(3-methyl-4-nitrophenyl)-1H-indazole

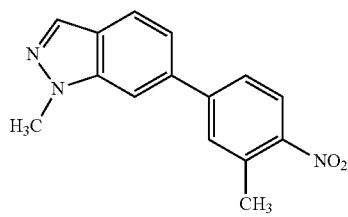

The title compound was prepared analogously to Example 014, step 1, where 6-bromo-1-methyl-1H-indazole was substituted in place of 2-chloro-6-fluoroquinoline and 4,4,5,5-tetramethyl-2-(3-methyl-4-nitrophenyl)-1,3,2-dioxaborolane was substituted in place of tert-butyl (2-methyl-4-(4,4,5,5-tetramethyl-1,3,2-dioxaborolan-2-yl)phenyl)carbamate. Yield=82%.

Step 2: 2-Methyl-4-(1-methyl-1H-indazol-6-yl)aniline

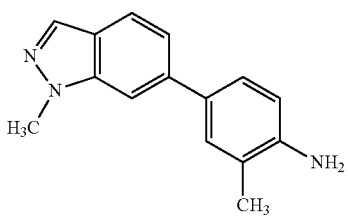 [SMILES: Cc1cc(-c2ccc3cnn(C)c3c2)ccc1[N+](=O)[O-]]

The title compound was prepared analogously to Example 050, step 2, where 1-methyl-6-(3-methyl-4-nitrophenyl)-1H-indazole was substituted in place of 6-fluoro-2-(2-methyl-4-nitrophenyl)quinoline. Yield=95%.

Example 091: 1-Methyl-N-(2-methyl-4-(7-(2,2,2-trifluoroethyl)-7H-pyrrolo[2,3-d]pyrimidin-2-yl)phenyl)-1H-pyrazole-5-carboxamide

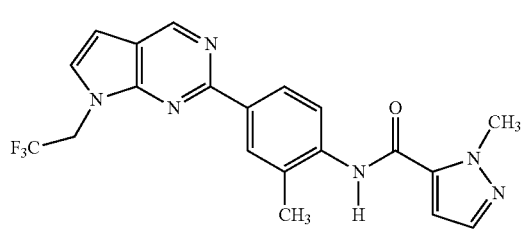 [SMILES: Cc1cc(-c2ncc3ccn(CC(F)(F)F)c3n2)ccc1NC(=O)c1ccnn1C]

The title compound was prepared analogously to Example 003, where 2-Methyl-4-(7-(2,2,2-trifluoroethyl)-7H-pyrrolo[2,3-d]pyrimidin-2-yl)aniline was substituted in place of 4-(quinoxalin-2-yl)aniline. Yield=46%. LCMS (ES, m/z): [M+H]+ 415; 1H-NMR (400 MHz, CDCl3, ppm): 9.06 (s, 1H), 8.47-8.41 (m, 2H), 8.16 (m, 1H), 7.64 (s, 1H), 7.53 (d, 1H), 7.28 (d, 1H), 6.69-6.65 (m, 2H), 4.96 (q, 2H), 4.26 (s, 3H), 2.45 (s, 3H)

Step 1: 2-chloro-7-(2,2,2-trifluoroethyl)-7H-pyrrolo[2,3-d]pyrimidine

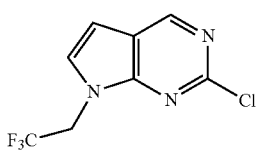 [SMILES: FC(F)(F)Cn1ccc2cnc(Cl)nc21]

The title compound was prepared analogously to Example 088, step 2, where 2-chloro-7H-pyrrolo[2,3-d]pyrimidine was substituted in place of 5-(3-methyl-4-nitrophenyl)-1H-indole and THF was substituted in place of DMF as solvent. Yield=46%.

Step 2: 2-Methyl-4-(7-(2,2,2-trifluoroethyl)-7H-pyrrolo[2,3-d]pyrimidin-2-yl)aniline

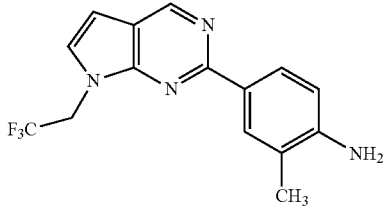 [SMILES: Cc1cc(-c2ncc3ccn(CC(F)(F)F)c3n2)ccc1N]

The title compound was prepared analogously to Example 014, step 1, where 2-chloro-7-(2,2,2-trifluoroethyl)-7H-pyrrolo[2,3-d]pyrimidine was substituted in place of 2-chloro-6-fluoroquinoline and 2-methyl-4-(4,4,5,5-tetramethyl-1,3,2-dioxaborolan-2-yl)aniline was substituted in place of tert-butyl (2-methyl-4-(4,4,5,5-tetramethyl-1,3,2-dioxaborolan-2-yl)phenyl)carbamate. Yield=60%.

Example 098: N-(4-(6-fluorobenzo[d]thiazol-2-yl)-2-methylphenyl)-1-methyl-1H-pyrazole-5-carboxamide

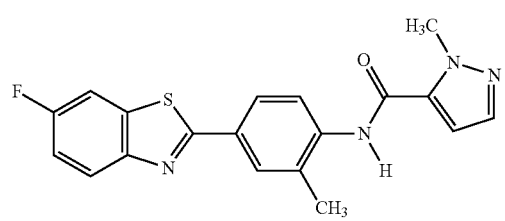 [SMILES: Cc1cc(-c2nc3ccc(F)cc3s2)ccc1NC(=O)c1ccnn1C]

The title compound was prepared analogously to Example 001, where 4-(6-fluorobenzo[d]thiazol-2-yl)-2-methylaniline was substituted in place of 2-methyl-4-(6-(trifluoromethyl)quinolin-2-yl)aniline. Yield=44%. LCMS (ES, m/z): [M+H]+ 367; 1H-NMR (DMSO-d6, 400 MHz, ppm): δ2.08 (s, 3H), δ4.10 (s, 3H), δ7.10-7.11 (d, 1H), δ7.40-7.46 (m, 1H), δ7.56-7.61 (m, 2H), δ7.93-7.96 (m, 1H), δ8.02 (d, 1H), δ8.07-8.11 (m, 2H), δ10.01 (s, 1H).

Step 1: 4-(6-fluorobenzo[d]thiazol-2-yl)-2-methylaniline

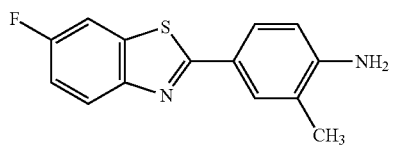 [SMILES: Cc1cc(-c2nc3ccc(F)cc3s2)ccc1N]

The title compound was prepared analogously to Example 001, step 4, where 2-chloro-6-fluorobenzo[d]thiazole was substituted in place of 2-chloro-6-(trifluoromethyl)quinoline. Yield=80%.

Example 099: N-(4-(5-fluorobenzo[d]thiazol-2-yl)-2-methylphenyl)-1-methyl-1H-pyrazole-5-carboxamide

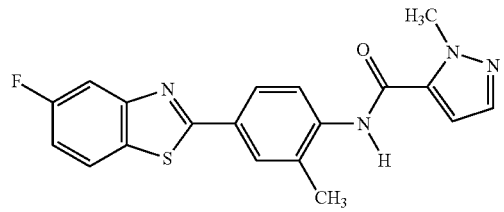 [SMILES: Cc1cc(-c2nc3cc(F)ccc3s2)ccc1NC(=O)c1ccnn1C]

The title compound was prepared analogously to Example 001, where 4-(5-fluorobenzo[d]thiazol-2-yl)-2-methylaniline was substituted in place of 2-methyl-4-(6-(trifluoromethyl)quinolin-2-yl)aniline and 1-methyl-N-(2-methyl-4-(4,4,5,5-tetramethyl-1,3,2-dioxaborolan-2-yl)phenyl)-1H-pyrazole-5-carboxamide was substituted in place of 3-methyl-4-(tetramethyl-1,3,2-dioxaborolan-2-yl)aniline. Yield=23%. LCMS (ES, m/z): [M+H]+ 367; 1H-NMR (CDCl3, 300 MHz, ppm) δ2.43 (s, 3H), δ4.25 (s, 3H), δ6.67-6.68 (d, 1H), δ7.13-7.19 (m, 1H), δ7.53-7.54 (d, 1H), δ7.66 (s, 1H), δ7.72-7.76 (m, 1H), δ7.80-7.84 (m, 1H), δ7.92-7.94 (d, 1H), δ8.01 (s, 1H), δ8.20-8.23 (d, 1H)

Example 100: 1-methyl-N-(2-methyl-4-(5-(trifluoromethyl)benzo[d]thiazol-2-yl)phenyl)-1H-pyrazole-5-carboxamide

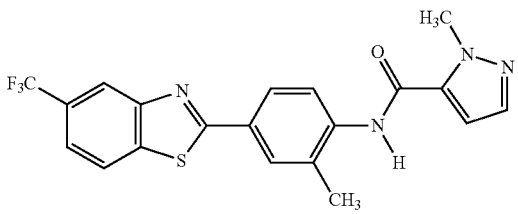 [SMILES: Cc1cc(-c2nc3cc(C(F)(F)F)ccc3s2)ccc1NC(=O)c1ccnn1C]

The title compound was prepared analogously to Example 001, where 2-methyl-4-(5-(trifluoromethyl)benzo[d]thiazol-2-yl)aniline was substituted in place of 2-methyl-4-(6-(trifluoromethyl)quinolin-2-yl)aniline. Yield=56%. LCMS (ES, m/z): [M+H]+ 417; 1H-NMR: (300 MHz, DMSO-d6, ppm): δ2.39 (s, 3H), δ4.11 (s, 3H), δ7.11-7.12 (d, 1H), δ7.57-7.58 (d, 1H), δ7.64-7.67 (d, 1H), δ7.79-7.82 (q, 1H), δ7.99-8.08 (m, 2H), δ8.42-8.45 (d, 2H), δ10.03 (s, 1H)

Step 1: 2-methyl-4-(5-(trifluoromethyl)benzo[d]thiazol-2-yl)aniline

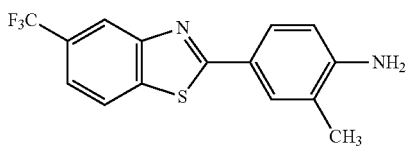 [SMILES: Cc1cc(-c2nc3cc(C(F)(F)F)ccc3s2)ccc1N]

The title compound was prepared analogously to Example 001, step 4, where 2-chloro-5-(trifluoromethyl)-1,3-benzothiazole was substituted in place of 2-chloro-6-(trifluoromethyl)quinoline. Yield=87%.

Example 101: 1-methyl-N-(2-methyl-4-(6-(trifluoromethyl)benzo[d]thiazol-2-yl)phenyl)-1H-pyrazole-5-carboxamide

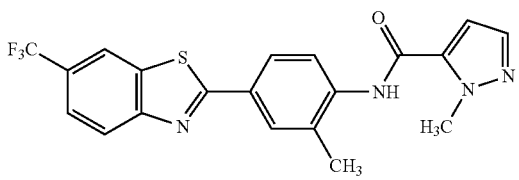 [SMILES: Cc1cc(-c2nc3ccc(C(F)(F)F)cc3s2)ccc1NC(=O)c1ccnn1C]

The title compound was prepared analogously to Example 001, where 2-methyl-4-(6-(trifluoromethyl)benzo[d]thiazol-2-yl)aniline was substituted in place of 2-methyl-4-(6-(trifluoromethyl)quinolin-2-yl)aniline. Yield=50%. LCMS (ES, m/z): [M+H]⁺ 417; ¹H-NMR (300 MHz, CDCl₃, ppm): δ2.46 (s, 3H), δ4.27 (s, 3H), δ6.70-6.71 (d, 1H), δ7.29 (s, 1H), δ7.70-7.77 (m, 2H), δ7.97-8.01 (q, 1H), δ8.06 (s, 1H), δ8.15-8.31 (m, 3H)

Step 1: 2-methyl-4-(6-(trifluoromethyl)benzo[d]thiazol-2-ylaniline

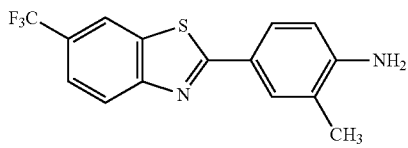 [SMILES: Cc1cc(-c2nc3ccc(C(F)(F)F)cc3s2)ccc1N]

The title compound was prepared analogously to Example 001, step 4, where 2-chloro-6-(trifluoromethyl)-1,3-benzothiazole was substituted in place of 2-chloro-6-(trifluoromethyl)quinoline. Yield=50%.

Example 102: 1-methyl-N-(2-methyl-4-(6-(trifluoromethyl)-1,5-naphthyridin-2-yl)phenyl)-1H-pyrazole-5-carboxamide

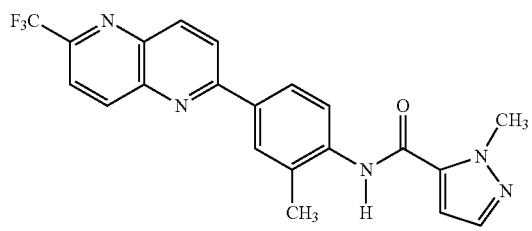 [SMILES: Cc1cc(-c2ccc3nc(C(F)(F)F)ccc3n2)ccc1NC(=O)c1ccnn1C]

The title compound was prepared analogously to Example 001 where 2-methyl-4-(6-(trifluoromethyl)-1,5-naphthyridin-2-yl)aniline was substituted in place of 2-methyl-4-(6-(trifluoromethyl)quinolin-2-yl)aniline. Yield=58%. LCMS (ES, m/z): [M+H]⁺ 412; ¹H-NMR (300 MHz, CDCl₃, ppm): δ2.50 (s, 3H), δ4.28 (s, 3H), δ6.72-6.73 (d, 1H), δ7.56-7.57 (d, 1H), δ7.70 (s, 1H), δ8.00-8.02 (d, 1H), δ8.09-8.13 (q, 1H), δ8.22-8.32 (m, 3H), δ8.57-8.60 (d, 1H), δ8.67-8.70 (d, 1H).

Step 1: ethyl (E)-3-(3-amino-6-(trifluoromethyl)pyridin-2-yl)acrylate

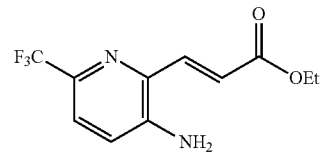 [SMILES: CCOC(=O)/C=C/c1nc(C(F)(F)F)ccc1N]

The title compound was prepared analogously to Example 001, step 1, where 2-bromo-6-(trifluoromethyl)pyridin-3-amine was substituted in place of 2-bromo-4-(trifluoromethyl)aniline. Yield=97%.

Step 2: 6-(trifluoromethyl)-1,5-naphthyridin-2(1H)-one

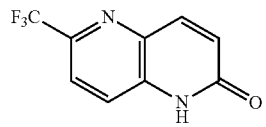

The title compound was prepared analogously to Example 001, step 2, where (E)-3-(3-amino-6-(trifluoromethyl)pyridin-2-yl)acrylate was substituted in place of (E)-3-(2-amino-5-(trifluoromethyl)phenyl)acrylate. Yield=89%.

Step 3: 2-chloro-6-(trifluoromethyl)-1,5-naphthyridine

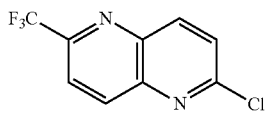 [SMILES: FC(F)(F)c1ccc2nc(Cl)ccc2n1]

The title compound was prepared analogously to Example 001, step 3, 6-(trifluoromethyl)-1,5-naphthyridin-2(1H)-one was substituted in place of 6-(trifluoromethyl)-1,2-dihydroquinolin-2-one. Yield=70%.

Step 4: 2-methyl-4-(6-(trifluoromethyl)-1,5-naphthyridin-2-yl)aniline

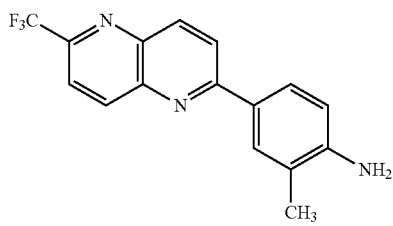

The title compound was prepared analogously to Example 001, step 4, where 2-chloro-6-(trifluoromethyl)-1,5-naphthyridine was substituted in place of 2-chloro-6-(trifluoromethyl)quinoline. Yield=99%.

Example 103: N-(2-fluoro-4-(6-(trifluoromethyl)-1,5-naphthyridin-2-yl)phenyl)-1-methyl-1H-pyrazole-5-carboxamide

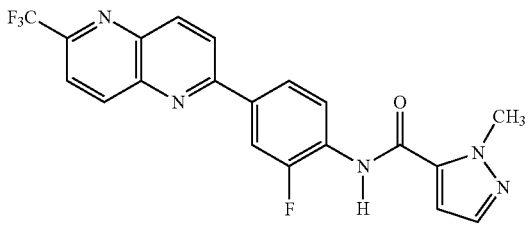

The title compound was prepared analogously to Example 001, step 4, where 2-chloro-6-(trifluoromethyl)-1,5-naphthyridine was substituted in place of 2-chloro-6-(trifluoromethyl)quinoline and N-(2-fluoro-4-(4,4,5,5-tetramethyl-1,3,2-dioxaborolan-2-yl)phenyl)-1-methyl-1H-pyrazole-5-carboxamide was substituted in place of 3-methyl-4-(tetramethyl-1,3,2-dioxaborolan-2-yl)aniline. Yield=68%. LCMS (ES, m/z): [M+H]$^+$ 416; $^1$H-NMR (300 MHz, DMSO-d$_6$, ppm): 10.30 (s, 1H), 8.79-8.77 (d, 1H), 8.70-8.68 (d, 1H), 8.64-8.62 (d, 1H), 8.34-8.26 (m, 3H), 7.91-7.87 (t, 1H), 7.57 (s, 1H), 7.16 (s, 1H), 4.12 (s, 3H).

Step 1: N-(4-bromo-2-fluorophenyl)-1-methyl-1H-pyrazole-5-carboxamide

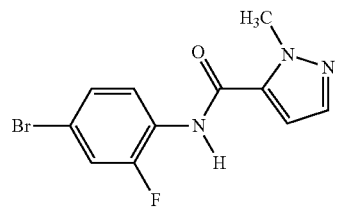 [SMILES: Cn1nccc1C(=O)Nc1ccc(Br)cc1F]

The title compound was prepared analogously to Example 001, where 4-bromo-2-fluoroaniline was substituted in place of 2-methyl-4-(6-(trifluoromethyl)quinolin-2-yl)aniline. Yield=75%.

Step 2: N-(2-fluoro-4-(4,4,5,5-tetramethyl-1,3,2-dioxaborolan-2-yl)phenyl)-1-methyl-1H-pyrazole-5-carboxamide

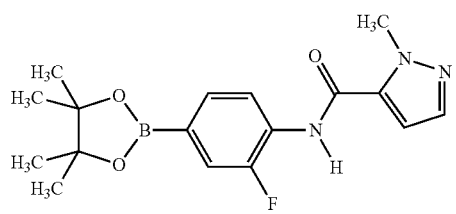 [SMILES: Cn1nccc1C(=O)Nc1ccc(B2OC(C)(C)C(C)(C)O2)cc1F]

The title compound was prepared analogously to Example 005, step 3, where N-(4-bromo-2-fluorophenyl)-1-methyl-1H-pyrazole-5-carboxamide was substituted in place of N-(4-bromo-2-fluoro-3-methylphenyl)-1-methyl-1H-pyrazole-5-carboxamide. Yield=95%.

Example 104: N-(4-(8-chloro-1,6-naphthyridin-2-yl)-2-methylphenyl)-1-methyl-1H-pyrazole-5-carboxamide

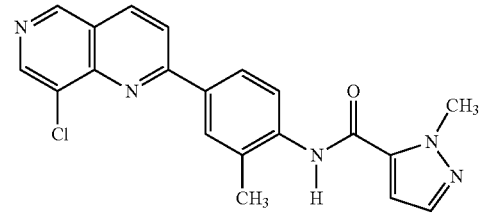 [SMILES: Cc1cc(-c2ccc3cncc(Cl)c3n2)ccc1NC(=O)c1ccnn1C]

The title compound was prepared analogously to Example 001, where 4-(8-chloro-1,6-naphthyridin-2-yl)-2-methylaniline was substituted in place of 2-methyl-4-(6-(trifluoromethyl)quinolin-2-yl)aniline. Yield=42%. LCMS (ES, m/z): [M+H]$^+$ 378; $^1$H-NMR (400 MHz, CDCl$_3$, ppm): δ9.15 (s, 1H), δ8.84 (s, 1H), δ8.38-8.35 (d, 1H), δ8.30-8.26 (m, 2H), δ8.16-8.09 (m, 2H), δ7.68 (s, 1H), δ7.55-7.54 (d, 1H), δ6.70-6.69 (d, 1H), δ4.26 (s, 3H), δ2.49 (s, 3H)

Step 1: ethyl (E)-3-(4-amino-5-chloropyridin-3-yl)acrylate

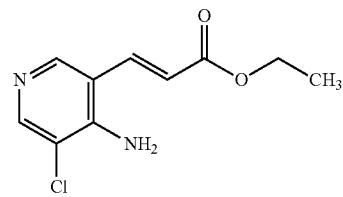

The title compound was prepared analogously to Example 001, step 1, where 3-bromo-5-chloropyridin-4-amine was substituted in place of 2-bromo-4-(trifluoromethyl)aniline. Yield=69%.

Step 2: 8-chloro-1,6-naphthyridin-2(1H)-one

The title compound was prepared analogously to Example 001, step 2, where ethyl (E)-3-(4-amino-5-chloropyridin-3-yl)acrylate was substituted in place of ethyl (E)-3-(2-amino-5-(trifluoromethyl)phenyl)acrylate. Yield=59%.

Step 3: 2,8-dichloro-1,6-naphthyridine

The title compound was prepared analogously to Example 001, step 3, where 8-chloro-1,6-naphthyridin-2(1H)-one was substituted in place 6-(trifluoromethyl)quinolin-2(1H)-one. Yield=60%.

Step 4: 4-(8-chloro-1,6-naphthyridin-2-yl)-2-methylaniline

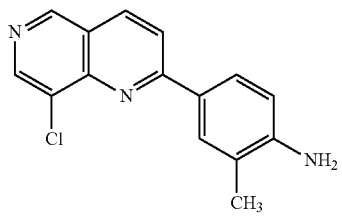

The title compound was prepared analogously to Example 001, step 4, where 2,8-dichloro-1,6-naphthyridine was substituted in place of 2-chloro-6-(trifluoromethyl)quinoline. Yield=30%.

Example 105: 1-methyl-N-(2-methyl-4-(8-methyl-6-(trifluoromethyl)-1,5-naphthyridin-2-yl)phenyl)-1H-pyrazole-5-carboxamide

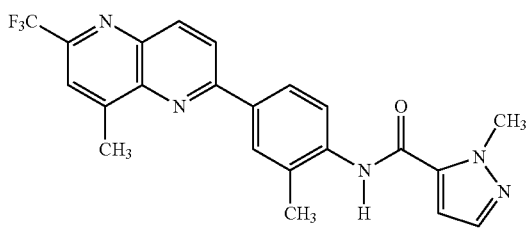 [SMILES: Cc1cc(-c2ccc3nc(C(F)(F)F)cc(C)c3n2)ccc1NC(=O)c1ccnn1C]

The title compound was prepared analogously to Example 005, where 6-chloro-4-methyl-2-(trifluoromethyl)-1,5-naphthyridine was substituted in place of 2-chloro-6-(trifluoromethyl)quinoline and 1-methyl-N-(2-methyl-4-(4,4,5,5-tetramethyl-1,3,2-dioxaborolan-2-yl)phenyl)-1H-pyrazole-5-carboxamide was substituted in place of N-(2-fluoro-3-methyl-4-(4,4,5,5-tetramethyl-1,3,2-dioxaborolan-2-yl)phenyl)-1-methyl-1H-pyrazole-5-carboxamide. Yield=62%. LCMS (ES, m/z): [M+H]+ 426; ¹H-NMR (400 MHz, CDCl₃, ppm): δ2.51 (s, 3H), δ3.03 (s, 3H), δ4.29 (s, 3H), δ6.73-6.72 (d, 1H), δ7.57-7.58 (d, 1H), δ7.68 (s, 1H), δ7.84 (s, 1H), δ8.17-8.28 (m, 4H), δ8.53-8.55 (d, 1H)

Step 1: 2-bromo-4-methyl-6-(trifluoromethyl)pyridin-3-amine

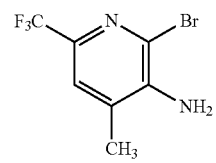

Over a solution of 4-methyl-6-(trifluoromethyl)pyridin-3-amine (2 g, 11.35 mmol, 1 equiv) in dichloromethane (20 mL), NBS (2.0 g, 11.24 mmol, 0.990 equiv) was added. The resulting solution was stirred for 4 hr at room temperature and volatiles evaporated under vacuum. The residue was purified by silica gel chromatography with ethyl acetate/petroleum ether (1:5) as eluent to afford the desired final product as a white solid in 86% yield.

Step 2: ethyl (E)-3-(3-amino-4-methyl-6-(trifluoromethyl)pyridin-2-yl)acrylate

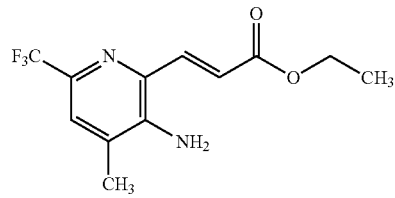 [SMILES: CCOC(=O)/C=C/c1nc(C(F)(F)F)cc(C)c1N]

The title compound was prepared analogously to Example 001, step 1, where 2-bromo-4-methyl-6-(trifluoromethyl)pyridin-3-amine was substituted in place of 2-bromo-4-(trifluoromethyl)aniline. Yield=74%.

Step 3: 8-methyl-6-(trifluoromethyl)-1,5-naphthyridin-2(1H)-one

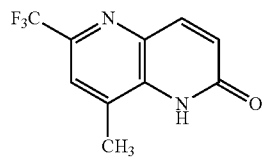

Into a 50-mL round-bottom flask, was placed ethyl-3-[3-amino-4-methyl-6-(trifluoromethyl)pyridin-2-yl]prop-2-enoate (1 g, 3.65 mmol, 1 equiv), dioxane (5 mL), HCl (6M, 5 mL). The resulting solution was stirred overnight at 100° C. The resulting solution was diluted with 30 mL of water. The solids were collected by filtration. This resulted in 700 mg of 8-methyl-6-(trifluoromethyl)-1,2-dihydro-1,5-naphthyridin-2-one as a grey solid. Yield=84%.

Step 4: 6-chloro-4-methyl-2-(trifluoromethyl)-1,5-naphthyridine

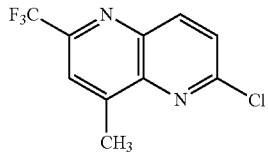 [SMILES: Cc1cc(C(F)(F)F)nc2ccc(Cl)nc12]

The title compound was prepared analogously to Example 001, step 3, where 8-methyl-6-(trifluoromethyl)-1,5-naphthyridin-2(1H)-one was substituted in place of 6-(trifluoromethyl)-1,2-dihydroquinolin-2-one. Yield=59%.

Example 106: N,1-dimethyl-N-(2-methyl-4-(8-methyl-6-(trifluoromethyl)-1,5-naphthyridin-2-yl)phenyl)-1H-pyrazole-5-carboxamide

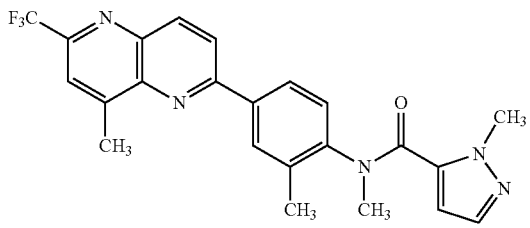 [SMILES: Cc1cc(-c2ccc3nc(C(F)(F)F)cc(C)c3n2)ccc1N(C)C(=O)c1ccnn1C]

The title compound was prepared analogously to Example 002, where 1-methyl-N-(2-methyl-4-(8-methyl-6-(trifluoromethyl)-1,5-naphthyridin-2-yl)phenyl)-1H-pyrazole-5-carboxamide was substituted in place of 1-methyl-N-(2-methyl-4-(6-(trifluoromethyl)quinolin-2-yl)phenyl)-1H-pyrazole-5-carboxamide. Yield=31%. LCMS (ES, m/z): [M+H]+ 440; 1H-NMR (400 MHz, DMSO-d6, ppm): δ2.29 (s, 3H), δ2.96 (s, 3H), δ3.33 (s, 3H), δ4.02 (s, 3H), δ5.57-5.58 (d, 1H), δ7.16-7.17 (s, 1H), δ7.50-7.53 (d, 1H), δ8.17 (s, 1H), δ8.24-8.32 (m, 2H), δ8.55-8.65 (m, 2H)

Example 107: N-(4-(6-fluoroquinazolin-2-yl)-2-methylphenyl)-1-methyl-1H-pyrazole-5-carboxamide

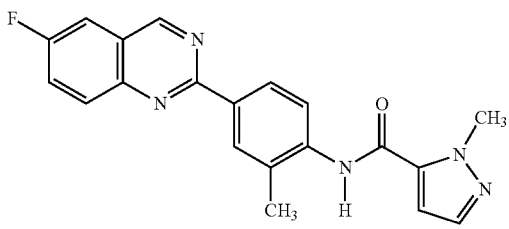 [SMILES: Cc1cc(-c2ncc3cc(F)ccc3n2)ccc1NC(=O)c1ccnn1C]

The title compound was prepared analogously to Example 001, where 4-(6-fluoroquinazolin-2-yl)-2-methylaniline was substituted in place of 2-methyl-4-(6-(trifluoromethyl)quinolin-2-yl)aniline. Yield=32%. LCMS (ES, m/z): [M+H]+ 362; 1H-NMR (400 MHz, DMSO-d6, ppm): δ2.43 (s, 3H), δ4.11 (s, 3H), δ7.10-7.11 (d, 1H), δ7.55-7.60 (m, 2H), δ7.94-8.02 (m, 2H), δ8.14-8.18 (m, 1H), δ8.39-8.42 (d, 1H), δ8.47-8.48 (d, 1H), δ9.70 (s, 1H), δ9.97 (s, 1H)

Step 1: 4-(6-fluoroquinazolin-2-yl)-2-methylaniline

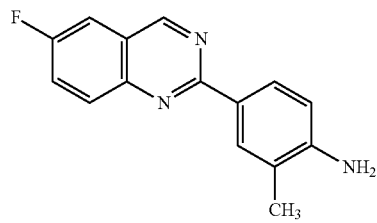

The title compound was prepared analogously to Example 001, step 4, where 2-chloro-6-fluoroquinazoline was substituted in place of 2-chloro-6-(trifluoromethyl)quinoline. Yield=40%.

Example 108: 1-methyl-N-(2-methyl-4-(7-(trifluoromethyl)quinazolin-2-yl)phenyl)-1H-pyrazole-5-carboxamide

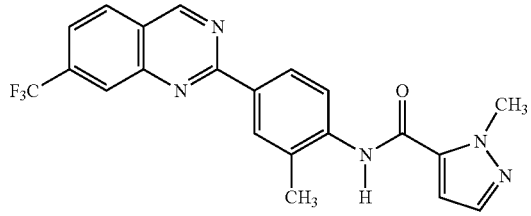 [SMILES: Cc1cc(-c2ncc3ccc(C(F)(F)F)cc3n2)ccc1NC(=O)c1ccnn1C]

The title compound was prepared analogously to Example 001, step 4, where 2-chloro-7-(trifluoromethyl)quinazoline was substituted in place of 2-chloro-6-(trifluoromethyl)quinoline and 1-methyl-N-(2-methyl-4-(4,4,5,5-tetramethyl-1,3,2-dioxaborolan-2-yl)phenyl)-1H-pyrazole-5-carboxamide was substituted in place of 3-methyl-4-(tetramethyl-1,3,2-dioxaborolan-2-yl)aniline. Yield=4%. LCMS (ES, m/z): [M+H]+ 412; 1H-NMR (DMSO-d6, 300 MHz, ppm): δ2.40 (s, 3H), δ4.11 (s, 3H), δ7.11-7.12 (d, 1H), δ7.56-7.57 (d, 1H), δ7.62-7.64 (d, 1H), δ8.01-8.04 (d, 1H), δ8.44-8.46 (d, 3H), δ8.47-8.53 (d, 1H), δ9.89 (s, 1H), δ10.00 (s, 1H)

Step 1: 7-(trifluoromethyl)quinazoline-2,4(1H,3H)-dione

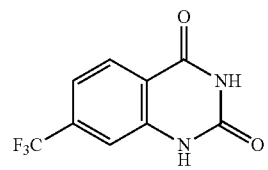 [SMILES: O=c1[nH]c(=O)c2ccc(C(F)(F)F)cc2[nH]1]

A mixture of 2-amino-4-(trifluoromethyl)benzoic acid (5 g, 24.37 mmol, 1.00 equiv) and urea (14.6 g, 243.11 mmol, 10.00 equiv) was stirred for 15 min at 200° C. The resulting solution was allowed to react, with stirring, for an additional 0.5 hours while the temperature was maintained at 100° C.

The reaction was then quenched by the addition of 25 mL of water. The solids were collected by filtration to afford the desired final product as a yellow solid in 89% yield.

Step 2: 2,4-dichloro-7-(trifluoromethyl)quinazoline

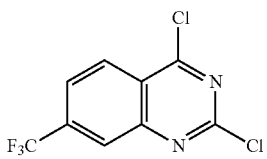 [SMILES: FC(F)(F)c1ccc2c(Cl)nc(Cl)nc2c1]

7-(trifluoromethyl)-1,2,3,4-tetrahydroquinazoline-2,4-dione (3.8 g, 16.51 mmol, 1.00 equiv) in phosphoroyl trichloride (38 mL) was stirred at 120° C. overnight. The resulting mixture was concentrated under vacuum and 100 mL of ice/water added. The pH of the solution was adjusted to pH 7 with sodium bicarbonate. The resulting solution was extracted with dichloromethane (3×300 mL) and the organic layers combined and concentrated under reduced pressure. The resulting residue was purified by silica gel chromatography with ethyl acetate/petroleum ether (1:20) to afford the desired final product as a yellow solid in 41% yield.

Step 3: 2-chloro-7-(trifluoromethyl)quinazoline

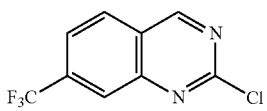

Over a solution of 2,4-dichloro-7-(trifluoromethyl)quina (370 mg, 1.3 mmol, 1.00 equiv) in THF (4 mL), Pd(PPh3)$_2$Cl$_2$ (97 mg, 0.14 mmol, 0.10 equiv), PPh$_3$ (363 mg, 1.38 mmol, 1.00 equiv) and Bu$_3$SnH (809 mg, 2.00 equiv) were added. The resulting solution was stirred for 4 hours at room temperature, quenched with 10 ml of H$_2$O and extracted with ethyl acetate (3×30 mL). The organic layers were combined and concentrated under reduced pressure. The residue was purified by preparative TLC with ethyl acetate/petroleum ether (1:20) as eluent to afford the desired product as a white solid in 79% yield.

Example 109: N-(4-(6-fluoro-8-methylquinazolin-2-yl)-2-methylphenyl)-1-methyl-1H-pyrazole-5-carboxamide

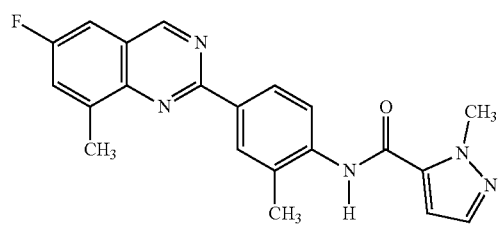 [SMILES: Cc1cc(-c2ncc3cc(F)cc(C)c3n2)ccc1NC(=O)c1ccnn1C]

2-chloro-6-fluoro-8-methylquinazoline (100 mg, 0.51 mmol, 1 equiv), 1-methyl-N-[2-methyl-4-(tetramethyl-1,3,2-dioxaborolan-2-yl)phenyl]-1H-pyrazole-5-carboxamide (173.5 mg, 0.51 mmol, 1 equiv) were dissolved in DME (3 mL) and H$_2$O (1 mL). Na$_2$CO$_3$ (107.8 mg, 1.02 mmol, 2 equiv) and Pd(PPh$_3$)$_4$ (58.8 mg, 0.05 mmol, 0.1 equiv) were added next. The resulting solution was stirred overnight at 85° C. and quenched by the addition of 5 mL of H$_2$O. Extraction with ethyl acetate (2×5 mL) and elimination of volatiles under reduced pressure afforded a crude residue that was purified by preparative TLC with dichloromethane/methanol (30/1) as eluent to afford the desired product as a white solid in 32% yield. LCMS (ES, m/z): [M+H]$^+$ 376; $^1$H-NMR (400 MHz, DMSO-d$_6$, ppm): δ2.39 (s, 3H), δ2.83 (s, 3H), δ4.11 (s, 3H), δ7.11 (s, 1H), δ7.56-7.60 (m, 2H), δ7.78-7.81 (m, 1H), δ7.84-7.86 (m, 1H), δ8.43-8.45 (m, 1H), δ8.50 (s, 1H), δ9.64 (s, 1H), δ9.98 (s, 1H).

Step 1: 8-bromo-2-chloro-6-fluoroquinazoline

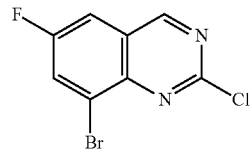 [SMILES: Fc1cc(Br)c2nc(Cl)ncc2c1]

The title compound was prepared analogously to Example 001 step 3, where 8-bromo-6-fluoro-1,2-dihydroquinolin-2-one was substituted in place of 6-(trifluoromethyl)-1,2-dihydroquinolin-2-one. Yield=84%.

Step 2: 2-chloro-6-fluoro-8-methylquinazoline

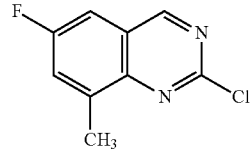

A mixture of 8-bromo-2-chloro-6-fluoroquinazoline (500 mg, 1.91 mmol, 1 equiv), methylboronic acid (114.5 mg, 1.91 mmol, 1 equiv), K$_2$CO$_3$ (528.6 mg, 3.82 mmol, 2 equiv), Pd(dppf)Cl$_2$ (139.9 mg, 0.19 mmol, 0.1 equiv) in 20 mL of DMF was stirred overnight at 120° C. The reaction was then quenched by the addition of 50 mL of water, extracted with ethyl acetate (2×20 mL) and the combined organic layers concentrated. The residue was purified by silica gel chromatography with ethyl acetate/petroleum ether (1:3) to afford the desired product as a yellow solid in 53% yield.

Example 110: 1-methyl-N-(2-methyl-4-(8-methyl-6-(trifluoromethyl)quinazolin-2-yl)phenyl)-1H-pyrazole-5-carboxamide

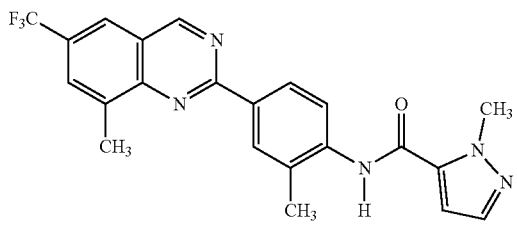 [SMILES: Cc1cc(-c2ncc3cc(C(F)(F)F)cc(C)c3n2)ccc1NC(=O)c1ccnn1C]

A mixture of 2-chloro-8-methyl-6-(trifluoromethyl)quinazoline (100 mg, 0.41 mmol, 1 equiv), 1-methyl-N-(2-methyl-4-(4,4,5,5-tetramethyl-1,3,2-dioxaborolan-2-yl)phenyl)-1H-pyrazole-5-carboxamide (138.4 mg, 0.41 mmol, 1 equiv), Na$_2$CO$_3$ (86.0 mg, 0.81 mmol, 2 equiv) and Pd(PPh$_3$)$_4$ (46.9 mg, 0.04 mmol, 0.1 equiv) in toluene (2 mL) and EtOH (1 mL) was stirred at 80° C. overnight. The resulting solution was diluted with 10 mL of water and extracted with ethyl acetate (2×5 mL). Elimination of volatiles under reduced pressure afforded a residue that was purified by silica gel chromatography with dichloromethane/methanol (30/1) to afford the desired product as a white solid in 35% yield. LCMS (ES, m/z): [M+H]$^+$ 426; $^1$H-NMR (400 MHz, CDCl$_3$, ppm): δ2.51 (s, 3H), δ2.94 (s, 3H), δ4.29 (s, 3H), δ6.71-6.72 (d, 1H), δ7.57 (s, 1H), δ7.70 (s, 1H), δ7.93 (s, 1H), δ8.10 (s, 1H), δ8.28-8.32 (m, 1H), δ8.61-8.64 (m, 2H), δ9.53 (s, 1H).

Step 1:
2-amino-3-methyl-5-(trifluoromethyl)benzonitrile

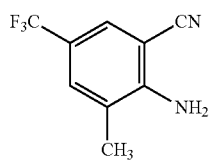

2-bromo-6-methyl-4-(trifluoromethyl)aniline (2.8 g, 11.02 mmol, 1 equiv) and CuCN (1974.3 mg, 22.04 mmol, 2 equiv) were dissolved in DMF (20 mL) and irradiated under microwave conditions for 40 min at 220° C. The reaction was then quenched by the addition of 50 mL of water. The resulting solution was extracted with ethyl acetate (3×50 mL) and the combined organic layers concentrated. The residue was purified by silica gel chromatograpy with dichloromethane/methanol (50/1) to afford the desired product as a yellow solid in 60% yield.

Step 2: 2,4-dichloro-8-methyl-6-(trifluoromethyl)quinazoline

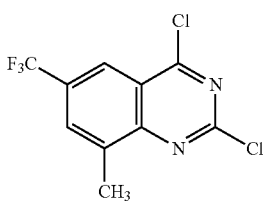 [SMILES: Cc1cc(C(F)(F)F)cc2c(Cl)nc(Cl)nc12]

Over a solution of 2-amino-3-methyl-5-(trifluoromethyl)benzonitrile (300 mg, 1.50 mmol, 1 equiv) in CH$_3$CN (5 mL, 0.12 mmol, 0.081 equiv), chloro(trichloromethoxy)methanone (444.8 mg, 2.25 mmol, 1.500 equiv) was added. The resulting solution was stirred overnight at 120° C. The reaction was quenched by addition of 30 ml of H$_2$O, the aqueous layer extracted with ethyl acetate (3×30 mL) and the combined organic layers concentrated under reduced pressure. The resulting residue was purified by preparative-TLC with ethyl acetate/petroleum ether (1/10) as eluent to afford the desired product as a yellow solid in 71% yield.

Step 3:
2-chloro-8-methyl-6-(trifluoromethyl)quinazoline

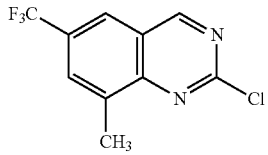 [SMILES: Cc1cc(C(F)(F)F)cc2cnc(Cl)nc12]

A mixture of 2,4-dichloro-8-methyl-6-(trifluoromethyl)quinazoline (200 mg, 0.71 mmol, 1 equiv), PPh$_3$ (280.0 mg, 1.07 mmol, 1.5 equiv), Bu$_3$SnH (207.1 mg, 0.71 mmol, 1 equiv) and Pd(PPh$_3$)$_4$ (82.2 mg, 0.07 mmol, 0.1 equiv) in THF (10 mL) was stirred for 8 hours at room temperature. Elimination of volatiles under reduced pressure afforded a residue that was purified by silica gel chromatography with ethyl acetate/petroleum ether (1:10) to afford the desired final product as a white solid in 45% yield.

Example 111: N,1-dimethyl-N-(2-methyl-4-(8-methyl-6-(trifluoromethyl)quinazolin-2-yl)phenyl)-1H-pyrazole-5-carboxamide

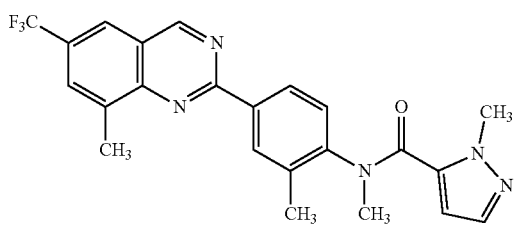 [SMILES: Cc1cc(-c2ncc3cc(C(F)(F)F)cc(C)c3n2)ccc1N(C)C(=O)c1ccnn1C]

The title compound was prepared analogously to Example 002, where 1-methyl-N-(2-methyl-4-(8-methyl-6-(trifluoromethyl)quinazolin-2-yl)phenyl)-1H-pyrazole-5-carboxamide was substituted in place of 1-methyl-N-(2-methyl-4-(6-(trifluoromethyl)quinolin-2-yl)phenyl)-1H-pyrazole-5-carboxamide. Yield=41%. LCMS (ES, m/z): [M+H]$^+$ 440; $^1$H-NMR (400 MHz, DMSO-d$_6$, ppm): δ2.27 (s, 3H), δ2.85 (s, 3H), δ3.33 (s, 3H), δ4.01 (s, 3H), δ5.54-5.55 (d, 1H), δ7.14-7.15 (d, 1H), δ7.49-7.50 (d, 1H), δ8.17 (s, 1H), δ8.40-8.48 (d, 1H), δ8.51-8.52 (d, 2H), δ9.84 (s, 1H)

Example 112: 1-methyl-N-(2-methyl-4-(6-(trifluoromethyl)quinazolin-2-yl)phenyl)-1H-pyrazole-5-carboxamide

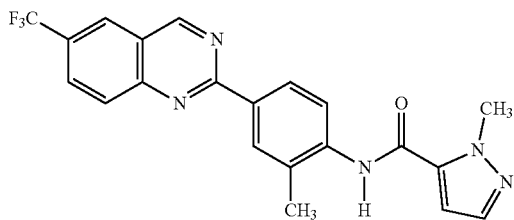

The title compound was prepared analogously to Example 014, step 1, where 2-chloro-6-(trifluoromethyl)quinazoline was substituted in place of 2-chloro-6-fluoroquinoline and 1-methyl-N-(2-methyl-4-(4,4,5,5-tetramethyl-1,3,2-dioxaborolan-2-yl)phenyl)-1H-pyrazole-5-carboxamide was substituted in place of tert-butyl (2-methyl-4-(4,4,5,5-tetramethyl-1,3,2-dioxaborolan-2-yl)phenyl)carbamate.
Yield=20%. LCMS (ES, m/z): [M+H]$^+$ 412; $^1$H-NMR (400 MHz, CDCl$_3$, ppm): 2.40 (s, 3H), 4.18 (s, 3H), 6.60 (d, 1H), 7.46 (d, 1H), 7.61 (s, 1H), 8.00 (dd, 1H), 8.19 (m, 3H), 8.51 (m, 2H), 9.49 (s, 1H).

Step 1: 2-amino-5-(trifluoromethyl)benzonitrile

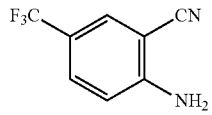 [SMILES: N#Cc1cc(C(F)(F)F)ccc1N]

The title compound was prepared analogously to Example 110, step 1, where 2-bromo-4-(trifluoromethyl)aniline was substituted in place-bromo-6-methyl-4-(trifluoromethyl)aniline. Yield=55%.

Step 2: 2,4-dichloro-6-(trifluoromethyl)quinazoline

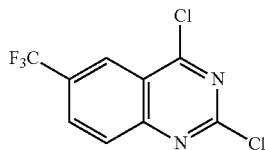 [SMILES: FC(F)(F)c1ccc2nc(Cl)nc(Cl)c2c1]

The title compound was prepared analogously to Example 110, step 2, where 2-amino-5-(trifluoromethyl)benzonitrile was substituted in place 2-amino-3-methyl-5-(trifluoromethyl)benzonitrile. Yield=46%.

Step 3: 2-chloro-6-(trifluoromethyl)quinazoline

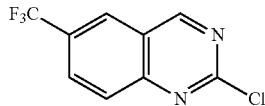 [SMILES: FC(F)(F)c1ccc2nc(Cl)ncc2c1]

The title compound was prepared analogously to Example 110, step 3, 2,4-dichloro-6-(trifluoromethyl)quinazoline was substituted in place of 2,4-dichloro-8-methyl-6-(trifluoromethyl)quinazoline. Yield=50%.

Example 113: N-(2-fluoro-3-methyl-4-(6-(trifluoromethyl)quinazolin-2-yl)phenyl)-1-methyl-1H-pyrazole-5-carboxamide

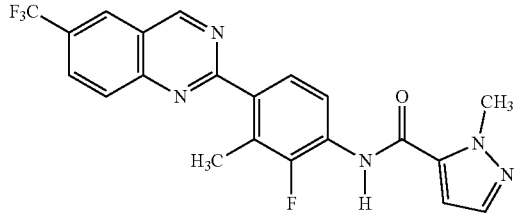

The title compound was prepared analogously to Example 110, where 2-chloro-6-(trifluoromethyl)quinazoline was substituted in place of 2-chloro-8-methyl-6-(trifluoromethyl)quinazoline and N-(2-fluoro-3-methyl-4-(4,4,5,5-tetramethyl-1,3,2-dioxaborolan-2-yl)phenyl)-1-methyl-1H-pyrazole-5-carboxamide was substituted in place of 1-methyl-N-(2-methyl-4-(4,4,5,5-tetramethyl-1,3,2-dioxaborolan-2-yl)phenyl)-1H-pyrazole-5-carboxamide.
Yield=31%. LCMS (ES, m/z): [M+H]$^+$ 430; $^1$H-NMR (DMSO-d$_6$, 300 MHz, ppm): δ2.56-2.57 (d, 3H), δ4.11 (s, 3H), δ7.15-7.16 (d, 2H), δ7.56-7.57 (d, 1H), δ7.66-7.71 (t, 1H), δ7.88-7.90 (d, 1H), δ8.25-8.3 (m, 2H), δ8.77 (s, 1H), δ9.92 (s, 1H), δ10.22 (s, 1H)

Example 114: N-(2-fluoro-3-methyl-4-(6-(trifluoromethyl)quinazolin-2-yl)phenyl)-N,1-dimethyl-1H-pyrazole-5-carboxamide

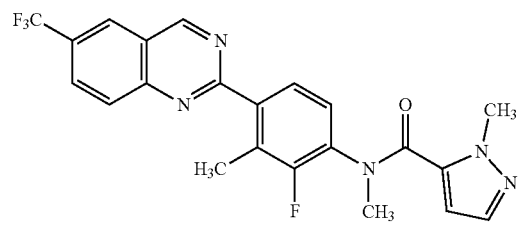 [SMILES: Cc1c(-c2ncc3cc(C(F)(F)F)ccc3n2)ccc(NC(=O)c2ccnn2C)c1F]

The title compound was prepared analogously to Example 002, where N-(2-fluoro-3-methyl-4-(6-(trifluoromethyl)quinazolin-2-yl)phenyl)-1-methyl-1H-pyrazole-5-carboxamide was substituted in place of 1-methyl-N-(2-methyl-4-(6-(trifluoromethyl)quinolin-2-yl)phenyl)-1H-pyrazole-5-carboxamide. Yield=17%. LCMS (ES, m/z): [M+H]$^+$ 444; $^1$H-NMR (DMSO-d$_6$, 300 MHz, ppm): δ2.43 (s, 3H), δ3.30-3.33 (d, 3H), δ3.97 (s, 3H), δ5.84 (s, 1H), δ7.26 (s, 1H), δ7.50-7.55 (t, 1H), δ7.80-7.82 (d, 1H), δ8.24-8.34 (m, 2H), δ8.77 (s, 1H), δ9.92 (s, 1H)

Example 115: N-(2-methyl-4-(6-(trifluoromethyl)quinazolin-2-yl)phenyl)isonicotinamide

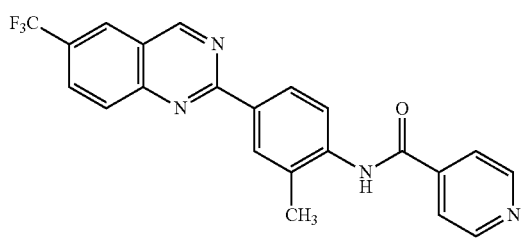 [SMILES: Cc1cc(-c2ncc3cc(C(F)(F)F)ccc3n2)ccc1NC(=O)c1ccncc1]

The title compound was prepared analogously to Example 001, step 4, where 2-methyl-4-(6-(trifluoromethyl)quinazolin-2-yl)aniline was substituted in place of 2-methyl-4-(6-(trifluoromethyl)quinolin-2-yl)aniline and isonicotinic acid was substituted in place of 1-methyl-1H-pyrazole-5-carboxylic acid. Yield=42%. LCMS (ES, m/z): [M+H]$^+$ 409; $^1$H-NMR (DMSO-d$_6$, 400 MHz, ppm): δ2.42 (s, 3H), δ7.67-7.70 (t, 1H), δ7.91-7.95 (m, 2H), δ8.24-8.30 (m, 2H), δ8.46-8.49 (t, 1H), δ8.54 (s, 1H), δ8.72 (s, 1H), δ8.81-8.83 (d, 2H), δ9.99 (s, 1H), δ10.29 (s, 1H)

Step 1: 2-(3-methyl-4-nitrophenyl)-6-(trifluoromethyl)quinazoline

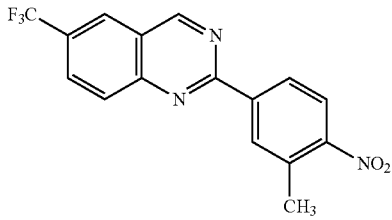 [SMILES: Cc1cc(-c2ncc3cc(C(F)(F)F)ccc3n2)ccc1[N+](=O)[O-]]

The title compound was prepared analogously to Example 136, step 4, where 2-chloro-6-(trifluoromethyl)quinazoline was substituted in place of 2-chloro-6-(trifluoromethyl)quinoline and 4,4,5,5-tetramethyl-2-(3-methyl-4-nitrophenyl)-1,3,2-dioxaborolane was substituted in place of 2-methyl-4-(4,4,5,5-tetramethyl-1,3,2-dioxaborolan-2-yl)aniline. Yield=42%.

Step 2: 2-methyl-4-(6-(trifluoromethyl)quinazolin-2-yl)aniline

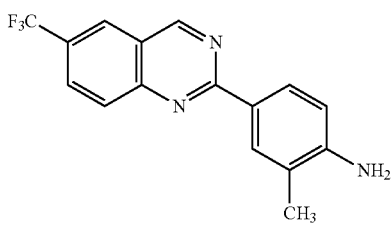

The title compound was prepared analogously to Example 045, step 3, where 2-(3-methyl-4-nitrophenyl)-6-(trifluoromethyl)quinazoline was substituted in place of 6-fluoro-2-(6-methyl-5-nitropyridin-2-yl)quinoline. Yield=98%.

Example 116: N-methyl-N-(2-methyl-4-(6-(trifluoromethyl)quinazolin-2-yl)phenyl)isonicotinamide

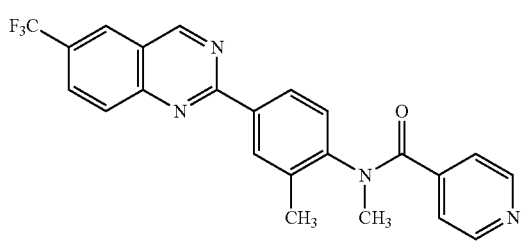 [SMILES: Cc1cc(-c2ncc3cc(C(F)(F)F)ccc3n2)ccc1N(C)C(=O)c1ccncc1]

To a stirred solution of N,2-dimethyl-4-[6-(trifluoromethyl)quinazolin-2-yl]aniline (60 mg, 0.19 mmol, 1 equiv) and isonicotinoyl chloride hydrochloride (40.4 mg, 0.23 mmol, 1.2 equiv) in CH$_2$Cl$_2$ (2 mL) were added triethylamine (67 mg, 0.665 mmol, 3.5 equiv). The resulting mixture was stirred at 50° C. overnight. The reaction was quenched with water (10 ml) and the aqueous layer extracted with CH$_2$Cl$_2$ (2×20 mL). The combined organic layers were concentrated under vacuum and the residue was purified by Prep-TLC (CH$_2$Cl$_2$/MeOH=25:1) to afford the desired product as a white solid in 58% yield. LCMS (ES, m/z): [M+H]$^+$ 423; $^1$H-NMR (DMSO-d$_6$, 400 MHz, ppm): δ2.35 (s, 3H), δ3.35 (s, 3H), δ7.24-7.26 (m, 2H), δ7.45-7.47 (d, 1H), δ8.20-8.26 (d, 1H), δ8.27-8.31 (m, 2H), δ8.40-8.56 (m, 3H), δ8.70-8.78 (m, 1H), δ9.85-9.91 (d, 1H)

Step 1: N,2-dimethyl-4-(6-(trifluoromethyl)quinazolin-2-yl)aniline

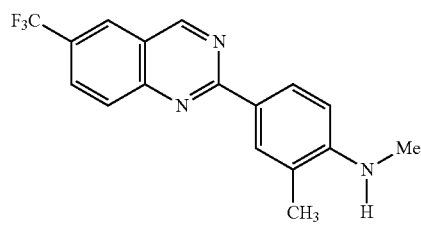 [SMILES: CNc1ccc(-c2ncc3cc(C(F)(F)F)ccc3n2)cc1C]

A solution of tert-butyl N-methyl-N-[2-methyl-4-[6-(trifluoromethyl)quinazolin-2-yl]phenyl]carbamate (5 g, 11.98 mmol, 1 equiv) in HCl (50 mL, 4M dioxane solution) was stirred at room temperature for 2 hours. The resulting mixture was concentrated under reduced pressure and the residue diluted with water (100 mL). The mixture was basified to pH=8 with saturated NaHCO$_3$ and extracted with EtOAc (2×100 mL). The combined organic layers were concentrated under reduced pressure to afford the desired product as a yellow solid in 82% yield.

Example 117: 3-methyl-N-(2-methyl-4-(6-(trifluoromethyl)quinazolin-2-yl)phenyl)picolinamide

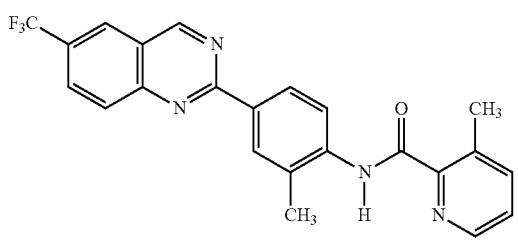 [SMILES: Cc1cc(-c2ncc3cc(C(F)(F)F)ccc3n2)ccc1NC(=O)c1ncccc1C]

The title compound was prepared analogously to Example 001, where 2-methyl-4-(6-(trifluoromethyl)quinazolin-2-yl)aniline was substituted in place of 2-methyl-4-(6-(trifluoromethyl)quinolin-2-yl)aniline and 3-methylpyridine-2-carboxylic acid was substituted in place of 1-methyl-1H-pyrazole-5-carboxylic acid. Yield=46%. LCMS (ES, m/z): [M+H]$^+$ 423; $^1$H-NMR (300 MHz, CDCl$_3$, ppm): 10.66 (s, 1H), 9.57 (s, 1H), 8.65-8.61 (m, 3H), 8.53-8.52 (d, 1H), 8.26-8.25 (d, 2H), 8.10-8.07 (m, 1H), 7.72-7.70 (d, 1H), 7.54-7.41 (m, 1H), 2.91 (s, 3H), 2.59 (s, 3H)

Example 118: N,3-dimethyl-N-(2-methyl-4-(6-(trifluoromethyl)quinazolin-2-yl)phenyl)picolinamide

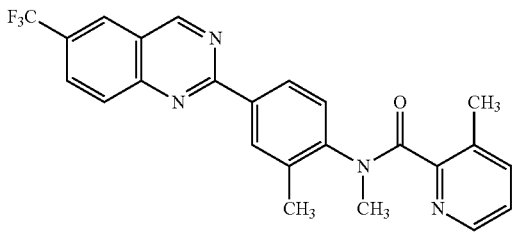 [SMILES: Cc1cc(-c2ncc3cc(C(F)(F)F)ccc3n2)ccc1N(C)C(=O)c1ncccc1C]

The title compound was prepared analogously to Example 002, where 3-methyl-N-(2-methyl-4-(6-(trifluoromethyl)quinazolin-2-yl)phenyl)picolinamide was substituted in place of 1-methyl-N-(2-methyl-4-(6-(trifluoromethyl)quinolin-2-yl)phenyl)-1H-pyrazole-5-carboxamide. Yied=56%. LCMS (ES, m/z): [M+H]$^+$ 437; $^1$H-NMR (300 MHz, CDCl$_3$, ppm): 9.61-8.53 (d, 1H), 8.66-8.57 (m, 0.6H), 8.42 (s, 0.8H), 8.27-8.23 (m, 2H), 8.19-8.07 (m, 2.6H), 7.72-7.70 (d, 0.4H), 7.56-7.54 (d, 1H), 7.39-7.37 (d, 0.8H), 7.25-7.23 (d, 0.8H), 3.49 (s, 2.4H), 3.23 (s, 0.6H), 2.57 (s, 3.7H), 2.45 (s, 2.5H).

Example 119: 2-methyl-N-(2-methyl-4-(6-(trifluoromethyl)quinazolin-2-yl)phenyl)isonicotinamide

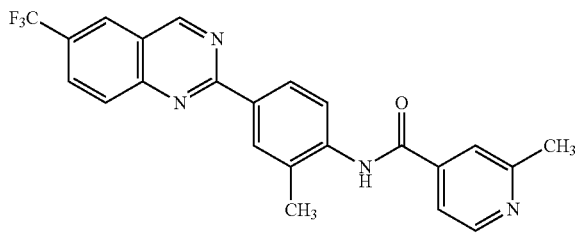 [SMILES: Cc1cc(C(=O)Nc2ccc(-c3ncc4cc(C(F)(F)F)ccc4n3)cc2C)ccn1]

The title compound was prepared analogously to Example 001, where 2-methyl-4-(6-(trifluoromethyl)quinazolin-2-yl)aniline was substituted in place of 2-methyl-4-(6-(trifluoromethyl)quinolin-2-yl)aniline and 2-methylpyridine-4-carboxylic acid was substituted in place of 1-methyl-1H-pyrazole-5-carboxylic acid. Yield=34%. LCMS (ES, m/z): [M+H]$^+$ 423; $^1$H-NMR (DMSO-d$_6$, 300 MHz, ppm): δ2.41 (s, 3H), δ2.60 (s, 3H), δ7.65-7.72 (t, 2H), δ7.79 (s, 1H), δ8.24-8.31 (t, 2H), δ8.45-8.49 (t, 1H), δ8.53 (s, 1H), δ8.66-8.68 (d, 1H), δ8.72 (s, 1H), δ9.99 (s, 1H), δ10.24 (s, 1H)

Example 120: N,2-dimethyl-N-(2-methyl-4-(6-(trifluoromethyl)quinazolin-2-yl)phenyl)isonicotinamide

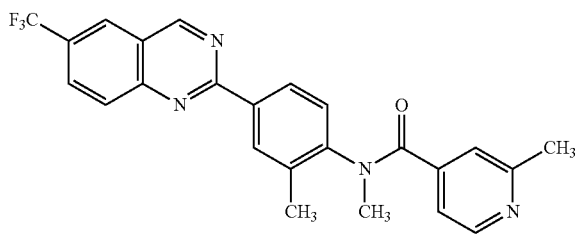 [SMILES: Cc1cc(C(=O)N(C)c2ccc(-c3ncc4cc(C(F)(F)F)ccc4n3)cc2C)ccn1]

The title compound was prepared analogously to Example 002, where 2-methyl-N-(2-methyl-4-(6-(trifluoromethyl)quinazolin-2-yl)phenyl)isonicotinamide was substituted in place of 1-methyl-N-(2-methyl-4-(6-(trifluoromethyl)quinolin-2-yl)phenyl)-1H-pyrazole-5-carboxamide. Yield=21%. LCMS (ES, m/z): [M+H]$^+$ 437; $^1$H-NMR (DMSO-d$_6$, 300 MHz, ppm): δ2.35 (s, 6H), δ3.31-3.33 (d, 3H), δ6.96-6.97 (d, 1H), δ7.19 (s, 1H), δ8.45-7.47 (d, 1H), δ8.21-8.8.33 (m, 4H), δ8.41 (s, 1H), δ8.72 (s, 1H), δ9.87 (s, 1H)

Example 121: 3-methyl-N-(2-methyl-4-(6-(trifluoromethyl)quinazolin-2-yl)phenyl)isonicotinamide

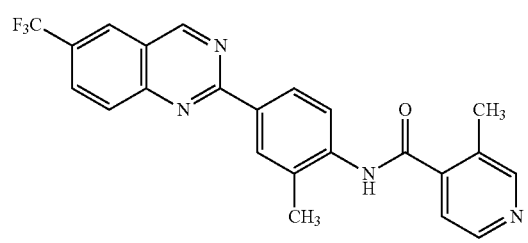

The title compound was prepared analogously to Example 001, where 2-methyl-4-(6-(trifluoromethyl)quinazolin-2-yl)aniline was substituted in place of 2-methyl-4-(6-(trifluoromethyl)quinolin-2-yl)aniline and 3-methylpyridine-4-carboxylic acid was substituted in place of 1-methyl-1H-pyrazole-5-carboxylic acid. Yield=43%. LCMS (ES, m/z): [M+H]$^+$ 423; $^1$H-NMR (300 MHz, DMSO-d$_6$, ppm): 10.16 (s, 1H), 9.89 (s, 1H), 8.71 (s, 1H), 8.60-8.47 (m, 4H), 8.30-8.27 (m, 2H), 7.99-7.77 (d, 1H), 7.65-7.54 (d, 1H), 2.45-2.44 (d, 6H)

Example 122: N,3-dimethyl-N-(2-methyl-4-(6-(trifluoromethyl)quinazolin-2-yl)phenyl)isonicotinamide

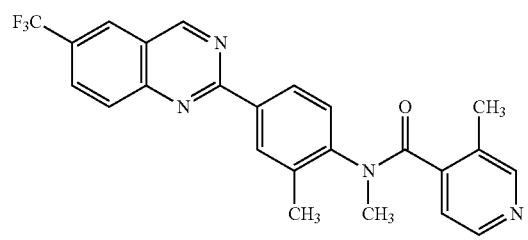

To a stirred solution of N,2-dimethyl-4-[6-(trifluoromethyl)quinazolin-2-yl]aniline (60 mg, 0.19 mmol, 1 equiv) and 3-methylpyridine-4-carboxylic acid (25.9 mg, 0.19 mmol, 1 equiv) in DMF (1 mL) were added DIEA (48.9 mg, 0.38 mmol, 2 equiv) and HATU (107.8 mg, 0.28 mmol, 1.5 equiv). The resulting mixture was stirred overnight at 60° C. under nitrogen atmosphere. The mixture was concentrated under reduced pressure and the residue was purified by preparative TLC (CH$_2$Cl$_2$/MeOH=20:1) to afford the desired final product as a white solid in 64% yield. LCMS (ES, m/z): [M+H]$^+$ 437; $^1$H-NMR (300 MHz, CDCl$_3$, ppm): 9.60-9.55 (d, 1H), 8.68-8.62 (m, 0.6H), 8.02 (s, 0.9H), 8.34 (s, 0.8H), 8.32-8.27 (m, 2H), 8.24-8.18 (m, 1.7H), 8.12-8.10 (m, 1H), 7.46-7.43 (d, 0.2H), 7.35-7.33 (d, 0.2H), 7.15-7.13 (d, 0.8H), 6.91-6.90 (d, 0.8H), 3.49 (s, 2.5H), 3.19 (s, 0.4H), 2.53-2.47 (d, 6H)

Example 123: 5-methyl-N-(2-methyl-4-(6-(trifluoromethyl)quinazolin-2-yl)phenyl)pyrimidine-4-carboxamide

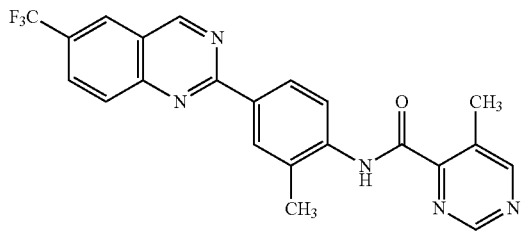

A mixture of 5-bromo-N-[2-methyl-4-[6-(trifluoromethyl)quinazolin-2-yl]phenyl]pyrimidine-4-carboxamide (245 mg, 0.50 mmol, 1 equiv), KOAc (98.5 mg, 1.00 mmol, 2 equiv), trimethyl-1,3,5,2,4,6-trioxatriborinane (252.0 mg, 1.00 mmol, 2.000 equiv, 50%), Pd(dppf)Cl$_2$ (36.7 mg, 0.05 mmol, 0.100 equiv) in dioxane (3.0 mL) was stirred overnight at 100° C. The reaction was quenched by the addition of 15 mL of water, extracted with ethyl acetate (3×5 mL) and the combined organic layers concentrated under reduced pressure. The residue was purified by silica gel chromatography with dichloromethane/methanol (30/1) to afford the desired final product as a white solid in 90% yield. LCMS (ES, m/z): [M+H]$^+$ 424; $^1$H-NMR (400 MHz, DMSO-d$_6$, ppm): δ2.47 (s, 3H), δ2.60 (s, 3H), δ8.04-8.06 (d, 1H), δ8.24-8.29 (m, 2H), δ8.48-8.53 (m, 2H), δ8.71 (s, 1H), δ8.95 (s, 1H), δ9.24 (s, 1H), δ9.88 (s, 1H), δ10.46 (s, 1H).

Step 1: 5-bromo-N-(2-methyl-4-(6-(trifluoromethyl)quinazolin-2-yl)phenyl)pyrimidine-4-carboxamide

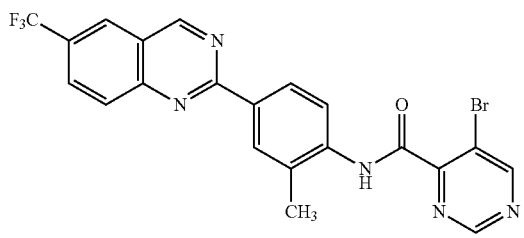 [SMILES: Cc1cc(-c2ncc3cc(C(F)(F)F)ccc3n2)ccc1NC(=O)c1ncncc1Br]

The title compound was prepared analogously to Example 001, where 2-methyl-4-(6-(trifluoromethyl)quinazolin-2-yl)aniline was substituted in place of 2-methyl-4-(6-(trifluoromethyl)quinolin-2-yl)aniline and 5-bromopyrimidine-4-carboxylic acid was substituted in place of 1-methyl-1H-pyrazole-5-carboxylic acid. Yield=79%

Example 124: N,5-dimethyl-N-(2-methyl-4-(6-(trifluoromethyl)quinazolin-2-yl)phenyl)pyrimidine-4-carboxamide

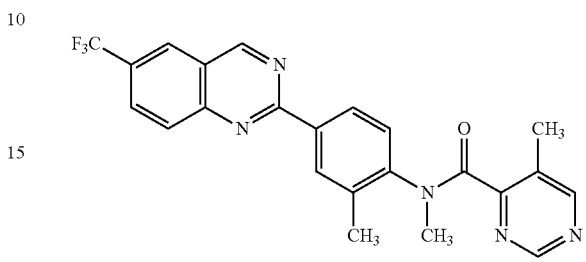

The title compound was prepared analogously to Example 002, where 5-methyl-N-(2-methyl-4-(6-(trifluoromethyl)quinazolin-2-yl)phenyl)pyrimidine-4-carboxamide was substituted in place of 1-methyl-N-(2-methyl-4-(6-(trifluoromethyl)quinolin-2-yl)phenyl)-1H-pyrazole-5-carboxamide. Yield=58%. LCMS (ES, m/z): [M+H]$^+$ 438; $^1$H-NMR (400 MHz, CDCl$_3$, ppm): δ2.42 (s, 3H), δ2.55 (s, 3H), δ3.49 (s, 3H), δ7.15-7.17 (d, 1H), δ8.06-8.10 (m, 1H), δ8.16-8.22 (m, 1H), δ8.25-8.28 (m, 2H), δ8.45-8.66 (m, 2H), δ8.74 (s, 1H), δ9.52 (s, 1H)

Example 125: 2,5-dimethyl-N-(2-methyl-4-(6-(trifluoromethyl)quinazolin-2-yl)phenyl)isonicotinamide

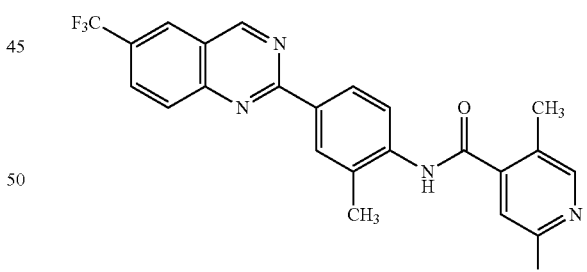

The title compound was prepared analogously to Example 001, where 2-methyl-4-(6-(trifluoromethyl)quinazolin-2-yl)aniline was substituted in place of 2-methyl-4-(6-(trifluoromethyl)quinolin-2-yl)aniline and 2,5-dimethylisonicotinic acid was substituted in place of 1-methyl-1H-pyrazole-5-carboxylic acid. Yield=49%. LCMS (ES, m/z): [M+H]$^+$ 437; $^1$H-NMR (400 MHz, CDCl$_3$, ppm): δ2.48 (s, 3H), δ2.53 (s, 3H), δ2.64 (s, 3H), δ7.33 (s, 1H), δ7.53 (s, 1H), δ8.08-8.11 (q, 1H), δ8.21-8.23 (d, 1H), δ8.27 (s, 1H), δ8.34 (brs, 1H), δ8.49 (s, 1H), δ8.58-8.61 (m, 2H), δ9.57 (s, 1H)

Example 126: N,2,5-trimethyl-N-(2-methyl-4-(6-(trifluoromethyl)quinazolin-2-yl)phenyl)isonicotinamide

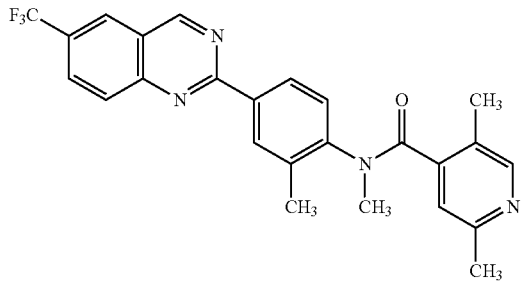 [SMILES: Cc1cc(C(=O)N(C)c2ccc(-c3ncc4cc(C(F)(F)F)ccc4n3)cc2C)c(C)cn1]

To a stirred solution of 2,5-dimethylisonicotinoyl chloride (96 mg, 1.2 equiv) and N,2-dimethyl-4-[6-(trifluoromethyl)quinazolin-2-yl]aniline (150 mg, 1 equiv) in CH$_2$Cl$_2$ (2 mL) was added triethylamine (100 mg, 2 equiv). The resulting mixture was stirred for 2 h at room temperature. The reaction was quenched by the addition of water (20 mL). The resulting mixture was extracted with EtOAc (2×20 mL) and the combined organic layers concentrated under reduced pressure. The residue was purified by preparative TLC (CH$_2$Cl$_2$/MeOH=30/1) to afford the desired product as a white solid in 46% yield. LCMS: (ES, m/z): [M+H]$^+$ 451; $^1$H-NMR: (400 MHz, CD$_3$OD, ppm): δ2.27 (s, 2H), δ2.39 (s, 2H), δ2.43 (s, 1H), δ2.46 (s, 2H), δ2.50 (s, 1H), δ2.60 (s, 1H), δ3.20 (s, 1H), δ3.46 (s, 2H), δ6.96-7.54 (m, 2H), δ8.15-8.67 (m, 6H), δ9.67-9.74 (d, 1H)

Example 127: 1,3-dimethyl-1-(2-methyl-4-(6-(trifluoromethyl)quinazolin-2-yl)phenyl)urea

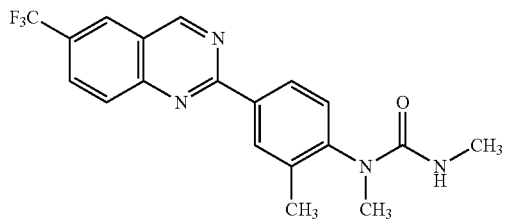 [SMILES: CNC(=O)N(C)c1ccc(-c2ncc3cc(C(F)(F)F)ccc3n2)cc1C]

Over a solution of 4-nitrophenyl methyl(2-methyl-4-(6-(trifluoromethyl)quinazolin-2-yl)phenyl)carbamate in THF, methanamine (2M in THF, 0.4 mL, 4.00 equiv) was added. The resulting solution was stirred overnight at 70° C. The reaction was then diluted by the addition of 20 mL of water and extracted with ethyl acetate (3×50 mL). The organic layers were combined and concentrated under reduced pressure. The residue was purified by preparative TLC with chloroform/methanol (20:1) to afford the desired final product as a white solid in 57% yield. LCMS, (ES, m/z): [M+H]$^+$ 375; $^1$H-NMR (DMSO-d$_6$, 300 MHz, ppm): δ2.31 (s, 3H), δ2.55 (s, 3H), δ3.12 (s, 3H), δ5.75 (s, 1H), δ7.36-7.39 (d, 1H), δ8.27-8.28 (s, 2H), δ8.43-8.47 (q, 1H), δ8.52 (s, 1H), δ8.72 (s, 1H), δ9.90 (s, 1H)

Step 1: 4-nitrophenyl methyl(2-methyl-4-(6-(trifluoromethyl)quinazolin-2-yl)phenyl)carbamate

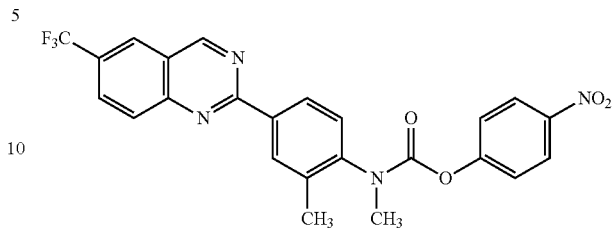

A mixture of N,2-dimethyl-4-[6-(trifluoromethyl)quinazolin-2-yl]aniline (60 mg, 0.19 mmol, 1.00 equiv), triethylamine (38 mg, 0.38 mmol, 2.00 equiv) and 4-nitrophenyl chloroformate (42 mg, 0.21 mmol, 1.10 equiv) in 0.5 mL of THF was stirred for at room temperature 2 hours and used immediately in the next step.

Example 128: methyl methyl(2-methyl-4-(6-(trifluoromethyl)quinazolin-2-yl)phenyl)carbamate

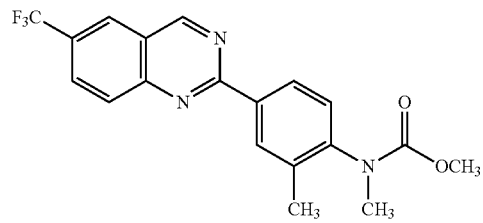 [SMILES: COC(=O)N(C)c1ccc(-c2ncc3cc(C(F)(F)F)ccc3n2)cc1C]

Methyl chloroformate (31.3 mg, 0.33 mmol, 1.5 equiv) was added to a solution of N,2-dimethyl-4-[6-(trifluoromethyl)quinazolin-2-yl]aniline (70 mg, 0.22 mmol, 1 equiv) in pyridine (0.7 mL). The resulting mixture was stirred at 50° C. overnight, and concentrated under reduced pressure. The residue was purified by preparative-TLC (CH$_2$Cl$_2$/MeOH=80/1) to afford the desired final product as yellow solid in 32% yield. LCMS (ES, m/z): [M+H]$^+$ 376; $^1$H-NMR (300 MHz, DMSO-d$_6$, ppm): δ2.29 (s, 3H), δ3.19 (s, 3H), δ3.56-3.72 (d, 3H), δ7.42-7.45 (d, 1H), δ8.27-8.28 (d, 2H), δ8.42-8.45 (q, 1H), δ8.50-8.51 (d, 1H), δ8.71-8.72 (d, 1H), δ9.89 (s, 1H)

Example 129: 1,1,3-trimethyl-3-(2-methyl-4-(6-(trifluoromethyl)quinazolin-2-yl)phenyl)urea

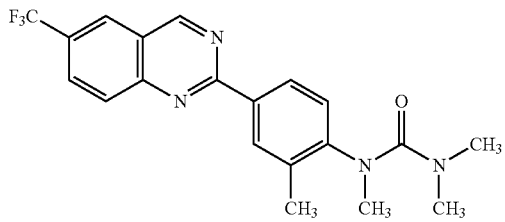 [SMILES: Cc1cc(-c2ncc3cc(C(F)(F)F)ccc3n2)ccc1N(C)C(=O)N(C)C]

A mixture of N, 2-dimethyl-4-[6-(trifluoromethyl)quinazolin-2-yl]aniline (70 mg, 0.22 mmol, 1 equiv), N,N-dimethylcarbamoyl chloride (47.4 mg, 0.44 mmol, 2 equiv)

and Et₃N (44.6 mg, 0.44 mmol, 2 equiv) in toluene (2 mL) was stirred at 100° C. overnight. The resulting mixture was concentrated under reduced pressure. The residue was purified by silica gel chromatography with ethyl acetate/hexane (1/10) to afford the desired product as a yellow solid in 44% yield. LCMS (ES, m/z): [M+H]⁺ 389; ¹H-NMR (400 MHz, CDCl₃, ppm): δ9.58 (s, 1H), δ8.56 (s, 1H), δ8.55-8.47 (d, 1H), δ8.28 (s, 1H), δ8.24-8.22 (d, 1H), δ8.12-8.09 (d, 1H), δ7.24-7.22 (d, 1H), δ3.16 (s, 3H), δ2.67 (s, 6H), δ2.43 (s, 3H)

Example 130: N-methyl-N-(2-methyl-4-(6-(trifluoromethyl)quinazolin-2-yl)phenyl)acetamide

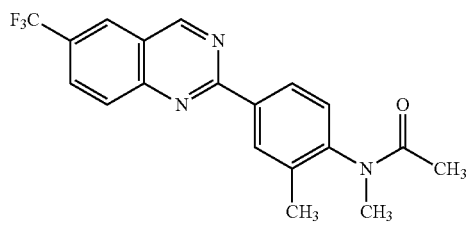 [SMILES: CC(=O)N(C)c1ccc(-c2ncc3cc(C(F)(F)F)ccc3n2)cc1C]

The title compound was prepared analogously to Example 002, where N-(2-methyl-4-(6-(trifluoromethyl)quinazolin-2-yl)phenyl)acetamide was substituted in place of 1-methyl-N-(2-methyl-4-(6-(trifluoromethyl)quinolin-2-yl)phenyl)-1H-pyrazole-5-carboxamide. Yield=59%. LCMS (ES, m/z): [M+H]⁺ 360; ¹H-NMR (300 MHz, CDCl₃, ppm): δ1.87 (s, 3H), δ2.41 (s, 3H), δ3.27 (s, 3H), δ7.33-7.36 (d, 1H), δ8.11-8.14 (m, 1H), δ8.25-8.31 (t, 2H), δ8.54-8.57 (d, 1H), δ8.62 (s, 1H), δ9.61 (s, 1H)

Step 1: N-(2-methyl-4-(6-(trifluoromethyl)quinazolin-2-yl)phenyl)acetamide

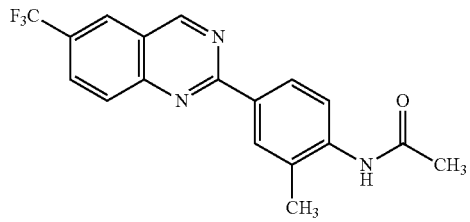 [SMILES: CC(=O)Nc1ccc(-c2ncc3cc(C(F)(F)F)ccc3n2)cc1C]

To a stirred solution of 2-methyl-4-[6-(trifluoromethyl)quinazolin-2-yl]aniline (100 mg, 0.33 mmol, 1 equiv) in CH₂Cl₂ (2 mL) was added triethylamine (50.0 mg, 0.49 mmol, 1.5 equiv) and acetyl chloride (31.1 mg, 0.40 mmol, 1.2 equiv). The resulting mixture was stirred at room temperature for 2 hours. The reaction was quenched by the addition of water (20 mL). The resulting mixture was extracted with CH₂Cl₂ (2×20 mL). The combined organic layers were concentrated under reduced pressure. The residue was purified by preparative TLC (CH₂Cl₂/MeOH=30/1) to afford the desired final product as a yellow solid in 99% yield.

Example 131: N-methyl-N-(2-methyl-4-(6-(trifluoromethyl)quinazolin-2-yl)phenyl)-1H-imidazole-5-carboxamide

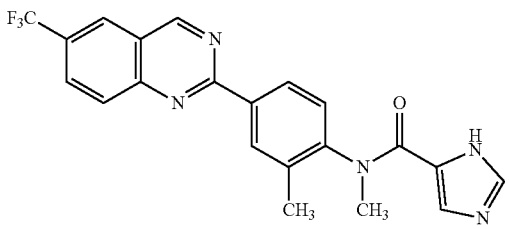 [SMILES: Cc1cc(-c2ncc3cc(C(F)(F)F)ccc3n2)ccc1N(C)C(=O)c1cnc[nH]1]

The title compound was prepared analogously to Example 001, where N,2-dimethyl-4-(6-(trifluoromethyl)quinazolin-2-yl)aniline was substituted in place of 2-methyl-4-(6-(trifluoromethyl)quinolin-2-yl)aniline. Yield=7%. LCMS (ES, m/z): [M+H]⁺ 412; ¹H-NMR (400 MHz, CDCl₃, ppm): δ9.60 (s, 1H), δ8.67 (s, 1H), δ8.63-8.61 (d, 1H), δ8.30 (s, 1H), δ8.25-8.23 (d, 1H), δ8.12-8.10 (m, 1H), δ7.70-7.71 (d, 1H), δ7.40-7.38 (d, 1H), δ5.79 (s, 1H). δ3.43 (s, 3H), δ2.28 (s, 3H Example 132: N-methyl-N-(2-methyl-4-(6-(trifluoromethyl)quinazolin-2-yl)phenyl)-1H-imidazole-2-carboxamide

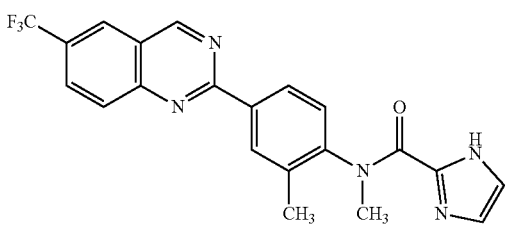 [SMILES: Cc1cc(-c2ncc3cc(C(F)(F)F)ccc3n2)ccc1N(C)C(=O)c1ncc[nH]1]

The title compound was prepared analogously to Example 122, where 1H-imidazole-2-carboxylic acid was substituted in place of 3-methylpyridine-4-carboxylic acid. Yield=9%. LCMS (ES, m/z): [M+H]⁺ 412; ¹H-NMR (400 MHz, DMSO-d₆, ppm): δ10.54-10.21 (d, 1H), δ9.59 (s, 1H), δ8.64-8.55 (m, 2H), δ8.29 (s, 1H), δ8.25-8.22 (t, 1H), δ8.12-8.09 (d, 1H), δ7.42-7.28 (dd, 1.5H), δ7.23 (s, 0.5H), δ7.02-6.89 (d, 1H). δ4.08 (s, 1H), δ3.45 (s, 2H), δ2.98-2.91 (d, 3H)

Example 133: N-methyl-N-(2-methyl-4-(6-(trifluoromethyl)quinazolin-2-yl)phenyl)-1H-tetrazole-5-carboxamide

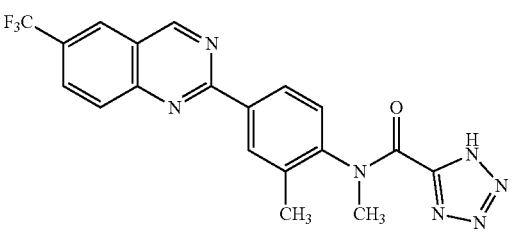

The title compound was prepared analogously to Example 122, where 1H-1,2,3,4-tetrazole-5-carboxylic acid was substituted in place of 3-methylpyridine-4-carboxylic acid. Yield=15%. LCMS (ES, m/z): [M+H]⁺ 414; ¹H-NMR (400 MHz, CD$_3$OD, ppm): δ2.34-2.45 (d, 3H), δ3.46-3.53 (d, 3H), δ7.31-7.51 (q, 1H), δ8.15-8.27 (m, 2H), δ8.37-8.66 (m, 3H), δ9.68-9.73 (d, 1H)

Example 134: N-methyl-N-(2-methyl-4-(6-(trifluoromethyl)quinazolin-2-yl)phenyl)-1H-1,2,4-triazole-5-carboxamide

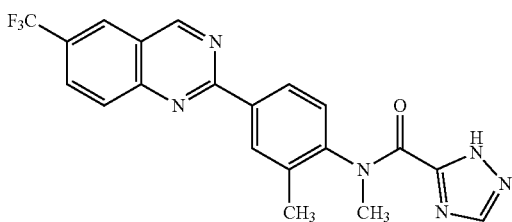 [SMILES: Cc1cc(-c2ncc3cc(C(F)(F)F)ccc3n2)ccc1N(C)C(=O)c1ncn[nH]1]

The title compound was prepared analogously to Example 122, where 1H-1,2,4-triazole-5-carboxylic acid acid was substituted in place of 3-methylpyridine-4-carboxylic acid. Yield=19%. LCMS (ES, m/z): [M+H]⁺ 413; ¹H-NMR (300 MHz, CDCl$_3$, ppm): δ2.38-2.40 (d, 3H), δ3.48-3.96 (d, 3H), δ5.80 (s, 1H), δ7.32-7.43 (t, 1H), δ7.91 (brs, 1H), δ8.09-8.12 (q, 1H), δ8.21-8.24 (d, 1H), δ8.29 (s, 1H), δ8.48-8.64 (m, 2H), δ9.59 (s, 1H)

Example 135: 1-methyl-N-(2-methyl-4-(6-(trifluoromethyl)pyrido[3,2-d]pyrimidin-2-yl)phenyl)-1H-pyrazole-5-carboxamide

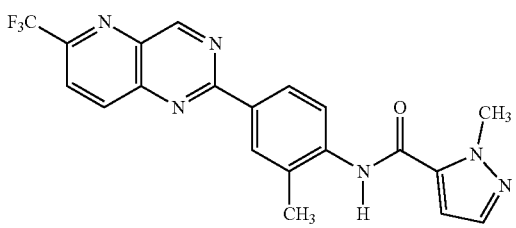

DIEA (135.9 mg, 1.05 mmol, 2 equiv) and HATU (299.9 mg, 0.79 mmol, 1.5 equiv) were added to a solution of 2-methyl-4-[6-(trifluoromethyl)pyrido[3,2-d]pyrimidin-2-yl]aniline (160 mg, 0.53 mmol, 1 equiv) and 1-methyl-1H-pyrazole-5-carboxylic acid (99.5 mg, 0.79 mmol, 1.5 equiv) in DMF (2 mL). The resulting solution was stirred overnight at 50° C. The reaction was quenched by the addition of 10 mL of water. The resulting solution was extracted with ethyl acetate (2×3 mL) and concentrated under reduced pressure. The residue was purified by preparative TLC with dichloromethane/methanol (30/1) to afford the desired product as a yellow solid in 24% yield. LCMS (ES, m/z): [M+H]⁺ 413; ¹H-NMR (400 MHz, CDCl$_3$, ppm): δ2.51 (s, 3H), δ4.29 (s, 3H), δ6.71-6.72 (s, 1H), δ7.58 (s, 1H), δ7.72 (s, 1H), δ8.14-8.16 (d, 1H), δ8.33-8.37 (m, 1H), δ8.59-8.62 (m, 3H), δ9.81 (s, 1H)

Step 1: 3-amino-6-(trifluoromethyl)picolinonitrile

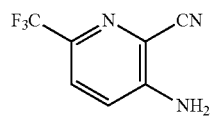

2-bromo-6-(trifluoromethyl)pyridin-3-amine (10 g, 41.49 mmol, 1 equiv) and CuCN (10.0 g, 111.66 mmol, 2.691 equiv) were dissolved in DMSO (100 mL). The resulting solution was stirred for 4 hours at 120° C. followed by dilution with 400 mL of H$_2$O. The aqueous solution was extracted with ethyl acetate (2×300 mL) and concentrated under reduced pressure. The residue was purified by silica gel chromatography with ethyl acetate/petroleum ether (1/5) to afford the desired final product as a grey solid in 64% yield.

Step 2: 3-amino-6-(trifluoromethyl)picolinic acid

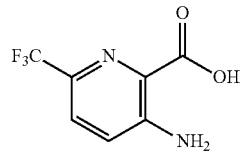

A solution of 3-amino-6-(trifluoromethyl)pyridine-2-carbonitrile (5 g, 26.72 mmol, 1 equiv) and KOH (50 mL, 2M) in EtOH (25 mL) was refluxed overnight. The ethanol was eliminated under reduced pressure and the pH of the solution was adjusted to 5 with 5% HCl. The solid was collected by filtration to afford the desired product in 78% yield.

Step 3: 6-(trifluoromethyl)pyrido[3,2-d]pyrimidine-2,4(1H,3H)-dione

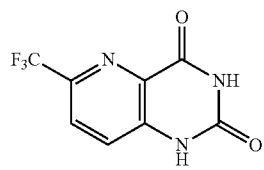 [SMILES: O=c1[nH]c(=O)c2nc(C(F)(F)F)ccc2[nH]1]

3-amino-5-(trifluoromethyl)pyridine-2-carboxylic acid (4.2 g, 20.38 mmol, 1 equiv) and urea (12.2 g, 203.15 mmol, 9.970 equiv) were heated at 200° C. for three hours. The resulting solution was diluted with 150 mL of water and the solid filtrated to afford the desired product in 85% yield.

Step 4: 2,4-dichloro-6-(trifluoromethyl)pyrido[3,2-d]pyrimidine

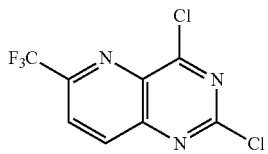 [SMILES: FC(F)(F)c1ccc2nc(Cl)nc(Cl)c2n1]

POCl₃ (20 mL) was added over 6-(trifluoromethyl)-1H, 2H,3H,4H-pyrido[3,2-d]pyrimidine-2,4-dione (4 g, 17.31 mmol, 1 equiv) and the resulting solution stirred for 3 hours at 100° C. The mixture was concentrated and the residue diluted with 50 mL of saturated NaHCO₃. After extraction with ethyl acetate (2×20 mL), the volatiles were eliminated under reduced pressure to afford a crude material that was purified by silica gel with ethyl acetate/petroleum ether (1/100) to afford the desired product as a white solid in 11% yield.

Step 5: 2-chloro-6-(trifluoromethyl)pyrido[3,2-d]pyrimidine

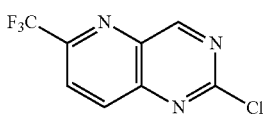 [SMILES: FC(F)(F)c1ccc2nc(Cl)ncc2n1]

Over a solution of 2,4-dichloro-6-(trifluoromethyl)pyrido[3,2-d]pyrimidine (500 mg, 1.87 mmol, 1 equiv) in THF (5 mL), Bu₃SnH (544 mg, 1.87 mmol, 1 equiv) and Pd(PPh₃)₄ (215.6 mg, 0.19 mmol, 0.1 equiv) were added. The resulting solution was stirred overnight at room temperature and concentrated under reduced pressure. The residue was purified by silica gel with ethyl acetate/petroleum ether (100/1) as eluent to afford the desired product as a white solid in 46% yield.

Step 6: 2-(3-methyl-4-nitrophenyl)-6-(trifluoromethyl)pyrido[3,2-d]pyrimidine

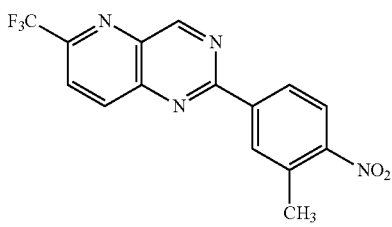

A mixture of 2-chloro-6-(trifluoromethyl)pyrido[3,2-d]pyrimidine (400 mg, 1.71 mmol, 1 equiv), 4,4,5,5-tetramethyl-2-(3-methyl-4-nitrophenyl)-1,3,2-dioxaborolane (450.6 mg, 1.71 mmol, 1 equiv), Na₂CO₃ (363.0 mg, 3.42 mmol, 2 equiv), Pd(PPh₃)₄ (197.9 mg, 0.17 mmol, 0.1 equiv) in toluene (8 mL) and EtOH (4 mL) was stirred overnight at 100° C. The solids were filtered out and the solution concentrated. The residue was purified by preparative TLC with ethyl acetate/petroleum ether (1/5) as eluent to afford the desired product as a yellow solid in 40% yield.

Step 7: 2-methyl-4-(6-(trifluoromethyl)pyrido[3,2-d]pyrimidin-2-yl)aniline

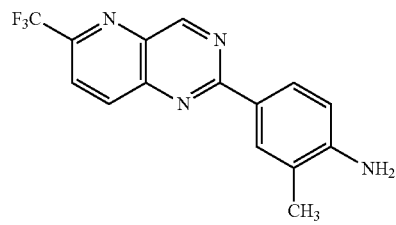 [SMILES: Cc1cc(-c2ncc3nc(C(F)(F)F)ccc3n2)ccc1N]

Over a solution of 2-(3-methyl-4-nitrophenyl)-6-(trifluoromethyl)pyrido[3,2-d]pyrimidine (230 mg, 0.69 mmol, 1 equiv) in 10 mL of ethanol, SnCl₂.2H₂O (621.1 mg, 2.75 mmol, 4 equiv) was added and resulting solution stirred for 2 hours at 80° C. The reaction was quenched by the addition of 20 mL of saturated solution of NaHCO₃, extracted with 3×10 mL of ethyl acetate and concentrated. The residue was purified by preparative TLC with ethyl acetate/petroleum ether (1:2) as eluent to afford the desired final product as a yellow solid in 72% yield.

Example 136: N,1-dimethyl-N-(2-methyl-4-(6-(trifluoromethyl)pyrido[3,2-d]pyrimidin-2-yl)phenyl)-1H-pyrazole-5-carboxamide

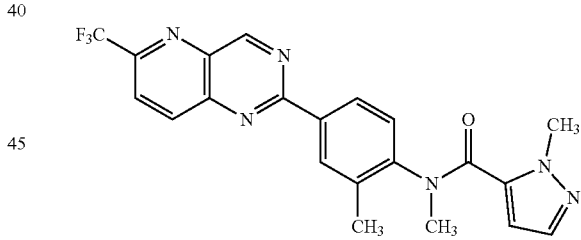

NaH (2.1 mg, 0.05 mmol, 1.1 equiv, 60%) was added to a solution of 1-methyl-N-[2-methyl-4-[6-(trifluoromethyl)pyrido[3,2-d]pyrimidin-2-yl]phenyl]-1H-pyrazole-5-carboxamide (20 mg, 0.05 mmol, 1 equiv) in DMF (3 mL) at 0° C. The reaction was stirred for 0.5 h at 0° C. and MeI (7.6 mg, 0.05 mmol, 1.104 equiv) was added. At that point the cooling bath was removed and stirring continued for another 4 hours at room temperature. The reaction was then quenched by the addition of 10 mL of saturated NH₄Cl. The resulting solution was extracted with ethyl acetate (2×3 mL) and concentrated. The residue was purified by preparative TLC with dichloromethane/methanol (30/1) to afford the desired final product as a white solid in 51% yield. LCMS (ES, m/z): [M+H]⁺ 427; ¹H-NMR (400 MHz, DMSO-d₆, ppm): δ2.28 (s, 3H), δ3.34 (s, 3H), δ4.01 (s, 3H), δ5.53-5.54 (d, 1H), δ7.14-7.15 (d, 1H), δ7.51-7.54 (d, 1H), δ8.35-8.50 (m, 3H), δ8.75-8.81 (d, 1H), δ9.96 (s, 1H)

Example 137: N-(2-fluoro-4-(6-(trifluoromethyl)pyrido[3,2-d]pyrimidin-2-yl)phenyl)-1-methyl-1H-pyrazole-5-carboxamide

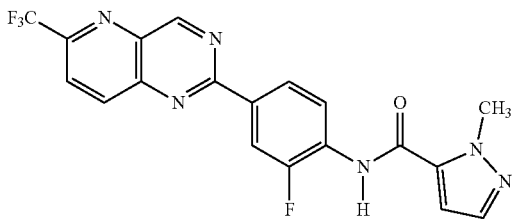 [SMILES: Cn1nccc1C(=O)Nc1ccc(-c2ncc3nc(C(F)(F)F)ccc3n2)cc1F]

The title compound was prepared analogously to Example 122, where 2-fluoro-4-(6-(trifluoromethyl)pyrido[3,2-d]pyrimidin-2-yl)aniline was substituted in place of N,2-dimethyl-4-[6-(trifluoromethyl)quinazolin-2-yl]aniline and 1-methyl-1H-pyrazole-5-carboxylic acid was substituted in place of 3-methylpyridine-4-carboxylic acid. Yield=34%. LCMS (ES, m/z): [M+H]+ 417; 1H-NMR (400 MHz, DMSO-d6, ppm): δ4.11 (s, 3H), δ7.16-7.17 (d, 1H), δ7.57-7.58 (s, 1H), δ7.92-7.96 (t, 1H), δ8.39-8.43 (q, 1H), δ8.47-8.49 (q, 2H), δ8.80-8.82 (d, 1H), δ9.96 (s, 1H), δ10.35 (s, 1H)

Step 1: 2-(3-fluoro-4-nitrophenyl)-6-(trifluoromethyl)pyrido[3,2-d]pyrimidine

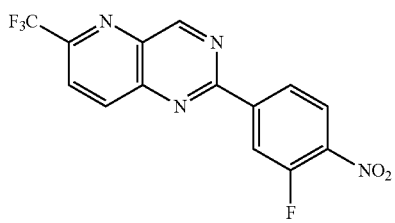 [SMILES: O=[N+]([O-])c1ccc(-c2ncc3nc(C(F)(F)F)ccc3n2)cc1F]

The title compound was prepared analogously to Example 110, where 2-chloro-6-(trifluoromethyl)pyrido[3,2-d]pyrimidine was substituted in place of 2-chloro-8-methyl-6-(trifluoromethyl)quinazoline and 2-(3-fluoro-4-nitrophenyl)-4,4,5,5-tetramethyl-1,3,2-dioxaborolane was substituted in place of 1-methyl-N-(2-methyl-4-(4,4,5,5-tetramethyl-1,3,2-dioxaborolan-2-yl)phenyl)-1H-pyrazole-5-carboxamide. Yield=34%.

Step 2: 2-fluoro-4-(6-(trifluoromethyl)pyrido[3,2-d]pyrimidin-2-yl)aniline

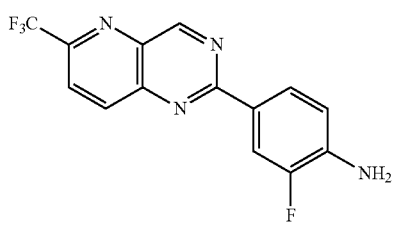

2-(3-fluoro-4-nitrophenyl)-6-(trifluoromethyl)pyrido[3,2-d]pyrimidine (170 mg, 0.50 mmol, 1 equiv) was dissolved in 10 mL of ethanol and SnCl2·2H2O (453.7 mg, 2.01 mmol, 4 equiv) was added. The resulting solution was stirred for 3 hours at 80° C. and quenched by the addition of 20 mL of saturated NaHCO3. Extraction with ethyl acetate (2×10 mL) and elimination of volatiles under reduced pressure afforded a residue that was purified by silica gel chromatography with ethyl acetate/petroleum ether (1/2). The desired final product was isolated as a yellow solid in 65% yield.

Example 138: N-(2-fluoro-4-(6-(trifluoromethyl)pyrido[3,2-d]pyrimidin-2-yl)phenyl)-N,1-dimethyl-1H-pyrazole-5-carboxamide

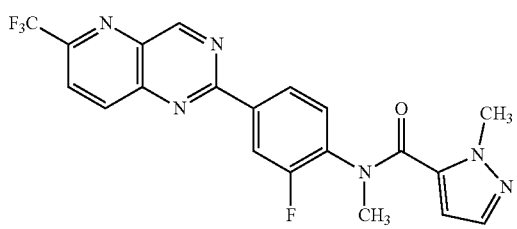

The title compound was prepared analogously to Example 136, where N-(2-fluoro-4-(6-(trifluoromethyl)pyrido[3,2-d]pyrimidin-2-yl)phenyl)-1-methyl-1H-pyrazole-5-carboxamide was substituted in place of 1-methyl-N-[2-methyl-4-[6-(trifluoromethyl)pyrido[3,2-d]pyrimidin-2-yl]phenyl]-1H-pyrazole-5-carboxamide. Yield=51%. LCMS (ES, m/z): [M+H]+ 431; 1H-NMR (400 MHz, DMSO-d6, ppm): δ3.42 (s, 3H), δ3.97 (s, 3H), δ5.88 (s, 1H), δ7.22 (s, 1H), δ7.77-7.81 (t, 1H), δ8.28-8.31 (d, 1H), δ8.44-8.51 (m, 2H), δ8.80-8.82 (d, 1H), δ9.97 (s, 1H)

Example 139: 1-methyl-N-(2-methyl-4-(2-(trifluoromethyl)pyrido[3,2-d]pyrimidin-6-yl)phenyl)-1H-pyrazole-5-carboxamide

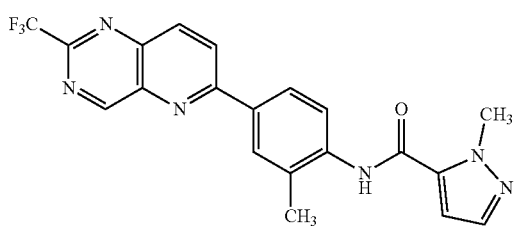 [SMILES: Cc1cc(-c2ccc3nc(C(F)(F)F)ncc3n2)ccc1NC(=O)c1ccnn1C]

The title compound was prepared analogously to Example 109, where 6-chloro-2-(trifluoromethyl)pyrido[3,2-d]pyrimidine was substituted in place of 2-chloro-6-fluoro-8-methylquinazoline. Yield=53%. LCMS (ES, m/z): [M+H]+ 413; 1H-NMR (400 MHz, DMSO-d6, ppm): δ2.41 (s, 3H), δ4.11 (s, 3H), δ7.11-7.12 (d, 1H), δ7.56-7.57 (d, 1H), δ7.64-7.67 (d, 1H), δ8.25-8.28 (q, 1H), δ8.34-8.35 (d, 1H), 8.72-8.74 (d, 1H), 8.83-8.85 (d, 1H), 9.93 (s, 1H), 10.02 (s, 1H)

Step 1:
4-bromo-2-(trifluoromethyl)pyrimidin-5-amine

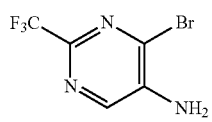

To a solution of 2-(trifluoromethyl)pyrimidin-5-amine (5 g, 30.66 mmol, 1 equiv) in DME (300 mL) was added $Br_2$ (4.90 g, 30.66 mmol, 1 equiv) and Fe (171.2 mg, 3.07 mmol, 0.1 equiv). The resulting mixture was stirred at 80° C. overnight, quenched by the addition of saturated $NaHCO_3$ (300 mL) and extracted with $CH_2Cl_2$ (2×300 mL). The combined organic layers were concentrated under reduced pressure and the residue was purified by silica gel column chromatography with EtOAc/PE (1/10) to afford the desired product as a yellow solid in 20% yield Step 2: ethyl (E)-3-(5-amino-2-(trifluoromethyl)pyrimidin-4-yl)acrylate

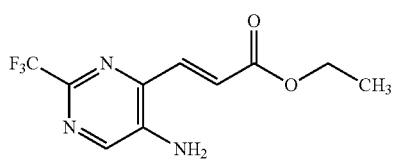

The title compound was prepared analogously to Example 001, step 1, where 4-bromo-2-(trifluoromethyl)pyrimidin-5-amine was substituted in place 2-bromo-4-(trifluoromethyl)aniline. Yield=76%.

Step 3: 2-(trifluoromethyl)pyrido[3,2-d]pyrimidin-6(5H)-one

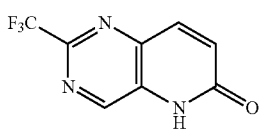 [SMILES: O=c1ccc2nc(C(F)(F)F)ncc2[nH]1]

To a solution of ethyl (E)-3-(5-amino-2-(trifluoromethyl)pyrimidin-4-yl)acrylate (350 mg, 1.34 mmol, 1 equiv) in EtOH (30 mL, 516.41 mmol, 385.387 equiv), EtONa (364.7 mg, 5.36 mmol, 4 equiv) was added. The resulting mixture was stirred at 80° C. for 2 hours. The reaction was quenched by the addition of saturated $NH_4Cl$ (100 mL). The resulting mixture was extracted with EtOAc (2×100 mL). The combined organic layers were concentrated under reduced pressure. The residue was purified by preparative TLC ($CH_2Cl_2$/MeOH 20/1) to afford the desired product as a yellow solid in 85% yield.

Step 4: 6-chloro-2-(trifluoromethyl)pyrido[3,2-d]pyrimidine

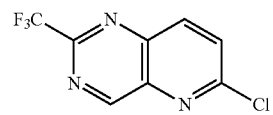

The title compound was prepared analogously to Example 001, step 3, where 2-(trifluoromethyl)pyrido[3,2-d]pyrimidin-6(5H)-one was substituted in place of 6-(trifluoromethyl)-1,2-dihydroquinolin-2-one. Yield=41%.

Example 140: N,1-Dimethyl-N-(2-methyl-4-(6-(trifluoromethyl)quinazolin-2-yl)phenyl)-1H-pyrazole-5-carboxamide

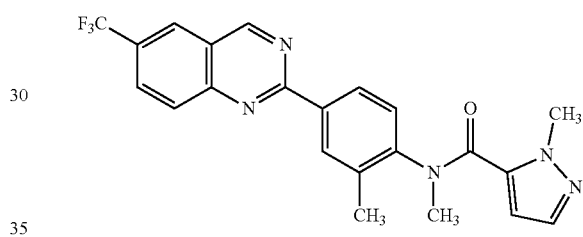

The title compound was prepared analogously to Example 002, where 1-methyl-N-[2-methyl-4-[6-(trifluoromethyl)quinazolin-2-yl]phenyl]-1H-pyrazole-5-carboxamide was substituted in place of 1-methyl-N-(2-methyl-4-(6-(trifluoromethyl)quinolin-2-yl)phenyl)-1H-pyrazole-5-carboxamide. Yield=57%. LCMS (ES, m/z): [M+H]⁺ 426; ¹H-NMR (400 MHz, DMSO-$d_6$, ppm): δ9.89 (s, 1H), δ8.72 (s, 1H), δ8.48-8.40 (m, 2H), δ8.30-8.23 (q, 2H), δ7.51-7.48 (d, 1H), δ7.14 (s, 1H), δ5.53 (s, 1H), δ4.01 (s, 3H), δ3.33 (s, 3H), δ2.27 (s, 3H)

Example 141: 1-(2-methyl-4-(6-(trifluoromethyl)quinazolin-2-yl)phenyl)imidazolidin-2-one

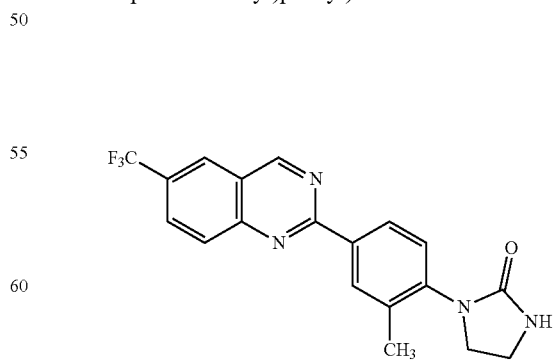

1-(2-chloroethyl)-3-(2-methyl-4-(6-(trifluoromethyl)quinazolin-2-yl)phenyl)urea (110 mg, 0.27 mmol, 1.00 equiv) was dissolved in DMF (1 mL) and sodium hydride (13 mg, 0.54 mmol, 1.20 equiv) added. The resulting solution was stirred overnight at room temperature. The reaction was then quenched by the addition of a saturated solution of NH₄Cl, extracted with 2×300 mL of ethyl acetate and the organic layers combined and concentrated under reduced pressure. The residue was purified by preparative TLC with dichloromethane/methanol (20:1) as eluent. The crude product was purified by recrystallization from methanol to afford the final product as a yellow solid in 26% yield. LCMS: (ES, m/z): [M+H]⁺ 373; ¹H-NMR (DMSO-d₆, 300 MHz ppm): δ2.37 (s, 3H), δ2.45-2.50 (t, 2H), δ3.81-3.86 (t, 2H), δ6.82 (s, 1H), δ7.43-7.46 (d, 1H), δ8.23-8.29 (m, 2H), δ8.41-8.44 (q, 1H), δ8.48-8.49 (d, 1H), δ8.70 (s, 1H), δ9.87 (s, 1H)

Step 1: 1-(2-chloroethyl)-3-(2-methyl-4-(6-(trifluoromethyl)quinazolin-2-yl)phenyl)urea

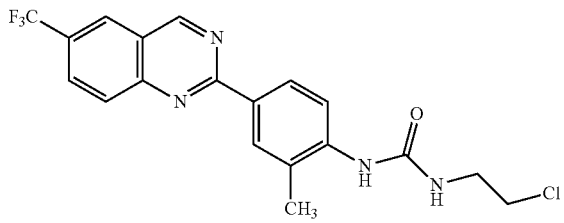 [SMILES: Cc1cc(-c2ncc3cc(C(F)(F)F)ccc3n2)ccc1NC(=O)NCCCl]

A mixture of 2-methyl-4-[6-(trifluoromethyl)quinazolin-2-yl]aniline (100 mg, 0.33 mmol, 1.00 equiv), triethylamine (70 mg, 0.69 mmol, 2.00 equiv), 1-chloro-2-isocyanatoethane (70 mg, 0.66 mmol, 2.00 equiv) in dichloromethane (1 mL) was stirred at room temperature overnight. The resulting solution was diluted with 10 mL of H₂O and extracted with 200 mL of ethyl acetate. The combined organic layers were concentrated under vacuum and the resulting crude product purified by recrystallization from methanol affording the desired product as a yellow solid in 96% yield.

Example 142: 2-methoxy-N-(2-methyl-4-(6-(trifluoromethyl)quinazolin-2-yl)phenyl)isonicotinamide

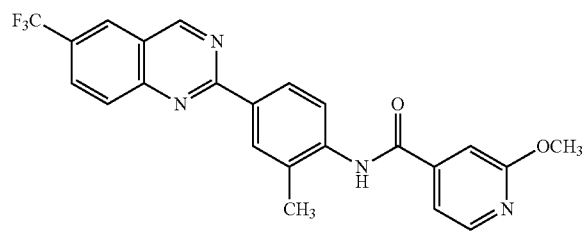 [SMILES: COc1cc(C(=O)Nc2ccc(-c3ncc4cc(C(F)(F)F)ccc4n3)cc2C)ccn1]

The title compound was prepared analogously to Example 001, where 2-methoxyisonicotinic acid was substituted in place of 1-methyl-1H-pyrazole-5-carboxylic acid. LCMS (ES, m/z): [M+H]⁺ 439; ¹H-NMR (400 MHz, DMSO-d₆, ppm): 10.22 (s, 1H), 9.89 (s, 1H), 8.72 (s, 1H), 8.54-8.53 (d, 1H), 8.48-8.46 (q, 1H), 8.39-8.38 (d, 1H), 8.30-8.25 (m, 2H), 7.68-7.66 (d, 1H), 7.50-7.49 (m, 1H), 7.36 (s, 1H), 3.95 (s, 3H), 2.41 (s, 3H)

Example 143: 2-Methoxy-N-methyl-N-(2-methyl-4-(6-(trifluoromethyl)quinazolin-2-yl)phenyl)isonicotinamide

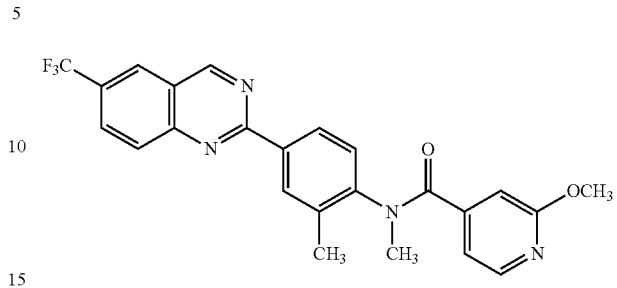

To a solution of N,2-dimethyl-4-[6-(trifluoromethyl)quinazolin-2-yl]aniline (60 mg, 0.19 mmol, 1 equiv) and Et₃N (57.4 mg, 0.57 mmol, 3 equiv) in dichloromethane kept at 0° C., 2-methoxypyridine-4-carbonyl chloride (48.7 mg, 0.28 mmol, 1.5 equiv) was added. The resulting mixture was stirred at room temperature for 12 hours. The reaction was quenched with saturated NH₄Cl and the aqueous layer extracted with ethyl acetate (2×10 mL). The combined organic layers were combined and concentrated under reduced pressure. The residue was purified by preparative TLC (dichloromethane/MeOH=20:1) to afford the desired final product as a white solid in 45% yield. LCMS (ES, m/z): [M+H]⁺ 453; ¹H-NMR (400 MHz, CDCl₃, ppm): δ9.60 (s, 1H), 8.63 (s, 1H), 8.42-8.40 (d, 1H), 8.26 (s, 1H), 8.23-8.21 (d, 1H), 8.12-8.10 (d, 1H), 7.98-7.97 (d, 1H), 7.31-7.28 (d, 1H), 6.76-6.74 (d, 1H), 6.70 (s, 1H), 4.03 (s, 3H), 3.47 (s, 3H), 2.44 (s, 3H)

Example 144: 3-methoxy-N-(2-methyl-4-(6-(trifluoromethyl)quinazolin-2-yl)phenyl)isonicotinamide

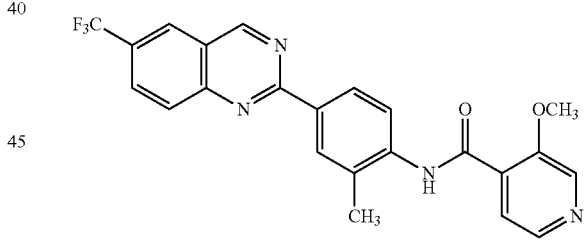

A solution of 2-methyl-4-[6-(trifluoromethyl)quinazolin-2-yl]aniline (100 mg, 0.33 mmol, 1 equiv), 3-methoxypyridine-4-carboxylic acid (75.7 mg, 0.49 mmol, 1.5 equiv), DIEA (85.2 mg, 0.66 mmol, 2 equiv), HATU (188.1 mg, 0.49 mmol, 1.5 equiv) in DMF (2 mL) was stirred overnight at 65° C. The reaction was quenched by the addition of 10 mL of water and extracted with ethyl acetate (2×20 mL). The combined organic layers were evaporated under reduced pressure. The crude product was purified under the following conditions: Column=XBridge Prep C₁₈ OBD Column; mobile phase=water (0.1% NH₄HCO₃) and acetonitrile (10% up to 30% in 15 min); Detector=UV 254 nm. The desired final product was isolated as a white solid in 18% yield. LCMS (ES, m/z): [M+H]⁺439; ¹H-NMR (400 MHz, DMSO-d₆, ppm): δ10.06 (s, 1H), δ9.88 (s, 1H), δ8.71-8.69 (d, 2H), δ8.53-8.42 (m, 3H), δ8.27-8.18 (m, 3H), δ7.78-7.77 (d, 1H), δ4.14 (s, 3H), δ2.48 (s, 3H)

Example 145: 3-Methoxy-N-methyl-N-(2-methyl-4-(6-(trifluoromethyl)quinazolin-2-yl)phenyl)isonicotinamide

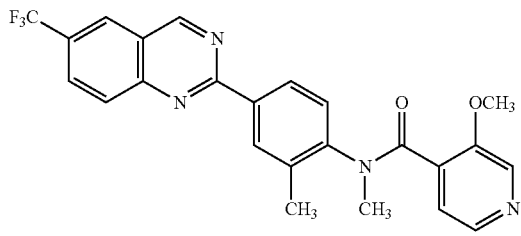 [SMILES: COc1cnccc1C(=O)N(C)c1ccc(-c2ncc3cc(C(F)(F)F)ccc3n2)cc1C]

The title compound was prepared analogously to Example 144, where N,2-dimethyl-4-(6-(trifluoromethyl)quinazolin-2-yl)aniline was substituted in place of 2-methyl-4-[6-(trifluoromethyl)quinazolin-2-yl]aniline. The crude product was purified by reverse phase chromatography with the following conditions: Column=XBridge Prep $C_{18}$ OBD Column, mobile phase=water (0.01% $NH_4HCO_3$) and acetonitrile (10% up to 35% in 15 min), detector=UV 254 nm. Yield=19%. LCMS (ES, m/z): [M+H]$^+$ 453; $^1$H-NMR (400 MHz, CDCl$_3$, ppm): δ9.60 (s, 1H), δ8.59 (s, 1H), δ8.44-8.29 (m, 2H), δ8.27-8.08 (m, 4H), δ7.28-7.24 (d, 1H), δ7.15-7.14 (d, 1H), δ4.10-3.88 (d, 3H), δ3.46-3.20 (d, 3H), δ2.52-2.46 (d, 3H)

Example 146: N-methyl-N-(2-methyl-4-(6-(trifluoromethyl)quinazolin-2-yl)phenyl)-1H-1,2,3-triazole-5-carboxamide

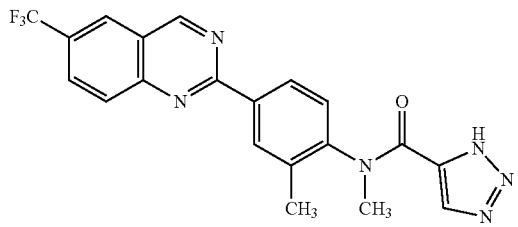 [SMILES: Cc1cc(-c2ncc3cc(C(F)(F)F)ccc3n2)ccc1N(C)C(=O)c1cnn[nH]1]

The title compound was prepared analogously to Example 144, where 1H-1,2,3-triazole-5-carboxylic acid was substituted in place of 3-methoxypyridine-4-carboxylic acid and N,2-dimethyl-4-(6-(trifluoromethyl)quinazolin-2-yl)aniline was substituted in place of 2-methyl-4-[6-(trifluoromethyl)quinazolin-2-yl]aniline. The crude product was purified by preparative HPLC with the following conditions (2 #-AnalyseHPLC-SHIMADZU(HPLC-10)): Column, XBridge Prep $C_{18}$ OBD Column, 5 um, 19*150 mm; mobile phase, water (10 mmol/L, $NH_4HCO_3$) and $CH_3CN$ (30% Phase B up to 42% in 7 min); Detector, UV. Yield=7%. LCMS (ES, m/z): [M+H]$^+$ 413; $^1$H-NMR (400 MHz, DMSO-d$_6$, ppm): δ9.91 (s, 1H), δ8.74 (s, 1H), δ8.51-8.44 (d, 2H), δ8.42 (s, 2H), δ8.32-8.26 (m, 1H), δ7.42-7.40 (d, 1H), δ7.30 (s, 1H), δ3.32 (s, 3H), δ2.33 (s, 3H)

Example 147: 1-methyl-N-(2-methyl-4-(8-methyl-6-(trifluoromethyl)pyrido[3,2-d]pyrimidin-2-yl)phenyl)-1H-pyrazole-5-carboxamide

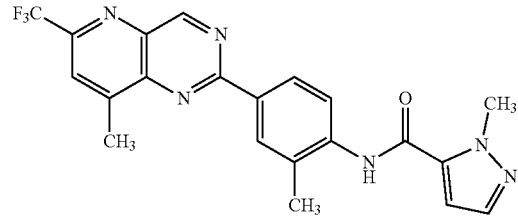 [SMILES: Cc1cc(-c2ncc3nc(C(F)(F)F)cc(C)c3n2)ccc1NC(=O)c1ccnn1C]

The title compound was prepared analogously to Example 009, where 2-chloro-8-methyl-6-(trifluoromethyl)pyrido[3,2-d]pyrimidine was substituted in place of 2-chloro-6-(trifluoromethyl)quinazoline and 1-methyl-N-[2-methyl-4-(tetramethyl-1,3,2-dioxaborolan-2-yl)phenyl]-1H-pyrazole-5-carboxamide was substituted in place of tert-butyl N-methyl-N-[2-methyl-4-(tetramethyl-1,3,2-dioxaborolan-2-yl)phenyl]carbamate. LCMS (ES, m/z): [M+H]$^+$427; $^1$H-NMR (400 MHz, DMSO-d$_6$, ppm): δ2.41 (s, 3H), δ2.95 (s, 3H), δ4.12 (s, 3H), 67.12-7.13 (d, 1H), δ7.57-7.58 (d, 1H), δ7.65-7.67 (d, 1H), δ8.39 (s, 1H), δ8.50-8.52 (q, 1H), δ8.56-8.57 (d, 1H), δ9.89 (s, 1H), δ10.02 (s, 1H)

Step 1: 3-amino-4-methyl-6-(trifluoromethyl)picolinonitrile

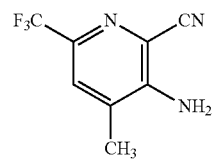

$Zn(CN)_2$ (4.6 g, 39.17 mmol, 1.998 equiv) and $Pd(PPh_3)_4$ (2.3 g, 1.99 mmol, 0.102 equiv) were added over a solution of 2-bromo-4-methyl-6-(trifluoromethyl)pyridin-3-amine (5 g, 19.61 mmol, 1 equiv) in DMF (50 mL). The resulting solution was stirred overnight at 80° C., diluted with 150 mL of water, extracted with 2×50 ml of ethyl acetate and concentrated under reduced pressure. The residue was purified by silica gel chromatgraphy with ethyl acetate/petroleum ether (1:2) to afford the desired final product as a white solid in 94% yield.

Step 2: 8-methyl-6-(trifluoromethyl)pyrido[3,2-d]pyrimidine-2,4(1H,3H)-dione

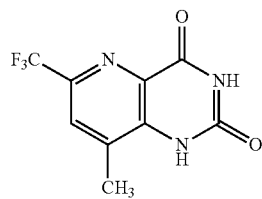

3-amino-4-methyl-6-(trifluoromethyl)pyridine-2-carbonitrile (1.4 g, 6.96 mmol, 1 equiv) was dissolved in DMF (30 mL) and DBU (3.2 g, 21.02 mmol, 3.020 equiv) was added. $CO_2$ was introduced into the flask and the resulting solution stirred overnight at 100° C. After quenching with 90 mL of water, the pH value of the solution was adjusted to 5 with 5% HCl. The solids were collected by filtration to afford the desired final product as a white solid in 88% yield.

Step 3: 2,4-dichloro-8-methyl-6-(trifluoromethyl) pyrido[3,2-d]pyrimidine

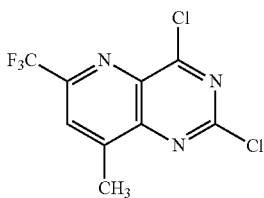 [SMILES: Cc1cc(C(F)(F)F)nc2c(Cl)nc(Cl)nc12]

The title compound was prepared analogously to Example 135, step 4, where 8-methyl-6-(trifluoromethyl)pyrido[3,2-d]pyrimidine-2,4(1H,3H)-dione was substituted in place of 6-(trifluoromethyl)-1H,2H,3H,4H-pyrido[3,2-d]pyrimidine-2,4-dione. Yield=30%.

Step 4: 2-chloro-8-methyl-6-(trifluoromethyl)pyrido [3,2-d]pyrimidine

A mixture of 2,4-dichloro-8-methyl-6-(trifluoromethyl) pyrido[3,2-d]pyrimidine (300 mg, 1.06 mmol, 1 equiv), $PPh_3$ (418.5 mg, 1.60 mmol, 1.5 equiv), $Bu_3SnH$ (325.0 mg, 1.12 mmol, 1.050 equiv) and $Pd(PPh_3)_4$ (122.9 mg, 0.11 mmol, 0.100 equiv) in 5 mL of DMF was stirred for 5 hours at room temperature. The volatiles were removed under reduced pressure to afford a residue that was purified by silica gel chromatography with ethyl acetate/petroleum ether (50/1) affording the desired final product as a white solid in 65% yield.

Example 148: N,1-Dimethyl-N-(2-methyl-4-(8-methyl-6-(trifluoromethyl)pyrido[3,2-d]pyrimidin-2-yl)phenyl)-1H-pyrazole-5-carboxamide

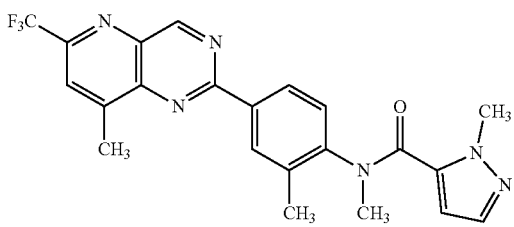 [SMILES: Cc1cc(-c2ncc3nc(C(F)(F)F)cc(C)c3n2)ccc1N(C)C(=O)c1ccnn1C]

The title compound was prepared analogously to Example 009, where 2-chloro-8-methyl-6-(trifluoromethyl)pyrido[3,2-d]pyrimidine was substituted in place of 2-chloro-6-(trifluoromethyl)quinazoline and N,1-dimethyl-N-(2-methyl-4-(4,4,5,5-tetramethyl-1,3,2-dioxaborolan-2-yl)phenyl)-1H-pyrazole-5-carboxamide was substituted in place of tert-butyl N-methyl-N-[2-methyl-4-(tetramethyl-1,3,2-dioxaborolan-2-yl)phenyl]carbamate. Yield=50%. LCMS (ES, m/z): [M+H]⁺ 441; ¹H-NMR (400 MHz, DMSO-d₆, ppm): δ2.29 (s, 3H), δ2.95 (s, 3H), δ3.35 (s, 3H), δ3.99 (s, 3H), δ5.54-5.55 (d, 1H), δ7.14-7.15 (d, 1H), δ7.52-7.54 (d, 1H), δ8.39-8.40 (d, 1H), δ8.45-8.47 (m, 1H), δ8.53 (s, 1H), δ9.89 (s, 1H)

Example 149: 2-methyl-N-(2-methyl-4-(8-methyl-6-(trifluoromethyl)pyrido[3,2-d]pyrimidin-2-yl)phenyl)isonicotinamide

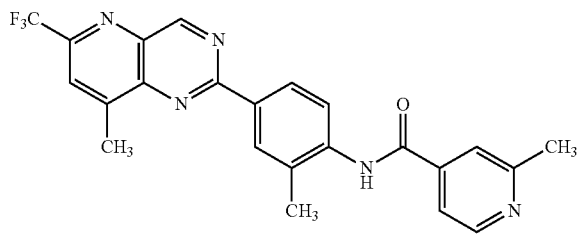 [SMILES: Cc1cc(C(=O)Nc2ccc(-c3ncc4nc(C(F)(F)F)cc(C)c4n3)cc2C)ccn1]

The title compound was prepared analogously to Example 122, where 2-methyl-4-(8-methyl-6-(trifluoromethyl)pyrido [3,2-d]pyrimidin-2-yl)aniline was substituted in place of N,2-dimethyl-4-[6-(trifluoromethyl)quinazolin-2-yl]aniline and 2-methylisonicotinic acid was substituted in place of 3-methylpyridine-4-carboxylic acid. Yield=40%. LCMS (ES, m/z): [M+H]⁺ 438; ¹H-NMR (400 MHz, DMSO-d₆, ppm): δ2.42 (s, 3H), δ2.60 (s, 3H), δ2.95 (s, 3H), δ7.68-7.73 (m, 2H), δ7.80 (s, 1H), δ8.39 (s, 1H), δ8.50-8.52 (d, 1H), δ8.57 (s, 1H), δ8.67-8.68 (d, 1H), δ9.89 (s, 1H), δ10.26 (s, 1H)

Step 1: 8-methyl-2-(3-methyl-4-nitrophenyl)-6-(trifluoromethyl)pyrido[3,2-d]pyrimidine

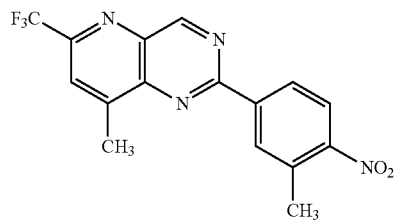 [SMILES: Cc1cc(-c2ncc3nc(C(F)(F)F)cc(C)c3n2)ccc1[N+](=O)[O-]]

The title compound was prepared analogously to Example 009, where 2-chloro-8-methyl-6-(trifluoromethyl)pyrido[3,2-d]pyrimidine was substituted in place of 2-chloro-6-(trifluoromethyl)quinazoline and 4,4,5,5-tetramethyl-2-(3-methyl-4-nitrophenyl)-1,3,2-dioxaborolane was substituted in place of tert-butyl N-methyl-N-[2-methyl-4-(tetramethyl-1,3,2-dioxaborolan-2-yl)phenyl]carbamate. Yield=99%

Step 2: 2-methyl-4-(8-methyl-6-(trifluoromethyl)pyrido[3,2-d]pyrimidin-2-yl)aniline

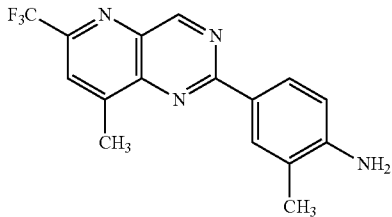 [SMILES: Cc1cc(-c2ncc3nc(C(F)(F)F)cc(C)c3n2)ccc1N]

The title compound was prepared analogously to Example 135, step 7, where 8-methyl-2-(3-methyl-4-nitrophenyl)-6-(trifluoromethyl)pyrido[3,2-d]pyrimidine was substituted in place 2-(3-methyl-4-nitrophenyl)-6-(trifluoromethyl)pyrido[3,2-d]pyrimidine. Yield=59%.

Example 150: N,2-dimethyl-N-(2-methyl-4-(8-methyl-6-(trifluoromethyl)pyrido[3,2-d]pyrimidin-2-yl)phenyl)isonicotinamide

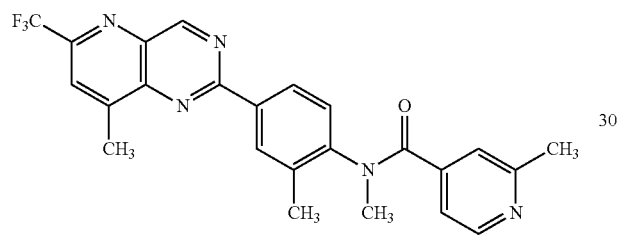

LiHMDS (0.24 mL, 1.5 equiv, 1 M) was added over a solution of 2-methyl-N-[2-methyl-4-[8-methyl-6-(trifluoromethyl)pyrido[3,2-d]pyrimidin-2-yl]phenyl]pyridine-4-carboxamide (70 mg, 0.16 mmol, 1 equiv) in THF (5 mL). After 0.5 hours, methyl iodide (22.7 mg, 0.16 mmol, 1 equiv) was added. The resulting solution was stirred overnight at room temperature. The reaction was quenched by addition of 10 mL of saturated NH$_4$Cl, extracted with ethyl acetate (2×5 mL) and the combined organic layers concentrated under reduced pressure. The residue was purified by preparative TLC with dichloromethane/methanol (25:1) as eluent to afford the desired final product as a white solid in 72% yield. LCMS (ES, m/z): [M+H]$^+$ 452; $^1$H-NMR (400 MHz, DMSO-d$_6$, ppm): δ2.35-2.38 (d, 6H), δ2.90 (s, 3H), δ3.33 (s, 3H), δ6.96-6.97 (d, 1H), δ7.21 (s, 1H), δ7.47-7.49 (d, 1H), δ8.25-8.27 (d, 1H), δ8.30-8.37 (m, 2H), δ8.45 (s, 1H), δ9.84 (s, 1H)

Example 151: N4-(2-methyl-4-(6-(trifluoromethyl)quinazolin-2-yl)phenyl)pyridine-2,4-dicarboxamide

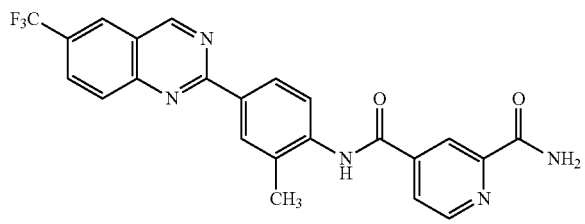 [SMILES: Cc1cc(-c2ncc3cc(C(F)(F)F)ccc3n2)ccc1NC(=O)c1ccnc(C(N)=O)c1]

A solution of 2-cyano-N-[2-methyl-4-[6-(trifluoromethyl)quinazolin-2-yl]phenyl]pyridine-4-carboxamide (30 mg, 0.07 mmol, 1 equiv) in concentrated H$_2$SO$_4$ (0.2 mL) was stirred for 30 min at room temperature. The reaction was quenched by the addition of 5 mL of ice/water, extracted with ethyl acetate (3×5 mL) and the combined organic layers concentrated under reduced pressure. Addition of MeOH afforded the desired final product as a solid, that was isolated after filtration in 57% yield. LCMS (ES, m/z): [M+H]$^+$ 452; $^1$H-NMR (300 MHz, DMSO-d$_6$, ppm): δ2.42 (s, 3H), δ7.65-7.68 (d, 1H), δ7.82 (s, 1H), δ8.09-8.11 (d, 1H), δ8.28 (s, 3H), δ8.47-8.50 (d, 1H), δ8.54-8.59 (d, 2H), δ8.72 (s, 1H), δ8.86-8.88 (d, 1H), δ9.90 (s, 1H), δ10.52 (s, 1H)

Step 1: 2-Cyano-N-(2-methyl-4-(6-(trifluoromethyl)quinazolin-2-yl)phenyl)isonicotinamide

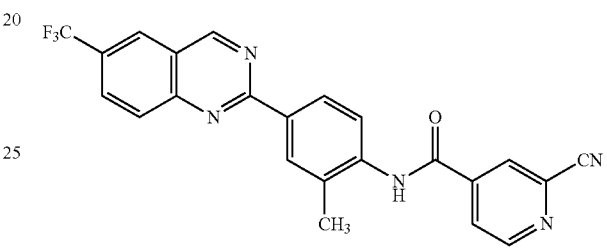

2-cyanopyridine-4-carbonyl chloride (54.9 mg, 0.33 mmol, 1 equiv) was added over a solution of 2-methyl-4-[6-(trifluoromethyl)quinazolin-2-yl]aniline (100 mg, 0.33 mmol, 1 equiv) in 2 mL of dichloromethane, followed by Et$_3$N (66.7 mg, 0.66 mmol, 2 equiv). The resulting solution was stirred for 3 hr at room temperature. The reaction was quenched by the addition of 5 mL of water, extracted with dichloromethane (2×5 mL) and the combined organic layers concentrated. The residue was purified by preparative TLC with dichloromethane/methanol (20/1) to afford the desired final product as a white solid in 24% yield.

Example 152: N4-methyl-N4-(2-methyl-4-(6-(trifluoromethyl)quinazolin-2-yl)phenyl)pyridine-2,4-dicarboxamide

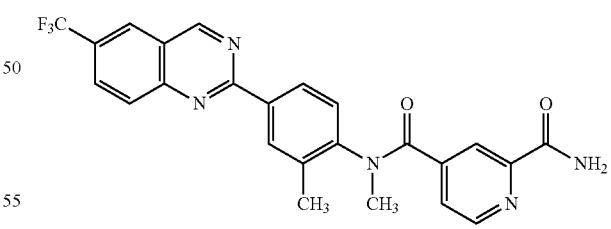

The title compound was prepared analogously to Example 151, where 2-cyano-N-methyl-N-(2-methyl-4-(6-(trifluoromethyl)quinazolin-2-yl)phenyl)isonicotinamide was substituted in place of 2-cyano-N-[2-methyl-4-[6-(trifluoromethyl)quinazolin-2-yl]phenyl]pyridine-4-carboxamide.
Yield=89%. LCMS (ES, m/z): [M+H]$^+$ 466; $^1$H-NMR (300 MHz, DMSO-d$_6$, ppm): δ2.36 (s, 3H), δ3.36 (s, 3H), δ7.40-7.43 (m, 1H), δ7.48-7.50 (d, 1H), δ7.62 (s, 1H), δ7.90 (s, 1H), δ8.02 (s, 1H), δ8.20-8.31 (m, 3H), δ8.40-8.41 (d, 1H), δ8.47-8.49 (d, 1H), δ8.70 (s, 1H), δ9.85 (s, 1H).

Step 1: 2-Cyano-N-methyl-N-(2-methyl-4-(6-(trifluoromethyl)quinazolin-2-yl)phenyl)isonicotinamide

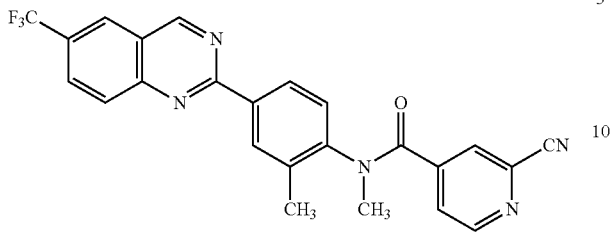

The title compound was prepared analogously to Example 151, step 1, where N,2-dimethyl-4-[6-(trifluoromethyl)quinazolin-2-yl]aniline was substituted in place of 2-methyl-4-[6-(trifluoromethyl)quinazolin-2-yl]aniline. Yield=46%.

Example 153: N-(4-(4-amino-8-methyl-6-(trifluoromethyl)pyrido[3,2-d]pyrimidin-2-yl)-2-methylphenyl)-1-methyl-1H-pyrazole-5-carboxamide

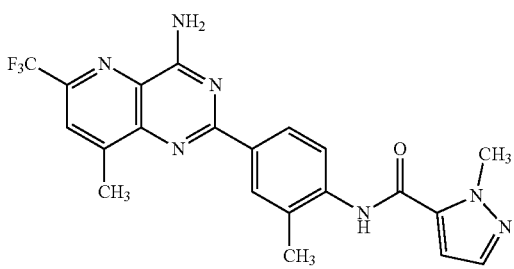 [SMILES: Cc1cc(-c2nc(N)c3nc(C(F)(F)F)cc(C)c3n2)ccc1NC(=O)c1ccnn1C]

A mixture of 2-chloro-8-methyl-6-(trifluoromethyl)pyrido[3,2-d]pyrimidin-4-amine (40 mg, 0.15 mmol, 1 equiv), 1-methyl-N-[2-methyl-4-(tetramethyl-1,3,2-dioxaborolan-2-yl)phenyl]-1H-pyrazole-5-carboxamide (52.0 mg, 0.15 mmol, 1 equiv), $K_2CO_3$ (42.1 mg, 0.30 mmol, 2 equiv) and Pd(PPh$_3$)$_4$ (17.6 mg, 0.02 mmol, 0.1 equiv) in dioxane (1 mL) and H$_2$O (0.2 mL) was stirred at 100° C. overnight. The resulting solution was diluted with 10 mL of water, extracted with 2×10 ml of ethyl acetate, the combined organic layers concentrated and the resulting residue purified by preparative TLC with dichloromethane/methanol (20/1) as eluent to afford the desired final product as a white solid in 58% yield. LCMS (ES, m/z): [M+H]$^+$ 442; $^1$H-NMR (400 MHz, DMSO-d$_6$, ppm): δ2.36 (s, 3H), δ2.80 (s, 3H), δ4.11 (s, 3H), δ7.11-7.12 (d, 1H), δ7.53-7.56 (m, 2H), δ7.99 (s, 1H), δ8.14-8.15 (d, 1H), δ8.27 (s, 1H), δ8.36-8.39 (m, 1H), δ8.43 (s, 1H), δ9.97 (s, 1H)

Step 1: 2-chloro-8-methyl-6-(trifluoromethyl)pyrido[3,2-d]pyrimidin-4-amine

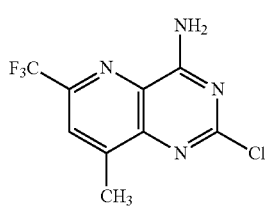

A solution of 2,4-dichloro-8-methyl-6-(trifluoromethyl)pyrido[3,2-d]pyrimidine (200 mg, 1 equiv) in NH$_3$/MeCN (2 mL) was stirred for 30 min at room temperature. The resulting mixture was concentrated and the residue purified by preparative TLC with ethyl acetate/petroleum ether (1:2) as eluent to afford the desired final product as a white solid in 59% yield.

Example 154: N-(4-(4-amino-8-methyl-6-(trifluoromethyl)pyrido[3,2-d]pyrimidin-2-yl)-2-methylphenyl)-N,1-dimethyl-1H-pyrazole-5-carboxamide

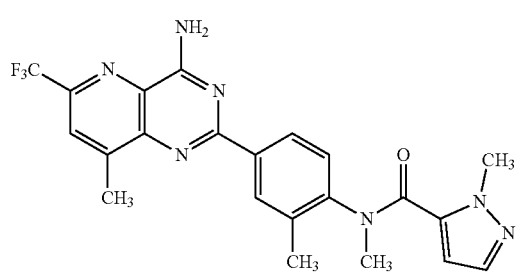 [SMILES: Cc1cc(-c2nc(N)c3nc(C(F)(F)F)cc(C)c3n2)ccc1N(C)C(=O)c1ccnn1C]

The title compound was prepared analogously to Example 153, where 1-methyl-N-[2-methyl-4-(tetramethyl-1,3,2-dioxaborolan-2-yl)phenyl]-1H-pyrazole-5-carboxamide was substituted in place of 1-methyl-N-[2-methyl-4-(tetramethyl-1,3,2-dioxaborolan-2-yl)phenyl]-1H-pyrazole-5-carboxamide. Yield=58%. LCMS (ES, m/z): [M+H]$^+$ 456; $^1$H-NMR (400 MHz, CD$_3$OD, ppm): δ2.29 (s, 3H), δ2.84 (s, 3H), δ3.44 (s, 3H), δ4.10 (s, 3H), δ5.61-5.62 (d, 1H), δ7.15-7.16 (d, 2H), δ7.34-7.37 (d, 1H), δ7.99 (s, 1H), δ8.42-8.47 (m, 2H)

Example 155: 1-(Cyanomethyl)-N-(2-methyl-4-(6-(trifluoromethyl)quinazolin-2-yl)phenyl)-1H-pyrazole-5-carboxamide

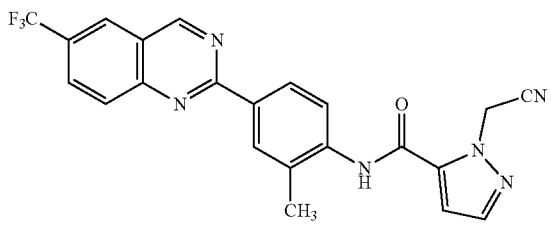 [SMILES: Cc1cc(-c2ncc3cc(C(F)(F)F)ccc3n2)ccc1NC(=O)c1ccnn1CC#N]

The title compound was prepared analogously to Example 116, where 1-(cyanomethyl)-1H-pyrazole-5-carbonyl chloride was substituted in place of isonicotinoyl chloride hydrochloride and 2-methyl-4-(6-(trifluoromethyl)quinazolin-2-yl)aniline was substituted in place of N,2-dimethyl-4-[6-(trifluoromethyl)quinazolin-2-yl]aniline. Yield=30%. LCMS (ES, m/z): [M+H]$^+$ 451; $^1$H-NMR (400 MHz, DMSO-d6, ppm): δ2.31 (s, 3H), δ3.36 (s, 3H), δ5.48-5.49 (d, 1H), δ5.63-5.75 (m, 2H), δ7.35-7.36 (d, 1H), δ7.53-7.55 (d, 1H), δ8.25-8.32 (m, 2H), δ8.44-8.46 (d, 1H), δ8.54 (s, 1H), δ8.74 (s, 1H), δ9.91 (s, 1H).

Step 1: Methyl 1-(cyanomethyl)-1H-pyrazole-5-carboxylate

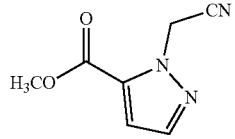 [SMILES: COC(=O)c1ccnn1CC#N]

A mixture of methyl 1H-pyrazole-5-carboxylate (10 g, 79.29 mmol, 1.00 equiv), 2-bromoacetonitrile (9.43 g, 78.62 mmol, 1.10 equiv) and potassium carbonate (10.84 g, 78.43 mmol, 1.10 equiv) in acetonitrile (100 mL) was stirred for 6 h at 80° C. The solids were filtered out and the solution concentrated under vacuum. The residue was purified by silica gel chromatography with ethyl acetate/petroleum ether (1:20) to afford the desired final product as a white solid in 42% yield.

Step 2: 1-(Cyanomethyl)-1H-pyrazole-5-carboxylic acid

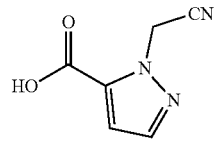

LiOH (704 mg, 29.39 mmol, 1.00 equiv) in water (7 mL) was added over a solution of ethyl 1-(cyanomethyl)-1H-pyrazole-5-carboxylate (3 g, 16.74 mmol, 1.00 equiv) in THF (7 mL). The mixture was stirred at room temperature overnight. Addition of 30 mL of $H_2O$ was followed by neutralization with 1 M HCl. The aqueous solution was extracted three times with ethyl acetate and the combined organic layers concentrated. The crude product was purified by Flash-Prep-HPLC with the following conditions (IntelFlash-1): Column=C18 silica gel; mobile phase=acetonitrile:water=0:100 increasing to acetonitrile:water=30:70 within 30 min; Detector=UV 220 nm. The final product was isolated as a white solid in 22% yield.

Step 3: 1-(Cyanomethyl)-1H-pyrazole-5-carbonyl chloride

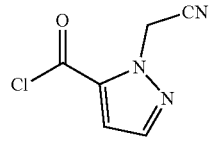 [SMILES: N#CCn1nccc1C(=O)Cl]

1-(cyanomethyl)-1H-pyrazole-5-carboxylic acid (100 mg, 0.66 mmol, 1 equiv) was dissolved in $CH_2Cl_2$ (2 mL) followed by addition of DMF (4.8 mg, 0.07 mmol, 0.1 equiv) and oxalyl chloride (92.4 mg, 0.73 mmol, 1.1 equiv). The resulting solution was stirred for 2 hours at room temperature. Evaporation of volatiles afforded the desired acid chloride as a solid, which was used in the next step without further purification.

Example 156: 1-(2-amino-2-oxoethyl)-N-methyl-N-(2-methyl-4-(6-(trifluoromethyl)quinazolin-2-yl)phenyl)-1H-pyrazole-5-carboxamide

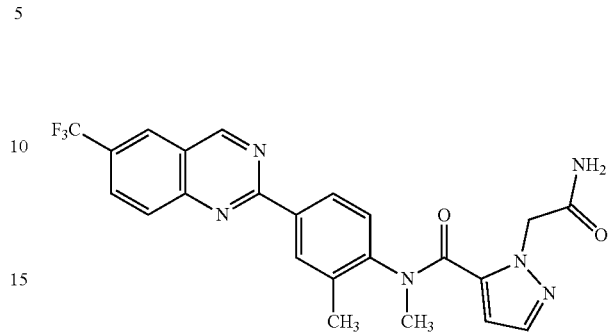

A mixture of 1-(cyanomethyl)-N-methyl-N-[2-methyl-4-[6-(trifluoromethyl)quinazolin-2-yl]phenyl]-1H-pyrazole-5-carboxamide (100 mg, 0.22 mmol, 1 equiv) and conc. $H_2SO_4$ (0.5 mL) was stirred at room temperature for 1 hour. The resulting solution was diluted with 20 mL of ice/water, extracted with (2×10 mL) of ethyl acetate and the combined organic layers concentrated. The residue was purified by preparative TLC with dichloromethane/methanol (20:1) as eluent to afford the desired final product as a white solid in 58% yield. LCMS (ES, m/z): [M+H]$^+$ 469; $^1$H-NMR: (300 MHz, DMSO-d$_6$, ppm): δ2.39 (s, 3H), δ3.28 (s, 3H), δ5.13-5.14 (d, 2H), δ5.41-5.42 (d, 1H), δ7.17-7.21 (m, 2H), δ7.55-7.58 (d, 2H), δ8.27-8.29 (m, 2H), δ8.37-8.39 (d, 1H), δ8.55 (s, 1H), δ8.74 (s, 1H), δ9.91 (s, 1H)

Example 157: N-methyl-N-(2-methyl-4-(6-(trifluoromethyl)quinazolin-2-yl)phenyl)-1-(2-morpholinoethyl)-1H-pyrazole-5-carboxamide

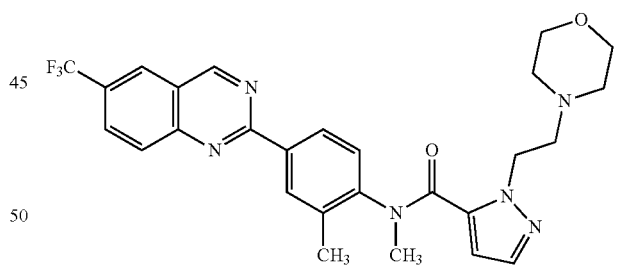

To a solution of N,2-dimethyl-4-[6-(trifluoromethyl)quinazolin-2-yl]aniline (150 mg, 0.47 mmol, 1 equiv) in $CH_2Cl_2$ (3 mL) was added 1-(2-morpholinoethyl)-1H-pyrazole-5-carbonyl chloride (230.4 mg, 0.95 mmol, 2 equiv) and triethylamine (143.5 mg, 1.42 mmol, 3 equiv). The resulting mixture was stirred for 3 h at room temperature and quenched by the addition of MeOH (0.5 mL). The resulting mixture was concentrated under reduced pressure and the residue purified by preparative TLC ($CH_2Cl_2$/MeOH=30:1) to afford the desired final product as a yellow solid in 24% yield. LCMS: (ES, m/z): [M+H]$^+$ 525; $^1$H-NMR (400 MHz, DMSO-d$_6$, ppm): δ2.35 (s, 3H), δ2.45-2.50 (m, 2H), δ2.50-2.52 (m, 2H), δ2.70-2.76 (m, 2H), δ3.32 (s, 3H), δ3.55-3.65 (m, 4H), δ4.48-4.50 (m, 1H), 4.64-4.66 (m, 1H), 5.46-5.47

(d, 1H), 7.17 (s, 1H), 7.51-7.53 (d, 1H), 8.24-8.31 (m, 2H), 8.37-8.39 (d, 1H), 8.52 (s, 1H), 8.73 (s, 1H), 9.90 (s, 1H)

Step 1: Methyl 1-(2-morpholinoethyl)-1H-pyrazole-5-carboxylate

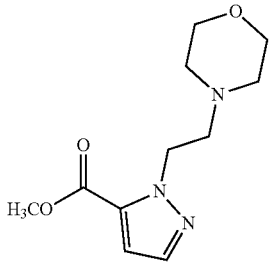 [SMILES: COC(=O)c1ccnn1CCN1CCOCC1]

To a solution of methyl 1H-pyrazole-5-carboxylate (2 g, 15.86 mmol, 1 equiv) and 2-(morpholin-4-yl)ethan-1-ol (2.5 g, 19.03 mmol, 1.2 equiv) in THF (20 mL), was added DIAD (4.8 g, 23.79 mmol, 1.5 equiv) and PPh$_3$ (8.3 g, 31.72 mmol, 2 equiv). The reaction was stirred at room temperature overnight. The resulting mixture was concentrated under reduced pressure and the residue purified by silica gel column chromatography with petroleum ether/EtOAc (3:1) to afford a crude product. This crude product was purified by flash chromatography with the following conditions (CH$_3$CN:NH$_4$HCO$_3$ (aq)=0%-20%, 20 min) affording the pure final product as a white solid in 40% yield.

Step 2: 1-(2-Morpholinoethyl)-1H-pyrazole-5-carboxylic acid

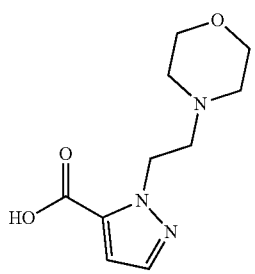 [SMILES: O=C(O)c1ccnn1CCN1CCOCC1]

To a stirred solution of methyl 1-(2-morpholinoethyl)-1H-pyrazole-5-carboxylate (880 mg, 3.68 mmol, 1 equiv) in THF (20 mL) was added LiOH.H$_2$O (186 mg, 4.42 mmol, 1.2 equiv) dissolved in 10 mL of H$_2$O. The resulting mixture was stirred for 2 h at room temperature and acidified to pH 6 with 1M HCl. The mixture was concentrated under reduced pressure to afford the desired final product as a white solid in 99% yield.

Step 3: 1-(2-Morpholinoethyl)-1H-pyrazole-5-carbonyl chloride

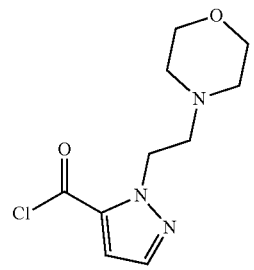 [SMILES: O=C(Cl)c1ccnn1CCN1CCOCC1]

To a stirred solution of 1-(2-morpholinoethyl)-1H-pyrazole-5-carboxylic acid and DMF (16.2 mg, 0.22 mmol, 0.1 equiv) in CH$_2$Cl$_2$ (10 mL), oxalyl chloride (422.6 mg, 3.33 mmol, 1.5 equiv) was added. The resulting mixture was stirred at room temperature for 5 hours and concentrated under reduced pressure to afford the acid chloride as a white solid. This material was immediately used in the next step without further purification.

Example 158: 1-((1H-tetrazol-5-yl)methyl)-N-methyl-N-(2-methyl-4-(6-(trifluoromethyl)-quinazolin-2-yl)phenyl)-1H-pyrazole-5-carboxamide

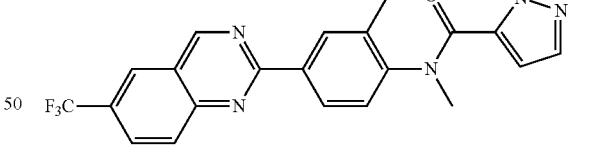

Into an 8-mL vial, was placed 1-(cyanomethyl)-N-methyl-N-(2-methyl-4-(6-(trifluoro-methyl)-quinazolin-2-yl)phenyl)-1H-pyrazole-5-carboxamide (100 mg, 0.22 mmol, 1 equiv.), DMF (2 mL), NaN$_3$ (43.3 mg, 0.67 mmol, 3 equiv.), NH$_4$C$_1$ (47.5 mg, 0.89 mmol, 4 equiv.) and the resulting solution was stirred for 4 h at 100° C. The crude product was purified by Flash-Prep-HPLC (Column, C$_{18}$; mobile phase, MeCN/H$_2$O=0:100 increasing to 70:30 within 25 mins; Detector, UV 254 nm) to give the title compound as a white solid in 25% yield. LC-MS: (ES, m/z): [M+H]$^+$ 494; $^1$H-NMR: (400 MHz, DMSO, ppm): δ 2.30 (s, 3H), 3.34 (s, 3H), 5.50-5.51 (d, 1H), 5.86-5.99 (m, 2H), 7.20-7.21 (d, 1H), 7.42-7.44 (d, 1H), 8.24-8.32 (m, 3H), 8.50 (s, 1H), 8.73 (s, 1H), 9.89 (s, 1H)

Example 159: N,1-dimethyl-N-(2-methyl-4-(8-methyl-6-(trifluoromethoxy)pyrido[3,2-d]-pyrimidin-2-yl)phenyl)-1H-pyrazole-5-carboxamide

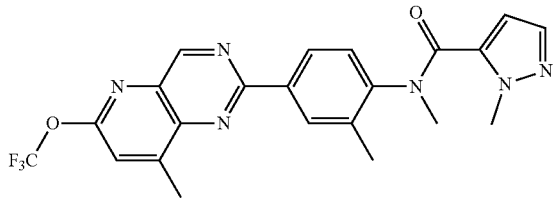 [SMILES: Cc1cc(-c2ncc3nc(OC(F)(F)F)cc(C)c3n2)ccc1N(C)C(=O)c1ccnn1C]

To a stirred mixture of 2-chloro-8-methyl-6-(trifluoromethoxy)pyrido[3,2-d]pyrimidine (100 mg, 0.38 mmol, 1 equiv.) and N-[2-fluoro-4-(tetramethyl-1,3,2-dioxaborolan-2-yl)phenyl]-N,1-dimethyl-1H-pyrazole-5-carboxamide (136.3 mg, 0.38 mmol, 1 equiv.) in t-BuOH (2 mL) was added $K_2CO_3$ (104.9 mg, 0.76 mmol, 2 equiv.) and Xantphos G3 Pd (32 mg, 0.038 mmol, 0.1 equiv.) at room temperature under nitrogen atmosphere. The resulting mixture was stirred overnight at 70° C. under nitrogen atmosphere and then concentrated under vacuum. The residue was purified by Prep-TLC ($CH_2Cl_2$/MeOH=20:1) to afford the title compound as a white solid in 42.60% yield. LC-MS: (ES, m/z): [M+H]$^+$ 457; $^1$H-NMR: (400 MHz, DMSO, ppm): δ 2.27 (s, 1H), 2.84 (s, 3H), 3.31 (s, 3H), 4.11 (s, 3H), 5.54 (s, 1H), 7.14 (s, 1H), 7.48-7.50 (d, 1H), 7.81 (s, 1H), 8.39-8.41 (d, 1H), 8.47 (s, 1H), 9.61 (s, 1H)

Example 160: 2-methyl-N-(2-methyl-4-(8-methyl-6-(trifluoromethoxy)pyrido[3,2-d]-pyrimidin-2-yl)phenyl)isonicotinamide

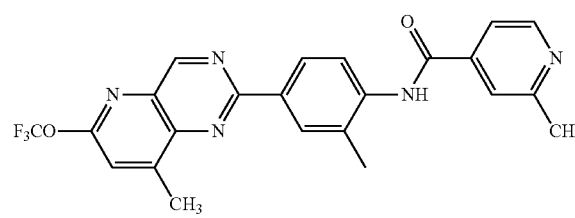

To a stirred solution of 2-chloro-8-methyl-6-(trifluoromethoxy)pyrido[3,2-d]pyrimidine (100 mg, 0.38 mmol, 1 equiv.) and 2-methyl-N-[2-methyl-4-(tetramethyl-1,3,2-dioxaborolan-2-yl)phenyl]pyridine-4-carboxamide (133.6 mg, 0.38 mmol, 1 equiv.) in t-BuOH (2 mL) were added XPhos Pd G3 (32.1 mg, 0.04 mmol, 0.1 equiv.) and $K_2CO_3$ (104.9 mg, 0.76 mmol, 2 equiv.) at room temperature under nitrogen atmosphere. The resulting mixture was stirred overnight at 70° C. under nitrogen atmosphere. The resulting mixture was concentrated under vacuum and the residue was purified by Prep-TLC ($CH_2Cl_2$/MeOH=20:1) to the title compound as a white solid in 11.10% yield. LC-MS: (ES, m/z): [M+H]$^+$ 454; $^1$H-NMR: (400 MHz, DMSO, ppm): δ2.40 (s, 3H), 2.60 (s, 3H), δ2.86-2.87 (d, 3H), 7.64-7.66 (d, 1H), 7.70-7.71 (d, 1H), 7.79-7.81 (d, 2H), 8.44-8.45 (d, 1H), 8.51 (s, 1H), 8.66-8.67 (d, 1H), 9.62 (s, 1H), 10.23 (s, 1H)

Step 1: 4-methyl-5-nitro-2-(trifluoromethoxy)pyridine

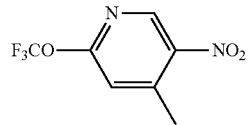

To a stirred solution of 4-methyl-5-nitropyridin-2-ol (48.7 g, 316 mmol, 2 equiv.) in $CH_3NO_2$ (500 mL) was added 1-trifluoromethyl-1,2-benziodoxol-3-(1H)-one (50 g, 158 mmol, 1 equiv.) in portions at room temperature under nitrogen atmosphere. The resulting mixture was stirred for 12 h at 100° C. under nitrogen atmosphere. The mixture was allowed to cool down to room temperature, filtered, and the filter cake was washed with DCM. The filtrate was concentrated under reduced pressure and the residue was purified by silica gel column chromatography by eluting with PE/EA (10:1) to afford the title compound as a white solid in 38.4% yield.

Step 2: 4-methyl-6-(trifluoromethoxy)pyridin-3-amine

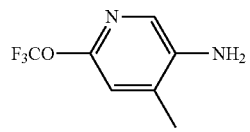

To a stirred suspension of 4-methyl-5-nitro-2-(trifluoromethoxy)pyridine (13.5 g, 60.79 mmol, 1 equiv.) and $NH_4Cl$ (19.6 g, 364.76 mmol, 6 equiv.) in $H_2O$ (135 mL) was added Fe (10.02 g, 182.38 mmol, 3 equiv.) at room temperature. The resulting mixture was stirred for 2 h at 100° C. under nitrogen atmosphere and then allowed to cool down to room temperature. The resulting mixture was filtered and the filter cake was washed with EA. The filtrate was extracted with EA and the organic layer was concentrated under reduced pressure. The residue was purified by silica gel column chromatography by eluting with PE/EA (5:1) to afford the title compound as a white solid in 78.83% yield.

Step 3: 2-bromo-4-methyl-6-(trifluoromethoxy)pyridin-3-amine

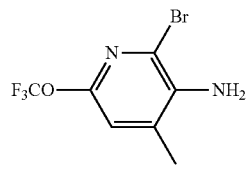

To a stirred solution of 4-methyl-6-(trifluoromethoxy)pyridin-3-amine (9.2 g, 47.88 mmol, 1 equiv.) in DCM (100 mL) was added NBS (8.36 g, 47.88 mmol, 1 equiv.) in portions at 0° C. under nitrogen atmosphere. The resulting mixture was stirred for 1 h at 0° C. under nitrogen atmosphere and then quenched with sat. NH₄Cl (aq.) at 0° C. The resulting mixture was extracted with ethyl acetate, dried over anhydrous Na₂SO₄. After filtration, the filtrate was concentrated under reduced pressure to afford the title compound as a yellow solid in 92.45% yield.

Step 4: 3-amino-4-methyl-6-(trifluoromethoxy)pyridine-2-carbonitrile

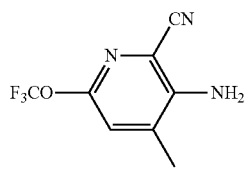

To a stirred solution of 2-bromo-4-methyl-6-(trifluoromethoxy)pyridin-3-amine (12 g, 44.25 mmol, 1 equiv.) and Zn(CN)₂ (10.24 g, 88.49 mmol, 1.97 equiv.) in DMF (120 mL) were added Pd(PPh₃)₄ (5.12 g, 4.44 mmol, 0.10 equiv.). The final reaction mixture was irradiated with microwave radiation for 2 h at 200° C. and then quenched with water. The resulting mixture was extracted with EA and the combined organic layer was concentrated under reduced pressure. The residue was purified by silica gel column chromatography by eluting with PE/EA (5:1) to afford the title compound as a white solid in 36.72% yield.

Step 5: 8-methyl-6-(trifluoromethoxy)pyrido[3,2-d]pyrimidine-2,4(1H,3H)-dione

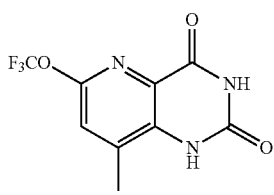

To a stirred solution of 3-amino-4-methyl-6-(trifluoromethoxy)pyridine-2-carbonitrile (3 g, 13.8 mmol, 1 equiv.) in DMF (30 mL) was added DBU (6.29 g, 41.4 mmol, 3 equiv.). The resulting mixture was stirred overnight at 100° C. under CO₂ atmosphere. The reaction was quenched with water and the resulting mixture was extracted with EA. The combined organic layer was concentrated under reduced pressure and the residue was purified by silica gel column chromatography with PE/EA (5:1) as the eluent to afford the title compound as a white solid in 86.11% yield.

Step 6: 2,4-dichloro-8-methyl-6-(trifluoromethoxy)pyrido[3,2-d]pyrimidine

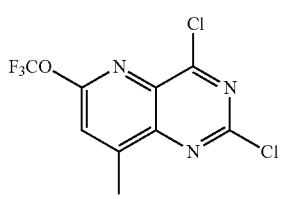 [SMILES: Cc1cc(OC(F)(F)F)nc2c(Cl)nc(Cl)nc12]

To a stirred solution of 8-methyl-6-(trifluoromethoxy)pyrido[3,2-d]pyrimidine-2,4(1H,3H)-dione (3.1 g, 11.88 mmol, 1 equiv.) in POCl₃ (30 mL) was added PCl₅ (12.35 g, 59.39 mmol, 5 equiv.) in portions at room temperature under nitrogen atmosphere. The reaction mixture was then heated to reflux for 120 min under nitrogen atmosphere. The reaction was quenched with water/ice at 0° C. and the resulting mixture was extracted with EA and then concentrated under reduced pressure. The residue was purified by silica gel column chromatography, eluted with petroleum ether/ethyl acetate (5:1) to afford the title compound as a white solid in 34.30% yield.

Step 7: 2-chloro-8-methyl-6-(trifluoromethoxy)pyrido[3,2-d]pyrimidine

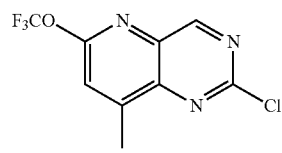 [SMILES: Cc1cc(OC(F)(F)F)nc2cnc(Cl)nc12]

To a stirred solution of 2,4-dichloro-8-methyl-6-(trifluoromethoxy)pyrido[3,2-d]-pyrimidine (1.37 g, 4.60 mmol, 1 equiv.) and Pd(PPh₃)₄ (0.5 g, 0.46 mmol, 0.1 equiv.) in THF (20 mL) was added PPh₃ (1.8 g, 6.89 mmol, 1.5 equiv.) under nitrogen atmosphere. To the above mixture was added SnBu₃H (2.8 g, 4.83 mmol, 1.05 equiv.) dropwise over 15 min at 0° C. The resulting mixture was stirred for addition 2 h at 0° C. and then quenched with water/ice (20 mL) at 0° C. The aqueous layer was extracted with EA and the combined organic layer was concentrated under vacuum. The residue was purified by silica gel column chromatography by eluting with PE/EA (5:1) to afford the title compound as a white solid in 55.30% yield.

Step 8: N-(4-bromo-2-methylphenyl)-2-methylpyridine-4-carboxamide

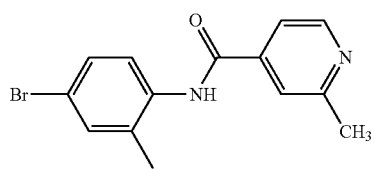 [SMILES: Cc1cc(C(=O)Nc2ccc(Br)cc2C)ccn1]

To a stirred mixture of 2-methylpyridine-4-carboxylic acid (1.47 g, 10.72 mmol, 1 equiv.) and 4-bromo-2-methylaniline (2.0 g, 10.72 mmol, 1 equiv.) in DMF (50 mL) were added HATU (6.1 g, 16.08 mmol, 1.50 equiv.) and DIEA (2.8 g, 21.66 mmol, 2.02 equiv.). The resulting mixture was stirred overnight at room temperature and then quenched with water and extracted with EA. The combined organic layer was concentrated under reduced pressure and the residue was purified by silica gel column chromatography, eluted with CH₂Cl₂/MeOH (100:1) to afford the title compound as a white solid in 91.71% yield.

Step 9: 2-methyl-N-[2-methyl-4-(tetramethyl-1,3,2-dioxaborolan-2-yl)phenyl]pyridine-4-carboxamide

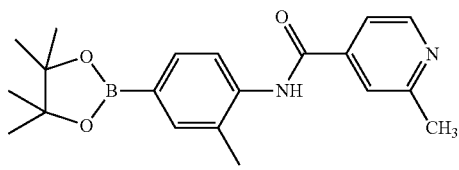

To a stirred solution of N-(4-bromo-2-methylphenyl)-2-methylpyridine-4-carboxamide (1.5 g, 4.92 mmol, 1 equiv.) and Pd(dppf)Cl$_2$ (0.4 g, 0.54 mmol, 0.11 equiv.) in dioxane (20 mL) were added KOAc (964.8 mg, 9.83 mmol, 2 equiv.) and B$_2$Pin$_2$ (0.528 g, 5.41 mmol, 1.1 equiv.) under N$_2$ atmosphere. The resulting mixture was stirred for 4 h at 80° C. under N$_2$ atmosphere. The resulting mixture was concentrated under reduced pressure and the residue was purified by silica gel column chromatography, eluted with CH$_2$Cl$_2$/MeOH (100:1) to afford the title compound as a white solid in 11.55% yield.

Example 161: N,2-dimethyl-N-(2-methyl-4-(8-methyl-6-(trifluoromethoxy)pyrido[3,2-d]pyrimidin-2-yl)phenyl)isonicotinamide

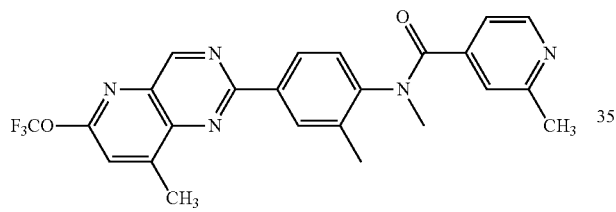

The title compound was prepared analogously to Example 160 by substituting 2-methyl-N-(2-methyl-4-(4,4,5-trimethyl-1,3,2-dioxaborolan-2-yl)phenyl)isonicotinamide with N,2-dimethyl-N-[2-methyl-4-(tetramethyl-1,3,2-dioxaborolan-2-yl)phenyl]pyridine-4-carboxamide as a white solid. LC-MS: (ES, m/z): [M+H]$^+$ 468; $^1$H-NMR: (300 MHz, DMSO, ppm): δ 2.35 (s, 6H), 2.81 (s, 3H), 3.37 (s, 3H), 6.97-7.01 (d, 1H), 7.21 (s, 1H), 7.44-7.47 (d, 1H), 7.77 (s, 1H), 8.25-8.27 (m, 2H), 8.39 (s, 1H), 9.57 (s, 1H)

Step 1: N-(4-bromo-2-methylphenyl)-N,2-dimethylpyridine-4-carboxamide

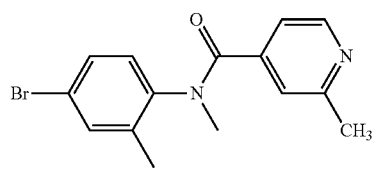 [SMILES: Cc1cc(C(=O)N(C)c2ccc(Br)cc2C)ccn1]

To a stirred solution of N-(4-bromo-2-methylphenyl)-2-methylpyridine-4-carboxamide (1 g, 3.28 mmol, 1 equiv.) in DMF (10 mL) was added NaH (0.0787 g, 3.28 mmol, 1 equiv.) and the resulting mixture was stirred for 30 min. MeI (0.5 g, 3.52 mmol, 1.08 equiv.) was added dropwise at 0° C. and the resulting mixture was stirred for additional 1 h at 0° C. The reaction mixture was quenched with NH$_4$Cl (aq.) and then extracted with EA and dried over anhydrous Na$_2$SO$_4$. After filtration, the filtrate was concentrated under reduced pressure to give the title compound as a white solid in (920 mg, 87.96%).

Step 2: N,2-dimethyl-N-[2-methyl-4-(tetramethyl-1,3,2-dioxaborolan-2-yl)phenyl]pyridine-4-carboxamide

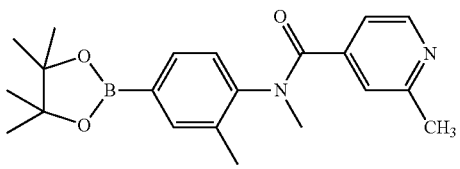

To a stirred solution of N-(4-bromo-2-methylphenyl)-N,2-dimethylpyridine-4-carboxamide (920 mg, 2.88 mmol, 1 equiv.) and B$_2$Pin$_2$ (309.4 mg, 3.17 mmol, 1.10 equiv.) in 1,4-dioxane (10 mL) were added KOAc (565.7 mg, 5.76 mmol, 2 equiv.) and Pd(dppf)Cl$_2$ (210.9 mg, 0.29 mmol, 0.1 equiv.) in portions at room temperature under nitrogen atmosphere. The resulting mixture was stirred for overnight at 80° C. under nitrogen atmosphere and then concentrated under reduced pressure. The residue was purified by silica gel column chromatography by eluting with PE/EA (10:1) to afford the title compound as a white solid in 76.73% yield.

Example 162: N-(2-fluoro-4-(8-methyl-6-(trifluoromethyl)pyrido[3,2-d]pyrimidin-2-yl)-phenyl)-N,1-dimethyl-1H-pyrazole-5-carboxamide

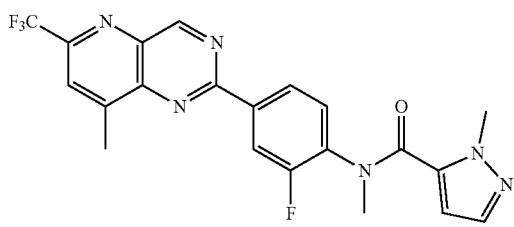 [SMILES: Cc1cc(C(F)(F)F)nc2cnc(-c3ccc(N(C)C(=O)c4ccnn4C)c(F)c3)nc12]

Into a 8-mL sealed tube purged and maintained with an inert atmosphere of nitrogen, was placed 2-chloro-8-methyl-6-(trifluoromethyl)pyrido[3,2-d]pyrimidine (100 mg, 0.40 mmol, 1 equiv.), N-(2-fluoro-4-(4,4,5,5-tetramethyl-1,3,2-dioxaborolan-2-yl)phenyl)-N,1-dimethyl-1H-pyrazole-5-carboxamide (174.1 mg, 0.48 mmol, 1.2 equiv.), toluene (2 mL), EtOH (1 mL), K$_2$CO$_3$ (167.5 mg, 1.21 mmol, 3 equiv.), and Pd(PPh$_3$)$_4$ (93.3 mg, 0.08 mmol, 0.2 equiv.). The resulting solution was stirred overnight at 80° C. and then quenched with NH$_4$Cl (aq.). The resulting solution was extracted with ethyl acetate and the organic layers were combined, and concentrated. The residue was purified by Flash-Prep-HPLC ((IntelFlash-1): Column, C$_{18}$; mobile phase, MeCN:H$_2$O (30:70) increasing to MeCN:H$_2$O (70:30) within 30 min; Detector, 254 nm) to give the title compound as a white solid in 41.18% yield. LC-MS: (ES, m/z): [M+H]$^+$ 445; $^1$H-NMR: (300 MHz, DMSO, ppm): δ2.92 (s, 3H), 3.42 (s, 3H), 3.98 (s, 3H), 5.84 (s, 1H), 7.22-7.23 (d, 1H), 7.77-7.82 (t, 1H), 8.31-8.35 (m, 1H), 8.41 (d, 1H), 8.46-8.49 (m, 1H), 9.90 (s, 1H)

Step 1: N-(2-fluoro-4-(4,4,5,5-tetramethyl-1,3,2-dioxaborolan-2-yl)phenyl)-N,1-dimethyl-1H-pyrazole-5-carboxamide

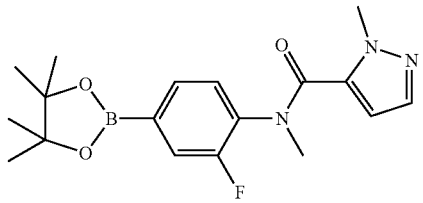 [SMILES: CN(C(=O)c1ccnn1C)c1ccc(B2OC(C)(C)C(C)(C)O2)cc1F]

Into a 50-mL 3-necked round-bottom flask purged and maintained with an inert atmosphere of nitrogen, was placed N-[2-fluoro-4-(tetramethyl-1,3,2-dioxaborolan-2-yl)phenyl]-1-methyl-1H-pyrazole-5-carboxamide (2 g, 5.79 mmol, 1 equiv.) in THF (20 mL). LiHMDS (11.59 mL, 1M, 2 equiv.) was added at 0° C., followed by addition of MeI (904.7 mg, 6.37 mmol, 1.100 equiv.) after 30 min. The resulting solution was stirred for 2 h at room temperature and then quenched with NH$_4$Cl (aq.). The resulting solution was extracted with ethyl acetate and the combined organic layer was concentrated under reduced pressure. The residue was applied onto a silica gel column and eluted with ethyl acetate/petroleum ether (1/10) to give the title compound as a pale-yellow solid in 20.47% yield.

Example 163: N-[2-fluoro-4-[8-methyl-6-(trifluoromethyl)pyrido[3,2-d]pyrimidin-2-yl]phenyl]-1-methyl-1H-pyrazole-5-carboxamide

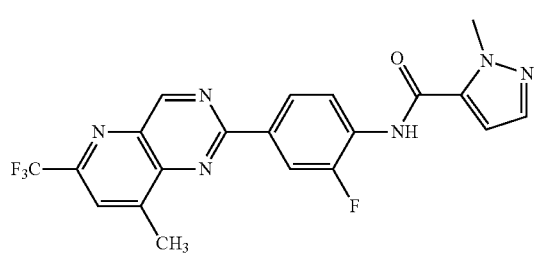 [SMILES: Cc1cc(C(F)(F)F)nc2cnc(-c3ccc(NC(=O)c4ccnn4C)c(F)c3)nc12]

To a stirred solution of 2-chloro-8-methyl-6-(trifluoromethyl)pyrido[3,2-d]pyrimidine (100 mg, 0.40 mmol, 1 equiv.) and N-[2-fluoro-4-(tetramethyl-1,3,2-dioxaborolan-2-yl)phenyl]-1-methyl-1H-pyrazole-5-carboxamide (139.4 mg, 0.40 mmol, 1 equiv.) in toluene (0.8 mL) and EtOH (0.4 mL) was added Pd(PPh$_3$)$_4$ (46.7 mg, 0.04 mmol, 0.1 equiv.) and K$_2$CO$_3$ (111.6 mg, 0.81 mmol, 2 equiv.) at room temperature under nitrogen atmosphere. The resulting mixture was stirred overnight at 100° C. under nitrogen atmosphere. The mixture cooled to room temperature and then concentrated under reduced pressure. The residue was purified by Prep-TLC (CH$_2$Cl$_2$/MeOH=20:1) to afford the title compound as a yellow solid in 28% yield. LC-MS: (ES, m/z): [M+H]$^+$ 431; $^1$H-NMR: (400 MHz, DMSO, ppm): δ 2.94 (s, 3H), 4.11 (s, 3H), 7.16 (d, 1H), 7.57 (d, 1H), 7.91-7.95 (t, 1H), 8.39-8.45 (m, 2H), 8.49-8.51 (m, 1H), 9.89 (s, 1H), 10.33 (s, 1H)

Example 164: N-(2-fluoro-4-(8-methyl-6-(trifluoromethyl)pyrido[3,2-d]pyrimidin-2-yl)phenyl)-2-methylisonicotinamide

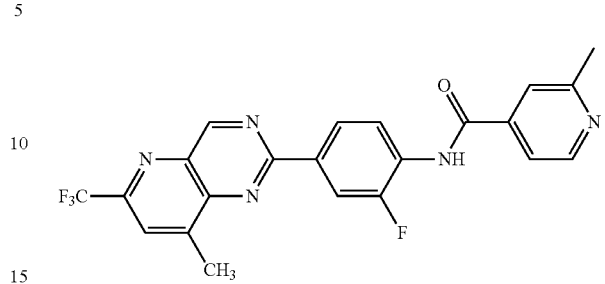

The title compound was prepared analogously to Example 163 by substituting N-[2-fluoro-4-(tetramethyl-1,3,2-dioxaborolan-2-yl)phenyl]-1-methyl-1H-pyrazole-5-carboxamide with N-(2-fluoro-4-(4,4,5,5-tetramethyl-1,3,2-dioxaborolan-2-yl)phenyl)-2-methylisonicotinamide to give crude product which was purified by Flash-Prep-HPLC ((IntelFlash-1): Column, C$_{18}$ silica gel; mobile phase, MeCN:H$_2$O (40:60) increasing to MeCN:H$_2$O (60:40) within 50 min; Detector, 254 nm) to give a white solid in 18.10%) yield. LC-MS: (ES, m/z): [M+H]$^+$ 442; $^1$H-NMR: (300 MHz, CDCl$_3$, ppm): δ 2.71 (s, 3H), 2.97 (s, 3H), 7.56-7.58 (d, 1H), 7.61-7.65 (d, 1H), 7.96 (s, 1H), 8.26-8.27 (d, 1H), 8.47-8.52 (m, 1H), 8.56-8.59 (d, 1H), 8.67-8.72 (m, 2H), 9.74 (s, 1H)

Step 1: N-(2-fluoro-4-(4,4,5,5-tetramethyl-1,3,2-dioxaborolan-2-yl)phenyl)-2-methylisonicotinamide

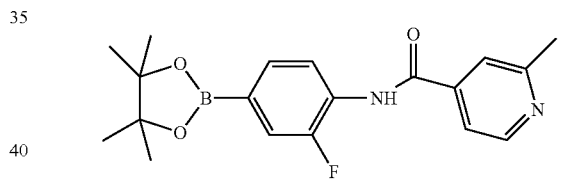

The title compound was prepared analogously to Example 160, Step 8 by substituting 4-bromo-2-methylaniline with 2-fluoro-4-(4,4,5,5-tetramethyl-1,3,2-dioxaborolan-2-yl) aniline to provide a crude product which was purified by silica gel column with dichloromethane/methanol (80/1) as eluent to give the title compound as a yellow solid in 50.60% yield.

Example 165: N-(2-fluoro-4-(8-methyl-6-(trifluoromethyl)pyrido[3,2-d]pyrimidin-2-yl)phenyl)-2-methylisonicotinamide

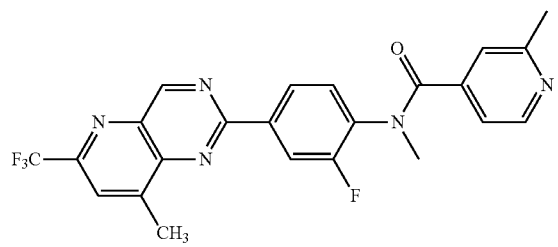 [SMILES: Cc1cc(C(=O)N(C)c2ccc(-c3ncc4nc(C(F)(F)F)cc(C)c4n3)cc2F)ccn1]

Into a 8-mL sealed tube purged and maintained with an inert atmosphere of nitrogen, was placed 2-chloro-8-methyl-6-(trifluoromethyl)pyrido[3,2-d]pyrimidine (132 mg, 0.53 mmol, 1 equiv.), N,2-dimethyl-N-[2-fluoro-4-(tetramethyl-1,3,2-dioxaborolan-2-yl)phenyl]pyridine-4-carboxamide (217.1 mg, 0.59 mmol, 1.1 equiv.), toluene (2.64 mL), EtOH (1.32 mL), K$_2$CO$_3$ (221.0 mg, 1.60 mmol, 3 equiv.), Pd(PPh$_3$)$_4$ (92.4 mg, 0.08 mmol, 0.15 equiv.). The resulting solution was stirred overnight at 85° C. The reaction was then quenched with NH$_4$Cl (aq.) and extracted with ethyl acetate. The residue was applied onto Prep-TLC with dichloromethane/methanol (50/1). The crude product was purified by Flash-Prep-HPLC with the following conditions (IntelFlash-1): Column, C18 silica gel; mobile phase, MeCN:H$_2$O=40:60 increasing to MeCN:H$_2$O=70:30 within 60 min; Detector, 254 nm to give the title compound in 32.46% yield as a yellow solid. LC-MS: (ES, m/z): [M+H]+$^1$H-NMR: (400 MHz, DMSO, ppm): δ 2.39 (s, 3H), 2.91 (s, 3H), 3.40 (s, 3H), 7.05 (s, 1H), 7.25 (s, 1H), 7.71-7.76 (t, 1H), 8.28-8.34 (m, 2H), 8.39-8.42 (m, 2H), 9.88 (s, 1H)

Step 1:
N-(4-bromo-2-fluorophenyl)-2-methylisonicotinamide

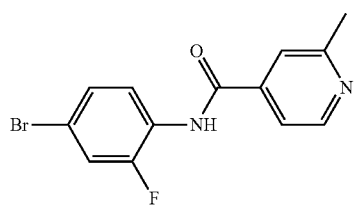 [SMILES: Cc1cc(C(=O)Nc2ccc(Br)cc2F)ccn1]

The title compound was prepared analogously to Example 160, Step 8 by substituting 4-bromo-2-fluoroaniline with 4-bromo-2-fluoroaniline to give crude product which was purified by re-crystallization from dichloromethane to give the title compound as a yellow solid in 59.90% yield.

Step 2: N-(4-bromo-2-fluorophenyl)-N,2-dimethylisonicotinamide

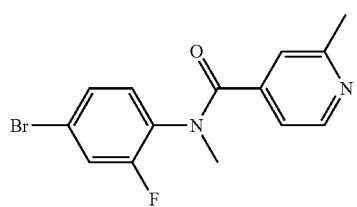 [SMILES: Cc1cc(C(=O)N(C)c2ccc(Br)cc2F)ccn1]

Into a 50-mL 3-necked round-bottom flask purged and maintained with an inert atmosphere of nitrogen, was placed N-(4-bromo-2-fluorophenyl)-2-methylisonicotinamide (1.08 g, 3.49 mmol, 1 equiv.) and DMF (11 mL). NaH (167.7 mg, 6.99 mmol, 2 equiv.) was added at 0° C., followed by addition of MeI (520.7 mg, 3.67 mmol, 1.05 equiv.) after 30 min. The resulting solution was stirred for 6 h at room temperature. The reaction was then quenched with NH$_4$Cl (aq.). The resulting solution was extracted with ethyl acetate and the combined organic layer was concentrated under reduced pressure. The residue was applied onto a silica gel column and eluted with ethyl acetate/petroleum ether (1/10) to give the title compound as a yellow solid in 40.74% yield.

Step 3: N,2-dimethyl-N-[2-fluoro-4-(tetramethyl-1,3,2-dioxaborolan-2-yl)phenyl]pyridine-4-carboxamide

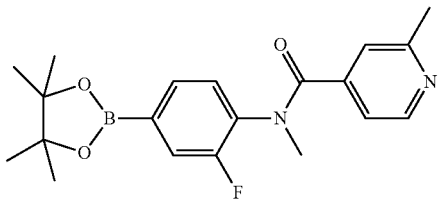

Proceeding as described in Example 161, Step 2 but substituting N-(4-bromo-2-methylphenyl)-N,2-dimethylpyridine-4-carboxamide with N-(4-bromo-2-fluorophenyl)-N,2-dimethylpyridine-4-carboxamide provided the title compound as a yellow solid in 41.27% yield.

Example 166: N4-(2-methyl-4-(8-methyl-6-(trifluoromethyl)pyrido[3,2-d]pyrimidin-2-yl)phenyl)pyridine-2,4-dicarboxamide

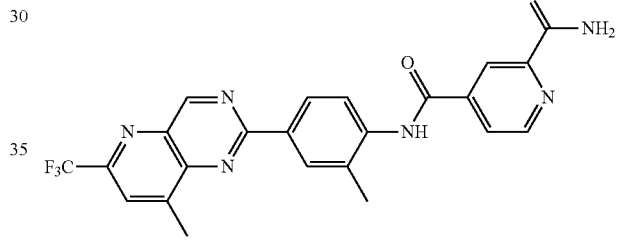

To a stirred solution of 2-cyano-N-[2-methyl-4-[8-methyl-6-(trifluoromethyl)pyrido[3,2-d]pyrimidin-2-yl]phenyl]pyridine-4-carboxamide (100 mg, 0.22 mmol, 1 equiv.) in MeOH (10 mL) were added NaOH (17.8 mg, 0.45 mmol, 2.00 equiv.) and H$_2$O$_2$ (0.5 mL). The resulting mixture was stirred for 5 h at room temperature and then diluted with water. The resulting mixture was extracted with ethyl acetate and the combined organic layer was concentrated under reduced pressure. The residue was purified by Prep-TLC (CH$_2$Cl$_2$/MeOH=10:1) to afford the title compound as a yellow solid in 23.27% yield. LC-MS: (ES, m/z): [M−H]$^-$ 465; $^1$H-NMR: (400 MHz, DMSO, ppm): δ 2.43 (s, 3H), 2.95 (s, 3H), 7.68-7.70 (d, 1H), 7.81 (s, 1H), 8.10-8.12 (d, 1H), 8.26 (s, 1H), 8.38-8.39 (d, 1H), 8.50-8.53 (m, 1H), 8.57-8.60 (d, 1H), 8.86-8.88 (d, 1H), 9.89 (s, 1H), 10.53 (s, 1H).

Step 1: 2-cyanopyridine-4-carbonyl chloride

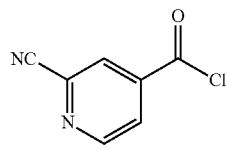 [SMILES: N#Cc1cc(C(=O)Cl)ccn1]

To a stirred solution of 2-cyanopyridine-4-carboxylic acid (250 mg, 1.69 mmol, 1 equiv.) in DCM (5 mL) were added DMF (12.3 mg, 0.17 mmol, 0.1 equiv.) and oxalyl chloride (431.9 mg, 3.38 mmol, 2.00 equiv.) at 0° C. The resulting mixture was stirred for 3 h at 0° C. and then concentrated under reduced pressure. The crude product was used in the next step directly without further purification.

Step 2: 2-cyano-N-[2-methyl-4-[8-methyl-6-(trifluoromethyl)pyrido[3,2-d]pyrimidin-2-yl]-phenyl]pyridine-4-carboxamide

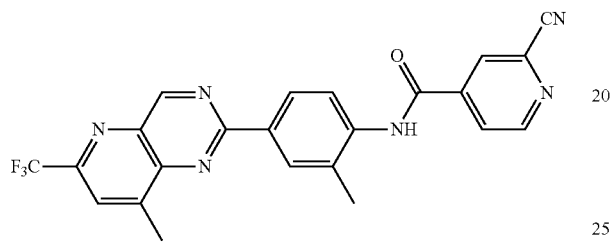

To a stirred solution of 2-cyanopyridine-4-carbonyl chloride (300 mg, 1.80 mmol, 1 equiv.) and 2-methyl-4-[8-methyl-6-(trifluoromethyl)pyrido[3,2-d]pyrimidin-2-yl]aniline (516.0 mg, 1.62 mmol, 0.90 equiv.) in DCM (5 mL) was added TEA (240.6 mg, 2.38 mmol, 1.32 equiv.). The resulting mixture was stirred for 1 h at 0° C. and then quenched with NH$_4$Cl (aq.). The resulting mixture was extracted with CH$_2$Cl$_2$ and the combined organic layer was concentrated under reduced pressure. The residue was purified by Prep-TLC (CH$_2$Cl$_2$/MeOH=30:1) to afford the title compound as a yellow solid in 38.38% yield.

Example 167: N2-methyl-N4-(2-methyl-4-(8-methyl-6-(trifluoromethyl)pyrido[3,2-d]pyrimidin-2-yl)phenyl)pyridine-2,4-dicarboxamide

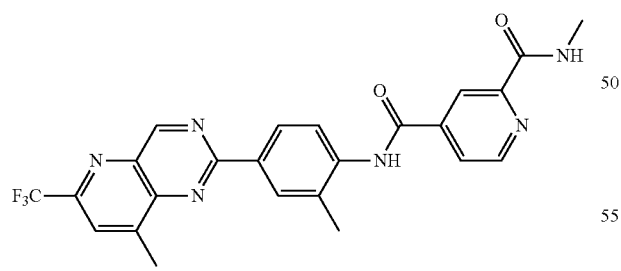

To a stirred mixture of 2-chloro-8-methyl-6-(trifluoromethyl)pyrido[3,2-d]pyrimidine (100 mg, 0.40 mmol, 1 equiv.) and N2-methyl-N4-(2-methyl-4-(4,4,5,5-tetramethyl-1,3,2-dioxaborolan-2-yl)phenyl)pyridine-2,4-dicarboxamide (176.0 mg, 0.45 mmol, 1.10 equiv.) in dioxane (2 mL) were added H$_2$O (0.5 mL), Na$_2$CO$_3$ (128.7 mg, 1.21 mmol, 3 equiv.), and Pd(PPh$_3$)$_4$ (93.6 mg, 0.08 mmol, 0.2 equiv.). The resulting mixture was stirred overnight at 80° C. under N$_2$ and then quenched with water. The resulting mixture was extracted with EA and the combined organic layer was concentrated under reduced pressure. The residue was purified by Prep-TLC (CH$_2$Cl$_2$/MeOH=30:1) to afford the title compound as a yellow solid in 13.98% yield. LC-MS: (ES, m/z): [M+H]$^+$ 481; $^1$H-NMR: (300 MHz, DMSO, ppm): δ 2.43 (s, 3H), 2.86-2.88 (d, 3H), 2.95 (s, 3H), 7.68-7.70 (d, 1H), 8.10-8.12 (m, 1H), 8.39 (s, 1H), 8.50-8.53 (d, 1H), 8.58 (s, 2H), 8.86-8.88 (d, 1H), 8.91-8.94 (m, 1H), 9.88 (s, 1H), 10.55 (s, 1H).

Step 1: 4-[(4-bromo-2-methylphenyl)carbamoyl]pyridine-2-carboxylic acid

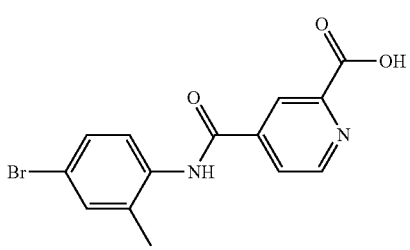 [SMILES: Cc1cc(Br)ccc1NC(=O)c1ccnc(C(=O)O)c1]

To a stirred solution of N-(4-bromo-2-methylphenyl)-2-cyanopyridine-4-carboxamide (1 g, 3.16 mmol, 1 equiv.) in EtOH (20 mL) was added NaOH (20 mL, 2 M). The resulting mixture was stirred for 2 h at 60° C. and then concentrated under reduced pressure. The aqueous layer was extracted with EA and the residue was acidified to pH 6 with HCl (1M). The resulting mixture was filtered, the filter cake was washed with water and the resulting solid was dried under infrared light to give the title compound as a yellow solid in 57.92% yield.

Step 2: 4-N-(4-bromo-2-methylphenyl)-2-N-methylpyridine-2,4-dicarboxamide

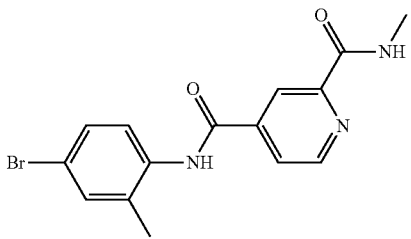 [SMILES: CNC(=O)c1cc(C(=O)Nc2ccc(Br)cc2C)ccn1]

To a stirred mixture of 4-[(4-bromo-2-methylphenyl)carbamoyl]pyridine-2-carboxylic acid (614 mg, 1.83 mmol, 1 equiv.) in DMF (10 mL) were added methanamine hydrochloride (185.5 mg, 2.75 mmol, 1.50 equiv.), DIEA (473.5 mg, 3.66 mmol, 2 equiv.) and HATU (1044.9 mg, 2.75 mmol, 1.5 equiv.). The resulting mixture was stirred overnight at room temperature and then washed with water and extracted with EA. The combined organic layer was concentrated under reduced pressure and the residue was purified by Prep-TLC (CH$_2$Cl$_2$/MeOH=20:1) to afford the title compound as a white solid in 69.45% yield.

Step 3: N2-methyl-N4-(2-methyl-4-(4,4,5,5-tetramethyl-1,3,2-dioxaborolan-2-yl)phenyl)pyridine-2,4-dicarboxamide

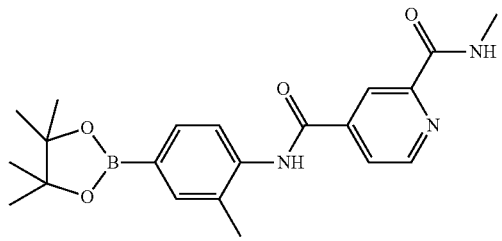

Proceeding analogously as described in Example 161, Step 2 but substituting N-(4-bromo-2-methylphenyl)-N,2-dimethylpyridine-4-carboxamide with 4-N-(4-bromo-2-methylphenyl)-2-N-methylpyridine-2,4-dicarboxamide afforded the title compound as a yellow solid after purification by Prep-TLC (PE/EA=2:1) in 69.60% yield.

Example 168: N4-methyl-N4-(2-methyl-4-(8-methyl-6-(trifluoromethyl)pyrido[3,2-d]pyrimidin-2-yl)phenyl)pyridine-2,4-dicarboxamide

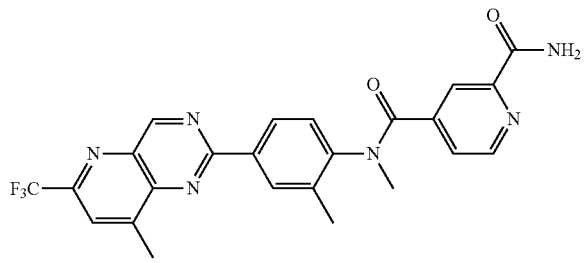 [SMILES: Cc1cc(-c2ncc3nc(C(F)(F)F)cc(C)c3n2)ccc1N(C)C(=O)c1ccnc(C(N)=O)c1]

Proceeding analogously as described in Example 167 but substituting N2-methyl-N4-(2-methyl-4-(4,4,5,5-tetramethyl-1,3,2-dioxaborolan-2-yl)phenyl)pyridine-2,4-dicarboxamide with N4-methyl-N4-(2-methyl-4-(4,4,5,5-tetramethyl-1,3,2-dioxaborolan-2-yl)phenyl)pyridine-2,4-dicarboxamide provided the title compound as a yellow solid 13.3% yield. LC-MS: (ES, m/z): [M+H]$^+$ 481; $^1$H-NMR: (300 MHz, DMSO, ppm): δ 2.38 (s, 3H), 2.89 (s, 3H), 3.37 (s, 3H), 7.42-7.45 (m, 1H), 7.51-7.53 (d, 1H), 7.63-7.64 (d, 1H), 7.90 (s, 1H), 8.02-8.03 (d, 1H), 8.33-8.37 (m, 2H), 8.45-8.50 (m, 2H), 9.83 (s, 1H)

Step 1: N-(4-bromo-2-methylphenyl)-2-cyano-N-methylpyridine-4-carboxamide

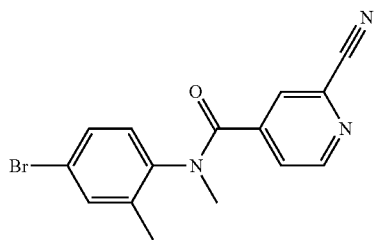 [SMILES: Cc1cc(Br)ccc1N(C)C(=O)c1ccnc(C#N)c1]

To a stirred mixture of N-(4-bromo-2-methylphenyl)-2-cyanopyridine-4-carboxamide (2 g, 6.33 mmol, 1 equiv.) in DMF (20 mL) was added NaH (305 mg, 12.71 mmol, 2.01 equiv.) in portions at 0° C. The resulting mixture was stirred for 3 h and MeI (1 g, 7.05 mmol, 1.11 equiv.) was added. The resulting mixture was stirred for additional 2 h at room temperature and then quenched with NH$_4$Cl (aq.). The resulting mixture was extracted with EA and the combined organic layer was concentrated under reduced pressure. The residue was purified by silica gel column chromatography, eluted with PE/EA (5:1) to afford the title compound as a yellow solid in 71.81% yield.

Step 2: 4-N-(4-bromo-2-methylphenyl)-4-N-methylpyridine-2,4-dicarboxamide

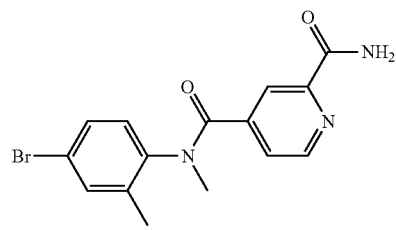 [SMILES: Cc1cc(Br)ccc1N(C)C(=O)c1ccnc(C(N)=O)c1]

To a stirred mixture of N-(4-bromo-2-methylphenyl)-2-cyano-N-methylpyridine-4-carboxamide (1.5 g, 4.54 mmol, 1 equiv.) in MeOH (110 mL) were added NaOH (0.4 g, 10.00 mmol, 2.20 equiv.), H$_2$O (11 mL) and H$_2$O$_2$ (5.5 mL). The resulting mixture was stirred overnight at room temperature and then neutralized to pH 7 with HCl (aq.). MeOH was evaporated under reduced pressure and the resulting mixture was extracted with EA. The combined organic layer was concentrated under reduced pressure and the. residue was purified on a silica gel column with CH$_2$Cl$_2$/MeOH=30:1 as eluent to provide the title compound as a white solid in 85.98% yield.

Step 3: N4-methyl-N4-(2-methyl-4-(4,4,5,5-tetramethyl-1,3,2-dioxaborolan-2-yl)phenyl)pyridine-2,4-dicarboxamide

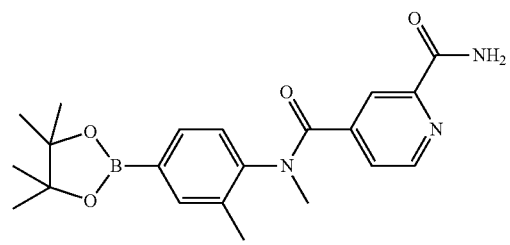 [SMILES: Cc1cc(B2OC(C)(C)C(C)(C)O2)ccc1N(C)C(=O)c1ccnc(C(N)=O)c1]

Proceeding analogously as described in Example 160, Step 9 but substituting N-(4-bromo-2-methylphenyl)-2-methylpyridine-4-carboxamide with 4-N-(4-bromo-2-methylphenyl)-4-N-methylpyridine-2,4-dicarboxamide, followed by purification of crude product on a silica gel column by eluting with (PE/EA=2:1) provided the title compound as a yellow solid in 64.77% yield.

Example 169: N2,N4-dimethyl-N4-(2-methyl-4-(8-methyl-6-(trifluoromethyl)pyrido-[3,2-d]pyrimidin-2-yl)phenyl)pyridine-2,4-dicarboxamide

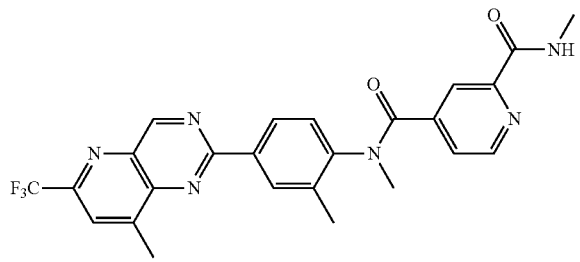 [SMILES: CNC(=O)c1cc(C(=O)N(C)c2ccc(-c3ncc4nc(C(F)(F)F)cc(C)c4n3)cc2C)ccn1]

Proceeding analogously as described in Example 167 but substituting N2-methyl-N4-(2-methyl-4-(4,4,5,5-tetramethyl-1,3,2-dioxaborolan-2-yl)phenyl)pyridine-2,4-dicarboxamide with 2-N,4-N-dimethyl-4-N-[2-methyl-4-(tetramethyl-1,3,2-dioxaborolan-2-yl)phenyl]pyridine-2,4-dicarboxamide provided the title compound as a white solid in 23.28% yield. LC-MS: (ES, m/z): [M+H]+ 495; 1H-NMR: (300 MHz, DMSO, ppm): δ 2.38 (s, 3H), 2.71-2.73 (d, 3H), 2.89 (s, 3H), 3.65 (s, 3H), 7.43-7.45 (q, 1H), 7.50-7.53 (d, 1H), 7.89 (s, 1H), 8.32-8.37 (m, 2H), 8.45-8.51 (m, 2H), 8.68-8.72 (m, 1H), 9.84 (s, 1H)

Step 1: 4-[(4-bromo-2-methylphenyl)(methyl)carbamoyl]pyridine-2-carboxylic acid

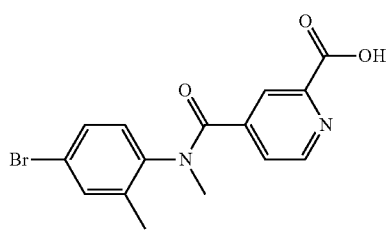 [SMILES: CNC(=O)c1cc(C(=O)N(C)c2ccc(Br)cc2C)ccn1]

Proceeding analogously as described in Example 167, Step 1 but substituting N-(4-bromo-2-methylphenyl)-2-cyanopyridine-4-carboxamide with N-(4-bromo-2-methylphenyl)-2-cyano-N-methylpyridine-4-carboxamide provided the title compound as a yellow solid in 63.04% yield.

Step 2: N4-(4-bromo-2-methylphenyl)-N2,N4-dimethylpyridine-2,4-dicarboxamide

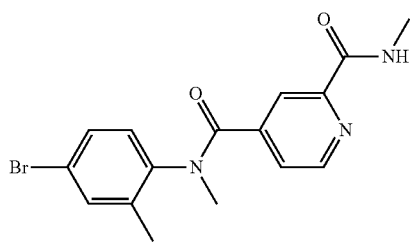

Proceeding analogously as described in Example 167, Step 2 but substituting 4-[(4-bromo-2-methylphenyl)carbamoyl]pyridine-2-carboxylic acid with 4-[(4-bromo-2-methylphenyl)(methyl)carbamoyl]pyridine-2-carboxylic acid provided crude product Purification by silica gel column chromatography, with CH2Cl2/MeOH (50:1) as eluent provided the title compound as a yellow oil in 96.40% yield.

Step 3: 2-N,4-N-dimethyl-4-N-[2-methyl-4-(tetramethyl-1,3,2-dioxaborolan-2-yl)phenyl]pyridine-2,4-dicarboxamide

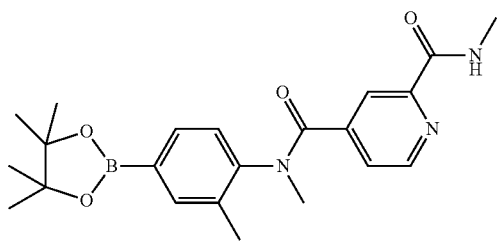

Proceeding analogously as described in Example 168, Step 3 but substituting 4-N-(4-bromo-2-methylphenyl)-2-N-methylpyridine-2,4-dicarboxamide with 4-N-(4-bromo-2-methylphenyl)-2-N,4-N-dimethylpyridine-2,4-dicarboxamide provided the title compound as a yellow solid in 64.61% yield.

Example 170: 1-(2-amino-2-oxoethyl)-N-(2-methyl-4-(8-methyl-6-(trifluoromethyl)-pyrido[3,2-d]pyrimidin-2-yl)phenyl)-1H-pyrazole-5-carboxamide

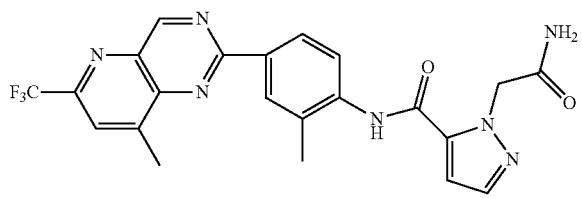 [SMILES: Cc1cc(-c2ncc3nc(C(F)(F)F)cc(C)c3n2)ccc1NC(=O)c1ccnn1CC(N)=O]

To a stirred mixture of 2-(5-((2-methyl-4-(8-methyl-6-(trifluoromethyl)pyrido[3,2-d]pyrimidin-2-yl)phenyl)carbamoyl)-1H-pyrazol-1-yl)acetic acid (75 mg, 0.16 mmol, 1 equiv.) and NH4Cl (17.1 mg, 0.32 mmol, 2 equiv.) in DMF (2 mL) were added HATU (90.9 mg, 0.24 mmol, 1.5 equiv.) and DIEA (82.4 mg, 0.64 mmol, 4 equiv.). The resulting mixture was stirred overnight at room temperature and then washed with water. The resulting mixture was extracted with CH2Cl2 and the combined organic layers were concentrated under reduced pressure. The residue was purified by Prep-TLC (CH2Cl2/MeOH=20:1) to afford the title compound as a white solid in 58.12% yield. LC-MS: (ES, m/z): [M+H]+ 470; 1H-NMR: (300 MHz, DMSO, ppm): δ 2.29-2.32 (d, 3H), 2.79 (s, 3H), 4.46-4.51 (d, 1H), 4.75-4.81 (m, 1H), 5.37-5.58 (m, 1H), 6.88-6.89 (d, 1H), 7.00-7.06 (m, 1H), 7.49-7.56 (m, 1H), 7.67 (s, 1H), 8.04 (s, 1H), δ8.17 (s, 1H), 8.32 (s, 1H), 8.38-8.44 (m, 2H).

Step 1: N-(2-methyl-4-(8-methyl-6-(trifluoromethyl)pyrido[3,2-d]pyrimidin-2-yl)phenyl)-1-(2-oxoethyl)-1H-pyrazole-5-carboxamide

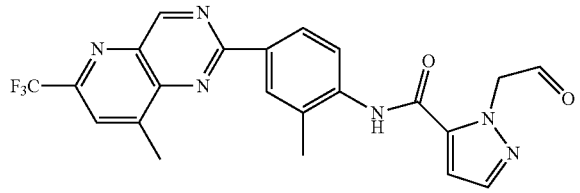 [SMILES: Cc1cc(-c2ncc3nc(C(F)(F)F)cc(C)c3n2)ccc1NC(=O)c1ccnn1CC=O]

To a stirred mixture of 1-(2-hydroxyethyl)-N-[2-methyl-4-[8-methyl-6-(trifluoromethyl)-pyrido[3,2-d]pyrimidin-2-yl]phenyl]-1H-pyrazole-5-carboxamide (120 mg, 0.26 mmol, 1 equiv.) in DCM (2.0 mL) was added Dess-Martin reagent (223.0 mg, 0.53 mmol, 2 equiv.). The resulting mixture was stirred for 6 h at room temperature and then filtered, and the filter cake was washed with water. The resulting mixture was extracted with $CH_2Cl_2$ and the combined organic layers were concentrated under reduced pressure. The residue was purified by Prep-TLC (PE/EtOAc=1:1) to afford the title compound as a white solid in 83.70% yield.

Step 2: 2-(5-((2-methyl-4-(8-methyl-6-(trifluoromethyl)pyrido[3,2-d]pyrimidin-2-yl)phenyl)carbamoyl)-1H-pyrazol-1-yl)acetic acid

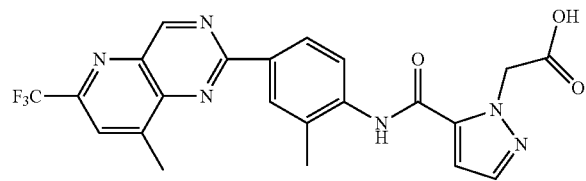 [SMILES: Cc1cc(-c2ncc3nc(C(F)(F)F)cc(C)c3n2)ccc1NC(=O)c1ccnn1CC(=O)O]

To a stirred mixture of N-(2-methyl-4-(8-methyl-6-(trifluoromethyl)pyrido[3,2-d]pyrimidin-2-yl)phenyl)-1-(2-oxoethyl)-1H-pyrazole-5-carboxamide (100 mg, 0.22 mmol, 1 equiv.) in DMF (1 mL) was added Oxone (111.0 mg, 0.66 mmol, 3 equiv.). The resulting mixture was stirred overnight at room temperature and then washed with water. The resulting mixture was extracted with EtOAc and the combined organic layers were concentrated under reduced pressure. The residue was purified by Prep-TLC ($CH_2Cl_2$/MeOH=15:1) to afford the title compound as a white solid in 82.11% yield.

Example 171: 1-(2-amino-2-oxoethyl)-N-methyl-N-(2-methyl-4-(8-methyl-6-(trifluoromethyl)pyrido[3,2-d]pyrimidin-2-yl)phenyl)-1H-pyrazole-5-carboxamide

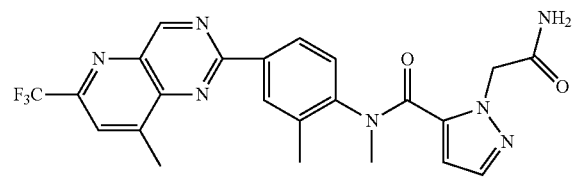 [SMILES: Cc1cc(-c2ncc3nc(C(F)(F)F)cc(C)c3n2)ccc1N(C)C(=O)c1ccnn1CC(N)=O]

Proceeding analogously as described in Example 167, Step 2 but substituting 4-[(4-bromo-2-methylphenyl)carbamoyl]pyridine-2-carboxylic acid with 2-(5-(methyl(2-methyl-4-(8-methyl-6-(trifluoromethyl)pyrido[3,2-d]pyrimidin-2-yl)phenyl)carbamoyl)-1H-pyrazol-1-yl)acetic acid and methanamine with ammonium chloride provided the title compound as a white solid in 43.55% yield. LC-MS: (ES, m/z): $[M+H]^+$ 484; $^1$H-NMR: (400 MHz, DMSO, ppm): δ 2.40 (s, 3H), 2.93 (s, 3H), 3.28 (s, 3H), 5.12-5.14 (d, 2H), 5.42-5.43 (d, 1H), 7.18 (d, 2H), 7.58-7.60 (d, 2H), 8.40 (d, 2H), 8.58 (s, 1H), 9.89 (s, 1H).

Step 1: 1-(2-(benzyloxy)ethyl)-N-methyl-N-(2-methyl-4-(8-methyl-6-(trifluoromethyl)-pyrido[3,2-d]pyrimidin-2-yl)phenyl)-1H-pyrazole-5-carboxamide

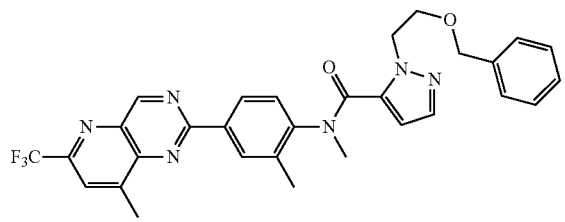 [SMILES: Cc1cc(-c2ncc3nc(C(F)(F)F)cc(C)c3n2)ccc1N(C)C(=O)c1ccnn1CCOCc1ccccc1]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1-[2-(benzyloxy)ethyl]-N-methyl-N-[2-methyl-4-(tetramethyl-1,3,2-dioxaborolan-2-yl)phenyl]-1H-pyrazole-5-carboxamide provided crude product which was purified by silica gel column chromatography, eluting with $CH_2Cl_2$/MeOH (20:1) to afford the title compound as a white solid in 57.42% yield.

Step 2: 1-(2-hydroxyethyl)-N-methyl-N-(2-methyl-4-(8-methyl-6-(trifluoromethyl)pyrido-[3,2-d]pyrimidin-2-yl)phenyl)-1H-pyrazole-5-carboxamide

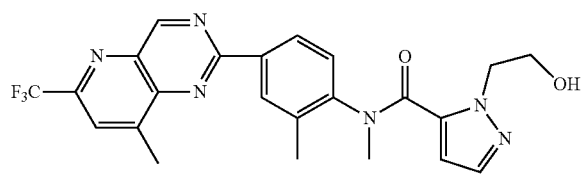 [SMILES: Cc1cc(-c2ncc3nc(C(F)(F)F)cc(C)c3n2)ccc1N(C)C(=O)c1ccnn1CCO]

To a stirred solution of 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide (520 mg, 0.93 mmol, 1 equiv.) in DCM (30 mL) was added $BBr_3$ (697.2 mg, 2.78 mmol, 3 equiv.) dropwise at 0° C. under nitrogen atmosphere. The resulting mixture was stirred for 1 h at 0° C. under nitrogen atmosphere and then quenched with sat. $NH_4Cl$ (aq.) at 0° C. The resulting mixture was extracted with EA and the residue was purified by Prep-TLC ($CH_2Cl_2$/MeOH=20:1) to afford the title compound as a white solid in 61.87% yield.

Step 3: N-methyl-N-(2-methyl-4-(8-methyl-6-(trifluoromethyl)pyrido[3,2-d]pyrimidin-2-yl)phenyl)-1-(2-oxoethyl)-1H-pyrazole-5-carboxamide

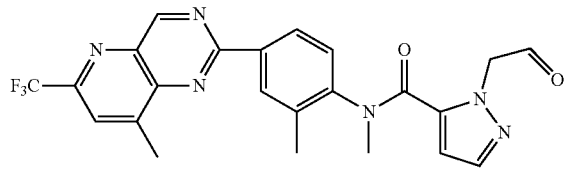 [SMILES: Cc1cc(-c2ncc3nc(C(F)(F)F)cc(C)c3n2)ccc1N(C)C(=O)c1ccnn1CC=O]

To a stirred solution of 1-(2-hydroxyethyl)-N-methyl-N-(2-methyl-4-(8-methyl-6-(trifluoromethyl)pyrido-[3,2-d]pyrimidin-2-yl)phenyl)-1H-pyrazole-5-carboxamide (270 mg, 0.57 mmol, 1 equiv.) in DCM (5 mL) was added Dess-Martin (730.3 mg, 1.72 mmol, 3 equiv.) in portions at room temperature. The resulting mixture was stirred for 3 h at room temperature. The resulting mixture was filtered, the filter cake was washed with DCM and the filtrate was concentrated under reduced pressure. The residue was purified by Prep-TLC (CH$_2$Cl$_2$/MeOH=20:1) to afford the title compound as a white solid in 37.20% yield.

Step 4: 2-(5-(methyl(2-methyl-4-(8-methyl-6-(trifluoromethyl)pyrido[3,2-d]pyrimidin-2-yl)phenyl)carbamoyl)-1H-pyrazol-1-yl)acetic acid

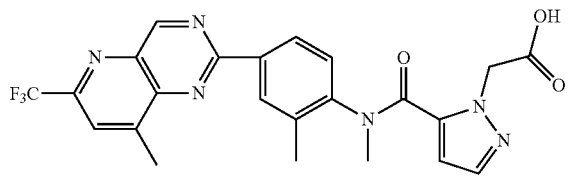 [SMILES: Cc1cc(-c2ncc3nc(C(F)(F)F)cc(C)c3n2)ccc1N(C)C(=O)c1ccnn1CC(=O)O]

To a stirred solution of N-methyl-N-(2-methyl-4-(8-methyl-6-(trifluoromethyl)pyrido-[3,2-d]pyrimidin-2-yl)phenyl)-1-(2-oxoethyl)-1H-pyrazole-5-carboxamide (100 mg, 0.21 mmol, 1 equiv.), DMF (1 mL) was added Oxone (71.8 mg, 0.43 mmol, 2 equiv.) at room temperature. The resulting mixture was stirred for 2 h at room temperature under air atmosphere and then extracted with EA. The residue was purified by Prep-TLC (CH$_2$Cl$_2$/MeOH=20:1) to afford the title compound as a white solid in 50.28% yield.

Example 172: 1-(2-hydroxyethyl)-N-[2-methyl-4-[8-methyl-6-(trifluoromethyl)pyrido-[3,2-d]pyrimidin-2-yl]phenyl]-1H-pyrazole-5-carboxamide

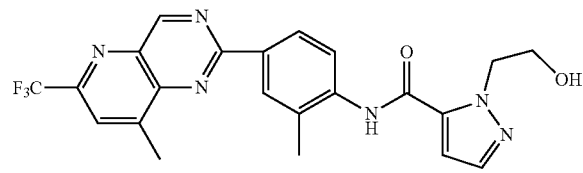 [SMILES: Cc1cc(-c2ncc3nc(C(F)(F)F)cc(C)c3n2)ccc1NC(=O)c1ccnn1CCO]

Into a 50-mL round-bottom flask, was placed 1-[2-(benzyloxy)ethyl]-N-[2-methyl-4-[8-methyl-6-(trifluoromethyl)pyrido[3,2-d]pyrimidin-2-yl]phenyl]-1H-pyrazole-5-carboxamide (100 mg, 0.18 mmol, 1 equiv.) and DCM (1 mL) and BBr$_3$ (275.0 mg, 1.10 mmol, 6 equiv.) was added at 0° C. The resulting solution was stirred for 1 h at room temperature and then quenched with NH$_4$Cl (aq.). The resulting solution was extracted with ethyl acetate and the organic layers were combined and concentrated. The residue was applied onto Prep-TLC and eluted with dichloromethane/methanol (40/1) to give the title compound as an off-white solid in 47.90% yield. LC-MS: (ES, m/z): [M+H]$^+$ 457; $^1$H-NMR: (400 MHz, DMSO, ppm): δ 2.41 (s, 3H), 2.95 (s, 3H), 3.72-3.76 (m, 2H), 4.58-4.61 (t, 2H), 4.91-4.93 (t, 1H), 7.06-7.07 (d, 1H), 7.59 (s, 1H), 7.65-7.67 (d, 1H), 8.38 (s, 1H), 8.49-8.52 (d, 1H), 8.56 (s, 1H), 9.87 (s, 1H), 10.04 (s, 1H)

Step 1: ethyl 1-[2-(benzyloxy)ethyl]-1H-pyrazole-5-carboxylate

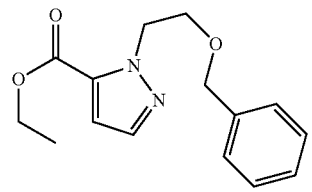 [SMILES: CCOC(=O)c1ccnn1CCOCc1ccccc1]

Into a 100-mL 3-necked round-bottom flask, was placed ethyl 1H-pyrazole-5-carboxylate (5.0 g, 35.68 mmol, 1 equiv.), THF (50 mL), 2-(benzyloxy)ethan-1-ol (5.97 g, 39.25 mmol, 1.1 equiv.), DIAD (10.82 g, 53.52 mmol, 1.5 equiv.), PPh$_3$ (18.7 g, 71.36 mmol, 2 equiv.). The resulting solution was stirred for 3 h at room temperature and then concentrated under vacuum. The residue was applied onto a silica gel column and eluted with ethyl acetate/petroleum ether (1/50) to give the title compound as a yellow liquid in 64.37% yield.

Step 2: 1-[2-(benzyloxy)ethyl]-1H-pyrazole-5-carboxylic acid

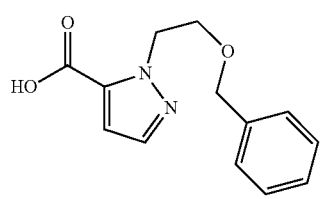 [SMILES: O=C(O)c1ccnn1CCOCc1ccccc1]

Into a 250-mL 3-necked round-bottom flask, was placed ethyl 1-[2-(benzyloxy)ethyl]-1H-pyrazole-5-carboxylate (6 g, 21.87 mmol, 1 equiv.), THF (60 mL), LiOH.H$_2$O (1.84 g, 43.75 mmol, 2 equiv.), and H$_2$O (12 mL). The resulting solution was stirred overnight at room temperature and the pH was adjusted to 5-6 with acetic acid. The solids were collected by filtration to give 5.5 g of the title compound as a white solid.

Step 3: 1-[2-(benzyloxy)ethyl]-N-(4-bromo-2-methylphenyl)-1H-pyrazole-5-carboxamide

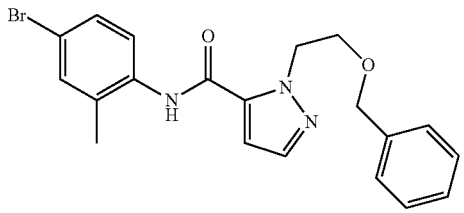 [SMILES: Cc1cc(Br)ccc1NC(=O)c1ccnn1CCOCc1ccccc1]

Proceeding analogously as described in Example 160, Step 8 but substituting 2-methylpyridine-4-carboxylic acid with 1-[2-(benzyloxy)ethyl]-1H-pyrazole-5-carboxylic acid provided crude product. Crystallization from petroleum and ether provided the title compound as an off-white solid in 77.27% yield.

Step 4: 1-(2-(benzyloxy)ethyl)-N-(2-methyl-4-(4,4,5,5-tetramethyl-1,3,2-dioxaborolan-2-yl)phenyl)-1H-pyrazole-5-carboxamide

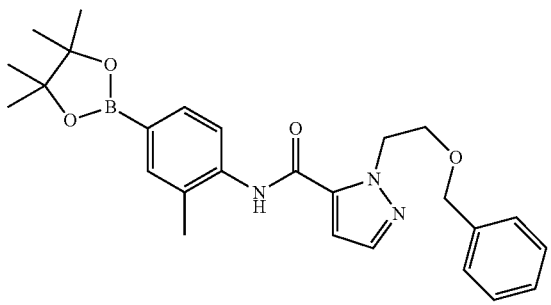 [SMILES: Cc1cc(B2OC(C)(C)C(C)(C)O2)ccc1NC(=O)c1ccnn1CCOCc1ccccc1]

Proceeding analogously as described in Example 161, Step 2 but substituting N-(4-bromo-2-methylphenyl)-N,2-dimethylpyridine-4-carboxamide with 1-[2-(benzyloxy)ethyl]-N-(4-bromo-2-methylphenyl)-1H-pyrazole-5-carboxamide provided the title compound as a yellow oil in 74.83% yield after purification with silica gel column chromatography with ethyl acetate/petroleum ether (1/5).

Step 5: 1-[2-(benzyloxy)ethyl]-N-[2-methyl-4-[8-methyl-6-(trifluoromethyl)pyrido[3,2-d]pyrimidin-2-yl]phenyl]-1H-pyrazole-5-carboxamide

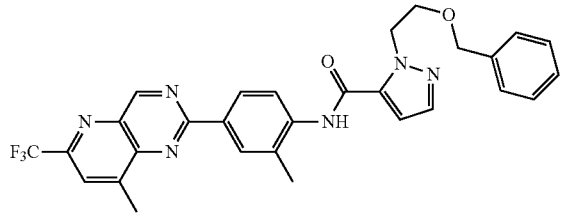 [SMILES: Cc1cc(-c2ncc3nc(C(F)(F)F)cc(C)c3n2)ccc1NC(=O)c1ccnn1CCOCc1ccccc1]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1-[2-(benzyloxy)ethyl]-N-[2-methyl-4-(tetramethyl-1,3,2-dioxaborolan-2-yl)phenyl]-1H-pyrazole-5-carboxamide provided crude product. Purification by silica gel column with ethyl acetate/petroleum ether (1/10) as the eluent provided the title compound as a yellow oil in 42.28% yield.

Example 173: 1-(2-hydroxyethyl)-N-methyl-N-(2-methyl-4-(8-methyl-6-(trifluoromethyl)-pyrido[3,2-d]pyrimidin-2-yl)phenyl)-1H-pyrazole-5-carboxamide

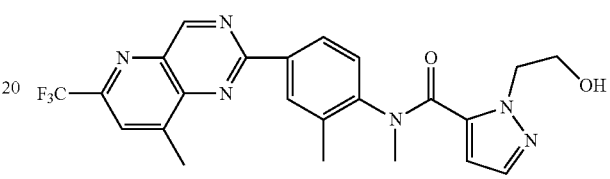

Proceeding analogously as described in Example 172 but substituting 1-[2-(benzyloxy)-ethyl]-N-[2-methyl-4-[8-methyl-6-(trifluoromethyl)pyrido[3,2-d]pyrimidin-2-yl]phenyl]-1H-pyrazole-5-carboxamide with 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide gave crude product. The crude product was purified by Flash chromatography (Column, C18 silica gel; mobile phase, $CH_3CN/H_2O=0/100$ up to $CH_3CN/H_2O=60/100$ in 30 min; Detector, 254 nm) to give the title compound as an off-white solid in 23.32% yield. LC-MS: (ES, m/z): $[M+H]^+$ 471; $^1$H-NMR: (400 MHz, DMSO, ppm): δ 2.36 (s, 3H), 2.92 (s, 3H), 3.33 (s, 3H), 3.75-3.79 (m, 2H), 4.40-4.43 (m, 1H), 4.52-4.53 (m, 1H), 4.95-4.98 (t, 1H), 5.53 (s, 1H), 7.18 (s, 1H), 7.48-7.50 (d, 1H), 8.38-8.41 (d, 2H), 8.54 (s, 1H), 9.87 (s, 1H)

Step 1: 1-(2-(benzyloxy)ethyl)-N-(4-bromo-2-methylphenyl)-N-methyl-1H-pyrazole-5-carboxamide

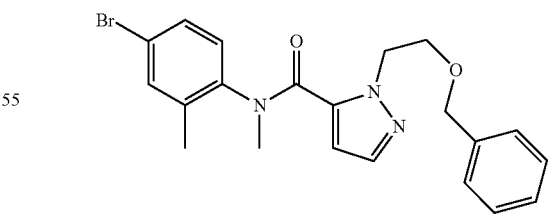

Proceeding analogously as described in Example 161, Step 1 but substituting N-(4-bromo-2-methylphenyl)-2-methylpyridine-4-carboxamide with 1-[2-(benzyloxy)ethyl]-N-(4-bromo-2-methylphenyl)-1H-pyrazole-5-carboxamide provided crude product which was purified by silica gel column chromatography using ethyl acetate/petroleum ether (1/10) as eluent to give the title compound as an off-white solid in 73.70% yield.

Step 2: 1-(2-(benzyloxy)ethyl)-N-methyl-N-(2-methyl-4-(4,4,5,5-tetramethyl-1,3,2-dioxaborolan-2-yl)phenyl)-1H-pyrazole-5-carboxamide

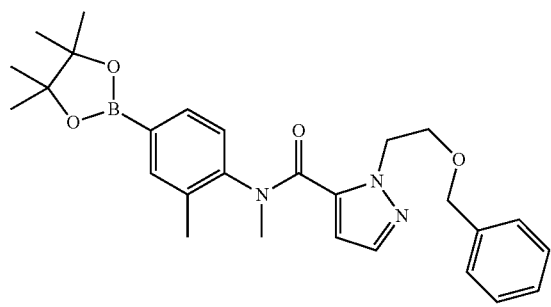 [SMILES: Cc1cc(B2OC(C)(C)C(C)(C)O2)ccc1N(C)C(=O)c1ccnn1CCOCc1ccccc1]

Proceeding analogously as described in Example 161, Step 2 but substituting N-(4-bromo-2-methylphenyl)-N,2-dimethylpyridine-4-carboxamide with 1-(2-(benzyloxy)ethyl)-N-(4-bromo-2-methylphenyl)-N-methyl-1H-pyrazole-5-carboxamide provided crude product. Purification by silica gel column chromatography with ethyl acetate/petroleum ether (1/5) as the eluent provided the title compound as a yellow oil in 67.57% yield.

Step 3: 1-(2-(benzyloxy)ethyl)-N-methyl-N-(2-methyl-4-(8-methyl-6-(trifluoromethyl)-pyrido[3,2-d]pyrimidin-2-yl)phenyl)-1H-pyrazole-5-carboxamide

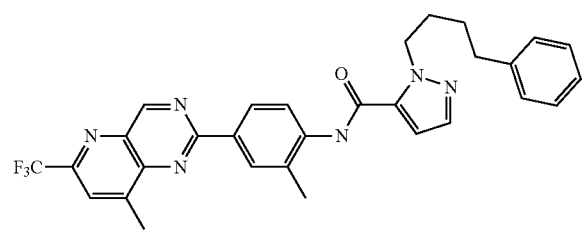 [SMILES: Cc1cc(-c2ncc3nc(C(F)(F)F)cc(C)c3n2)ccc1NC(=O)c1ccnn1CCCCc1ccccc1]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1-(2-(benzyloxy)ethyl)-N-methyl-N-(2-methyl-4-(4,4,5,5-tetramethyl-1,3,2-dioxaborolan-2-yl)phenyl)-1H-pyrazole-5-carboxamide provided crude product. Purification with Prep-TLC using dichloromethane/methanol (40/1) as eluent gave the title compound as an off-white solid in 66.26% yield.

Example 174: N-(3-fluoro-2-methyl-4-(8-methyl-6-(trifluoromethyl)pyrido[3,2-d]pyrimidin-2-yl)phenyl)-1-methyl-1H-pyrazole-5-carboxamide

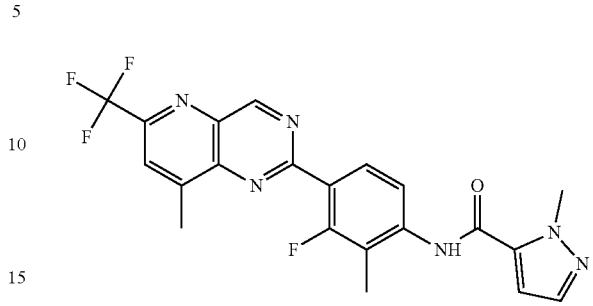

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-(3-fluoro-2-methyl-4-(4,4,5,5-tetramethyl-1,3,2-dioxaborolan-2-yl)phenyl)-1-methyl-1H-pyrazole-5-carboxamide provided crude product. Purification by Prep-TLC with dichloromethane/methanol (80:1) gave the title compound as a yellow solid in 50.15% yield. LC-MS: (ES, m/z): [M+H]$^+$ 445; $^1$H-NMR: (300 MHz, DMSO, ppm): δ 2.26 (s, 3H), 2.90 (s, 3H), 4.11 (s, 3H), 7.13 (s, 1H), 7.48-7.48 (d, 1H), 7.58 (s, 1H), 8.15-8.19 (m, 1H), 8.41 (s, 1H), 9.92 (s, 1H), 10.21 (s, 1H)

Step 1: 4-bromo-3-fluoro-2-methylaniline

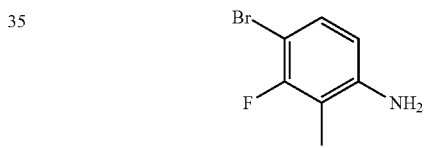

Into a 100-mL 3-necked round-bottom flask purged and maintained with an inert atmosphere of nitrogen, was placed 3-fluoro-2-methylaniline (5 g, 39.95 mmol, 1 equiv.) and DMF (50 mL) and NBS (7.1 g, 39.89 mmol, 0.998 equiv.) was added in three times at 0° C. Then the resulting solution was stirred overnight at room temperature and then extracted with ethyl acetate. The organic layers were combined and dried over anhydrous sodium sulfate. The solids were filtered and the filtrate was concentrated under vacuum to give the title compound as a purple solid in 96.91% yield.

Step 2: N-(4-bromo-3-fluoro-2-methylphenyl)-1-methyl-1H-pyrazole-5-carboxamide

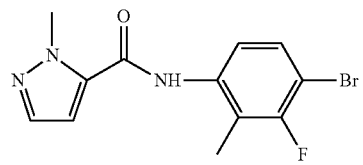 [SMILES: Cc1c(NC(=O)c2ccnn2C)ccc(Br)c1F]

Proceeding analogously as described in Example 160, Step 8 but substituting 4-bromo-2-methylaniline with 4-bromo-3-fluoro-2-methylaniline and 2-methylpyridine-4- carboxylic acid with 1-methyl-1H-pyrazole-5-carboxylic acid provided crude product. The residue was applied onto a silica gel column and eluted with CH₂Cl₂. Evaporation of volatiles afforded a solid that was re-crystallized from EA/PE (1:5) resulting in 1.6 g (52.29%) of the desired product as a white solid.

Step 3: N-(3-fluoro-2-methyl-4-(4,4,5,5-tetramethyl-1,3,2-dioxaborolan-2-yl)phenyl)-1-methyl-1H-pyrazole-5-carboxamide

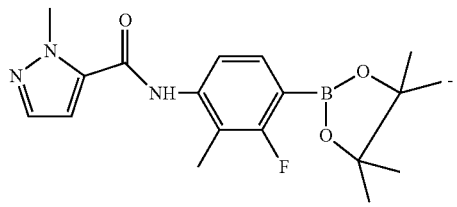

Proceeding analogously as described in Example 161, Step 2 but substituting N-(4-bromo-2-methylphenyl)-N,2-dimethylpyridine-4-carboxamide with N-(4-bromo-3-fluoro-2-methylphenyl)-1-methyl-1H-pyrazole-5-carboxamide provided crude product. The residue was applied onto a silica gel column and eluted with CH₂Cl₂. Evaporation of volatiles afforded a solid that was re-crystallized from EA/PE (1:5). This resulted in 0.9 g (111.73%) of the desired product as a white solid.

Example 175: N-(3-fluoro-2-methyl-4-(8-methyl-6-(trifluoromethyl)pyrido[3,2-d]pyrimidin-2-yl)phenyl)-N,1-dimethyl-1H-pyrazole-5-carboxamide

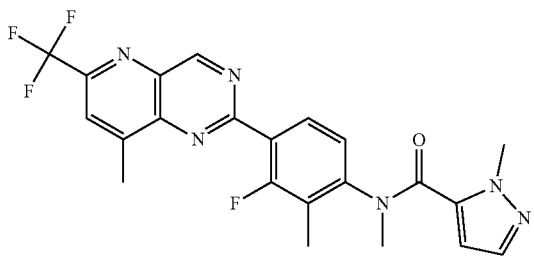 [SMILES: Cc1c(N(C)C(=O)c2ccnn2C)ccc(-c2ncc3nc(C(F)(F)F)cc(C)c3n2)c1F]

Proceeding analogously as described in Example 163 but substituting N-[2-fluoro-4-(tetramethyl-1,3,2-dioxaborolan-2-yl)phenyl]-1-methyl-1H-pyrazole-5-carboxamide with N-(3-fluoro-2-methyl-4-(4,4,5,5-tetramethyl-1,3,2-dioxaborolan-2-yl)phenyl)-N,1-dimethyl-1H-pyrazole-5-carboxamide provided crude product. Purification with Prep-TLC with dichloromethane/methanol (50:1) as eluent gave the title compound as a yellow solid in 35.59% yield. LC-MS: (ES, m/z): [M+H]⁺ 459; ¹H-NMR: (300 MHz, DMSO, ppm): δ 2.18 (s, 3H), 2.88 (s, 3H), 3.35 (s, 3H), 4.01 (s, 3H), 5.65 (s, 1H), 7.21 (s, 1H), 7.37-7.40 (d, 1H), 8.08-8.13 (t, 1H), 8.41 (s, 1H), 9.90 (s, 1H)

Step 1: N-(4-bromo-3-fluoro-2-methylphenyl)-N,1-dimethyl-1H-pyrazole-5-carboxamide

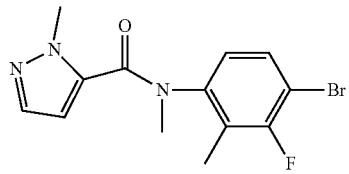 [SMILES: Cc1c(N(C)C(=O)c2ccnn2C)ccc(Br)c1F]

Into a 25-mL 3-necked round-bottom flask purged and maintained with an inert atmosphere of nitrogen was placed N-(4-bromo-3-fluoro-2-methylphenyl)-1-methyl-1H-pyrazole-5-carboxamide (0.87 g, 2.79 mmol, 1 equiv.), DMF (9 mL), and NaH (0.1 g, 3.34 mmol, 1.2 equiv.) was added at 0° C. The resulting mixture was stirred for 0.5 h and MeI (0.4 g, 2.93 mmol, 1.05 equiv.) was added. The resulting solution was stirred overnight at room temperature and then quenched with NH₄Cl (aq.). The resulting solution was extracted with ethyl acetate and the organic layers were combined and concentrated under vacuum to give the title compound as a white solid in 88.00% yield.

Step 2: N-(3-fluoro-2-methyl-4-(4,4,5,5-tetramethyl-1,3,2-dioxaborolan-2-yl)phenyl)-N,1-dimethyl-1H-pyrazole-5-carboxamide

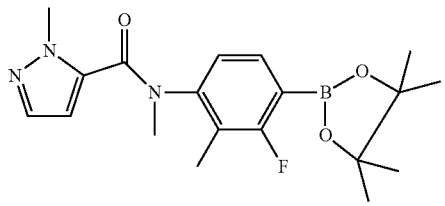 [SMILES: Cc1c(N(C)C(=O)c2ccnn2C)ccc(B2OC(C)(C)C(C)(C)O2)c1F]

Proceeding analogously as described in Example 161, Step 2 but substituting N-(4-bromo-2-methylphenyl)-N,2-dimethylpyridine-4-carboxamide with N-(4-bromo-3-fluoro-2-methylphenyl)-N,1-dimethyl-1H-pyrazole-5-carboxamide provided crude product. Purification on a silica gel column with ethyl acetate/petroleum ether (1:20) as eluent gave the title compound as a white solid in 81.93% yield.

Example 176: N-(2-fluoro-3-methyl-4-(8-methyl-6-(trifluoromethyl)pyrido[3,2-d]pyrimidin-2-yl)phenyl)-1-methyl-1H-pyrazole-5-carboxamide

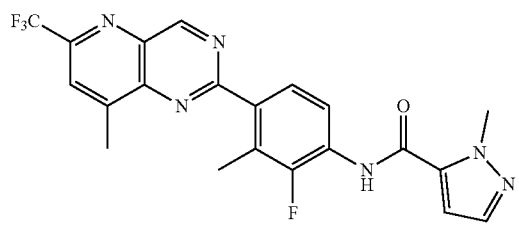 [SMILES: Cc1c(-c2ncc3nc(C(F)(F)F)cc(C)c3n2)ccc(NC(=O)c2ccnn2C)c1F]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-(2-fluoro-3-methyl-4-(4,4,5,5-tetramethyl-1,3,2-dioxaborolan-2-yl)phenyl)-1-methyl-1H-pyrazole-5-carboxamide provided the crude product. Purification on Prep-TLC with ethyl acetate/hexane (1/1) as eluent provided the title compound as a yellow solid in 11.81 yield. LC-MS: (ES, m/z): [M+H]$^+$ 445; $^1$H-NMR: (300 MHz, DMSO, ppm): δ 2.64-2.65 (d, 3H), 2.90 (s, 3H), 4.11 (s, 3H), 7.15-7.16 (d, 1H), 7.57-7.56 (d, 1H), 7.69-7.75 (t, 1H), 8.03-8.05 (d, 1H), 8.42 (s, 1H), 9.93 (s, 1H), 10.25 (s, 1H)

Step 1: 4-bromo-2-fluoro-3-methylaniline

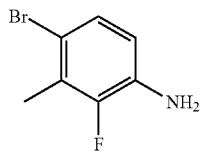

Proceeding as described in Example 174, Step 1 but substituting 3-fluoro-2-methylaniline with 2-fluoro-3-methylaniline provided the title compound as a red solid in 97.89% yield.

Step 2: N-(4-bromo-2-fluoro-3-methylphenyl)-1-methyl-1H-pyrazole-5-carboxamide

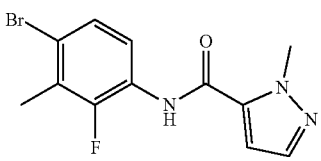 [SMILES: Cc1c(Br)ccc(NC(=O)c2ccnn2C)c1F]

Proceeding analogously as described in Example 160, Step 8 but substituting 4-bromo-2-methylaniline with 4-bromo-2-fluoro-3-methylaniline (2 g, 9.80 mmol, 1 equiv.) and 2-methylpyridine-4-carboxylic acid with 1-methyl-1H-pyrazole-5-carboxylic acid provided the crude product. Purification on a silica gel column with dichloromethane/methanol (100/1) as eluent provided the title compound as a red solid in 76.81% yield.

Step 3: N-(2-fluoro-3-methyl-4-(4,4,5,5-tetramethyl-1,3,2-dioxaborolan-2-yl)phenyl)-1-methyl-1H-pyrazole-5-carboxamide

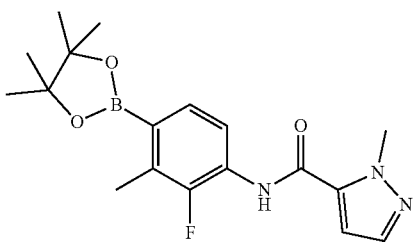 [SMILES: Cc1c(B2OC(C)(C)C(C)(C)O2)ccc(NC(=O)c2ccnn2C)c1F]

Proceeding analogously as described in Example 161, Step 2 but substituting N-(4-bromo-2-methylphenyl)-N,2-dimethylpyridine-4-carboxamide with N-(4-bromo-2-fluoro-3-methylphenyl)-1-methyl-1H-pyrazole-5-carboxamide provided the title compound as a white solid in 65.85% yield.

Example 177: N-(2-fluoro-3-methyl-4-(8-methyl-6-(trifluoromethyl)pyrido[3,2-d]pyrimidin-2-yl)phenyl)-N,1-dimethyl-1H-pyrazole-5-carboxamide

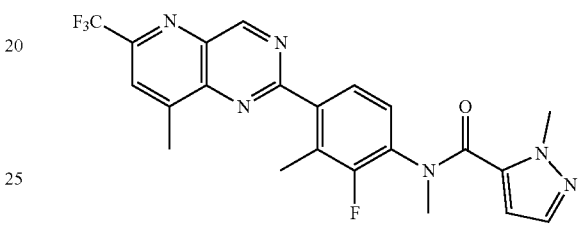

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-(2-fluoro-3-methyl-4-(4,4,5,5-tetramethyl-1,3,2-dioxaborolan-2-yl)phenyl)-N,1-dimethyl-1H-pyrazole-5-carboxamide gave crude product. Purification by Prep-TLC with ethyl acetate/hexane (1/5) and re-crystallization from hexane gave the title compound as a yellow solid. LC-MS: (ES, m/z): [M+H]$^+$ 459; $^1$H-NMR: (300 MHz, DMSO, ppm): δ 2.51 (s, 3H), 2.87 (s, 3H), 3.39 (s, 3H), 3.98 (s, 3H), 5.86 (s, 1H), 7.26 (s, 1H), 7.53-7.59 (t, 1H), 7.95-7.98 (d, 1H), 8.42 (s, 1H), 9.91 (s, 1H)

Step 1: N-(4-bromo-2-fluoro-3-methylphenyl)-N,1-dimethyl-1H-pyrazole-5-carboxamide

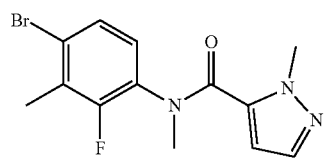

Proceeding analogously as described in Example 175, Step 1 but substituting N-(4-bromo3-fluoro-2-methylphenyl)-2-methylpyridine-4-carboxamide with N-(4-bromo-2-fluoro-3-methylphenyl)-1-methyl-1H-pyrazole-5-carboxamide provided the title compound as a yellow solid in 78.15% yield.

Step 2: N-(2-fluoro-3-methyl-4-(4,4,5,5-tetramethyl-1,3,2-dioxaborolan-2-yl)phenyl)-N,1-dimethyl-1H-pyrazole-5-carboxamide

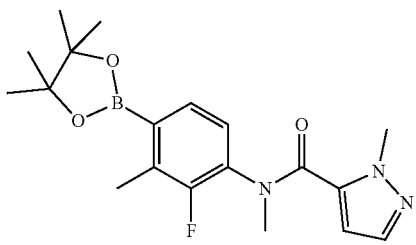 [SMILES: Cc1c(B2OC(C)(C)C(C)(C)O2)ccc(N(C)C(=O)c2ccnn2C)c1F]

Proceeding analogously as described in Example 161, Step 2 but substituting N-(4-bromo-2-methylphenyl)-N,2-dimethylpyridine-4-carboxamide with N-(4-bromo-2-fluoro-3-methylphenyl)-N,1-dimethyl-1H-pyrazole-5-carboxamide provided crude product which was purified by column chromatography by eluting with ethyl acetate/petroleum ether (1/10). The crude product was purified by recrystallization from PE to give the title compound as a white solid in 54.69% yield.

Example 178: N-(2-fluoro-5-methyl-4-(8-methyl-6-(trifluoromethyl)pyrido[3,2-d]pyrimidin-2-yl)phenyl)-1-methyl-1H-pyrazole-5-carboxamide

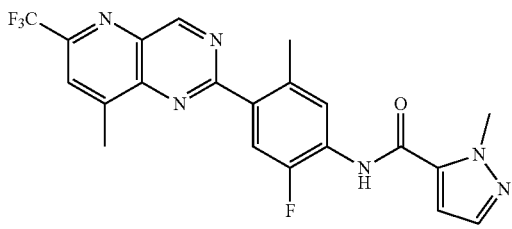 [SMILES: Cc1cc(NC(=O)c2ccnn2C)c(F)cc1-c1ncc2nc(C(F)(F)F)cc(C)c2n1]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-[2-fluoro-5-methyl-4-(tetramethyl-1,3,2-dioxaborolan-2-yl)phenyl]-1-methyl-1H-pyrazole-5-carboxamide provided the crude product. Purification by Prep-TLC (CH$_2$Cl$_2$/MeOH=20:1) afforded the title compound as a white solid 38.45% yield. LC-MS: (ES, m/z): [M+H]$^+$ 445; $^1$H-NMR: (400 MHz, DMSO, ppm): δ 2.74 (s, 3H), 2.89 (s, 3H), 4.11 (s, 3H), 7.15-7.16 (d, 1H), 7.56-7.57 (d, 1H), 7.71-7.73 (d, 1H), 8.10-8.13 (d, 1H), 9.90 (s, 1H), 10.28 (s, 1H).

Step 1: 4-bromo-2-fluoro-5-methylaniline

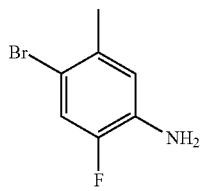

Proceeding analogously as described in Example 174, Step 1 but substituting 3-fluoro-2-methylaniline provided the title compound as a white solid in 90.77% yield.

Step 2: N-(4-bromo-2-fluoro-5-methylphenyl)-1-methyl-1H-pyrazole-5-carboxamide

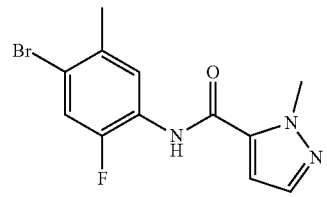 [SMILES: Cc1cc(NC(=O)c2ccnn2C)c(F)cc1Br]

Proceeding analogously as described in Example 160, Step 8 but substituting 4-bromo-2-methylaniline with 4-bromo-2-fluoro-5-methylaniline (2 g, 9.80 mmol, 1 equiv.) and 2-methylpyridine-4-carboxylic acid with 1-methyl-1H-pyrazole-5-carboxylic acid provided crude product. Purification by column chromatography by eluting with PE/EA (provided the title compound as a white solid in 94.78% yield.

Step 3: N-[2-fluoro-5-methyl-4-(tetramethyl-1,3,2-dioxaborolan-2-yl)phenyl]-1-methyl-1H-pyrazole-5-carboxamide

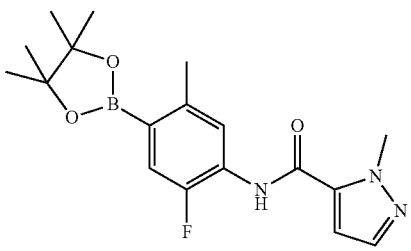 [SMILES: Cc1cc(NC(=O)c2ccnn2C)c(F)cc1B1OC(C)(C)C(C)(C)O1]

Proceeding analogously as described in Example 161, Step 2 but substituting N-(4-bromo-2-methylphenyl)-N,2-dimethylpyridine-4-carboxamide with N-(4-bromo-2-fluoro-5-methylphenyl)-1-methyl-1H-pyrazole-5-carboxamide provided crude product. Purification by column chromatography by eluting with petroleum ether/ethyl acetate (5:1) provided the title compound as a white solid in 84.29% yield.

Example 179: N-(2-fluoro-5-methyl-4-(8-methyl-6-(trifluoromethyl)pyrido[3,2-d]pyrimidin-2-yl)phenyl)-N,1-dimethyl-1H-pyrazole-5-carboxamide

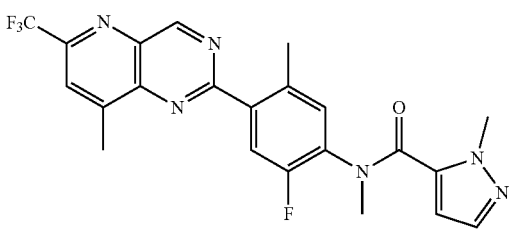 [SMILES: Cc1cc(N(C)C(=O)c2ccnn2C)c(F)cc1-c1ncc2nc(C(F)(F)F)cc(C)c2n1]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-[2-fluoro-5-methyl-4-(tetramethyl-1,3,2-dioxaborolan-2-yl)phenyl]-N,1-dimethyl-1H-pyrazole-5-carboxamide provided crude product. Purification by Prep-TLC (CH$_2$Cl$_2$/MeOH=20:1) provided the title compound as a white solid in 58.71% yield. LC-MS: (ES, m/z): [M+H]$^+$ 459; $^1$H-NMR: (300 MHz, DMSO, ppm): δ2.69 (s, 3H), 2.89 (s, 3H), 3.41 (s, 3H), 3.97 (s, 3H), 5.90 (s, 1H), 7.21 (s, 1H), 7.64-7.67 (d, 1H), 7.94-7.98 (d, 1H), 8.43 (s, 1H), 9.90 (s, 1H).

Step 1: N-(4-bromo-2-fluoro-5-methylphenyl)-N,1-dimethyl-1H-pyrazole-5-carboxamide

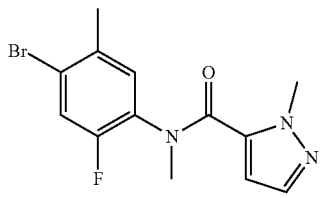 [SMILES: Cc1cc(N(C)C(=O)c2ccnn2C)c(F)cc1Br]

Proceeding analogously as described in Example 161, Step 1 but substituting N-(4-bromo-2-methylphenyl)-2-methylpyridine-4-carboxamide with N-(4-bromo-2-fluoro-5-methylphenyl)-1-methyl-1H-pyrazole-5-carboxamide provided the title compound as a white solid in 93.79% yield.

Step 2: N-[2-fluoro-5-methyl-4-(tetramethyl-1,3,2-dioxaborolan-2-yl)phenyl]-N,1-dimethyl-1H-pyrazole-5-carboxamide

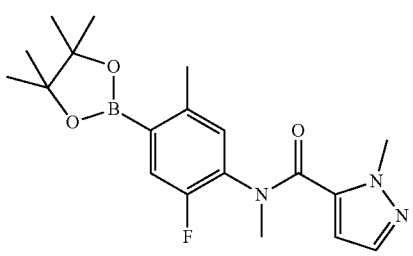 [SMILES: Cc1cc(N(C)C(=O)c2ccnn2C)c(F)cc1B1OC(C)(C)C(C)(C)O1]

Proceeding analogously as described in Example 161, Step 2 but substituting N-(4-bromo-2-methylphenyl)-N,2-dimethylpyridine-4-carboxamide with N-(4-bromo-2-fluoro-5-methylphenyl)-N,1-dimethyl-1H-pyrazole-5-carboxamide provided crude product. Purification by column chromatography by eluting with PE/EA (10:1) gave the title compound as a white solid in 74.01% yield.

Example 180: N-(5-fluoro-2-methyl-4-(8-methyl-6-(trifluoromethyl)pyrido[3,2-d]pyrimidin-2-yl)phenyl)-1-methyl-1H-pyrazole-5-carboxamide

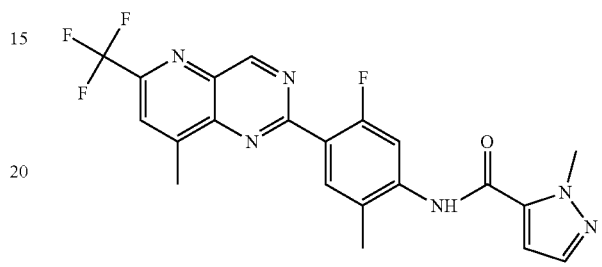

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-(5-fluoro-2-methyl-4-(4,4,5,5-tetramethyl-1,3,2-dioxaborolan-2-yl)phenyl)-1-methyl-1H-pyrazole-5-carboxamide gave crude product. Purification by Prep-TLC (CH$_2$Cl$_2$/MeOH=50:1) gave the title compound as a yellow solid in 31.15% yield. LC-MS: (ES, m/z): [M+H]$^+$ 445; $^1$H-NMR: (300 MHz, DMSO, ppm): δ2.38 (s, 3H), 2.90 (s, 3H), 4.12 (s, 3H), 7.13 (s, 1H), 7.57-7.61 (m, 2H), 8.25-8.27 (d, 1H), 8.41 (s, 1H), 9.91 (s, 1H), 10.00 (s, 1H).

Step 1: N-(4-bromo-5-fluoro-2-methylphenyl)-1-methyl-1H-pyrazole-5-carboxamide

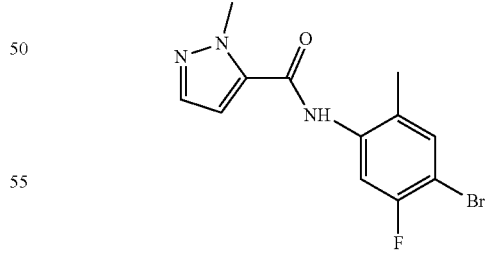

Proceeding analogously as described in Example 160, Step 8 but substituting 4-bromo-2-methylaniline with 4-bromo-5-fluoro-2-methylaniline (2 g, 9.80 mmol, 1 equiv.) and 2-methylpyridine-4-carboxylic acid with 1-methyl-1H-pyrazole-5-carboxylic acid provided crude product. Purification column chromatography with CH$_2$Cl$_2$, followed by re-crystallization from EA/PE gave the title compound as a white solid in 42.49% yield).

Step 2: N-(5-fluoro-2-methyl-4-(4,4,5,5-tetramethyl-1,3,2-dioxaborolan-2-yl)phenyl)-1-methyl-1H-pyrazole-5-carboxamide

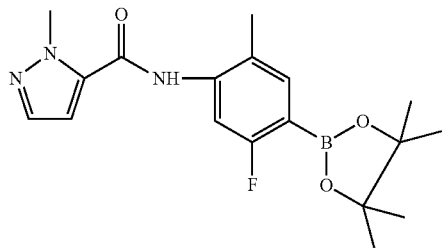 [SMILES: Cc1cc(B2OC(C)(C)C(C)(C)O2)c(F)cc1NC(=O)c1ccnn1C]

Proceeding analogously as described in Example 161, Step 2 but substituting N-(4-bromo-2-methylphenyl)-N,2-dimethylpyridine-4-carboxamide with N-(4-bromo-5-fluoro-2-methylphenyl)-1-methyl-1H-pyrazole-5-carboxamide provided crude product. Purification by column chromatograph with ethyl acetate/petroleum ether (1:10) as eluent gave the title compound as a white solid in 26.74% yield.

Example 181: N-(5-fluoro-2-methyl-4-(8-methyl-6-(trifluoromethyl)pyrido[3,2-d]pyrimidin-2-yl)phenyl)-N,1-dimethyl-1H-pyrazole-5-carboxamide

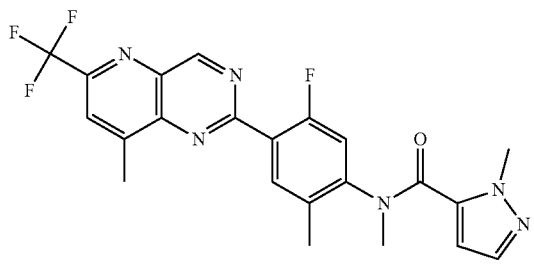 [SMILES: Cc1cc(-c2ncc3nc(C(F)(F)F)cc(C)c3n2)c(F)cc1N(C)C(=O)c1ccnn1C]

Proceeding analogously as in Example 163 but substituting N-[2-fluoro-4-(tetramethyl-1,3,2-dioxaborolan-2-yl)phenyl]-1-methyl-1H-pyrazole-5-carboxamide with N-(5-fluoro-2-methyl-4-(4,4,5,5-tetramethyl-1,3,2-dioxaborolan-2-yl)phenyl)-N,1-dimethyl-1H-pyrazole-5-carboxamide provided crude product. Purification by Prep-TLC with dichloromethane/methanol (50:1) gave the title compound in 52.01% yield. LC-MS: (ES, m/z): [M+H]+ 459; 1H-NMR: (300 MHz, DMSO, ppm): δ2.22 (s, 3H), 2.88 (s, 3H), 3.33 (s, 3H), 4.01 (s, 3H), 5.68 (s, 1H), 7.23 (s, 1H), 7.53-7.56 (d, 1H), 8.20 (d, 1H), 8.41 (s, 1H), 9.90 (s, 1H).

Step 1: N-(4-bromo-5-fluoro-2-methylphenyl)-N,1-dimethyl-1H-pyrazole-5-carboxamide

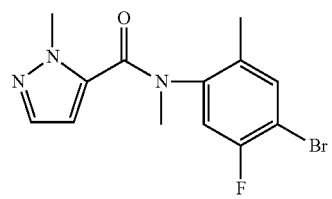 [SMILES: Cc1cc(Br)c(F)cc1N(C)C(=O)c1ccnn1C]

Proceeding analogously as described in Example 175, Step 1 but substituting N-(4-bromo-3-fluoro-2-methylphenyl)-1-methyl-1H-pyrazole-5-carboxamide with N-(4-bromo-5-fluoro-2-methylphenyl)-1-methyl-1H-pyrazole-5-carboxamide provided the title compound as a white solid in 99.38%.

Step 2: N-(5-fluoro-2-methyl-4-(4,4,5,5-tetramethyl-1,3,2-dioxaborolan-2-yl)phenyl)-N,1-dimethyl-1H-pyrazole-5-carboxamide

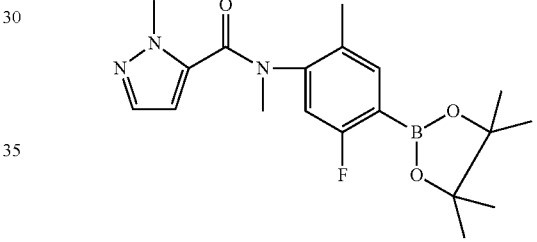

Proceeding analogously as described in Example 161, Step 2 but substituting N-(4-bromo-2-methylphenyl)-N,2-dimethylpyridine-4-carboxamide with N-(4-bromo-5-fluoro-2-methylphenyl)-N,1-dimethyl-1H-pyrazole-5- provided crude product. Purification by column chromatography with ethyl acetate/petroleum ether as eluent, followed by re-crystallization from EA/PE (1:5) provided the title compound as a white solid in 38.52% yield.

Example 182: N-methyl-N-(2-methyl-4-(8-methyl-6-(trifluoromethyl)pyrido[3,2-d]pyrimidin-2-yl)phenyl)-1-(2-(pyrrolidin-1-yl)ethyl)-1H-pyrazole-5-carboxamide

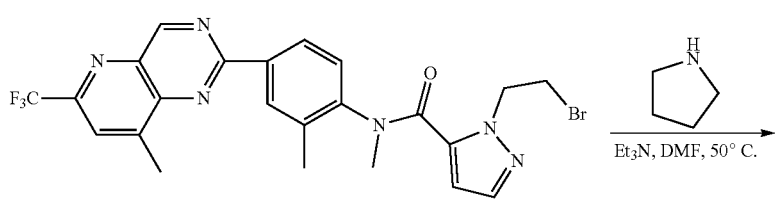

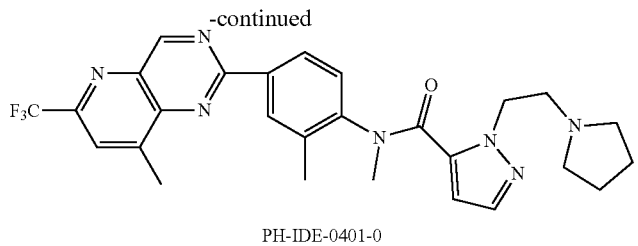

PH-IDE-0401-0

Into an 8-mL vial, was placed 1-(2-bromoethyl)-N-methyl-N-[2-methyl-4-[8-methyl-6-(trifluoromethyl)pyrido[3,2-d]pyrimidin-2-yl]phenyl]-1H-pyrazole-5-carboxamide (78 mg, 0.15 mmol, 1 equiv.), DMF (1 mL), Et$_3$N (29.6 mg, 0.29 mmol, 2 equiv.), and pyrrolidine (41.6 mg, 0.58 mmol, 4 equiv.). The resulting solution was stirred for 6 h at 50° C. and then quenched with water. The resulting solution was extracted with ethyl acetate and the organic layers combined. The residue was purified by prep-TLC with dichloromethane/methanol (40/1). The resulting material was further purified by prep-HPLC with the following conditions: Column, XBridge Prep OBD C18 Column; mobile phase, water (0.05% NH$_3$H$_2$O) and ACN (60% Phase B up to 72% in 8 min) to afford the title compound as a white solid in 10.97% yield. LC-MS: (ES, m/z): [M+H]$^+$ 524; $^1$H-NMR: (300 MHz, DMSO, ppm): δ9.88 (s, 1H), 8.56 (d, 1H), 8.41-8.38 (m, 2H), 7.52-7.50 (d, 2H), 7.17-7.18 (d, 1H), 5.49-5.48 (d, 2H), 4.69-4.60 (m, 1H), 4.51-4.43 (m, 1H), 3.32 (s, 6H), 2.93 (s, 4H), 2.74-2.73 (d, 2H), 2.37 (s, 3H), 1.73 (s, 3H)

Example 183: 3-methoxy-N-methyl-N-(2-methyl-4-(8-methyl-6-(trifluoromethyl)-pyrido[3,2-d]pyrimidin-2-yl)phenyl)isonicotinamide

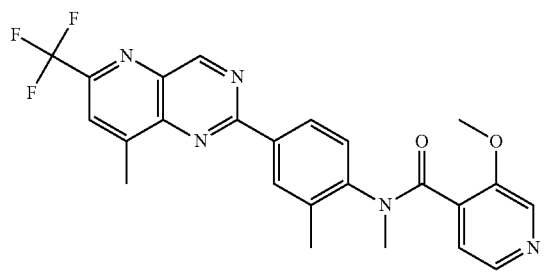 [SMILES: COc1cnccc1C(=O)N(C)c1ccc(-c2ncc3nc(C(F)(F)F)cc(C)c3n2)cc1C]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 3-methoxy-N-methyl-N-(2-methyl-4-(4,4,5,5-tetramethyl-1,3,2-dioxaborolan-2-yl)phenyl) isonicotinamide provided crude product. Purification by Prep-TLC (CH$_2$Cl$_2$/MeOH=20:1) afforded the title compound as a white solid in 34.91% yield. LC-MS: (ES, m/z): [M+H]$^+$ 468; $^1$H-NMR: (300 MHz, DMSO, ppm): δ2.41 (s, 3H), 2.90-2.96 (d, 3H), 3.10 (s, 3H), 3.81 (s, 3H), 7.29-7.39 (m, 2H), 8.07-8.09 (d, 1H), 8.21 (s, 1H) 8.25 (d, 1H), 8.37 (s, 1H), 8.42 (s, 1H), 9.83 (s, 1H).

Step 1: N-(4-bromo-2-methylphenyl)-3-methoxy-N-methylpyridine-4-carboxamide

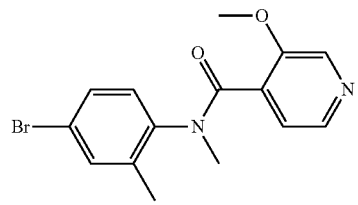 [SMILES: COc1cnccc1C(=O)N(C)c1ccc(Br)cc1C]

Proceeding analogously as described in Example 161, Step 1 but substituting N-(4-bromo-2-methylphenyl)-2-methylpyridine-4-carboxamide with N-(4-bromo-2-methylphenyl)-3-methoxypyridine-4-carboxamide (1000 mg, 3.11 mmol, 1 equiv.) in DMF (10.0 mL) was added NaH (124.5 mg, 3.11 mmol, 1.000 equiv., 60%) in portions at 0° C. with stirring for 30 min under nitrogen atmosphere. Then MeI (441.9 mg, 3.11 mmol, 1 equiv.) was added dropwise at 0° C. The resulting mixture was stirred for 1 h at room temperature under nitrogen atmosphere. The reaction was quenched by the addition of 10 mL of NH$_4$Cl (aq.) at 0° C. The resulting mixture was extracted with EA. The combined organic layers were washed with water. After filtration, the filtrate was concentrated under reduced pressure to afford (1.01 g, 96.77%) as a white solid.

Step 2: 3-methoxy-N-methyl-N-[2-methyl-4-(tetramethyl-1,3,2-dioxaborolan-2-yl)phenyl]pyridine-4-carboxamide Proceeding analogously as described in Example 161, Step 2 but substituting N-(4-bromo-2-methylphenyl)-N,2-dimethylpyridine-4-carboxamide with N-(4-bromo-2-methylphenyl)-3-methoxy-N-methylpyridine-4-carboxamide provided crude product. Purification by silica gel column chromatography by eluting with PE/EA (10:1) afforded the title compound as a white solid in 76.07% yield.

Example 184: 3-methoxy-N-(2-methyl-4-(8-methyl-6-(trifluoromethyl)pyrido[3,2-d]pyrimidin-2-yl)phenyl)isonicotinamide

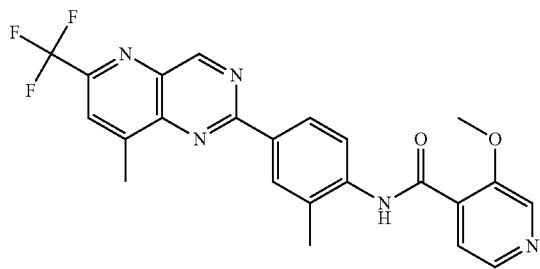 [SMILES: COc1cnccc1C(=O)Nc1ccc(-c2ncc3nc(C(F)(F)F)cc(C)c3n2)cc1C]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 3-methoxy-N-[2-methyl-4-(tetramethyl-1,3,2-dioxaborolan-2-yl)phenyl]pyridine-4-carboxamide provided crude product. Purification by Prep-TLC (CH$_2$Cl$_2$/MeOH=20:1) gave the title compound in 27.09%. LC-MS: (ES, m/z): [M+H]$^+$ 454; $^1$H-NMR: (300 MHz, DMSO, ppm): δ 2.95 (s, 3H), 4.14 (s, 3H), 7.78-7.89 (s, 1H), 8.21-8.23 (s, 1H), 8.38 (s, 1H), 8.42-8.43 (d, 1H), 8.51-8.56 (m, 1H), 8.69 (s, 1H), 9.86 (s, 1H), 10.08 (s, 1H)

Step 1: N-(4-bromo-2-methylphenyl)-3-methoxypyridine-4-carboxamide

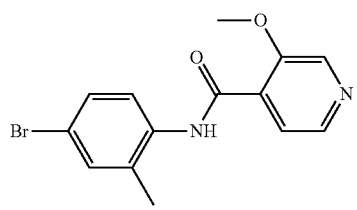 [SMILES: COc1cnccc1C(=O)Nc1ccc(Br)cc1C]

Proceeding analogously as described in Example 160, Step 8 but substituting 3-methylpyridine-4-carboxylic acid with 3-methoxypyridine-4-carboxylic acid provided the title compound as a solid in 90.59% yield.

Step 2: 3-methoxy-N-[2-methyl-4-(tetramethyl-1,3,2-dioxaborolan-2-yl)phenyl]pyridine-4-carboxamide

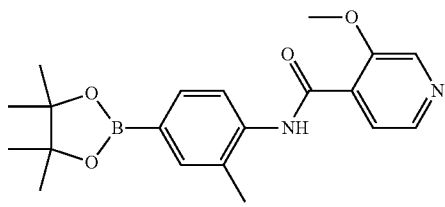 [SMILES: COc1cnccc1C(=O)Nc1ccc(B2OC(C)(C)C(C)(C)O2)cc1C]

Proceeding analogously as described in Example 161, Step 2 but substituting N-(4-bromo-2-methylphenyl)-N,2-dimethylpyridine-4-carboxamide with N-(4-bromo-2-methylphenyl)-3-methoxypyridine-4-carboxamide provided crude product. Purification by silica gel column chromatography by eluting with PE/EtOAc (10:1) provided the title compound as a white solid in 81.99% yield.

Example 185: N-(2-fluoro-4-(8-methyl-6-(trifluoromethyl)pyrido[3,2-d]pyrimidin-2-yl)-phenyl)morpholine-4-carboxamide

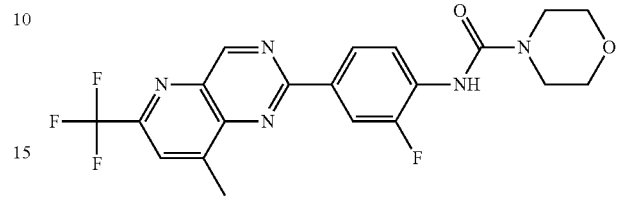

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-[2-fluoro-4-(tetramethyl-1,3,2-dioxaborolan-2-yl)phenyl]morpholine-4-carboxamide provided crude product. Purification by Prep-TLC with ethyl acetate/petroleum ether (1:2) provided the title compound as a yellow solid in 36.45% yield.

Step 1:
N-(4-bromo-2-fluorophenyl)morpholine-4-carboxamide

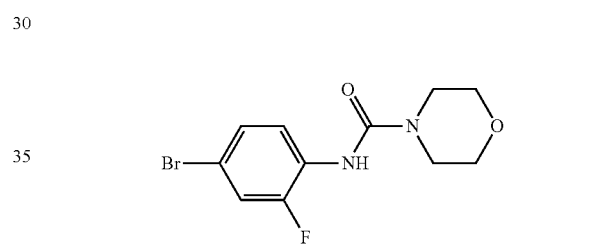

Into a 100-mL 3-necked round-bottom flask purged and maintained with an inert atmosphere of nitrogen, was placed 4-bromo-2-fluoroaniline (3 g, 15.79 mmol, 1 equiv.), DCM (30 mL), TRIPHOS (1.5 g, 5.21 mmol, 0.33 equiv.), Et$_3$N (4.8 g, 47.37 mmol, 3 equiv.), and morpholine (1.4 g, 15.79 mmol, 1 equiv.). The resulting solution was stirred overnight at room temperature. The crude product was purified by re-crystallization from EA/PE (1:5) to give the title compound as a white solid in 53.70% yield.

Step 2: N-[2-fluoro-4-(tetramethyl-1,3,2-dioxaborolan-2-yl)phenyl]morpholine-4-carboxamide

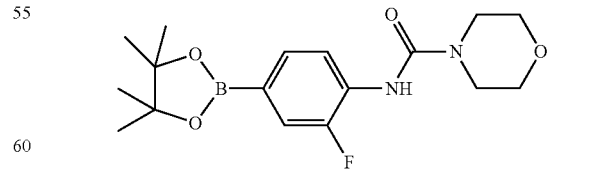

Proceeding analogously as described in Example 161, Step 2 but substituting N-(4-bromo-2-methylphenyl)-N,2-dimethylpyridine-4-carboxamide with N-(4-bromo-2-fluorophenyl)morpholine-4-carboxamide gave crude product. Purification by column chromatograph with ethyl acetate/ petroleum ether as eluent, followed by re-crystallization from EA/PE (1:5) provided the title compound as a white solid in 35.37% yield. LC-MS: (ES, m/z): [M+H]+ 436; 1H-NMR: (300 MHz, DMSO, ppm): δ 2.92 (s, 3H), 3.47-3.49 (d, 4H), 3.62-3.63 (d, 4H), 7.81-7.85 (t, 1H), 8.32-8.41 (m, 3H), 8.64 (s, 1H), 9.85 (s, 1H).

Example 186: N-(2-fluoro-4-(8-methyl-6-(trifluoromethyl)pyrido[3,2-d]pyrimidin-2-yl)phenyl)tetrahydro-2H-pyran-4-carboxamide

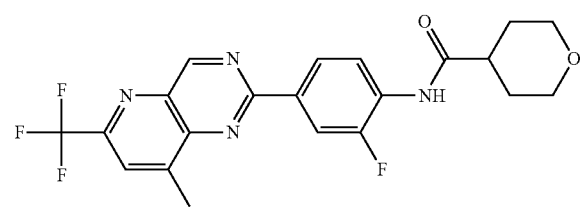 [SMILES: Cc1cc(C(F)(F)F)nc2cnc(-c3ccc(NC(=O)C4CCOCC4)c(F)c3)nc12]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with N-[2-fluoro-4-(tetramethyl-1,3,2-dioxaborolan-2-yl)phenyl]oxane-4-carboxamide gave crude product. Purification by Prep-HPLC (2 #SHIMADZU (HPLC-01)): Column, Xselect CSH OBD Column 30*150 mm 5 um, n; mobile phase, water (0.1% FA) and ACN (59% Phase B up to 69% in 7 min); Detector, UV) provided the title compound as a white solid in 6.50% yield. LC-MS: (ES, m/z): [M+H]+ 435; 1H-NMR: (300 MHz, DMSO, ppm): δ 1.69-1.73 (m, 4H), 2.87 (s, 1H), 2.92 (s, 3H), 3.33-3.40 (m, 2H), 3.91-3.94 (t, 2H), 8.27-8.31 (t, 1H), 8.35-8.36 (d, 2H), 8.38-8.44 (m, 1H), 9.86 (s, 1H), 10.00 (s, 1H).

Step 1: N-(4-bromo-2-fluorophenyl)oxane-4-carboxamide

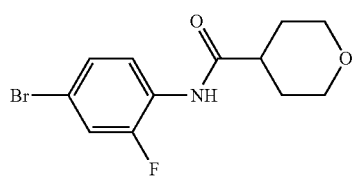 [SMILES: O=C(Nc1ccc(Br)cc1F)C1CCOCC1]

Proceeding analogously as described in Example 160, Step 8 but substituting 4-bromo-2-methylaniline with 4-bromo-2-fluoroaniline and 3-methylpyridine-4-carboxylic acid with oxane-4-carboxylic acid gave crude product. Purification by column chromatograph with ethyl acetate/petroleum ether (1:20) gave the title compound as a white solid in 48.21% yield.

Step 2: N-(2-fluoro-4-(4,4,5,5-tetramethyl-1,3,2-dioxaborolan-2-yl)phenyl)tetrahydro-2H-pyran-4-carboxamide

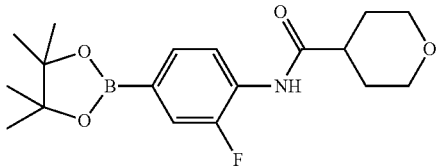 [SMILES: CC1(C)OB(c2ccc(NC(=O)C3CCOCC3)c(F)c2)OC1(C)C]

Proceeding analogously as described in Example 161, Step 2 but substituting N-(4-bromo-2-methylphenyl)-N,2-dimethylpyridine-4-carboxamide with N-(4-bromo-2-fluorophenyl)oxane-4-carboxamide provided crude product. Purification by column chromatography with ethyl acetate/petroleum ether (1:5), followed by re-crystallization from EA/PE (1:5) gave the title compound as a white solid in 48.15% yield.

Example 187: N,1-dimethyl-N-(3-methyl-4-(6-(trifluoromethyl)pyrido[3,2-d]pyrimidin-2-yl)phenyl)-1H-pyrazole-5-carboxamide

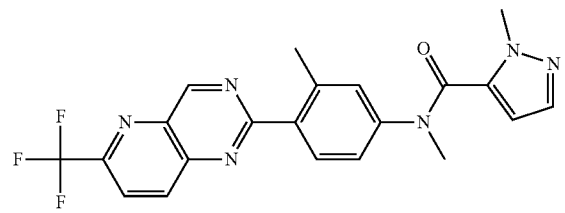 [SMILES: Cc1cc(N(C)C(=O)c2ccnn2C)ccc1-c1ncc2nc(C(F)(F)F)ccc2n1]

Proceeding analogously as described in Example 161, Step 1 but substituting N-(4-bromo-2-methylphenyl)-2-methylpyridine-4-carboxamide with 1-methyl-N-[3-methyl-4-[6-(trifluoromethyl)pyrido[3,2-d]pyrimidin-2-yl]phenyl]-1H-pyrazole-5-carboxamide provided crude product. Purification by prep-TLC with ethyl acetate/petroleum ether (1:2) as eluent gave the title compound as a white solid in 29.36% yield. LC-MS: (ES, m/z): [M+H]+ 427; 1H-NMR: (300 MHz, CDCl3, ppm): δ 2.01 (s, 1H), 2.66 (s, 3H), 3.51 (s, 3H), 4.15 (s, 3H), 5.70 (d, 1H), 7.10-7.12 (t, 2H), 7.17-7.18 (d, 1H), 8.07-8.10 (m, 1H), 8.15-8.18 (d, 1H), 8.57-8.60 (d, 1H), 9.84 (d, 1H).

Step 1: 2-(2-methyl-4-nitrophenyl)-6-(trifluoromethyl)pyrido[3,2-d]pyrimidine

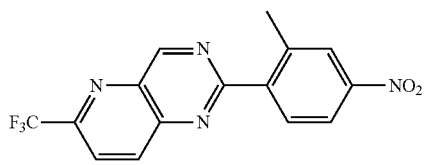 [SMILES: Cc1cc([N+](=O)[O-])ccc1-c1ncc2nc(C(F)(F)F)ccc2n1]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 4,4,5,5-tetramethyl-2-(2-methyl-4-nitrophenyl)-

1,3,2-dioxaborolane gave crude product. Purification by Prep-TLC (PE/EA=5:1) gave the title compound as a yellow solid in 20.96% yield.

Step 2: 3-methyl-4-(6-(trifluoromethyl)pyrido[3,2-d]pyrimidin-2-yl)aniline

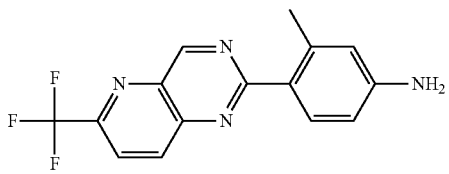 [SMILES: Cc1cc(N)ccc1-c1ncc2nc(C(F)(F)F)ccc2n1]

Into an 8-mL sealed tube, was placed 2-(2-methyl-4-nitrophenyl)-6-(trifluoro-methyl)pyrido[3,2-d]pyrimidine (180 mg, 0.54 mmol, 1 equiv.), Fe (90.2 mg, 1.62 mmol, 2.999 equiv.), NH₄Cl (144.0 mg, 2.69 mmol, 5 equiv.), and H₂O (1 mL, 55.51 mmol, 103.077 equiv.). The resulting solution was stirred for 2 h at 80° C. and then extracted with ethyl acetate. The residue was applied onto a prep-TLC and eluted with ethyl acetate/petroleum ether (1:3) to give the tile compound as a yellow solid in 67.13% yield.

Step 3: 1-methyl-N-[3-methyl-4-[6-(trifluoromethyl)pyrido[3,2-d]pyrimidin-2-yl]phenyl]-1H-pyrazole-5-carboxamide

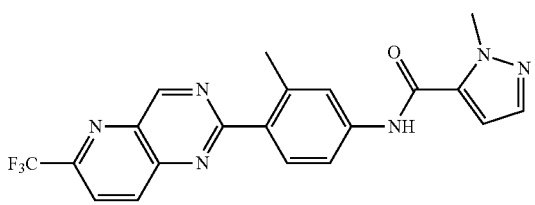 [SMILES: Cc1cc(NC(=O)c2ccnn2C)ccc1-c1ncc2nc(C(F)(F)F)ccc2n1]

Proceeding analogously as described in Example 160, Step 8 but substituting 4-bromo-2-methylaniline with 3-methyl-4-(6-(trifluoromethyl)pyrido[3,2-d]pyrimidin-2-yl)aniline (70 mg, 0.23 mmol, 1 equiv.) and 3-methylpyridine-4-carboxylic acid with 1-methyl-1H-pyrazole-5-carboxylic provided crude product. Purification by prep-TLC with ethyl acetate/petroleum ether (1:2) provided the title compound as a white solid in 59.03% yield.

Example 188: N-(2,5-dimethyl-4-(6-(trifluoromethyl)pyrido[3,2-d]pyrimidin-2-yl)phenyl)-N,1-dimethyl-1H-pyrazole-5-carboxamide

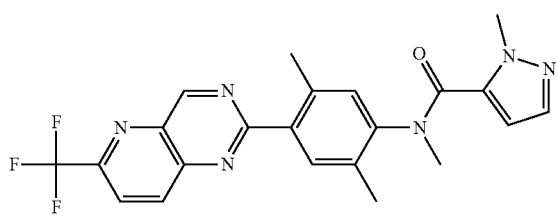 [SMILES: Cc1cc(N(C)C(=O)c2ccnn2C)c(C)cc1-c1ncc2nc(C(F)(F)F)ccc2n1]

Proceeding analogously as described in Example 161, Step 1 but substituting N-(4-bromo-2-methylphenyl)-2-methylpyridine-4-carboxamide with N-[2,5-dimethyl-4-[6-(trifluoromethyl)pyrido[3,2-d]pyrimidin-2-yl]phenyl]-1-methyl-1H-pyrazole-5-carboxamide provide crude product. Purification by Prep. TLC with ethyl acetate/petroleum ether (1/2) gave the title compound as a yellow solid in 40.95% yield. LC-MS: (ES, m/z): [M+H]⁺ 441; ¹H-NMR: (400 MHz, DMSO, ppm): δ2.17 (s, 3H), δ2.57 (s, 3H), δ3.33 (s, 3H), δ4.01 (s, 3H), δ5.57-5.58 (d, 1H), δ7.19-7.20 (d, 1H), δ7.37 (s, 1H), δ7.93 (s, 1H), δ8.48-8.50 (d, 1H), δ8.80-8.82 (d, 1H), δ9.95 (s, 1H).

Example 189: N-(2,5-dimethyl-4-(6-(trifluoromethyl)pyrido[3,2-d]pyrimidin-2-yl)phenyl)-1-methyl-1H-pyrazole-5-carboxamide

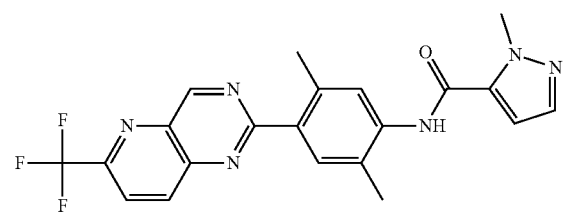 [SMILES: Cc1cc(-c2ncc3nc(C(F)(F)F)ccc3n2)c(C)cc1NC(=O)c1ccnn1C]

Proceeding analogously as described in Example 160, Step 8 but substituting 4-bromo-2-methylaniline with 2,5-dimethyl-4-[6-(trifluoromethyl)pyrido[3,2-d]pyrimidin-2-yl]aniline (70 mg, 0.23 mmol, 1 equiv.) and 3-methylpyridine-4-carboxylic acid with 1-methyl-1H-pyrazole-5-carboxylic acid gave crude product. Purification by Prep. TLC with ethyl acetate/petroleum ether (1/2) gave the title compound as a yellow solid in 93.31% yield. LC-MS: (ES, m/z): [M+H]⁺ 427; ¹H-NMR: (400 MHz, DMSO, ppm): δ 2.32 (s, 3H), 2.64 (s, 3H), 4.11 (s, 3H), 7.10-7.11 (d, 1H), 7.43 (s, 1H), 7.55-7.56 (d, 1H), 8.02 (s, 1H), 8.47-8.49 (d, 1H), 8.80-8.82 (d, 1H), 9.96-9.98 (d, 2H).

Example 190: N-(2,3-dimethyl-4-(6-(trifluoromethyl)pyrido[3,2-d]pyrimidin-2-yl)phenyl)-1-methyl-1H-pyrazole-5-carboxamide

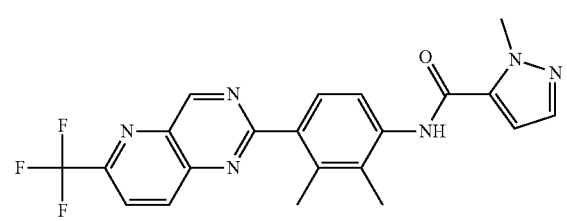 [SMILES: Cc1c(NC(=O)c2ccnn2C)ccc(-c2ncc3nc(C(F)(F)F)ccc3n2)c1C]

To a stirred solution of 2,3-dimethyl-4-[6-(trifluoromethyl)pyrido[3,2-d]pyrimidin-2-yl]aniline (120 mg, 0.38 mmol, 1 equiv.) and 1-methyl-1H-pyrazole-5-carboxylic acid (52.3 mg, 0.41 mmol, 1.1 equiv.) in DMF (1.2 mL) were added DIEA (97.5 mg, 0.75 mmol, 2.00 equiv.) and HATU (215.0 mg, 0.57 mmol, 1.5 equiv.) at room temperature. The resulting mixture was stirred for overnight at 40° C. under nitrogen atmosphere and then quenched with water at room temperature. The resulting mixture was extracted with EA and the combined organic layer were washed with NaCl (aq.). After concentrating the organic layer, the residue was purified by Prep. TLC with ethyl acetate/hexane. The resulting material was further purified by HPLC under following conditions: Column, $C_{18}$ silica gel; mobile phase, MeCN: $NH_4HCO_3$ (aq.)=0% increasing to MeCN:$NH_4HCO_3$ (aq.)=50% within 20 min; Detector, 254 nm to give the title compound as a yellow solid in 34.84% yield. LC-MS: (ES, m/z): [M+H]+ 427; $^1$H-NMR: (300 MHz, CDCL$_3$, ppm): δ 2.35 (s, 3H), 2.54 (s, 3H), 4.26 (s, 3H), 6.70-6.71 (d, 1H), 7.54-7.55 (d, 1H), 7.67 (s, 1H), 7.80-7.82 (d, 1H), 7.87-7.92 (m, 1H), 8.15-8.18 (d, 1H), 8.59-8.62 (d, 1H), 9.86 (s, 1H).

Example 191: N-(2,3-dimethyl-4-(6-(trifluoromethyl)pyrido[3,2-d]pyrimidin-2-yl)phenyl)-N,1-dimethyl-1H-pyrazole-5-carboxamide

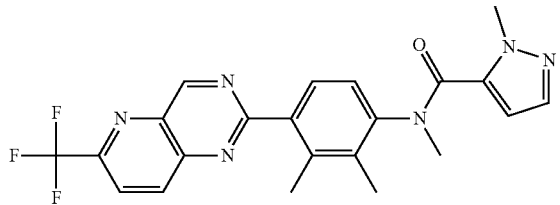 [SMILES: Cc1c(-c2ncc3nc(C(F)(F)F)ccc3n2)ccc(N(C)C(=O)c2ccnn2C)c1C]

Proceeding analogously as described in Example 161, Step 1 but substituting N-(4-bromo-2-methylphenyl)-2-methylpyridine-4-carboxamide with N-(2,3-dimethyl-4-(6-(trifluoromethyl)pyrido[3,2-d]pyrimidin-2-yl)phenyl)-1-methyl-1H-pyrazole-5-carboxamide provided crude product. Purification by Prep.TLC (hexane/EA=5:1) gave the title compound as a white solid in 56.92% yield. LC-MS: (ES, m/z): [M+H]+ 441; $^1$H-NMR: (300 MHz, DMSO, ppm): δ2.20 (s, 3H), 2.37 (s, 3H), 3.31 (s, 3H), 4.00 (s, 3H), 5.56-5.57 (d, 1H), 7.19-7.20 (d, 1H), 7.28-7.31 (d, 1H), 7.62-7.64 (d, 1H), 8.49-8.52 (d, 1H), 8.79-8.82 (d, 1H), 9.96 (d, 1H).

Example 192: 1-(2-hydroxypropyl)-N-methyl-N-(2-methyl-4-(8-methyl-6-(trifluoromethyl)pyrido[3,2-d]pyrimidin-2-yl)phenyl)-1H-pyrazole-5-carboxamide

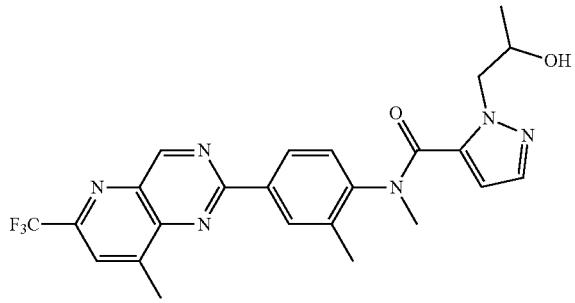 [SMILES: Cc1cc(-c2ncc3nc(C(F)(F)F)cc(C)c3n2)ccc1N(C)C(=O)c1ccnn1CC(C)O]

Proceeding analogously as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1-(2-hydroxypropyl)-N-methyl-N-(2-methyl-4-(4,4,5,5-tetramethyl-1,3,2-dioxaborolan-2-yl)phenyl)-1H-pyrazole-5-carboxamide provided crude product. Purification by Prep.TLC ($CH_2Cl_2$/MeOH=20:1) gave the title compound as a white solid in 24.24% yield. LC-MS: (ES, m/z): [M+H]+ 485; $^1$H-NMR: (400 MHz, DMSO, ppm): δ1.02-1.12 (d, 3H), 2.35 (s, 1H), 2.42 (s, 2H), 2.92 (s, 3H), 3.31 (s, 2H), 3.36 (s, 1H), 4.01-4.16 (m, 2H), 4.17-4.21 (m, 1H), 4.37-4.53 (m, 1H), 4.96-5.01 (m, 1H), 5.52-5.54 (m, 1H), 7.17 (s, 1H), 7.43-7.59 (m, 1H), 8.35-8.43 (m, 2H), 8.54-8.57 (d, 2H), 9.88 (s, 1H)

Step 1: N-methyl-N-(2-methyl-4-(4,4,5,5-tetramethyl-1,3,2-dioxaborolan-2-yl)phenyl)-1-(2-oxopropyl)-1H-pyrazole-5-carboxamide

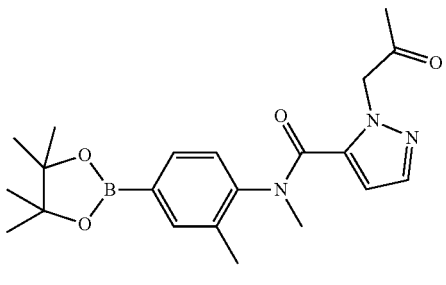 [SMILES: CC(=O)Cn1nccc1C(=O)N(C)c1ccc(B2OC(C)(C)C(C)(C)O2)cc1C]

Into an 8 mL sealed tube were added N-(4-bromo-2-methylphenyl)-N-methyl-1-(2-oxopropyl)-1H-pyrazole-5-carboxamide (200 mg, 0.57 mmol, 1 equiv.), XPhos Pd G$_3$ (48.3 mg, 0.06 mmol, 0.1 equiv.), KOAc (112.1 mg, 1.14 mmol, 2 equiv.), $B_2Pin_2$ (159.6 mg, 0.63 mmol, 1.1 equiv.) and 1,4-dioxane (2 mL) under nitrogen atmosphere. The resulting mixture was stirred overnight at 80° C. under nitrogen atmosphere and then concentrated under reduced pressure. The residue was purified by silica gel column (PE/EA=2:1) to afford the title compound as a yellow solid in 88.15% yield.

Step 2: 1-(2-hydroxypropyl)-N-methyl-N-(2-methyl-4-(4,4,5,5-tetramethyl-1,3,2-dioxaborolan-2-yl)phenyl)-1H-pyrazole-5-carboxamide

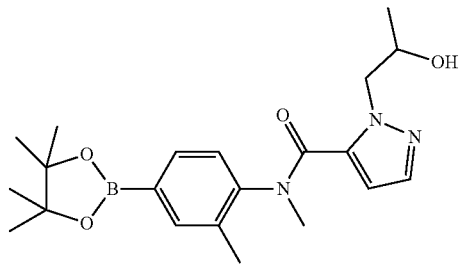 [SMILES: Cc1cc(B2OC(C)(C)C(C)(C)O2)ccc1N(C)C(=O)c1ccnn1CC(C)O]

To a stirred mixture of N-methyl-N-(2-methyl-4-(4,4,5,5-tetramethyl-1,3,2-dioxaborolan-2-yl)phenyl)-1-(2-oxopropyl)-1H-pyrazole-5-carboxamide (200 mg, 0.50 mmol, 1 equiv.) in MeOH (2 mL) was added NaBH$_4$ (19.0 mg, 0.50 mmol, 1.00 equiv.) and the resulting mixture was stirred for 2 h at room temperature. The reaction mixture was quenched with NH$_4$Cl (aq.) and extracted with EA. The combined organic layers were concentrated under reduced pressure and the residue was purified by silica gel column (PE/EA=2: 1) to afford the title compound as a white solid in 59.70% yield.

Example 193: 1-(2-hydroxypropyl)-N-(2-methyl-4-(6-(trifluoromethyl)pyrido[3,2-d]pyrimidin-2-yl)phenyl)-1H-pyrazole-5-carboxamide

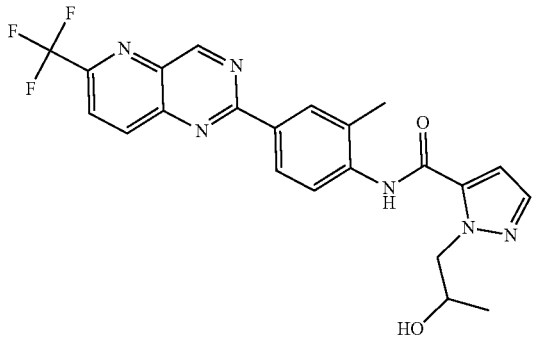 [SMILES: Cc1cc(-c2ncc3nc(C(F)(F)F)ccc3n2)ccc1NC(=O)c1ccnn1CC(C)O]

Into a 8-mL sealed tube purged and maintained with an inert atmosphere of nitrogen, was placed 1-(2-hydroxypropyl)-N-[2-methyl-4-(4,4,5,5-tetramethyl-1,3,2-dioxaborolan-2-yl)phenyl]-1H-pyrazole-5-carboxamide (100 mg, 0.26 mmol, 1 equiv.), 2-chloro-6-(trifluoromethyl)pyrido[3,2-d]pyrimidine (60.6 mg, 0.26 mmol, 1 equiv.), $K_2CO_3$ (107.6 mg, 0.78 mmol, 3 equiv.), t-BuOH (0.9 mL), $H_2O$ (0.1 mL), and $AmphosPdCl_2$ (55.0 mg, 0.08 mmol, 0.3 equiv.). The resulting solution was stirred for 12 min at 80° C. and then quenched with water. The resulting solution was extracted with ethyl acetate and after removal of the organics, the residue was applied onto Prep-TLC with ethyl acetate/petroleum ether (1:3) to give the title compound as a yellow solid in 19.92% yield. LC-MS: (ES, m/z): $[M+H]^+$ 457; $^1$H-NMR: (300 MHz, DMSO, ppm): δ1.01-1.03 (d, 3H), 1.23 (s, 1H), 2.80-2.88 (d, 3H), 2.40 (s, 3H), 3.98-4.04 (m, 1H), 4.39-4.40 (m, 1H), 4.42-4.44 (m, 1H), 4.90-4.94 (d, 1H), 7.04-7.05 (d, 1H), 7.57-7.59 (d, 1H), 7.66-7.68 (d, 1H), 8.45-8.49 (d, 1H), 8.54 (s, 1H), 8.78-8.81 (d, 1H), 9.81 (s, 1H), 10.08 (s, 1H).

Step 1: methyl 1-(2-oxopropyl)-1H-pyrazole-5-carboxylate

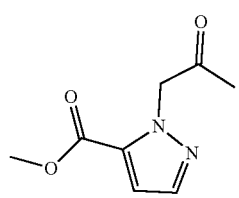

Into a 250-mL 3-necked round-bottom flask purged and maintained with an inert atmosphere of nitrogen, was placed methyl 1H-pyrazole-5-carboxylate (10 g, 79.29 mmol, 1 equiv.), 1-chloropropan-2-one (8.1 g, 87.22 mmol, 1.1 equiv.), $K_2CO_3$ (32.9 g, 237.88 mmol, 3 equiv.), and ACN (100 mL). The resulting solution was stirred for 12 h at 80° C. and then concentrated. After adding water, the resulting solution was extracted with ethyl acetate. The residue was applied onto a silica gel column and eluted with ethyl acetate/petroleum ether (1:20) to give the title compound as a yellow solid in 22.84% yield.

Step 2: 1-(2-oxopropyl)-1H-pyrazole-5-carboxylic acid

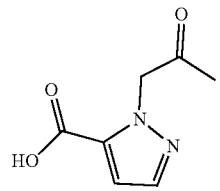

Into a 100-mL 3-necked round-bottom flask purged and maintained with an inert atmosphere of nitrogen, was placed methyl 1-(2-oxopropyl)-1H-pyrazole-5-carboxylate (3.3 g, 18.11 mmol, 1 equiv.), THF (33 mL), $LiOH \cdot H_2O$ (0.8 g, 18.11 mmol, 1 equiv.), and $H_2O$ (20 mL). The resulting solution was stirred for 1 h at 25° C. and the pH of the solution was adjusted to 6 with HCl. The resulting mixture was concentrated and the residue was applied onto a silica gel column and eluted with dichloromethane/methanol (20:1) to give the title compound as a yellow solid in 91.93% yield.

Step 3: N-(4-bromo-2-methylphenyl)-1-(2-oxopropyl)-1H-pyrazole-5-carboxamide

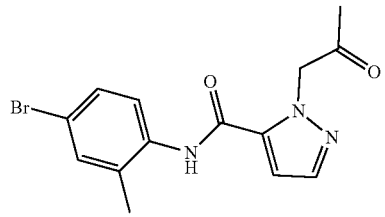 [SMILES: CC(=O)Cn1nccc1C(=O)Nc1ccc(Br)cc1C]

Proceeding analogously as described in Example 160, Step 8 but substituting 2-methylpyridine-4-carboxylic acid with 1-(2-oxopropyl)-1H-pyrazole-5-carboxylic acid provided crude product. The crude product was applied onto a silica gel column and eluted with ethyl acetate/petroleum ether (1:20) to give the title compound as a yellow solid in 17.86% yield.

Step 4: N-(4-bromo-2-methylphenyl)-1-(2-hydroxypropyl)-1H-pyrazole-5-carboxamide

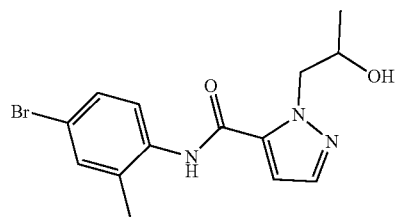 [SMILES: Cc1cc(Br)ccc1NC(=O)c1ccnn1CC(C)O]

Proceeding analogously as described in Example 192, Step 2 but substituting N-methyl-N-(2-methyl-4-(4,4,5,5- tetramethyl-1,3,2-dioxaborolan-2-yl)phenyl)-1-(2-oxopropyl)-1H-pyrazole-5-carboxamide with N-(4-bromo-2-methylphenyl)-1-(2-oxopropyl)-1H-pyrazole-5-carboxamide provided crude product. The crude product was applied onto a silica gel column and eluted with CH₂Cl₂ give the title compound as a white solid in 89.46% yield.

Step 5: 1-(2-hydroxypropyl)-N-[2-methyl-4-(4,4,5,5-tetramethyl-1,3,2-dioxaborolan-2-yl)phenyl]-1H-pyrazole-5-carboxamide

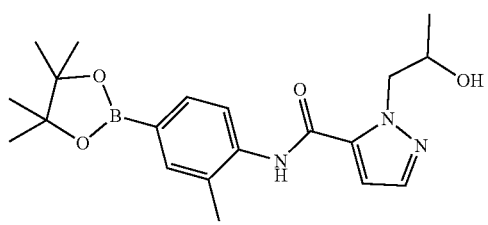 [SMILES: Cc1cc(B2OC(C)(C)C(C)(C)O2)ccc1NC(=O)c1ccnn1CC(C)O]

Proceeding as described in Example 161, Step 2 but substituting N-(4-bromo-2-methylphenyl)-N,2-dimethylpyridine-4-carboxamide with N-(4-bromo-2-methylphenyl)-1-(2-hydroxypropyl)-1H-pyrazole-5-carboxamide (0.9 g, 2.66 mmol, 1 equiv.) provided crude product. The crude product was applied onto a silica gel column and eluted with ethyl acetate/petroleum ether (1:10) to give the title compound as a yellow solid in 78.03% Yield.

Example 194: 2-[5-[methyl([2-methyl-4-[8-methyl-6-(trifluoromethyl)pyrido[3,2-d]pyrimidin-2-yl]phenyl])carbamoyl]-1H-pyrazol-1-yl]ethyl disodium phosphate

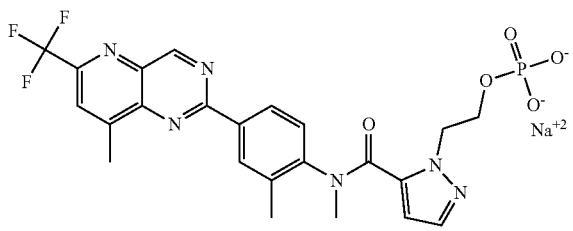

Into a 25 mL round-bottom flask were added (2-[5-[methyl([2-methyl-4-[8-methyl-6-(trifluoromethyl)pyrido[3,2-d]pyrimidin-2-yl]phenyl])carbamoyl]-1H-pyrazol-1-yl]ethoxy)phosphonic acid (11.7 mg, 0.02 mmol, 1 equiv.) and NaOH (0.04 mL, 1M, 2.00 equiv.). After lyophilization, the title compound was obtained in 98.94% yield as a yellow solid. LC-MS: (ES, m/z): 551; ¹H-NMR: (300 MHz, D₂O, ppm): δ 2.24-2.30 (m, 3H), 2.60-2.70 (m, 3H), 3.3.37-3.42 (m, 3H), 3.95-4.02 (m, 2H), 4.40-4.53 (m, 2H), 5.76-5.77 (d, 1H), 6.78 (s, 1H), 7.18 (s, 1H), 7.35-7.38 (m, 1H), 7.86-8.22 (m, 3H), 8.25-9.39 (m, 1H).

Step 1: (2-[5-[methyl([2-methyl-4-[8-methyl-6-(trifluoromethyl)pyrido[3,2-d]pyrimidin-2-yl]phenyl])carbamoyl]-1H-pyrazol-1-yl]ethoxy)phosphonic acid

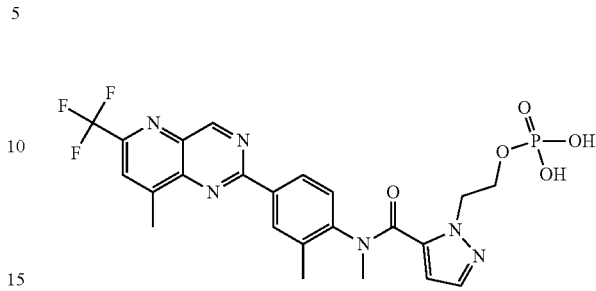

Into an 8 mL vial were added POCl₃ (163.0 mg, 1.06 mmol, 5 equiv.) and Et₃N (322.6 mg, 3.19 mmol, 15 equiv.) in CHCl₃ (2 mL). The resulting mixture was stirred for 10 min and 1-(2-hydroxyethyl)-N-methyl-N-[2-methyl-4-[8-methyl-6-(trifluoromethyl)pyrido-[3,2-d]pyrimidin-2-yl]phenyl]-1H-pyrazole-5-carboxamide (100 mg, 0.21 mmol, 1 equiv.) was added. The resulting mixture was stirred for 2 h at 0° C. and then with water. The resulting mixture was extracted with EtOAc and the combined organic layers were concentrated under reduced pressure. The crude product was purified by Prep-HPLC (Column: SunFire C18 OBD Prep Column, 100*5 um, 19 mm×250 mm; Mobile Phase A:Water (0.05% TFA), Mobile Phase B: ACN; Flow rate: 25 mL/min; Gradient: 48% B to 58% B in 8 min; 254/220 nm; Rt: 6.68 min) to afford the title compound as a yellow solid in 10.00% yield.

Example 195: 1-(2-amino-2-oxoethyl)-5-(methyl(2-methyl-4-(8-methyl-6-(trifluoro-methyl)pyrido[3,2-d]pyrimidin-2-yl)phenyl)carbamoyl)-1H-pyrazole-3-carboxylic acid

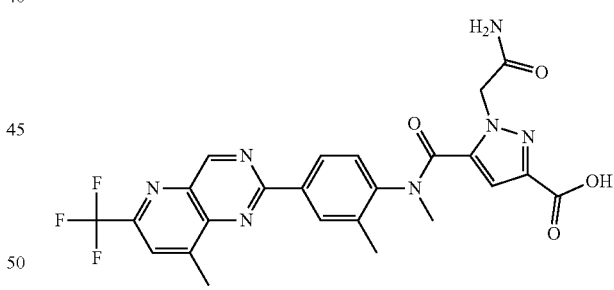

Proceeding analogously as described in Example 195, Step 4 but substituting 1-(cyanomethyl)-1H-pyrazole-3,5-dicarboxylate with methyl 1-(cyanomethyl)-5-(methyl(2-methyl-4-(8-methyl-6-(trifluoromethyl)pyrido[3,2-d]pyrimidin-2-yl)phenyl)carbamoyl)-1H-pyrazole-3-carboxylate provided crude product. The crude product was purified by Prep-TLC (CH₂Cl₂/MeOH 30/1), followed by purification by reverse flash chromatography column, C18 silica gel; mobile phase, MeCN in water, 0% to 50% gradient in 30 min; detector, UV 254 nm) to give the title compound as a white solid in 3.76% yield. LC-MS: (ES, m/z): [M+H]⁺ 528; ¹H-NMR: (400 MHz, DMSO, ppm): (400 MHz, DMSO, ppm): δ 2.40 (s, 3H), 2.94 (s, 3H), 3.26 (s, 1H), 5.13-5.19 (m, 2H), 5.64 (s, 1H), 7.22-7.28 (m, 1H), 7.59-7.66 (m, 2H), 8.38 (s, 1H), 8.43-8.45 (d, 1H), 8.57 (s, 1H), 9.89 (s, 1H).

Step 1: tert-butyl (4-bromo-2-methylphenyl)(methyl)carbamate

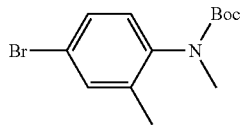

Proceeding analogously as described in Example 165, Step 2 but substituting N-(4-bromo-2-fluorophenyl)-2-methylisonicotinamide with tert-butyl N-(4-bromo-2-methylphenyl)carbamate (28 g, 97.85 mmol, 1.00 equiv.) provide crude product. The crude product was applied onto a silica gel column and eluted with ethyl acetate/petroleum ether (1/20) to give the title compound as a yellow oil in 92% yield.

Step 2: 4-bromo-N,2-dimethylaniline

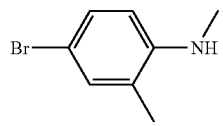

To a stirred solution of tert-butyl (4-bromo-2-methylphenyl)(methyl)carbamate (7.9 g, 26.32 mmol, 1 equiv.) in 1,4-dioxane was added 1,4-dioxane hydrochloride (40 mL) at room temperature. The resulting mixture was stirred overnight at room temperature under nitrogen atmosphere. The residue was basified to pH 8 with NaOH (aq.) and the resulting mixture was extracted with EtOAc. The combined organic layers were concentrated under reduced pressure and the residue was purified by silica gel column chromatography by eluting with PE/EtOAc (40/1) to give the title compound as a white solid in 98.76% yield.

Step 3: dimethyl 1-(cyanomethyl)-1H-pyrazole-3,5-dicarboxylate

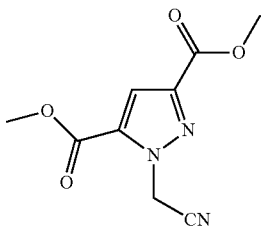

Into a 1-L 3-necked round-bottom flask purged and maintained with an inert atmosphere of nitrogen, was placed 3,5-dimethyl 1H-pyrazole-3,5-dicarboxylate (20 g, 108.61 mmol, 1 equiv.), $K_2CO_3$ (22.5 g, 162.91 mmol, 1.5 equiv.), $CH_3CN$ (400 mL), and 2-bromoacetonitrile (14.3 g, 119.22 mmol, 1.10 equiv.). The resulting solution was stirred for 1 h at 85° C. The solids were filtered out and the filtrate was concentrated. The residue was applied onto a silica gel column and eluted with ethyl acetate/petroleum ether (1/5) to give the title compound as a yellow solid in 86.63% yield.

Step 4: 1-(cyanomethyl)-3-(methoxycarbonyl)-1H-pyrazole-5-carboxylic acid

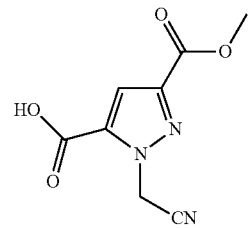

Proceeding analogously as described in Example 232, Step 4 but substituting methyl 1-(2-oxopropyl)-1H-pyrazole-5-carboylate with dimethyl 1-(cyanomethyl)-1H-pyrazole-3,5-dicarboxylate and stirring the reaction mixture overnight provided the title compound as a white solid in 87.78% yield.

Step 5: methyl 5-(chlorocarbonyl)-1-(cyanomethyl)-1H-pyrazole-3-carboxylate

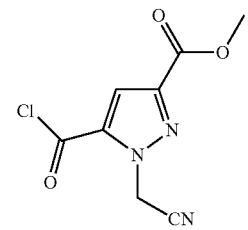

Proceeding analogously as described in Example 166, Step 1 but substituting 2-cyanopyridine-4-carboxylic acid with 1-(cyanomethyl)-3-(methoxycarbonyl)-1H-pyrazole-5-carboxylic acid and stirring the reaction mixture after addition of oxalyl chloride for 3 h at room temperature provided the title compound as a yellow solid in 98.46% yield.

Step 6: methyl 5-((4-bromo-2-methylphenyl)(methyl)carbamoyl)-1-(cyanomethyl)-1H-pyrazole-3-carboxylate

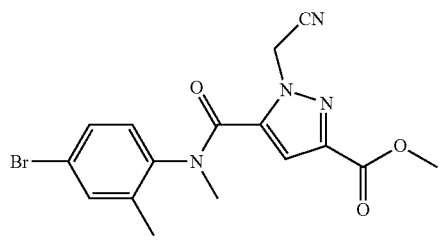 [SMILES: COC(=O)c1cc(C(=O)N(C)c2ccc(Br)cc2C)n(CC#N)n1]

To a stirred solution of 4-bromo-N,2-dimethylaniline (7.5 g, 37.49 mmol, 1 equiv.) and $Et_3N$ (6.76 g, 66.81 mmol, 1.78 equiv.) in DCM (140 mL) were added methyl 5-(chlorocarbonyl)-1-(cyanomethyl)-1H-pyrazole-3-carboxylate (6.67 g, 29.31 mmol, 0.78 equiv.) dissolved in 50 mL of DCM dropwise at 0° C. The resulting mixture was stirred for 2 h at room temperature and then quenched with water. The resulting mixture was extracted with CH₂Cl₂ and the combined organic layers were concentrated under reduced pressure. The residue was purified by silica gel column chromatography, eluting with PE/EtOAc (5/1) to afford the title compound as a white solid in 32.73% yield.

Step 7: methyl 1-(cyanomethyl)-5-(methyl(2-methyl-4-(4,4,5,5-tetramethyl-1,3,2-dioxaborolan-2-yl)phenyl)carbamoyl)-1H-pyrazole-3-carboxylate

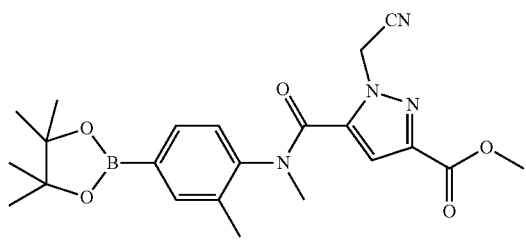

Proceeding as described in Example 161, Step 2 but substituting N-(4-bromo-2-methylphenyl)-N,2-dimethylpyridine-4-carboxamide with methyl 5-((4-bromo-2-methylphenyl)(methyl)carbamoyl)-1-(cyanomethyl)-1H-pyrazole-3-carboxylate provided crude product. The crude product was purified by silica gel column chromatography, eluting with PE/EtOAc (10/1) to afford the title compound in 74.38% yield as a yellow solid.

Step 8: methyl 1-(cyanomethyl)-5-(methyl(2-methyl-4-(8-methyl-6-(trifluoro-methyl)pyrido[3,2-d]pyrimidin-2-yl)phenyl)carbamoyl)-1H-pyrazole-3-carboxylate

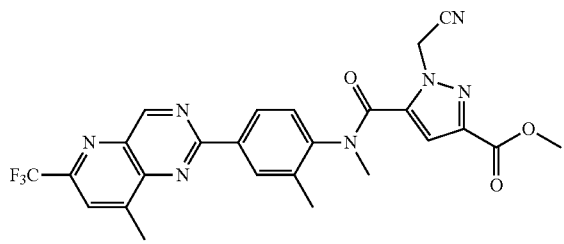 [SMILES: COC(=O)c1cc(C(=O)N(C)c2ccc(-c3ncc4nc(C(F)(F)F)cc(C)c4n3)cc2C)n(CC#N)n1]

Proceeding analogously as described in Example 193 but substituting 1-(2-hydroxypropyl)-N-[2-methyl-4-(4,4,5,5-tetramethyl-1,3,2-dioxaborolan-2-yl)phenyl]-1H-pyrazole-5-carboxamide with methyl 1-(cyanomethyl)-5-(methyl(2-methyl-4-(4,4,5,5-tetramethyl-1,3,2-dioxaborolan-2-yl)phenyl)carbamoyl)-1H-pyrazole-3-carboxylate and 2-chloro-6-(trifluoromethyl)pyrido[3,2-d]pyrimidine with 2-chloro-8-methyl-6-(trifluoromethyl)pyrido[3,2-d]pyrimidine provided crude product. The crude product was purified by Prep-TLC (PE/EtOAc 5/1) to afford the title compound as a yellow solid in 61.49% yield.

Example 196: 1-(2-amino-2-oxoethyl)-N5-methyl-N5-(2-methyl-4-(8-methyl-6-(trifluoromethyl)pyrido[3,2-d]pyrimidin-2-yl)phenyl)-1H-pyrazole-3,5-dicarboxamide

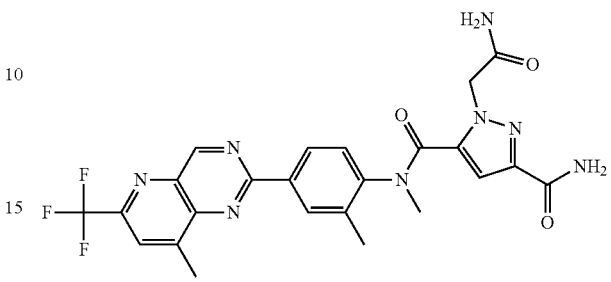

Proceeding analogously as described in Example 167, Step 2 but substituting 4-[(4-bromo-2-methylphenyl)carbamoyl]pyridine-2-carboxylic acid with 1-(carbamoylmethyl)-5-[methyl([2-methyl-4-[8-methyl-6-(trifluoromethyl)pyrido[3,2-d]pyrimidin-2-yl]phenyl])carbamoyl]-1H-pyrazole-3-carboxylic acid and methamine hydrochloride with NH₄Cl provided crude product. The crude product was purified by Prep-TLC (CH₂Cl₂/MeOH 40/1), followed by reverse flash chromatography (column, C18 silica gel; mobile phase, MeCN in water, 0% to 55% gradient in 30 min; detector, UV 254 nm) to provide the title compound as a yellow solid in 25.58% yield. LC-MS: (ES, m/z): [M+H]⁺ 527; ¹H-NMR: (400 MHz, DMSO, ppm): δ2.42 (s, 3H), δ2.94 (s, 3H), δ3.29 (s, 3H), δ5.13-5.25 (m, 2H), δ5.79 (s, 1H), δ7.21 (s, 1H), δ7.32 (s, 1H), δ7.47 (s, 1H), δ7.60-7.62 (d, 1H), δ7.67 (s, 1H), δ8.38 (s, 1H), δ8.43-8.46 (d, 1H), δ8.62 (s, 1H), δ9.88 (s, 1H).

Example 197: 1-(cyanomethyl)-5-(methyl(2-methyl-4-(8-methyl-6-(trifluoromethyl)-pyrido[3,2-d]pyrimidin-2-yl)phenyl)carbamoyl)-1H-pyrazole-3-carboxylic acid

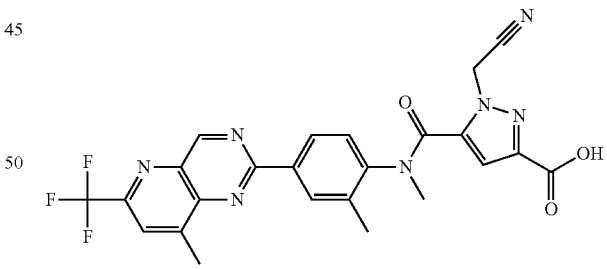

Proceeding analogously as described in Example 195, Step 4 but substituting N-(4-bromo-2-methylphenyl)-1-(2-oxopropyl)-1H-pyrazole-5-carboxamide with methyl 1-(cyanomethyl)-5-[methyl([2-methyl-4-[8-methyl-6-(trifluoromethyl)pyrido[3,2-d]pyrimidin-2-yl]phenyl])carbamoyl]-1H-pyrazole-3-carboxylate provided crude product. The crude product was purified by Prep-TLC (CH₂Cl₂/MeOH 30/1), followed by reverse flash chromatography column, C, 18 silica gel; mobile phase, MeCN in water, 0% to 40% gradient in 25 min; detector, UV 254 nm) to give the title compound as a white solid in 5.76% yield. LC-MS: (ES, m/z): [M+H]⁺510; ¹H-NMR: (400 MHz, DMSO, ppm): δ

9.75 (s, 1H), 8.72 (s, 1H), 8.63 (d, 1H), 8.20 (s, 1H), 6.01 (s, 1H), 5.68 (q, 2H), 3.47 (s, 3H), 3.00 (s, 3H), 2.42 (s, 3H)

Example 198: 1-(cyanomethyl)-N5-methyl-N5-(2-methyl-4-(8-methyl-6-(trifluoro-methyl)pyrido[3,2-d]pyrimidin-2-yl)phenyl)-1H-pyrazole-3,5-dicarboxamide

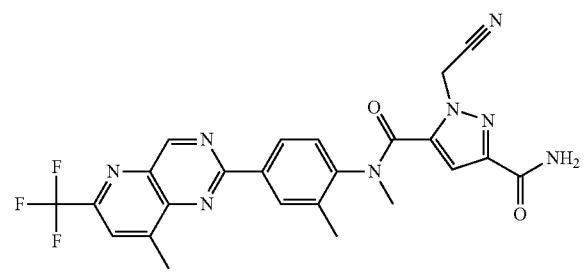 [SMILES: Cc1cc(-c2ncc3nc(C(F)(F)F)cc(C)c3n2)ccc1N(C)C(=O)c1cc(C(N)=O)nn1CC#N]

Proceeding analogously as described in Example 167, Step 2 but substituting 4-[(4-bromo-2-methylphenyl)carbamoyl]pyridine-2-carboxylic acid with 1-(cyanomethyl)-5-[methyl([2-methyl-4-[8-methyl-6-(trifluoromethyl)pyrido[3,2-d]pyrimidin-2-yl]phenyl])carbamoyl]-1H-pyrazole-3-carboxylic acid provided crude product. The crude product was purified by Prep-TLC (CH$_2$Cl$_2$/MeOH 40/1), followed by reverse flash chromatography (column, C$_{18}$ silica gel; mobile phase, MeCN in water, 0% to 65% gradient in 35 min; detector, UV 254 nm) to give the title compound as a white solid in 31.46% yield. LC-MS: (ES, m/z): [M+H]$^+$ 509; $^1$H-NMR: (400 MHz, DMSO, ppm): δ2.36 (s, 3H), δ2.94 (s, 3H), δ3.37 (s, 3H), δ5.65-5.80 (m, 2H), δ5.85 (s, 1H), δ7.36 (s, 1H), δ7.58-7.60 (m, 2H), δ8.39 (s, 1H), δ8.49-8.52 (m, 1H), δ8.62 (s, 1H), δ9.89 (s, 1H).

Example 199: 1-(2-hydroxyethyl)-3-(hydroxymethyl)-N-methyl-N-[2-methyl-4-[8-methyl-6-(trifluoromethyl)pyrido[3,2-d]pyrimidin-2-yl]phenyl]-1H-pyrazole-5-carboxamide

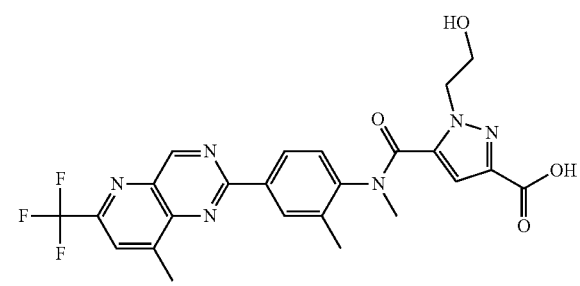 [SMILES: Cc1cc(-c2ncc3nc(C(F)(F)F)cc(C)c3n2)ccc1N(C)C(=O)c1cc(C(=O)O)nn1CCO]

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-[2-(benzyloxy)ethyl]-5-[methyl([2-methyl-4-[8-methyl-6-(trifluoromethyl)pyrido[3,2-d]pyrimidin-2-yl]phenyl])carbamoyl]-1H-pyrazole-3-carboxylic acid provided crude product. The crude product was purified by reverse flash chromatography (C$_{18}$ silica gel; mobile phase, MeCN in water, 0% to 55% gradient in 35 min; detector, UV 254 nm) to give the title compound as a white solid in 14.50% yield.

LC-MS: (ES, m/z): [M+H]$^+$ 515; $^1$H-NMR: (400 MHz, DMSO, ppm): δ 9.90-9.86 (d, 1H), 8.57 (s, 1H), 8.43-8.38 (m, 2H), 7.53-7.50 (d, 1H), 5.83 (s, 1H), 5.32-5.05 (m, 1H), 4.56-4.39 (m, 2H), 3.79 (s, 2H), 3.32 (s, 3H), 2.92 (s, 3H), 2.38 (s, 3H).

Step 1: 1-[2-(benzyloxy)ethyl]-5-[methyl([2-methyl-4-[8-methyl-6-(trifluoromethyl)pyrido-[3,2-d]pyrimidin-2-yl]phenyl])carbamoyl]-1H-pyrazole-3-carboxylic acid

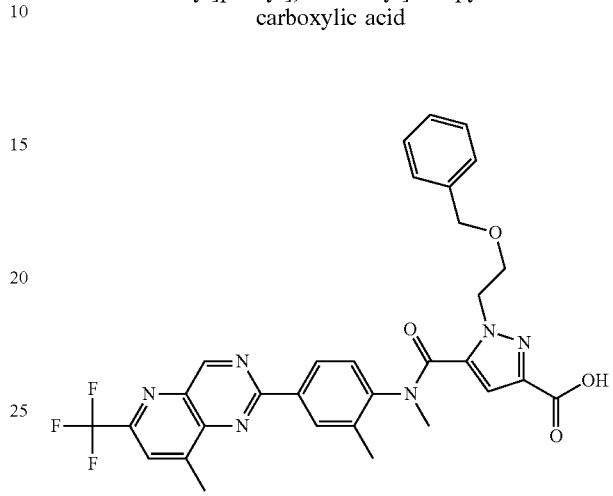

Proceeding analogously as described in Example 195, Step 4 but substituting 1-(cyanomethyl)-1H-pyrazole-3,5-dicarboxylate with methyl 1-[2-(benzyloxy)ethyl]-5-[methyl([2-methyl-4-[8-methyl-6-(trifluoromethyl)pyrido[3,2-d]pyrimidin-2-yl]phenyl])carbamoyl]-1H-pyrazole-3-carboxylate provided crude product. The crude product was applied onto a prep-TLC and eluted with EA:PE=1:1 to give the title compound as a white solid in 38.81% yield.

Example 200: 1-(2-hydroxyethyl)-N5-methyl-N5-(2-methyl-4-(8-methyl-6-(trifluoromethyl)pyrido[3,2-d]pyrimidin-2-yl)phenyl)-1H-pyrazole-3,5-dicarboxamide

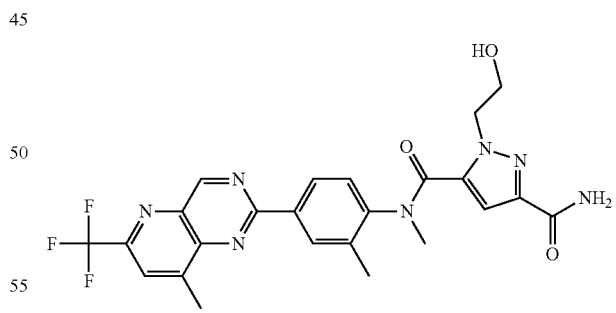

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-[2-(benzyloxy)ethyl]-N5-methyl-N5-[2-methyl-4-[8-methyl-6-(trifluoro-methyl)pyrido[3,2-d]pyrimidin-2-yl]phenyl]-1H-pyrazole-3,5-dicarboxamide provided crude product. The crude product was purified by prep-TLC with EA:PE (1:5) to give the title compound as a white solid in 39.15% yield. LC-MS: (ES, m/z): [M+H]$^+$ 514; $^1$H-NMR:

(400 MHz, DMSO, ppm): δ 9.88 (s, 1H), 8.58 (d, 1H), 8.33-8.44 (m, 2H), 7.54-7.57 (d, 1H), 7.46 (s, 1H), 7.18 (s, 1H), 5.87 (s, 1H), 5.04 (s, 1H), 4.56-4.66 (m, 1H), 4.38-4.50 (m, 1H), 3.81 (s, 2H), 3.38 (s, 3H), 2.91 (s, 3H), 2.38 (s, 3H).

Step 1: 3,5-dimethyl 1-[2-(benzyloxy)ethyl]-1H-pyrazole-3,5-dicarboxylate

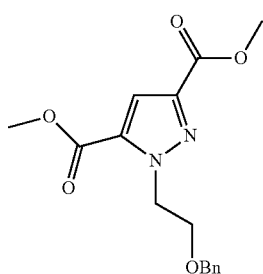

To a stirred solution of 3,5-dimethyl 1H-pyrazole-3,5-dicarboxylate (10 g, 54.30 mmol, 1 equiv.) and [(2-bromoethoxy)methyl]benzene (12.8 g, 59.51 mmol, 1.096 equiv.) in MeCN (200 mL) was added $K_2CO_3$ (11.3 g, 81.46 mmol, 1.5 equiv.) at room temperature under nitrogen atmosphere. The resulting mixture was stirred for 4 h at 90° C. The mixture was allowed to cool down to room temperature and then quenched with water. The resulting mixture was extracted with EtOAc and the combined organic layers were dried over anhydrous $Na_2SO_4$. After filtration, the filtrate was concentrated under reduced pressure and the residue was purified by silica gel column chromatography, eluting with PE/EtOAc (10:1) to afford the title compound as a yellow oil in 96.22% yield.

Step 2: 1-[2-(benzyloxy)ethyl]-3-(methoxycarbonyl)-1H-pyrazole-5-carboxylic acid

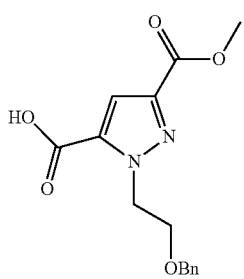

Proceeding analogously as described in Example 167, Step 1 but substituting N-(4-bromo-2-methylphenyl)-2-cyanopyridine-4-carboxamide with 3,5-dimethyl 1-[2-(benzyloxy)ethyl]-1H-pyrazole-3,5-dicarboxylate and stirring the reaction mixture in methanol at room temperature for 3 h provided the title compound as a colorless oil in 68.57% yield.

Step 3: methyl 1-[2-(benzyloxy)ethyl]-5-[(4-bromo-2-methylphenyl)carbamoyl]-1H-pyrazole-3-carboxylate

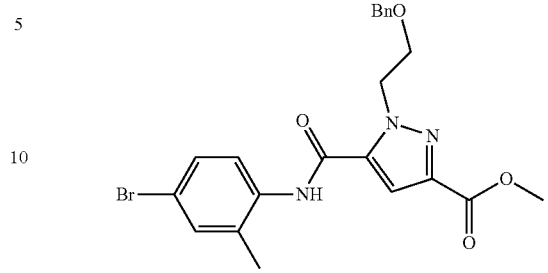

Proceeding analogously as described in Example 160, Step 8 but substituting 2-methylpyridine-4-carboxylic acid with 1-[2-(benzyloxy)ethyl]-3-(methoxycarbonyl)-1H-pyrazole-5-carboxylic acid provided crude product. The crude product was purified by a silica gel column by eluting with $CH_2Cl_2$/MeOH (15:1), followed by re-crystallization from DCM to afford the title compound as a white solid in 53.15% yield.

Step 4: methyl 1-[2-(benzyloxy)ethyl]-5-[(4-bromo-2-methylphenyl)(methyl)-carbamoyl]-1H-pyrazole-3-carboxylate

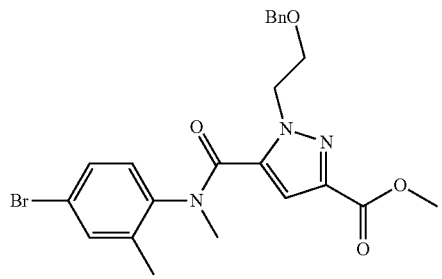 [SMILES: COC(=O)c1cc(C(=O)N(C)c2ccc(Br)cc2C)n(CCOCc2ccccc2)n1]

Proceeding analogously as described in Example 161, Step 1 but substituting N-(4-bromo-2-methylphenyl)-2-methylpyridine-4-carboxamide with methyl 1-[2-(benzyloxy)ethyl]-5-[(4-bromo-2-methylphenyl)carbamoyl]-1H-pyrazole-3-carboxylate provided crude product. The crude product was purified by silica gel column chromatography by eluting with PE/EtOAc (5:1) to afford the title compound in 77.69% yield.

Step 5: methyl 1-[2-(benzyloxy)ethyl]-5-[methyl[2-methyl-4-(4,4,5,5-tetramethyl-1,3,2-dioxaborolan-2-yl)phenyl]carbamoyl]-1H-pyrazole-3-carboxylate

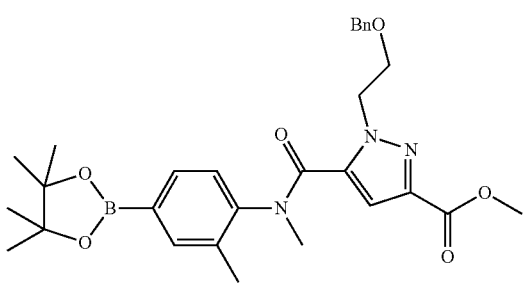

Proceeding as described in Example 161, Step 2 but substituting N-(4-bromo-2-methylphenyl)-N,2-dimethylpyridine-4-carboxamide with methyl 1-[2-(benzyloxy)ethyl]-5-[(4-bromo-2-methylphenyl)(methyl)carbamoyl]-1H-pyrazole-3-carboxylate provided crude product. The crude product was purified by silica gel column chromatography by eluting with PE/EtOAc (5:1) to afford the title compound as a yellow oil in 95.98% yield.

Step 6: methyl 1-[2-(benzyloxy)ethyl]-5-[methyl([2-methyl-4-[8-methyl-6-(trifluoro-methyl)pyrido[3,2-d]pyrimidin-2-yl]phenyl])carbamoyl]-1H-pyrazole-3-carboxylate

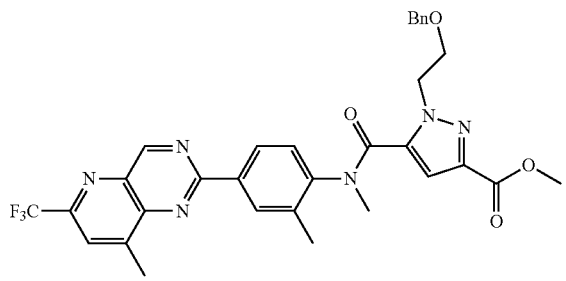 [SMILES: COC(=O)c1cc(C(=O)N(C)c2ccc(-c3ncc4nc(C(F)(F)F)cc(C)c4n3)cc2C)n(CCOCc2ccccc2)n1]

Proceeding analogously as described in Example 193 but substituting 1-(2-hydroxypropyl)-N-[2-methyl-4-(4,4,5,5-tetramethyl-1,3,2-dioxaborolan-2-yl)phenyl]-1H-pyrazole-5-carboxamide with methyl 1-[2-(benzyloxy)ethyl]-5-[methyl[2-methyl-4-(4,4,5,5-tetramethyl-1,3,2-dioxaborolan-2-yl)phenyl]carbamoyl]-1H-pyrazole-3-carboxylate provided crude product. The crude product was applied onto a silica gel column and eluted with ethyl acetate/petroleum ether (1:10) to give the title compound as a white solid in 50.43% yield.

Step 7: 1-[2-(benzyloxy)ethyl]-N5-methyl-N5-[2-methyl-4-[8-methyl-6-(trifluoro-methyl)pyrido[3,2-d]pyrimidin-2-yl]phenyl]-1H-pyrazole-3,5-dicarboxamide

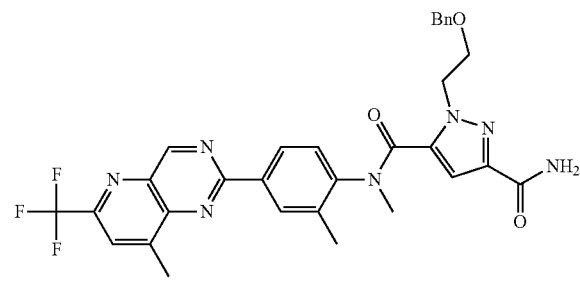 [SMILES: Cc1cc(-c2ncc3nc(C(F)(F)F)cc(C)c3n2)ccc1N(C)C(=O)c1cc(C(N)=O)nn1CCOCc1ccccc1]

Into an 8-mL sealed tube, was placed methyl 1-[2-(benzyloxy)ethyl]-5-[methyl([2-methyl-4-[6-(trifluoromethyl)pyrido[3,2-d]pyrimidin-2-yl]phenyl])carbamoyl]-1H-pyrazole-3-carboxylate (200 mg, 0.33 mmol, 1 equiv.) and NH₃ solution in MeCN (2 mL). The resulting solution was stirred overnight at 50° C. and then concentrated. The residue was applied onto a Prep-TLC and eluted with ethyl acetate/petroleum ether (1:1) to give the title compound as a white solid in 52.08% yield.

Example 201: 1-(2-hydroxyethyl)-N-methyl-N-(2-methyl-4-(8-methyl-6-(trifluoromethyl)-quinolin-2-yl)phenyl)-1H-pyrazole-5-carboxamide

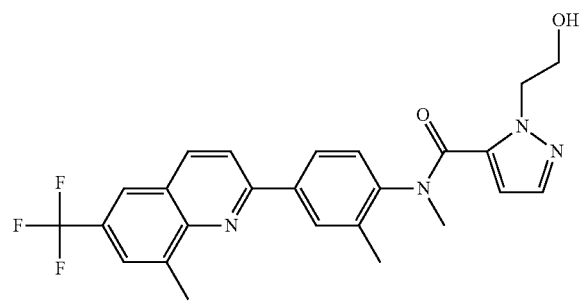 [SMILES: Cc1cc(-c2ccc3cc(C(F)(F)F)cc(C)c3n2)ccc1N(C)C(=O)c1ccnn1CCO]

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-[2-(benzyloxy)ethyl]-N-methyl-N-[2-methyl-4-[8-methyl-6-(trifluoromethyl)quinolin-2-yl]phenyl]-1H-pyrazole-5-carboxamide provided crude product. The crude product was applied onto Prep-TLC and eluted with acetate/petroleum ether (1:2) to give the title compound as a yellow solid in 79.73% yield. LC-MS: (ES, m/z): [M+H]⁺ 469; ¹H-NMR: (300 MHz, DMSO, ppm): (300 MHz, DMSO, ppm): δ 7.66-7.69 (m, 1H), 7.53 (s, 1H), 7.35-7.47 (m, 3H), 7.00 (s, 1H), 6.61-6.63 (d, 1H), 6.40 (s, 1H), 4.85 (s, 1H), 3.91-3.99 (m, 1H), 3.71-3.74 (m, 1H), 3.15 (s, 2H), 2.63 (s, 3H), 2.12 (s, 3H), 1.61 (s, 3H)

Step 1: methyl 1-(2-(benzyloxy)ethyl)-1H-pyrazole-5-carboxylate

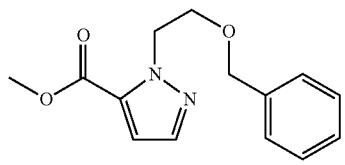 [SMILES: COC(=O)c1ccnn1CCOCc1ccccc1]

To a stirred solution of methyl 1H-pyrazole-5-carboxylate (10 g, 79.29 mol, 1 equiv.) and 2-(benzyloxy)ethan-1-ol (14.5 g, 95.28 mol, 1.2 equiv.) in THF (100 mL) was added DIAD (24.1 g, 119.18 mmol, 1.5 equiv.) and PPH₃ (41.6 g, 158.61 mmol, 2 equiv.) in portions at 0-10° C. under nitrogen atmosphere. The resulting mixture was stirred overnight at room temperature under nitrogen atmosphere and then concentrated under reduced pressure. The residue was purified by silica gel column chromatography by eluting with PE/EtOAc (10/1) to afford the title compound as a yellow oil in 61.05% yield.

Step 2: 1-(2-(benzyloxy)ethyl)-1H-pyrazole-5-carboxylic acid

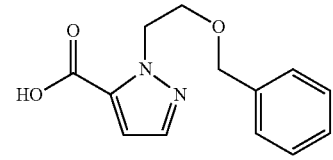 [SMILES: O=C(O)c1ccnn1CCOCc1ccccc1]

Proceeding analogously as described in Example 232, Step 4 but substituting methyl 1-(2-oxopropyl)-1H-pyrazole-5-carboylate with methyl 1-(2-(benzyloxy)ethyl)-1H-pyrazole-5-carboxylate provided the title compound as a white solid in 90.60% yield.

Step 3: 1-(2-(benzyloxy)ethyl)-N-(4-bromo-2-methylphenyl)-1H-pyrazole-5-carboxamide

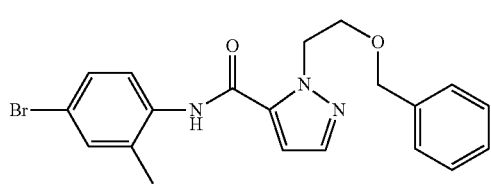 [SMILES: Cc1cc(Br)ccc1NC(=O)c1ccnn1CCOCc1ccccc1]

Proceeding analogously as described in Example 160, Step 8 but substituting 2-methylpyridine-4-carboxylic acid with 1-(2-(benzyloxy)ethyl)-1H-pyrazole-5-carboxylic acid provided title compound as a white solid in 88.06% yield

Step 4: 1-(2-(benzyloxy)ethyl)-N-(4-bromo-2-methylphenyl)-N-methyl-1H-pyrazole-5-carboxamide

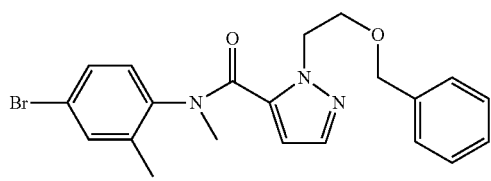 [SMILES: Cc1cc(Br)ccc1N(C)C(=O)c1ccnn1CCOCc1ccccc1]

Proceeding analogously as described in Example 165, Step 2 but substituting N-(4-bromo-2-fluorophenyl)-2-methylisonicotinamide with 1-(2-(benzyloxy)ethyl)-N-(4-bromo-2-methylphenyl)-1H-pyrazole-5-carboxamide provided crude product. The crude product was purified by silica gel column chromatography by eluting with PE/EtOAc (30/1) to afford the title compound as a yellow oil in 94.79% yield.

Step 5: 1-(2-(benzyloxy)ethyl)-N-methyl-N-(2-methyl-4-(4,4,5,5-tetramethyl-1,3,2-dioxaborolan-2-yl)phenyl)-1H-pyrazole-5-carboxamide

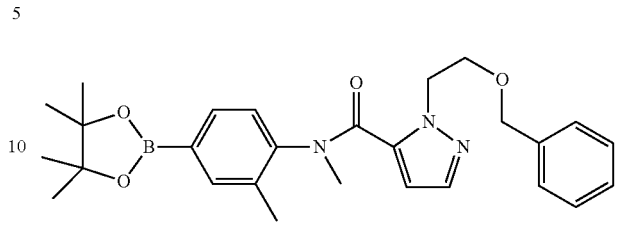

Proceeding as described in Example 161, Step 2 but substituting N-(4-bromo-2-methylphenyl)-N,2-dimethylpyridine-4-carboxamide with 1-(2-(benzyloxy)ethyl)-N-(4-bromo-2-methylphenyl)-N-methyl-1H-pyrazole-5-carboxamide provided crude product. The crude product was purified by silica gel column chromatography by eluting with PE/EtOAc (20/1) to afford the title compound as a yellow oil in 64.36% yield.

Step 6: 1-(2-(benzyloxy)ethyl)-N-(4-(8-bromo-6-(trifluoromethyl)quinolin-2-yl)-2-methylphenyl)-N-methyl-1H-pyrazole-5-carboxamide

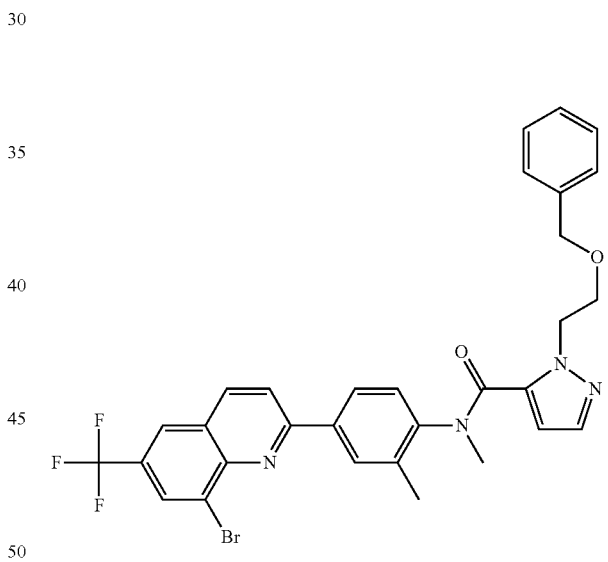

Into a 25-mL 3-necked round-bottom flask purged and maintained with an inert atmosphere of nitrogen, was placed 8-bromo-2-chloro-6-(trifluoromethyl)quinoline (300 mg, 0.97 mmol, 1 equiv.), 1-[2-(benzyloxy)ethyl]-N-methyl-N-[2-methyl-4-(tetramethyl-1,3,2-dioxaborolan-2-yl)phenyl]-1H-pyrazole-5-carboxamide (459.3 mg, 0.97 mmol, 1 equiv.), $Na_2CO_3$ (307.2 mg, 2.90 mmol, 3 equiv.), DME (6 mL), $H_2O$ (1.5 mL), $Pd(PPh_3)_4$ (111.6 mg, 0.10 mmol, 0.1 equiv.). The resulting solution was stirred for 12 h at 80° C. and then extracted with ethyl acetate. The combined organic layers were concentrated under reduced pressure and the residue was applied onto Prep-TLC and eluted with ethyl acetate/petroleum ether (1:2) to give the title compound as a yellow oil in 74.70% yield.

Step 7: 1-(2-(benzyloxy)ethyl)-N-methyl-N-(2-methyl-4-(8-methyl-6-(trifluoromethyl)-quinolin-2-yl)phenyl)-1H-pyrazole-5-carboxamide

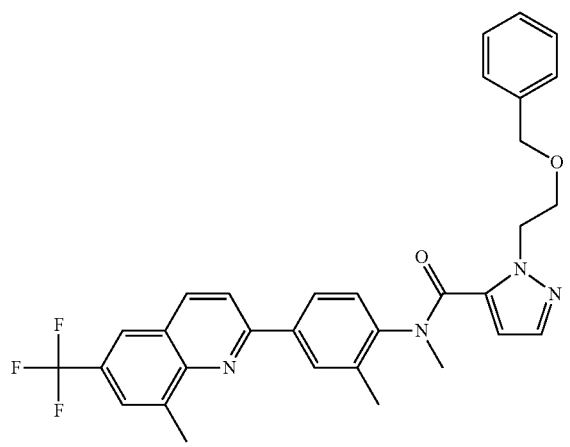 [SMILES: Cc1cc(-c2ccc3cc(C(F)(F)F)cc(C)c3n2)ccc1N(C)C(=O)c1ccnn1CCOCc1ccccc1]

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with methylboronic acid and 2-chloro-8-methyl-6-(trifluoromethyl)pyrido[3,2-d]pyrimidine with 1-[2-(benzyloxy)ethyl]-N-[4-[8-bromo-6-(trifluoromethyl)quinolin-2-yl]-2-methylphenyl]-N-methyl-1H-pyrazole-5-carboxamide provided crude product. The product was applied onto Prep-TLC and eluted with ethyl acetate/petroleum ether (1:3) to give the title compound as a yellow solid in 62.01% yield.

Example 202: N,1-dimethyl-N-(2-methyl-4-(8-methyl-6-(trifluoromethyl)quinolin-2-yl)phenyl)-1H-pyrazole-5-carboxamide

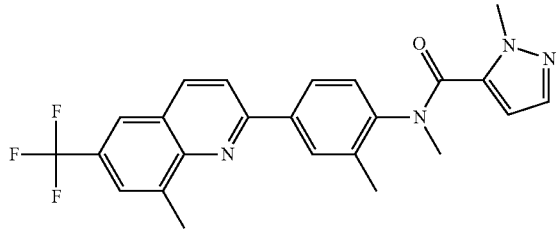 [SMILES: Cc1cc(-c2ccc3cc(C(F)(F)F)cc(C)c3n2)ccc1N(C)C(=O)c1ccnn1C]

Proceeding analogously as described in Example 165, Step 2 but substituting N-(4-bromo-2-fluorophenyl)-2-methylisonicotinamide with 1-methyl-N-[2-methyl-4-[8-methyl-6-(trifluoromethyl)quinolin-2-yl]phenyl]-1H-pyrazole-5-carboxamide provided crude product. The crude product was purified by Prep-TLC (CH$_2$Cl$_2$/MeOH 60/1) to afford the title compound as an off-white solid in 69.77% yield. LC-MS: (ES, m/z): [M+H]$^+$ 439; $^1$H-NMR: (400 MHz, DMSO, ppm): δ 2.28 (s, 3H), 2.89 (s, 3H), 3.33 (s, 3H), 4.01 (s, 3H), 5.57 (s, 1H), 7.15-7.16 (d, 1H), 7.48-7.50 (d, 1H), 7.91 (s, 1H), 8.21-8.24 (m, 1H), 8.28 (s, 1H), 8.32-8.34 (d, 2H), 8.65-8.65 (d, 1H).

Example 203: 1-methyl-N-(2-methyl-4-(8-methyl-6-(trifluoromethyl)quinolin-2-yl)phenyl)-1H-pyrazole-5-carboxamide

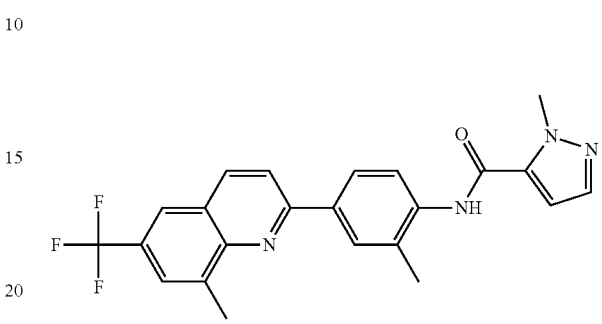

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with methylboronic acid and 2-chloro-8-methyl-6-(trifluoromethyl)pyrido[3,2-d]pyrimidine with N-(4-(8-bromo-6-(trifluoromethyl)quinolin-2-yl)-2-methylphenyl)-1-methyl-1H-pyrazole-5-carboxamide provided crude product. The crude product was purified by Prep-TLC (CH$_2$Cl$_2$/MeOH 50/1) to afford the title compound as an off-white solid in 55.14% yield. LC-MS: (ES, m/z): [M+H]$^+$ 425; $^1$H-NMR (400 MHz, DMSO, ppm): δ 2.39 (s, 3H), 2.89 (s, 3H), 4.11 (s, 3H), 7.11-7.12 (d, 1H), 7.56-7.59 (m, 2H), 7.90 (s, 1H), 8.23-8.35 (m, 4H), 8.63-8.65 (d, 1H), 10.00 (s, 3H)

Step 1: N-(4-(8-bromo-6-(trifluoromethyl)quinolin-2-yl)-2-methylphenyl)-1-methyl-1H-pyrazole-5-carboxamide Proceeding analogously as described in Example 167 but substituting N2-methyl-N4-(2-methyl-4-(4,4,5,5-tetramethyl-1,3,2-dioxaborolan-2-yl)phenyl)pyridine-2,4-dicarboxamide with methyl-N-[2-methyl-4-(4,4,5,5-tetramethyl-1,3,2-dioxaborolan-2-yl)phenyl]-1H-pyrazole-5-carboxamide and 2-chloro-8-methyl-6-(trifluoromethyl)pyrido[3,2-d]pyrimidine with 8-bromo-2-chloro-6-(trifluoromethyl)quinoline provided crude product. The crude product was purified by Prep-TLC (PE/EtOAc 2/1) to afford the title compound as a yellow solid in 63.46% yield.

Example 204: N-[2-methyl-4-[6-(trifluoromethyl)quinolin-2-yl]phenyl]-1H-pyrazole-5-carboxamide

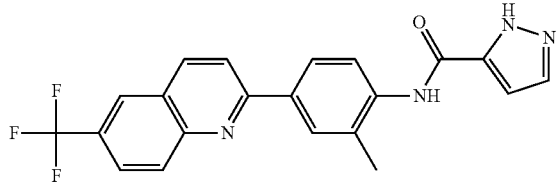 [SMILES: Cc1cc(-c2ccc3cc(C(F)(F)F)ccc3n2)ccc1NC(=O)c1ccn[nH]1]

Proceeding analogously as described in Example 160, Step 8 but substituting 2-methylpyridine-4-carboxylic acid with 1H-pyrazole-5-carboxylic acid and 4-bromo-2-methylaniline with 2-methyl-4-[6-(trifluoromethyl)quinolin-2-yl]aniline provided crude product. (The crude product was applied onto a prep-TLC and eluted with ethyl acetate/petroleum ether (1:5) to give the title compound as a white solid in 18.38% yield. $^1$H-NMR: (400 MHz, DMSO, ppm): δ 13.47 (s, 1H), 9.57 (s, 1H), 8.65-8.66 (d, 1H), 8.64 (s, 1H), 8.8.32-8.34 (d, 1H), 8.8.26-8.27 (d, 1H), 8.20-8.24 (m, 2H), 8.18-8.20 (m, 1H), 7.94-8.03 (m, 3H), 6.81 (s, 1H), 2.43 (s, 3H)

Example 205: N-methyl-N-[2-methyl-4-[6-(trifluoromethyl)quinolin-2-yl]phenyl]-1H-pyrazole-5-carboxamide

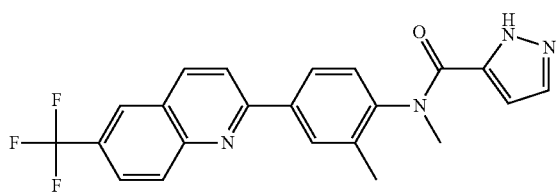 [SMILES: Cc1cc(-c2ccc3cc(C(F)(F)F)ccc3n2)ccc1N(C)C(=O)c1ccn[nH]1]

Into a 25-mL 3-necked round-bottom flask, was placed N,2-dimethyl-4-[6-(trifluoromethyl)quinolin-2-yl]aniline (200 mg, 0.63 mmol, 1 equiv.), 1H-pyrazole-5-carboxylic acid (212.6 mg, 1.90 mmol, 3 equiv.), HATU (721.2 mg, 1.90 mmol, 3 equiv.), and DIEA (245.1 mg, 1.90 mmol, 3 equiv.) in DMF (5 mL). The resulting solution was stirred overnight at 100° C. and then quenched with water. The resulting solution was extracted with ethyl acetate and the organics were evaporated. The residue was applied onto prep-TLC and eluted with ethyl acetate/petroleum ether (1:5) to give the title compound as a white solid in 57.81% yield as a white solid. LC-MS: (ES, m/z): [M+H]$^-$ 409; $^1$H-NMR: (300 MHz, DMSO, ppm): δ 13.65 (s, 1H), 12.94 (s, 1H), 8.68-8.73 (m, 1H), 8.55-8.66 (m, 1H), 8.24-8.41 (m, 3H), 8.01-8.19 (m, 1H), 7.50-7.57 (m, 2H), 7.31-7.34 (d, 1H), 7.23 (s, 1H), 6.23 (s, 1H), 4.94 (s, 1H), 3.29 (s, 3H), 2.25-2.27 (d, 3H)

Step 1: N,2-dimethyl-4-[6-(trifluoromethyl)quinolin-2-yl]aniline

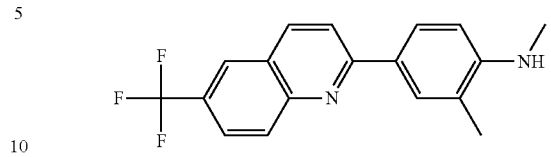

Proceeding analogously as described in Example 165, Step 2 but substituting N-(4-bromo-2-fluorophenyl)-2-methylisonicotinamide with 2-methyl-4-[6-(trifluoromethyl)quinolin-2-yl]aniline provided crude product. The crude product was applied onto a silica gel column and eluted with ethyl acetate/petroleum ether (1:10) to give the title compound as a white solid in 19.11% yield.

Example 206: N-(2,5-dimethyl-4-(6-(trifluoromethyl)quinolin-2-yl)phenyl)-1,4-dimethyl-1H-pyrazole-5-carboxamide

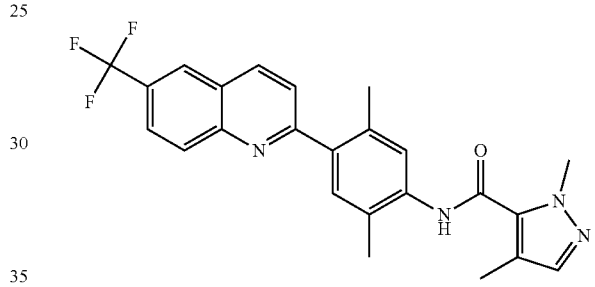

Into an 8-mL sealed tube purged and maintained with an inert atmosphere of nitrogen, was placed 2,5-dimethyl-4-[6-(trifluoromethyl)quinolin-2-yl]aniline (100 mg, 0.32 mmol, 1 equiv.), 1,4-dimethyl-1H-pyrazole-5-carboxylic acid (53.2 mg, 0.38 mmol, 1.2 equiv.), DIEA (81.7 mg, 0.63 mmol, 2 equiv.), DMF (2 mL), and HATU (180.3 mg, 0.47 mmol, 1.5 equiv.). The resulting solution was stirred for 12 h at 50° C. and then quenched with water. The resulting solution was extracted with ethyl acetate. The combined organic layers were concentrated under reduced pressure and the residue was applied onto Prep-TLC and eluted with ethyl acetate/petroleum ether (1:5) to give the title compound as a white solid in 57.72% yield. LC-MS: (ES, m/z): [M+H]$^+$ 439; $^1$H-NMR: (400 MHz, DMSO, ppm): δ 9.77 (s, 1H), 8.65-8.68 (d, 1H), 8.58 (s, 1H), 8.23-8.26 (d, 1H), 8.02-8.05 (dd, 1H), 7.89-7.91 (d, 1H), 7.49-7.52 (d, 2H), 7.36 (s, 1H), 3.96 (s, 3H), 2.45 (s, 3H), 2.32 (s, 3H), 2.26 (s, 3H).

Step 1: ethyl 1,4-dimethyl-1H-pyrazole-5-carboxylate

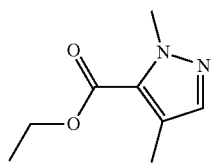

Into a 100-mL 3-necked round-bottom flask purged and maintained with an inert atmosphere of nitrogen, was placed ethyl 4-methyl-1H-pyrazole-5-carboxylate (3 g, 19.46 mmol, 1 equiv.), DIAD (7.9 g, 38.92 mmol, 2 equiv.), THF (30 mL), and MeOH (3.1 g, 97.30 mmol, 5 equiv.), and PPh₃ (10.2 g, 38.92 mmol, 2 equiv.) was added at 0° C. The resulting solution was stirred for 5 h at 25° C. and then concentrated under vacuum. The residue was applied onto a silica gel column and eluted with ethyl acetate/petroleum ether (1:50) to give the title compound as a yellow liquid in 76.38% yield.

Step 2: 1,4-dimethyl-1H-pyrazole-5-carboxylic acid

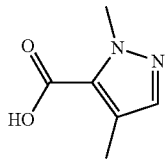

Proceeding analogously as described in Example 167, Step 1 but substituting N-(4-bromo-2-methylphenyl)-2-cyanopyridine-4-carboxamide with ethyl 1,4-dimethyl-1H-pyrazole-5-carboxylate provided the title compound as a white solid 96.01% yield.

Step 3: 2,5-dimethyl-4-(4,4,5,5-tetramethyl-1,3,2-dioxaborolan-2-yl)aniline

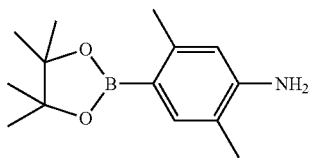 [SMILES: Cc1cc(B2OC(C)(C)C(C)(C)O2)c(C)cc1N]

Proceeding as described in Example 161, Step 2 but substituting N-(4-bromo-2-methylphenyl)-N,2-dimethylpyridine-4-carboxamide with 4-bromo-2,5-dimethylaniline provided the title compound as a white solid in 34.33% yield.

Step 4: 2,5-dimethyl-4-(6-(trifluoromethyl)quinolin-2-yl)aniline

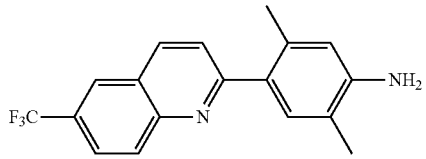 [SMILES: Cc1cc(-c2ccc3cc(C(F)(F)F)ccc3n2)c(C)cc1N]

Proceeding as described in Example 162 but substituting N-(2-fluoro-4-(4,4,5,5-tetramethyl-1,3,2-dioxaborolan-2-yl)phenyl)-N,1-dimethyl-TH-pyrazole-5-carboxamide with 2,5-dimethyl-4-(4,4,5,5-tetramethyl-1,3,2-dioxaborolan-2-yl)aniline and 2-chloro-8-methyl-6-(trifluoromethyl)pyrido[3,2-d]pyrimidine with 2-bromo-6-(trifluoromethyl)quinoline provided the title compound as a yellow solid in 23.44% yield.

Example 207: N-(2-fluoro-5-methyl-4-(6-(trifluoromethyl)quinolin-2-yl)phenyl)-1,4-dimethyl-1H-pyrazole-5-carboxamide

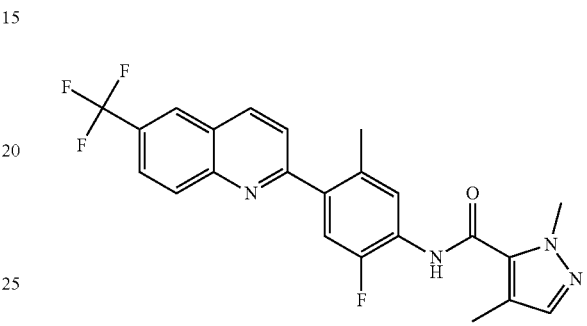

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 5-methyl-4-(4,4,5,5-tetramethyl-1,3,2-dioxaborolan-2-yl)phenyl]-1,4-dimethyl-1H-pyrazole-5-carboxamide and 2-chloro-8-methyl-6-(trifluoromethyl)pyrido[3,2-d]pyrimidine with 2-bromo-6-(trifluoromethyl)quinoline provided crude product. The crude product was applied onto Prep-TLC and eluted with ethyl acetate/petroleum ether (1:1) to give the title compound as a yellow solid in 42.52% yield. LC-MS: (ES, m/z): [M+H]⁺ 443; ¹H-NMR: (400 MHz, DMSO, ppm): δ 2.23 (s, 3H), 2.42 (s, 3H), 3.95 (s, 3H), 7.37 (s, 1H), 7.49-7.55 (d, 1H), 7.79-7.81 (d, 1H), 7.92-7.95 (d, 1H), 8.04-8.06 (d, 1H), 8.25-8.27 (d, 1H), 8.59 (s, 1H), 8.68-8.70 (d, 1H), 10.07 (s, 1H).

Step 1: N-(4-bromo-2-fluoro-5-methylphenyl)-1,4-dimethyl-1H-pyrazole-5-carboxamide

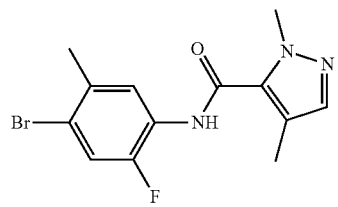 [SMILES: Cc1cc(NC(=O)c2c(C)cnn2C)c(F)cc1Br]

Proceeding analogously as described in Example 206 but substituting 2,5-dimethyl-4-[6-(trifluoromethyl)quinolin-2-yl]aniline with 4-bromo-2-fluoro-5-methylaniline provided crude product. The crude product was applied onto a silica gel column and eluted with ethyl acetate/petroleum ether (1:50) to give the title compound as a yellow solid in 42.97% yield.

Step 2: 5-methyl-4-(4,4,5,5-tetramethyl-1,3,2-dioxa-borolan-2-yl)phenyl]-1,4-dimethyl-1H-pyrazole-5-carboxamide

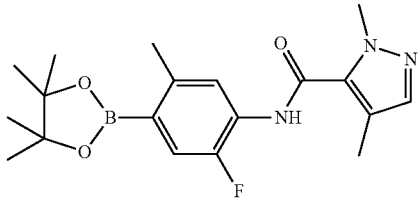 [SMILES: Cc1cc(NC(=O)c2c(C)cnn2C)c(F)cc1B1OC(C)(C)C(C)(C)O1]

Proceeding as described in Example 161, Step 2 but substituting N-(4-bromo-2-methylphenyl)-N,2-dimethylpyridine-4-carboxamide with N-(4-bromo-2-fluoro-5-methylphenyl)-1,4-dimethyl-1H-pyrazole-5-carboxamide provided crude product. The crude product was applied onto Prep-TLC and eluted with ethyl acetate/petroleum ether (1:20) to give the title compound as a yellow solid in 87.39% yield.

Example 208: N-(2,5-dimethyl-4-(6-(trifluoromethyl)quinolin-2-yl)phenyl)-1,4-dimethyl-1H-pyrazole-3-carboxamide

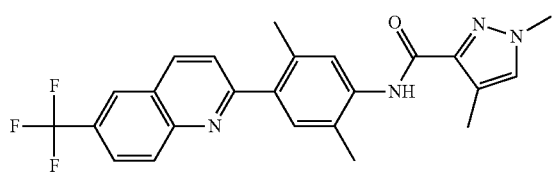 [SMILES: Cc1cc(-c2ccc3cc(C(F)(F)F)ccc3n2)c(C)cc1NC(=O)c1nn(C)cc1C]

Proceeding analogously as described in Example 206 but substituting 1,4-dimethyl-1H-pyrazole-5-carboxylic acid with 1-methyl-1H-pyrazole-3-carboxylic acid provided crude product. The crude product was applied onto a Prep-TLC and eluted with ethyl acetate/petroleum ether (1:1) gave the title compound as a yellow solid in 8.05% yield. LC-MS: (ES, m/z): [M+H]+ 439; $^1$H-NMR: (400 MHz, DMSO, ppm): δ 2.07 (s, 3H), 2.26 (s, 3H), 2.31 (s, 3H), 3.90 (s, 3H), 7.46 (s, 1H), 7.66 (s, 1H), 7.77 (s, 1H), 7.87-7.90 (d, 1H), 8.00-8.04 (d, 1H), 8.21-8.24 (d, 1H), 8.56 (s, 1H), 8.63-8.66 (d, 1H), 9.31 (s, 1H).

Step 1: ethyl 1-methyl-1H-pyrazole-3-carboxylate

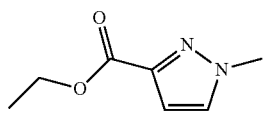

Proceeding as described in Example 206, Step 1 but substituting ethyl 1H-pyrazole-5-carboxylate with ethyl 4-methyl-1H-pyrazole-5-carboxylate provided crude product. The crude product was applied onto a silica gel column and eluted with ethyl acetate/petroleum ether (1:10) to give the title compound as a yellow solid in 4.58% yield.

Step 2: 1,4-dimethyl-1H-pyrazole-3-carboxylic acid

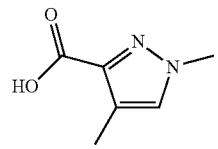

Proceeding analogously as described in Example 167, Step 1 but substituting N-(4-bromo-2-methylphenyl)-2-cyanopyridine-4-carboxamide with ethyl 1-methyl-1H-pyrazole-3-carboxylate provided the title compound as a white solid in 80.01% yield.

Example 209: 1-(2-hydroxyethyl)-N-methyl-N-(2-methyl-4-(6-(trifluoromethyl)quinolin-2-yl)phenyl)-1H-pyrazole-5-carboxamide

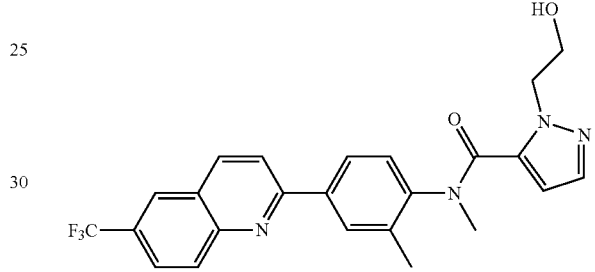

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-(2-(benzyloxy)ethyl)-N-methyl-N-(2-methyl-4-(6-(trifluoromethyl)quinolin-2-yl)phenyl)-1H-pyrazole-5-carboxamide provided crude product. The residue was purified by Prep-TLC (hexane/EtOAc=1:1) to afford the title compound as a white solid in 43.80% yield. LC-MS: (ES, m/z): [M+H]+ 455; $^1$H-NMR: (300 MHz, CDCl$_3$, ppm): δ2.32 (s, 3H), δ3.42 (s, 3H), δ4.05-4.08 (t, 2H), δ4.61-4.71 (m, 2H), δ5.56 (s, 1H), δ7.18 (s, 1H), δ7.29-7.32 (d, 1H), δ7.96-8.05 (m, 3H), δ8.14-8.18 (d, 2H), δ8.34-8.39 (t, 2H).

Step 1: 1-(2-(benzyloxy)ethyl)-N-methyl-N-(2-methyl-4-(6-(trifluoromethyl)quinolin-2-yl)phenyl)-1H-pyrazole-5-carboxamide

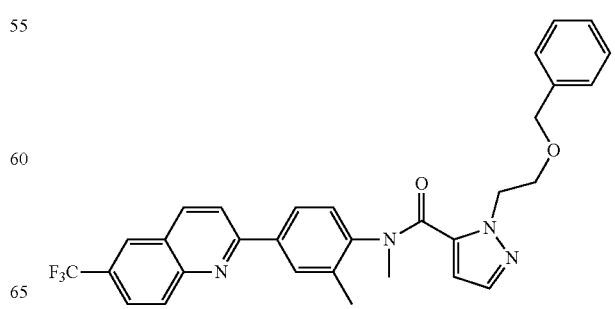

Proceeding analogously as described in Example 201, Step 6 but substituting 8-bromo-2-chloro-6-(trifluoromethyl)quinoline with 2-bromo-6-(trifluoromethyl)quinoline provided crude product which was purified by Prep-TLC (PE/EtOAc=5/1) to afford the title compound as a light yellow oil in 73.33% yield.

Example 210: 1-(2-hydroxyethyl)-N-methyl-N-(2-methyl-4-(6-(trifluoromethyl)-1,5-naphthyridin-2-yl)phenyl)-1H-pyrazole-5-carboxamide

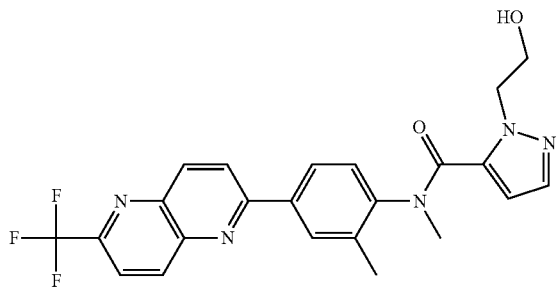 [SMILES: Cc1cc(-c2ccc3nc(C(F)(F)F)ccc3n2)ccc1N(C)C(=O)c1ccnn1CCO]

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-(2-(benzyloxy)ethyl)-N-methyl-N-(2-methyl-4-(6-(trifluoromethyl)-1,5-naphthyridin-2-yl)phenyl)-1H-pyrazole-5-carboxamide provided crude product. Purification by prep. TLC (PE/EA=3/1) gave the title compound as a white solid in 63.70% yield. LC-MS: (ES, m/z): [M+H]+ 456; ¹H-NMR: (300 MHz, CDCl₃, ppm): δ2.32 (s, 3H), δ3.47 (s, 3H), δ3.95-4.07 (m, 2H), δ4.60-4.74 (m, 2H), δ5.55 (s, 1H), δ7.18 (s, 1H), δ7.31-7.33 (d, 1H), δ8.00-8.03 (m, 2H), δ8.07 (s, 1H), δ8.20-8.23 (d, 1H), δ8.58-8.67 (m, 2H).

Step 1: 1-(2-(benzyloxy)ethyl)-N-methyl-N-(2-methyl-4-(6-(trifluoromethyl)-1,5-naphthyridin-2-yl)phenyl)-1H-pyrazole-5-carboxamide

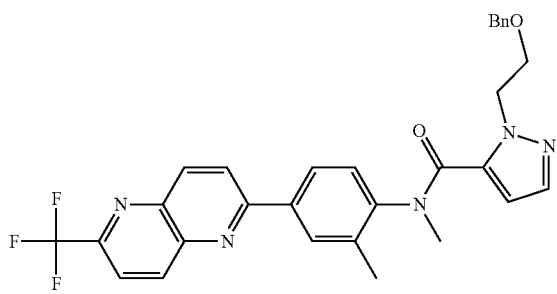 [SMILES: Cc1cc(-c2ccc3nc(C(F)(F)F)ccc3n2)ccc1N(C)C(=O)c1ccnn1CCOCc1ccccc1]

Proceeding analogously as described in Example 201, Step 6 but substituting 8-bromo-2-chloro-6-(trifluoromethyl)quinoline with 2-chloro-6-(trifluoromethyl)-1,5-naphthyridine provided crude product which was purified by Prep.TLC (PE/EA=3/1) to the title compound as a white solid in 85.27% yield.

Example 211: 1-(2-hydroxyethyl)-N-methyl-N-(2-methyl-4-(6-(trifluoromethyl)quinazolin-2-yl)phenyl)-1H-pyrazole-5-carboxamide

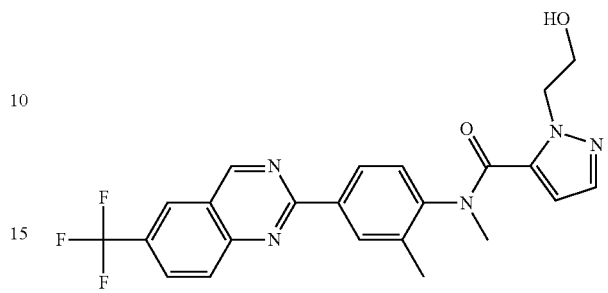

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-[2-(benzyloxy)ethyl]-N-methyl-N-[4-[6-(trifluoromethyl)quinazolin-2-yl]phenyl]-1H-pyrazole-5-carboxamide provided crude product. Purification by prep-TLC with ethyl acetate/petroleum ether (1:2) provided the title compound as a white solid in 43.01% yield. LC-MS: (ES, m/z): [M+H]+ 456. ¹H-NMR: (300 MHz, CDCl₃, ppm): δ 9.57 (s, 1H), 8.54-8.49 (m, 2H), 8.28-8.20 (d, 1H), 8.12-8.11 (d, 1H), 8.09-8.08 (d, 1H), 7.32-7.29 (m, 1H), 7.16-7.15 (d, 1H), 5.55-5.40 (d, 1H), 4.79-4.60 (m, 2H), 4.08-4.05 (t, 2H), 3.43 (s, 3H), 2.31 (s, 3H).

Step 1: 1-[2-(benzyloxy)ethyl]-N-methyl-N-[2-methyl-4-[6-(trifluoromethyl)quinazolin-2-yl]phenyl]-1H-pyrazole-5-carboxamide

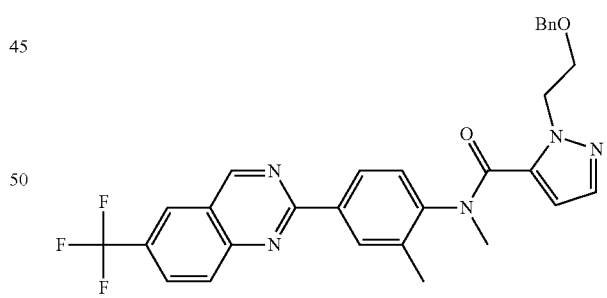

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1-[2-(benzyloxy)ethyl]-N-methyl-N-[2-methyl-4-(4,4,5,5-tetramethyl-1,3,2-dioxaborolan-2-yl)phenyl]-1H-pyrazole-5-carboxamide and 2-chloro-8-methyl-6-(trifluoromethyl)pyrido[3,2-d]pyrimidine with 2-chloro-6-trifluoromethylquinazoline provided crude product. The crude product was applied onto a prep-TLC and eluted with ethyl acetate/petroleum ether (1:2) to give the title compound as a white solid in 60.82% yield.

Example 212: 1-methyl-N-(methyl-d3)-N-(2-methyl-4-(6-(trifluoromethyl)quinolin-2-yl)phenyl)-1H-pyrazole-5-carboxamide

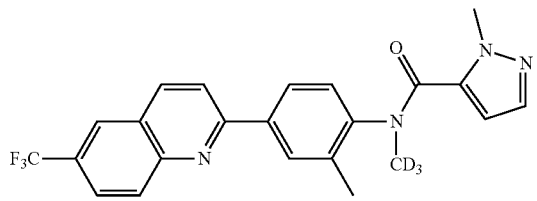 [SMILES: [2H]C([2H])([2H])N(C(=O)c1ccnn1C)c1ccc(-c2ccc3cc(C(F)(F)F)ccc3n2)cc1C]

Proceeding analogously as described in Example 165, Step 2 but substituting N-(4-bromo-2-fluorophenyl)-2-methylisonicotinamide with 1-methyl-N-[2-methyl-4-(6-(trifluoro-methyl)-quinolin-2-yl)phenyl)-1H-pyrazole-5-carboxamide and MeI with CD$_3$Cl, the title compound was obtained as an off-white solid in 77% yield. LC-MS: (ES, m/z): [M+H]$^+$ 428. $^1$H-NMR: (300 MHz, DMSO, ppm): δ2.27 (s, 3H), 4.02 (s, 3H), 5.55 (s, 1H), 7.16 (s, 1H), 7.48 (d, 1H), 8.03 (d, 1H), 8.16 (d, 1H), 8.25 (s, 1H), 8.26 (d, 1H), 8.33 (d, 1H), 8.55 (s, 1H), 8.69 (d, 1H).

Example 213: 2-(2-hydroxypropan-2-yl)-N-methyl-N-(2-methyl-4-(6-(trifluoromethyl)-quinazolin-2-yl)phenyl)isonicotinamide

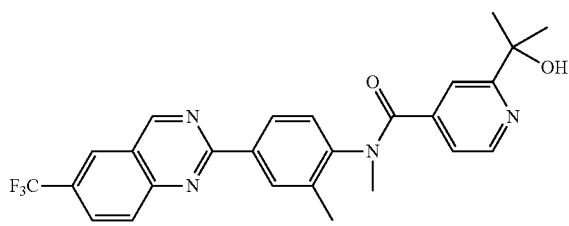 [SMILES: Cc1cc(-c2ncc3cc(C(F)(F)F)ccc3n2)ccc1N(C)C(=O)c1ccnc(C(C)(C)O)c1]

Into a round-bottom flask, was N,2-dimethyl-4-(6-(trifluoromethyl)quinazolin-2-yl)aniline (0.12 g, 0.38 mmol, 1 equiv.), 2-(2-hydroxypropan-2-yl)isonicotinic acid (0.09 g, 0.495 mmol, 1.3 equiv.), T3P, 50% solution in EtOAc (0.30 g, 0.95 mmol, 2.5 equiv.), DIPEA (0.074 g, 0.57 mmol, 1.5 equiv.) in THF (5 mL). The reaction mixture was stirred at 70° C. for 72 h and then diluted with EtOAc and washed with sodium bicarbonate. The organic layer was separated, dried and concentrated. The residue was chromatographed using ethyl acetate:hexanes mixture (10-100%) to give the title compound as a yellow solid in 4.4% yield. LC-MS: (ES, m/z): [M+H]$^+$ 482. $^1$H-NMR: (300 MHz, DMSO, ppm): δ1.23 (s, 3H), 1.26 (s, 3H), 2.33 (s, 3H), 3.36 (s, 3H), 5.15 (s, 1H), 7.04 (dd, 1H), 7.45 (d, 1H), 7.55 (m, 1H), Step 1: 2-(2-hydroxypropan-2-yl)isonicotinic acid

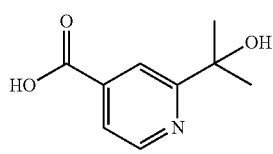

Into a round-bottom flask, was placed methyl 2-(2-hydroxypropan-2-yl)isonicotinate (0.435 g, 2.23 mmol, 1 equiv.) and KOH (0.14 g, 2.45 mmol, 1.1 equiv.) in methanol (5 mL) and the reaction mixture was stirred overnight at room temperature. After removal of the solvent under vacuo, the residue was diluted with water and extracted with ethyl ether. The aqueous phase was acidified to pH 1 with conc. HCl. The organics were extracted with ethyl acetate. The combined organic layer was washed with brine, dried over MgSO$_4$, filtered, and concentrated to give the title compound as a white solid in 89% yield.

Example 214: N,1,4-trimethyl-N-(2-methyl-4-(6-(trifluoromethyl)quinazolin-2-yl)phenyl)-1H-pyrazole-3-carboxamide

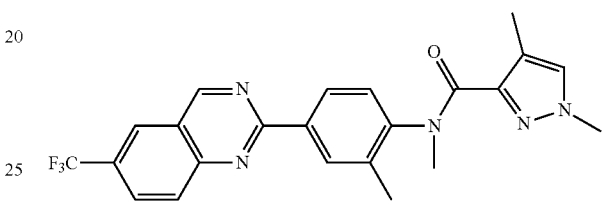

Proceeding analogously as described in Example 165, Step 2 but substituting N-(4-bromo-2-fluorophenyl)-2-methylisonicotinamide with 1,4-dimethyl-N-(2-methyl-4-(6-(trifluoromethyl)quinazolin-2-yl)phenyl)-1H-pyrazole-3-carboxamide, the title compound was obtained as a white solid in 33% yield. LC-MS: (ES, m/z): [M+H]$^+$ 440; $^1$H-NMR: (300 MHz, CDCl$_3$, ppm): δ 1.67 (s, 3H), 2.41 (s, 3H), 3.49 (s, 3H), 3.97 (s, 3H), 7.01 (s, 1H), 7.06 (d, 1H), 8.10 (d, 1H), 8.20 (d, 1H), 8.28 (s, 1H), 8.37 (d, 1H), 8.51 (s, 1H), 9.56 (s, 1H).

Example 215: 1,4-dimethyl-N-(2-methyl-4-(6-(trifluoromethyl)quinazolin-2-yl)phenyl)-1H-pyrazole-5-carboxamide

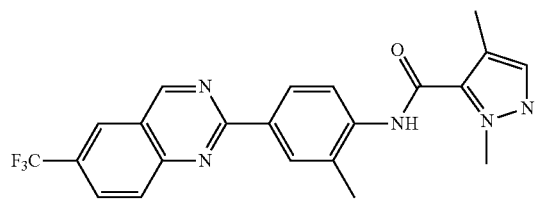

Proceeding as described in Example 162 but substituting 2-chloro-8-methyl-6-(trifluoromethyl)pyrido[3,2-d]pyrimidine with 2-chloro-6-(trifluoromethyl)quinazoline and N-(2-fluoro-4-(4,4,5,5-tetramethyl-1,3,2-dioxaborolan-2-yl)phenyl)-N,1-dimethyl-1H-pyrazole-5-carboxamide with 1,4-dimethyl-N-(2-methyl-4-(4,4,5,5-tetramethyl-1,3,2-dioxaborolan-2-yl)phenyl)-1H-pyrazole-5-carboxamide provided crude product. Purification by chromatography using 20-80% EtOAc-Hexanes as eluent gave the title compound as an off-white in 18% yield. LC-MS: (ES, m/z): [M+H]$^+$ 426; $^1$H-NMR: (300 MHz, DMSO, ppm): δ2.27 (s, 3H), 2.43 (s, 3H), 3.92 (s, 3H), 7.68 (s, 1H), 8.09 (d, 1H), 8.22-8.30 (m, 2H), 8.45 (dd, 1H), 8.50 (s, 1H), 8.70 (s, 1H), 9.39 (s, 1H), 9.87 (s, 1H).

Example 216: 1,4-dimethyl-N-(2-methyl-4-(6-(trifluoromethyl)quinazolin-2-yl)phenyl)-1H-pyrazole-3-carboxamide

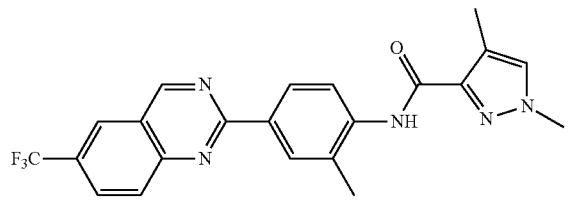 [SMILES: Cc1cc(-c2ncc3cc(C(F)(F)F)ccc3n2)ccc1NC(=O)c1nn(C)cc1C]

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1,4-dimethyl-N-(2-methyl-4-(4,4,5,5-tetramethyl-1,3,2-dioxaborolan-2-yl)phenyl)-1H-pyrazole-3-carboxamide and 2-chloro-8-methyl-6-(trifluoromethyl)pyrido[3,2-d]pyrimidine with 2-chloro-6-(trifluoromethyl)quinazoline provided crude product. Purification by chromatography using 20-80% EtOAc-Hexanes as eluent gave the title compound as an off-white in 17% yield. LC-MS: (ES, m/z): [M+H]$^+$ 426. $^1$H-NMR: (300 MHz, DMSO, ppm): δ2.27 (s, 3H), 2.44 (s, 3H), 3.97 (s, 3H), 7.38 (s, 1H), 7.83 (d, 1H), 8.24-8.31 (m, 2H), 8.48 (dd, 1H), 8.53 (s, 1H), 8.72 (s, 1H), 9.84 (s, 1H), 9.89 (s, 1H).

Step 1: 1,4-dimethyl-N-(2-methyl-4-(4,4,5,5-tetramethyl-1,3,2-dioxaborolan-2-yl)phenyl)-1H-pyrazole-3-carboxamide

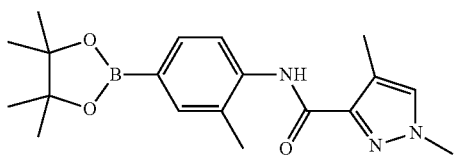

Proceeding analogously as described in Example 213, but substituting N,2-dimethyl-4-(6-(trifluoromethyl)quinazolin-2-yl)aniline with 2-methyl-4-(4,4,5,5-tetramethyl-1,3,2-dioxaboronlan-2-yl)aniline and 2-(2-hydroxypropan-2-yl)isonicotinic acid with 1,4-dimethyl-1H-pyrazole-3-carboxylic acid, the title compound was obtained as an off-white solid in 54% yield.

Example 217: N,1,4-trimethyl-N-(2-methyl-4-(6-(trifluoromethyl)quinazolin-2-yl)phenyl)-1H-pyrazole-5-carboxamide

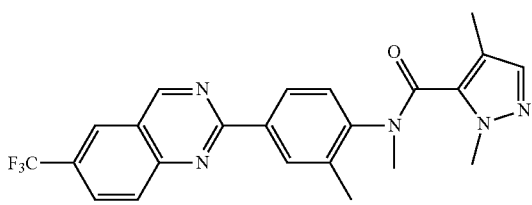 [SMILES: Cc1cc(-c2ncc3cc(C(F)(F)F)ccc3n2)ccc1N(C)C(=O)c1c(C)cnn1C]

Proceeding analogously as described in Example 165, Step 2 but substituting N-(4-bromo-2-fluorophenyl)-2-methylisonicotinamide with 1,4-dimethyl-N-[2-methyl-4-(6-(trifluoromethyl)-quinazolin-2-yl)phenyl)-1H-pyrazole-5-carboxamide provided the title compound as a white solid in 42% yield. LC-MS: (ES, m/z): [M+H]$^+$ 440; $^1$H-NMR: (300 MHz, CDCl$_3$, ppm): δ 1.27 (s, 3H), 2.17 (s, 3H), 2.38 (s, 3H), 3.42 (s, 3H), 3.53 (s, 3H), 8.10 (dd, 1H), 8.24 (d, 1H), 8.28 (s, 1H), 8.40 (d, 1H), 8.46 (s, 1H).

Example 218: N,1-dimethyl-N-(4-(6-(trifluoromethyl)quinazolin-2-yl)phenyl)-1H-pyrazole-5-carboxamide

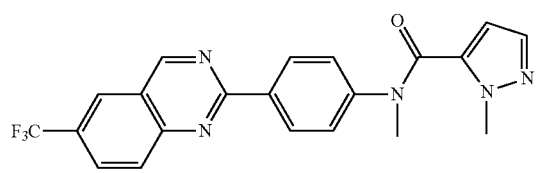 [SMILES: CN(C(=O)c1ccnn1C)c1ccc(-c2ncc3cc(C(F)(F)F)ccc3n2)cc1]

Proceeding analogously as described in Example 165, Step 2 but substituting N-(4-bromo-2-fluorophenyl)-2-methylisonicotinamide with 1-methyl-N-(4-(6-(trifluoromethyl)-quinazolin-2-yl)phenyl)-1H-pyrazole-5-carboxamide, the title compound was obtained as a white solid in 26% yield. LC-MS: (ES, m/z): [M+H]$^+$ 412; $^1$H-NMR: (300 MHz, CDCl$_3$, ppm): δ 3.56 (s, 3H), 4.19 (s, 3H), 5.68 (d, 1H), 7.19 (s, 1H), 7.30 (d, 2H), 8.12 (dd, 1H), 8.25 (dd, 1H), 8.30 (s, 1H), 8.67 (d, 2H), 9.59 (s, 1H).

Example 219: 1,3-dimethyl-N-(2-methyl-4-(6-(trifluoromethyl)quinazolin-2-yl)phenyl)-1H-pyrazole-4-carboxamide

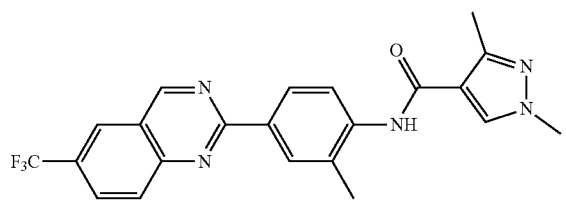 [SMILES: Cc1cc(-c2ncc3cc(C(F)(F)F)ccc3n2)ccc1NC(=O)c1cn(C)nc1C]

Proceeding analogously as described in Example 167 but substituting 2-chloro-8-methyl-6-(trifluoromethyl)pyrido[3,2-d]pyrimidine with 2-chloro-6-(trifluoromethyl)quinazoline and N2-methyl-N4-(2-methyl-4-(4,4,5,5-tetramethyl-1,3,2-dioxaborolan-2-yl)phenyl)pyridine-2,4-dicarboxamide with 1,3-dimethyl-N-(2-methyl-4-(4,4,5,5,-tetramethyl-1,3,2-dioxaborolan-2-yl)phenyl)-1H-pyrazole-4-carboxamide provided the title compound as an off-white solid in 21% yield. LC-MS: (ES, m/z): [M+H]$^+$ 426. $^1$H-NMR: (300 MHz, DMSO, ppm): δ 2.38 (s, 3H), 2.40 (s, 3H), 3.84 (s, 3H), 7.73 (d, 1H), 8.22-8.30 (m, 2H), 8.33 (s, 1H), 8.43 (dd, 1H), 8.50 (s, 1H), 8.71 (s, 1H), 9.29 (s, 1H), 9.87 (s, 1H).

Example 220: 1-methyl-N-(4-(6-(trifluoromethyl)quinazolin-2-yl)phenyl)-1H-pyrazole-5-carboxamide

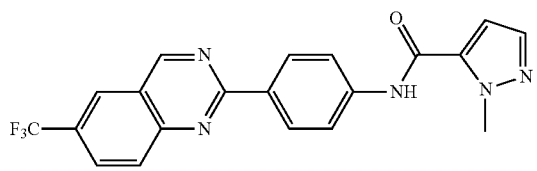

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1,4-dimethyl-N-(4-(4,4,5,5-tetramethyl-1,3,2-dioxaborolan-2-yl)phenyl)-1H-pyrazole-5-carboxamide and 2-chloro-8-methyl-6-(trifluoromethyl)pyrido[3,2-d]pyrimidine with 2-chloro-6-(trifluoromethyl)quinazoline provided crude product. Purification by chromatography using 5-80% EtOAc-Hexanes as eluent gave the title compound as an off-white in 16% yield. LC-MS: (ES, m/z): [M+H]⁺ 398; ¹H-NMR: (300 MHz, DMSO, ppm): δ4.13 (s, 3H), 7.15 (d, 1H), 7.57 (d, 1H), 8.00 (d, 2H), 8.20-8.30 (m, 2H), 8.62 (d, 2H), 8.71 (s, 1H), 9.87 (s, 1H), 10.48 (s, 1H).

Example 221: 1-methyl-5-(methyl-(2-methyl-4-(6-(trifluoromethyl)quinazolin-2-yl)phenyl)-carbamoyl)-1H-pyrazole-3-carboxylic acid

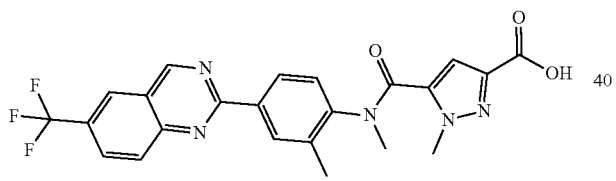

Proceeding analogously as described in Example 213, step 1 but substituting 2-(2-hydroxypropan-2-yl)isonicotinic acid with methyl 1-methyl-5-(methyl-(2-methyl-4-(6-(trifluoro-methyl)quinazolin-2-yl)phenyl)carbamoyl)-1H-pyrazole-3-carboxylate, the title compound was obtained as a yellow solid in 54% yield. LC-MS: (ES, m/z): [M+H]⁺ 470.

Step 1: 3-(methoxycarbonyl)-1-methyl-1H-pyrazole-5-carboxylic acid

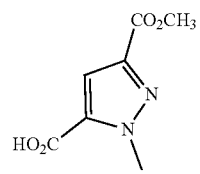

Proceeding analogously as described in Example 213, step 1 but substituting methyl 2-(2-hydroxypropan-2-yl)isonicotinate with dimethyl 1-methyl-1H-pyrazole-3,5-dicarboxylate, the title compound was obtained as a white solid in 31% yield.

Step 2: methyl 1-methyl-5-(methyl-(2-methyl-4-(6-(trifluoromethyl)quinazolin-2-yl)phenyl)-carbamoyl)-1H-pyrazole-3-carboxylate

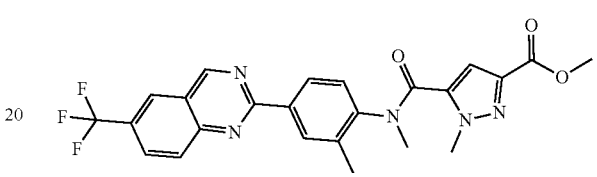

Proceeding analogously as described in Example 213, but substituting 2-(2-hydroxy-propan-2-yl)isonicotinic acid with 3-(methoxycarbonyl)-1-methyl-1H-pyrazole-5-carboxylic acid, the title compound was obtained as a yellow solid in 54% yield.

Example 222: N5,1-dimethyl-N5-(2-methyl-4-(6-(trifluoromethyl)quinazolin-2-yl)phenyl)-1H-pyrazole-3,5-dicarboxamide

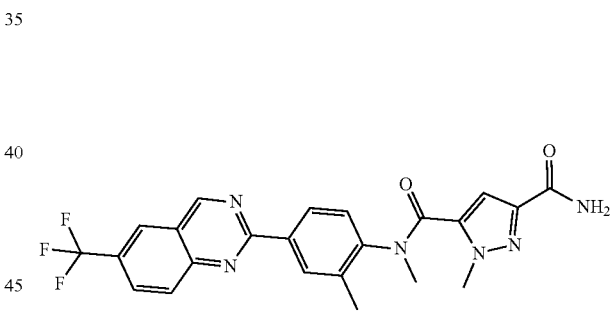

To a solution of 1-methyl-5-(methyl-(2-methyl-4-(6-(trifluoromethyl)quinazolin-2-yl)phenyl)-carbamoyl)-1H-pyrazole-3-carboxylic acid in DCM and 1 drop of DMF at 0° C., oxalyl chloride was added dropwise. The reaction mixture was brought to room temperature and stirred for 90 min. The reaction mixture was concentrated in vacuo, and the residue was dissolved in THF and the solution was cooled to 0° C. Conc. NH₄OH was added and the reaction mixture allowed to warm to room temperature. After 18 h, the reaction mixture was concentrated in vacuo and the residue was chromatographed on a silica gel column eluting with 20%-100% EtOAc-Hexanes to obtain crude product. The crude product was re-chromatography eluting with 1%-10% MeOH-DCM to obtain the title compound as an off-white solid which was triturated with diethyl ether, filtered, and then dried to give the pure product in 18% yield. LC-MS: (ES, m/z): [M+H]⁺ 469; ¹H-NMR: (300 MHz, DMSO, ppm): δ2.25 (s, 3H), 3.27 (s, 3H), 4.00 (s, 3H), 5.83 (s, 1H), 7.10 (s, 1H), 7.36 (s, 1H), 7.46 (d, 1H), 8.15-8.25 (m, 2H), 8.36 (dd, 1H), 8.44 (d, 1H), 8.66 (s, 1H), 9.82 (s, 1H).

Example 223: 1-(2-hydroxyethyl)-N-methyl-N-[2-methyl-4-[8-methyl-6-(trifluoromethyl)-1,5-naphthyridin-2-yl]phenyl]-1H-pyrazole-5-carboxamide

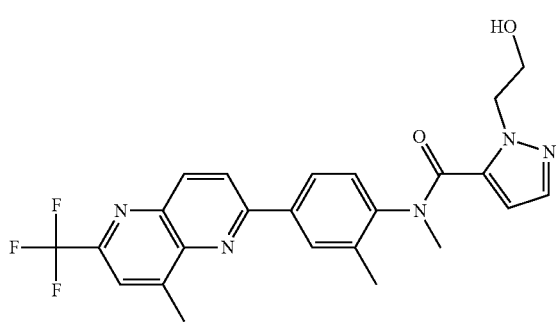 [SMILES: Cc1cc(-c2ccc3nc(C(F)(F)F)cc(C)c3n2)ccc1N(C)C(=O)c1ccnn1CCO]

Proceeding analogously as described in Example 171, Step 2 but substituting 1-(2-(benzyloxy)ethyl)-N-methyl-N-(2-methyl-4-(8-methyl-6-(trifluoromethyl)pyrido[3,2-d]pyrimidin-2-yl)phenyl)-1H-pyrazole-5-carboxamide with 1-[2-(benzyloxy)ethyl]-N-methyl-N-[2-methyl-4-[8-methyl-6-(trifluoromethyl)-1,5-naphthyridin-2-yl]phenyl]-1H-pyrazole-5-carboxamide provided crude product. The crude product was applied onto a prep-TLC and eluted with ethyl acetate/petroleum ether (1:2) to give the title compound in 57.83% yield. LC-MS: (ES, m/z): [M+H]$^+$ 470; $^1$H-NMR: (300 MHz, CDCl$_3$, ppm): δ 8.56-8.53 (d, 1H), 8.23-8.12 (m, 3H), 7.84-7.83 (d, 1H), 7.32-7.29 (d, 1H), 7.21-7.20 (d, 1H), 5.57-5.56 (d, 1H), 4.78-4.63 (m, 2H), 4.09-4.08 (t, 2H), 3.43 (s, 3H), 3.00 (s, 3H), 2.32 (s, 3H).

Step 1: 1-[2-(benzyloxy)ethyl]-N-methyl-N-[2-methyl-4-[8-methyl-6-(trifluoromethyl)-1,5-naphthyridin-2-yl]phenyl]-1H-pyrazole-5-carboxamide

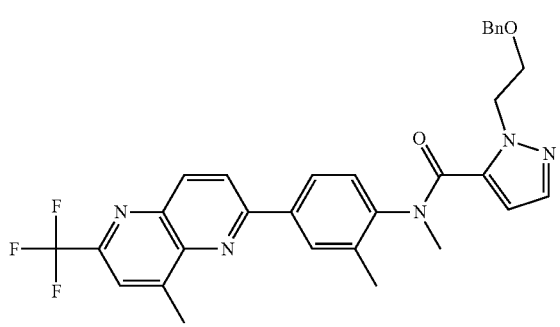 [SMILES: Cc1cc(-c2ccc3nc(C(F)(F)F)cc(C)c3n2)ccc1N(C)C(=O)c1ccnn1CCOCc1ccccc1]

Proceeding analogously as described in Example 201, Step 6 but substituting 8-bromo-2-chloro-6-(trifluoromethyl)quinoline with 6-chloro-4-methyl-2-(trifluoromethyl)-1,5-naphthyridine provided the title compound in 86.67% yield.

Example 224: 1-(2-hydroxy-2-methylpropyl)-N-methyl-N-(2-methyl-4-(8-methyl-6-(trifluoromethyl)pyrido[3,2-d]pyrimidin-2-yl)phenyl)-1H-pyrazole-5-carboxamide

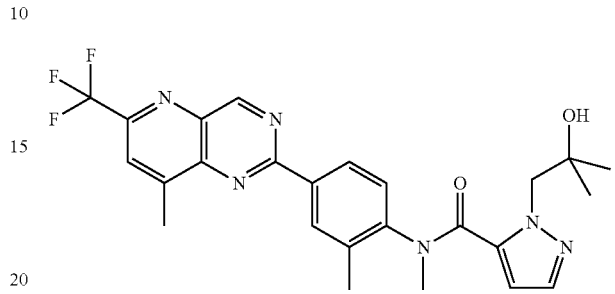

Into an 8-mL sealed tube was placed 1-[2-(benzyloxy)-2-methylpropyl]-N-methyl-N-[2-methyl-4-[8-methyl-6-(trifluoromethyl)pyrido[3,2-d]pyrimidin-2-yl]phenyl]-1H-pyrazole-5-carboxamide (120 mg, 0.20 mmol, 1 equiv.), DCM (1.5 mL), and BCl$_3$ (26.0 mg, 0.22 mmol, 1.10 equiv.). The resulting solution was stirred for 1 min at 0° C. and then quenched with NaHCO$_3$. The resulting solution was extracted with ethyl acetate and after removal of the organics, the residue was applied onto Prep-TLC and eluted with ethyl acetate/petroleum ether (1:2) to give the title compound as a white solid in 59.14% yield. LC-MS: (ES, m/z): [M+H]$^+$ 499; $^1$H-NMR: (400 MHz, DMSO, ppm): δ 0.99 (s, 2H), 1.20 (s, 3H), 2.38 (m, 3H), 2.92-2.95 (d, 3H), 3.29-3.32 (m, 2H), 3.36 (s, 1H), 4.16-4.20 (d, 1H), 4.63-4.67 (d, 1H), 4.83 (s, 1H), 5.54 (s, 1H), 7.17 (s, 1H), 7.56-7.57 (d, 1H), 8.31-8.33 (d, 1H), 8.39 (s, 1H), 8.58 (s, 1H), 9.88 (s, 1H).

Step 1: methyl 2-(benzyloxy)-2-methylpropanoate

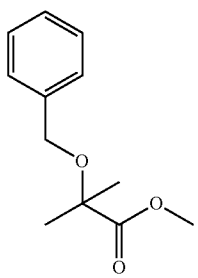

Into a 250-mL 3-necked round-bottom flask purged and maintained with an inert atmosphere of nitrogen, was placed methyl 2-hydroxy-2-methylpropanoate (10 g, 84.65 mmol, 1 equiv.), and DMF (100 mL), and NaH (2.0 g, 84.65 mmol, 1 equiv.) was added at 0° C. The resulting solution was stirred for 1 h at 0° C. and then benzyl bromide (15.9 g, 93.12 mmol, 1.1 equiv.) was added. The resulting solution was stirred for 12 h at 25° C. and then quenched with NH₄Cl. The resulting solution was extracted with ethyl acetate and the organic layer was concentrated. The residue was applied onto a silica gel column with ethyl acetate/petroleum ether (1:10) to give the title compound as a yellow liquid in 17.02% yield.

Step 2: 2-(benzyloxy)-2-methylpropan-1-ol

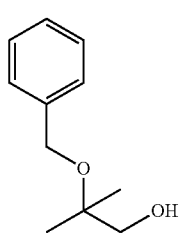

Into a 100-mL 3-necked round-bottom flask purged and maintained with an inert atmosphere of nitrogen, was placed methyl 2-(benzyloxy)-2-methylpropanoate (3 g, 14.41 mmol, 1 equiv.) and THF (30 mL) and LiAlH₄ (0.6 g, 15.81 mmol, 1.10 equiv.) was added at 0° C. The resulting solution was stirred for 1 h at 0° C. and then quenched with NaHCO₃. The resulting solution was extracted with ethyl acetate and the organic layer was concentrated. The residue was applied onto a silica gel column and eluted with ethyl acetate/petroleum ether (1:20) to give the title compound as a yellow oil in 38.51% yield.

Step 3: methyl 1-[2-(benzyloxy)-2-methylpropyl]-1H-pyrazole-5-carboxylate

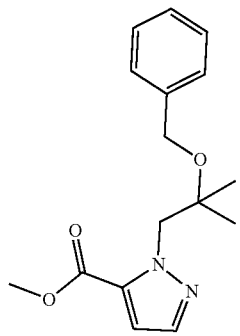 [SMILES: COC(=O)c1ccnn1CC(C)(C)OCc1ccccc1]

Into a 25-mL 3-necked round-bottom flask purged and maintained with an inert atmosphere of nitrogen, was placed 2-(benzyloxy)-2-methylpropan-1-ol (1 g, 5.55 mmol, 1 equiv.), methyl 1H-pyrazole-5-carboxylate (0.7 g, 5.55 mmol, 1 equiv.), and DIAD (2.2 g, 11.10 mmol, 2 equiv.) in THF (10 mL). PPh₃ (2.9 g, 11.10 mmol, 2 equiv.) was added at 0° C. and the resulting solution was stirred for 6 h at 25° C. The resulting mixture was concentrated and the residue was applied onto a silica gel column and eluted with ethyl acetate/petroleum ether (1:4) to give the title compound as a yellow solid in 21.88% yield.

Step 4: 1-[2-(benzyloxy)-2-methylpropyl]-1H-pyrazole-5-carboxylic acid

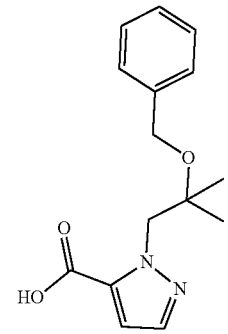 [SMILES: CC(C)(Cn1nccc1C(=O)O)OCc1ccccc1]

Into a 25-mL 3-necked round-bottom flask was placed methyl 1-[2-(benzyloxy)-2-methylpropyl]-1H-pyrazole-5-carboxylate (380 mg, 1.32 mmol, 1 equiv.), THF (8 mL), LiOH—H₂O (60.8 mg, 1.45 mmol, 1.1 equiv.), and H₂O (4 mL). The resulting solution was stirred for 3 h at 25° C. and then concentrated to give crude product.

Step 5: 1-[2-(benzyloxy)-2-methylpropyl]-N-(4-bromo-2-methylphenyl)-1H-pyrazole-5-carboxamide

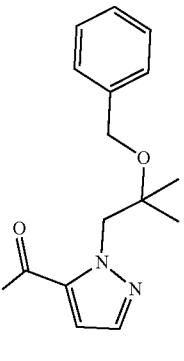

Proceeding analogously as described in Example 160, Step 8 but substituting 2-methylpyridine-4-carboxylic acid with 1-[2-(benzyloxy)-2-methylpropyl]-1H-pyrazole-5-carboxylic acid provided crude product. Purification by Prep-TLC with ethyl acetate/petroleum ether (1:3) gave the title compound as a yellow solid in 56.38% yield.

Step 6: 1-[2-(benzyloxy)-2-methylpropyl]-N-(4-bromo-2-methylphenyl)-N-methyl-1H-pyrazole-5-carboxamide

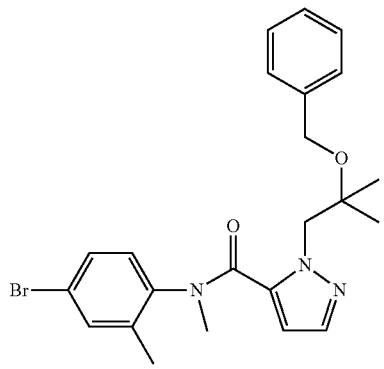 [SMILES: Cc1cc(Br)ccc1N(C)C(=O)c1ccnn1CC(C)(C)OCc1ccccc1]

Proceeding analogously as described in Example 165, Step 2 but substituting N-(4-bromo-2-fluorophenyl)-2-methylisonicotinamide with 1-[2-(benzyloxy)-2-methylpropyl]-N-(4-bromo-2-methylphenyl)-1H-pyrazole-5-carboxamide provided crude product. Purification by Prep-TLC with ethyl acetate/petroleum ether (1:3) as eluent provided the title compound as a yellow solid in 85.85% yield.

Step 7: 1-[2-(benzyloxy)-2-methylpropyl]-N-methyl-N-[2-methyl-4-(4,4,5,5-tetramethyl-1,3,2-dioxaborolan-2-yl)phenyl]-1H-pyrazole-5-carboxamide

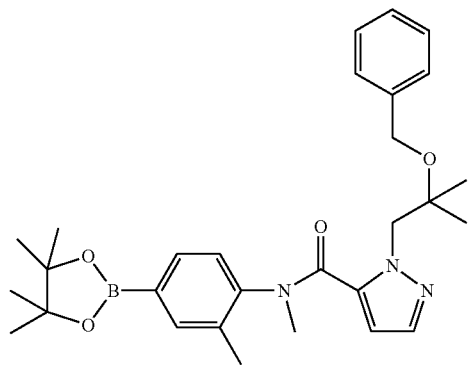 [SMILES: Cc1cc(B2OC(C)(C)C(C)(C)O2)ccc1N(C)C(=O)c1ccnn1CC(C)(C)OCc1ccccc1]

Proceeding as described in Example 161, Step 2 but substituting N-(4-bromo-2-methylphenyl)-N,2-dimethylpyridine-4-carboxamide with 1-[2-(benzyloxy)-2-methylpropyl]-N-(4-bromo-2-methylphenyl)-N-methyl-1H-pyrazole-5-carboxamide provided crude product. Purification by column chromatography with ethyl acetate/petroleum ether (1:10) provided the title compound as a yellow solid in 93.67% yield.

Step 8: 1-[2-(benzyloxy)-2-methylpropyl]-N-methyl-N-[2-methyl-4-[8-methyl-6-(trifluoromethyl)pyrido[3,2-d]pyrimidin-2-yl]phenyl]-1H-pyrazole-5-carboxamide

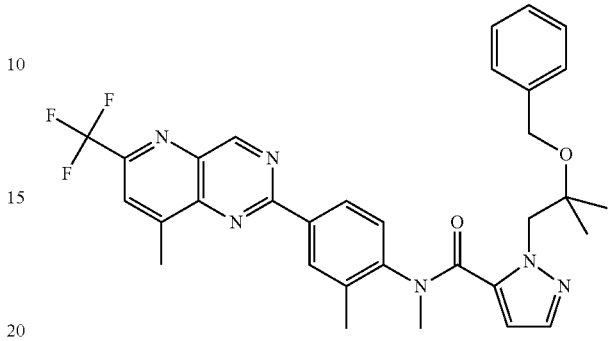

Proceeding as described in Example 162 but substituting N-(2-fluoro-4-(4,4,5,5-tetramethyl-1,3,2-dioxaborolan-2-yl)phenyl)-N,1-dimethyl-1H-pyrazole-5-carboxamide with 1-[2-(benzyloxy)-2-methylpropyl]-N-methyl-N-[2-methyl-4-(4,4,5,5-tetramethyl-1,3,2-dioxaborolan-2-yl)phenyl]-1H-pyrazole-5-carboxamide provided crude product. Purification by Prep-TLC with dichloromethane/methanol (30:1) as eluent provided the title compound as a yellow solid in 42.76% yield.

Example 225: 2-(5-(methyl(2-methyl-4-(6-(trifluoromethyl)quinazolin-2-yl)phenyl)-carbamoyl)-1H-pyrazol-1-yl)acetic acid

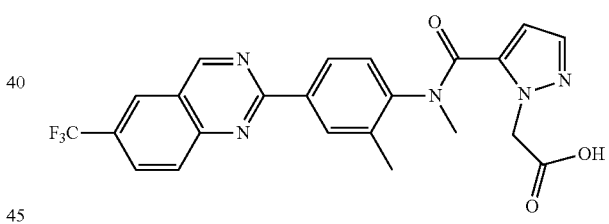

Into an 8-mL vial, was placed 1-(cyanomethyl)-N-methyl-N-(2-methyl-4-(6-(trifluoromethyl)-quinazolin-2-yl)phenyl)-1H-pyrazole-5-carboxamide (100 mg, 0.22 mmol, 1 equiv.), HCl (2 mL, 35%) and the resulting solution was stirred for 2 h at 100° C. The solids were collected by filtration and dried in an oven under reduced pressure to give the title compound as a white sold in 73.40% yield. LC-MS: (ES, m/z): [M+H]+ 470; 1H-NMR: (300 MHz, DMSO, ppm): δ2.34-2.44 (m, 3H), 3.25 (s, 3H), 4.63-4.76 (t, 1H), 4.95-5.00 (d, 1H), 5.38 (s, 1H), 7.04 (s, 1H), 7.40-7.78 (m, 1H), 8.23-8.36 (m, 3H), 8.47-8.57 (m, 1H), 8.71 (s, 1H), 9.70 (s, 1H).

BIOLOGICAL EXAMPLE

HEPG2 and HEPA1C1C7 cells were maintained in MEM and αMEM without nucleosides supplemented with 10% heat inactivated FBS respectively. Stably integrated DRE-luciferase cell lines were generated by transducing the both cell lines with Cignal XRE luciferase reporter (Qiagen) lentiviral particles according to the manufacturer protocol.

For both cell lines stably integrated reporter cell lines were selected for the presence of 2 μg/mL puromycin. Following selection of stably integrated cell line pools, clonal cell lines were isolated by limiting dilution in 96-well plates. Transcriptional assays were performed by seeding 100 μL of cells at a density of 250,000 or 100,000 cells/mL, for HEPG2 and HEPA1C1C7 DRE-Luc cells respectively, into 96-well cell culture plates in OptiMEM supplemented with 0.5% heat inactivated FBS and allowed to attach overnight. For modulator assays, the compounds were added in a semi-log dose response using a D300e Digital Dispenser (Tecan) followed normalization with vehicle (DMSO). Immediately following compound addition 10 μL of 2,3,7,8-Tetrachlorodibenzo-p-dioxin (TCDD) was added to the cells to a final concentration of 3 nM or 0.3 nM for the HEPG2 and HEPA1C1C7 DRE-Luc cells respectively. Following 24 hour incubation the medium was removed and the cells were lysed in 25 μL of Reporter Lysis Buffer (Promega). Firefly luciferase activity was measured immediately following the addition of 50 μL Luciferase Assay Reagent (Promega). The percent maximal activity for each point was determined using the following equation: $(RLU_{sample}-RLU_{vehicle-TCDD})/(RLU_{vehicle+TCDD} RLU_{vehicle-TCDD})*100$. The relative $IC_{50}$, defined as the compound concentration required to reduce the TCDD induced response between the top and bottom plateau of each individual dose response curve by half, for each compound was determined using Prism 7 (GraphPad Software).

| Example | IC$_{50}$ hAhR (antagonist mode) |
|---|---|
| 001 | +++ |
| 002 | ++++ |
| 003 | ++ |
| 004 | ++++ |
| 005 | + |
| 006 | + |
| 007 | ++++ |
| 008 | ++++ |
| 009 | ++ |
| 010 | +++ |
| 011 | +++ |
| 012 | ++++ |
| 013 | + |
| 014 | +++ |
| 015 | + |
| 016 | ++ |
| 017 | + |
| 018 | ++++ |
| 019 | +++ |
| 020 | ++++ |
| 021 | ++ |
| 022 | + |
| 023 | ++ |
| 024 | +++ |
| 025 | + |
| 026 | ++ |
| 027 | ++ |
| 028 | ++ |
| 029 | + |
| 030 | + |
| 031 | ++ |
| 032 | ++ |
| 033 | +++ |
| 034 | ++ |
| 035 | + |
| 036 | ++ |
| 037 | ++ |
| 038 | ++ |
| 039 | ++ |
| 040 | +++ |
| 041 | + |
| 042 | ++ |
| 043 | + |
| 044 | + |
| 045 | + |
| 046 | ++ |
| 047 | + |
| 048 | + |
| 049 | +++ |
| 050 | ++ |
| 051 | ++++ |
| 052 | ++++ |
| 053 | ++ |
| 054 | +++ |
| 055 | + |
| 056 | ++ |
| 057 | +++ |
| 058 | +++ |
| 059 | +++ |
| 060 | +++ |
| 061 | ++ |
| 062 | + |
| 063 | + |
| 064 | +++ |
| 065 | +++ |
| 066 | ++ |
| 067 | ++ |
| 068 | + |
| 069 | + |
| 070 | ++ |
| 071 | +++ |
| 072 | +++ |
| 073 | ++++ |
| 074 | + |
| 075 | + |
| 076 | ++++ |
| 077 | +++ |
| 078 | +++ |
| 079 | ++ |
| 080 | + |
| 081 | + |
| 082 | ++ |
| 083 | ++ |
| 084 | + |
| 085 | + |
| 086 | + |
| 087 | + |
| 088 | + |
| 089 | + |
| 090 | + |
| 091 | +++ |
| 098 | + |
| 099 | ++++ |
| 100 | +++ |
| 101 | +++ |
| 102 | ++++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | ++++ |
| 113 | +++ |
| 114 | ++++ |
| 115 | ++++ |
| 116 | ++++ |
| 117 | ++ |
| 118 | +++ |
| 119 | ++++ |
| 120 | ++++ |
| 121 | ++++ |
| 122 | ++++ |
| 123 | ++ |
| 124 | ++++ |
| 125 | ++++ |
| 126 | ++++ |

| Example | IC$_{50}$ hAhR (antagonist mode) |
|---|---|
| 127 | ++++ |
| 128 | ++++ |
| 129 | +++ |
| 130 | ++++ |
| 131 | +++ |
| 132 | ++++ |
| 133 | + |
| 134 | +++ |
| 135 | ++++ |
| 136 | ++++ |
| 137 | ++++ |
| 138 | ++++ |
| 139 | ++ |
| 140 | ++++ |
| 141 | ++++ |
| 142 | ++++ |
| 143 | ++++ |
| 144 | ++++ |
| 145 | ++++ |
| 146 | + |
| 147 | ++++ |
| 148 | ++++ |
| 149 | ++++ |
| 150 | ++++ |
| 151 | ++++ |
| 152 | ++++ |
| 153 | ++++ |
| 154 | ++++ |
| 155 | +++ |
| 155 | ++++ |
| 156 | ++++ |
| 157 | ++++ |
| 158 | + |
| 159 | na |
| 160 | ++++ |
| 161 | +++ |
| 162 | ++++ |
| 163 | ++++ |
| 164 | ++++ |
| 165 | — |
| 166 | ++++ |
| 167 | ++++ |
| 168 | ++++ |
| 169 | ++++ |
| 170 | ++++ |
| 171 | +++ |
| 172 | ++++ |
| 173 | ++++ |
| 174 | ++++ |
| 175 | ++++ |
| 176 | Na |
| 177 | ++++ |
| 178 | Na |
| 179 | +++ |
| 180 | Na |
| 181 | ++++ |
| 182 | ++++ |
| 183 | ++++ |
| 184 | ++++ |
| 185 | ++++ |
| 186 | + |
| 187 | ++++ |
| 188 | ++++ |
| 189 | + |
| 190 | + |
| 191 | + |
| 192 | ++++ |
| 193 | ++ |
| 194 | + |
| 195 | + |
| 196 | + |
| 197 | + |
| 198 | ++++ |
| 199 | na |
| 200 | ++++ |
| 201 | ++++ |
| 202 | ++++ |

| Example | IC$_{50}$ hAhR (antagonist mode) |
|---|---|
| 203 | ++++ |
| 204 | + |
| 205 | ++ |
| 206 | Na |
| 207 | +++ |
| 208 | + |
| 209 | ++++ |
| 210 | ++++ |
| 211 | ++++ |
| 212 | ++++ |
| 213 | na |
| 214 | +++ |
| 215 | ++++ |
| 216 | ++++ |
| 217 | ++++ |
| 218 | ++++ |
| 219 | ++++ |
| 220 | + |
| 221 | na |
| 222 | ++++ |
| 223 | ++++ |
| 224 | +++ |
| 225 | na |

(+) IC50 = 10 uM-1 uM
(++) IC50 = 1 uM-500 nM
(+++) IC50 = 500 nM-200 nM
(++++) IC50 < 200 nM

What is claimed is:

1. A compound having the formula:

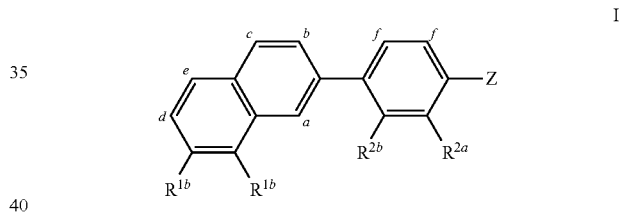

or a pharmaceutically acceptable salt, solvate or hydrate thereof;
a is N;
b is C(R$^{1a}$) or N;
c is C(R$^{1a}$);
ring vertex d is C(R$^{1b}$);
ring vertex e is selected from the group consisting of C(R$^{1b}$) and N;
each ring vertex f is selected from the group consisting of C(R$^{2c}$), C(R$^{2d}$) and N;
Z is

Z$^a$ is selected from the group consisting of:
(i) pyrazolyl, imidazolyl, oxazolyl, isoxazolyl, 1,2,4-triazolyl, pyridinyl, pyrimidinyl, pyridazinyl or pyrazinyl, which is substituted with from 0 to 4 R$^4$;
(ii) a 5-, 6- or 7-membered heterocycloalkyl group, which is optionally substituted with hydroxyl, deu terium, $C_{1-4}$ alkyl, $C_{1-4}$ haloalkyl, $C_{1-4}$ deuteroalkyl, and $C_{1-4}$ alkoxy; and (iii) a $C_{1-8}$ haloalkyl group or a $C_1$ alkoxy group;

each $R^{1a}$ and $R^{1b}$ is independently selected from the group consisting of hydrogen, halogen, —CN, —NO$_2$, —R$^c$, and —NR$^a$R$^b$; wherein each R$^a$ and R$^b$ is independently selected from hydrogen, $C_{1-8}$ alkyl, and $C_{1-8}$ haloalkyl; each R$^c$ is independently selected from the group consisting of $C_{1-8}$ alkyl, $C_{1-8}$ haloalkyl, $C_{2-6}$ alkenyl, $C_{2-6}$ alkynyl, $C_{3-6}$ cycloalkyl, 5- or 6-membered heterocycloalkyl, and 5- or 6-membered heteroaryl;

each $R^{2a}$, $R^{2b}$, $R^{2c}$ and $R^{2d}$ is independently selected from the group consisting of hydrogen, halogen, $C_{1-3}$ alkyl, $C_{1-3}$ haloalkyl, $C_{1-3}$ alkoxy, and $C_{1-3}$ haloalkoxy;

$R^3$ is selected from the group consisting of hydrogen, $C_{1-3}$ alkyl, and $C_{1-3}$ deuteroalkyl;

each $R^4$ is independently selected from the group consisting of halogen, —CN, —R$^f$, —CO$_2$R$^d$, —CONR$^d$R$^e$, —X$^1$—NR$^d$R$^e$, —X$^1$—OR$^d$, —X$^1$—P(O)(OH)$_2$, and —X$^1$—Y wherein each X$^1$ is independently $C_{1-6}$ alkylene and Y is selected from the group consisting of tetrazolyl, and morpholinyl;

each R$^d$ and R$^e$ is independently selected from hydrogen, $C_{1-8}$ alkyl, and $C_{1-8}$ haloalkyl;

each R$^f$ is independently selected from the group consisting of $C_{1-8}$ alkyl, and $C_{1-8}$ haloalkyl;

with the proviso that the compound is other than:
N-[4-[4-(ethylamino)-7-(trifluoromethyl)-2-quinazolinyl]phenyl]-2,2,2-trifluoroacetamide;
N-[4-(2-quinolinyl)phenyl]-3-pyridinecarboxamide;
1-(2-fluoroethyl)-N-(4-(quinolin-2-yl)phenyl-1H-1,2,3-triazole-4-carboxamide; or
a tautomer thereof.

2. A compound of claim 1, wherein d is selected from the group consisting of C(CN), C(C$_{1-4}$ haloalkyl).

3. A compound of claim 1, wherein d is C(CF$_3$).

4. A compound of claim 3, having a formula selected from the group consisting of:

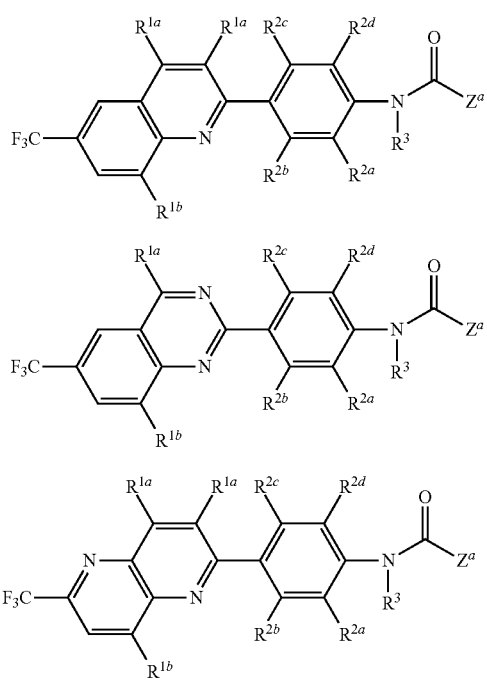

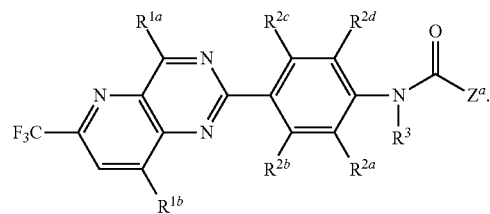

5. A compound of claim 4, wherein Z$^a$ is selected from the group consisting of pyrazolyl, imidazolyl, oxazolyl, isoxazolyl, 1,2,4-triazolyl, pyridinyl, pyrimidinyl, pyridazinyl and pyrazinyl, each of which is substituted with from 0 to 2 R$^4$.

6. A compound of claim 4, having formula I-1a, I-1b, I-1c, I-1f wherein Z$^a$ is pyrazolyl or pyridinyl, each of which is substituted with 0 to 3 R$^4$.

7. A compound of claim 4, wherein each R$^{1a}$ is hydrogen.

8. A compound of claim 4, wherein only one of R$^{2a}$, R$^{2b}$, R$^{2c}$ and R$^{2d}$ is other than hydrogen.

9. A compound of claim 4, wherein only one of R$^{2a}$, R$^{2b}$, R$^{2c}$ and R$^{2d}$ is other than hydrogen, and is selected from the group consisting of F and CH$_3$.

10. A compound of claim 4, wherein Z$^a$ is pyrazolyl or pyridinyl, each of which is substituted with 0 to 3 R$^4$; each R$^{1a}$ is hydrogen; one of R$^{2a}$, R$^{2b}$, R$^{2c}$ and R$^{2d}$ is other than hydrogen; and R$^3$ is hydrogen or methyl.

11. A compound of claim 1, wherein Z is:

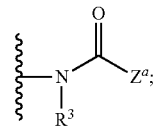

and
Z$^a$ is pyrazolyl, imidazolyl, pyridinyl, pyrimidinyl, pyridazinyl or pyrazinyl, which is substituted with from 0 to 4 R$^4$.

12. A compound of claim 1, wherein Z is:

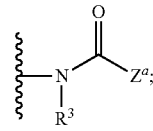

and
Z$^a$ is pyrazolyl, which is substituted with from 0 to 4 R$^4$.

13. A compound of claim 1, wherein Z is

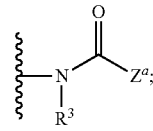

and
Z$^a$ is selected from the group consisting of: a $C_{1-8}$ haloalkyl group or a $C_1$ alkoxy group.

14. A compound of claim 13, wherein $Z^a$ is a $C_1$ alkoxy group.

15. A compound of claim 13, wherein $Z^a$ is a $C_{1-8}$ haloalkyl group.

16. A compound of claim 13, having a formula selected from the group consisting of:

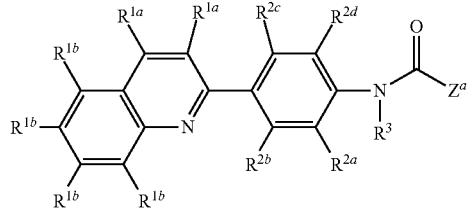

Ia

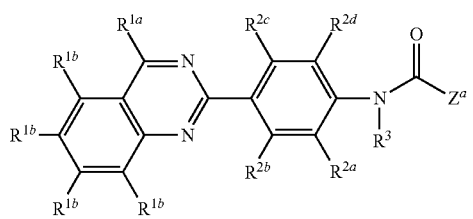

Ib

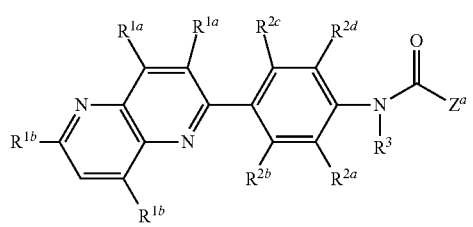

Ic

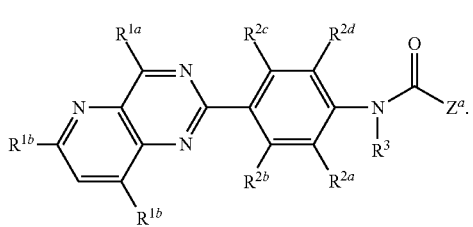

If

17. A pharmaceutical composition comprising a compound of claim 1 and a pharmaceutically acceptable excipient.

18. A method of treating cancer in a subject in need thereof, said method comprising administering to said subject an effective amount of a compound of claim 1.

19. A compound of claim 1, selected from the group consisting of

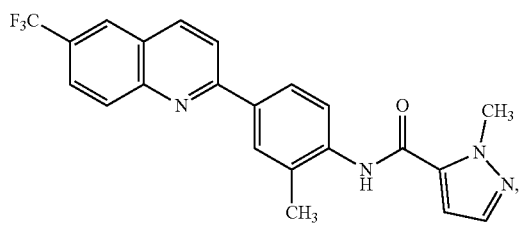

-continued

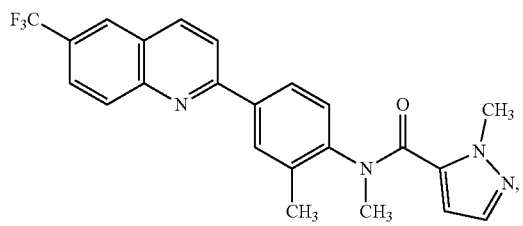

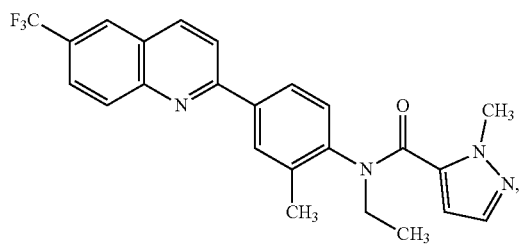

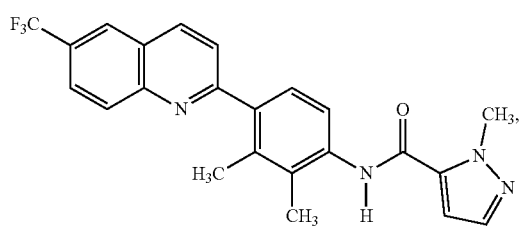

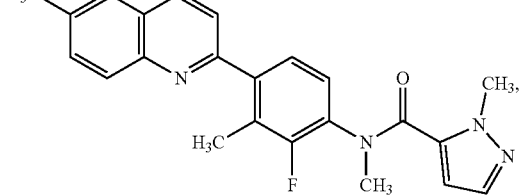

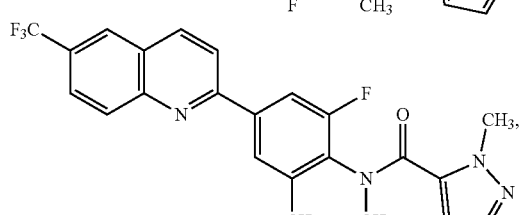

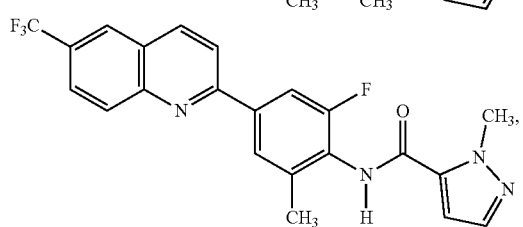

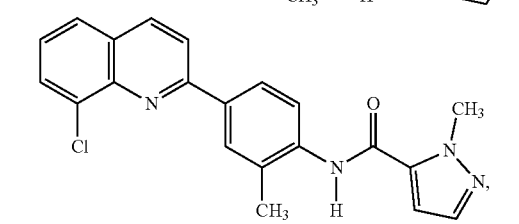

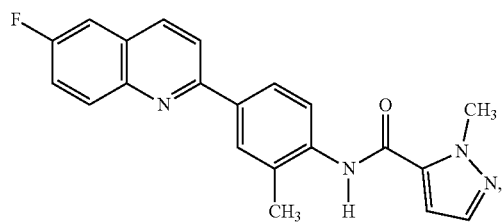
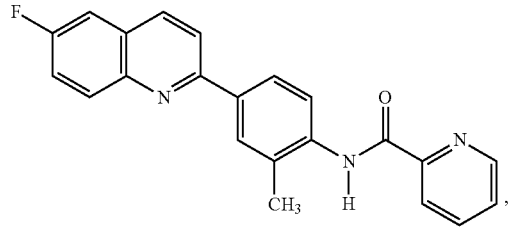
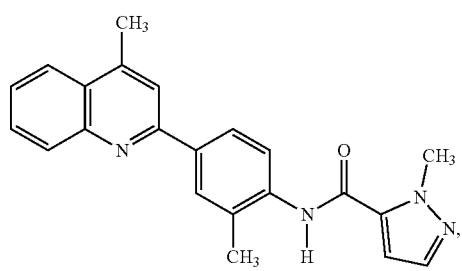
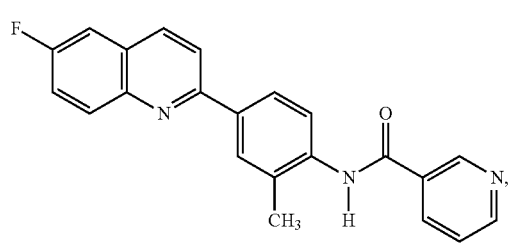
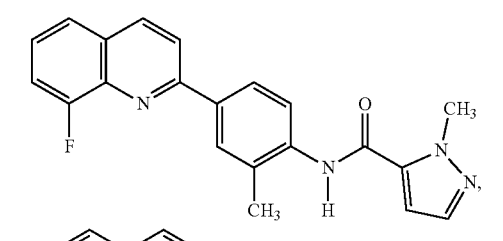
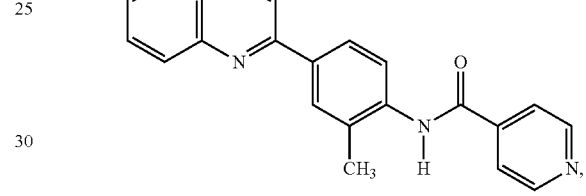
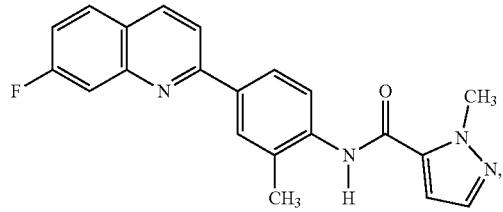
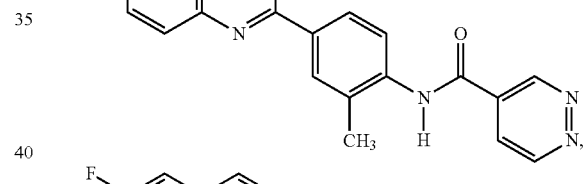
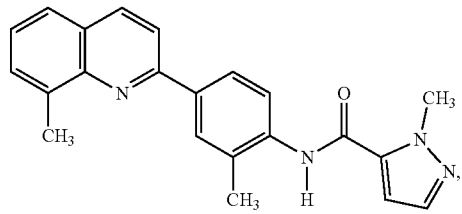
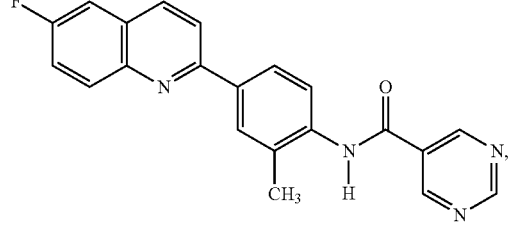
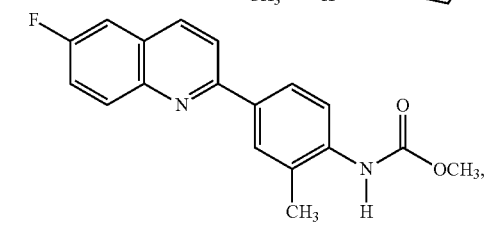
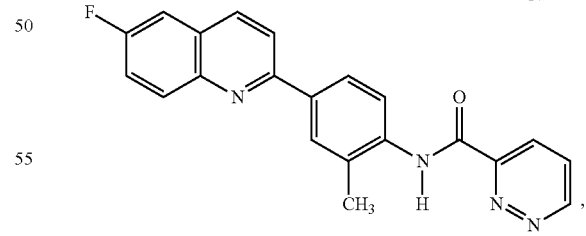
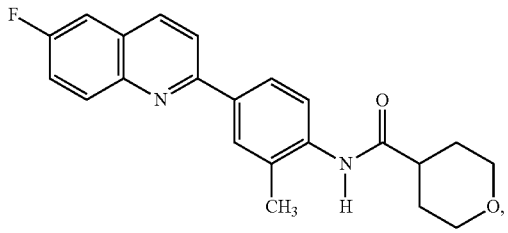
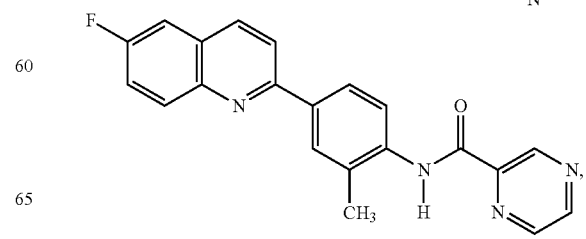

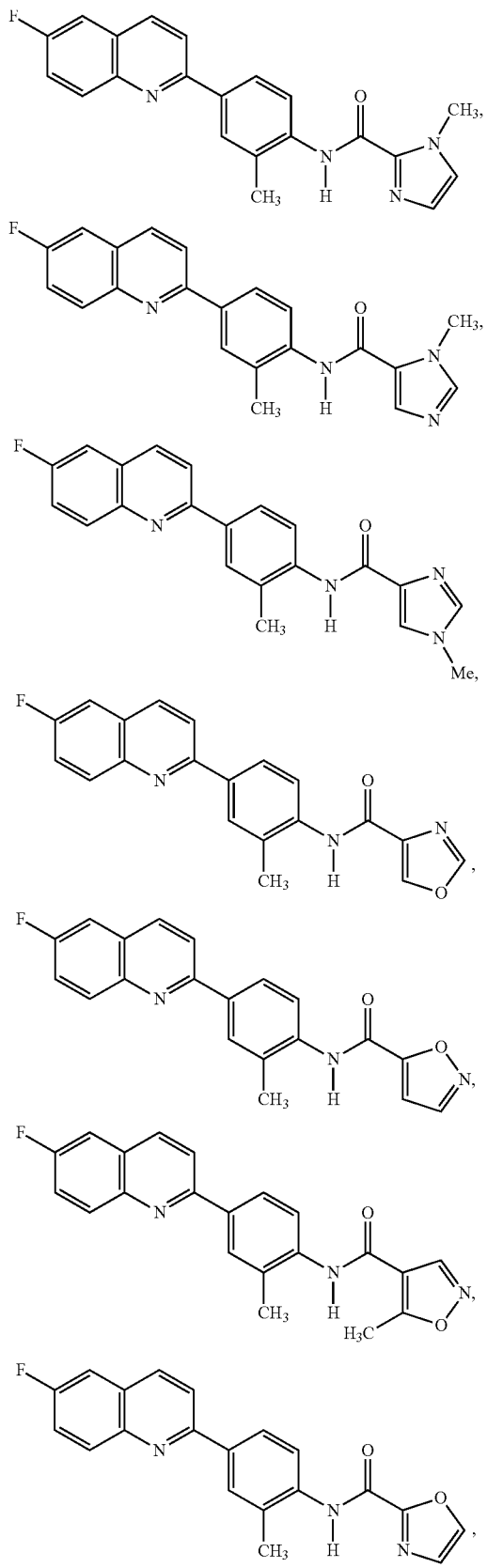
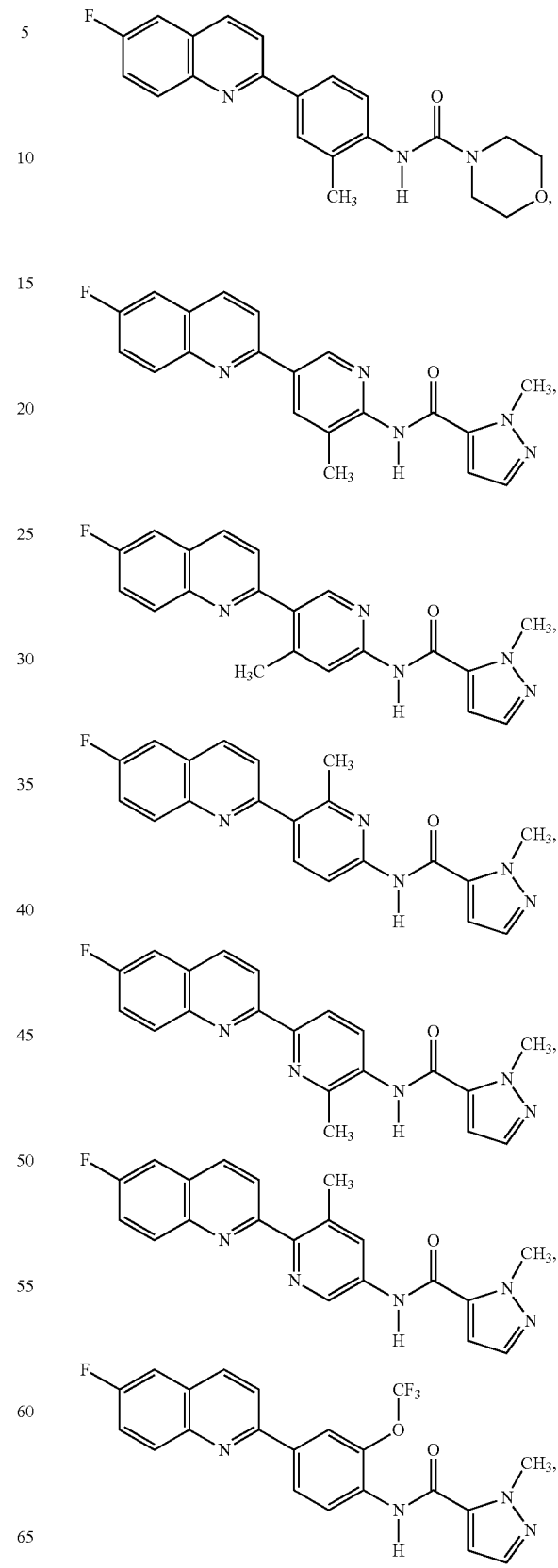

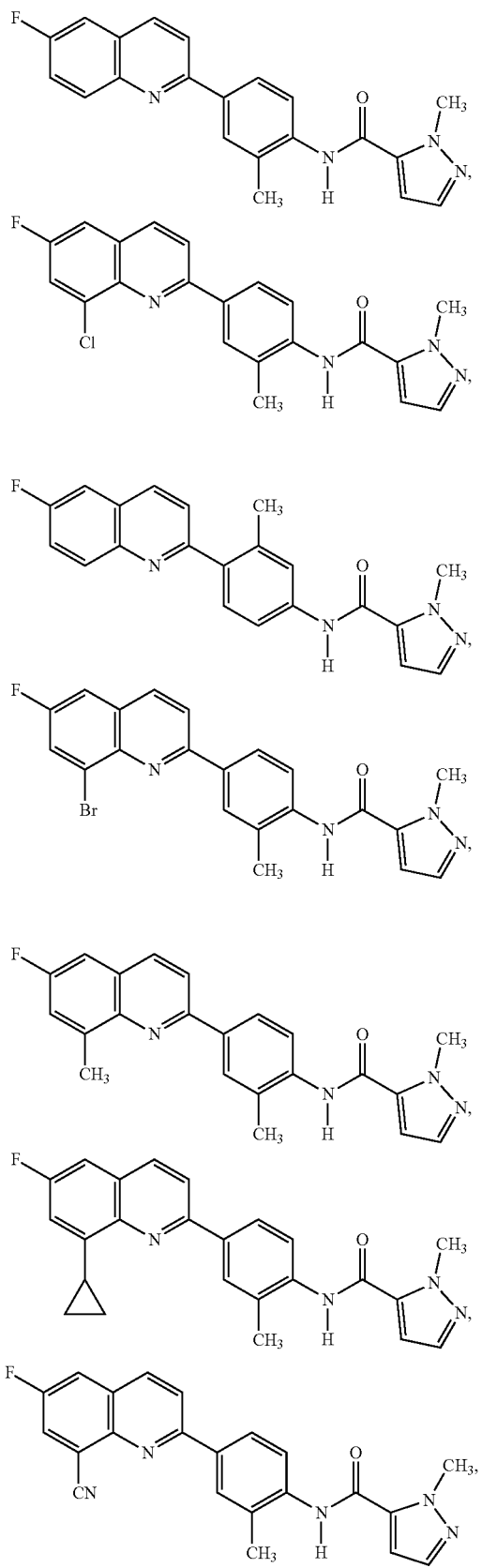
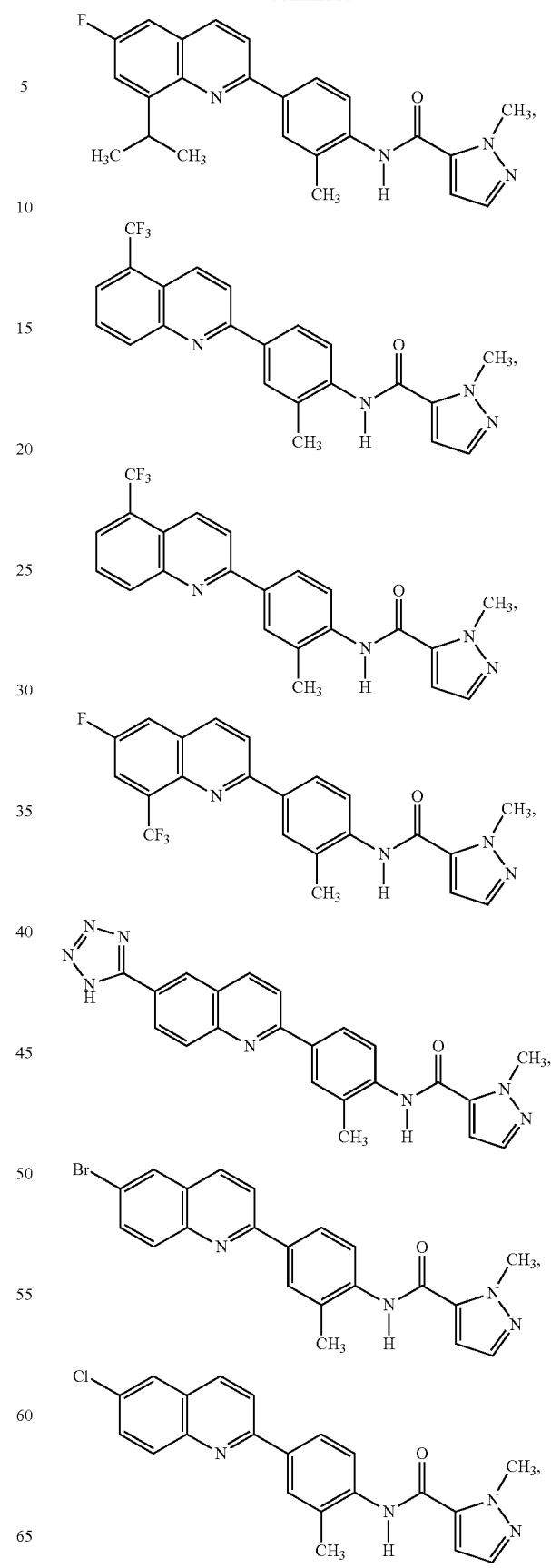

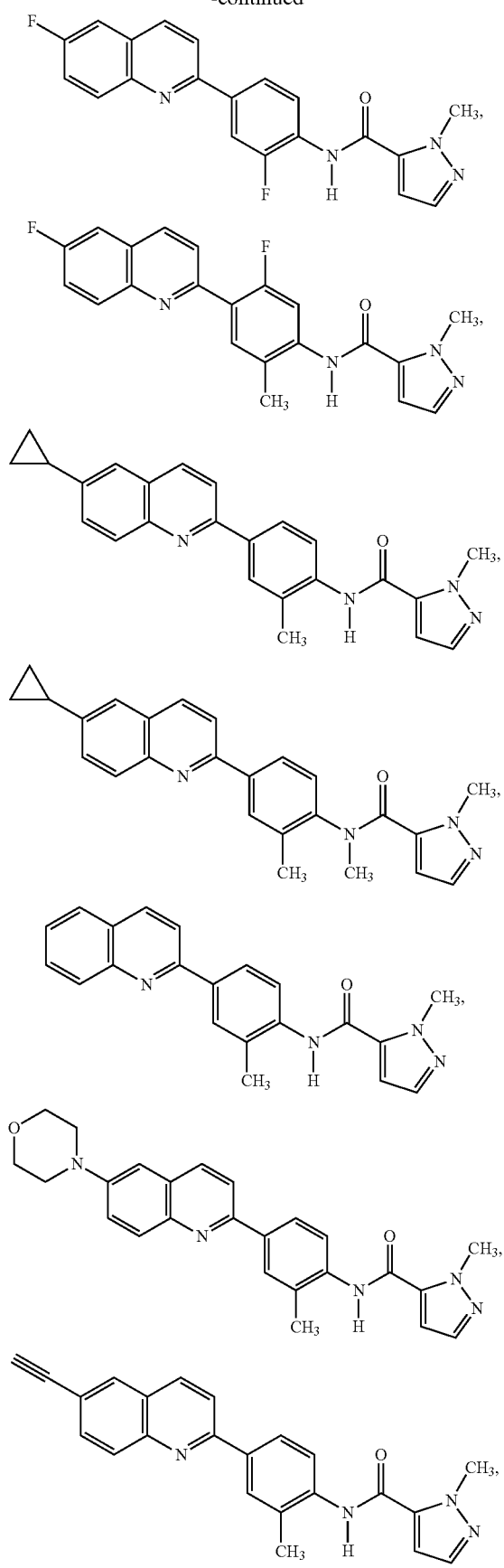
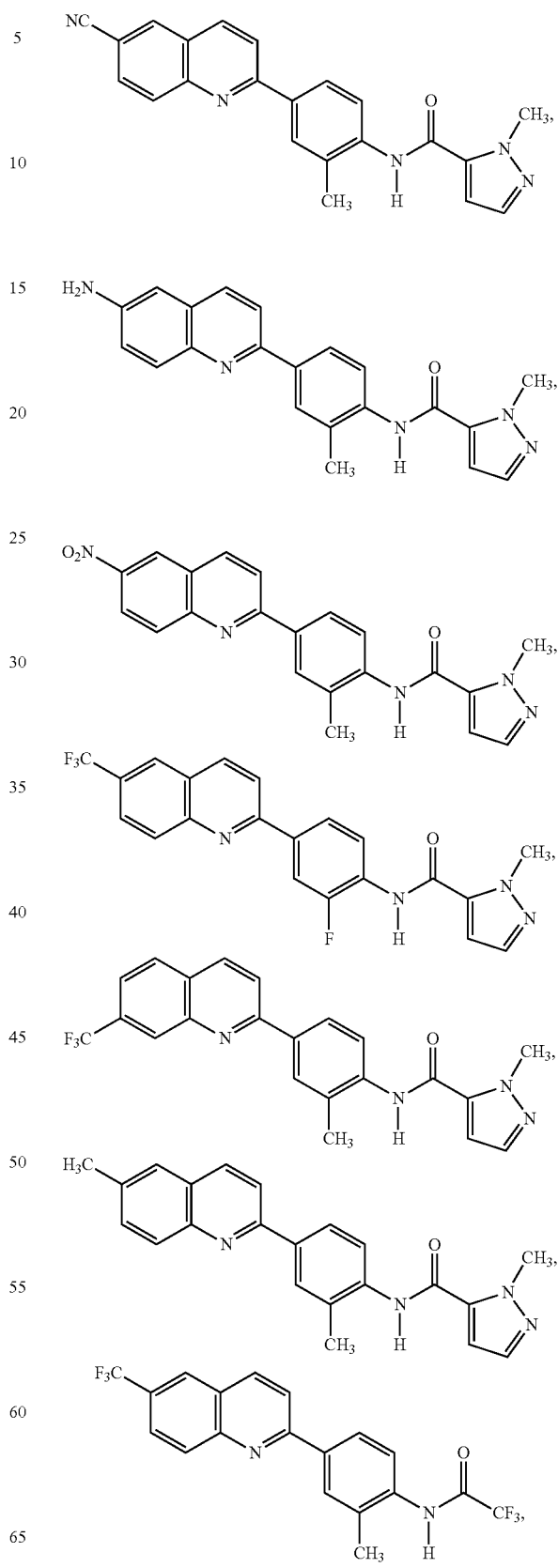

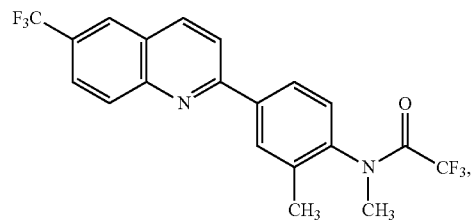
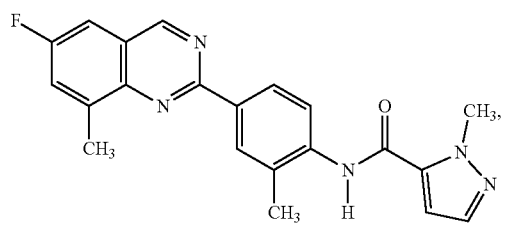
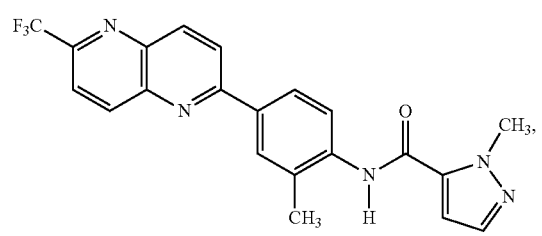
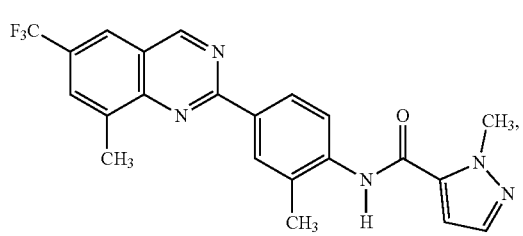
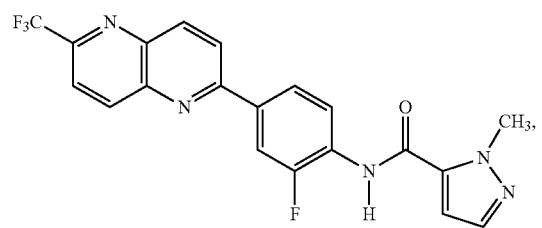
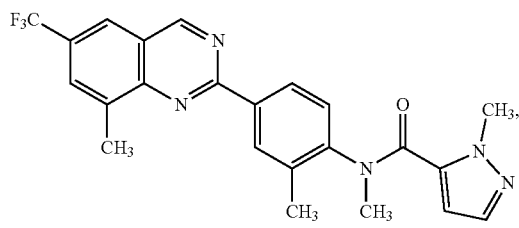
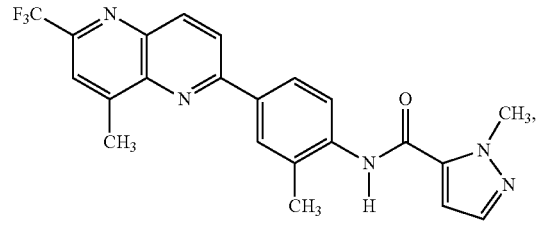
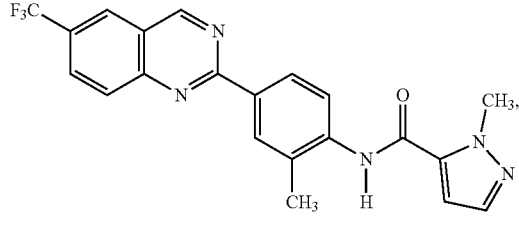
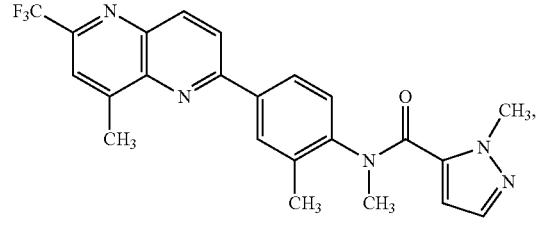
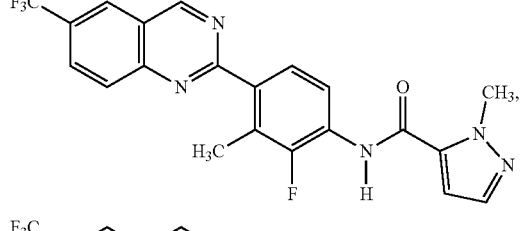
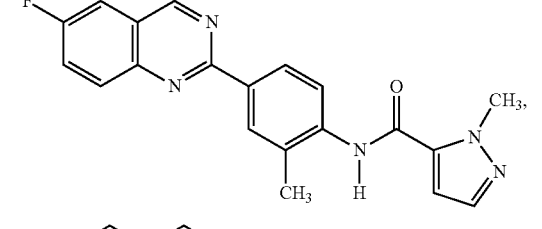
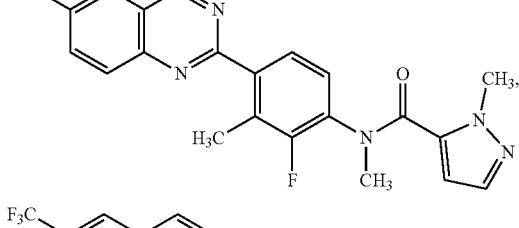
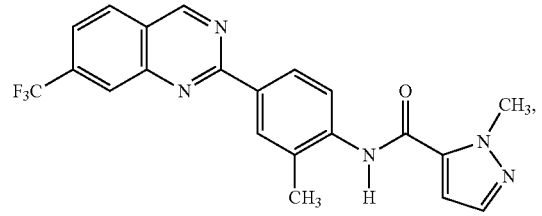
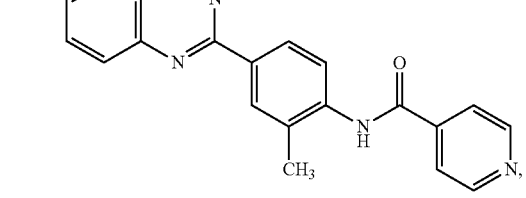

283
-continued
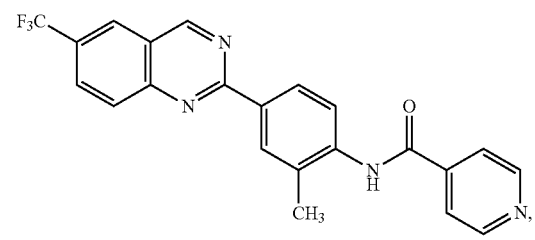
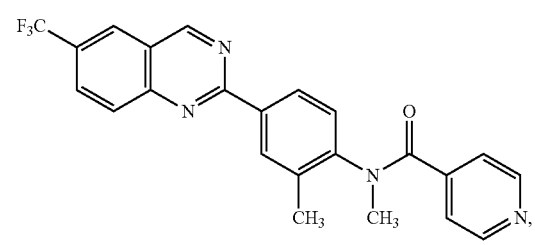
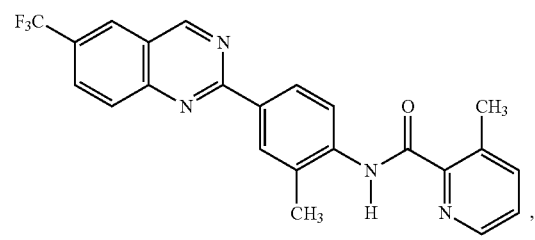
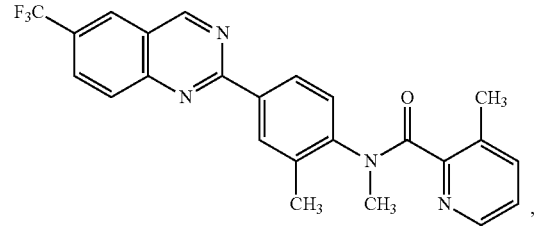
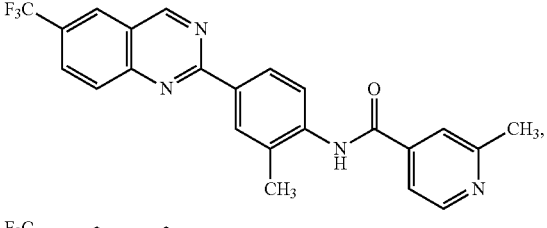
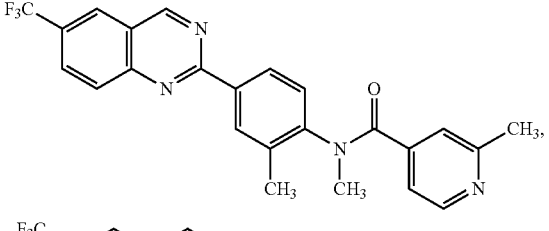
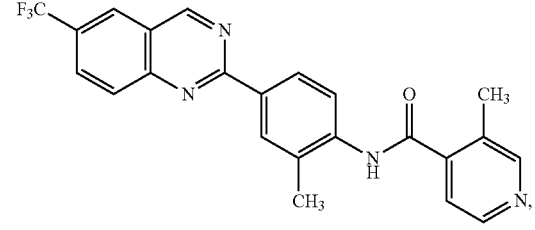
284
-continued
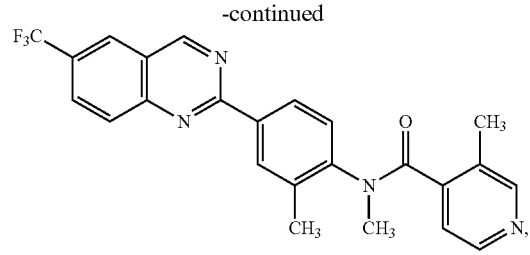
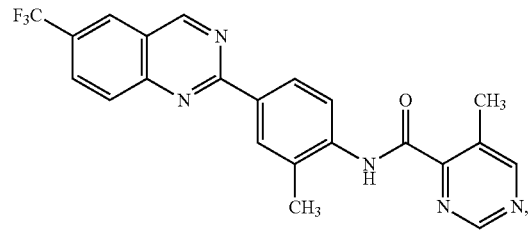
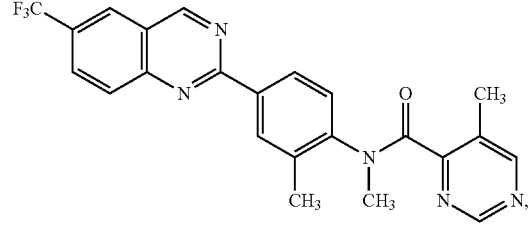
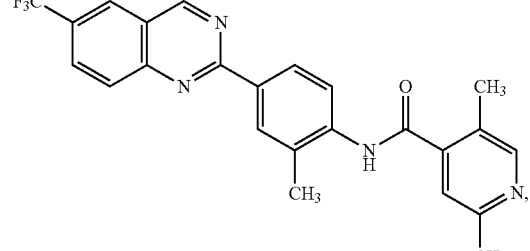
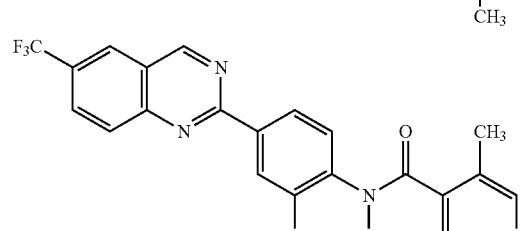
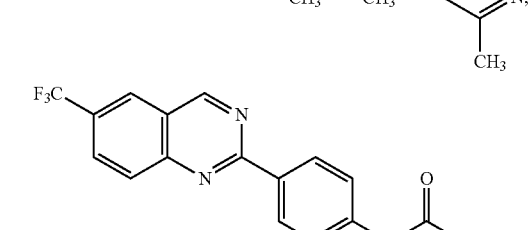
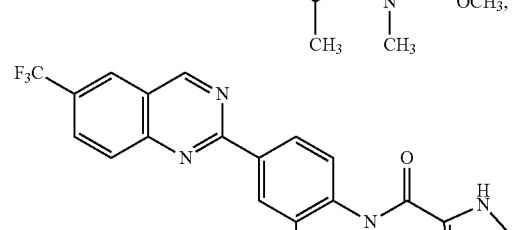

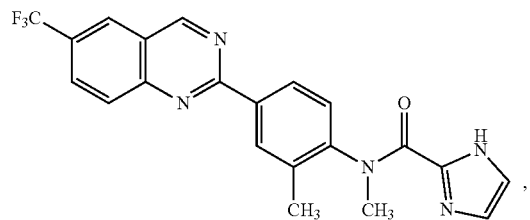
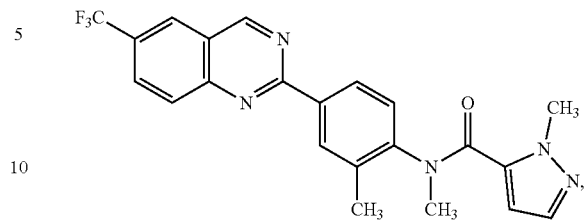
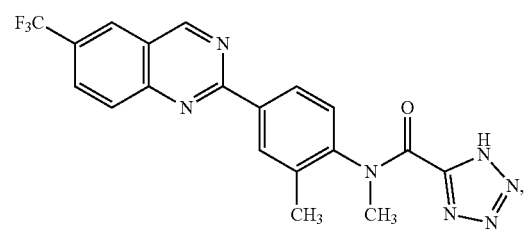
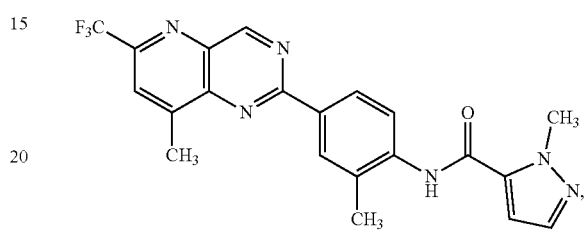
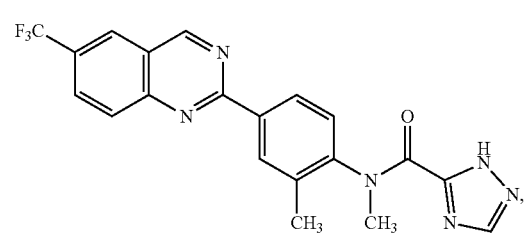
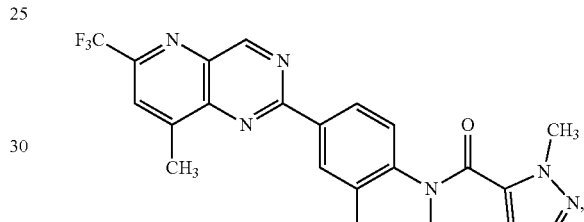
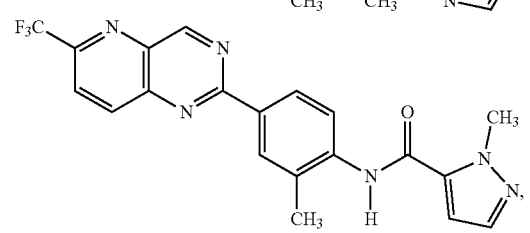
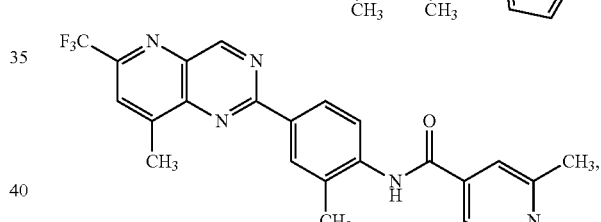
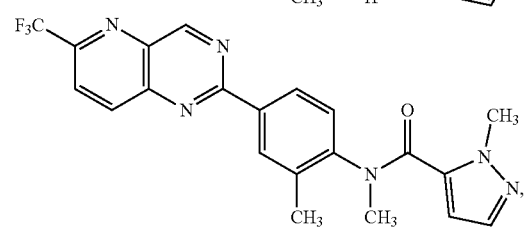
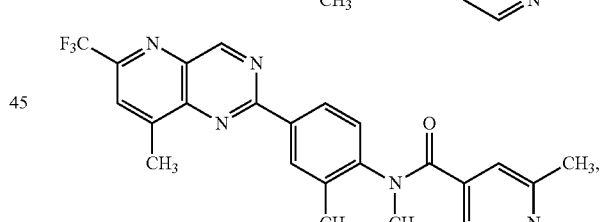
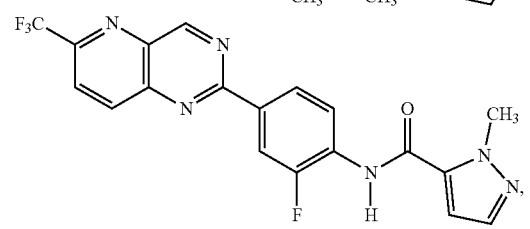
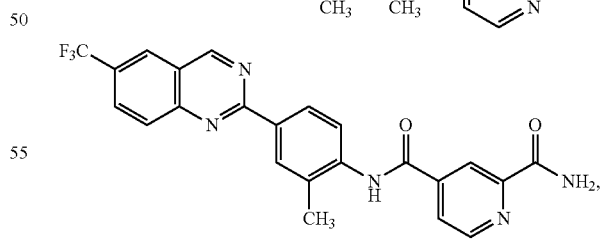
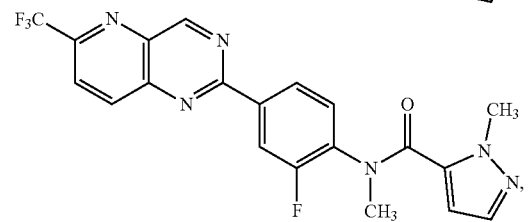
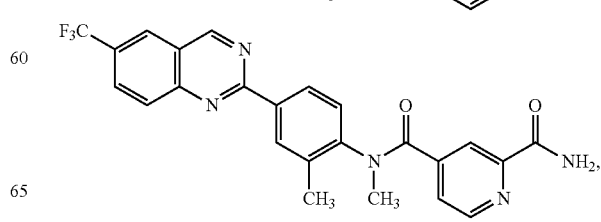

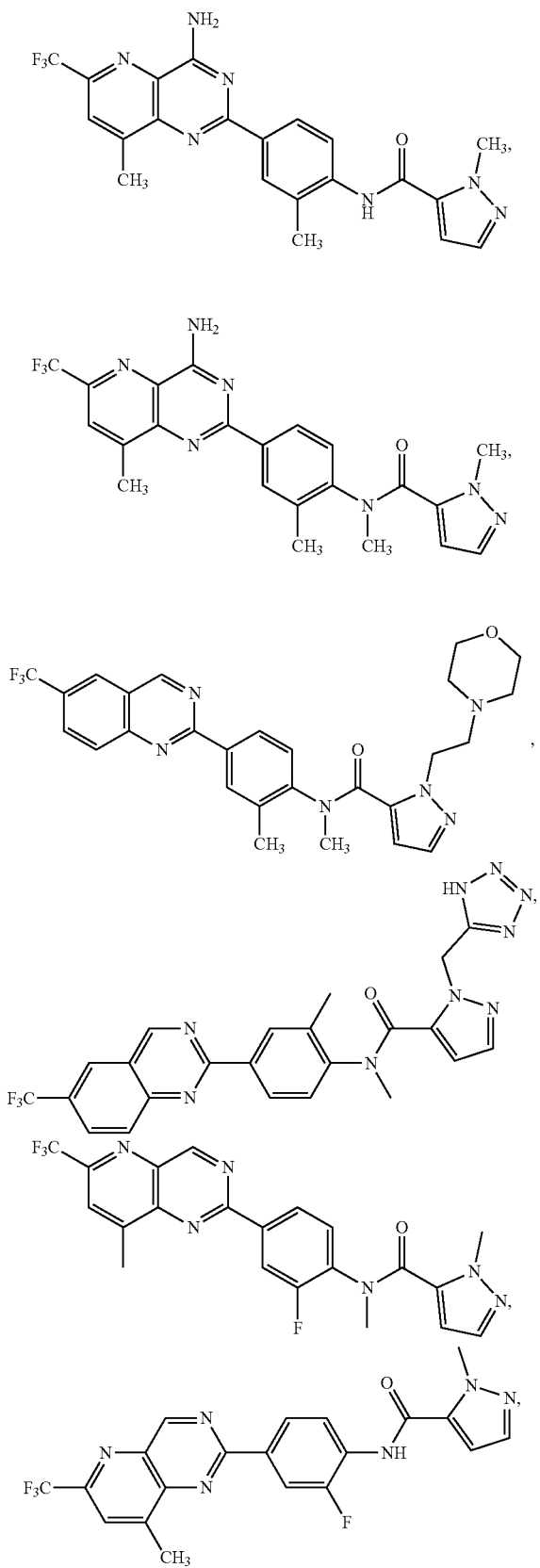
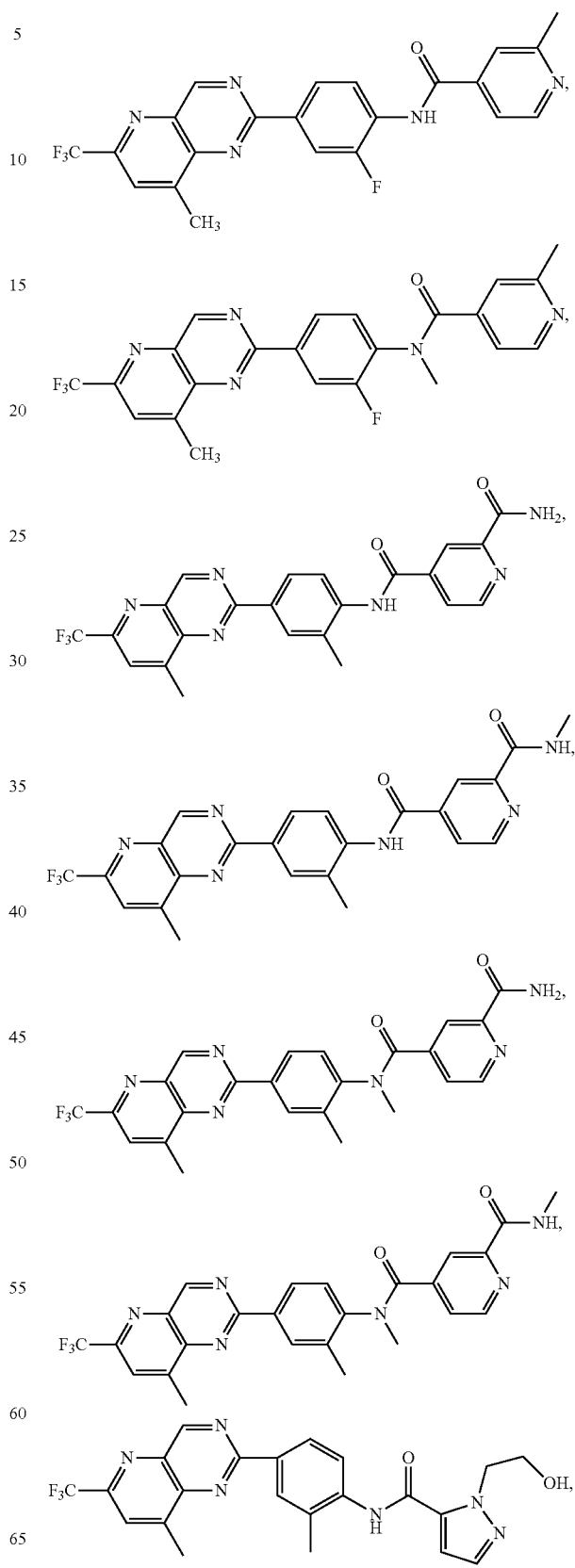

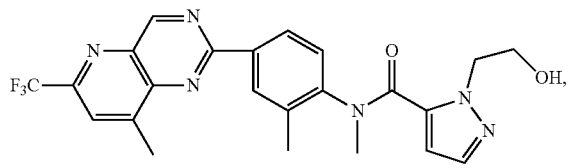
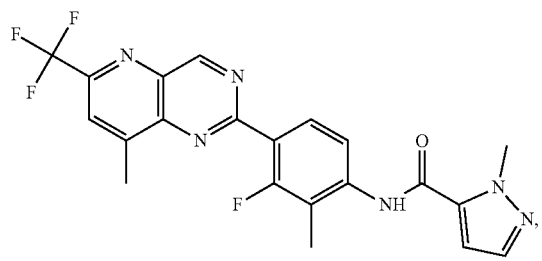
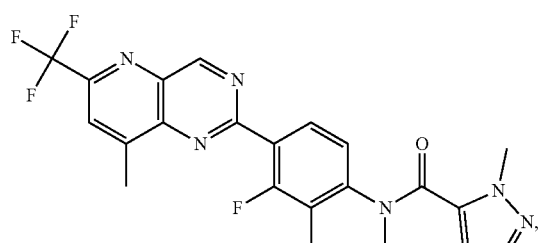
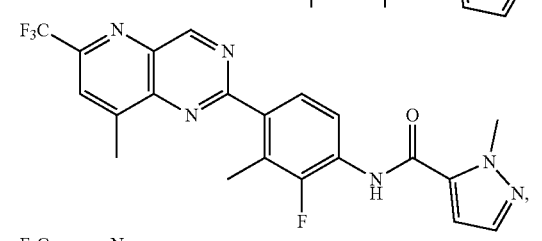
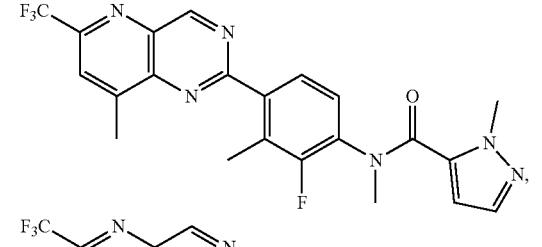
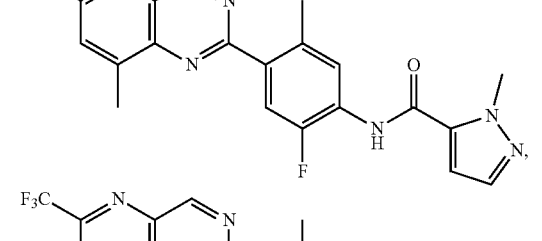
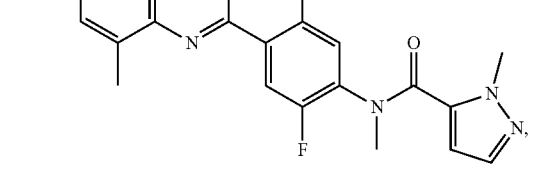
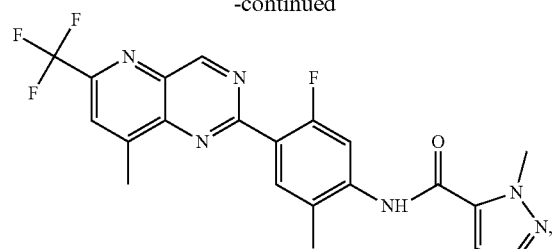
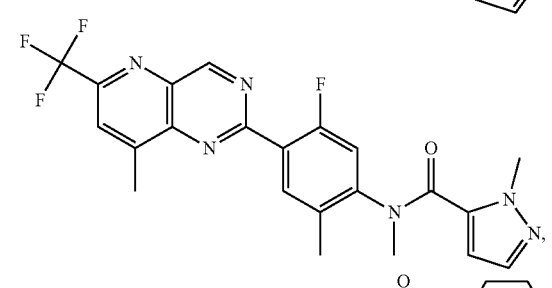
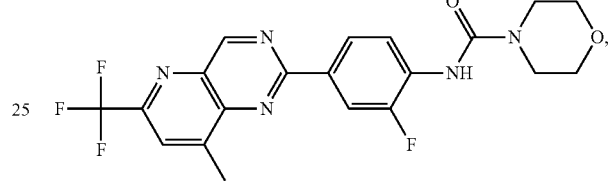
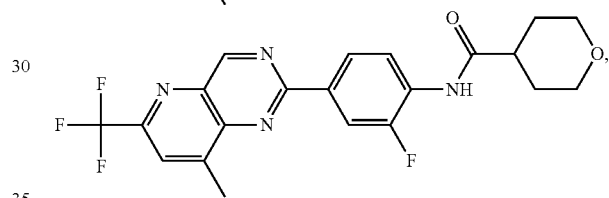
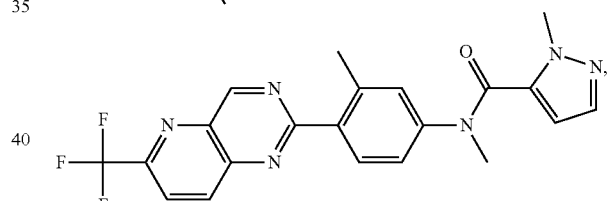
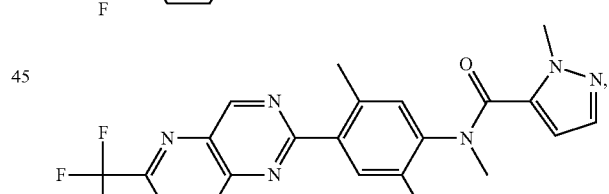
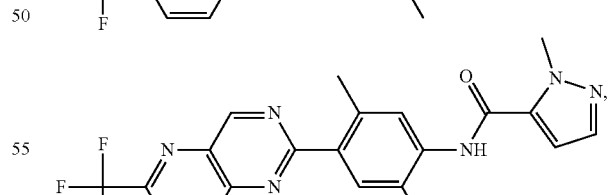

291
-continued
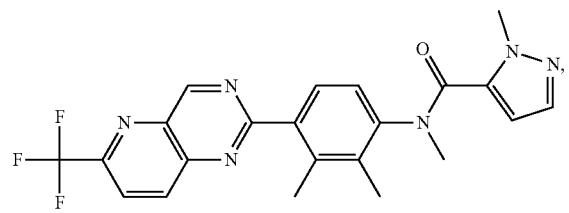
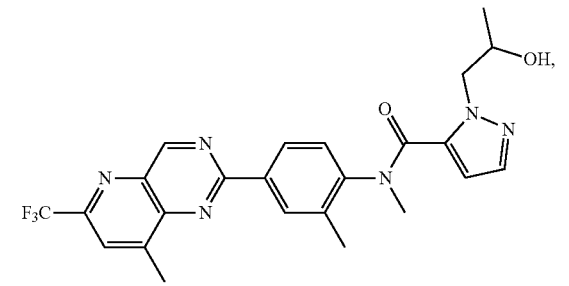
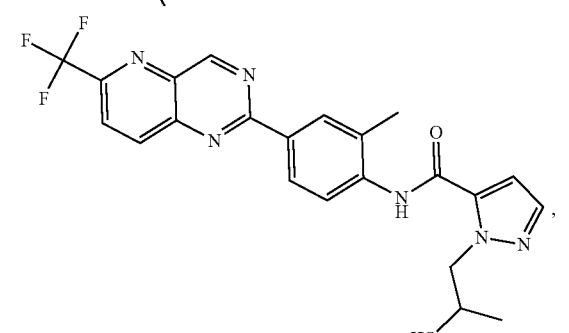
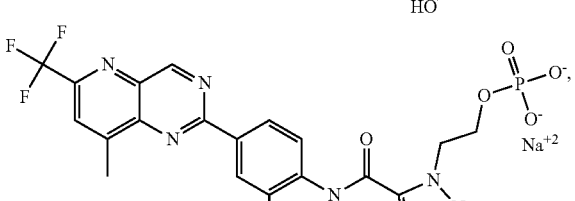
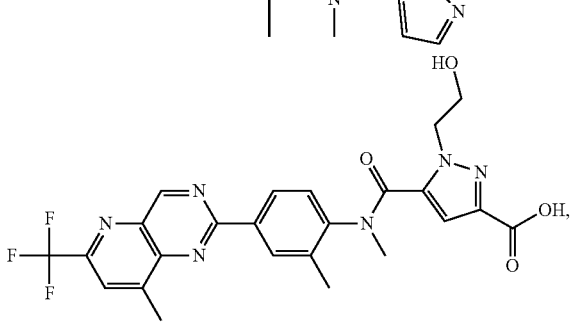
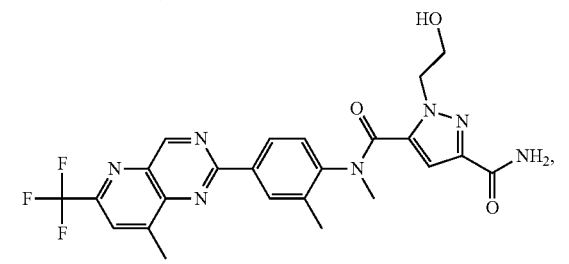
292
-continued
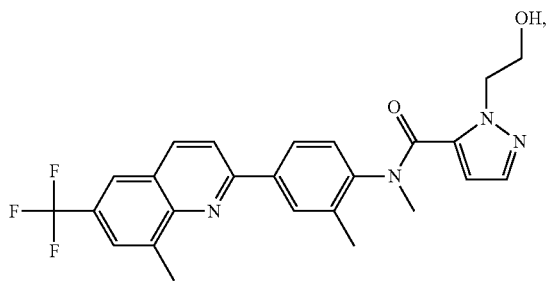
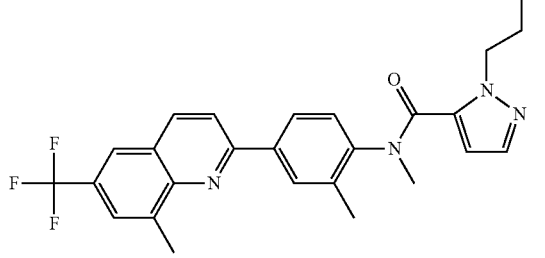
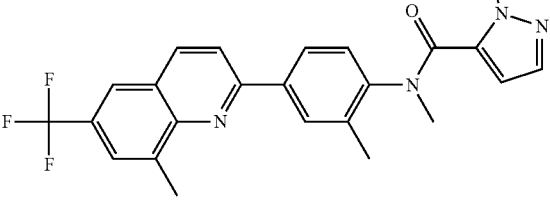
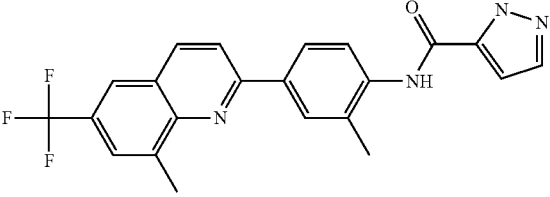
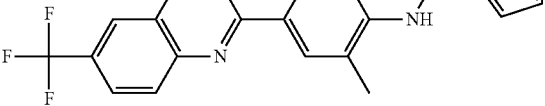
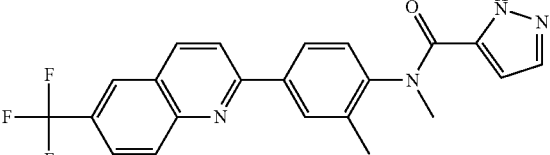
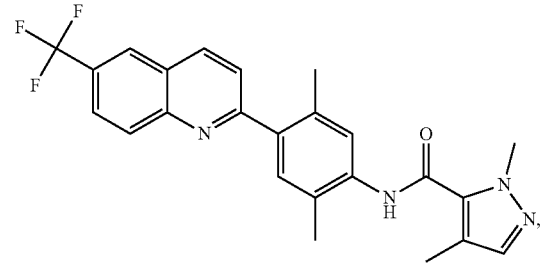

293
-continued
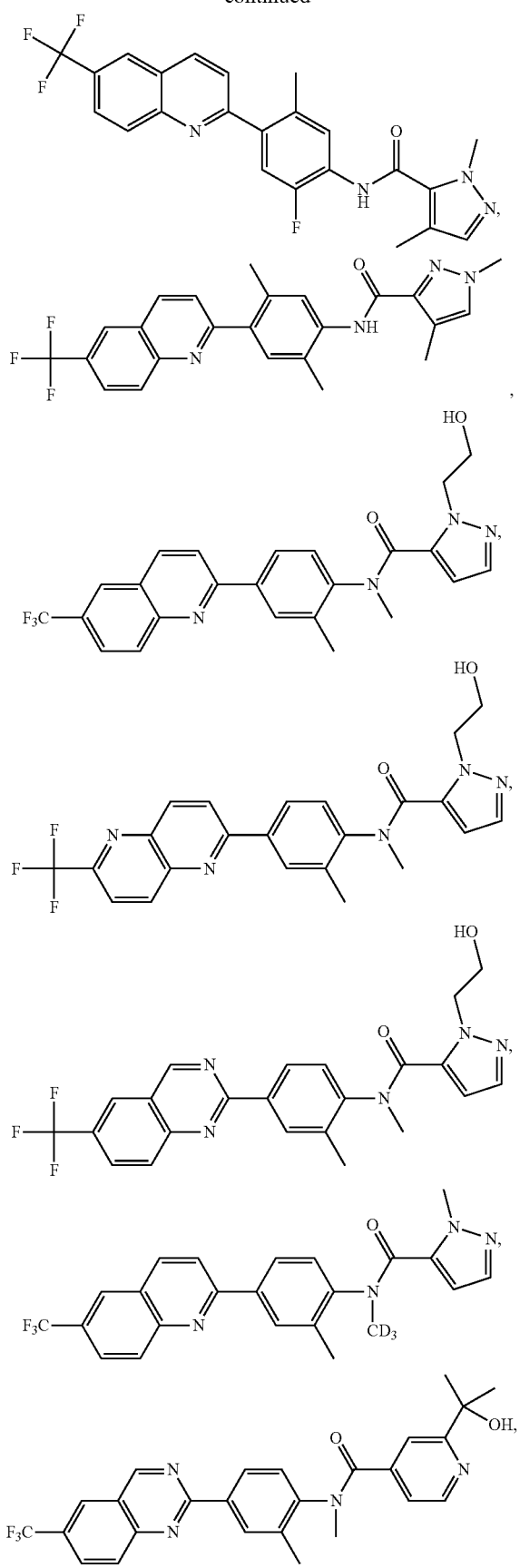
294
-continued
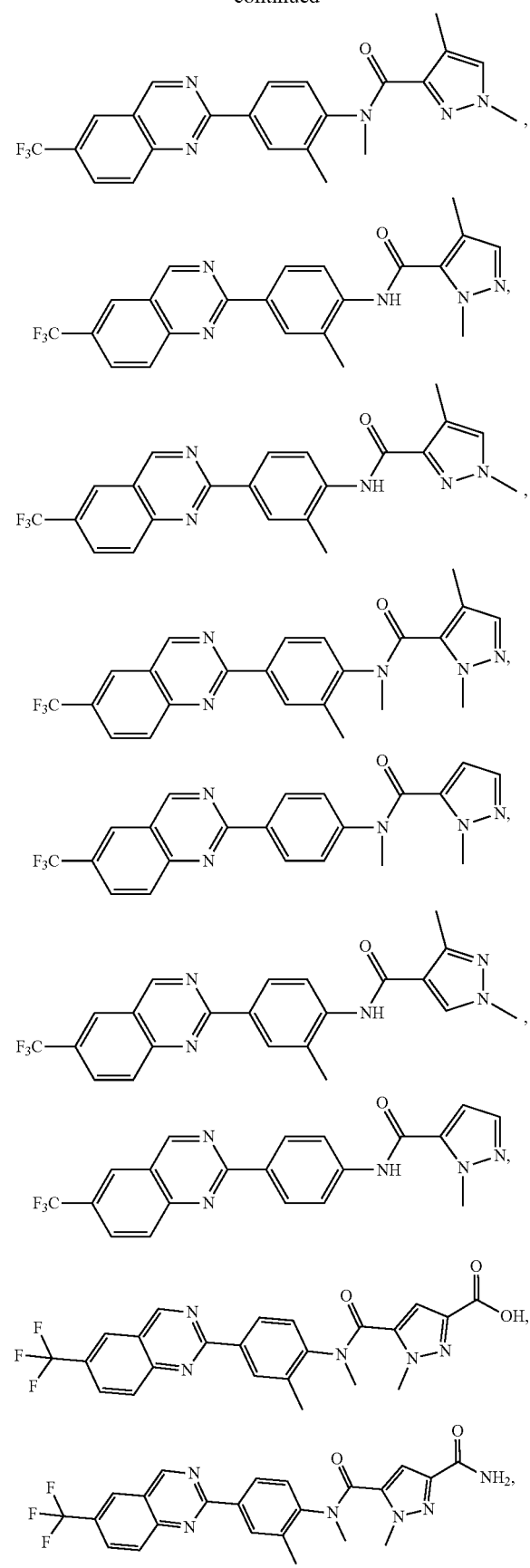

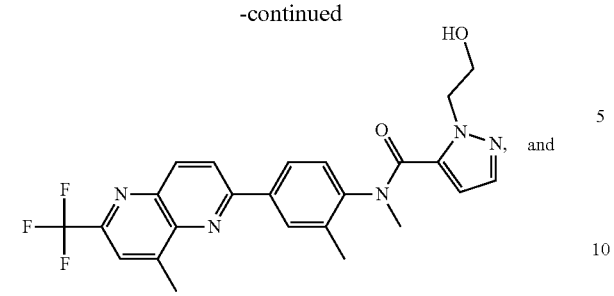
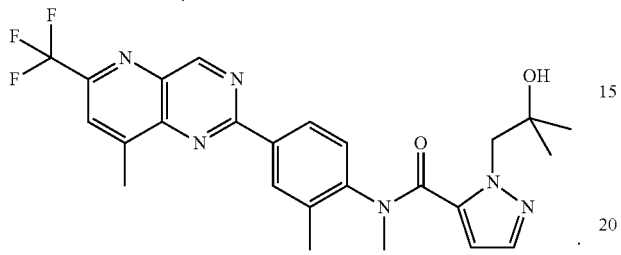
* * * * *